(12) United States Patent
Iwakuma et al.

(10) Patent No.: US 9,685,614 B2
(45) Date of Patent: Jun. 20, 2017

(54) MATERIAL FOR ORGANIC ELECTROLUMINESCENT ELEMENT, AND ELEMENT USING SAME

(71) Applicant: Idemitsu Kosan Co., Ltd., Chiyoda-ku, Tokyo (JP)

(72) Inventors: Toshihiro Iwakuma, Sodegaura (JP); Kazuki Nishimura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 393 days.

(21) Appl. No.: 14/371,399

(22) PCT Filed: Dec. 28, 2012

(86) PCT No.: PCT/JP2012/008442
§ 371 (c)(1),
(2) Date: Jul. 9, 2014

(87) PCT Pub. No.: WO2013/105206
PCT Pub. Date: Jul. 18, 2013

(65) Prior Publication Data
US 2014/0367667 A1 Dec. 18, 2014

(30) Foreign Application Priority Data
Jan. 10, 2012 (JP) .................................. 2012-001815

(51) Int. Cl.
*H01L 51/50* (2006.01)
*H01L 51/00* (2006.01)
(Continued)

(52) U.S. Cl.
CPC ........ *H01L 51/0067* (2013.01); *C07D 471/04* (2013.01); *C07D 491/048* (2013.01);
(Continued)

(58) Field of Classification Search
None
See application file for complete search history.

(56) References Cited

U.S. PATENT DOCUMENTS 7,279,704 B2 10/2007 Walters et al.
2011/0260138 A1* 10/2011 Xia ..................... C07D 405/14
257/40
(Continued)

FOREIGN PATENT DOCUMENTS

JP 2011-084531 A 4/2011
WO WO-2011/048821 A1 4/2011
(Continued)

OTHER PUBLICATIONS

International Search Report received in the International Application No. PCT/JP2012/008442 dated Mar. 12, 2013.
(Continued)

*Primary Examiner* — Gregory Clark
(74) *Attorney, Agent, or Firm* — Foley & Lardner LLP 1: Organic EL device 60: Cathode
50: Electron-transporting zone
40: Phosphorescent emitting layer
30: Hole-transporting zone
20: Anode
10: Substrate

(57) ABSTRACT

A compound represented by the following formula (1):

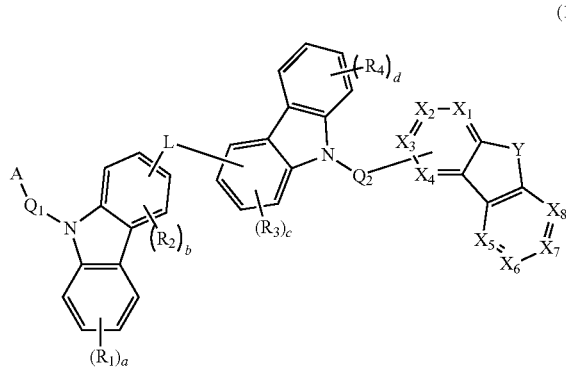

(1)

18 Claims, 1 Drawing Sheet

(51) Int. Cl.
| | | |
|---|---|---|
| *C07D 471/04* | (2006.01) | |
| *C07D 491/048* | (2006.01) | |
| *C07D 495/04* | (2006.01) | |
| *C09K 11/06* | (2006.01) | |

(52) U.S. Cl.
CPC .......... *C07D 495/04* (2013.01); *C09K 11/06* (2013.01); *H01L 51/0071* (2013.01); *H01L 51/0072* (2013.01); *H01L 51/5016* (2013.01); *H01L 51/5036* (2013.01); *C09K 2211/1029* (2013.01); *C09K 2211/1033* (2013.01); *C09K 2211/1044* (2013.01); *C09K 2211/1074* (2013.01); *C09K 2211/185* (2013.01); *H01L 51/0085* (2013.01); *H01L 51/5044* (2013.01)

(56) References Cited

U.S. PATENT DOCUMENTS

| | | |
|---|---|---|
| 2011/0278552 A1 | 11/2011 | Numata et al. |
| 2012/0211736 A1* | 8/2012 | Kim ............... C09K 11/06 257/40 |
| 2012/0223295 A1* | 9/2012 | Inoue ............. C09K 11/06 257/40 |
| 2012/0273767 A1 | 11/2012 | Yokoyama et al. |
| 2012/0305900 A1 | 12/2012 | Kim et al. |
| 2013/0020565 A1 | 1/2013 | Numata et al. |
| 2013/0056720 A1 | 3/2013 | Kim et al. |
| 2013/0140549 A1 | 6/2013 | Xia et al. |

FOREIGN PATENT DOCUMENTS

| | | |
|---|---|---|
| WO | WO-2011/055934 A2 | 5/2011 |
| WO | WO-2011/125680 A1 | 10/2011 |
| WO | WO-2011/137072 A1 | 11/2011 |
| WO | WO-2011/139055 A2 | 11/2011 |
| WO | WO-2012/023947 A1 | 2/2012 |
| WO | WO-2012/108389 A1 | 8/2012 |

OTHER PUBLICATIONS

Written Opinion of the International Searching Authority received in International Application No. PCT/JP2012/008442 dated Jul. 24, 2014.
Office Action issued in Japanese Patent Application No. 2013-553115 dated Jul. 19, 2016.

* cited by examiner

MATERIAL FOR ORGANIC ELECTROLUMINESCENT ELEMENT, AND ELEMENT USING SAME

TECHNICAL FIELD

The invention relates to a novel compound that is preferable for use as a material for an organic electroluminescence device and an organic electroluminescence device using the same.

BACKGROUND ART

An organic electroluminescence (EL) device includes a fluorescent organic EL device and a phosphorescent organic EL device, and a device design optimum for the emission mechanism of each type of organic EL device has been studied. It is known that a highly efficient phosphorescent organic EL device cannot be obtained by merely applying fluorescent device technology due to the emission characteristics. The reasons therefor are generally considered to be as follows.

Specifically, since phosphorescence emission utilizes triplet excitons, a compound used for forming an emitting layer must have a large energy gap. This is because the energy gap (hereinafter often referred to as "singlet energy") of a compound is normally larger than the triplet energy (in the invention, the difference in energy between the lowest excited triplet state and the ground state) of the compound.

In order to confine the triplet energy of a phosphorescent dopant material efficiently in an emitting layer, it is required to use, in an emitting layer, a host material having a triplet energy larger than that of the phosphorescent dopant material. Further, an electron-transporting layer and a hole-transporting layer are required to be provided adjacent to an emitting layer, and a compound having a triplet energy larger than that of a phosphorescent dopant material is required to be used in the electron-transporting layer and the hole-transporting layer.

As mentioned above, if based on the conventional design concept of an organic EL device, it leads to the use of a compound having a larger energy gap as compared with a compound used in a fluorescent organic EL device in a phosphorescent organic EL device. As a result, the driving voltage of the entire organic EL device is increased.

Further, a hydrocarbon-based compound having a high resistance to oxidation or reduction, which has been useful in a fluorescent device, the π electron cloud spreads largely, and hence it has a small energy gap. Therefore, in a phosphorescent organic EL device, such a hydrocarbon-based compound is hardly selected. As a result, an organic compound including a hetero atom such as oxygen and nitrogen is selected, and hence a phosphorescent organic EL device has a problem that it has a short lifetime as compared with a fluorescent organic EL device.

In addition, a significantly long exciton relaxation of a triplet exciton of a phosphorescent dopant material as compared with that of a singlet exciton greatly affects the device performance. That is, emission from the singlet exciton has a high relaxation speed that leads to emission, and hence, diffusion of excitons to peripheral layers of emitting layers (a hole-transporting layer or an electron-transporting layer, for example) hardly occurs, whereby efficient emission is expected. On the other hand, in the case of emission from the triplet exciton, since it is spin-forbidden and has a slow relaxation speed, diffusion of excitons to the peripheral layers tends to occur easily, and as a result, thermal energy deactivation occurs from other compounds than a specific phosphorescent emitting compound. That is, in a phosphorescent organic EL device, control of a recombination region of electrons and holes is more important than that of a fluorescent organic EL device.

For the reasons mentioned above, in order to improve the performance of a phosphorescent organic EL device, material selection and device design that are different from a fluorescent organic EL device have come to be required.

If a structure, in which the π conjugation is cut, is taken in order to increase the triplet energy of the compound, transporting properties of carriers may be deteriorated. That is, in order to improve the transporting properties of carriers, it is required to elongate the π conjugation. However, if the π conjugation is elongated, a problem then arises that the triplet energy is lowered.

Under such circumstances, as an organic EL device, Patent Documents 1 and 2 disclose a compound having, as a mother skeleton, a 3,3-biscarbazole formed by bonding of two carbazoles at the $3^{rd}$ position, in which a heteroaromatic ring substituent is bonded to the two carbazoles.

Patent Document 3 discloses a compound having a biscarbazole as a mother skeleton, in which a nitrogen-containing aromatic ring substituent is bonded to these two carbazoles.

Patent Document 4 discloses a compound having a biscarbazole as a mother skeleton, in which a carbazole skeleton is further bonded to the two biscarbazoles.

RELATED ART DOCUMENTS

Patent Documents

Patent Document 1: WO2011/125680
Patent Document 2: WO2011/137072
Patent Document 3: WO2011/139055
Patent Document 4: WO2011/055934

SUMMARY OF THE INVENTION

An object of the invention is to provide a material having a high triplet energy that can be used as a material of an organic EL device that emits phosphorescent light.

According to the invention, the following compounds or the like are provided.

1. A compound represented by the following formula (1):

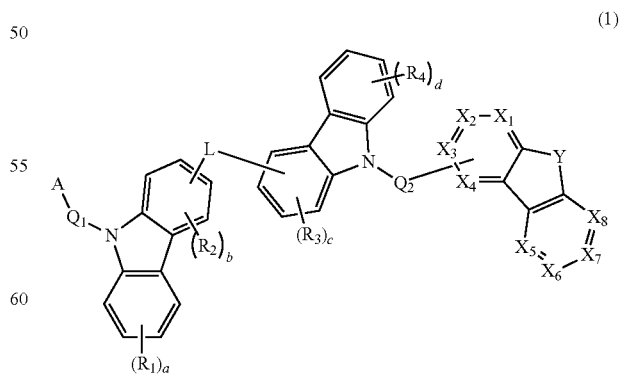

wherein in the formula (1),
L, $Q_1$ and $Q_2$ are independently a single bond or a linking group;

A is a substituted or unsubstituted nitrogen-containing heterocyclic group including 5 to 10 ring atoms;

$X_1$ to $X_8$ are independently a carbon atom that is bonded to $Q_2$, CH or N, provided that at least one of $X_1$ to $X_8$ is N;

Y is O, S, a nitrogen atom that is bonded to $Q_2$, or $NR_5$;

$R_1$ to $R_5$ are independently a substituted or unsubstituted aryl group including 6 to 18 ring carbon atoms, a substituted or unsubstituted heteroaryl group including 5 to 18 ring atoms, a substituted or unsubstituted alkyl group including 1 to 20 carbon atoms, a substituted or unsubstituted alkoxy group including 1 to 20 carbon atoms, a substituted or unsubstituted haloalkyl group including 1 to 20 carbon atoms, a substituted or unsubstituted haloalkoxy group including 1 to 20 carbon atoms, or a cyano group; and a and d are independently an integer of 0 to 4, and b and c are independently an integer of 0 to 3, when a is 2 or more, $R_1$s may be the same or different from each other, when b is 2 or more, $R_2$s may be the same or different from each other, when c is 2 or more, $R_3$s may be the same or different from each other, and when d is 2 or more, $R_4$s may be the same or different from each other.

2. The compound according to 1, wherein a to d in the formula (1) are 0.

3. The compound according to 1, which is a compound represented by any of the following formulas (2) to (17):

(2)

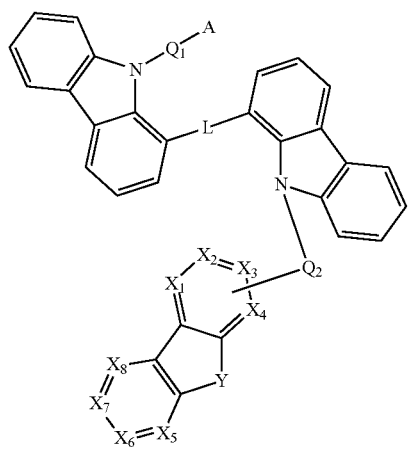

(3)

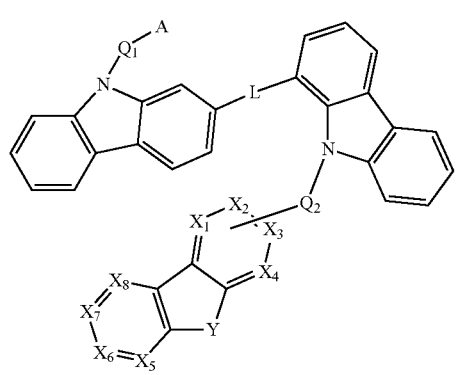

-continued (4)

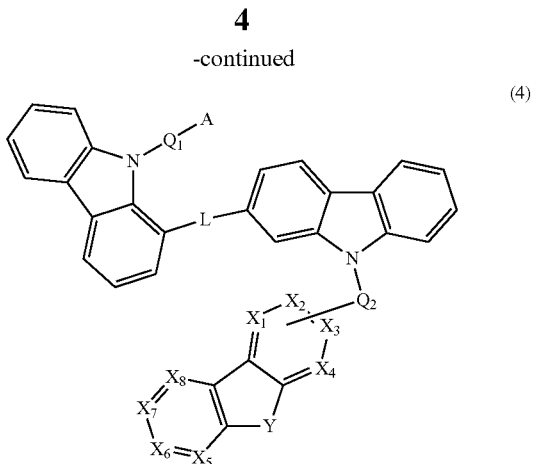

(5)

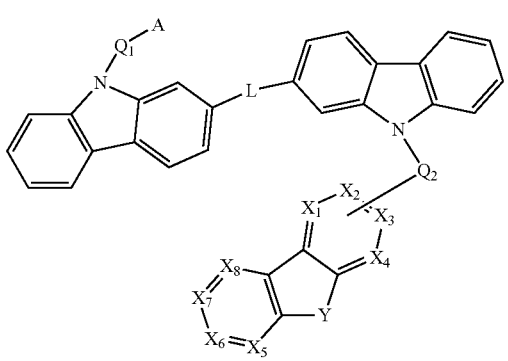

(6)

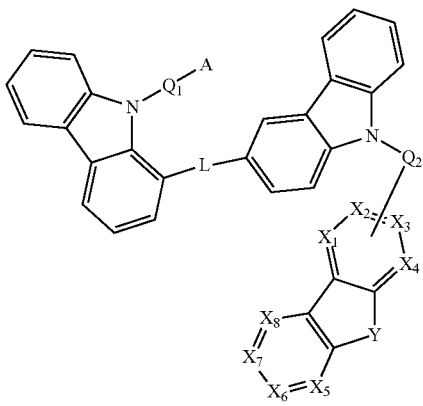

(7)

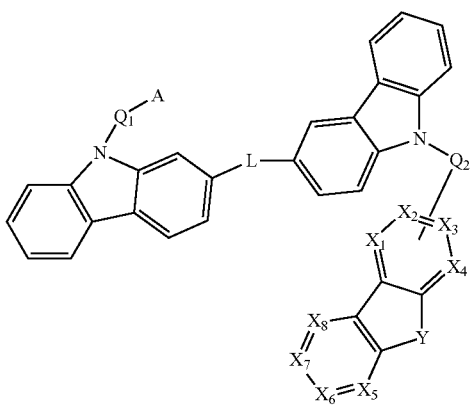

(8)
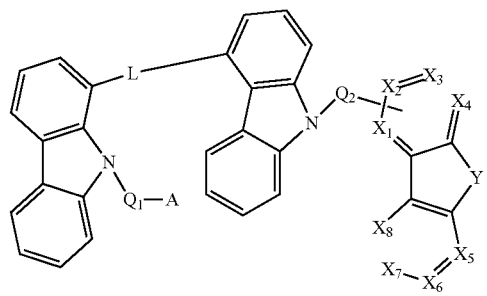
(9)
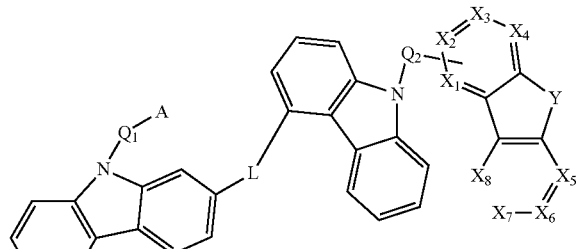
(10)
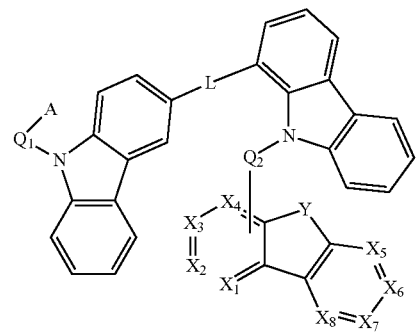
(11)
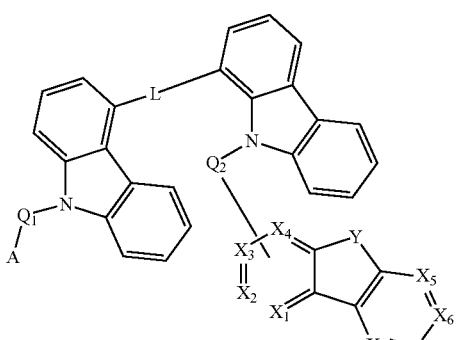
(12)
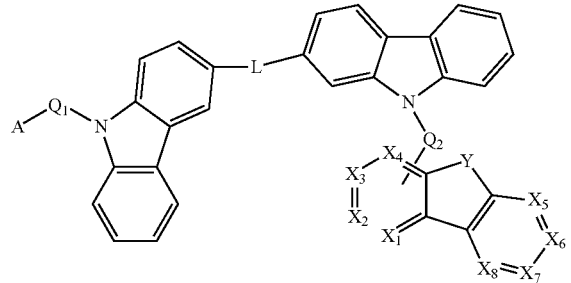
(13)
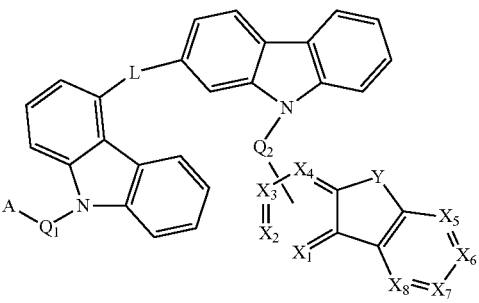
(14)
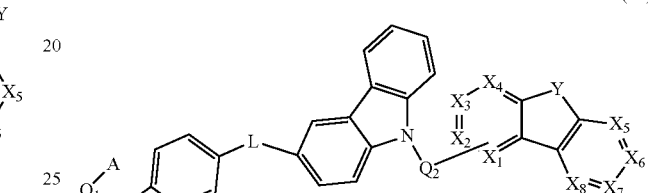
(15)
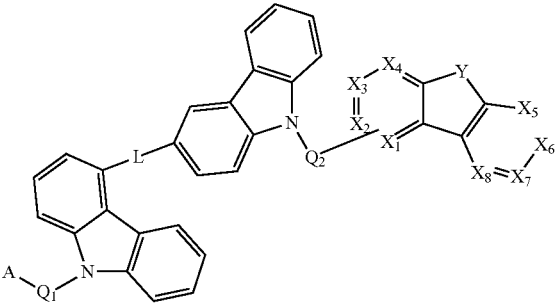
(16)
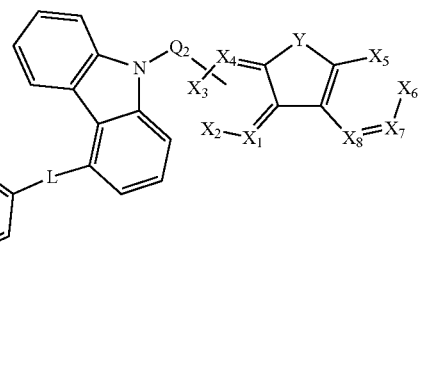

-continued (17)

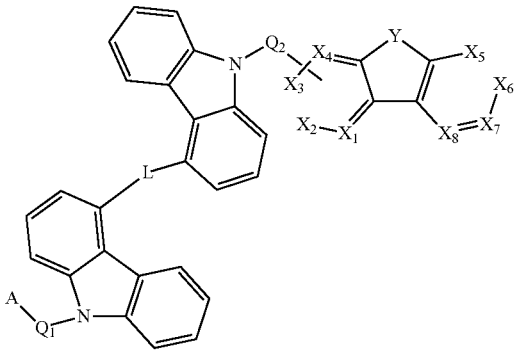

wherein in the formulas (2) to (17), A, $Q_1$, $Q_2$, L, $X_1$ to $X_8$ and Y are independently the same as in the formula (1).

4. The compound according to any of 1 to 3, wherein A is a group including a substituted or unsubstituted pyridine ring, a substituted or unsubstituted pyrimidine ring, a substituted or unsubstituted triazine ring, a substituted or unsubstituted pyrazine ring or a substituted or unsubstituted quinazoline ring.

5. An organic electroluminescence device comprising between a cathode and an anode one or more organic thin film layers including an emitting layer, wherein at least one layer of the organic thin film layers comprises the compound according to any of 1 to 4.

6. The organic electroluminescence device according to 5, wherein the organic thin film layers comprise one or more emitting layers, and at least one layer of the emitting layers comprises the compound according to any of 1 to 4 and a phosphorescent material.

7. The organic electroluminescence device according to 6, wherein the phosphorescent material has a triplet energy of 1.8 eV or more and less than 2.9 eV.

8. The organic electroluminescence device according to 6, wherein the phosphorescent material comprises a metal complex, and the metal complex comprises a metal atom selected from Ir, Pt, Os, Au, Cu, Re and Ru and a ligand.

9. The organic electroluminescence device according to 8, wherein the ligand has an ortho-metal bond with the metal atom.

10. The organic electroluminescence device according to any of 5 to 9, which has a maximum emission wavelength of 430 nm or more and 720 nm or less.

11. The organic electroluminescence device according to any of 5 to 10, wherein the organic thin film layers comprise one or more electron-transporting layers arranged between the emitting layer and the cathode, and at least one layer of the electron-transporting layers comprises the compound according to any of 1 to 4.

12. The electroluminescence device according to 11, wherein the organic thin film layers comprise two or more electron-transporting layers arranged between the emitting layer and the cathode, and at least one of the electron-transporting layers comprises the compound according to any of 1 to 4, and the identical or other electron-transporting layer comprises a heteroaromatic hydrocarbon ring compound including a nitrogen-containing six-member ring skeleton or a nitrogen-containing five-member ring skeleton, or a heterofused aromatic ring compound including a nitrogen-containing six-member ring skeleton or a nitrogen-containing five-member ring skeleton.

According to the invention, a compound having a high triplet energy can be provided. An organic EL device that uses the compound of the invention has a lower driving voltage and has an excellent luminous efficiency.

MODE FOR CARRYING OUT THE INVENTION

Figure 1:
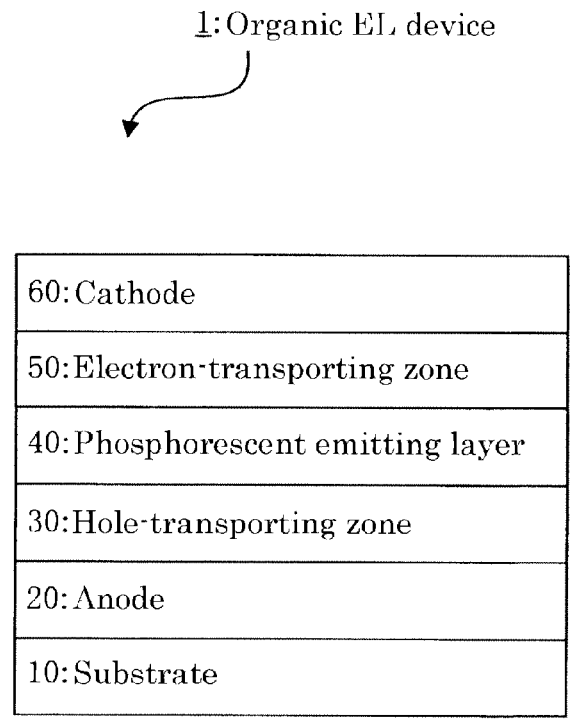
FIG. 1 is a schematic view showing the layer structure according to one embodiment of the organic EL device of the invention.

The compound of the invention is represented by the following formula (1):

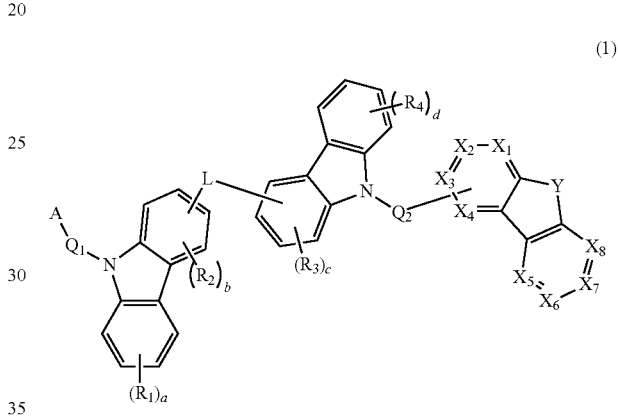

(1)

The compound represented by the formula (1) has two carbazole skeletons, and a nitrogen-containing fused heteroaromatic ring having a high triplet energy is bonded to the nitrogen atom of one of these carbazoles, and has a nitrogen-containing aromatic ring substituent in the nitrogen atom of another carbazole. Due to such a structure, barrier of injection of carriers to the emitting layer can be suppressed while maintaining a high energy level. As a result, the driving voltage of the device can be further lowered.

In a green to red phosphorescent device or a white phosphorescent device that requires a high triplet energy, the compound of the invention is effective for maintaining a high luminous efficiency and for lowering the driving voltage. In order to maintain a high luminous efficiency, a material capable of confining a high triplet energy is required. For maintaining a high triplet energy, it is important to control the molecular skeleton of the material in the triplet energy excited state.

In the formula (1), L, $Q_1$ and $Q_2$ are independently a single bond or a linking group.

As the linking group, a substituted or unsubstituted aromatic hydrocarbon ring group including 6 to 18 carbon atoms that form a ring (hereinafter referred to as the "ring carbon atoms") or a substituted or unsubstituted aromatic heterocyclic group including 5 to 18 atoms that form a ring (hereinafter referred to as "ring atoms").

As $Q_1$, a single bond and a phenylene group are preferable.

As $Q_2$ and L, a single bond, a phenylene group, or a group derived from a pyridine ring, a pyrimidine ring and a triazine ring are preferable.

A is a substituted or unsubstituted nitrogen-containing heterocyclic group including 5 to 10 ring atoms. For example, A is a group including a substituted or unsubstituted pyridine ring, a substituted or unsubstituted pyrimidine ring, a substituted or unsubstituted triazine ring, a substituted or unsubstituted pyrazine ring or a substituted or unsubstituted quinazoline ring, or the like.

Preferable examples of A include a substituted or unsubstituted pyridine ring, a substituted or unsubstituted pyrimidine ring, a substituted or unsubstituted triazine ring and a substituted or unsubstituted quinazoline ring.

$X_1$ to $X_8$ are independently a carbon atom that is bonded to $Q_2$, CH or N, provided that at least one of $X_1$ to $X_8$ is N.

Y is O, S, a nitrogen atom that is bonded to $Q_2$, or $NR_5$.

Among $X_1$ to $X_8$ and Y, one is bonded to $Q_2$ or the nitrogen atom in the carbazole ring by a single bond.

$R_1$ to $R_5$ are independently a substituted or unsubstituted aryl group including 6 to 18 ring carbon atoms, a substituted or unsubstituted heteroaryl group including 5 to 18 ring atoms, a substituted or unsubstituted alkyl group including 1 to 20 carbon atoms, a substituted or unsubstituted alkoxy group including 1 to 20 carbon atoms, a substituted or unsubstituted haloalkyl group including 1 to 20 carbon atoms, a substituted or unsubstituted haloalkoxy group including 1 to 20 carbon atoms, or a cyano group.

a and d are independently an integer of 0 to 4, and b and c are independently an integer of 0 to 3, when a is 2 or more, $R_1$s may be the same or different from each other, when b is 2 or more, $R_2$s may be the same or different from each other, when c is 2 or more, $R_3$s may be the same or different from each other, and when d is 2 or more, $R_4$s may be the same or different from each other.

In the invention, it is preferred that a to d be 0, i.e. the two carbazole rings do not have a substituent. As a result, since excessive electron conjugation of the substituent and the aromatic ring does not occur, a favorable triplet energy can be obtained.

As examples of the compound represented by the formula (1), compounds represented by any of the following formulas (2) to (17) can be given.

(2)

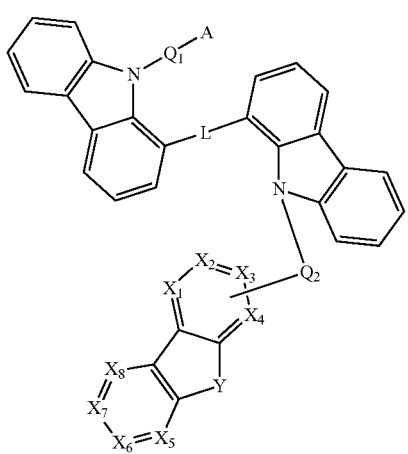

(3)

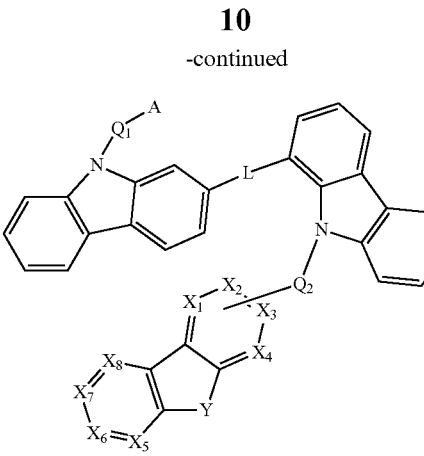

(4)

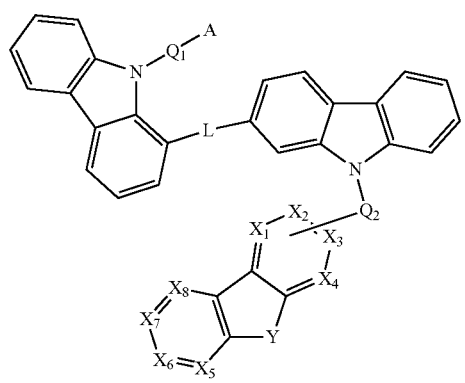

(5)

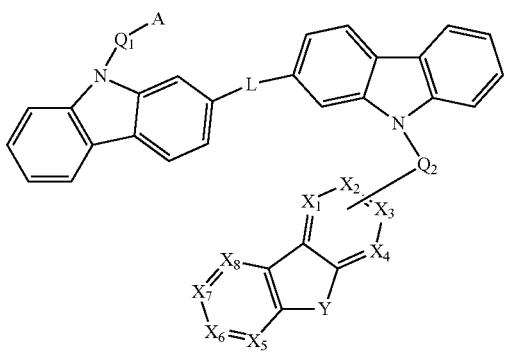

(6)

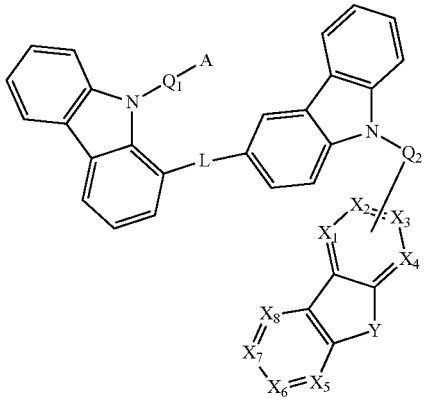

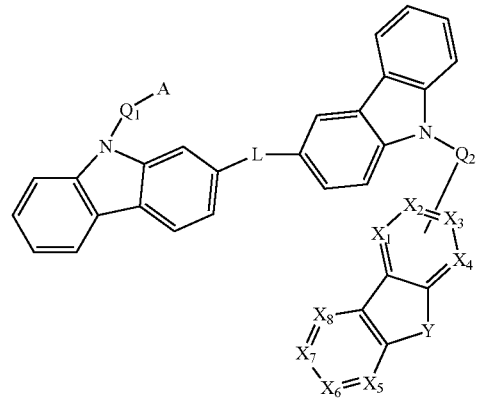
(7)
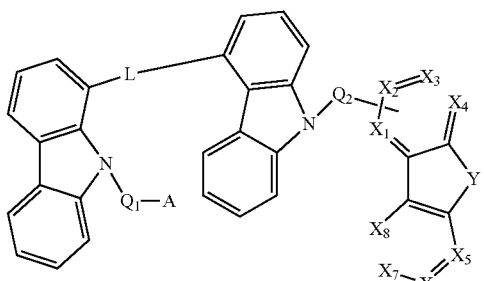
(8)
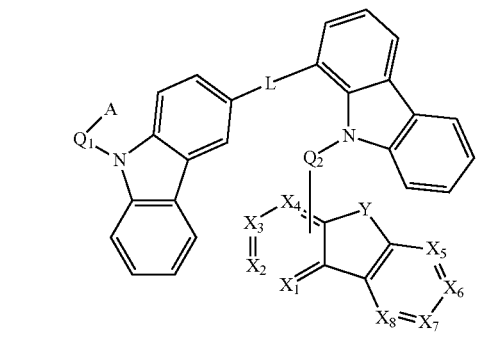
(9)
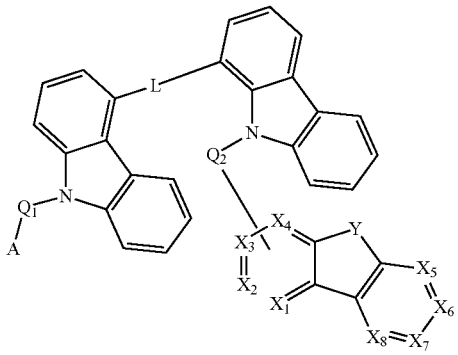
(10)
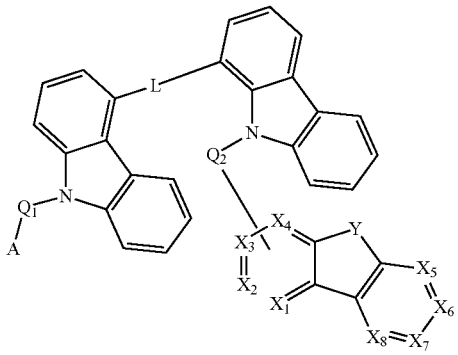
(11)
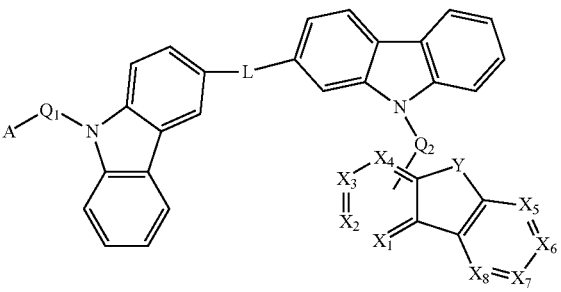
(12)
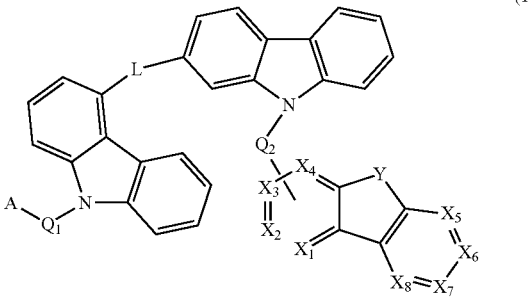
(13)
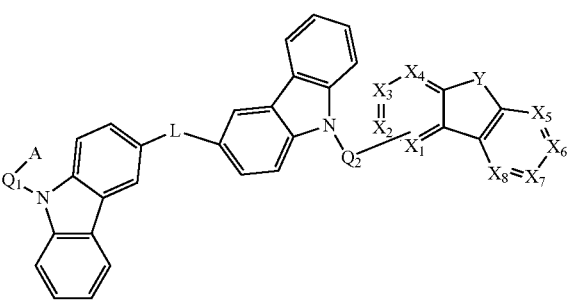
(14)
(15)

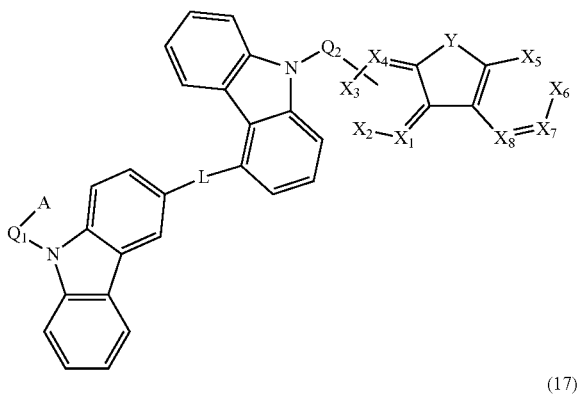

(16)

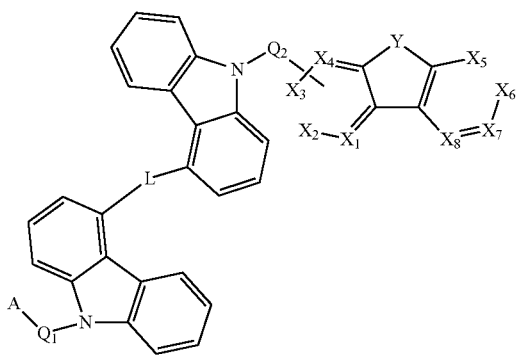

(17)

In the formulas (2) to (17), A, $Q_1$, $Q_2$, L, $X_1$ to $X_8$ and Y are independently the same as A, $Q_1$, $Q_2$, L, $X_1$ to $X_8$ and Y in the formula (1).

As the compound represented by the formula (1), compounds represented by any of the above formulas (7), (12) and (17) are preferable.

Hereinbelow, an explanation will be made on each group in the formulas (1) to (17).

In the specification, the aryl group includes a monocyclic aromatic hydrocarbon ring group and a fused aromatic hydrocarbon ring group obtained by fusing of a plurality of hydrocarbon rings. The heteroaryl group includes a monocyclic heteroaromatic ring group, a heterofused aromatic ring group obtained by fusing of a plurality of heteroaromatic rings, and a heterofused aromatic ring group obtained by fusing of an aromatic hydrocarbon ring and a heteroaromatic ring.

In the invention, a hydrogen atom includes an isomer differing in number of neutrons. That is, a hydrogen atom includes protium, deuterium and tritium.

As specific examples of the aryl group including 6 to 18 ring carbon atoms, a phenyl group, a triphenylenyl group, a fluorenyl group, a 9,9-dimethylfluorenyl group, a biphenyl group, a terphenyl group or the like can be given. Among them, a phenyl group and a biphenyl group are preferable.

It is preferred that the aryl group include 6 to 12 ring carbon atoms.

The "ring carbon atom" means a carbon atom that forms a saturated ring, an unsaturated ring or an aromatic ring.

As the aromatic hydrocarbon ring group including 6 to 18 ring carbon atoms as the linking group, a group obtained by excluding a hydrogen atom from the above-mentioned aryl group can be mentioned. Specifically, a benzene ring, a naphthalene ring and the like are preferable.

As specific examples of the heteroaryl group including 5 to 18 ring atoms, a pyrrolyl group, a pyrazinyl group, a pyridinyl group, an indolyl group, an isoindolyl group, an imidazolyl group, a furyl group, a benzofuranyl group, an isobenzofuranyl group, a dibenzofuranyl group, a dibenzothiophenyl group, a carbazolyl group, a phenylcarbazolyl group, an acridinyl group, a phenothiazinyl group, a phenoxazinyl group, an oxazolyl group, an oxadiazolyl group, a furazanyl group, a thienyl group, a benzothiophenyl group or the like can be given. Among these, a dibenzofuranyl group, a dibenzothiophenyl group, a carbazolyl group or a phenylcarbazolyl group can preferably be given.

It is preferred that the heteroaryl group include 5 to 13 ring atoms.

The "ring atom" means an atom that forms a saturated ring, an unsaturated ring or an aromatic ring As the aromatic heterocyclic group including 5 to 18 ring atoms as the linking group, a group obtained by excluding a hydrogen atom from the above-mentioned heteroaryl group can be mentioned. Specifically, a pyridine ring, a pyrimidine ring, a triazine ring, a pyrazine ring and the like are preferable.

As specific examples of the alkyl group including 1 to 20 carbon atoms, a linear or branched alkyl group can be mentioned. Specific examples thereof include a methyl group, an ethyl group, a propyl group, an isopropyl group, an n-butyl group, an isobutyl group, a sec-butyl group, a tert-butyl group, an n-pentyl group, an n-hexyl group, an n-heptyl group, and an n-octyl group. Of these, a methyl group, an ethyl group, a propyl group, an isopropyl group, an n-butyl group, an isobutyl group, a sec-butyl group and a tert-butyl group can preferably be given. A methyl group, an ethyl group, a propyl group, an isopropyl group, an n-butyl group, a sec-butyl group and a tert-butyl group are preferable.

As the alkoxy group including 1 to 20 carbon atoms, a methoxy group, an ethoxy group, a propoxy group, a butoxy group, a pentyloxy group, a hexyloxy group or the like can be given. As for an alkoxy group including 3 or more carbon atoms, it may be a linear, cyclic or branched alkoxy group. Among these, one including 1 to 6 carbon atoms is preferable.

As the haloalkyl group including 1 to 20 carbon atoms, a group in which the above-mentioned alkyl group including 1 to 20 carbon atoms is substituted by one or more halogen atoms can be given. Specifically, a fluoromethyl group, a difluoromethyl group, a trifluoromethyl group, a fluoroethyl group, a trifluoromethylmethyl group, a pentafluoroethyl group or the like can be given. A trifluoromethyl group and a pentafluoroethyl group are preferable.

As the haloalkoxy group including 1 to 20 carbon atoms, a group in which the above-mentioned alkoxy group is substituted by one or more halogen atoms can be given. Specifically, a trifluoromethoxy group, a pentafluoroethoxy group or the like can be mentioned.

As the substituent expressed by the "substituted or unsubstituted . . . " of each of the above-mentioned groups, the alkyl group, the alkoxy group, the aryl group, the heteroaryl group mentioned above, a substituted or unsubstituted amino group, a substituted or unsubstituted silyl group, a cycloalkyl group, a halogen atom (a fluorine atom, a chlorine atom, a bromine atom, an iodine atom, or the like can be given, with a fluorine atom being preferable), a fluoroalkyl group, a hydroxyl group, a nitro group, a cyano group, a carboxy group, an aryloxy group or the like can be given. These substituents may be further substituted by the above-mentioned substituents.

Specific examples of the compound of the invention will be given below.
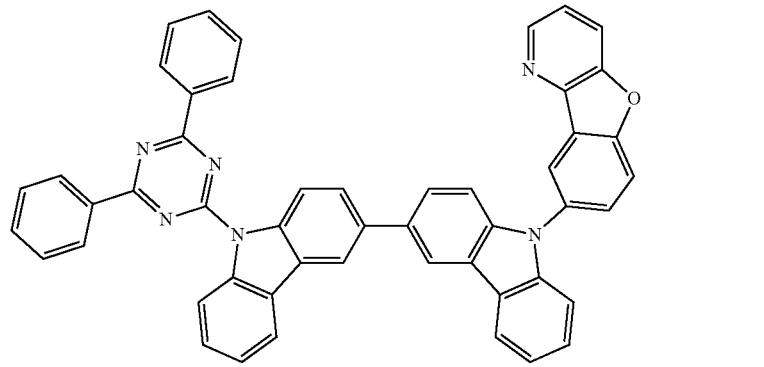
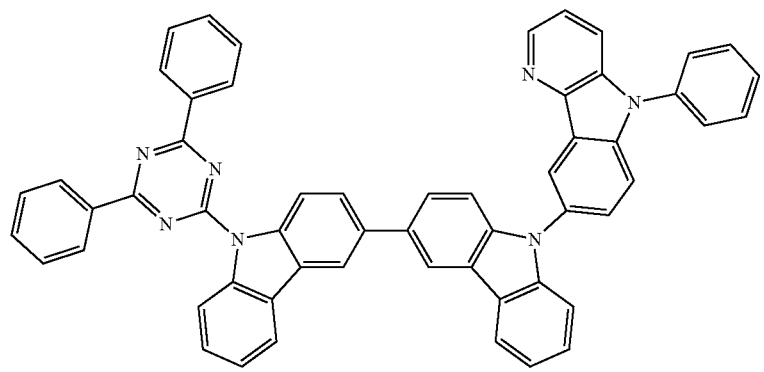
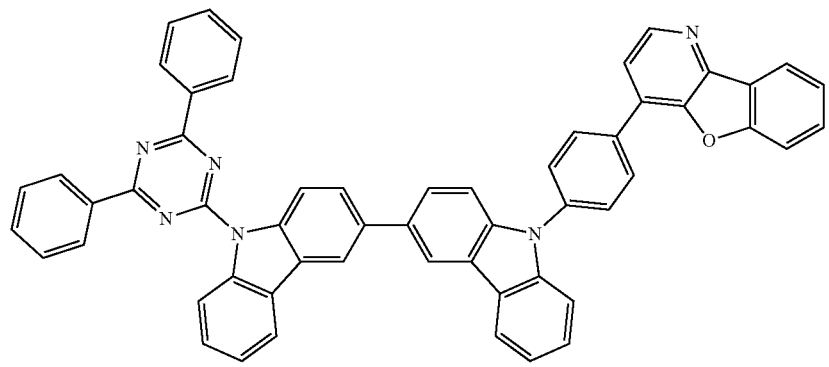
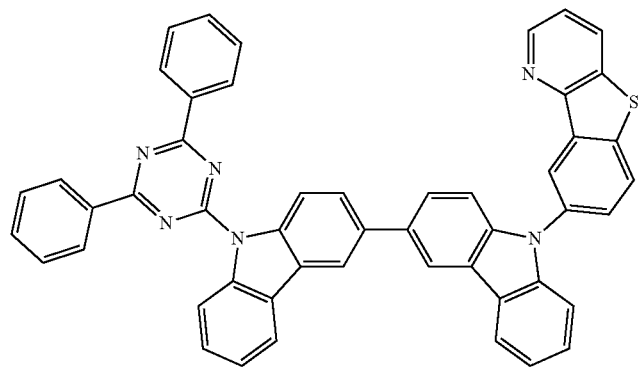

-continued
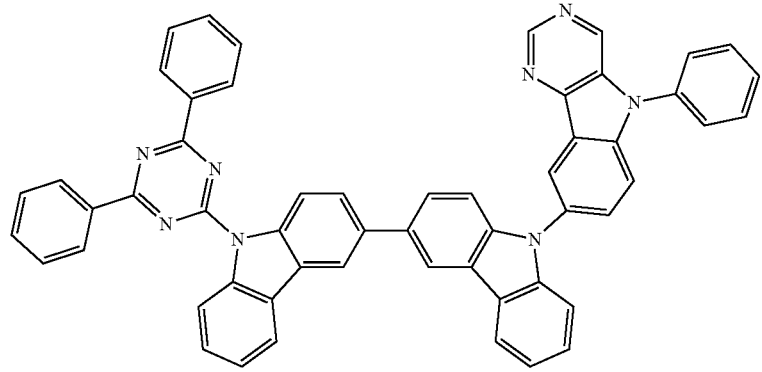
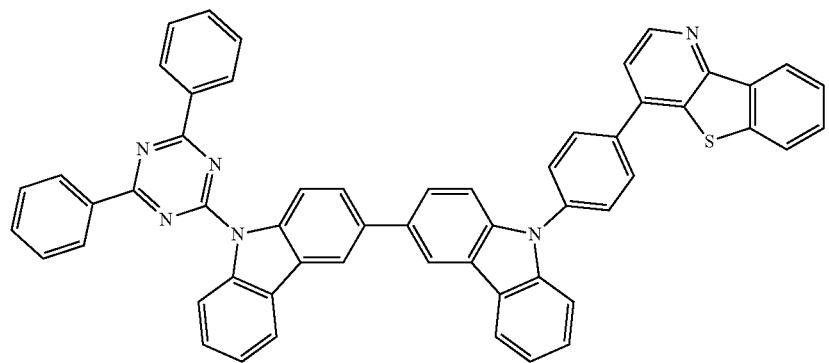
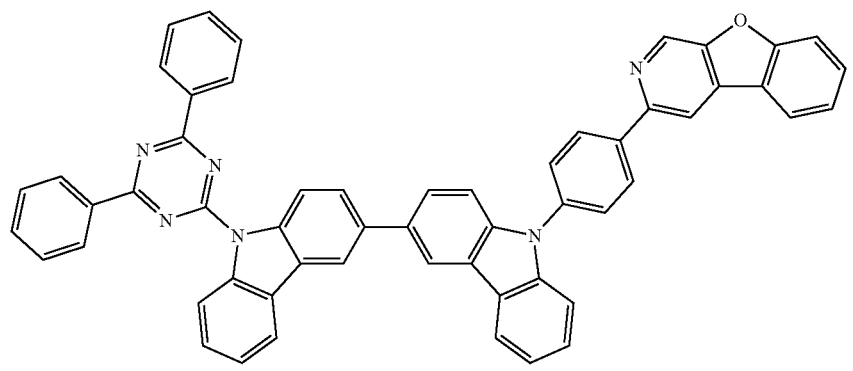
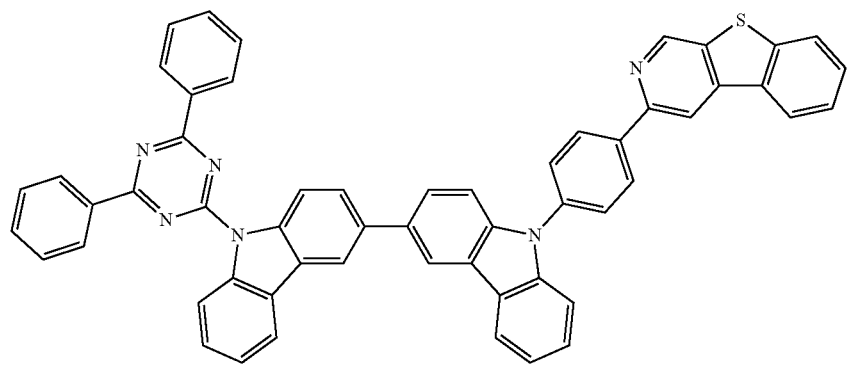

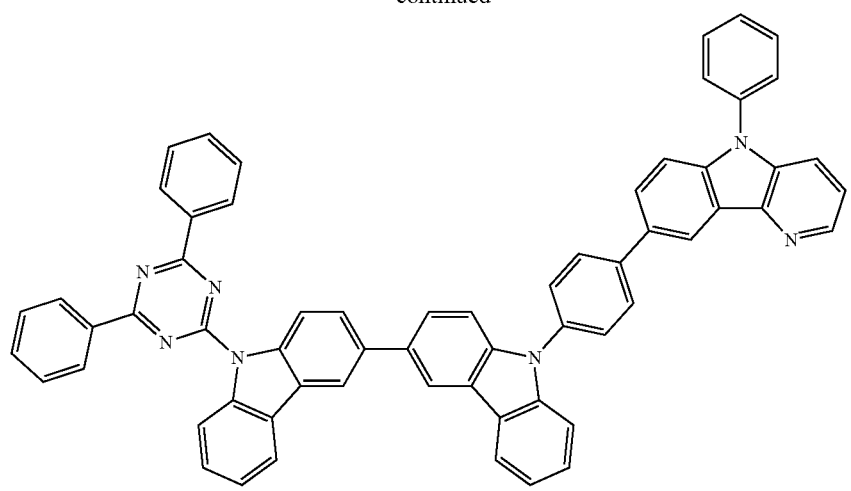
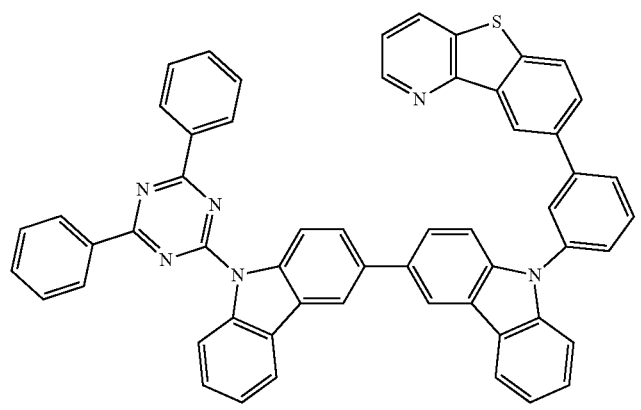

-continued
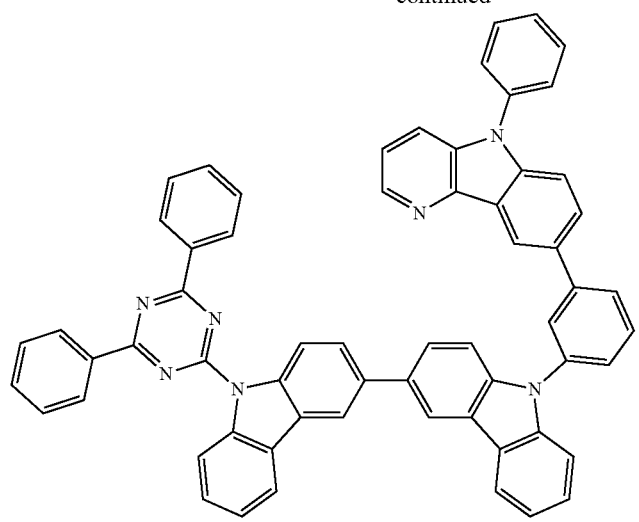
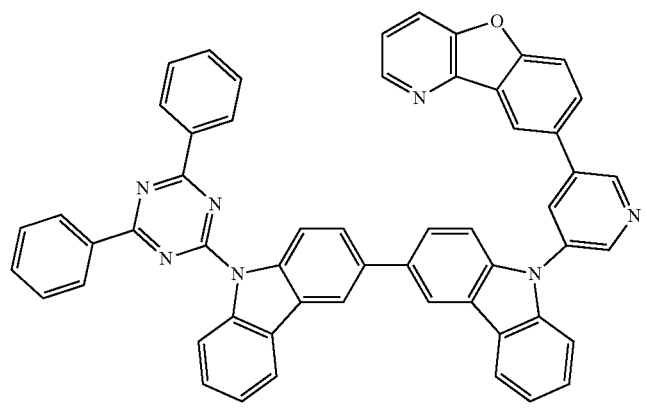

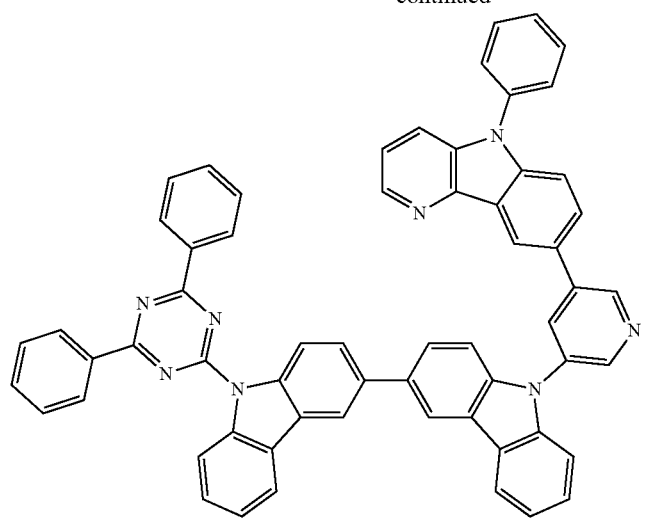
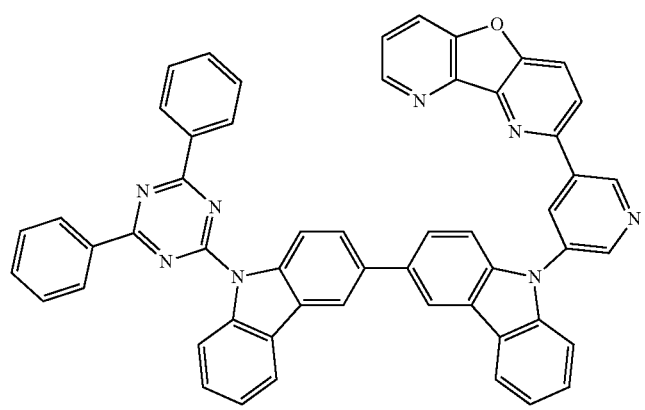
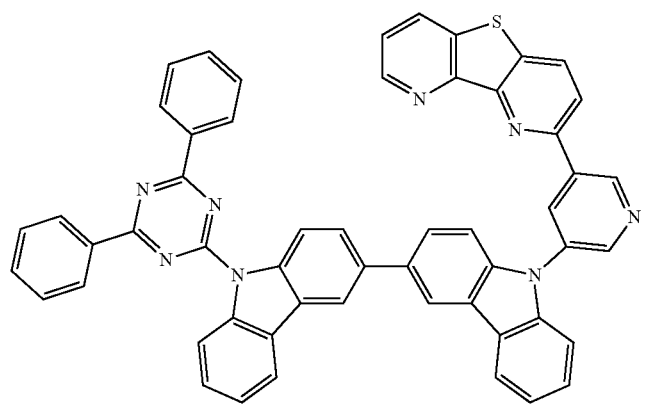

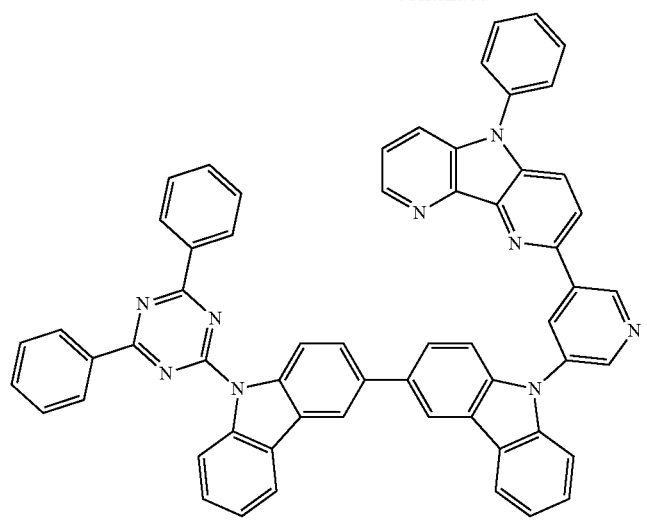
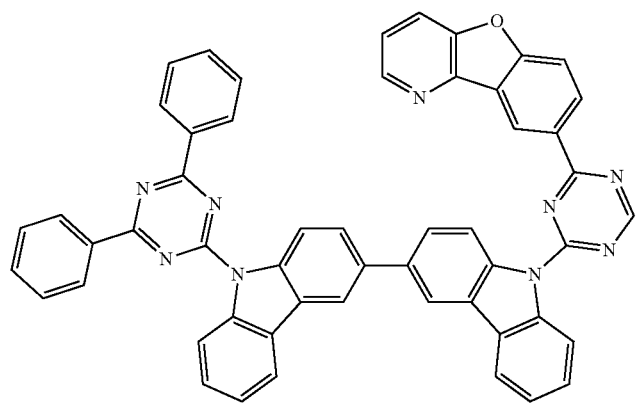
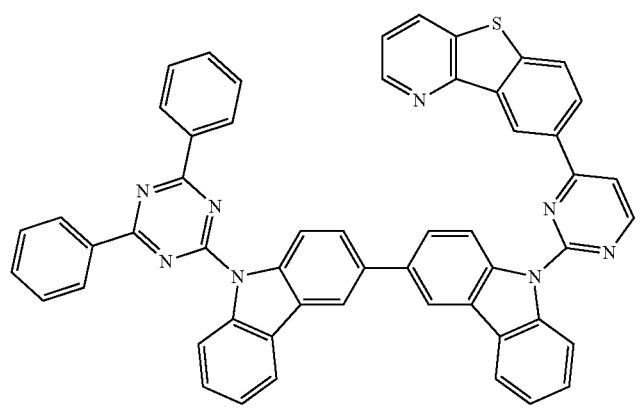

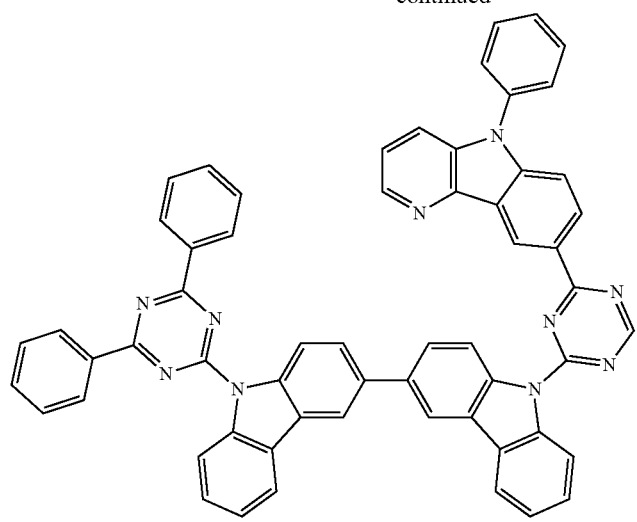
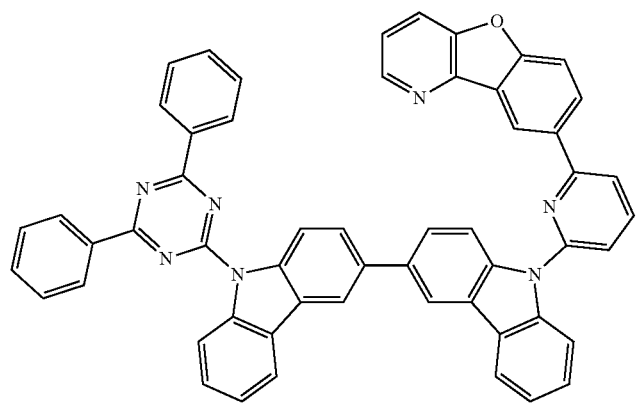
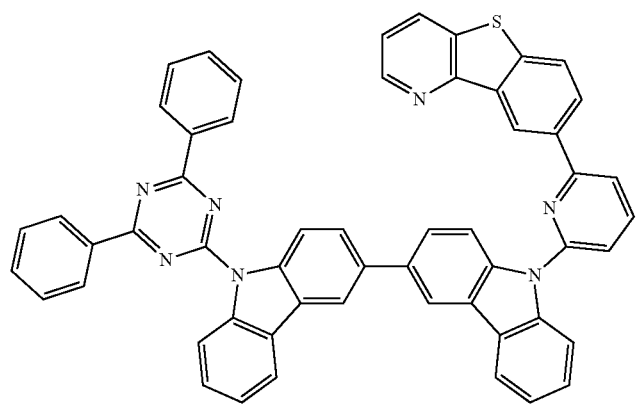

-continued
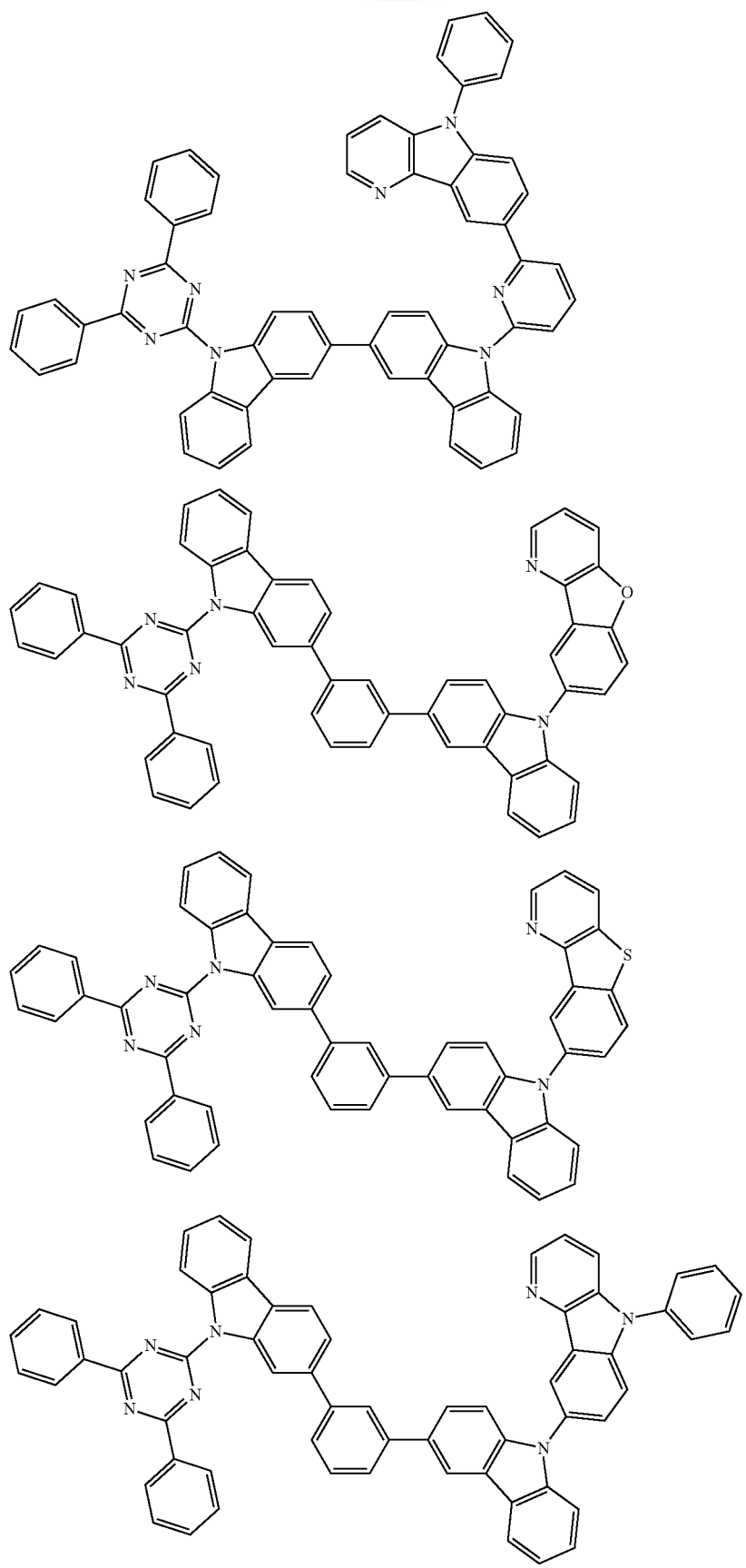

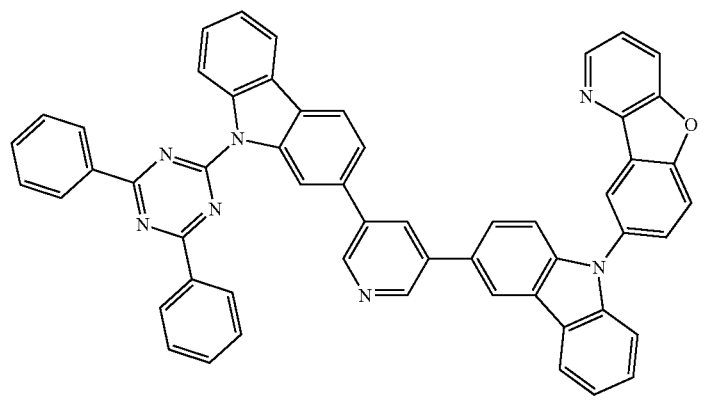
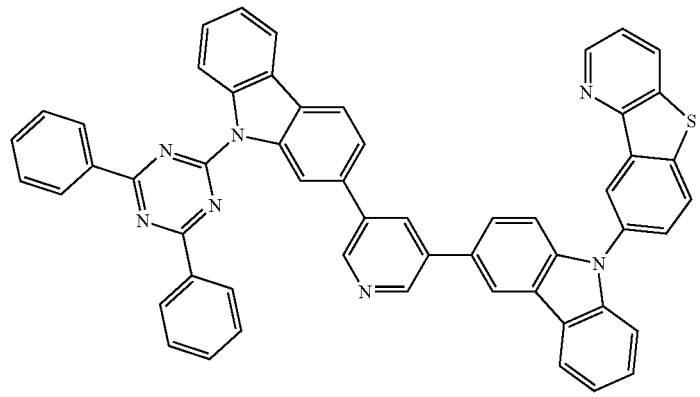
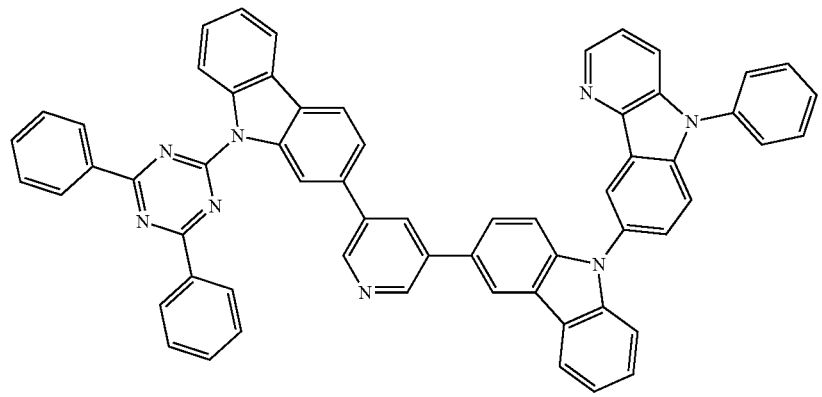
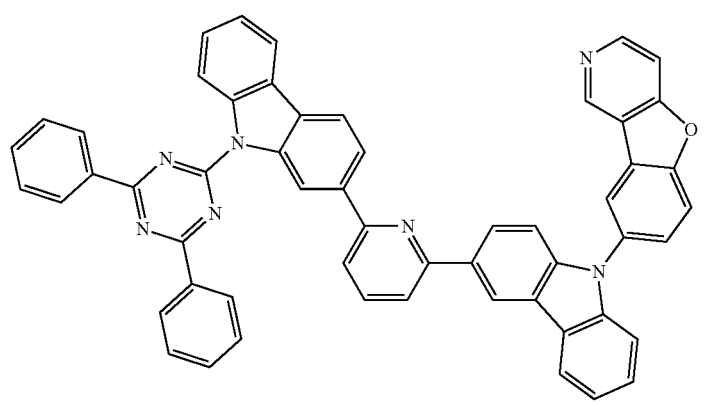

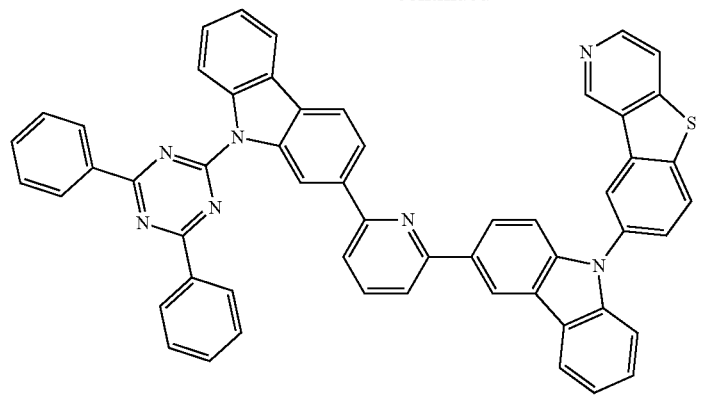
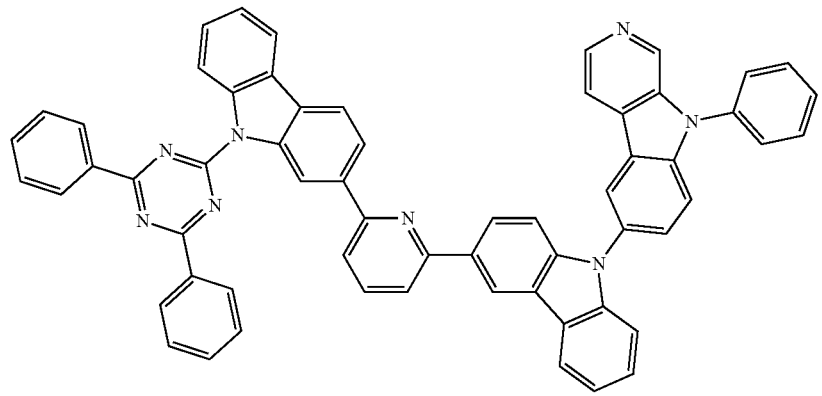
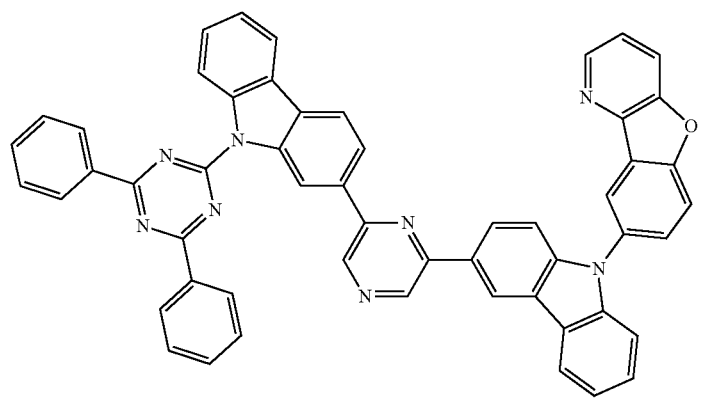
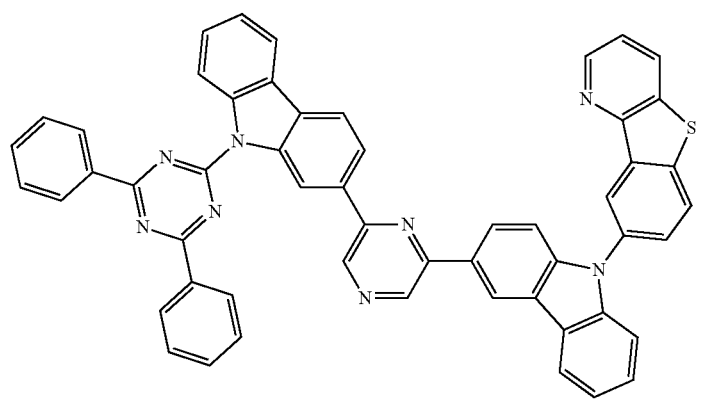

-continued
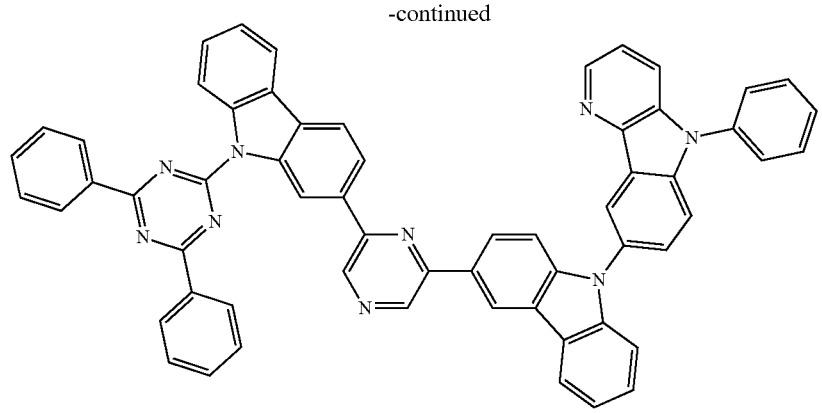
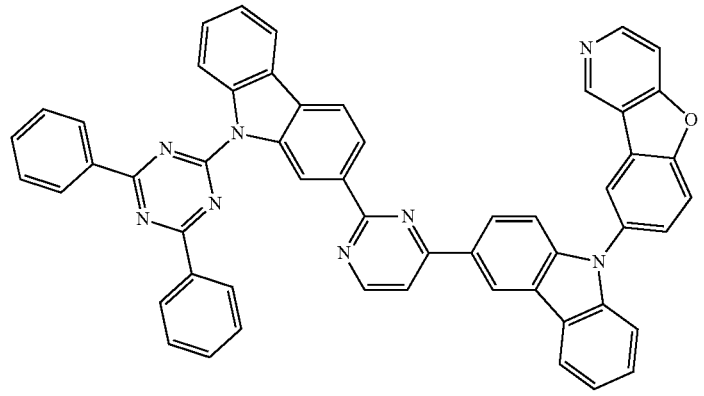
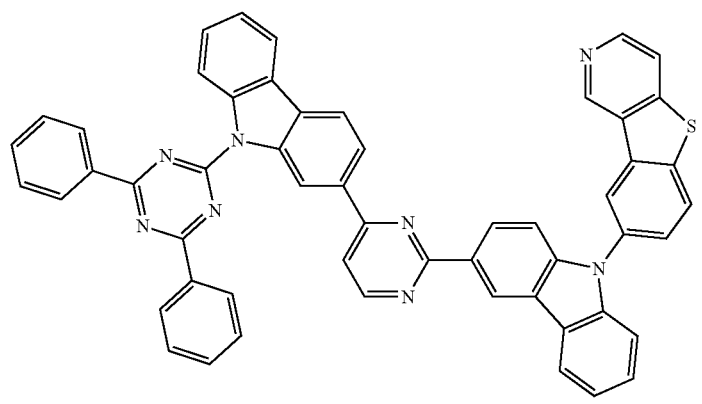
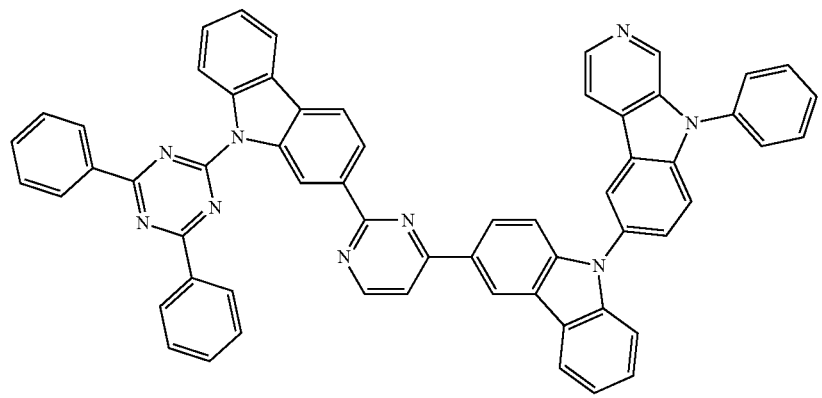

-continued
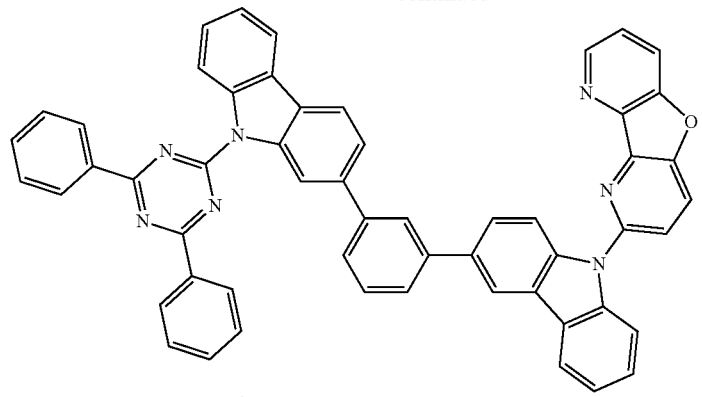
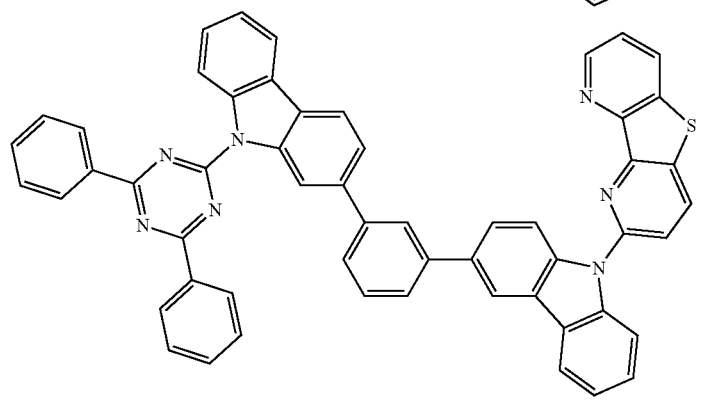
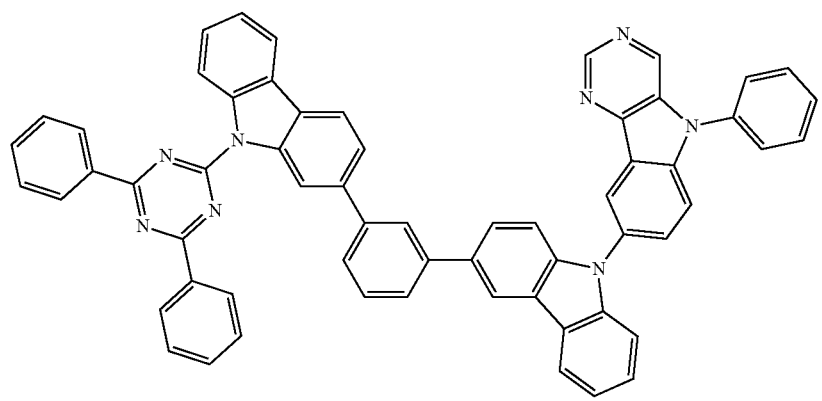
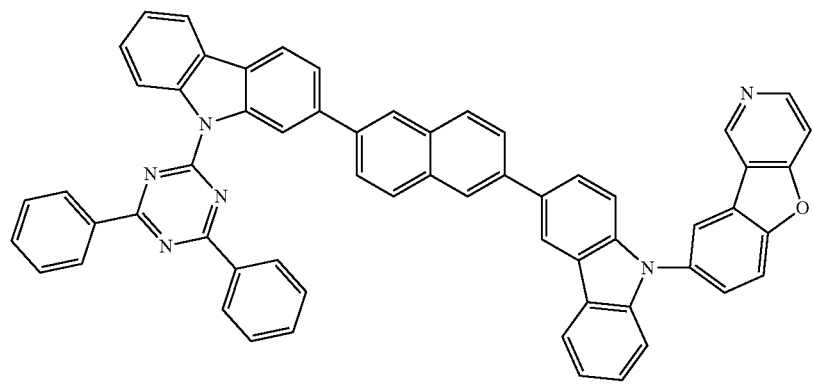

-continued
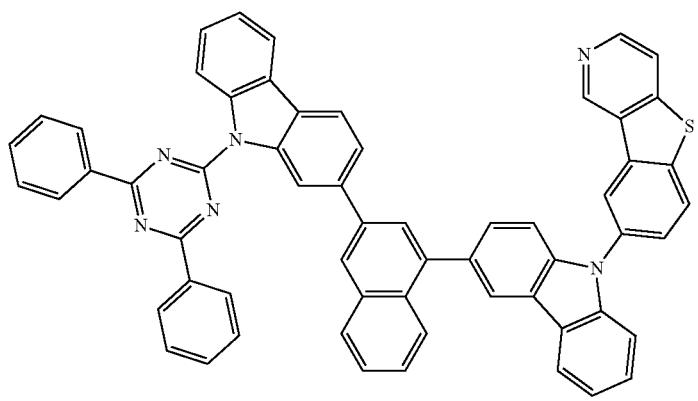
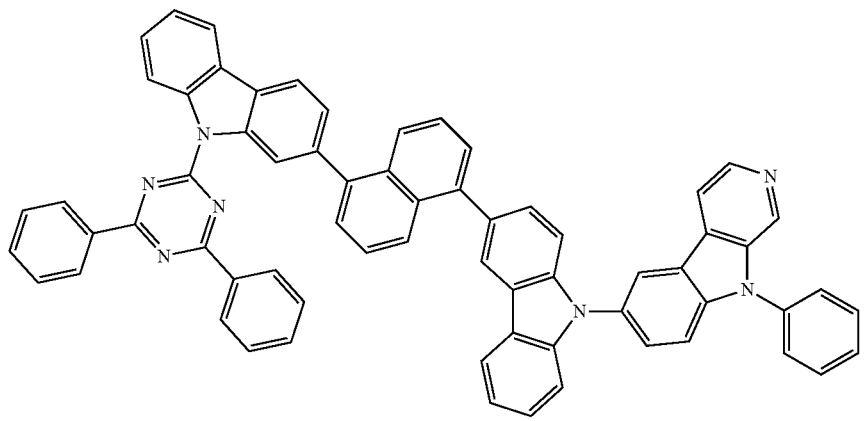
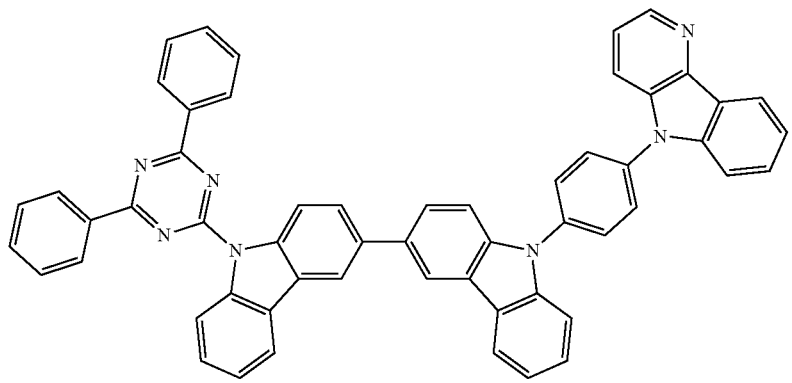
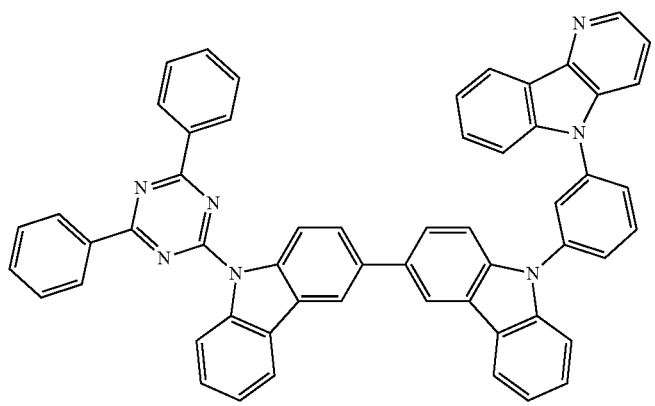

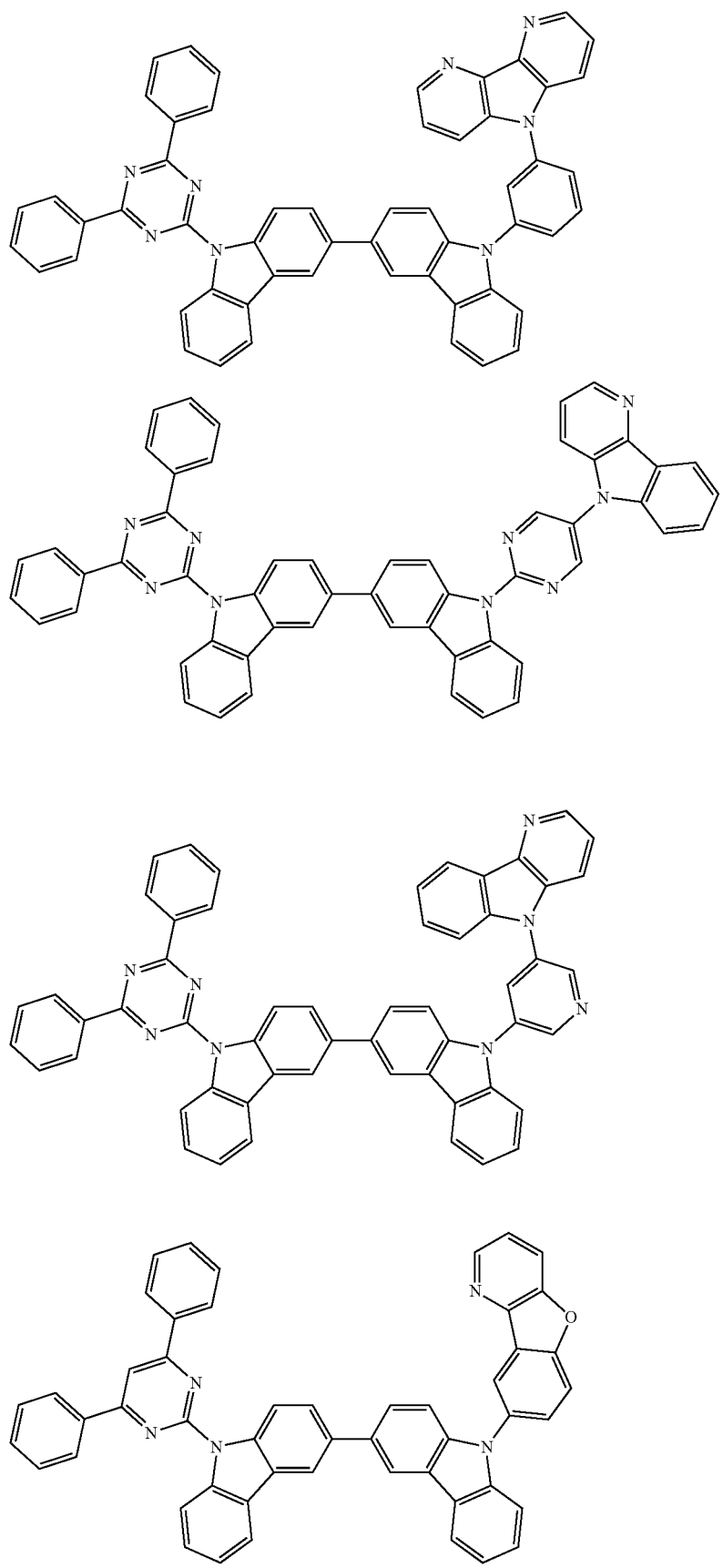

-continued
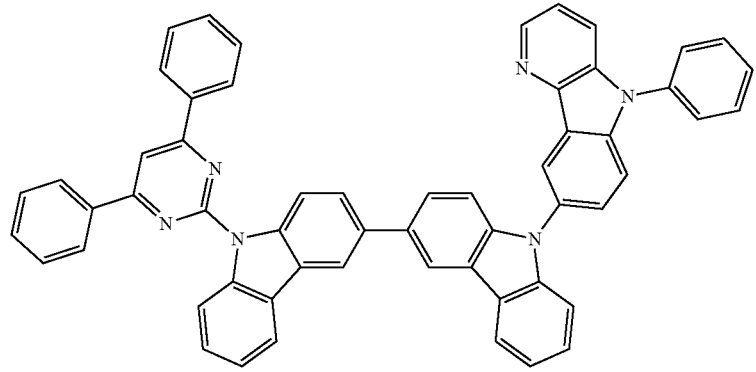

-continued
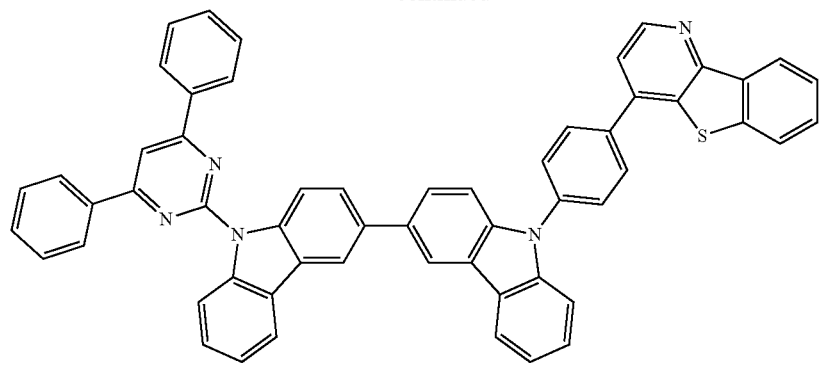
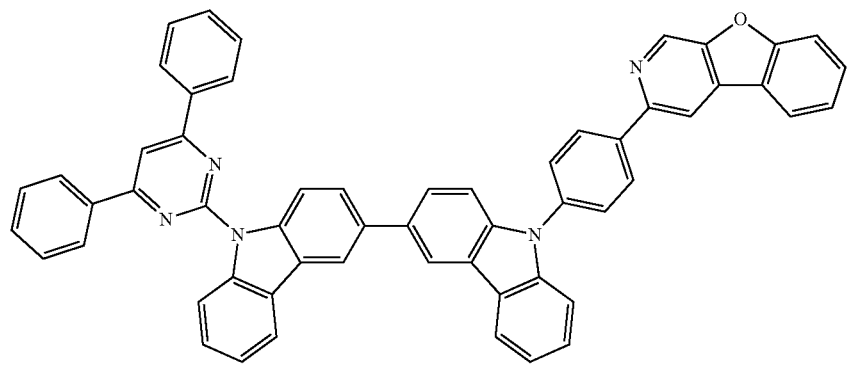
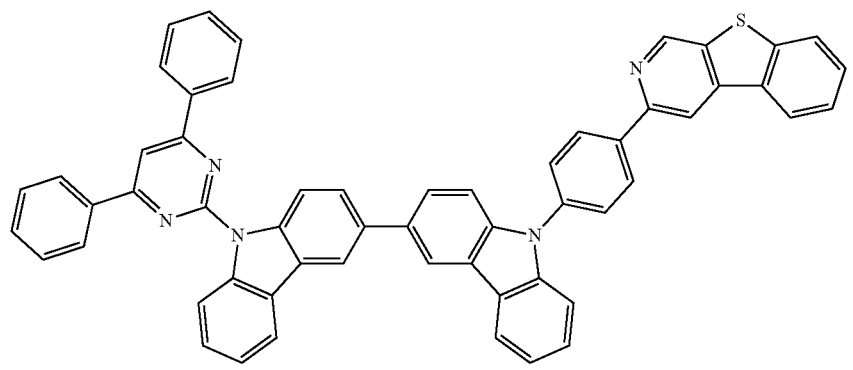
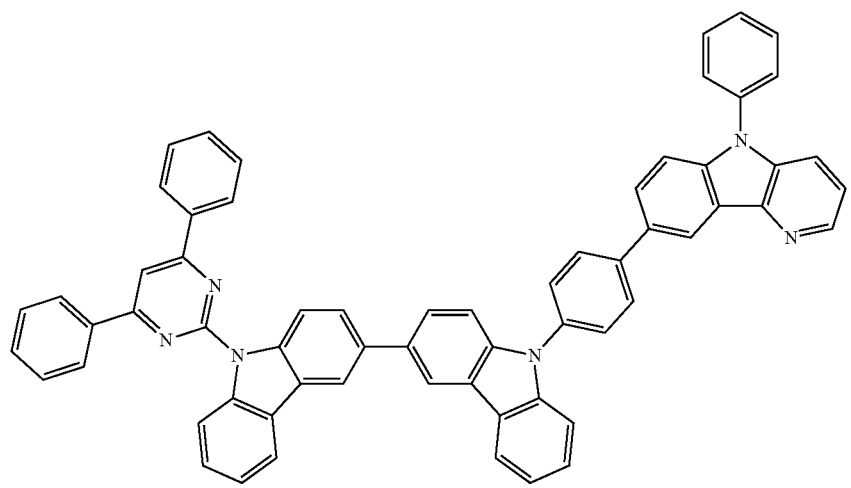

-continued
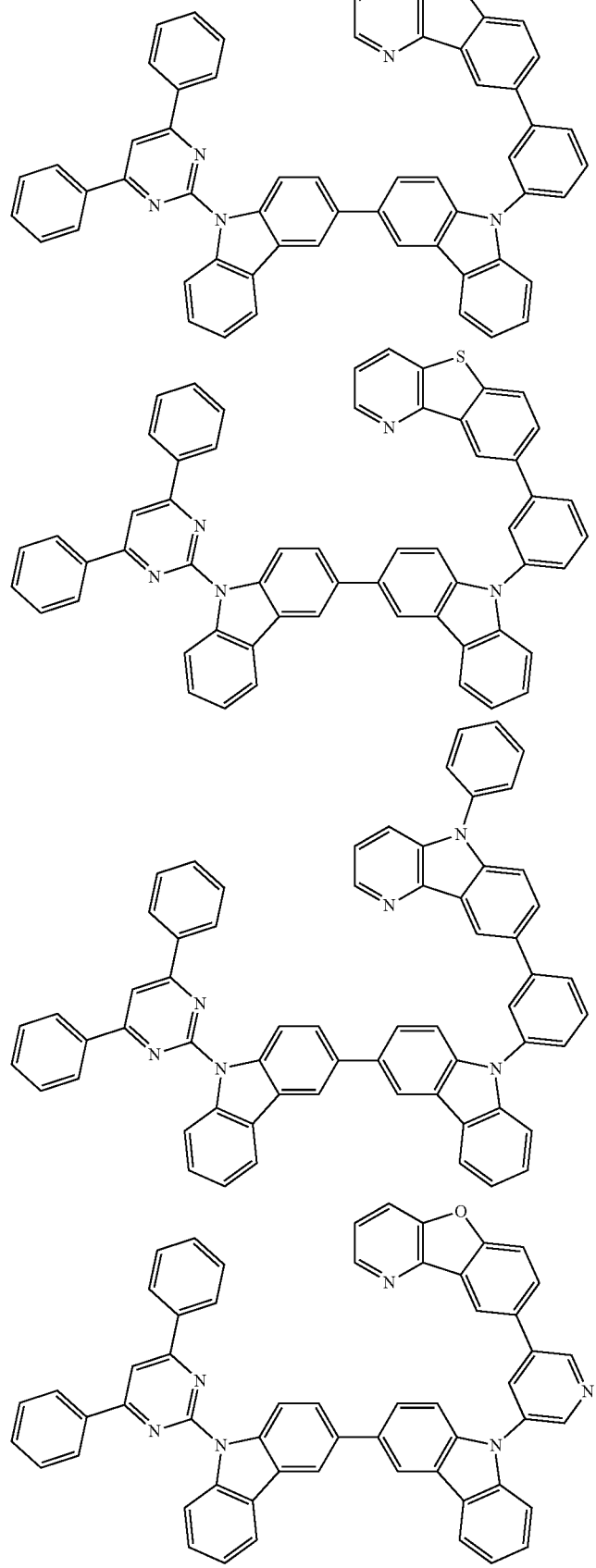

-continued
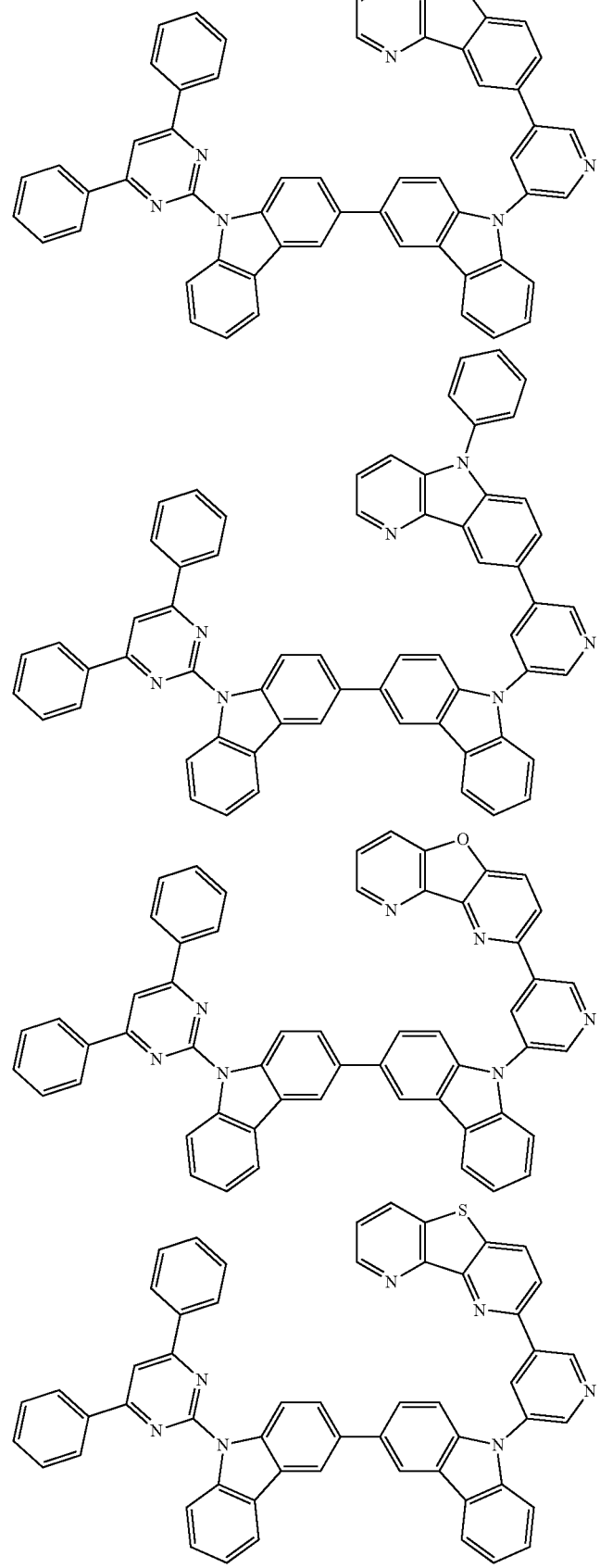

-continued
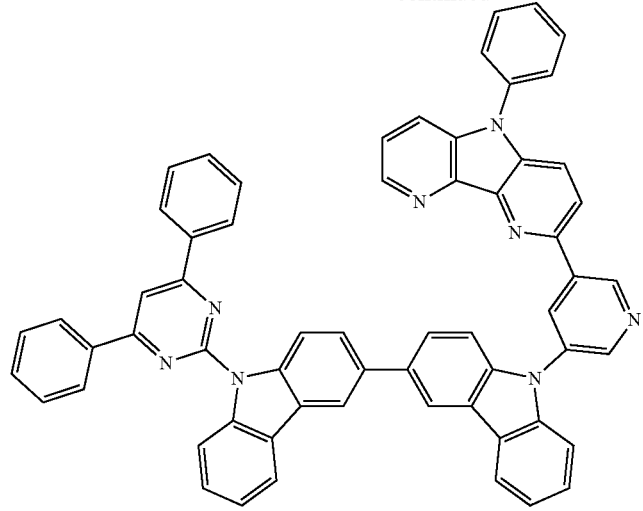
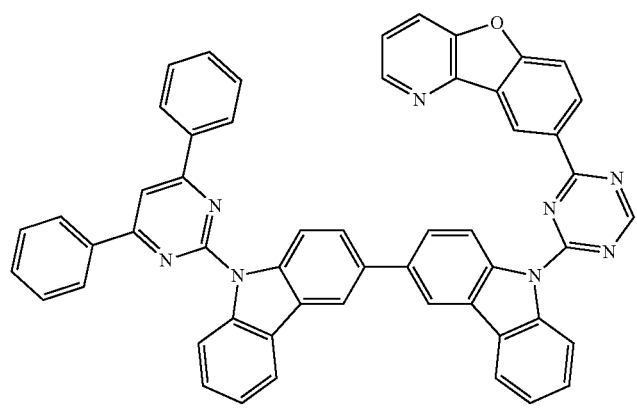
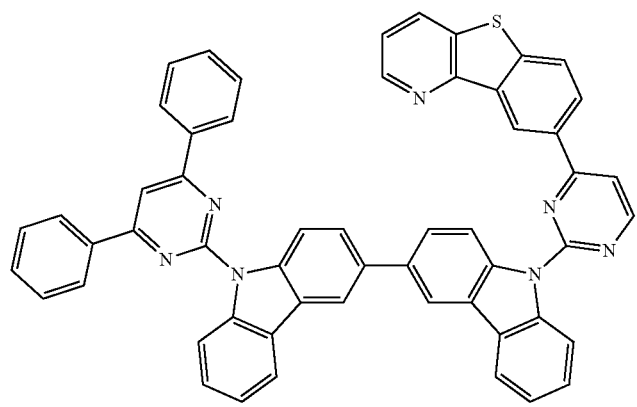

-continued
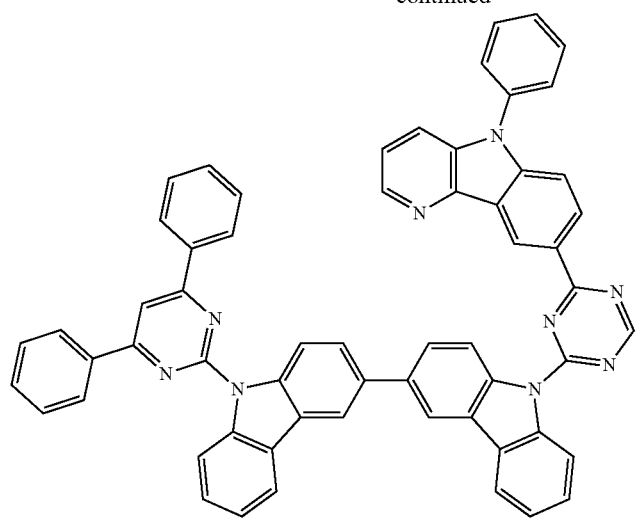
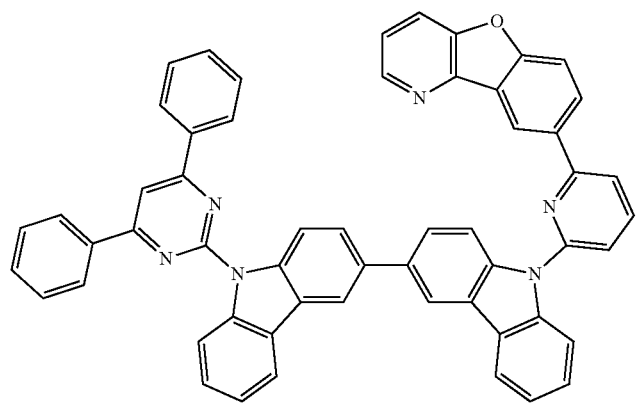
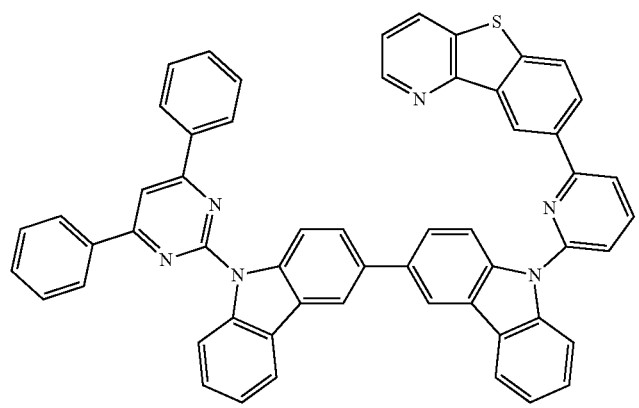

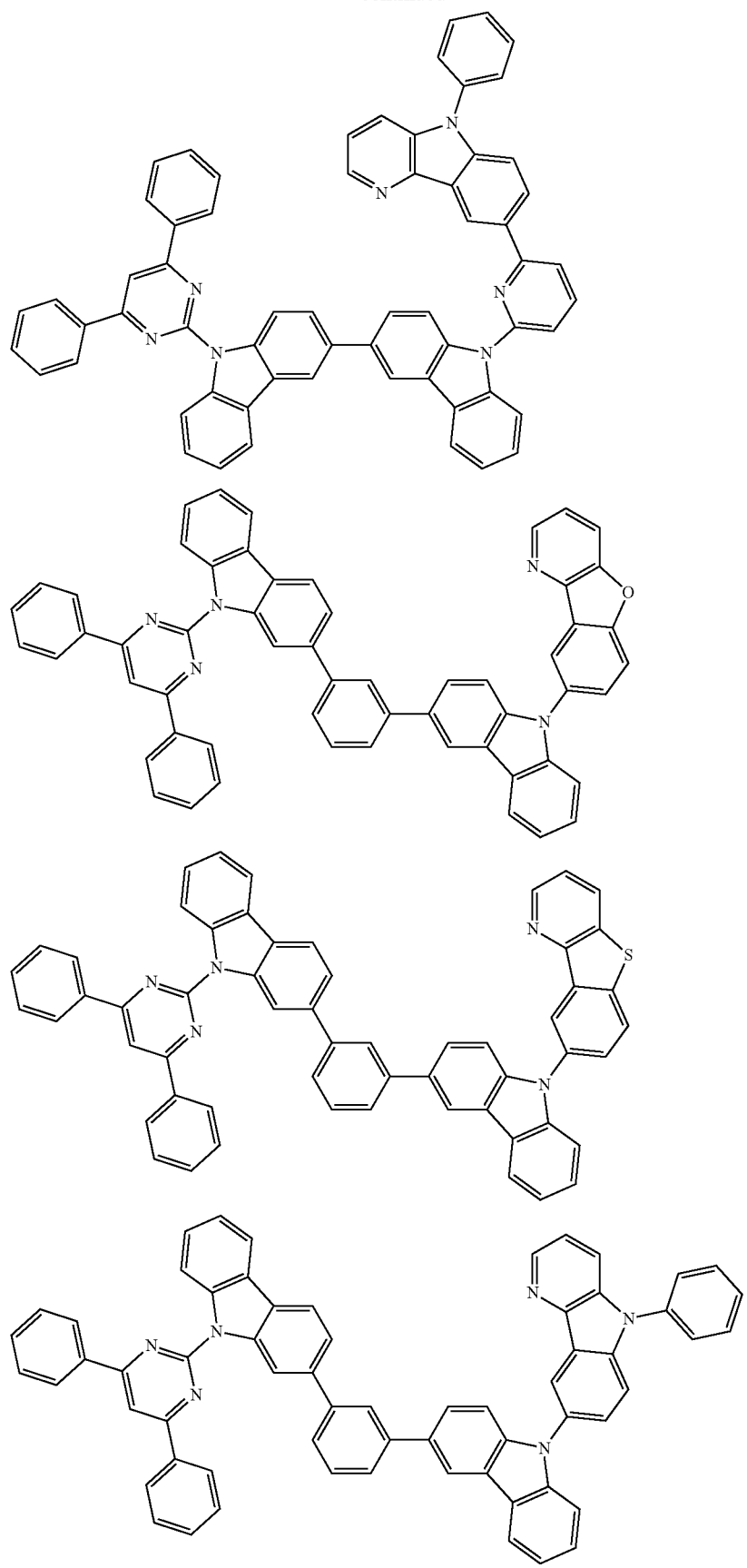

-continued
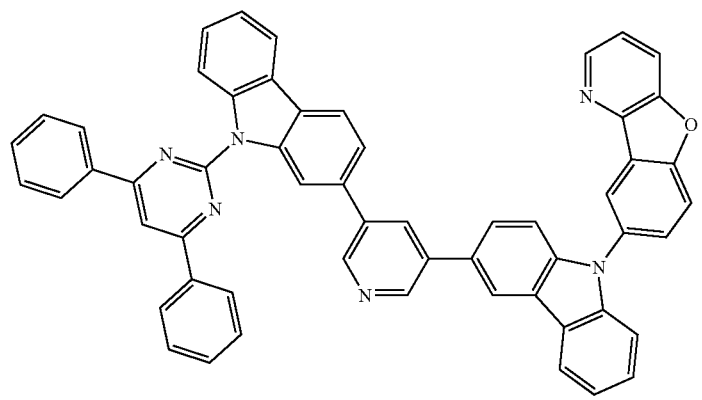
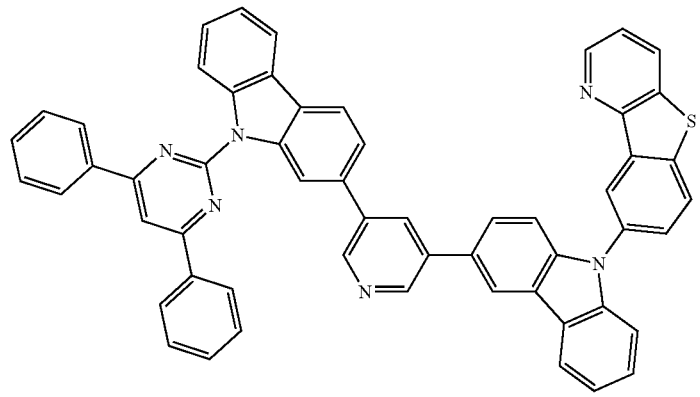
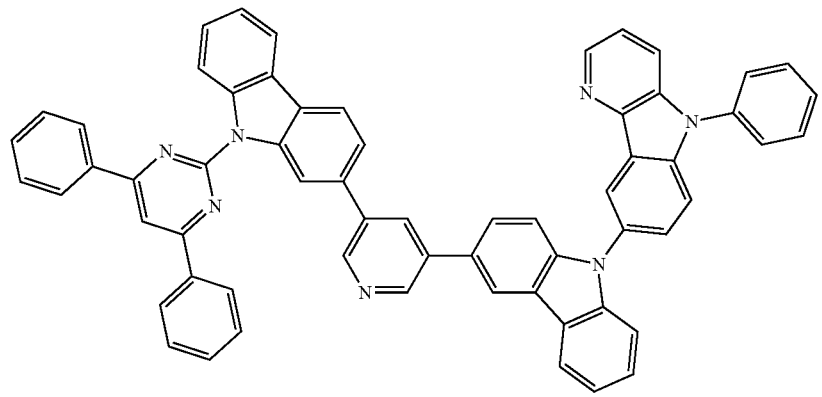
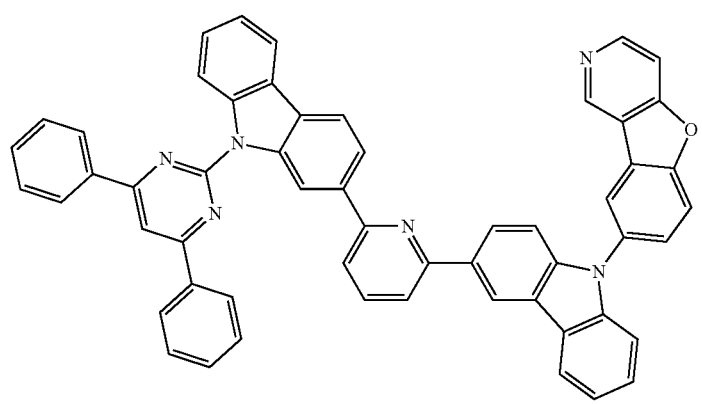

-continued
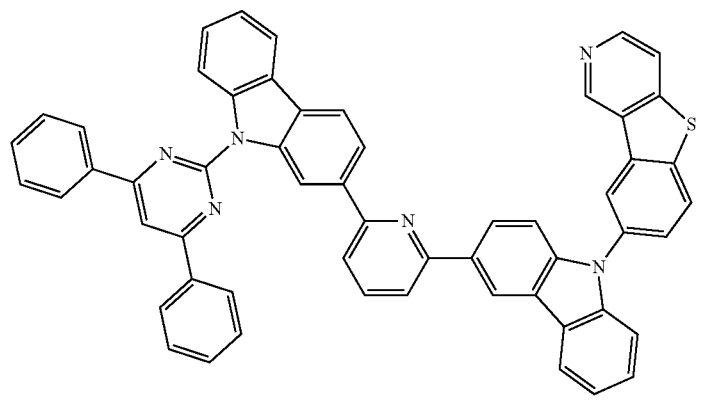
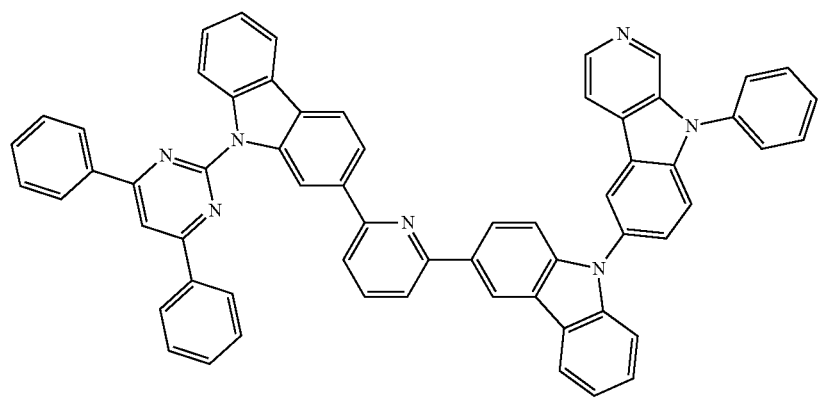
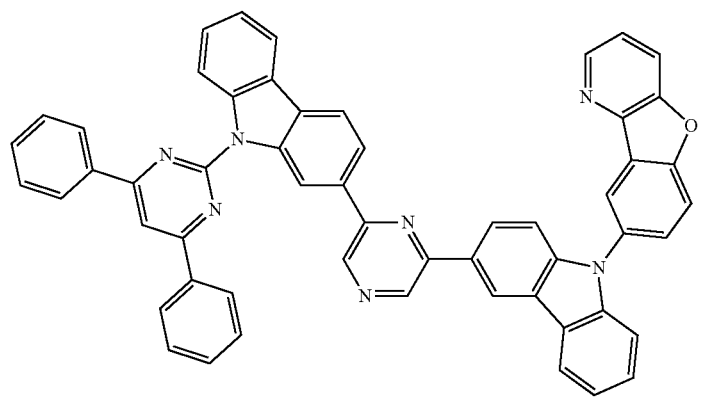
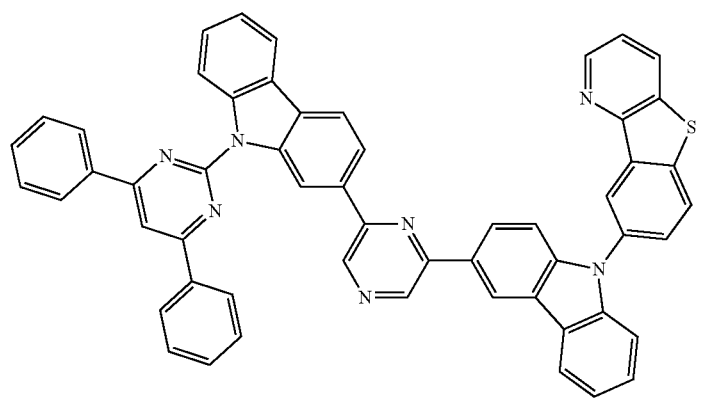

-continued
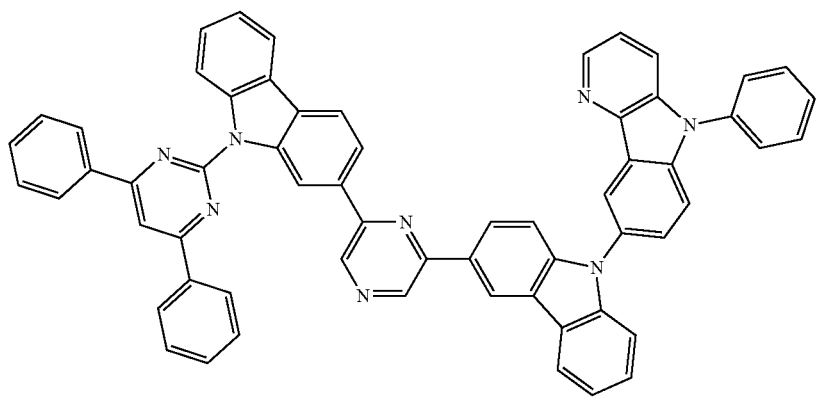
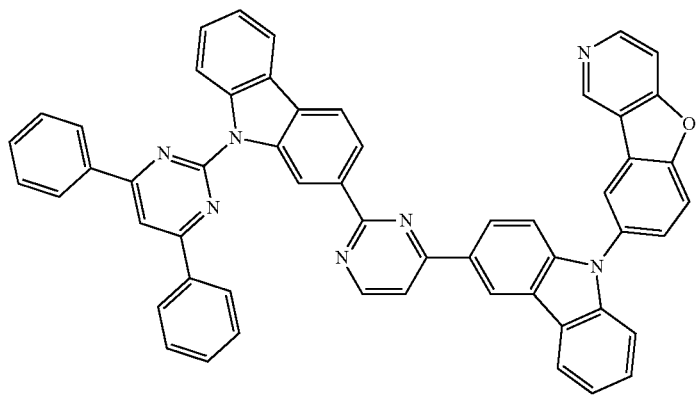
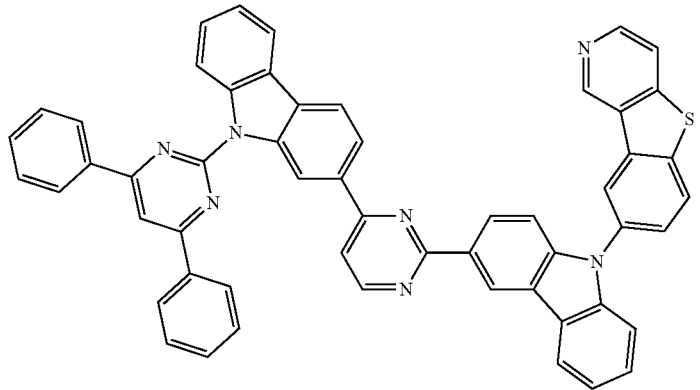
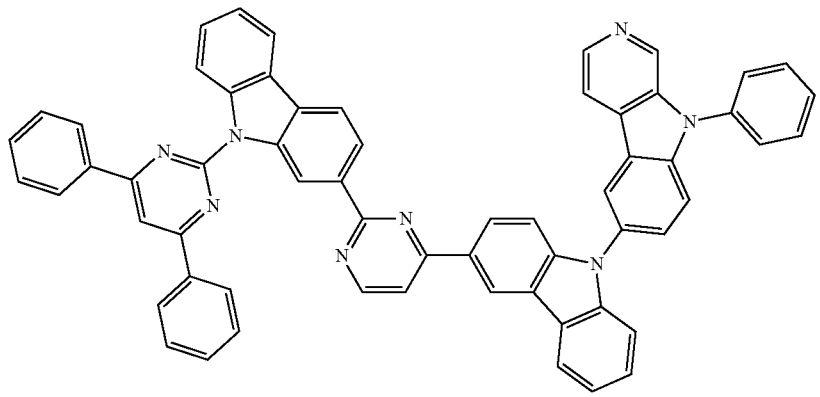

-continued
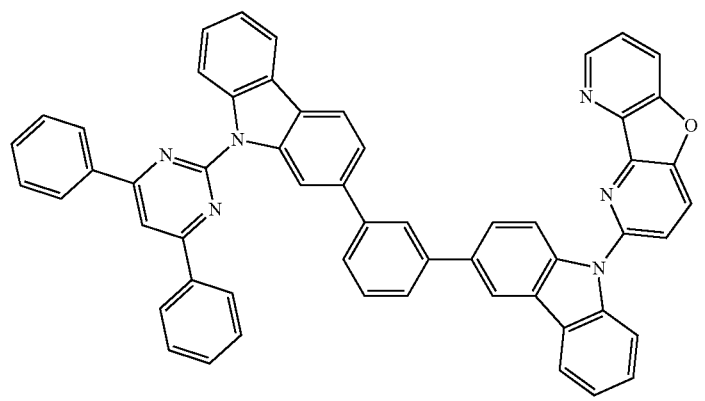
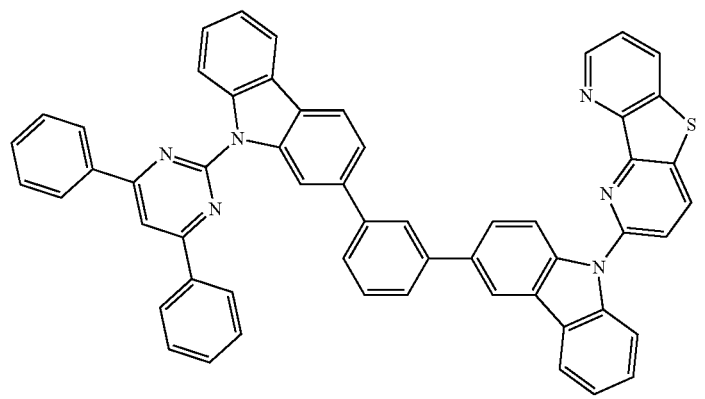
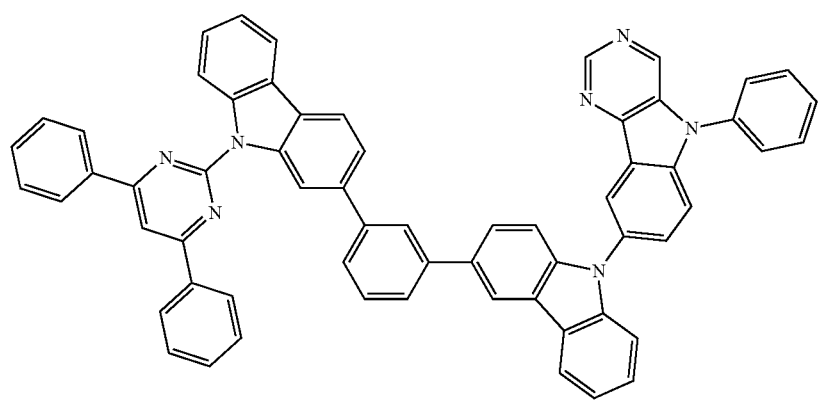
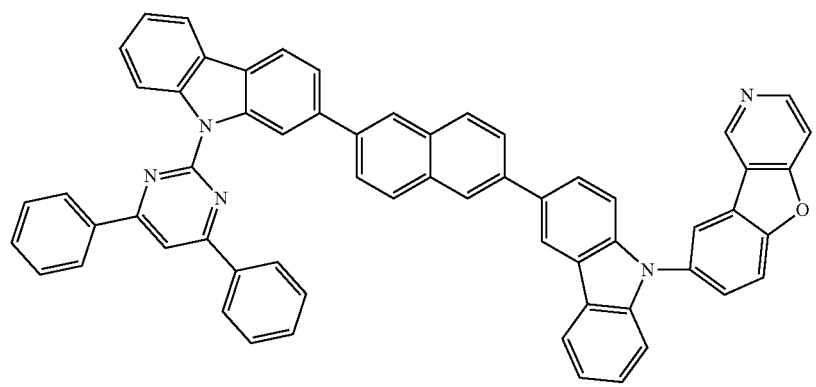

-continued
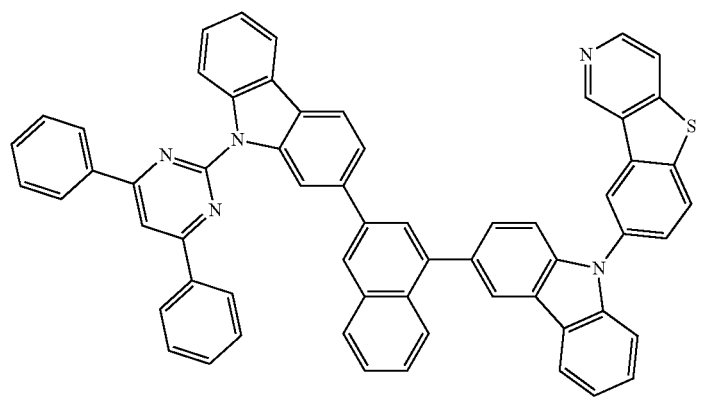
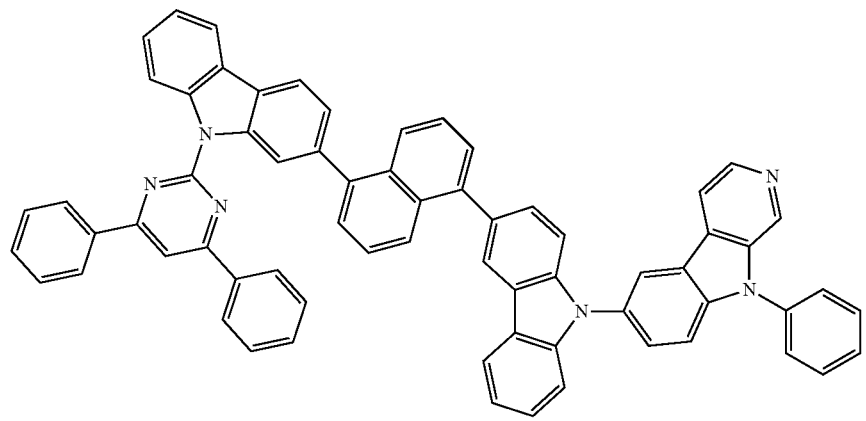
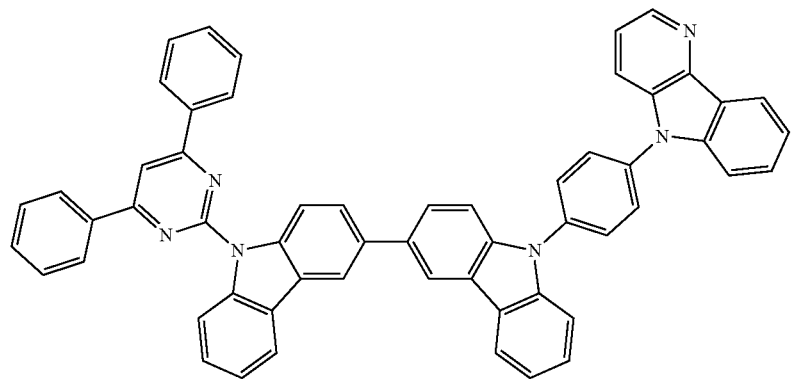
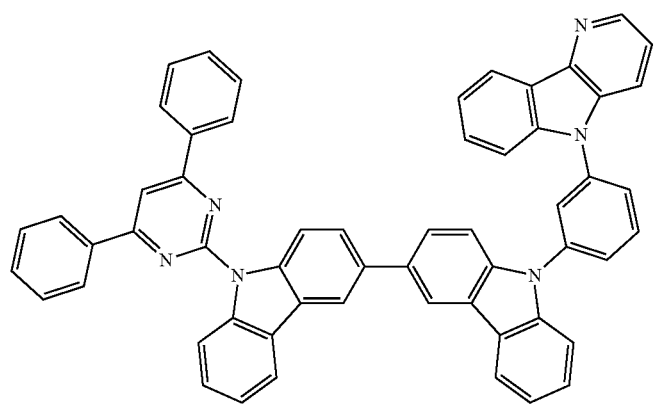

-continued
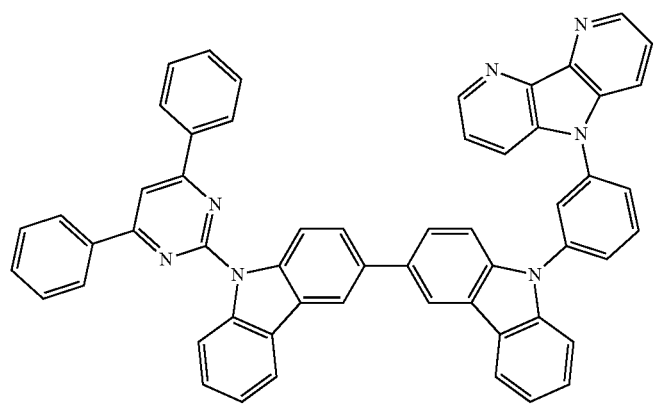
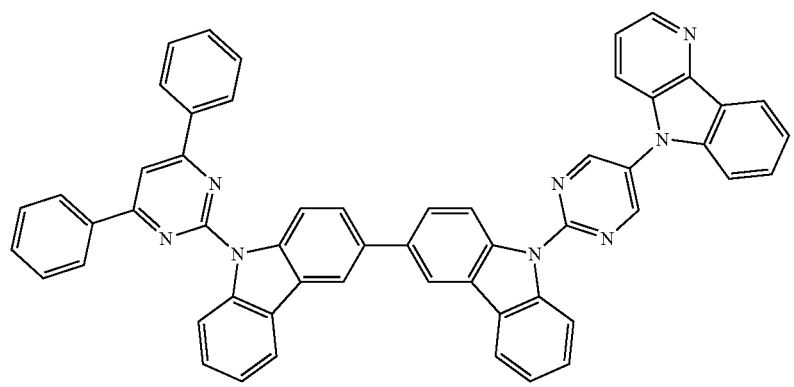
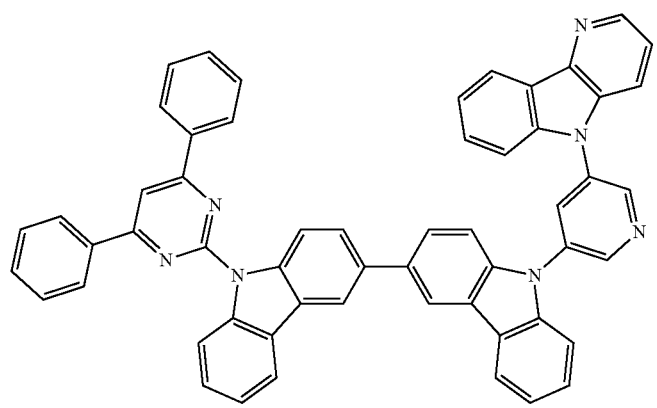
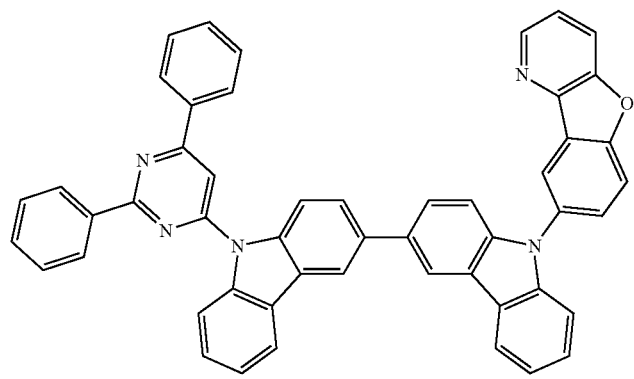

-continued
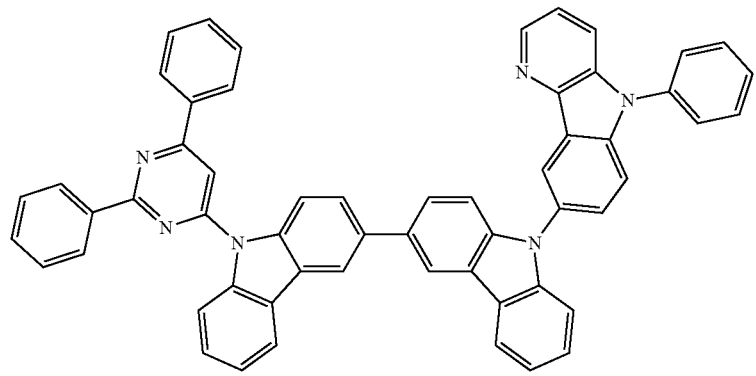
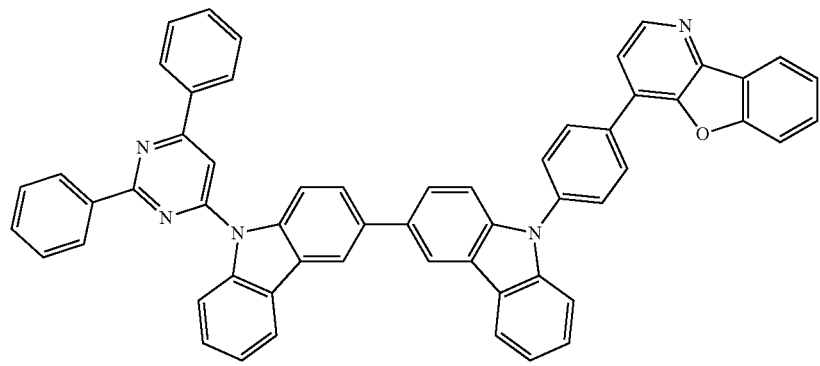
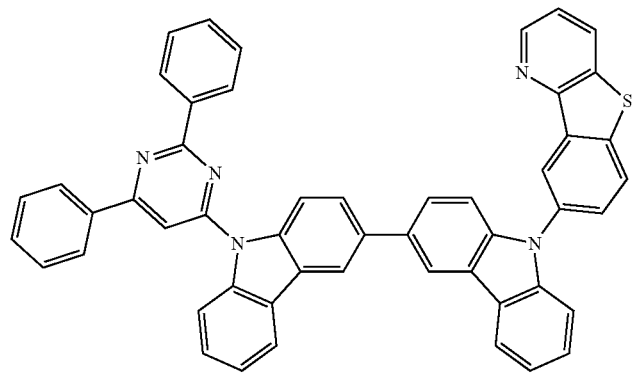
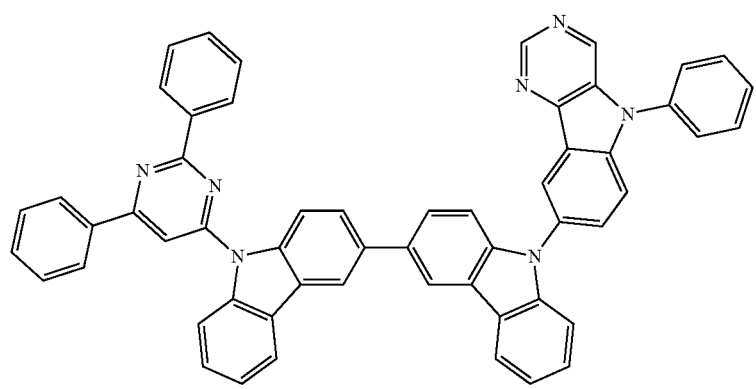

-continued
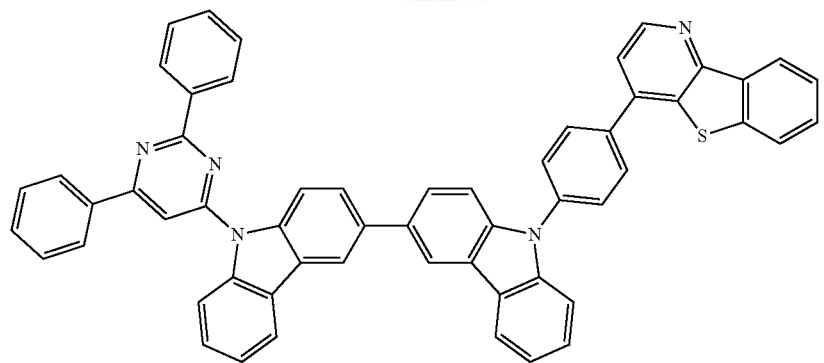
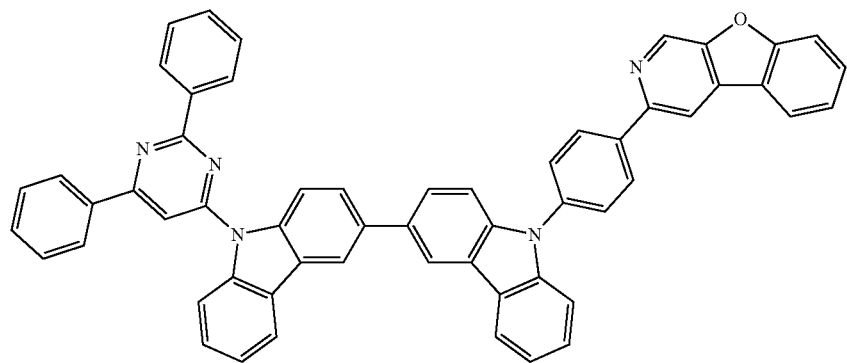
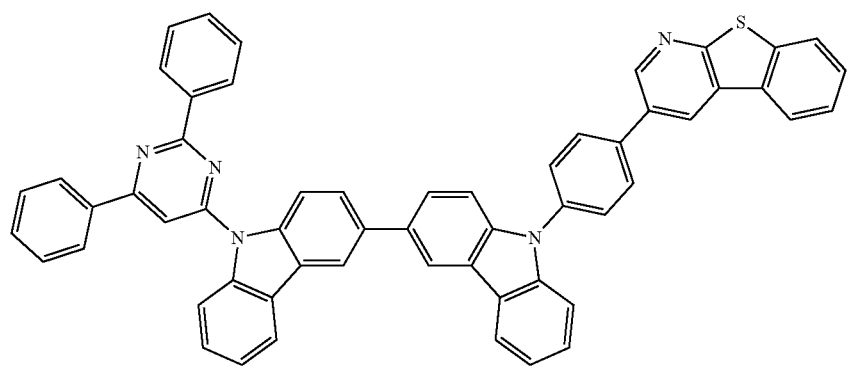
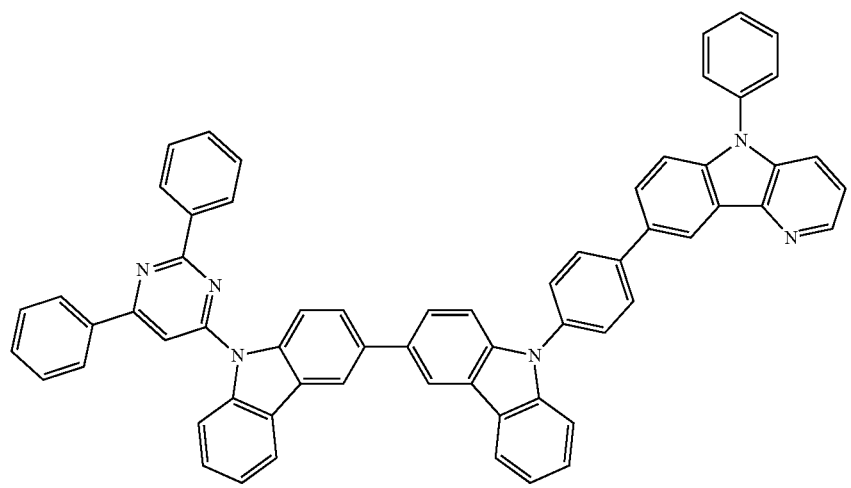

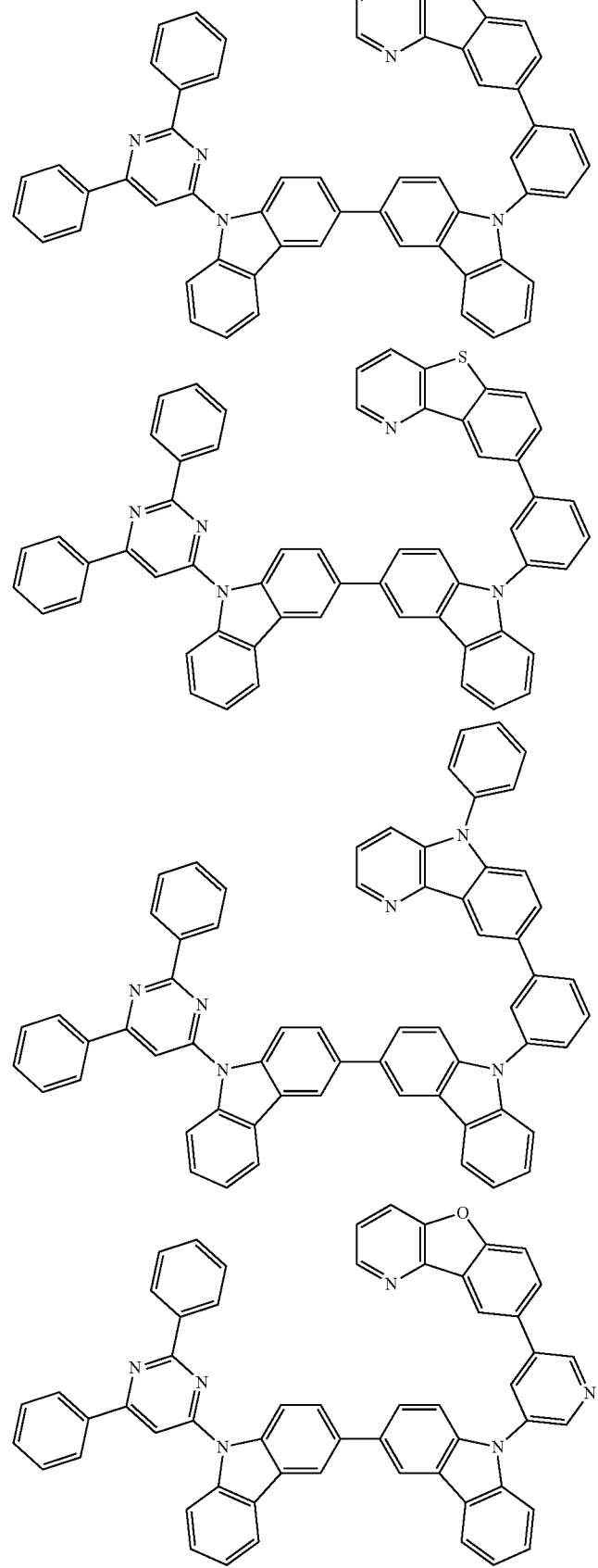

-continued
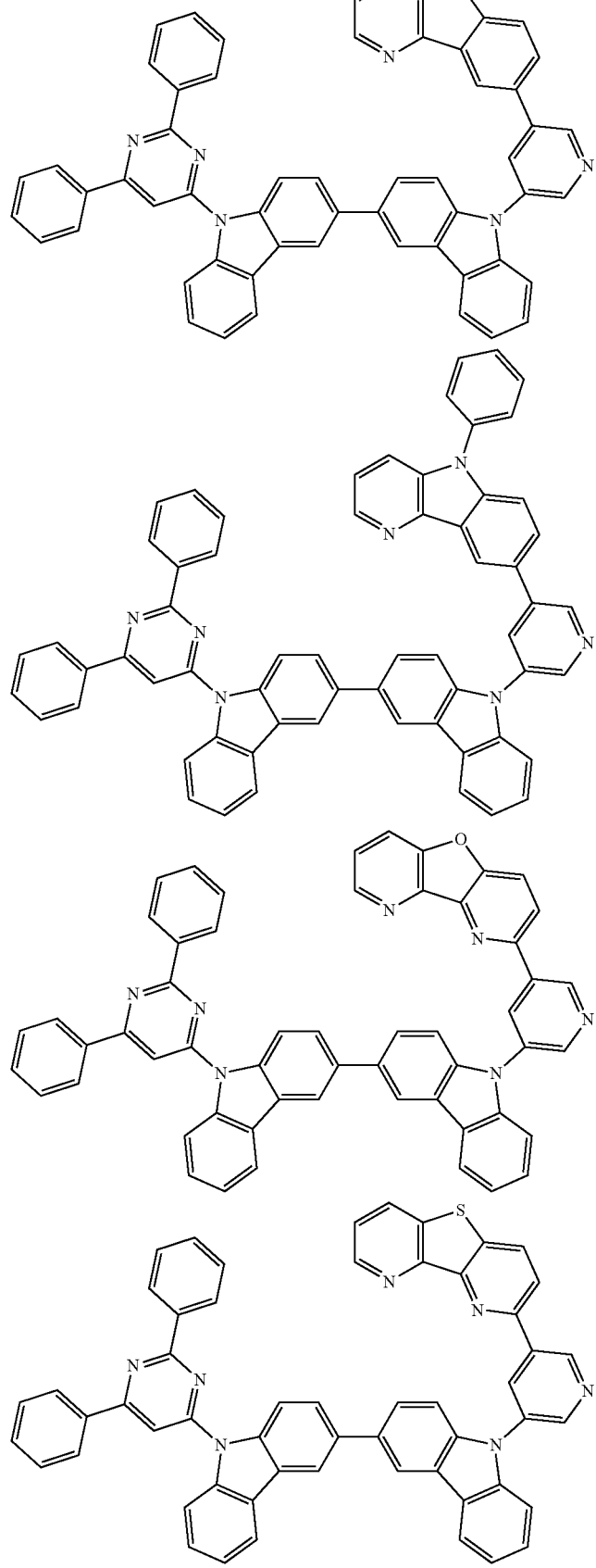

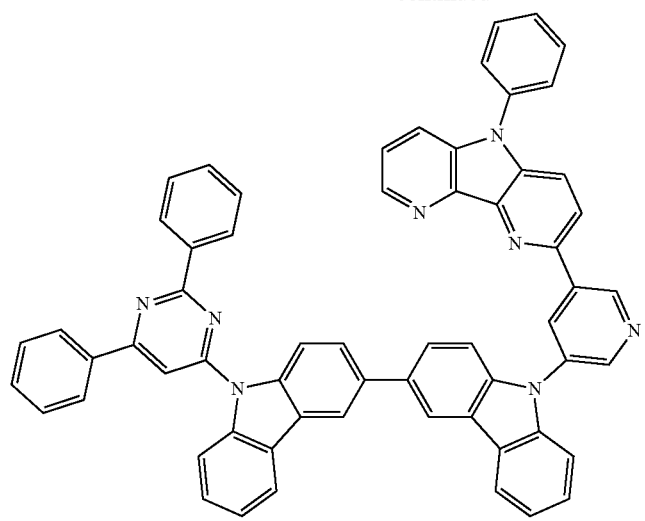
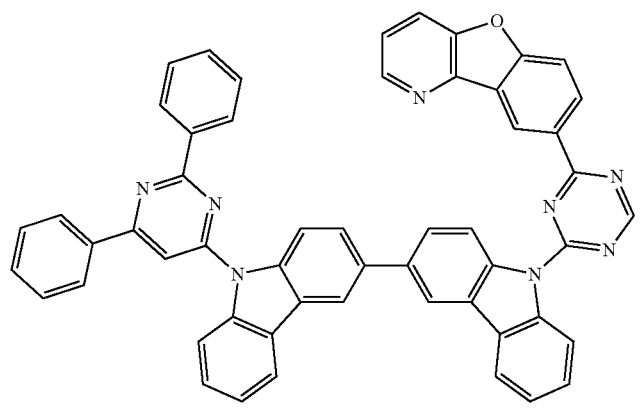
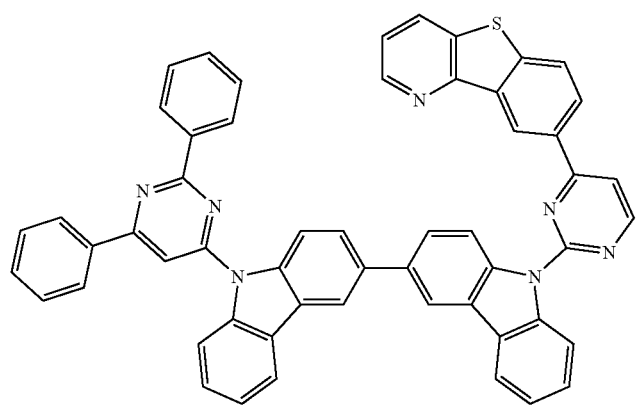

-continued
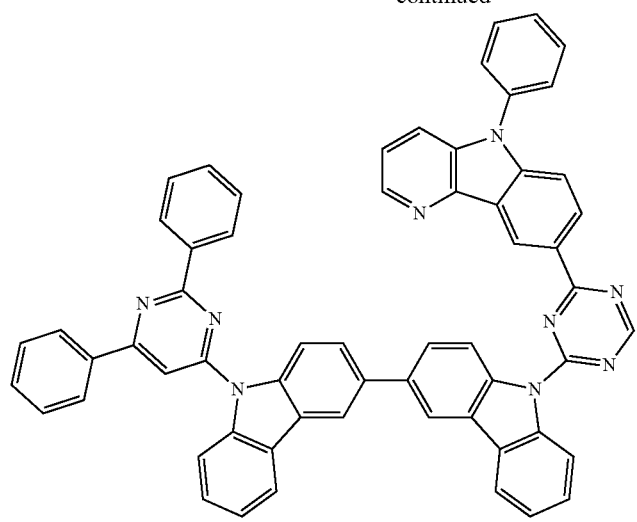
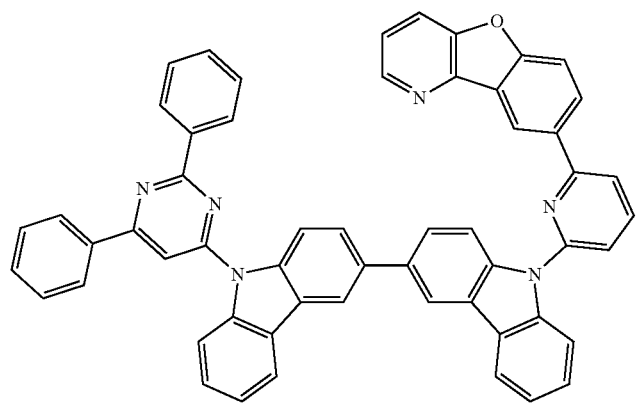
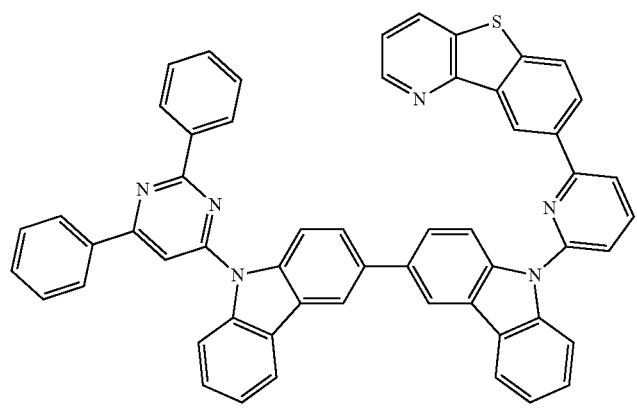

-continued
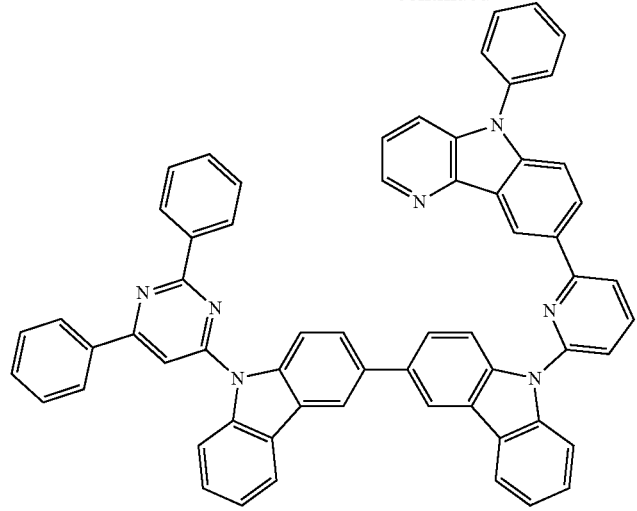
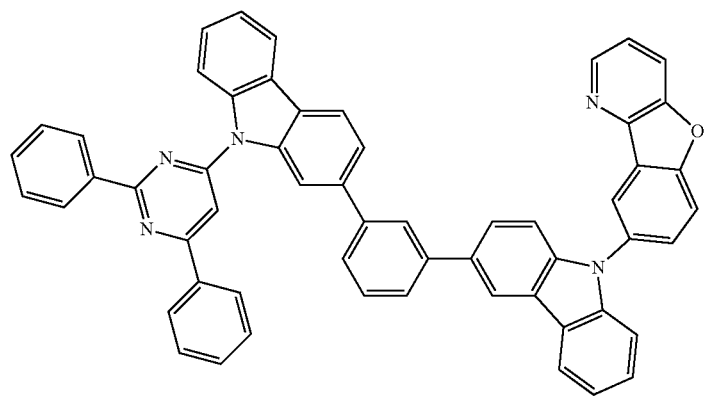
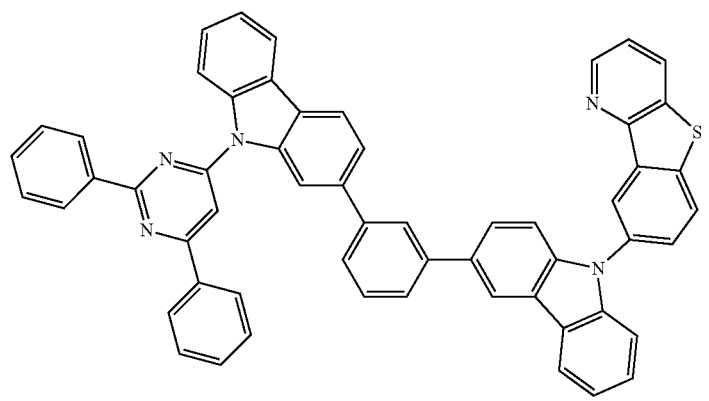

-continued
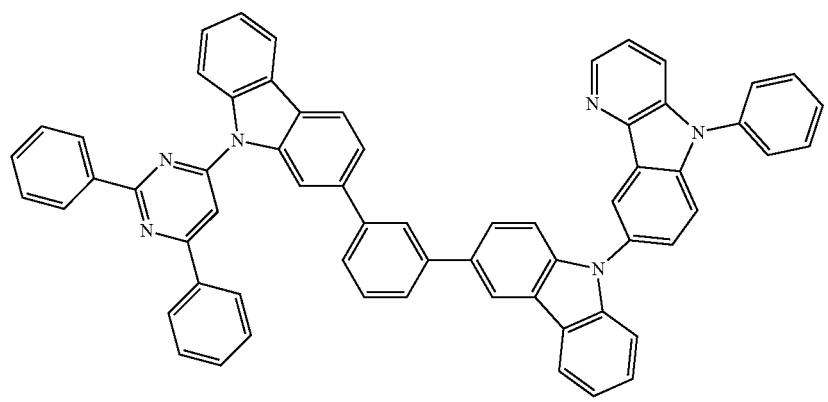
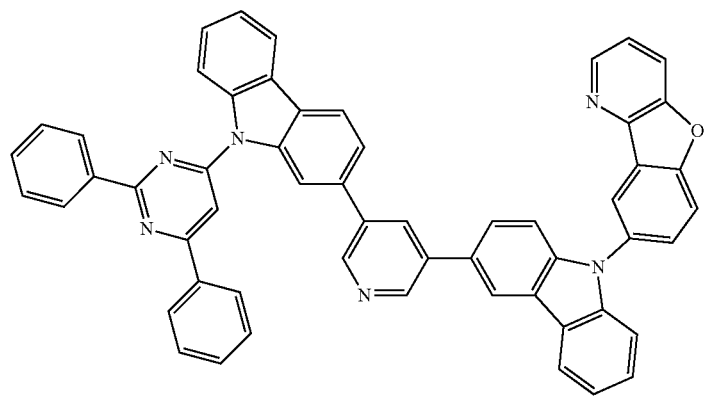
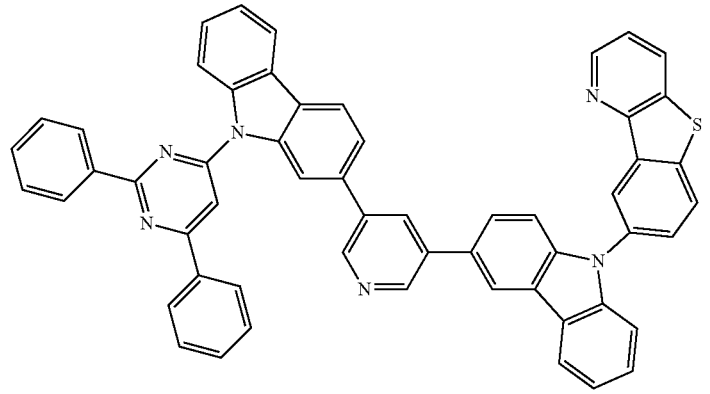
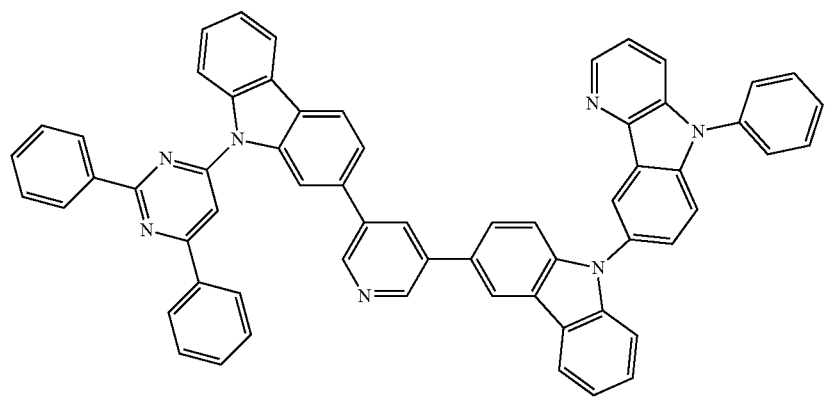

-continued
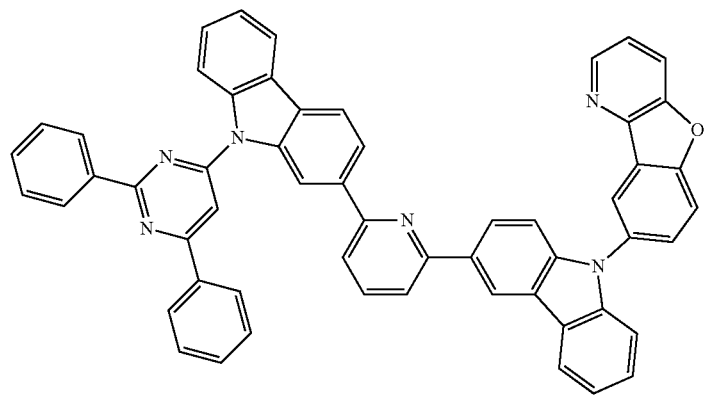
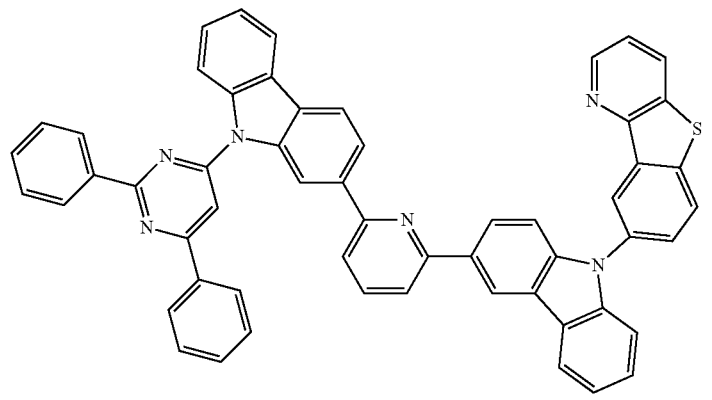
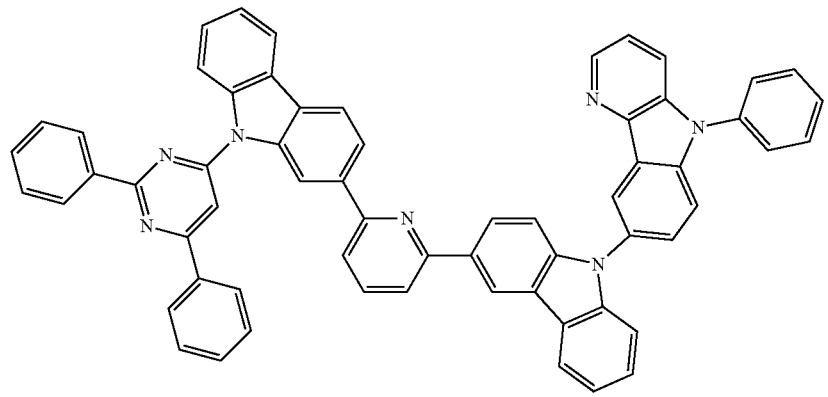
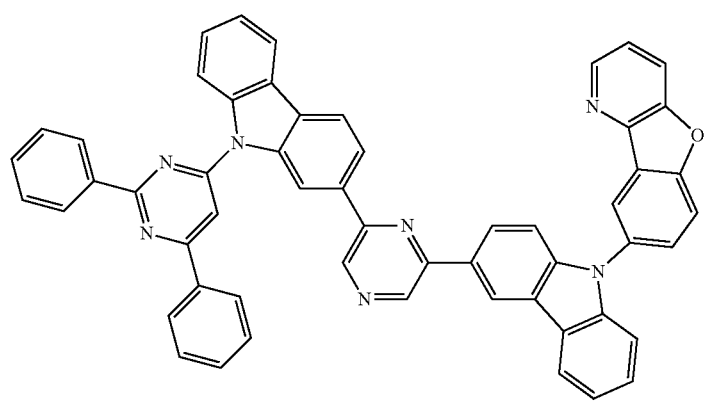

-continued
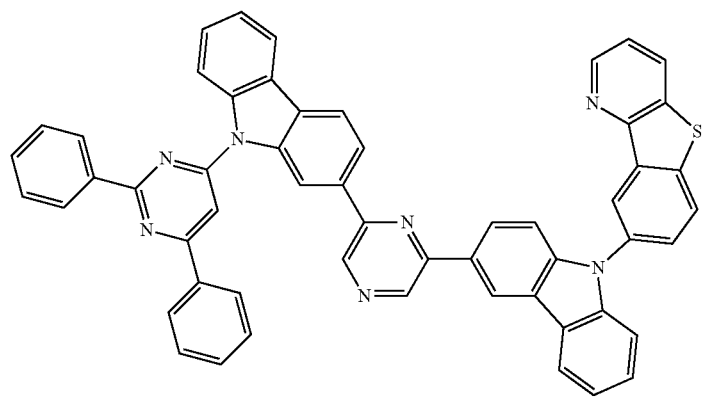
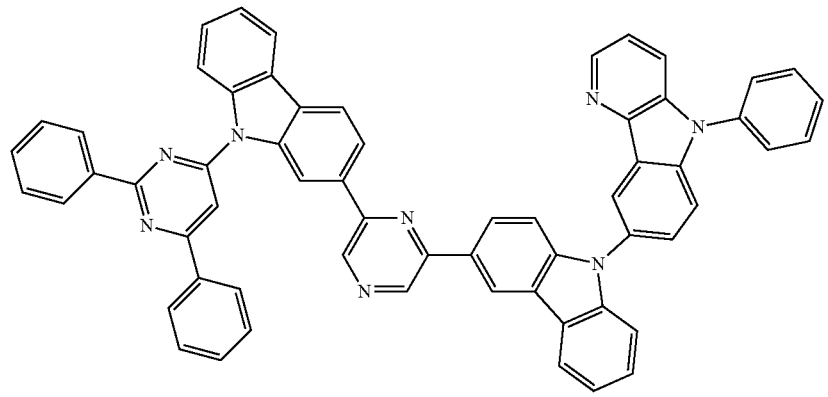
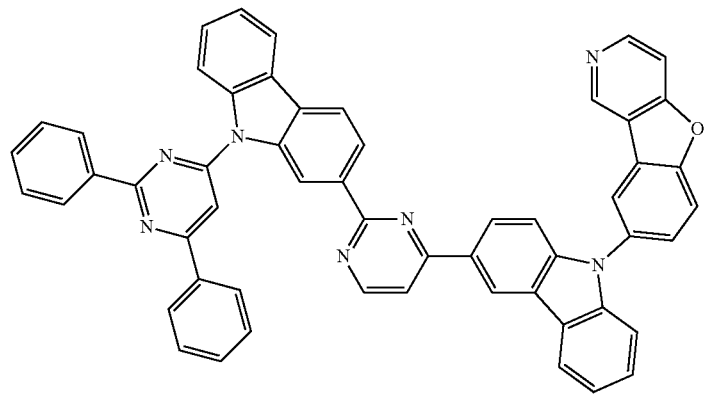
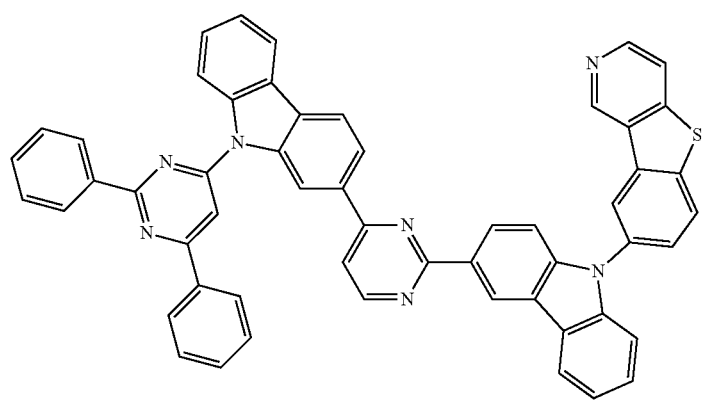

-continued
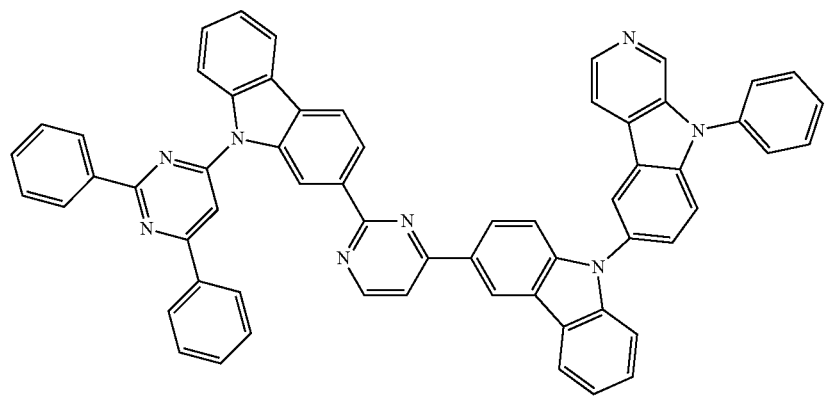
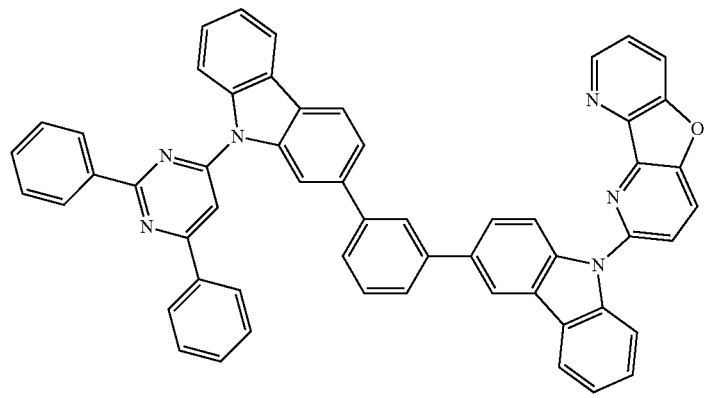
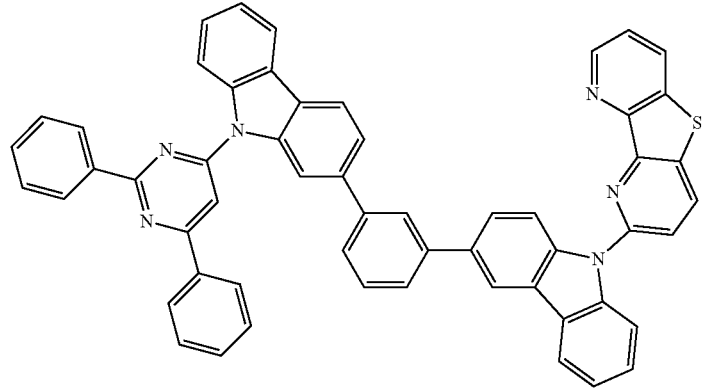
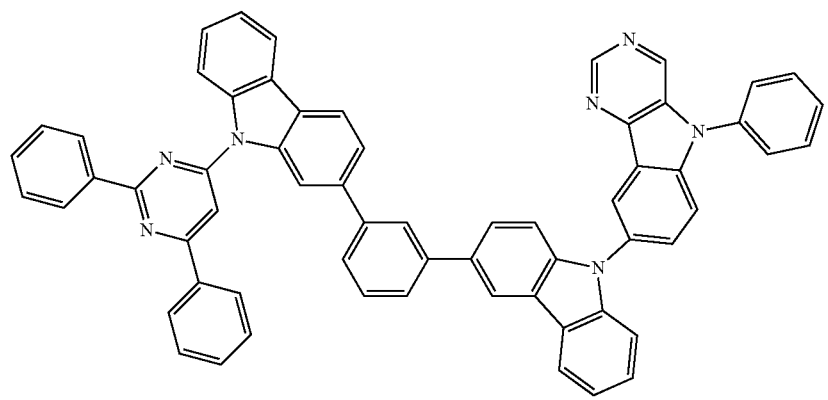

-continued
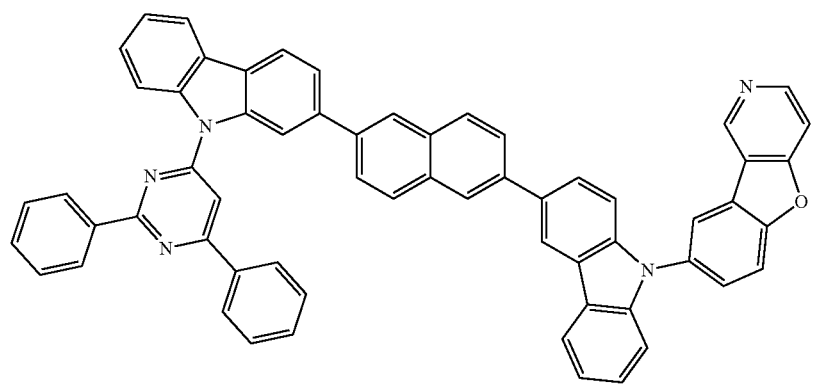
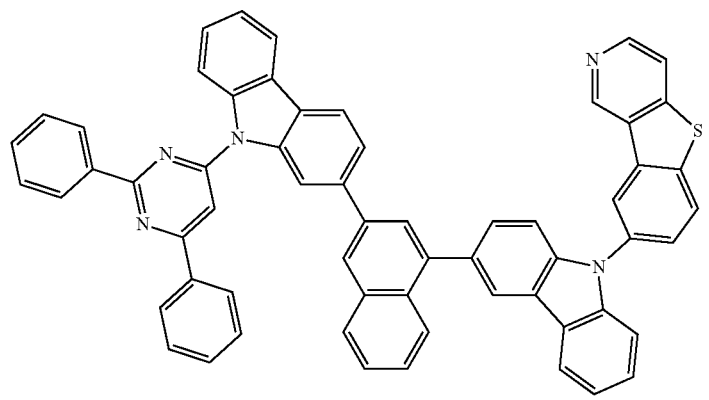
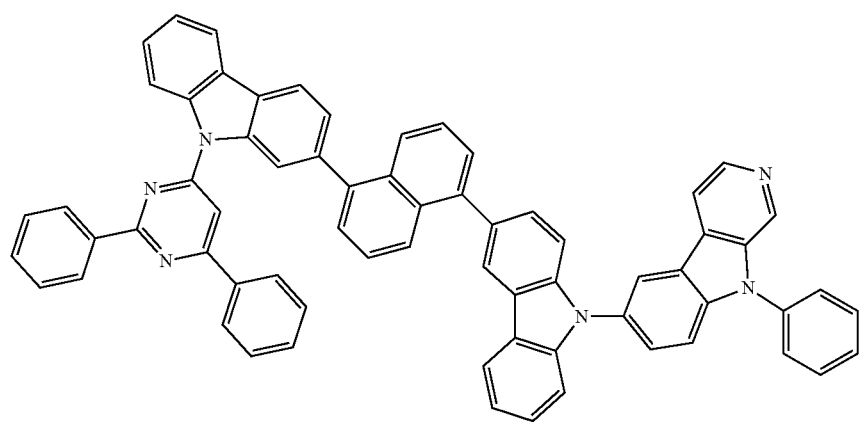
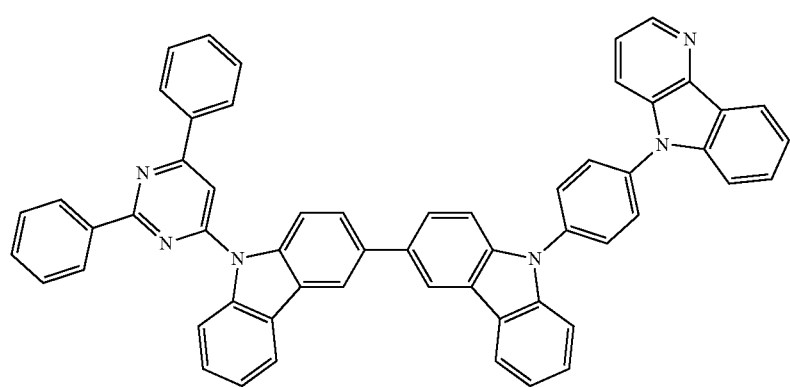

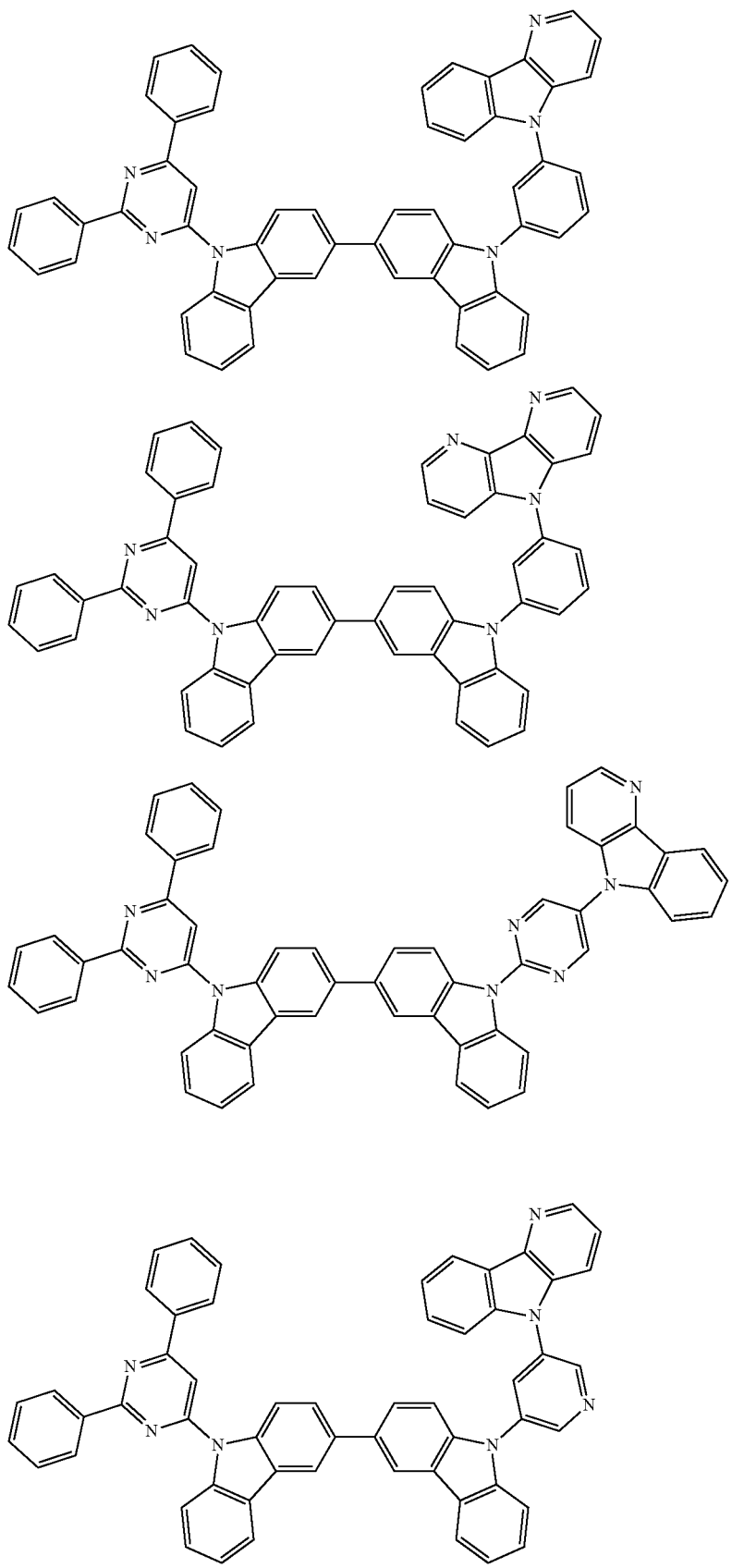

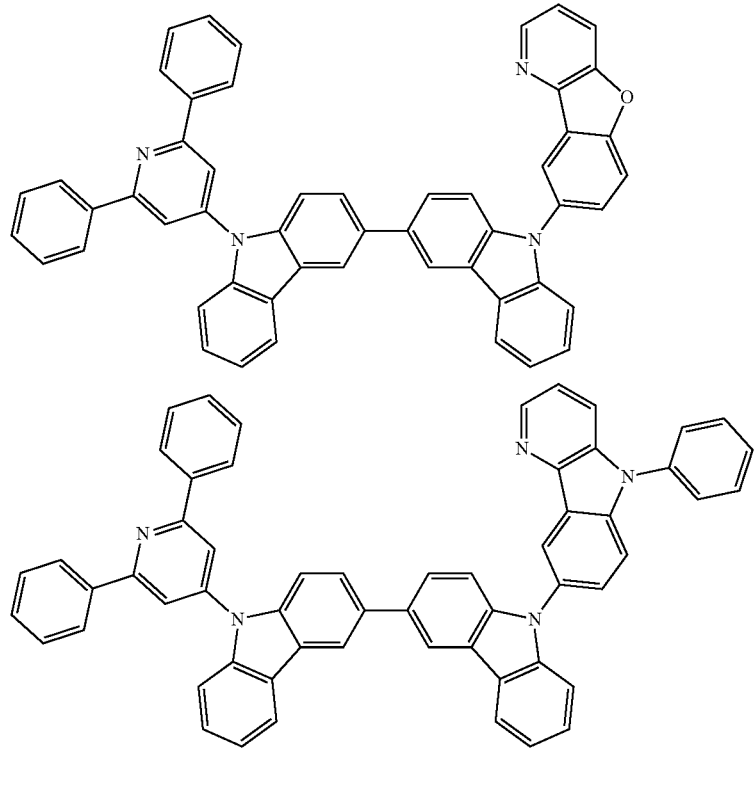
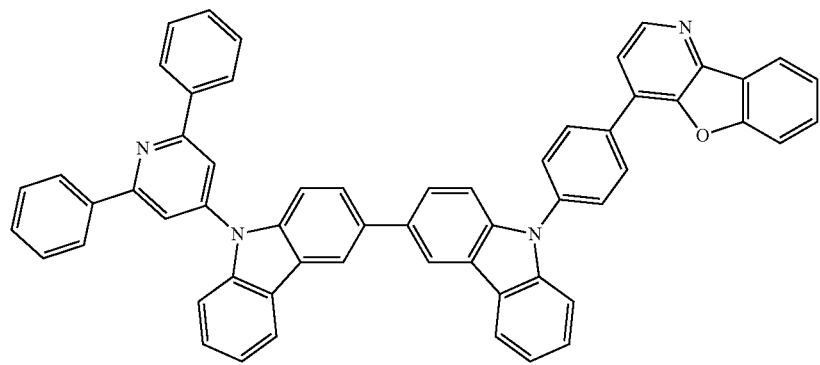
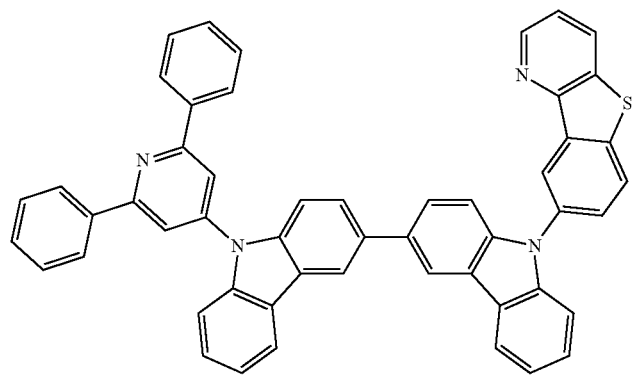

-continued
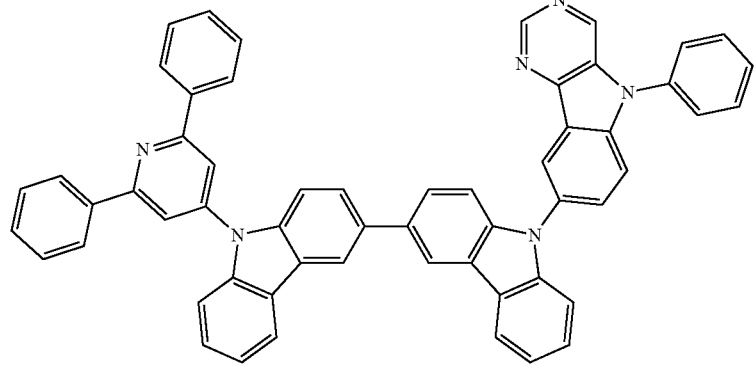
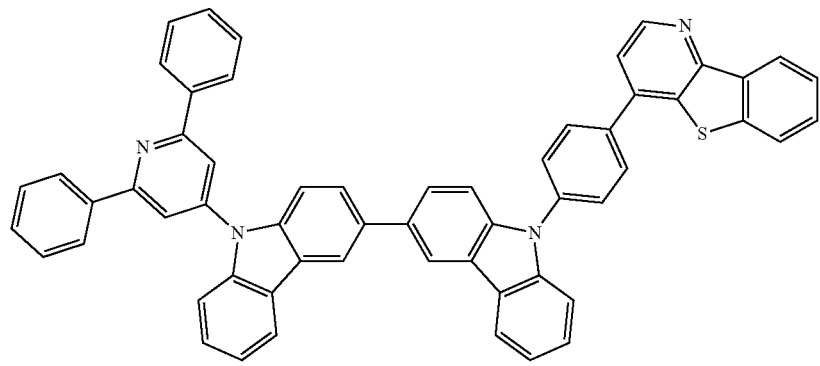
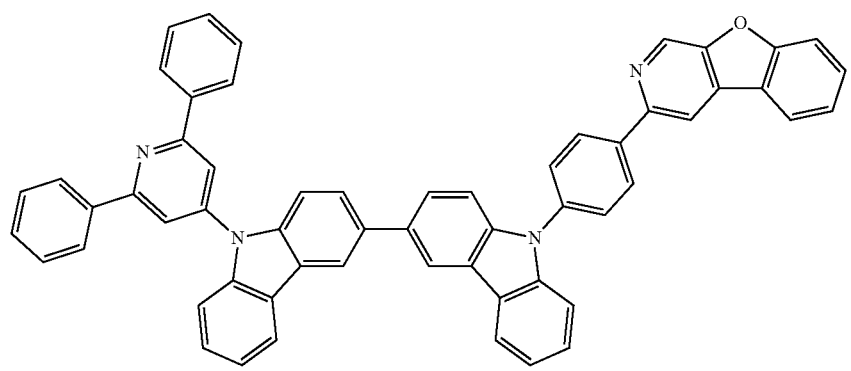
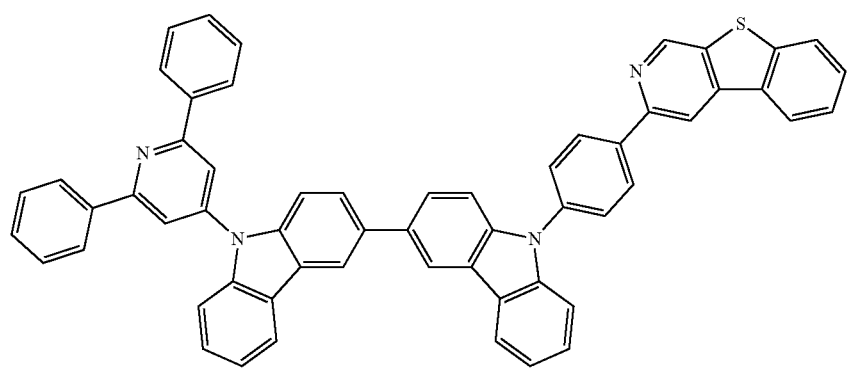

-continued
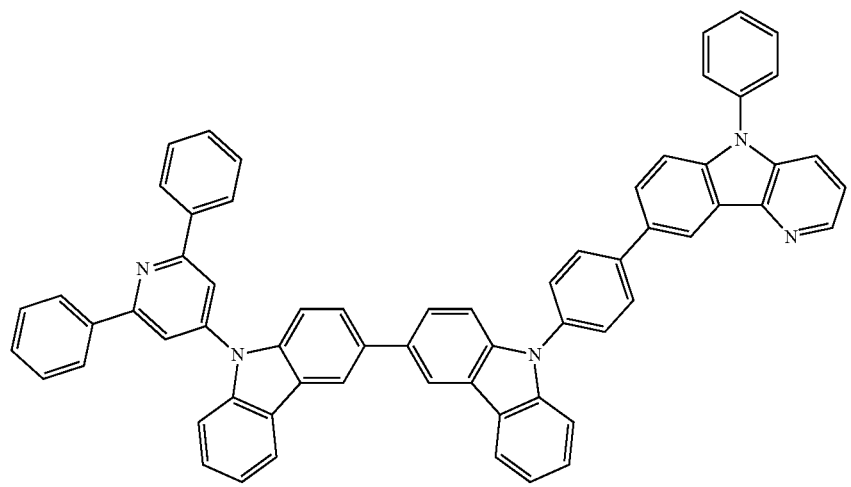
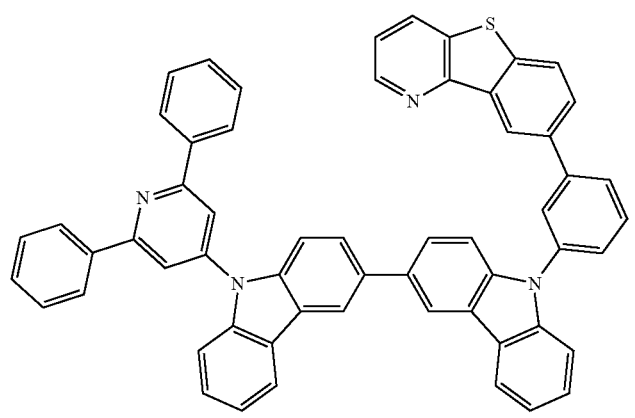

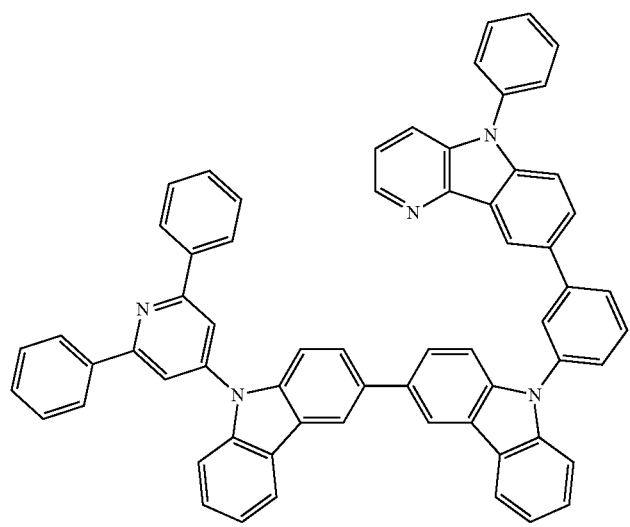
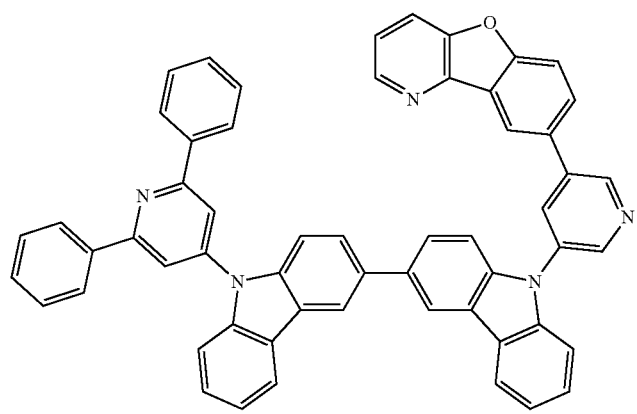
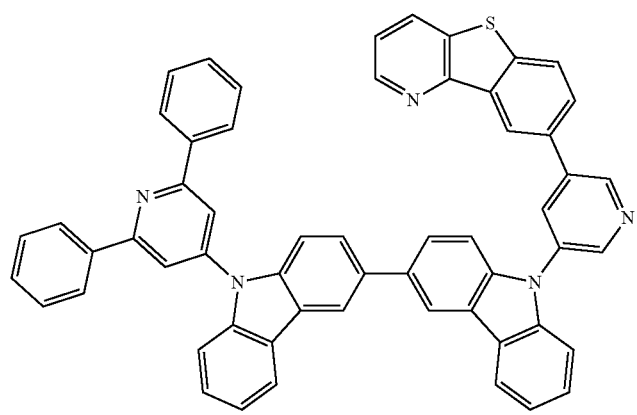

-continued
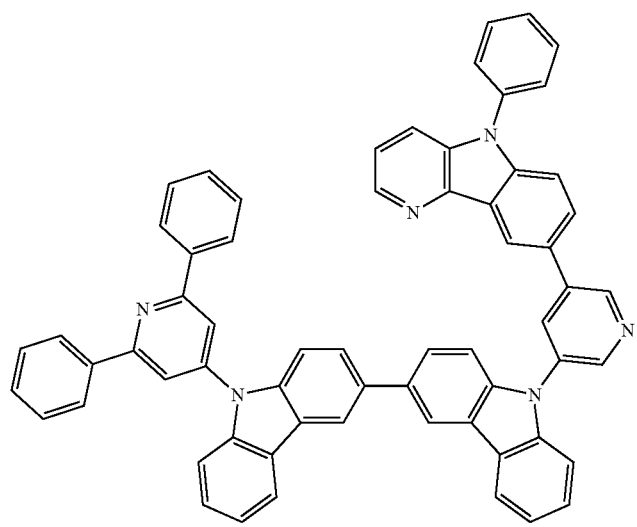
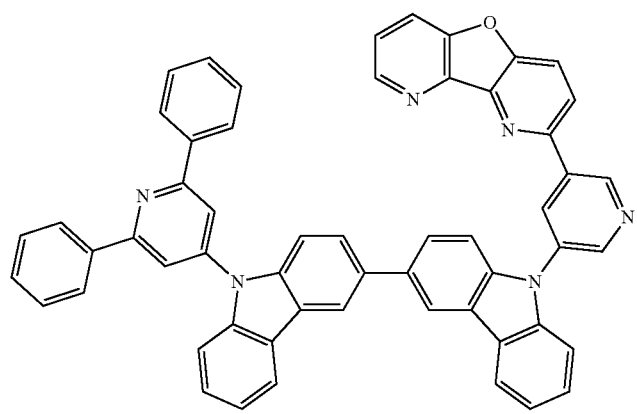
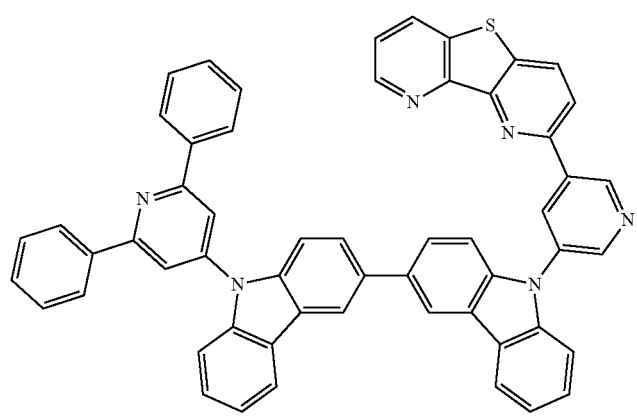

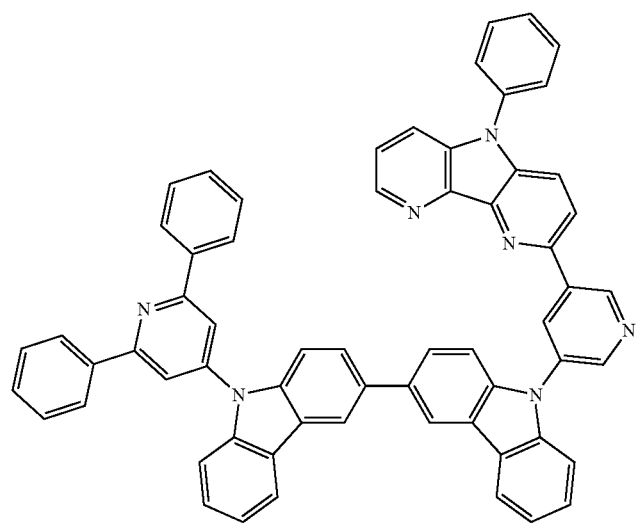
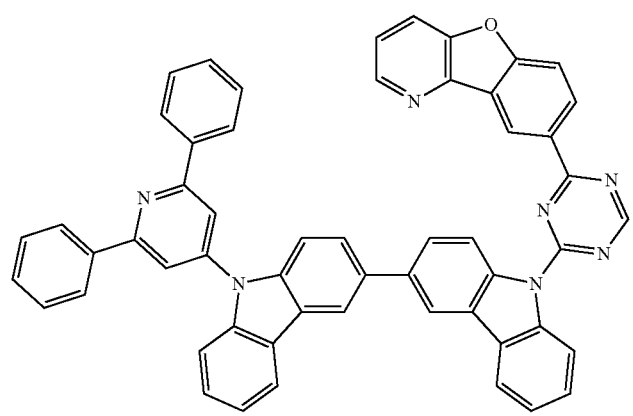
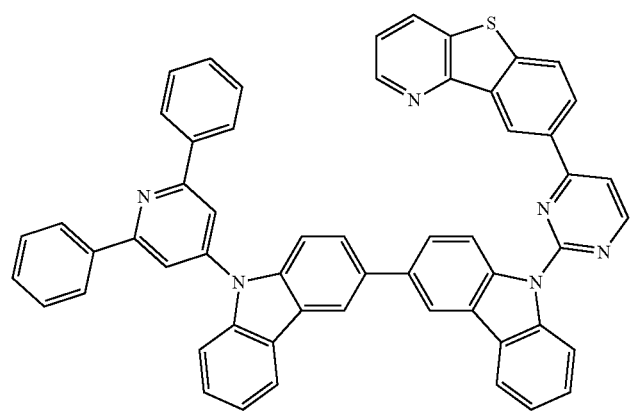

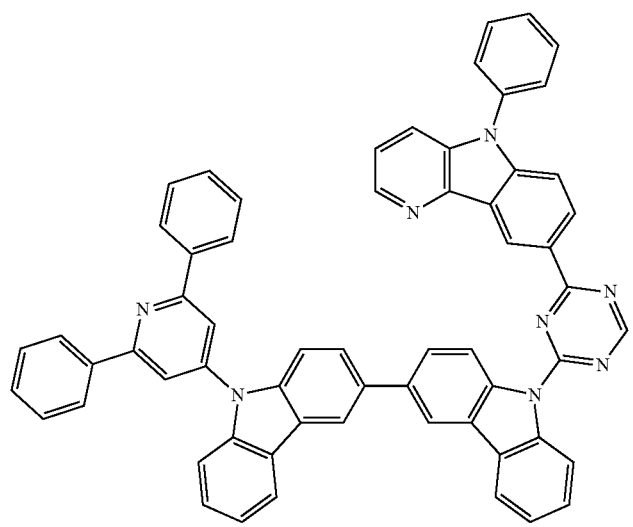
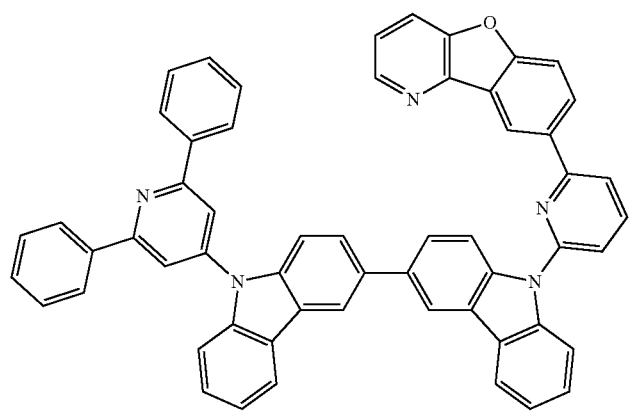
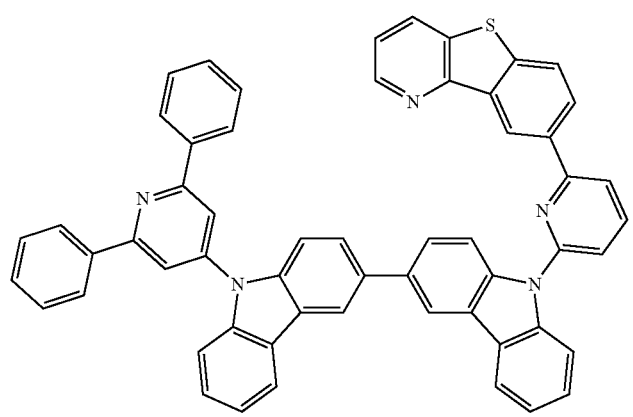

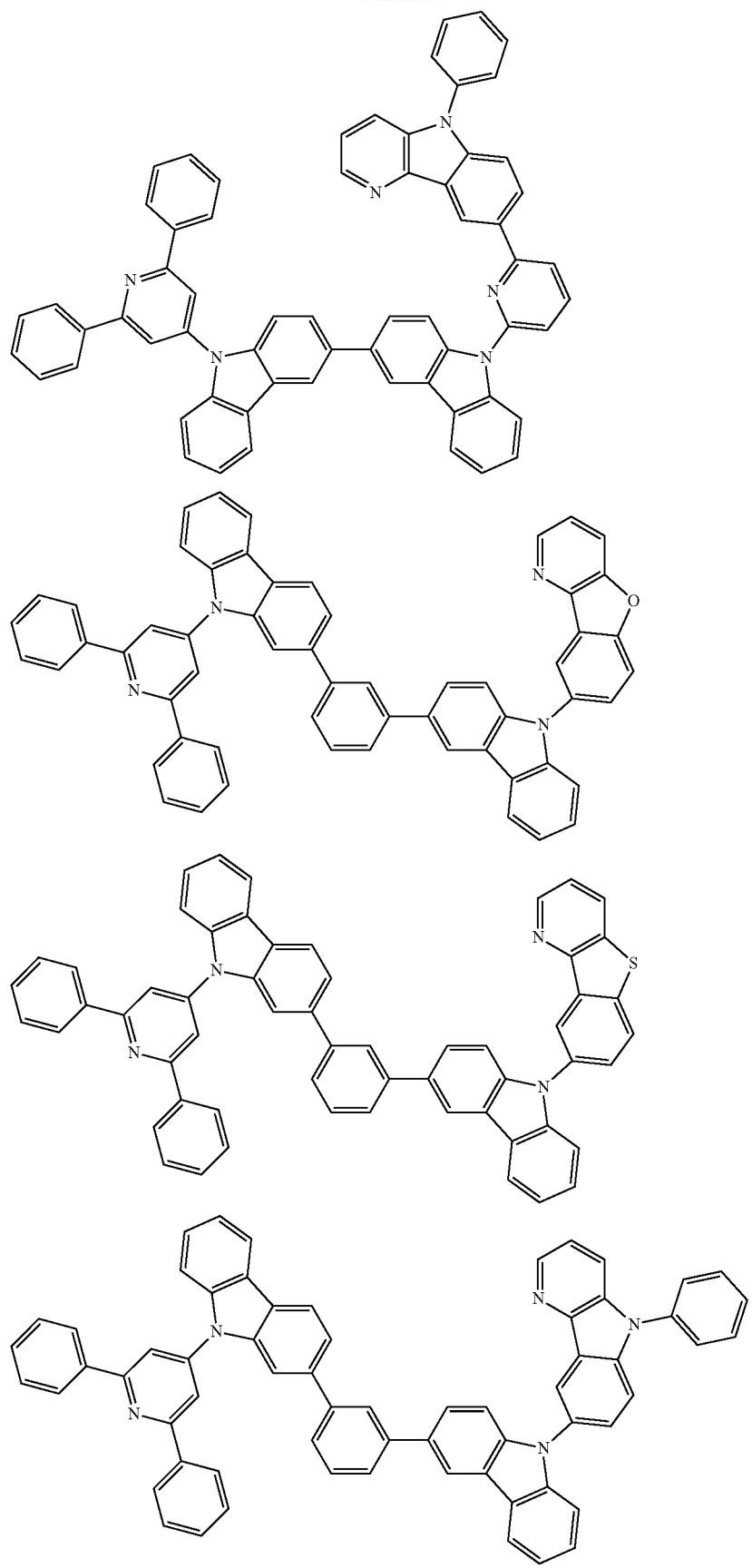

-continued
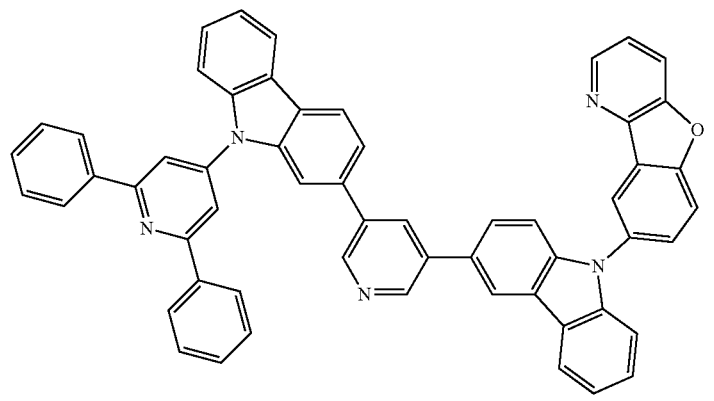
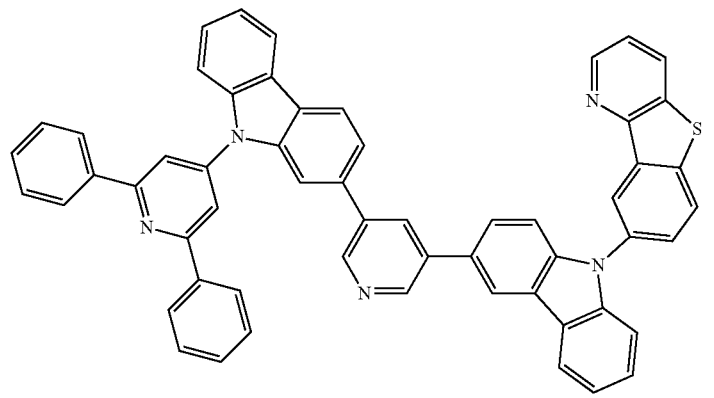
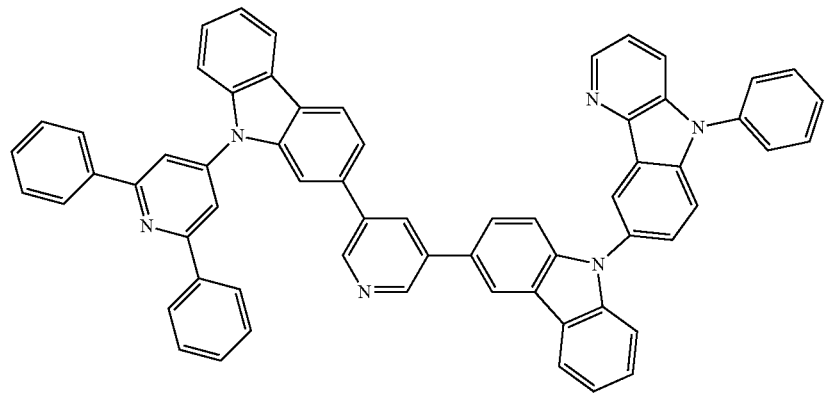
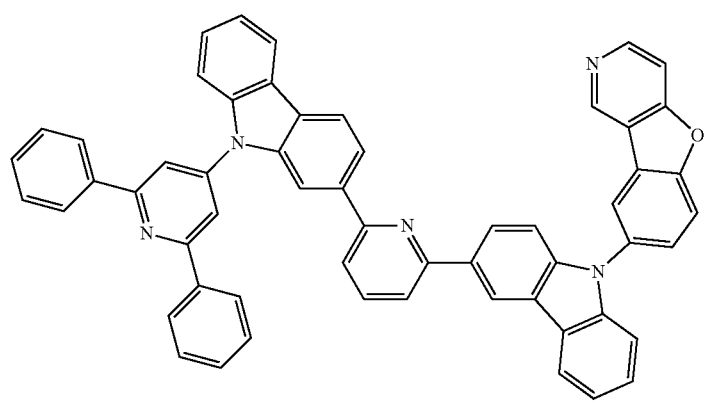

-continued
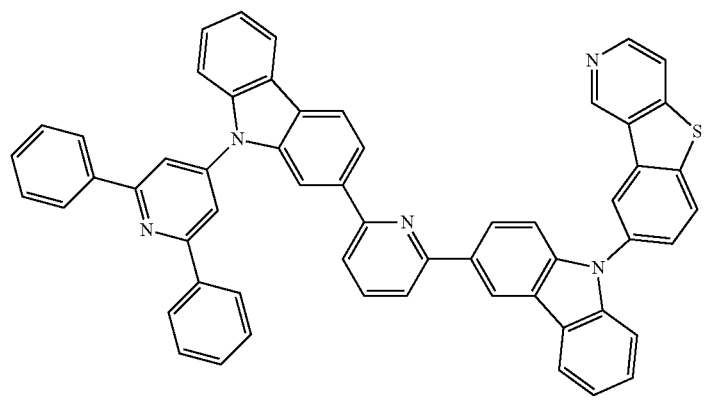
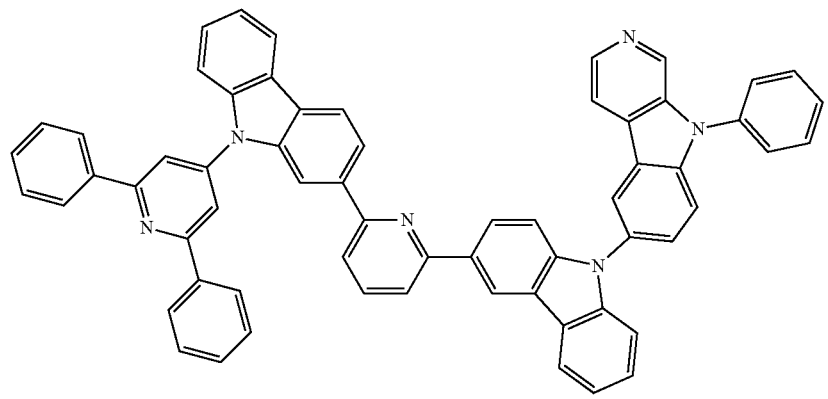
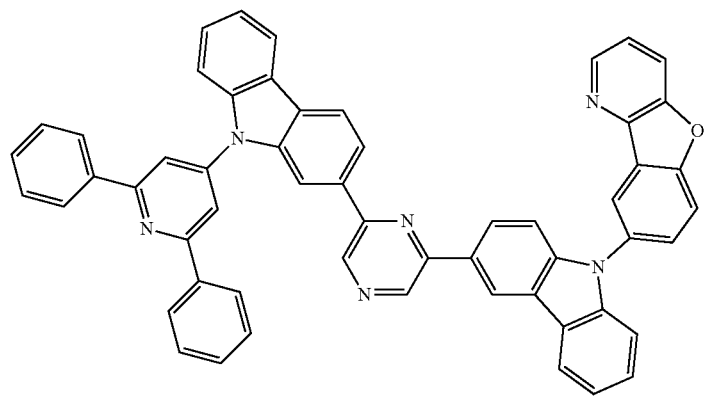
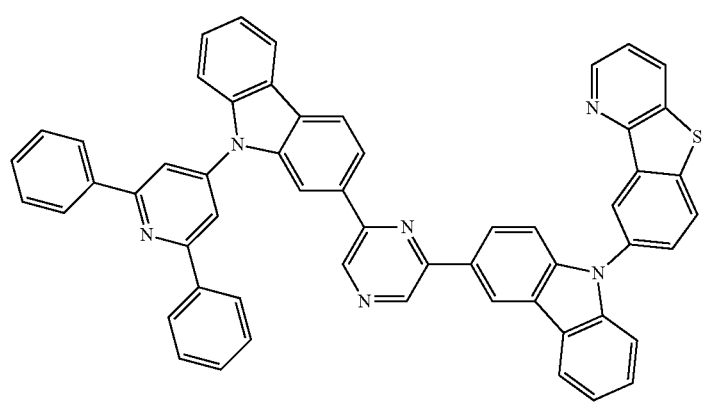

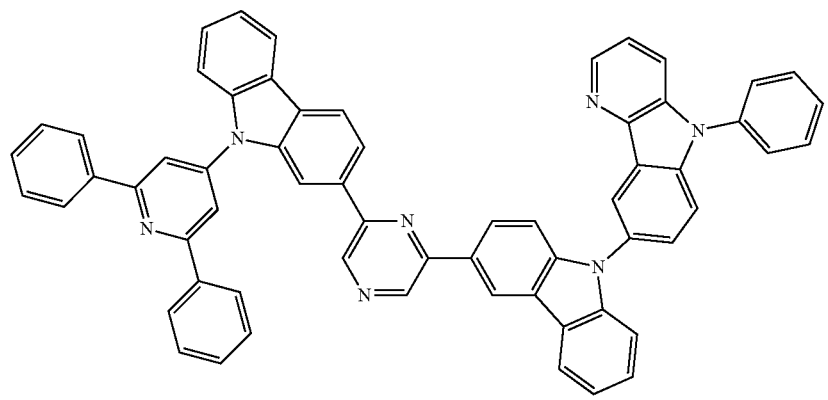
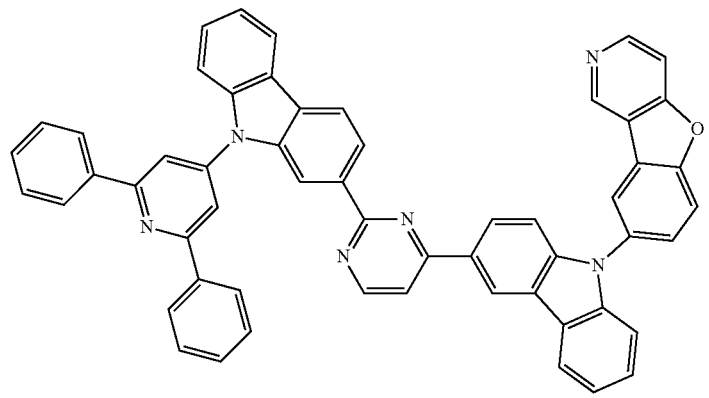
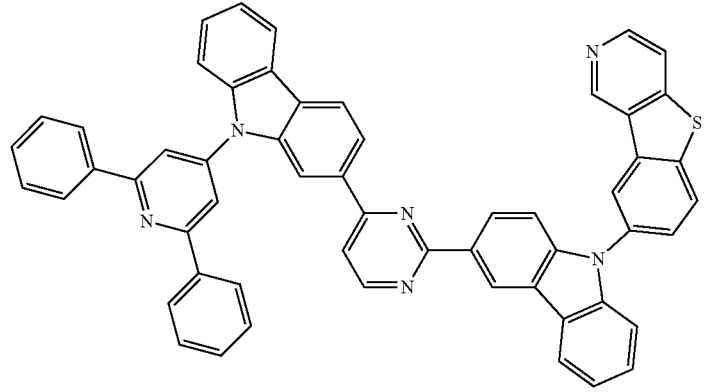
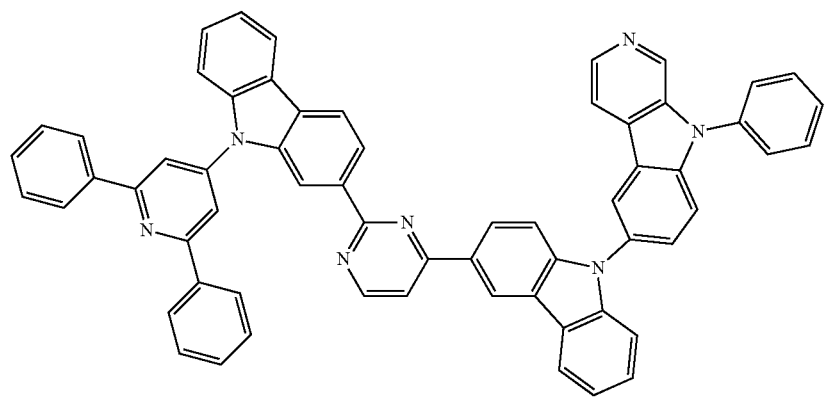

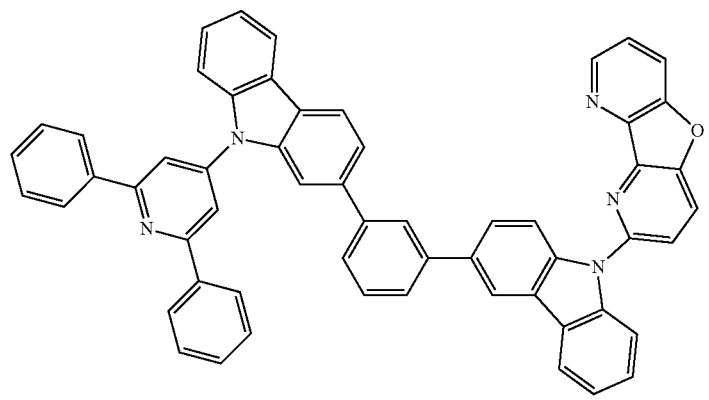

-continued
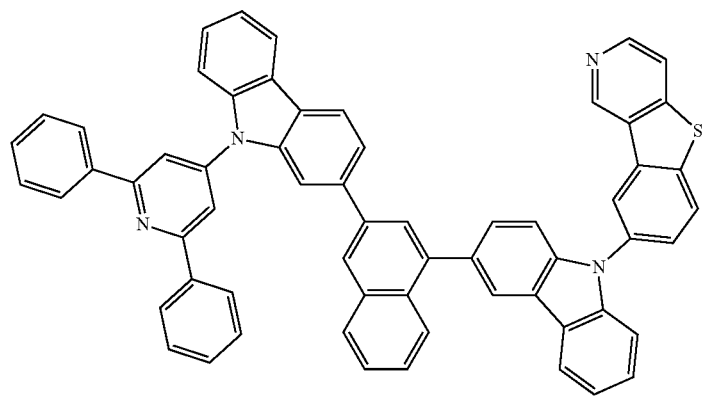
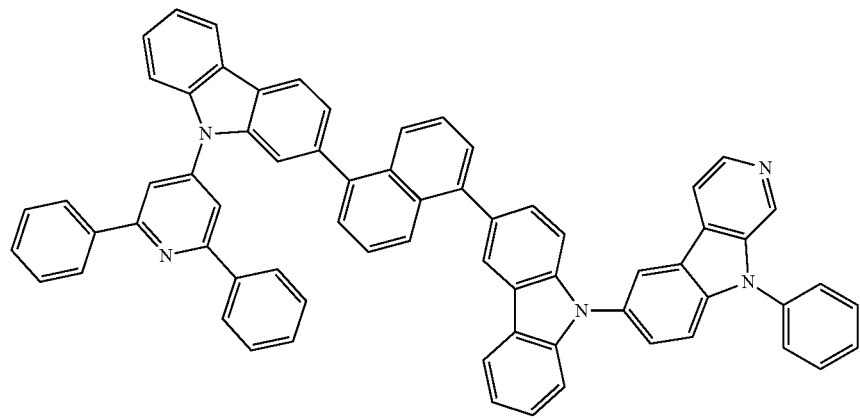
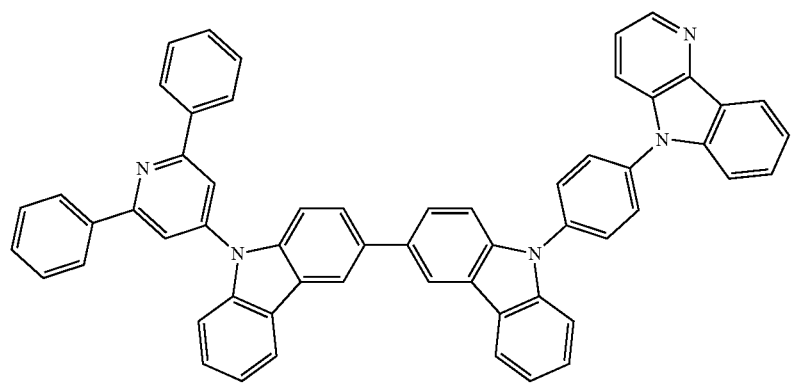
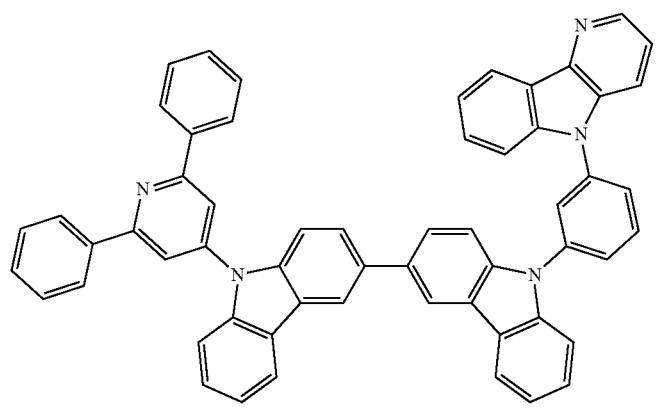

-continued
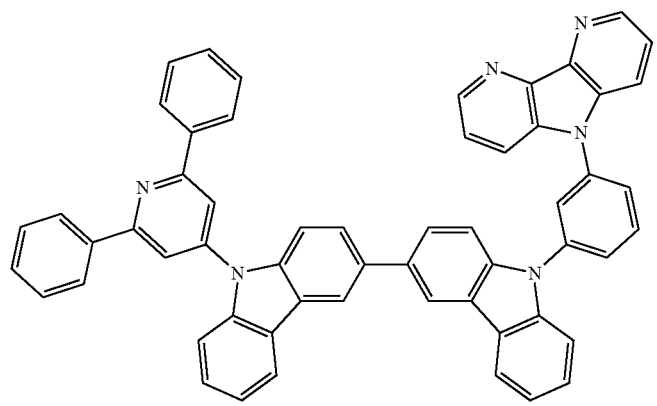
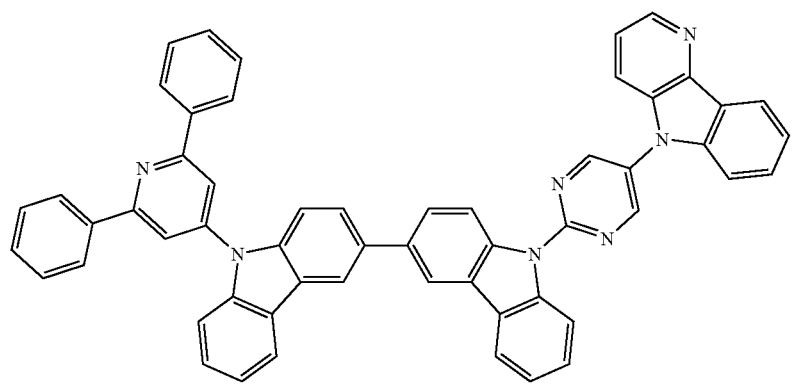
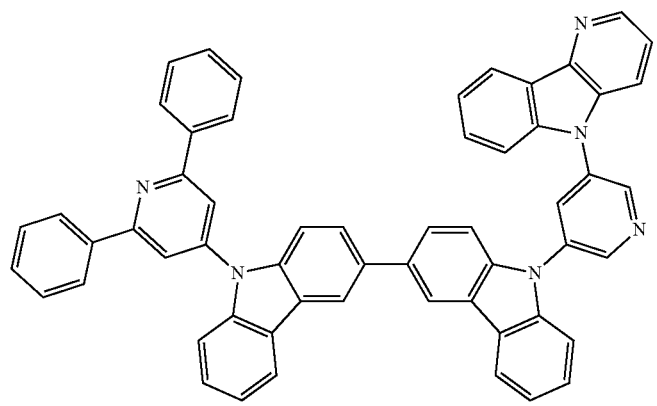
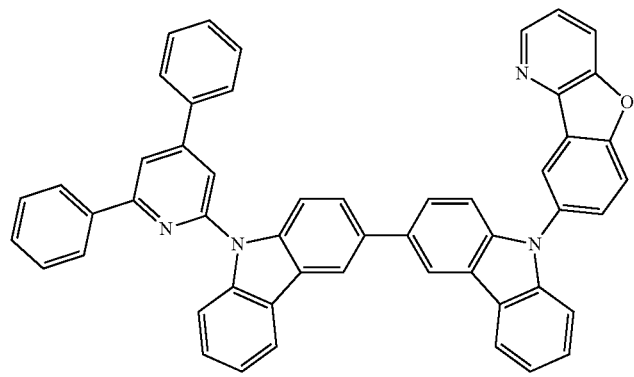

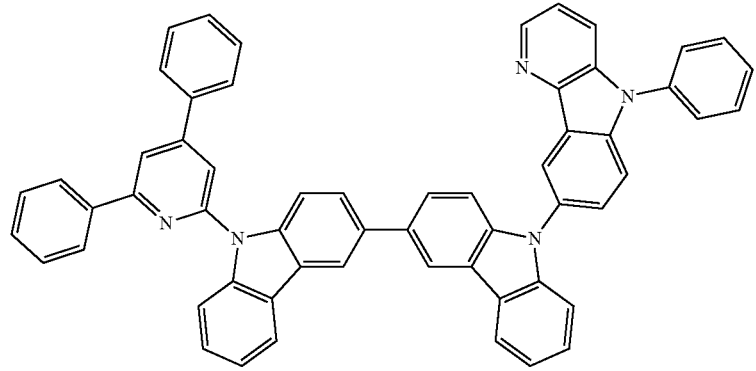
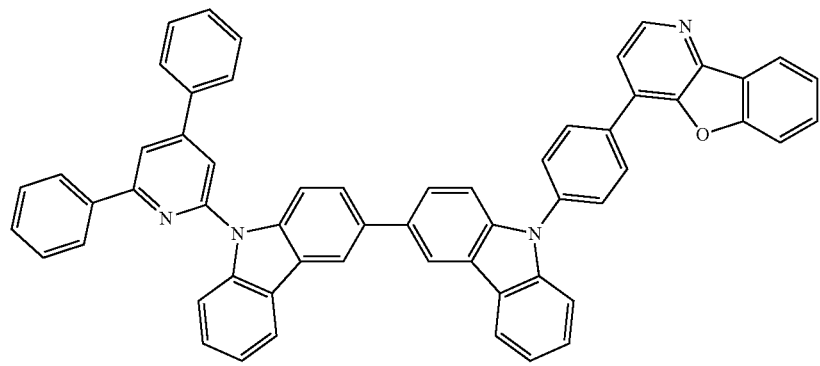
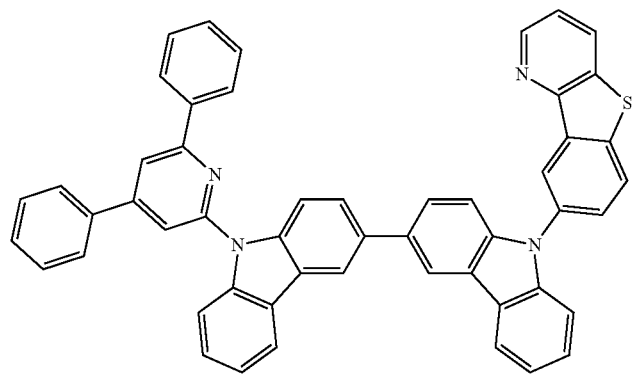
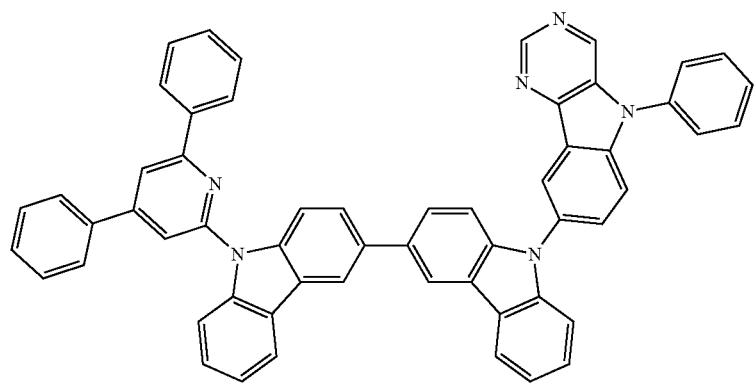

-continued
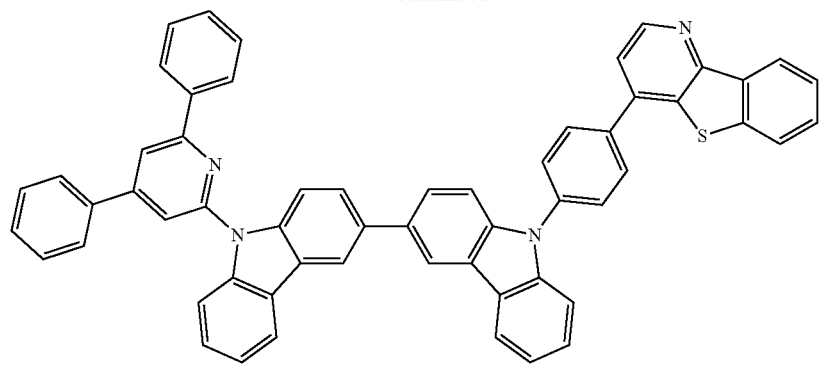
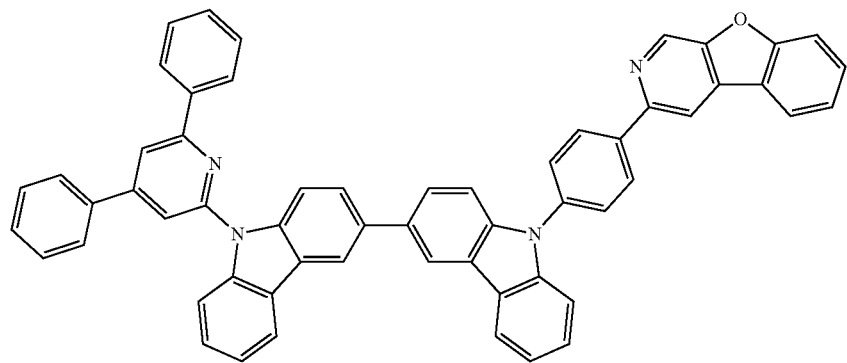
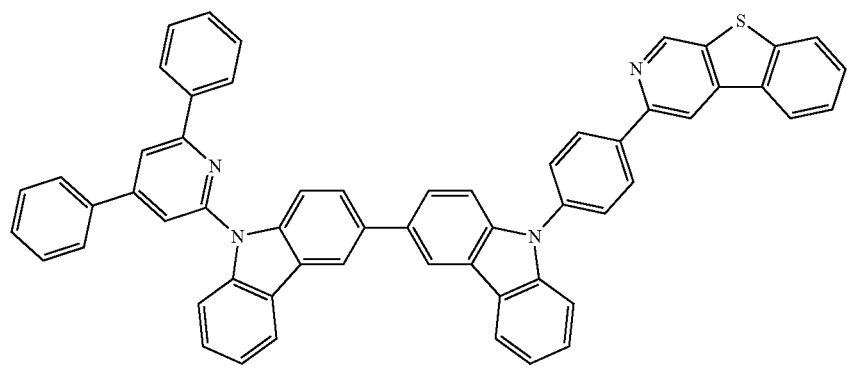
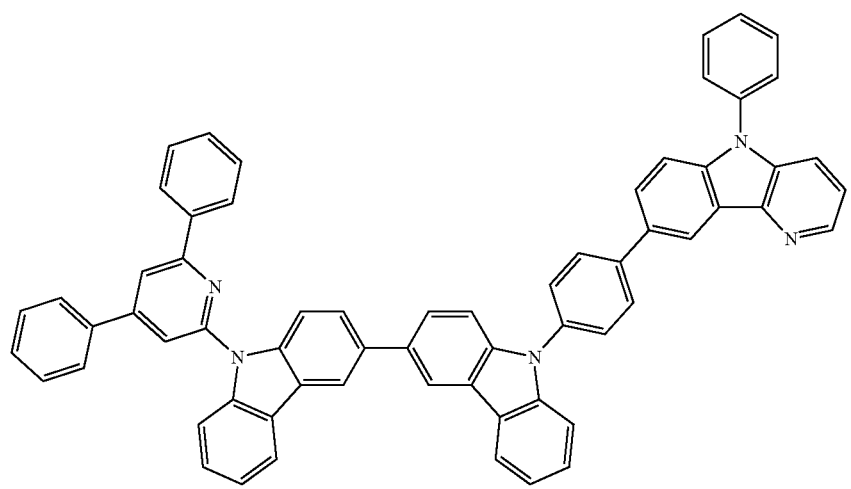

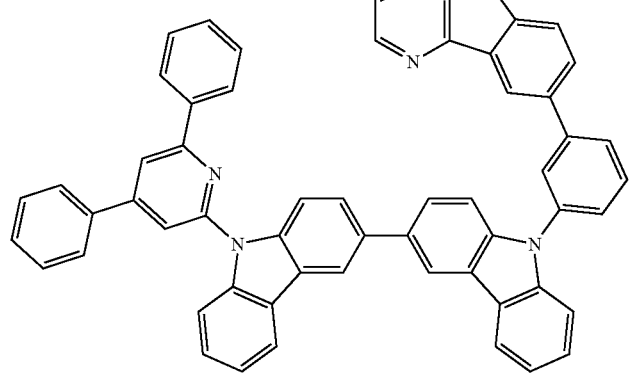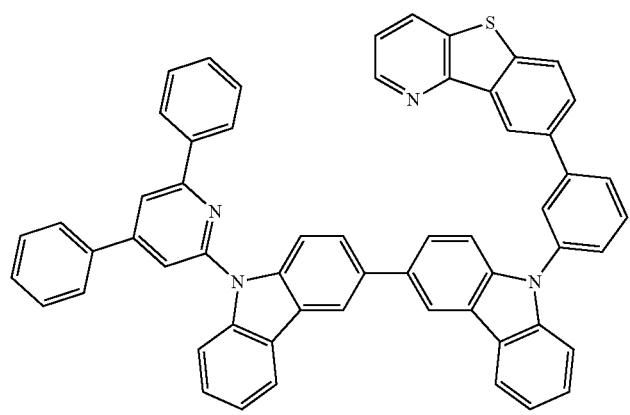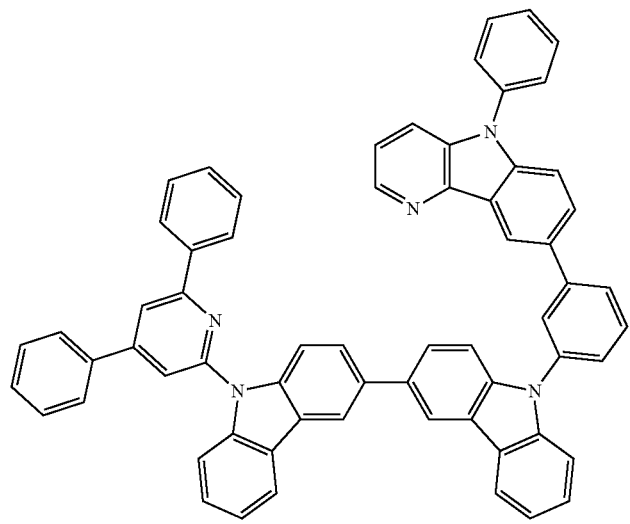

-continued
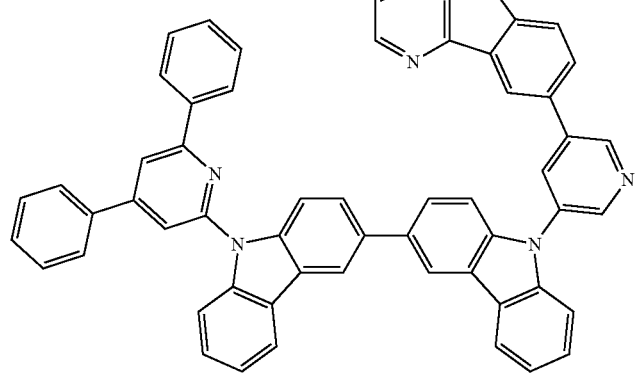
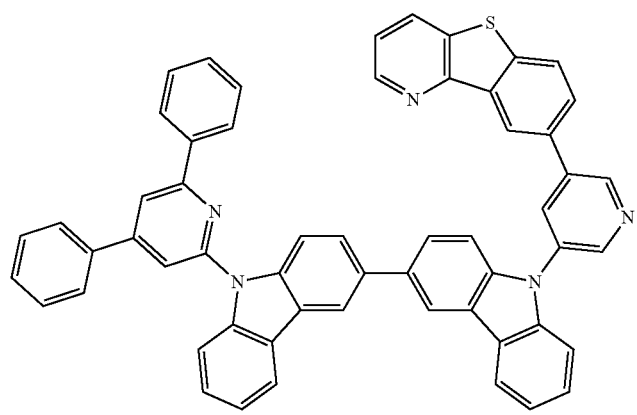
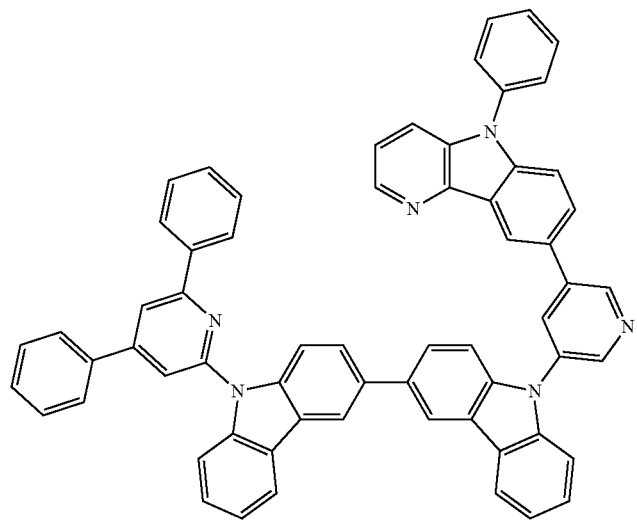

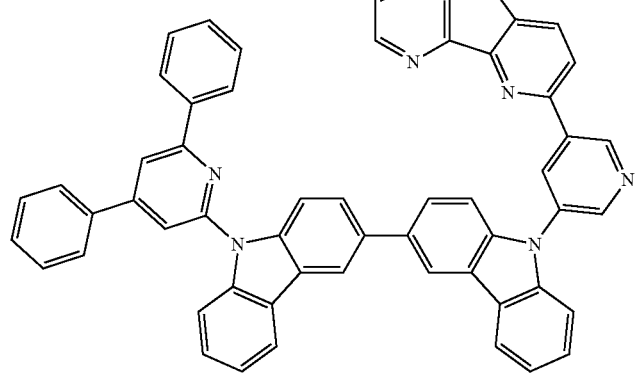
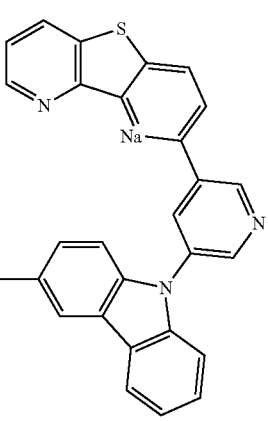
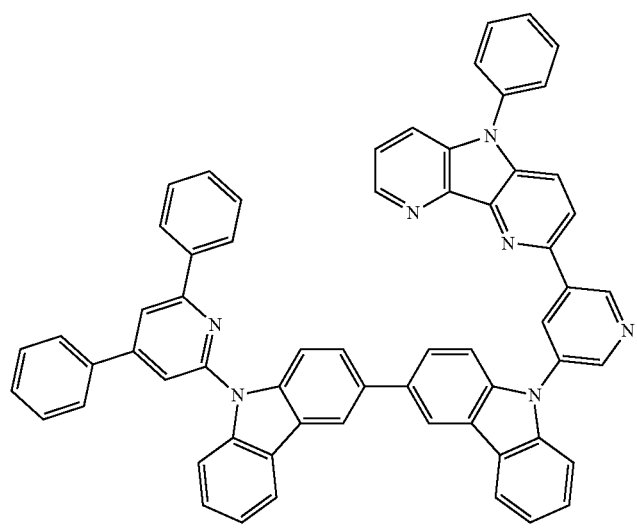

-continued
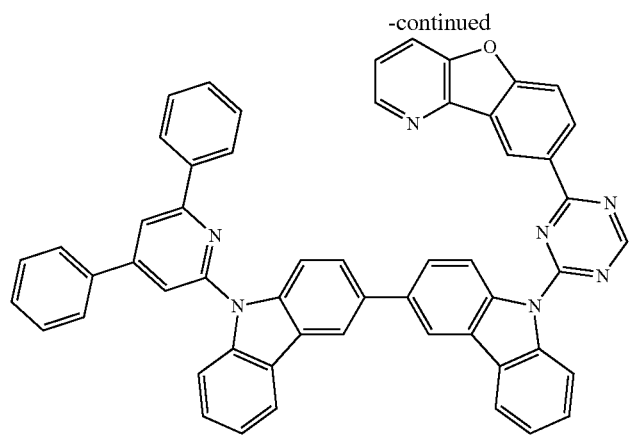
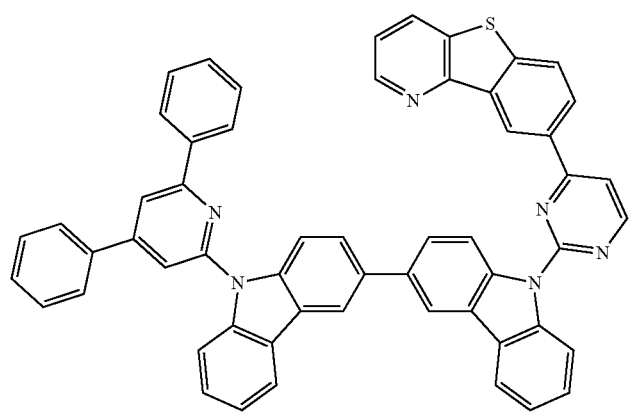
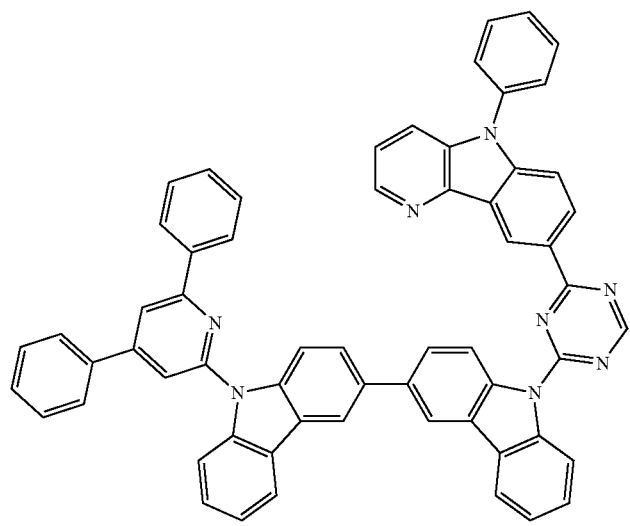

-continued
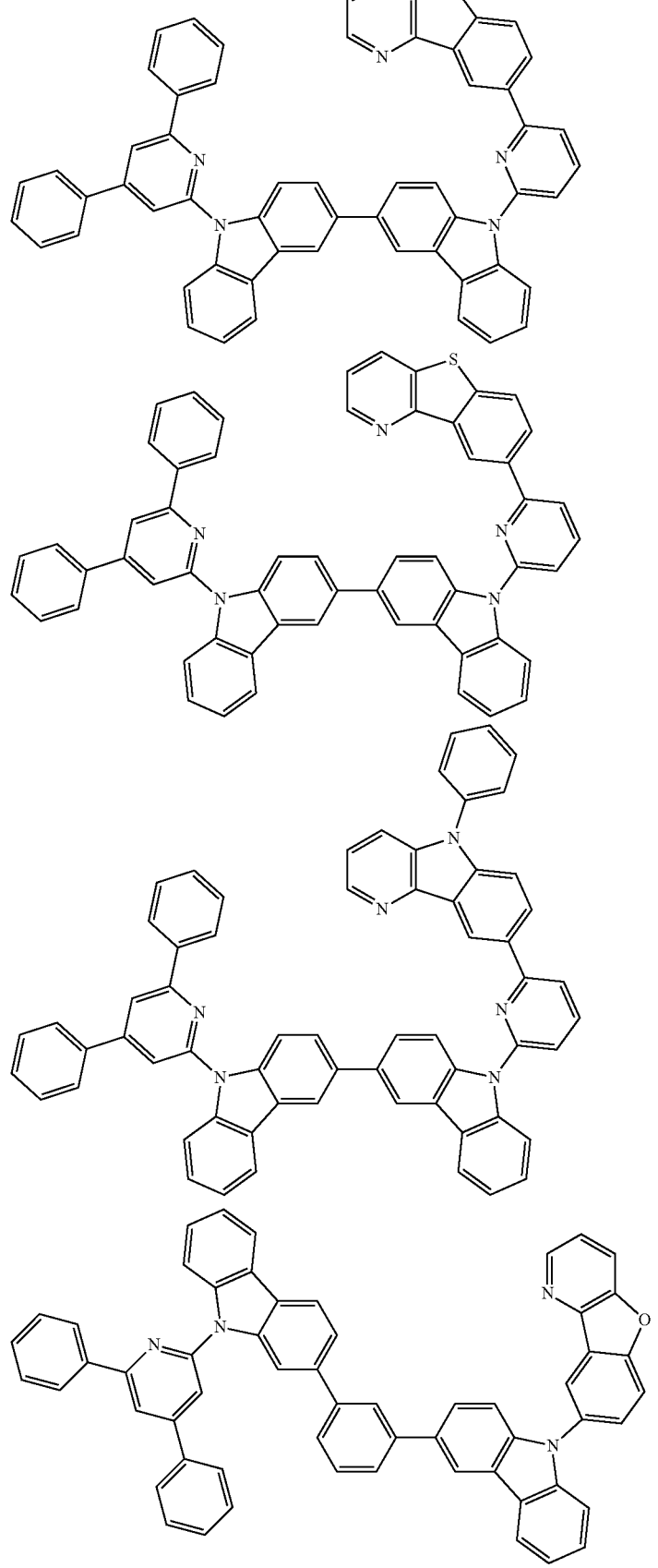

-continued
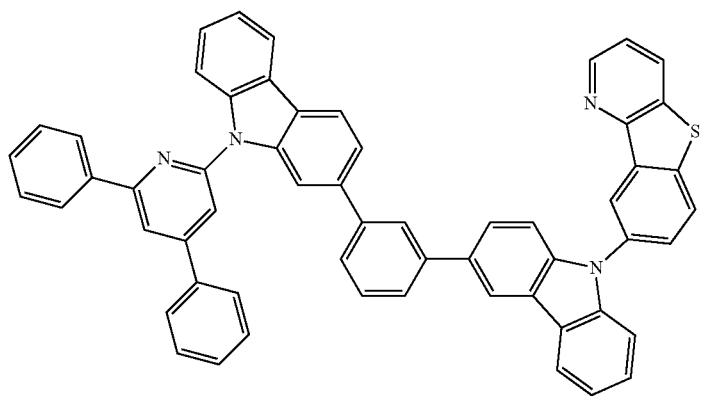
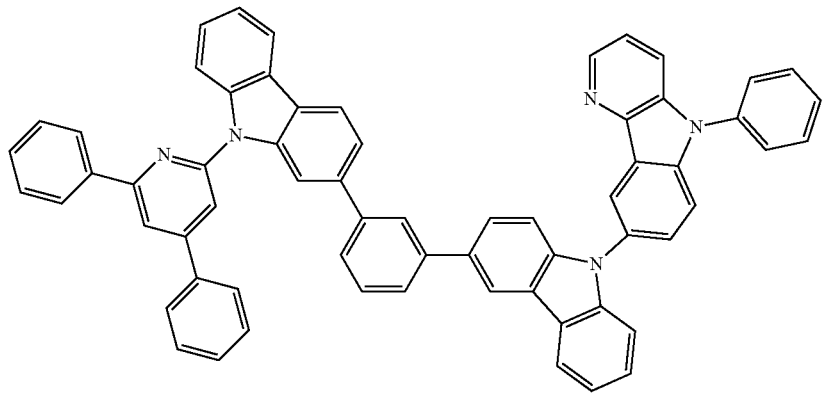
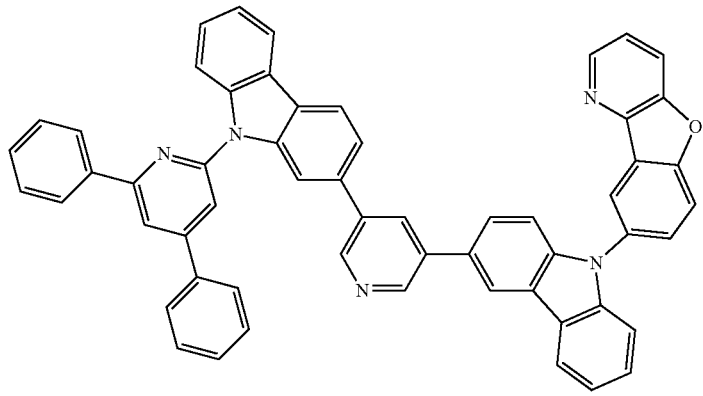
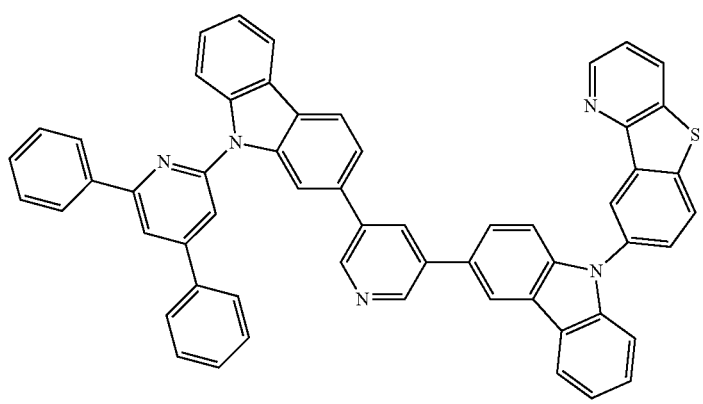

-continued
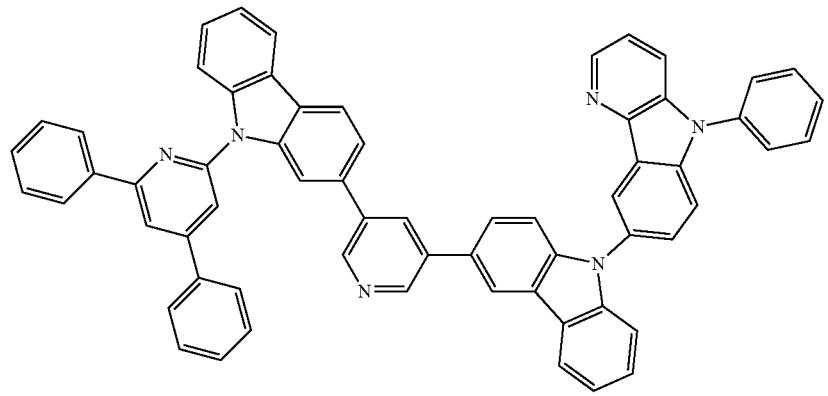
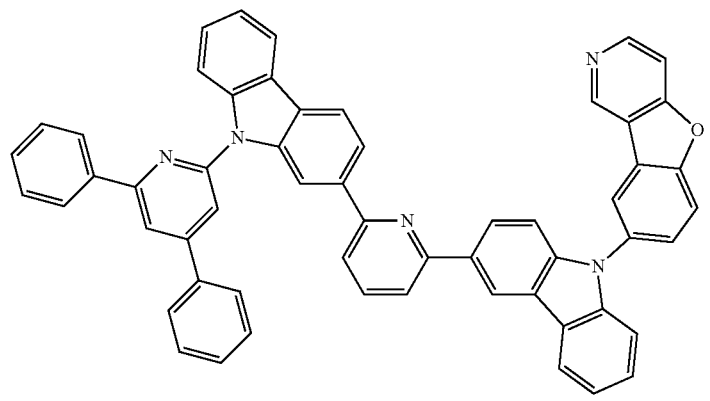
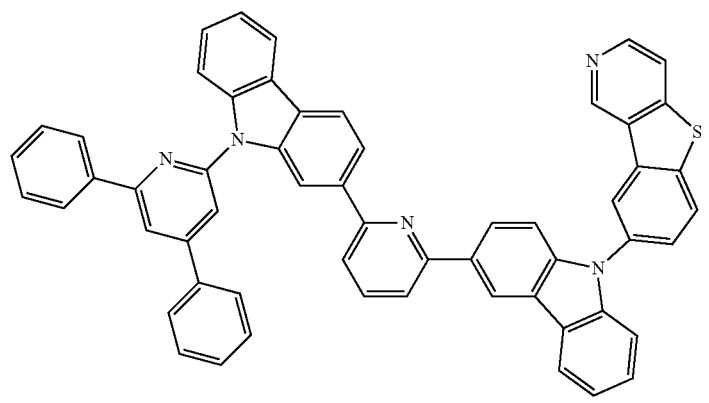
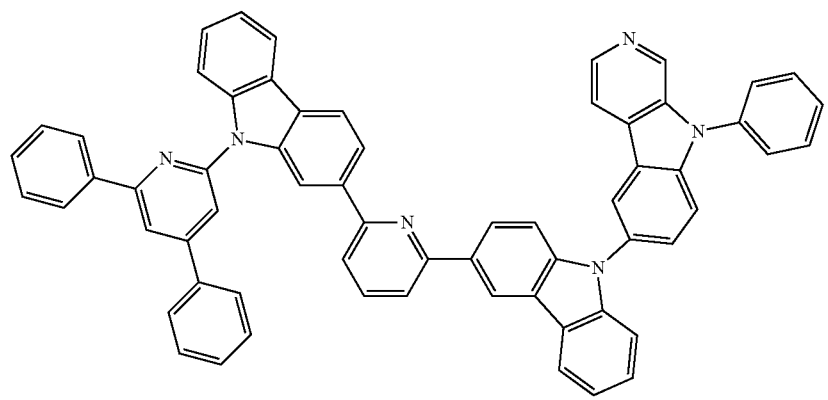

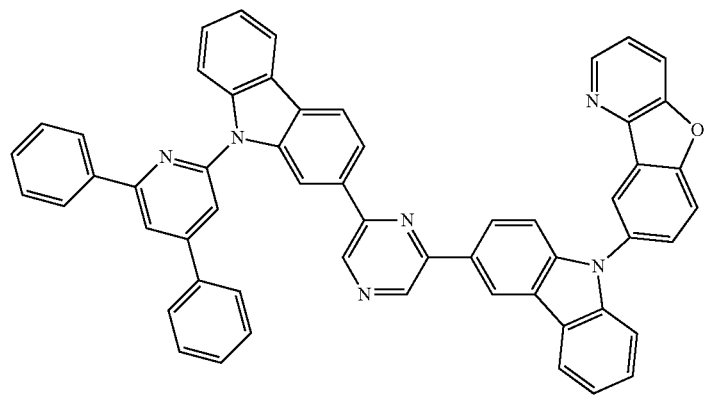
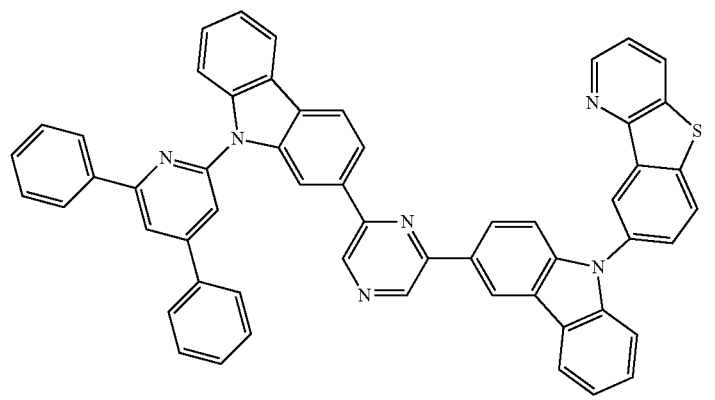
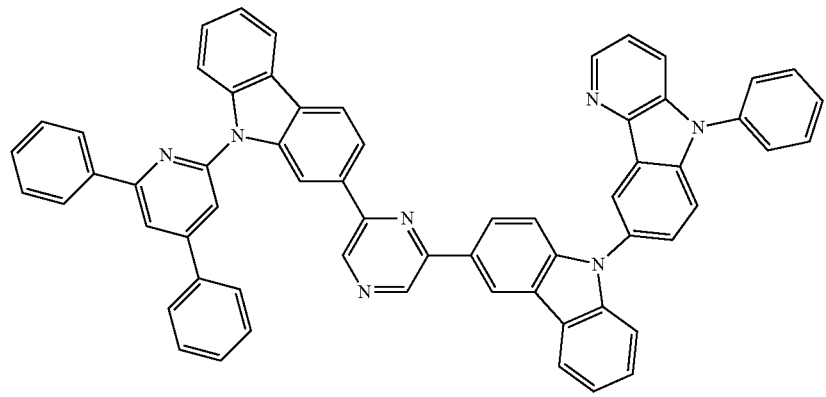
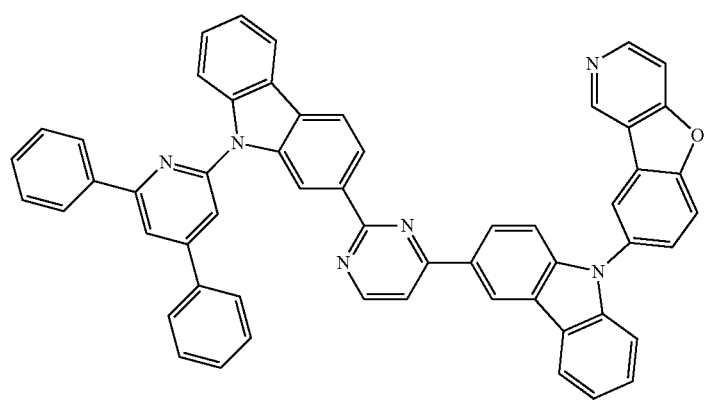

-continued
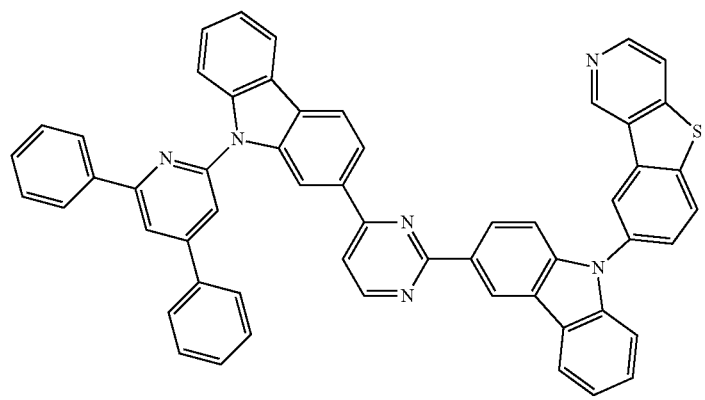
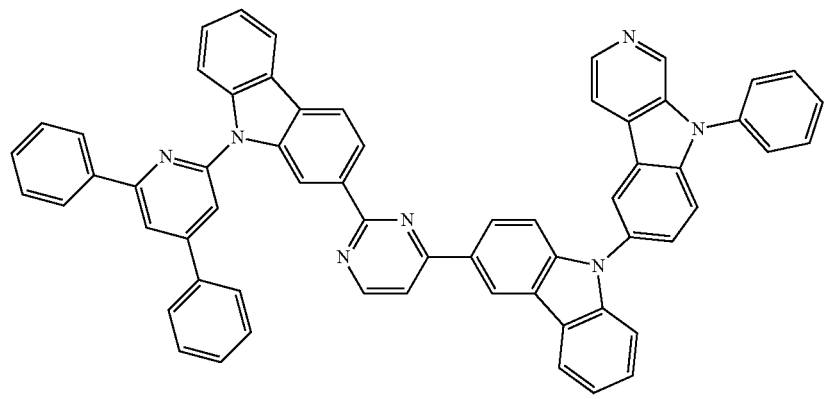
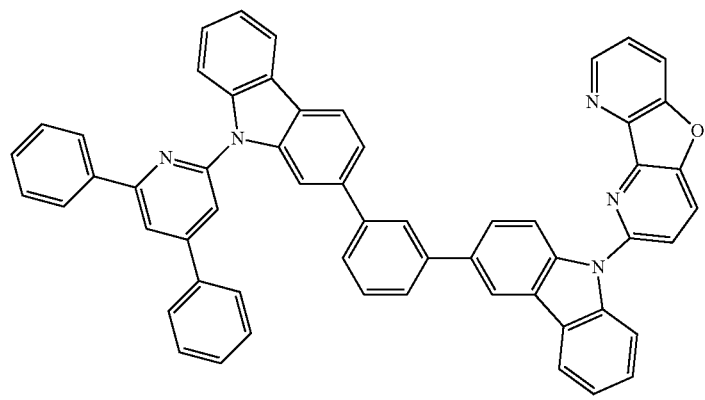
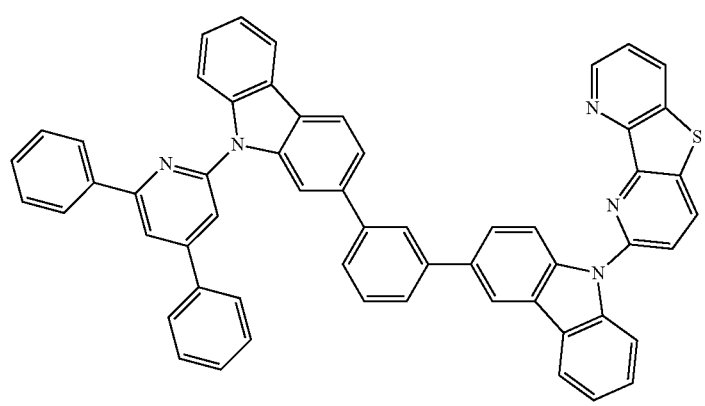

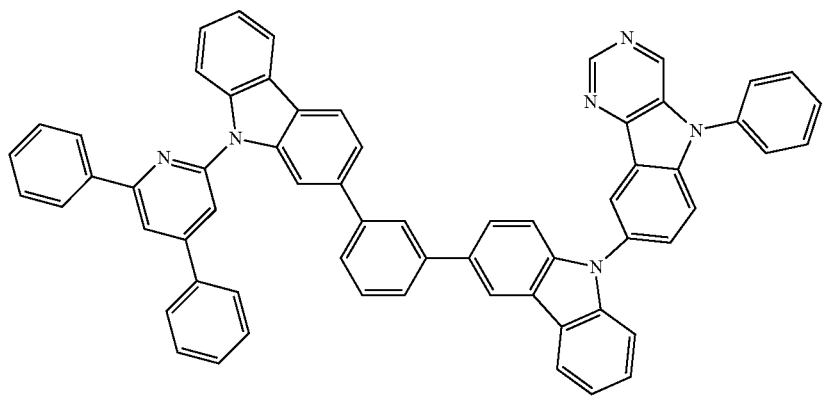
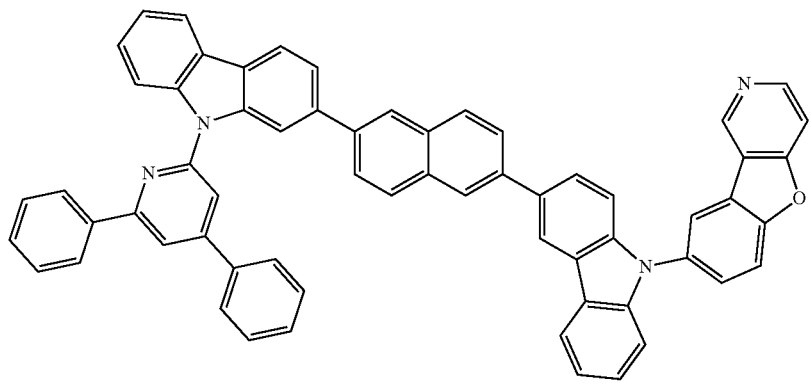
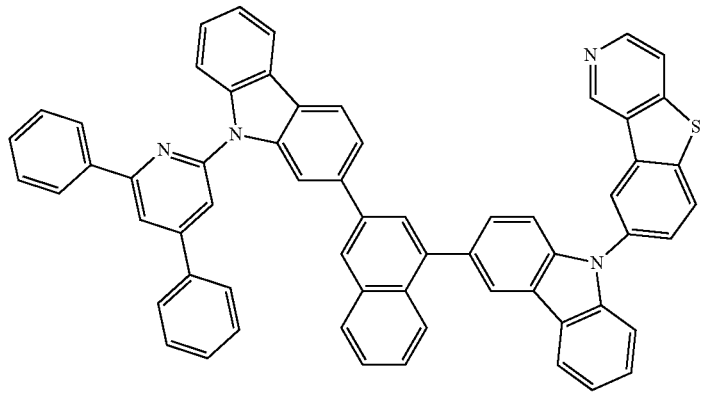
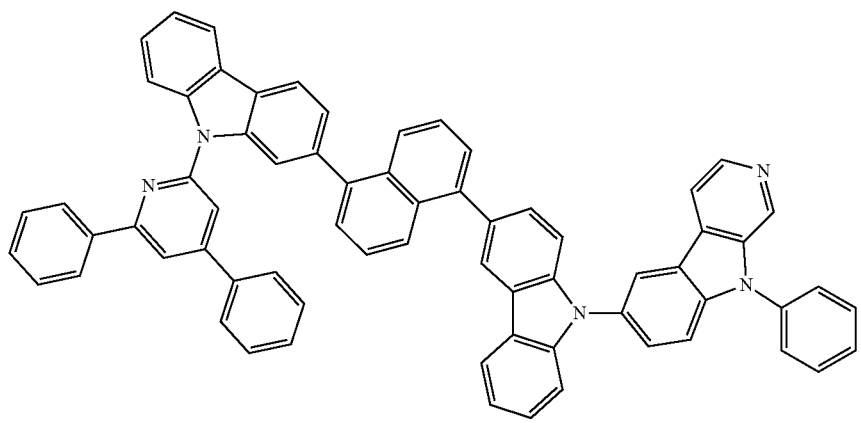

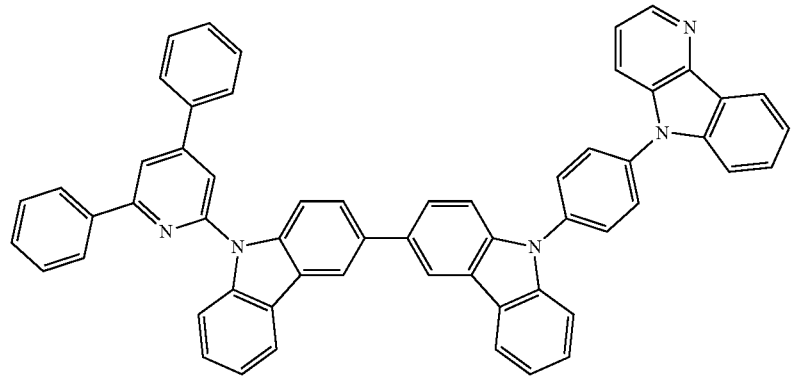
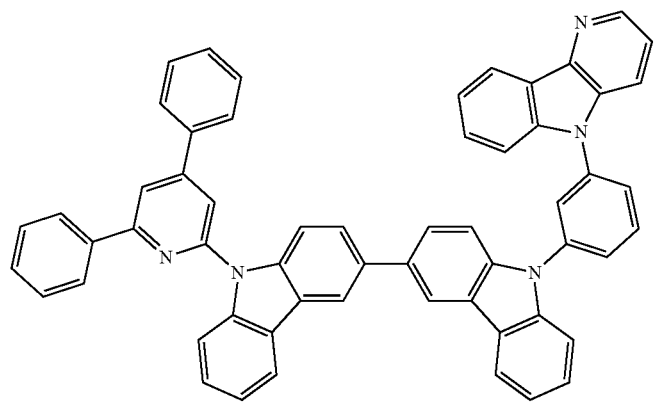
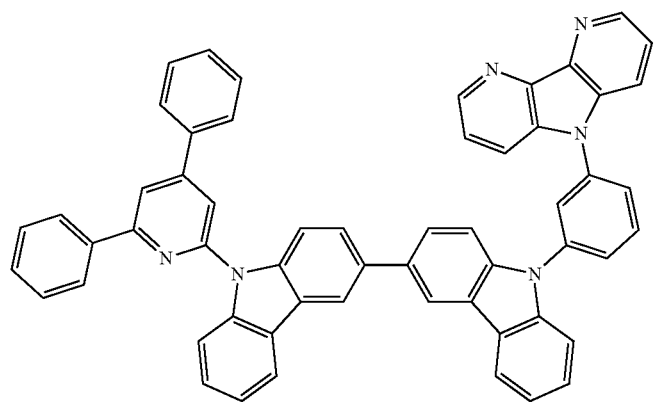
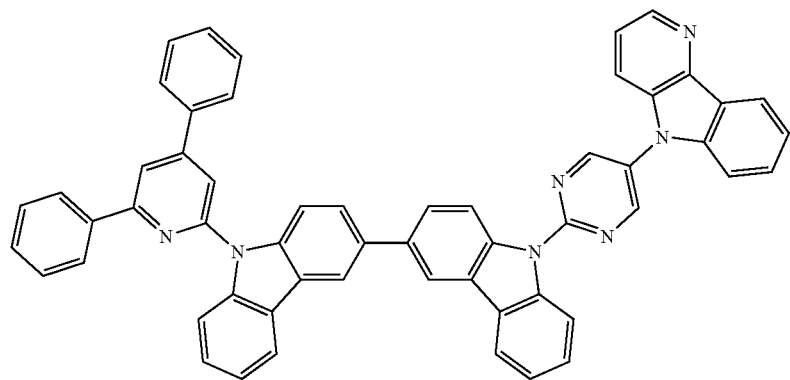

149 150
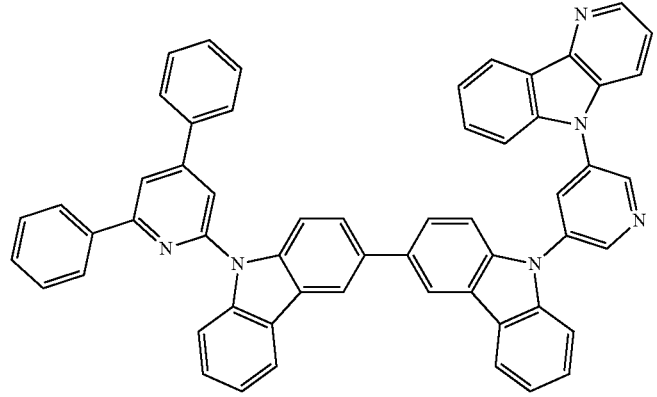
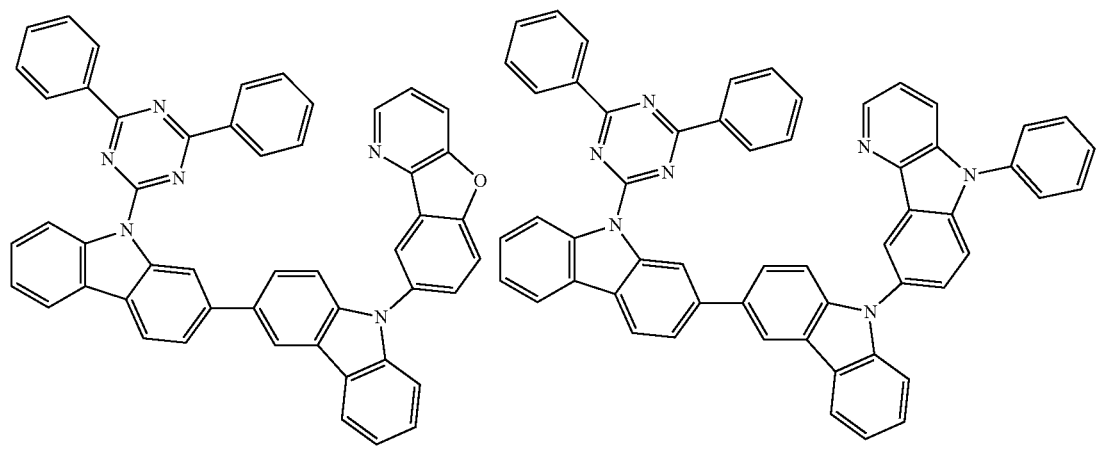
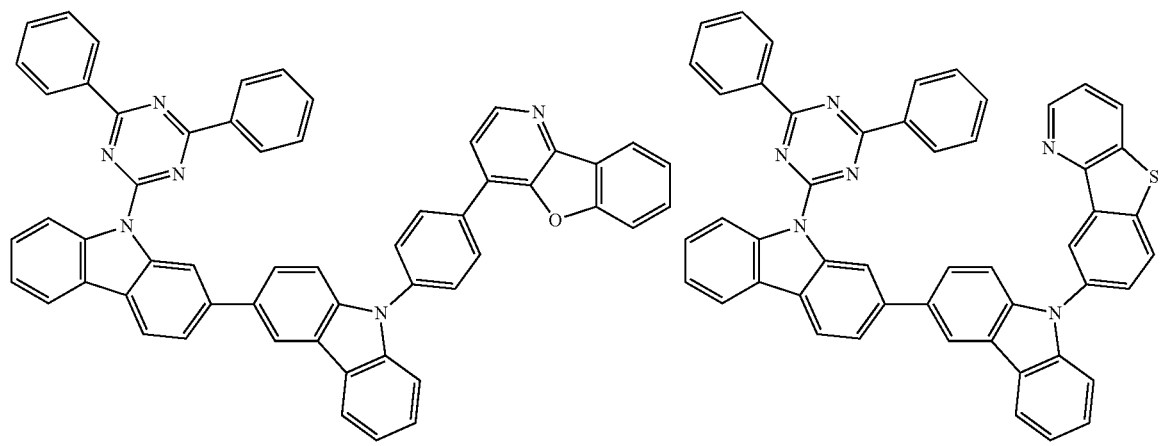

-continued
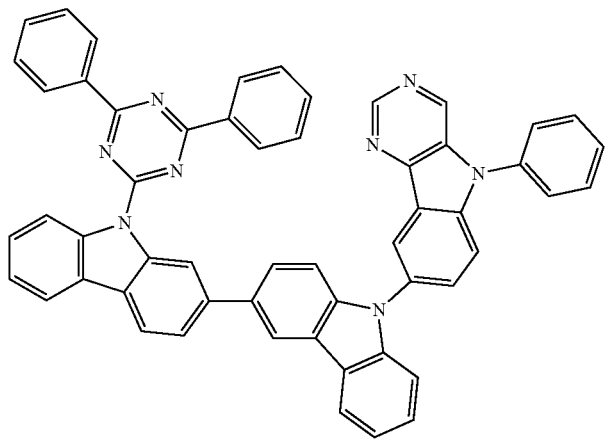
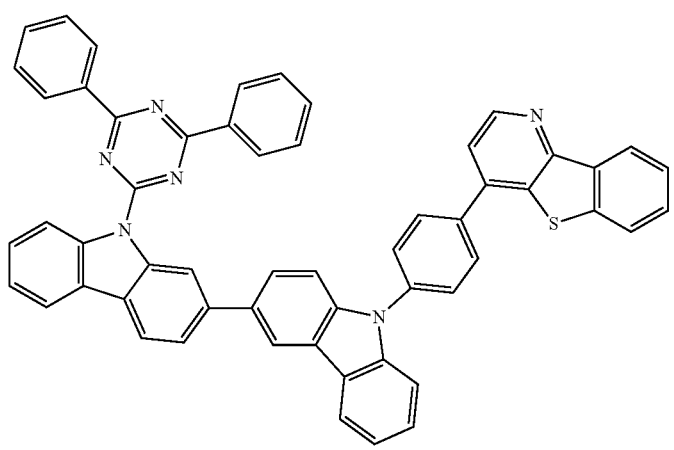
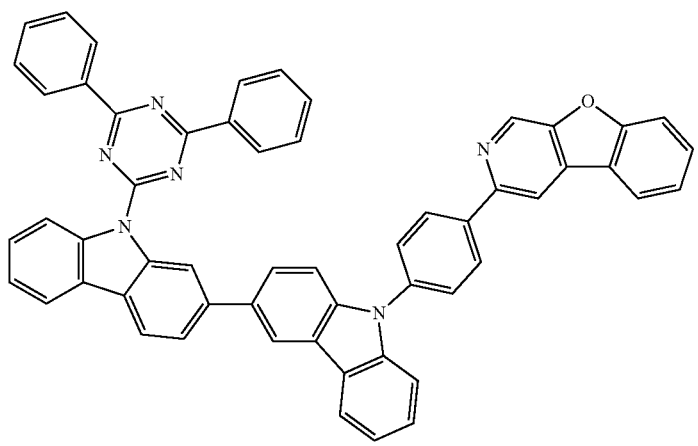

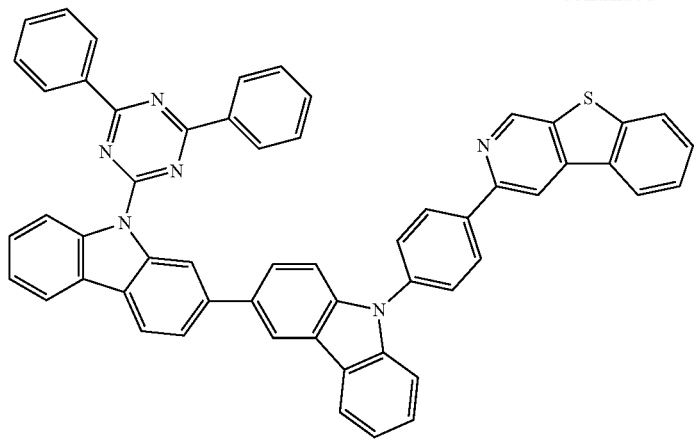
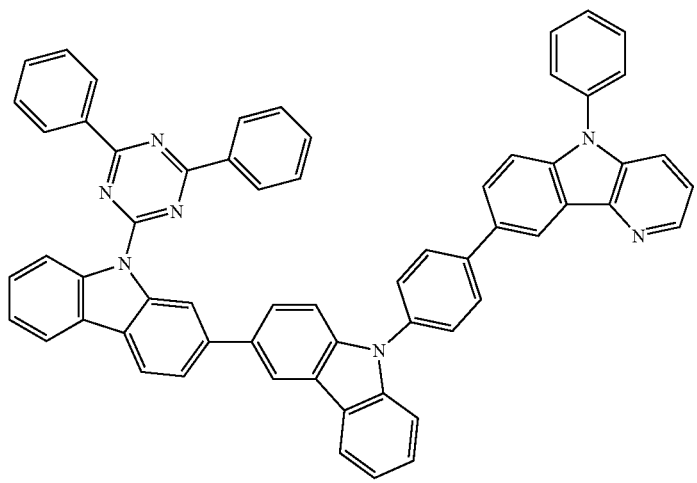
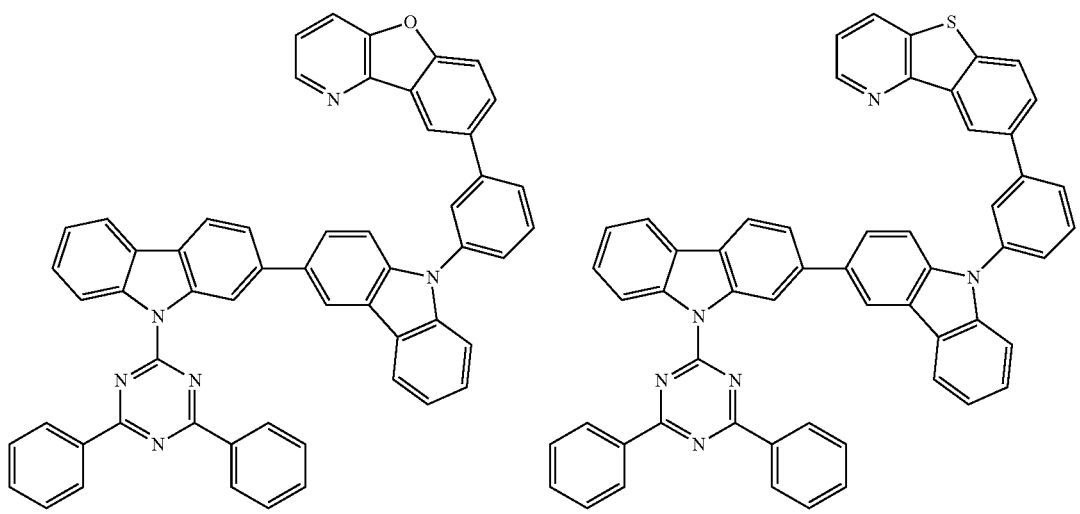

-continued
| 155 | 156 |
|---|---|
| 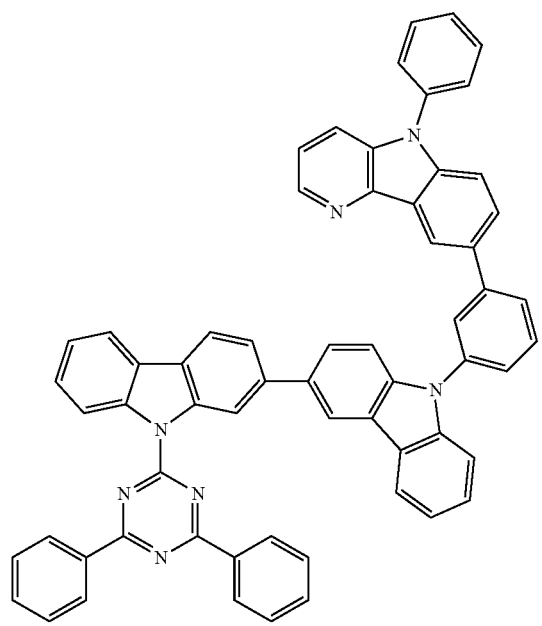 | 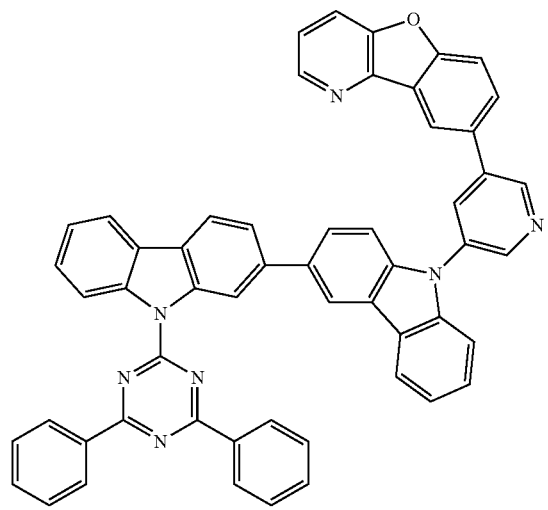 |
| 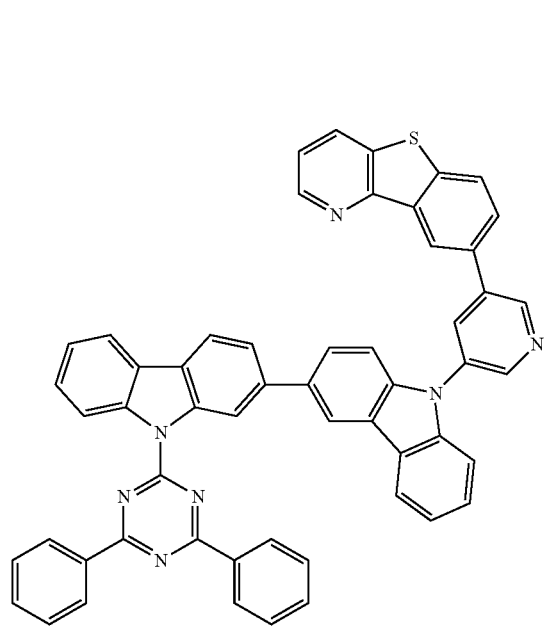 | 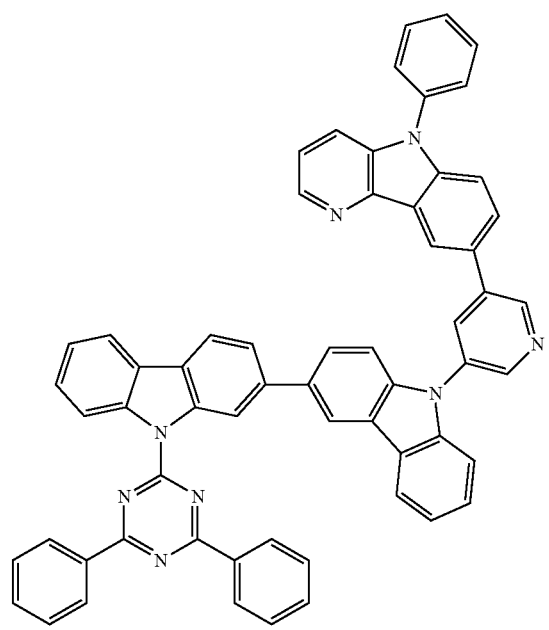 |

-continued
157
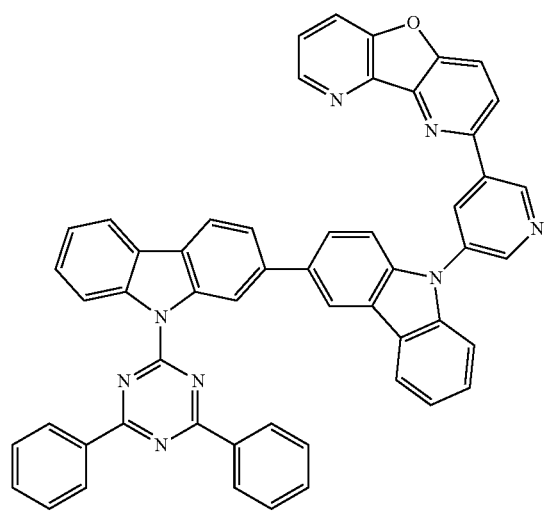
158
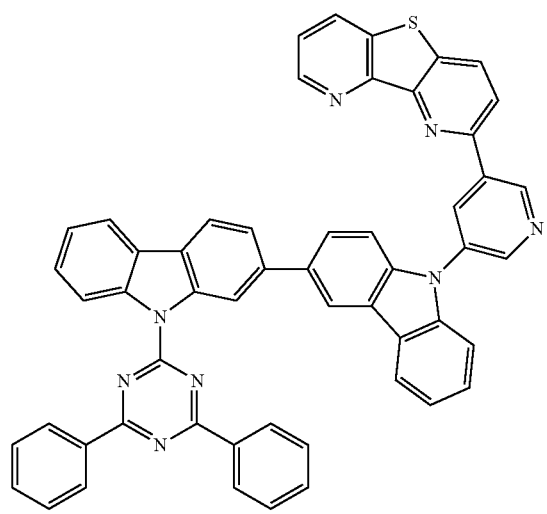
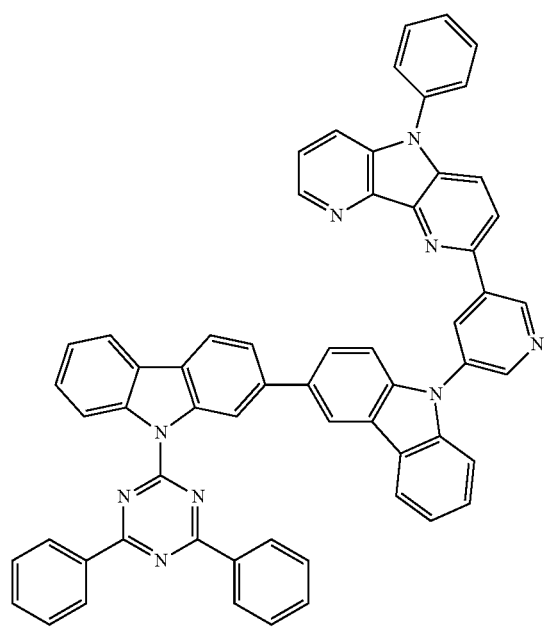
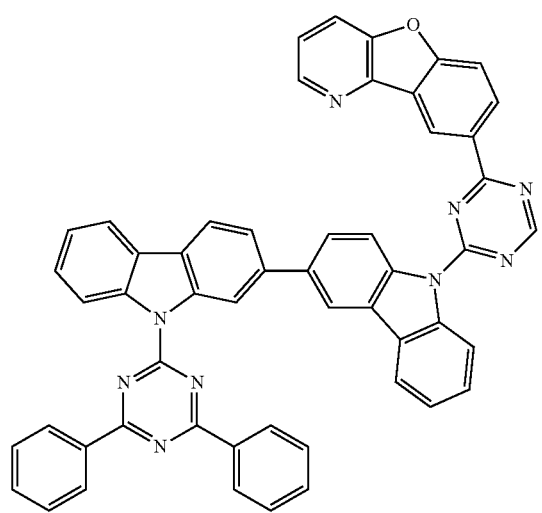

159
160
-continued
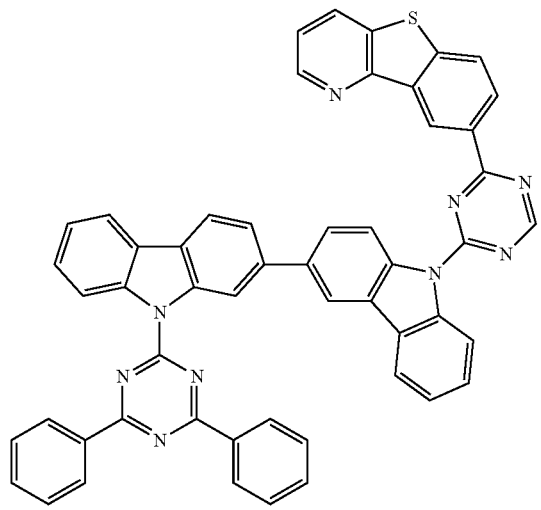
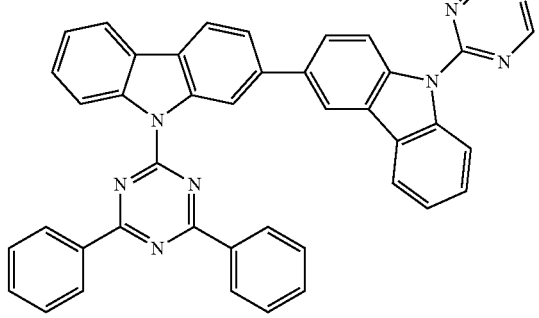
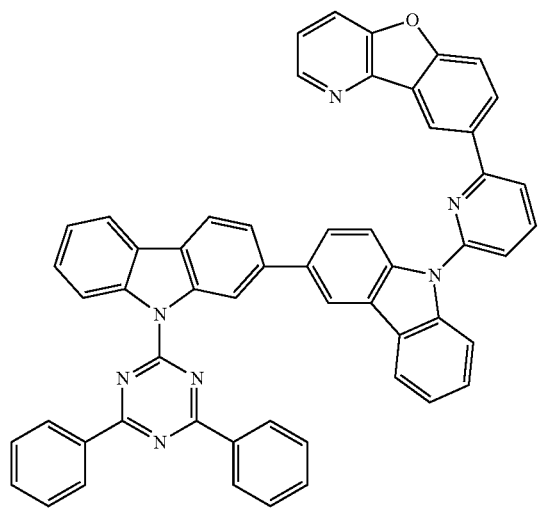
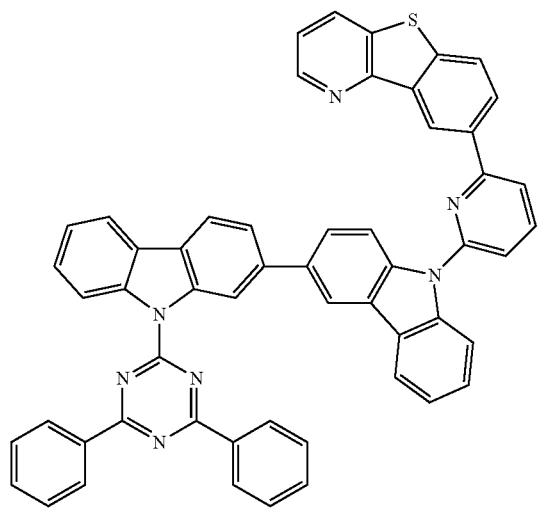

-continued
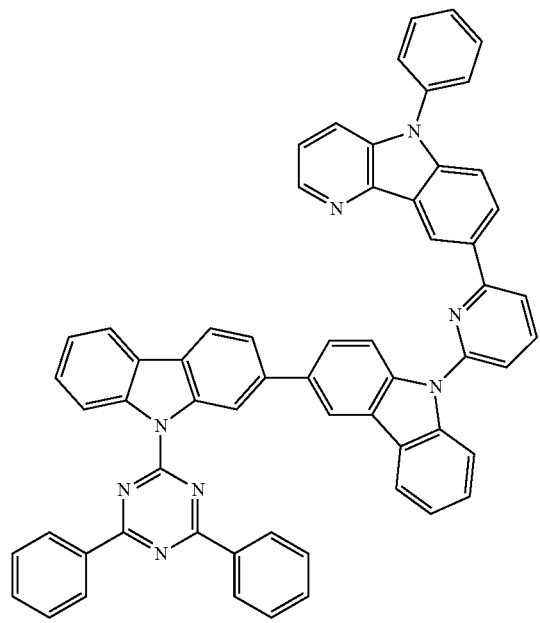
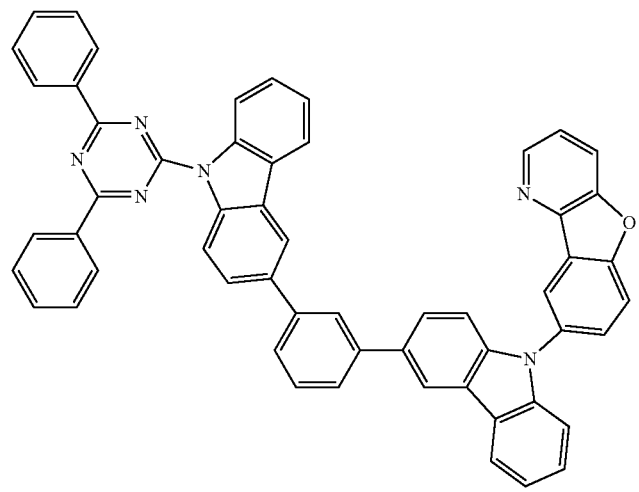
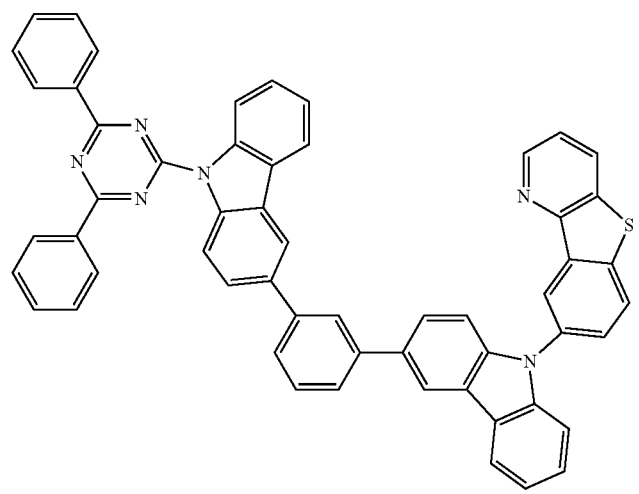

-continued
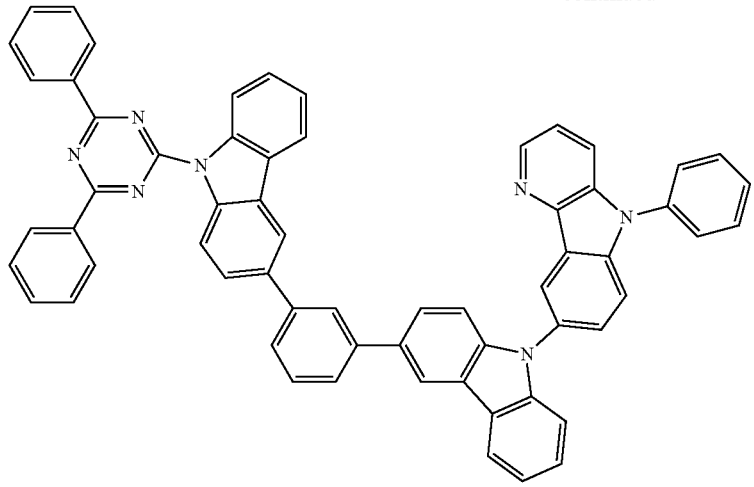
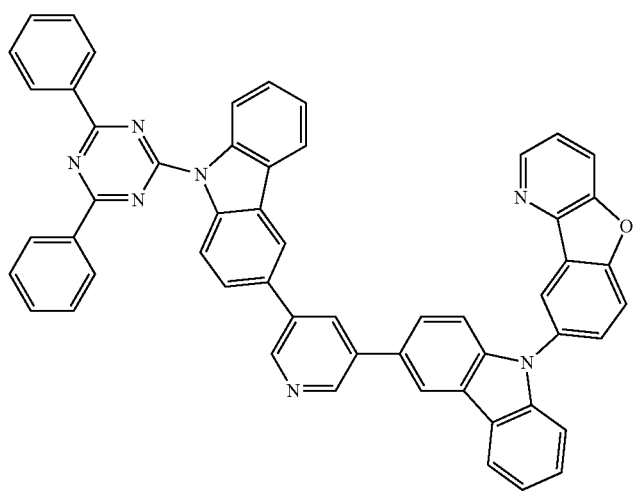
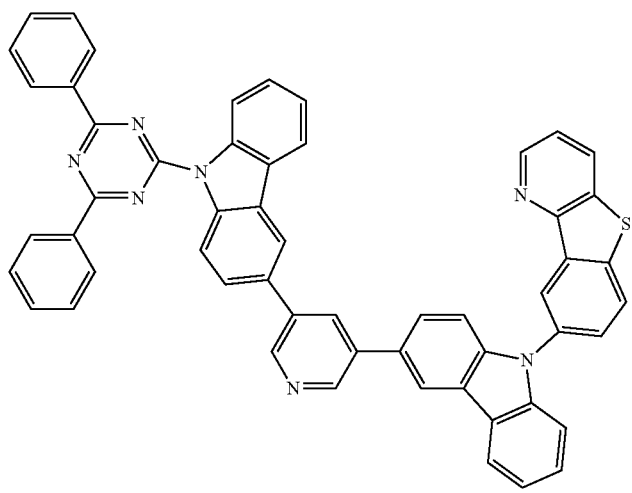

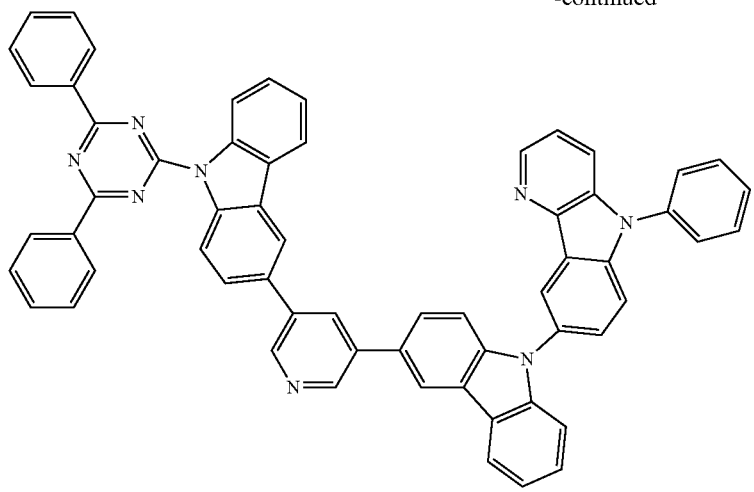
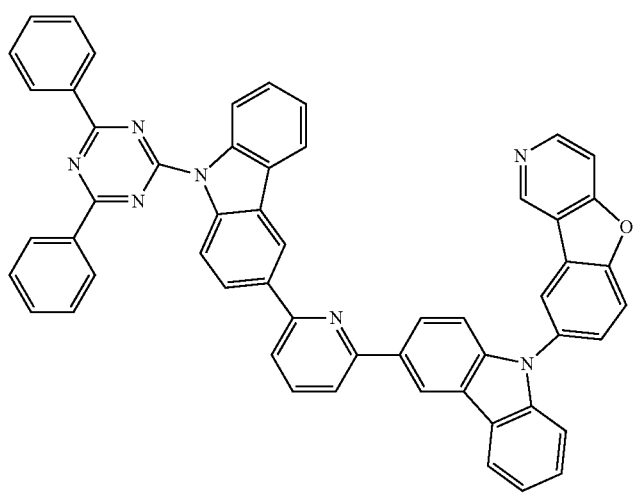
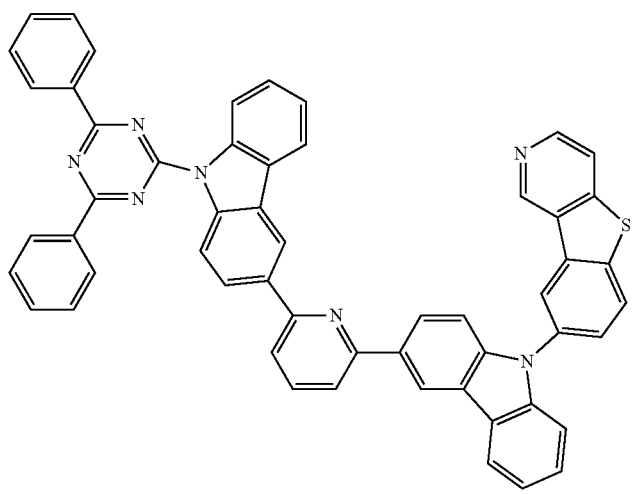

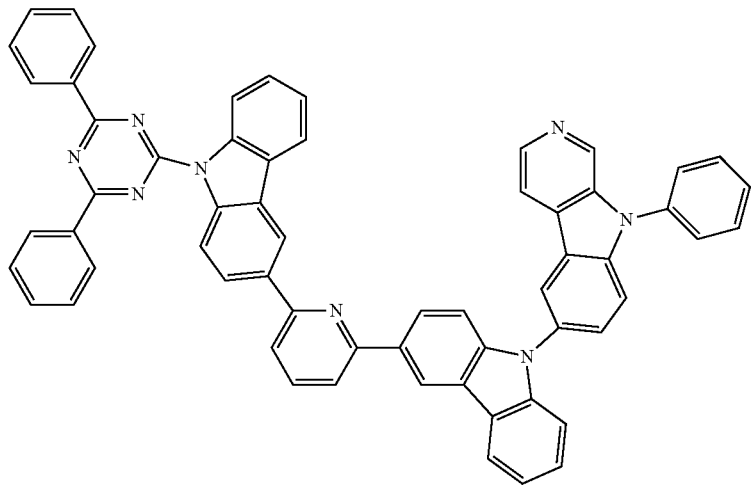
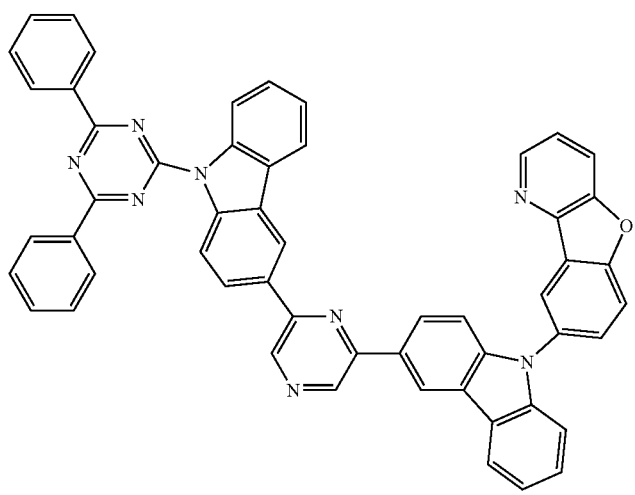
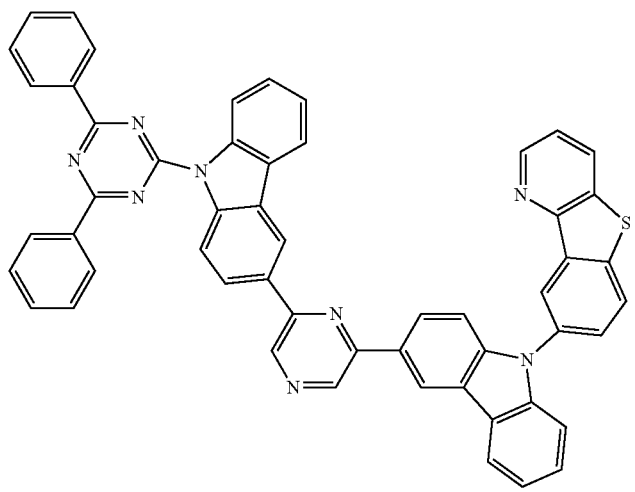

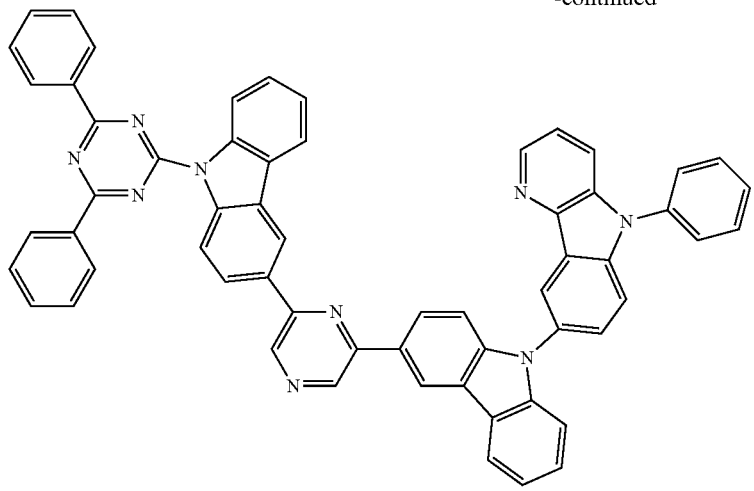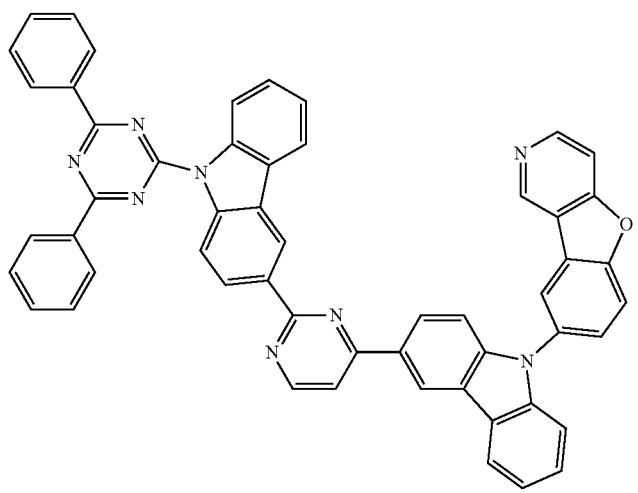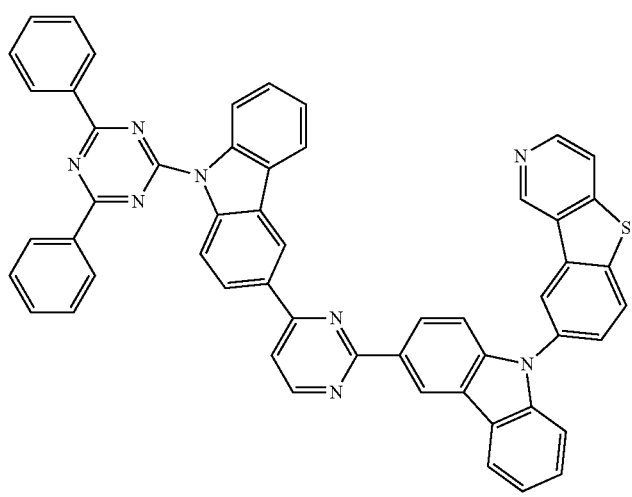

-continued
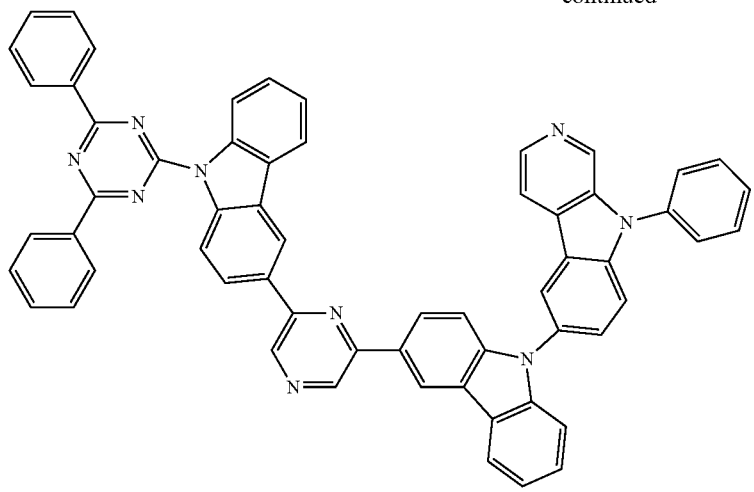
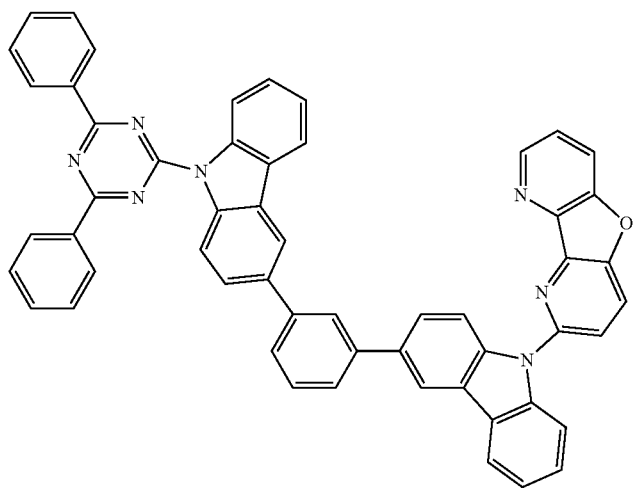
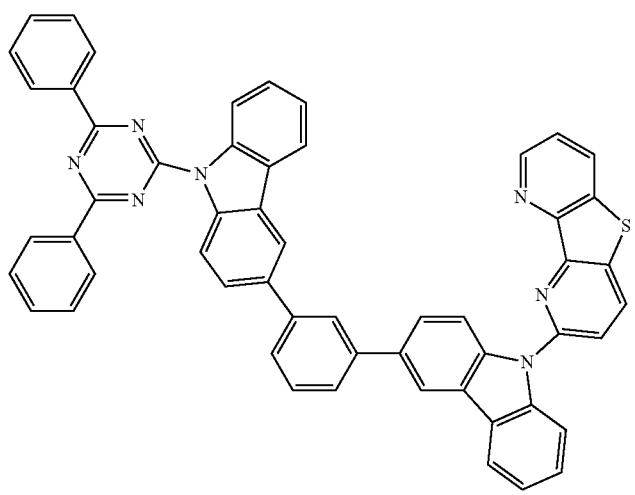

-continued
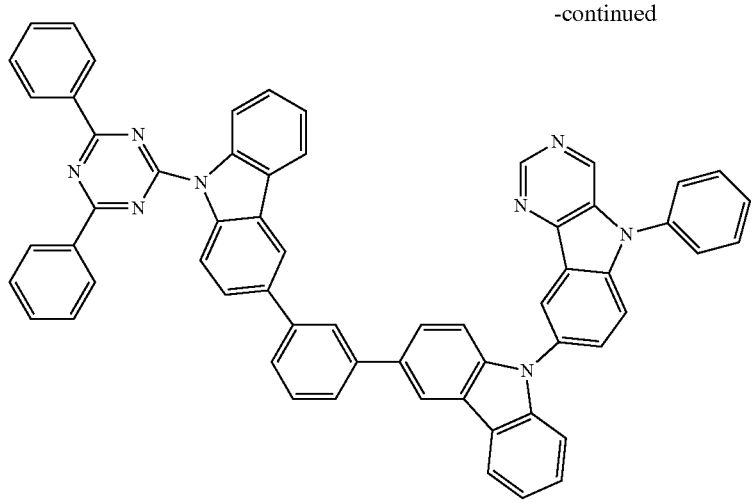
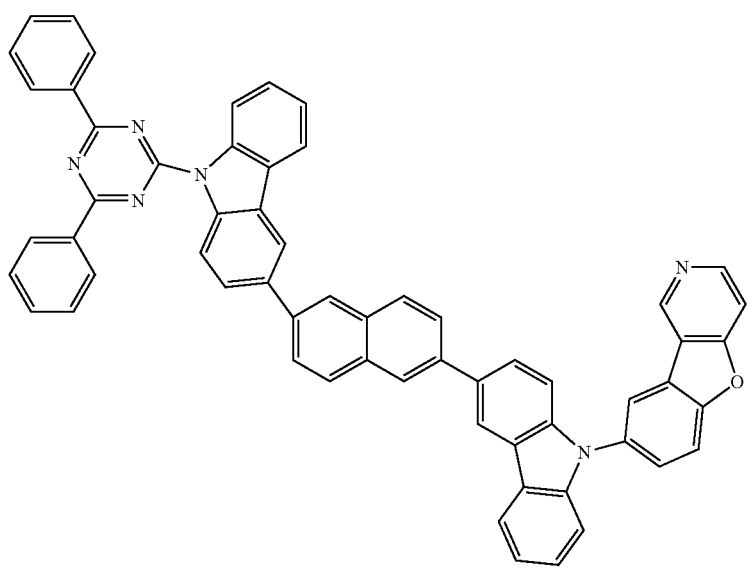
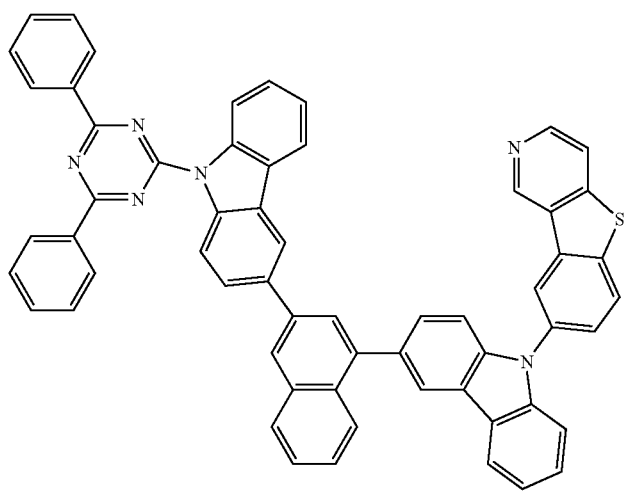

-continued
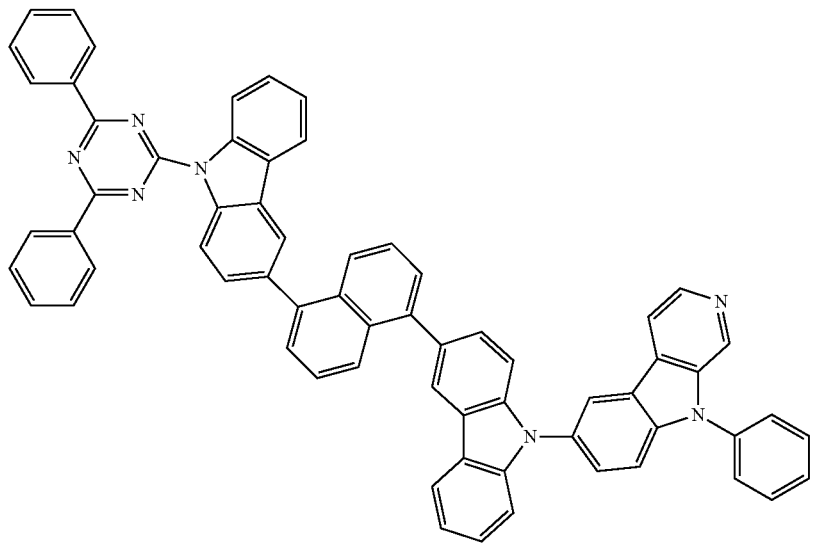
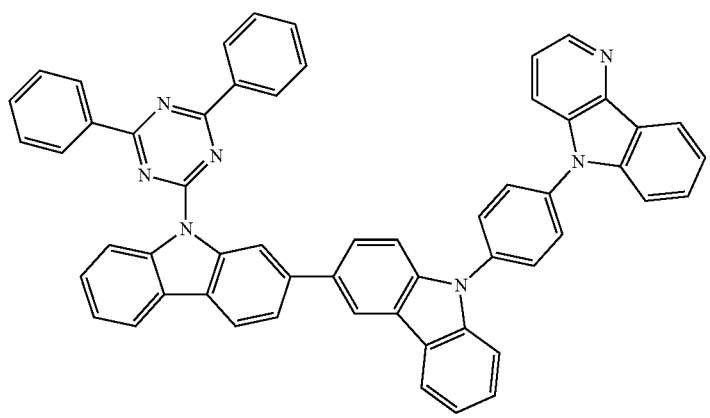
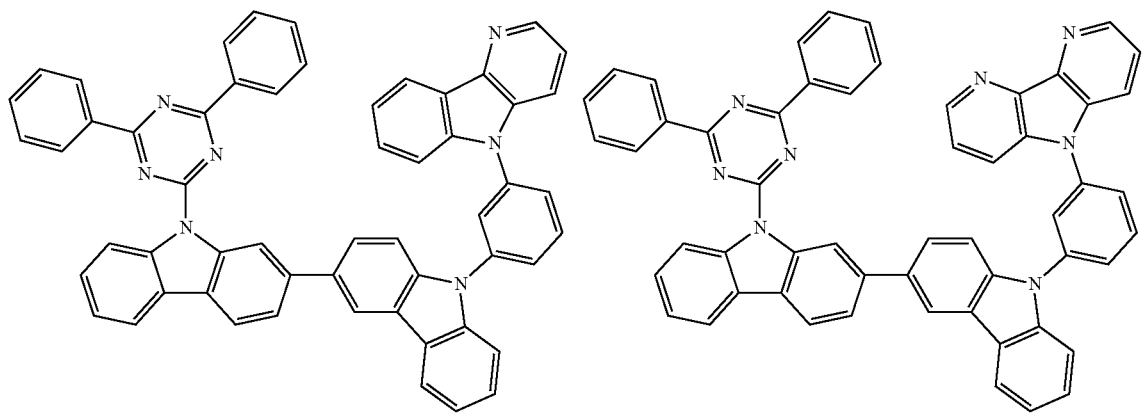

-continued
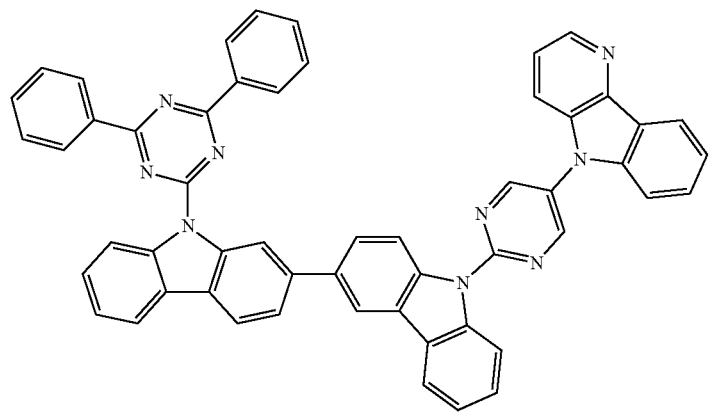
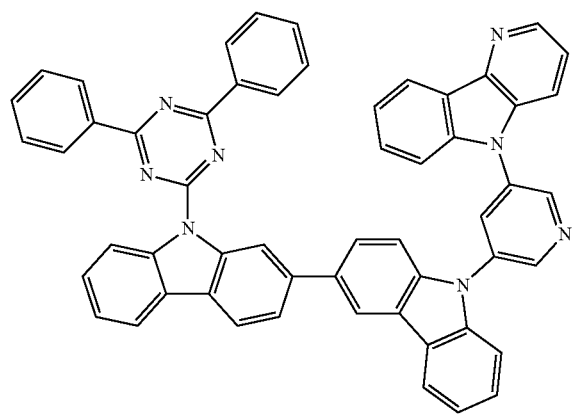
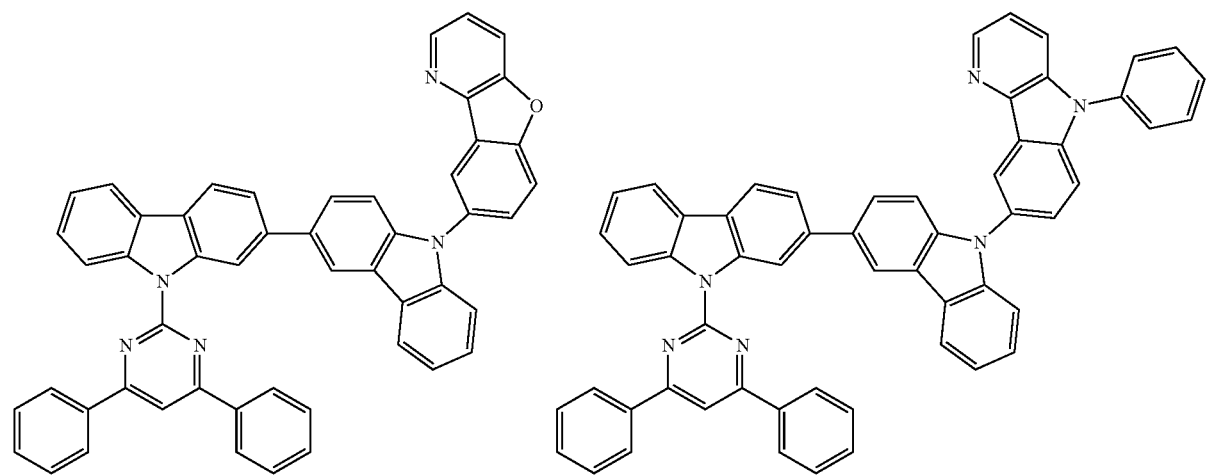

-continued
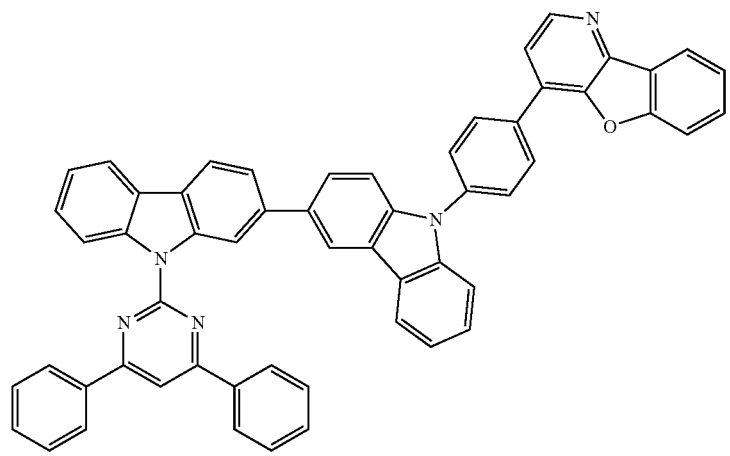
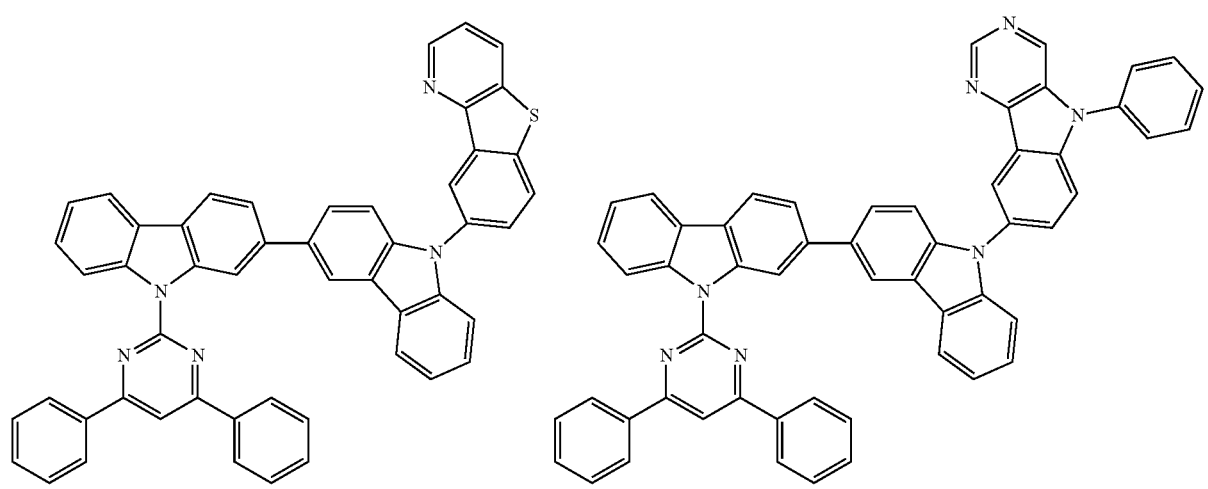
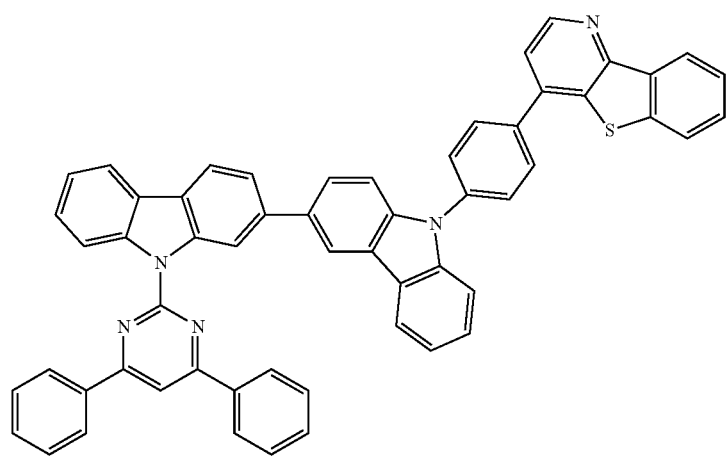

-continued
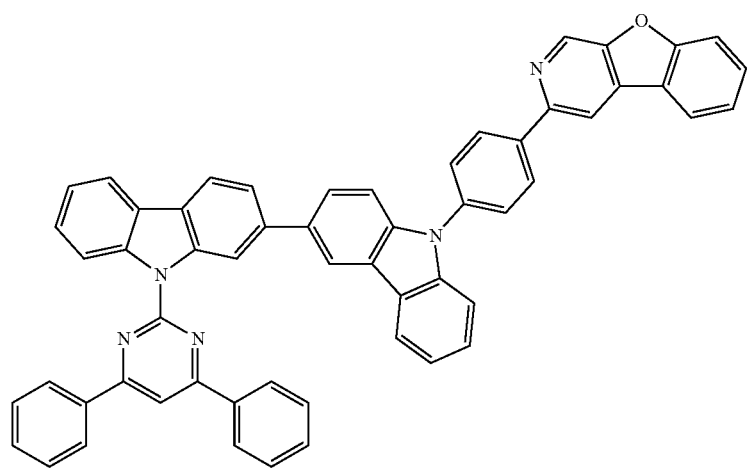
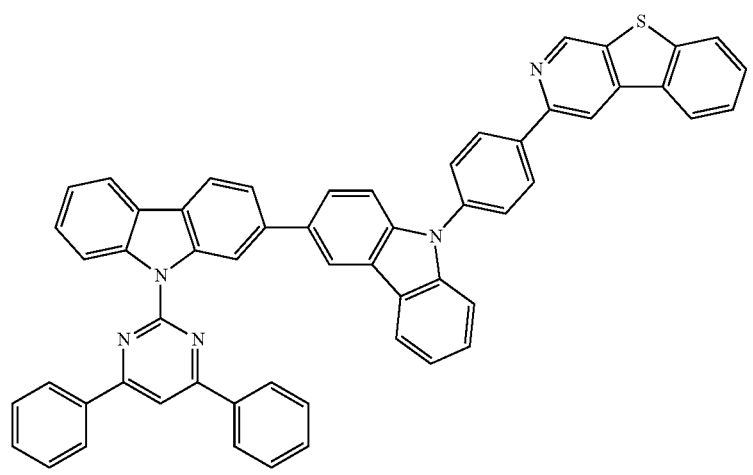
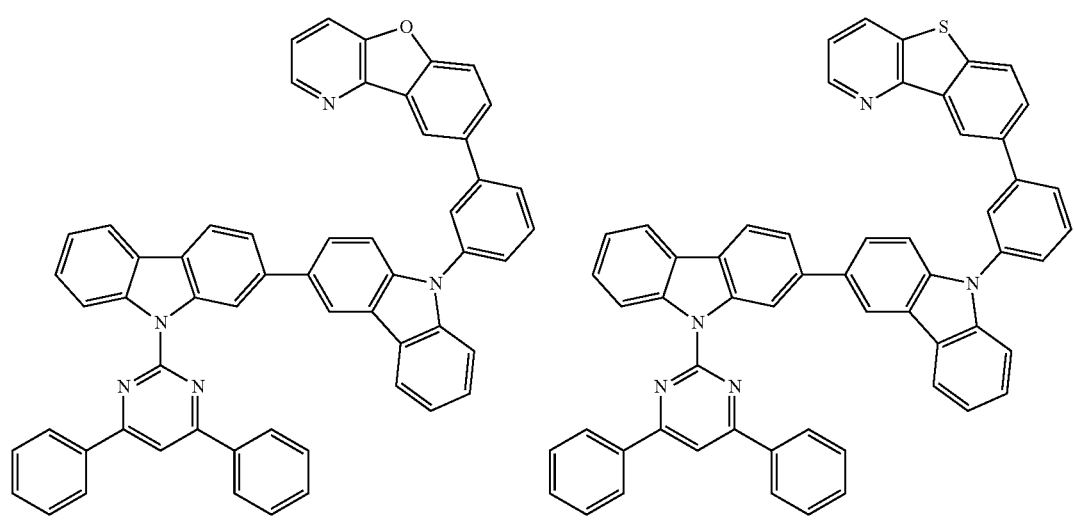

-continued
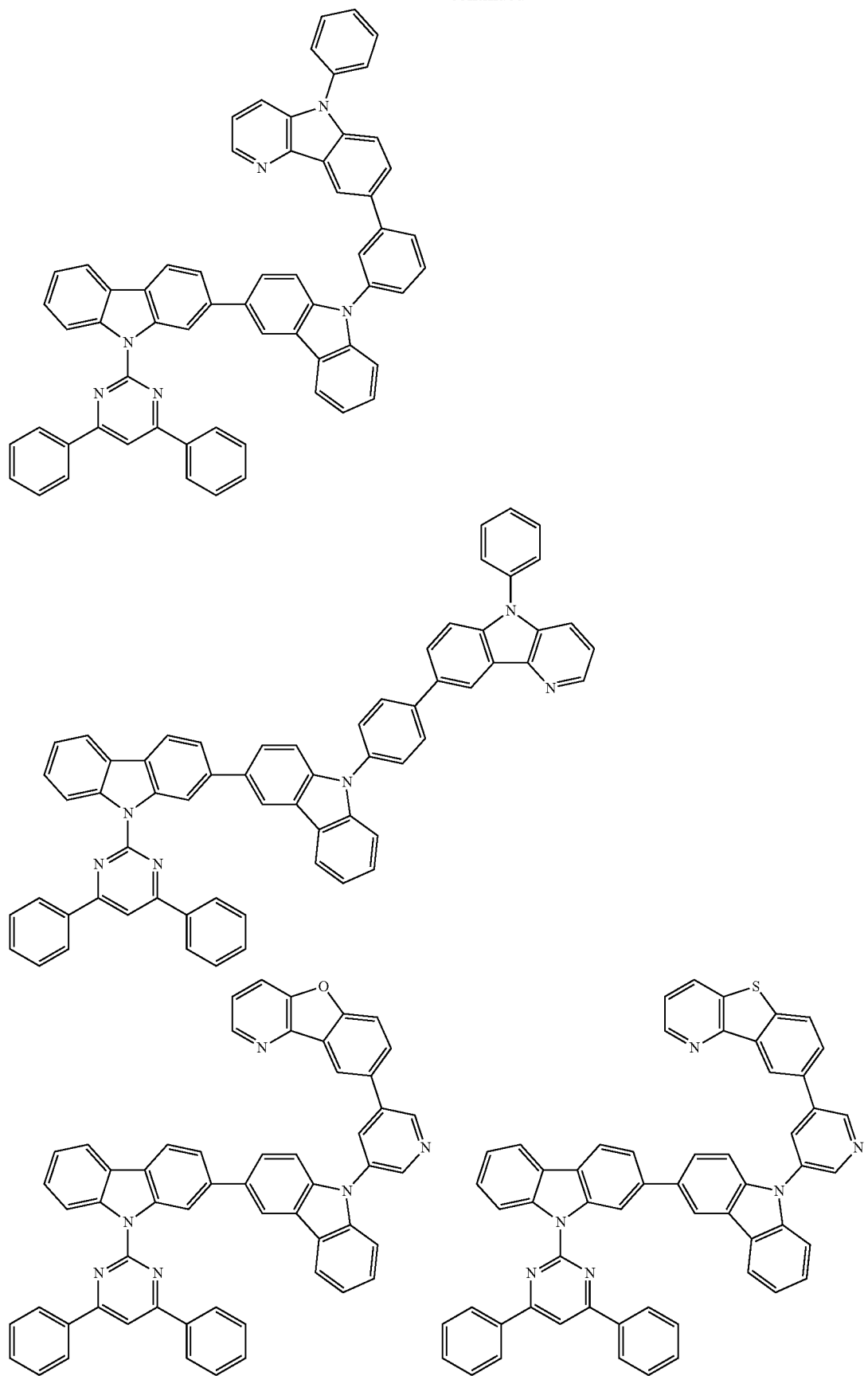

185
186
-continued
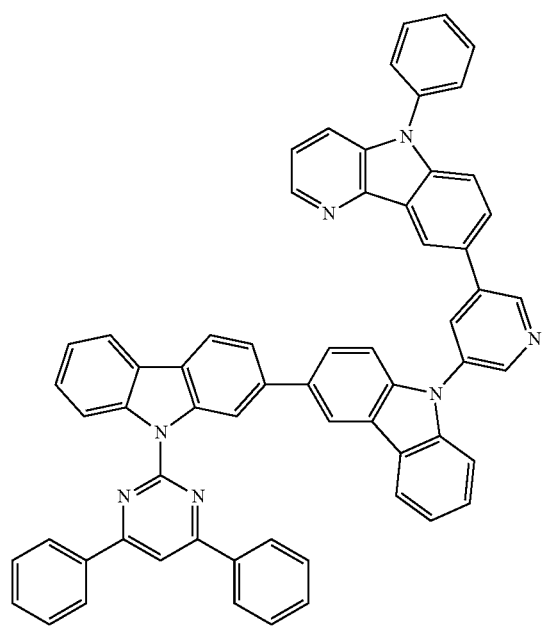
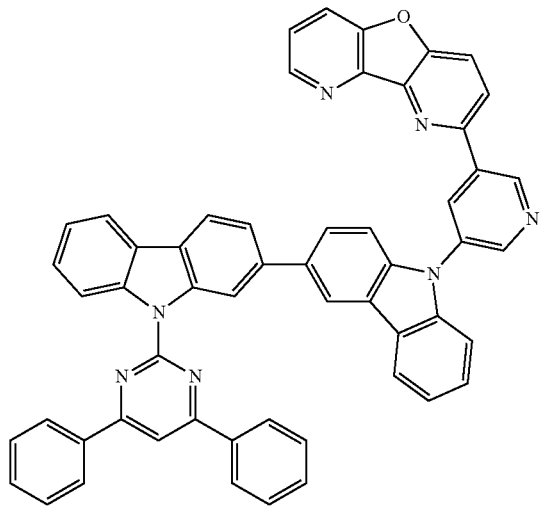
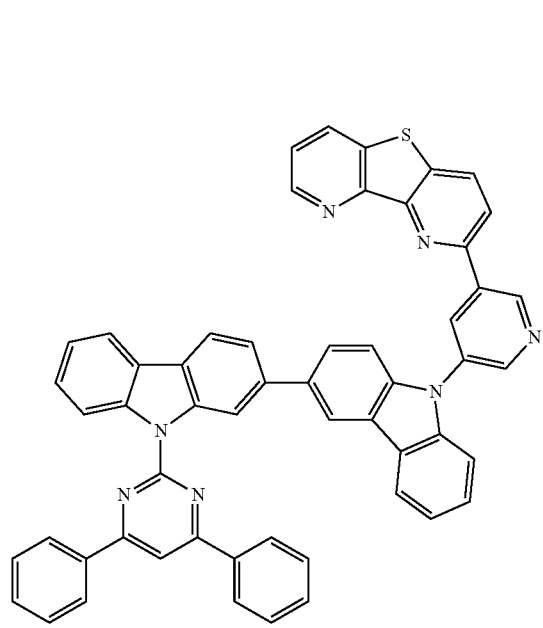
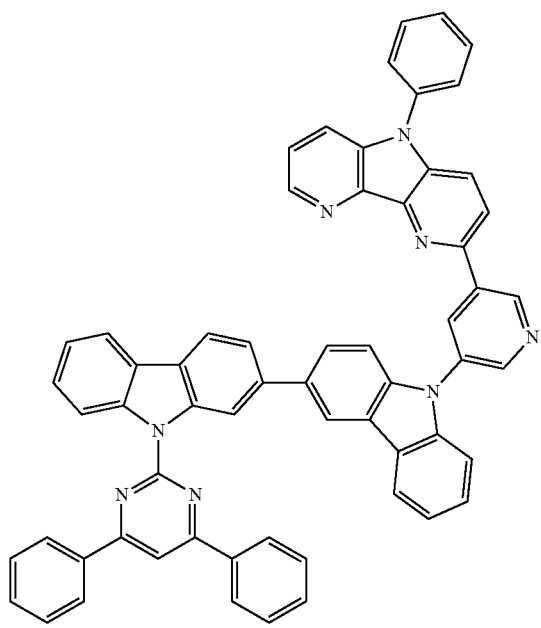

-continued
187
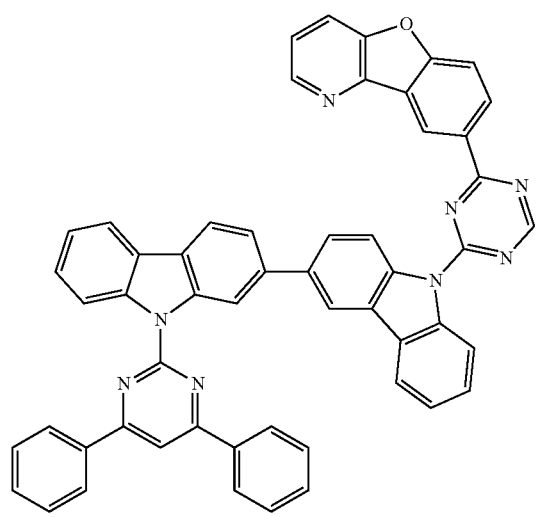
188
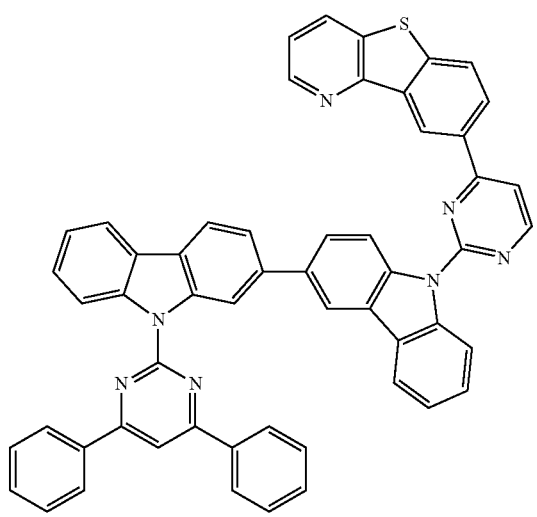
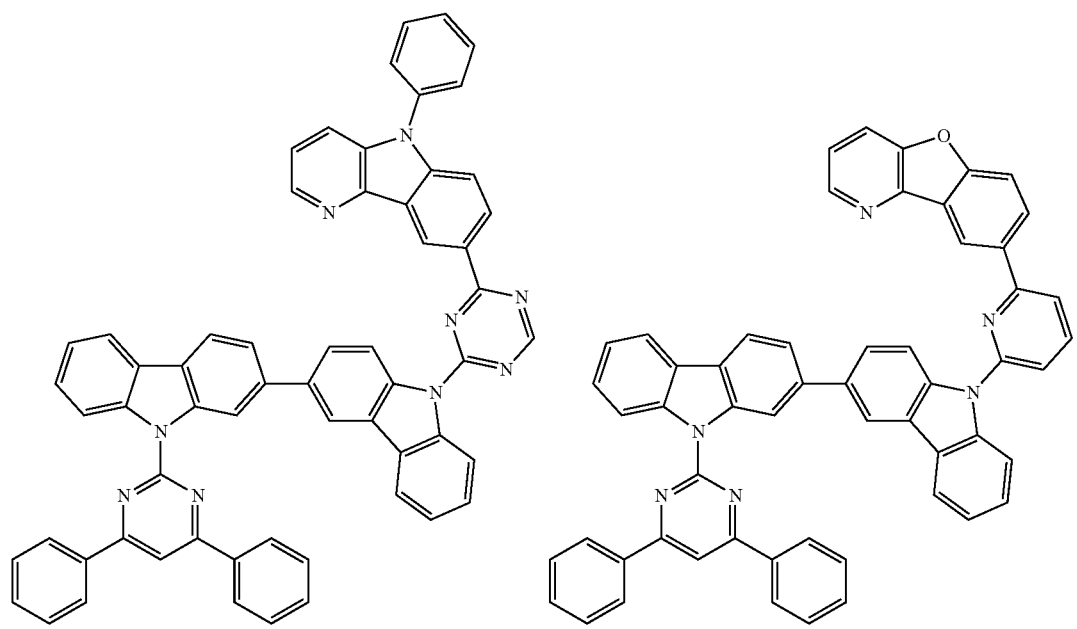

189 190
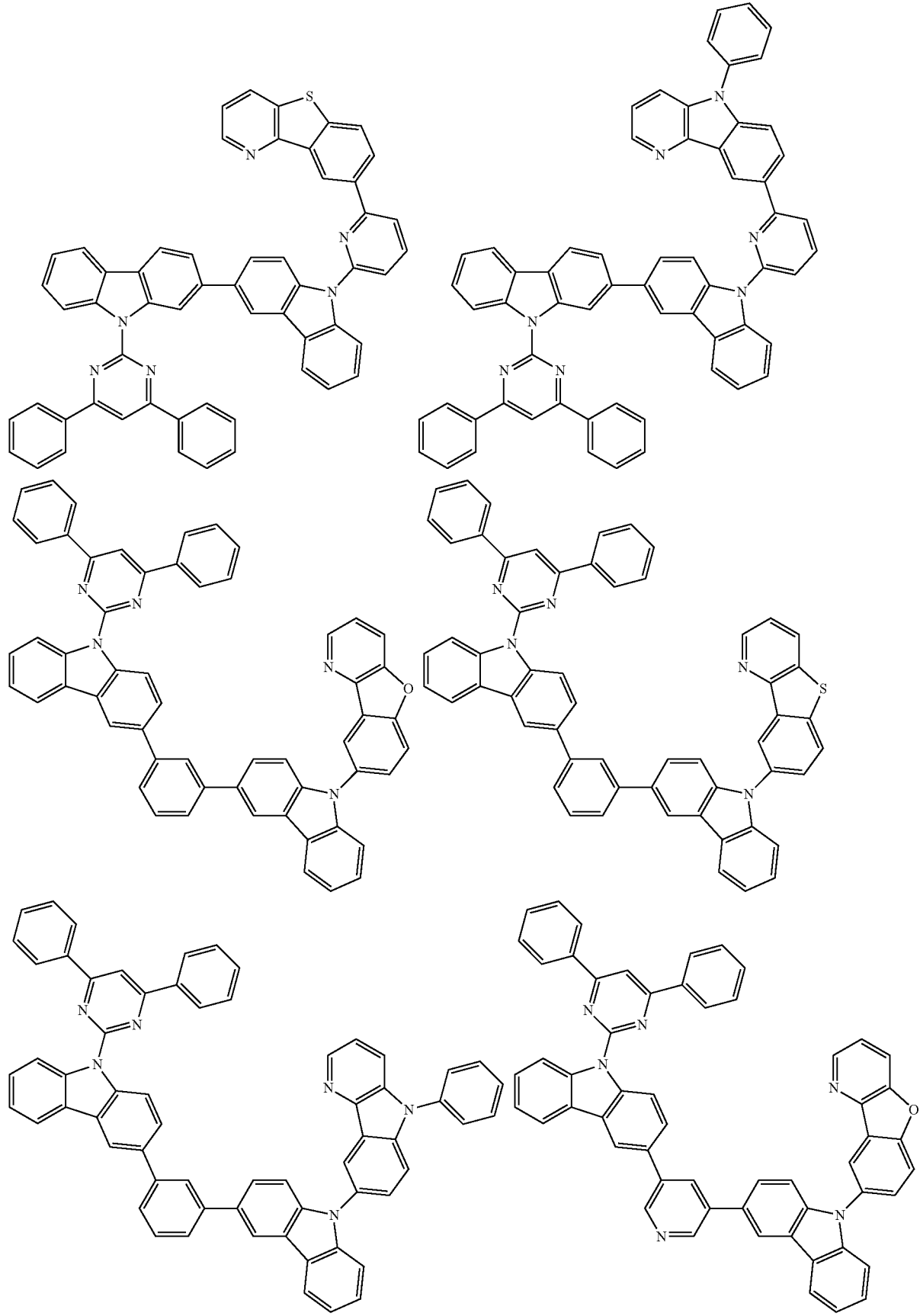
-continued

-continued
191
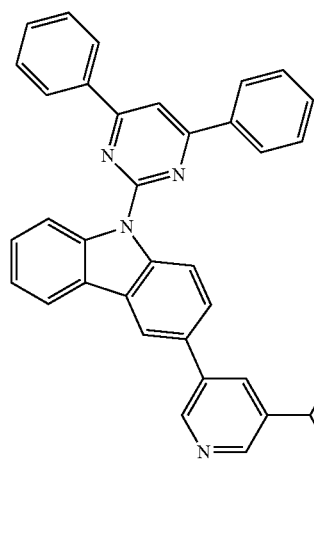
192
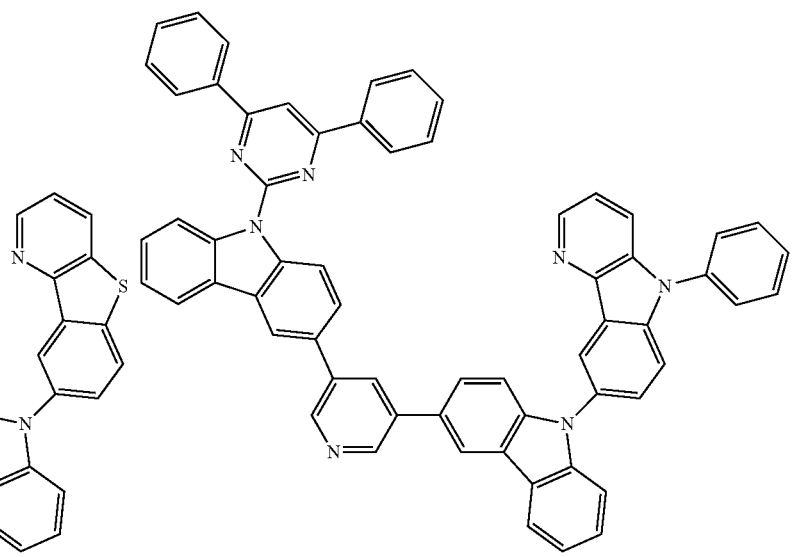
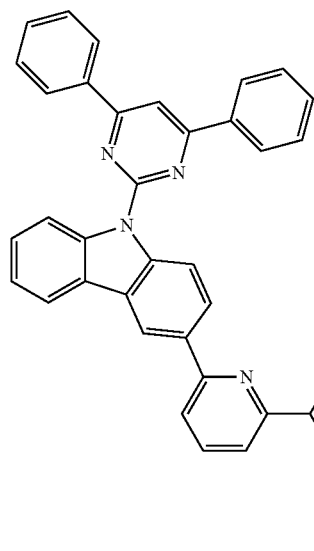
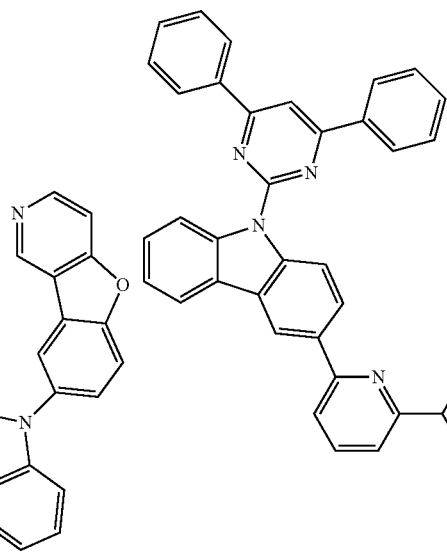
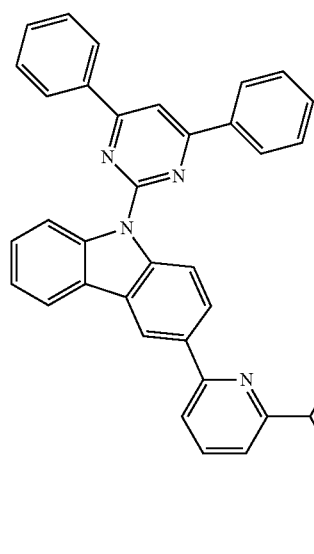

-continued
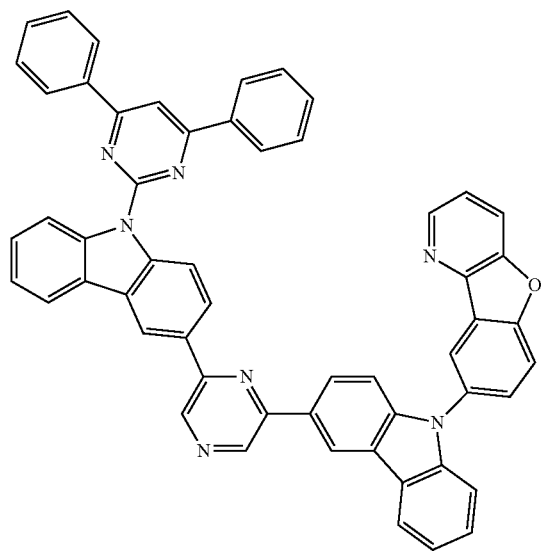
193
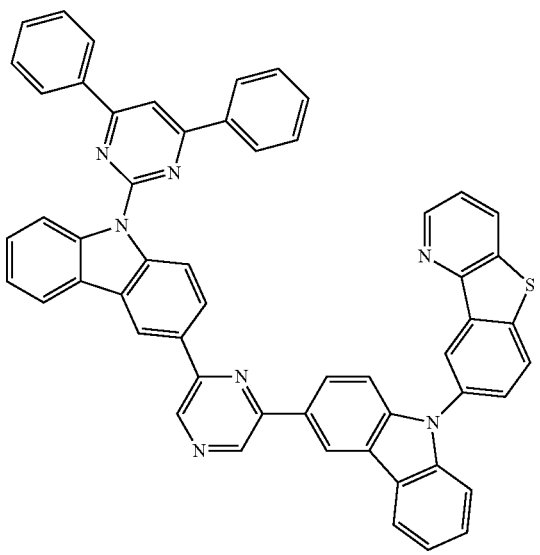
194
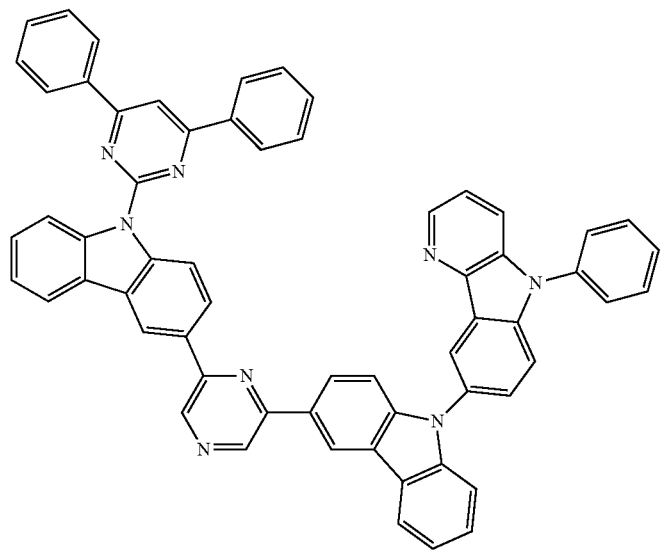
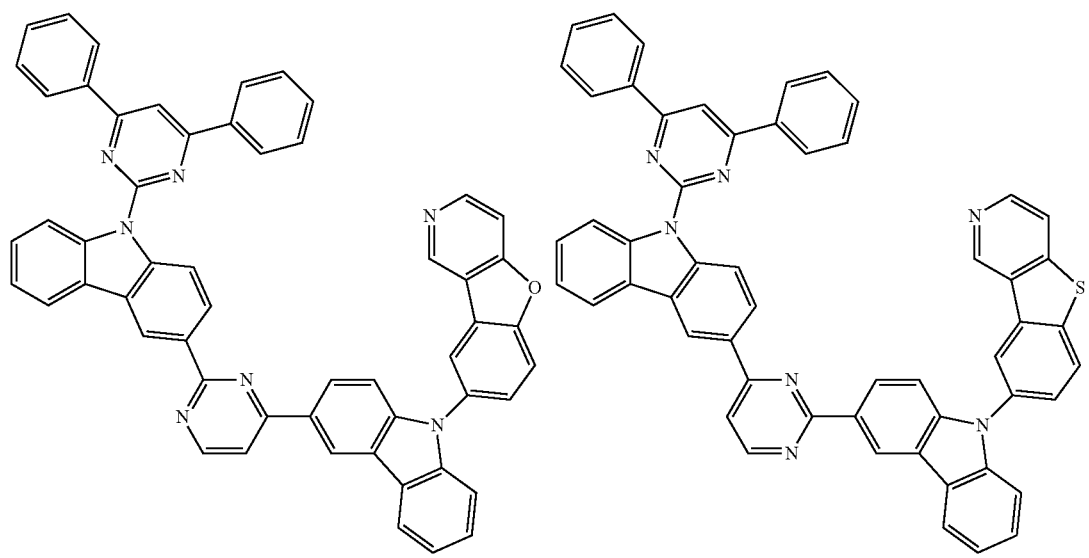

-continued
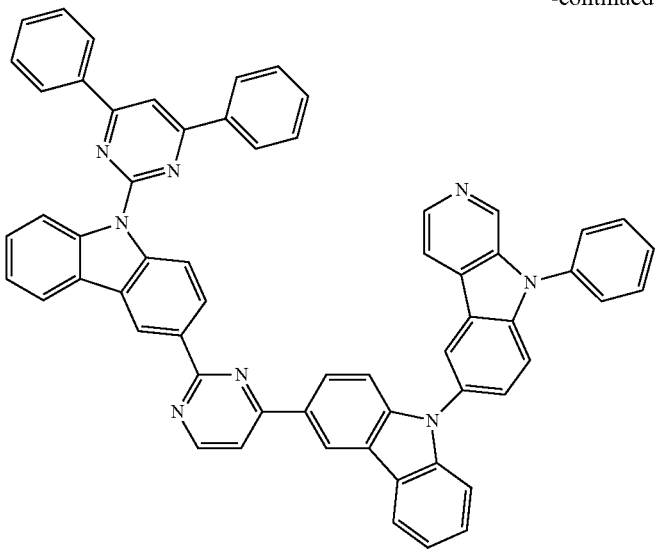
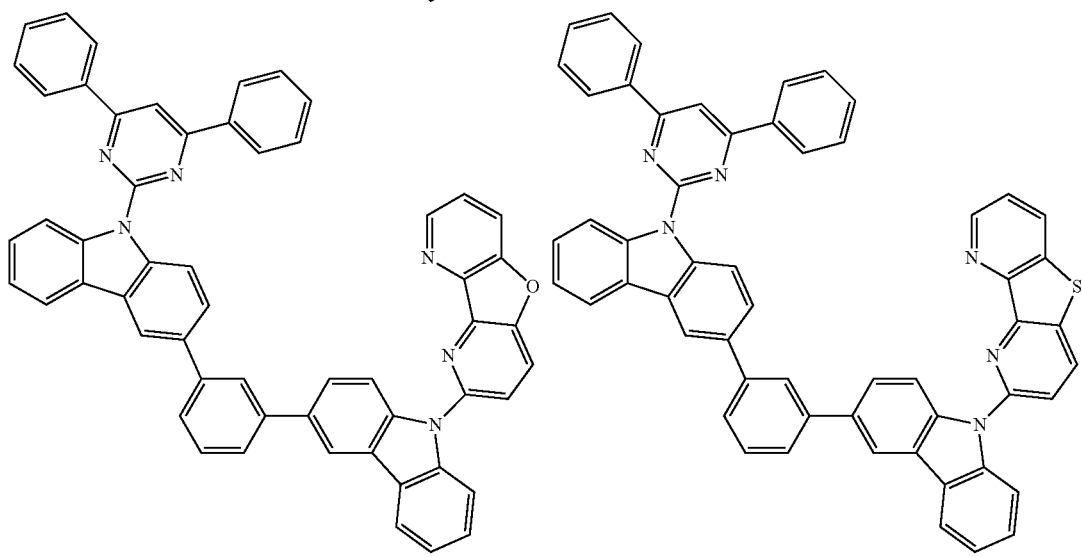
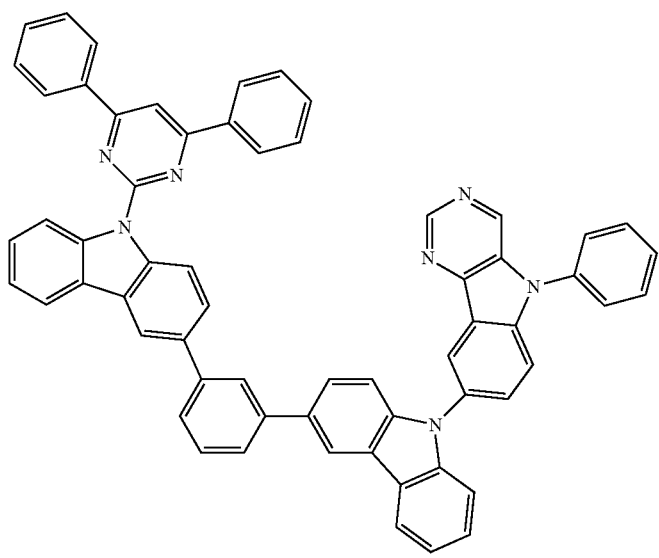

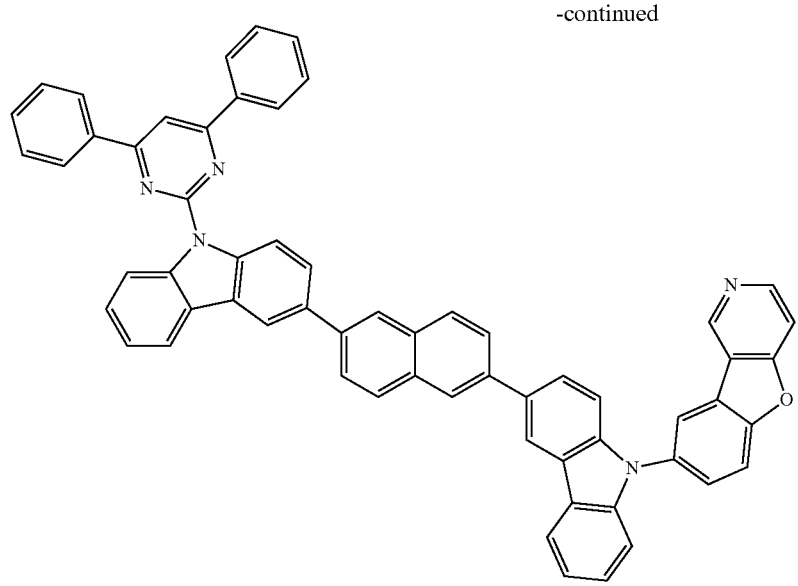
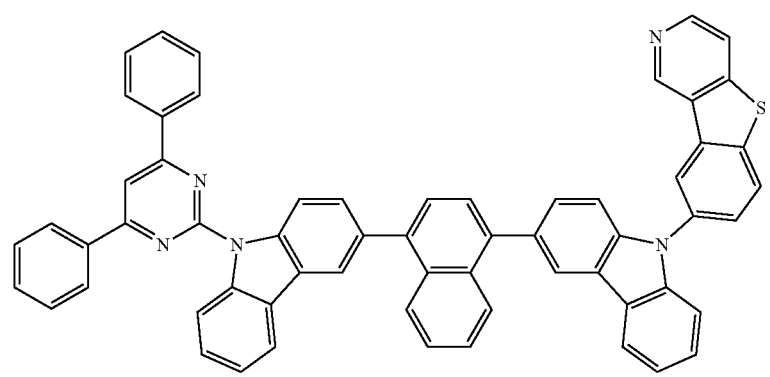
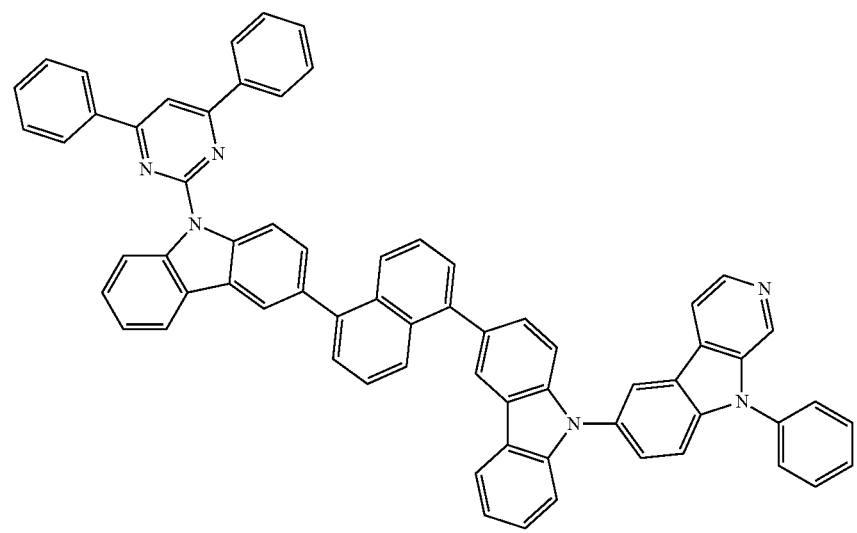

199
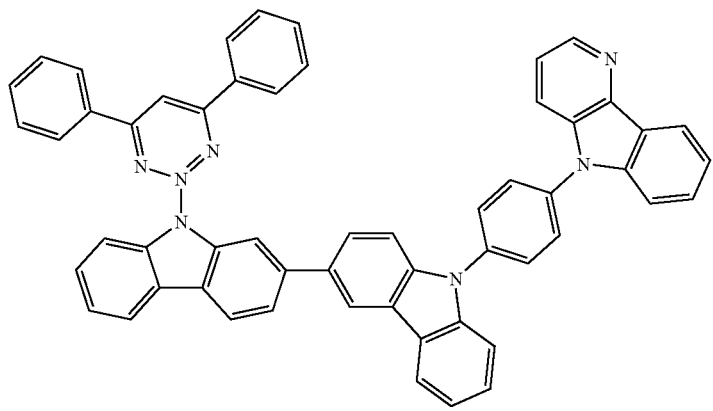
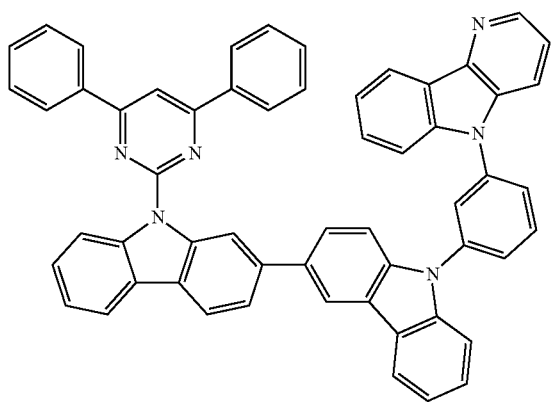
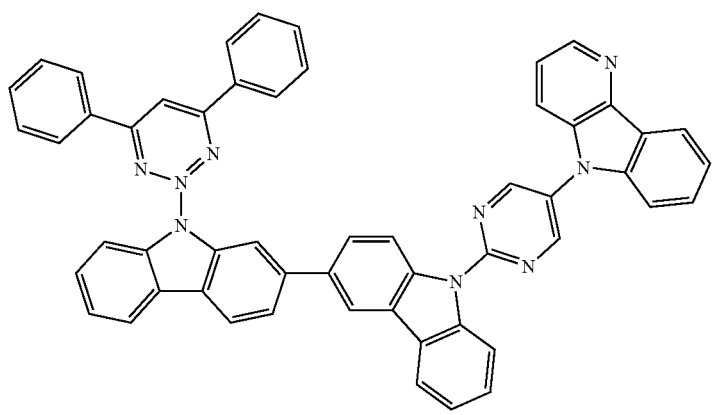
200
-continued
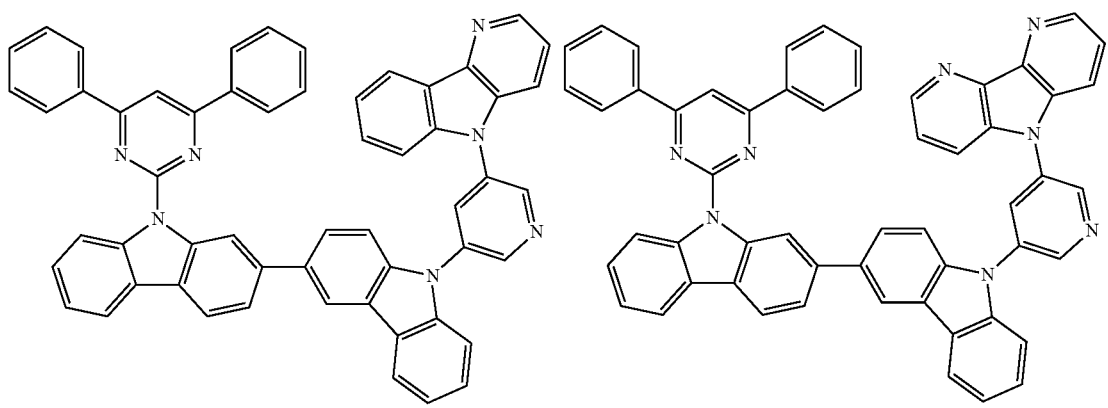

-continued
201
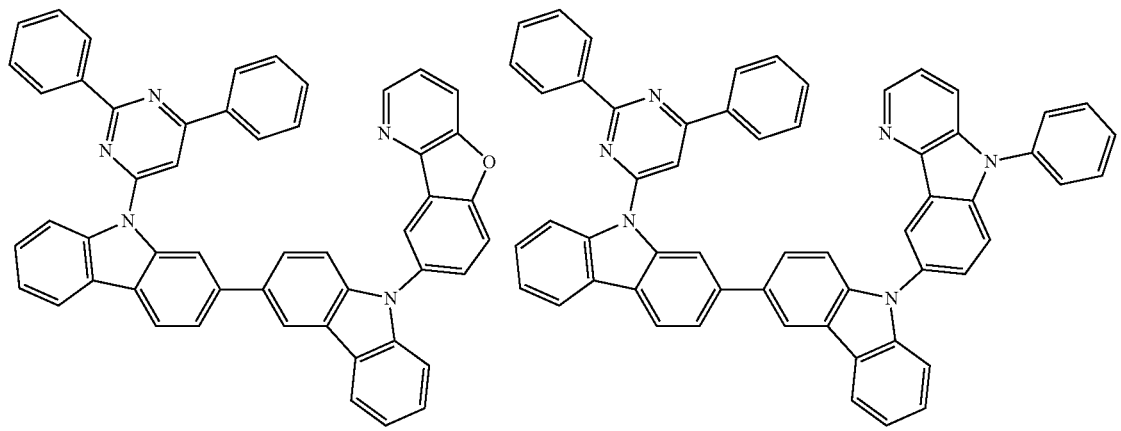
202
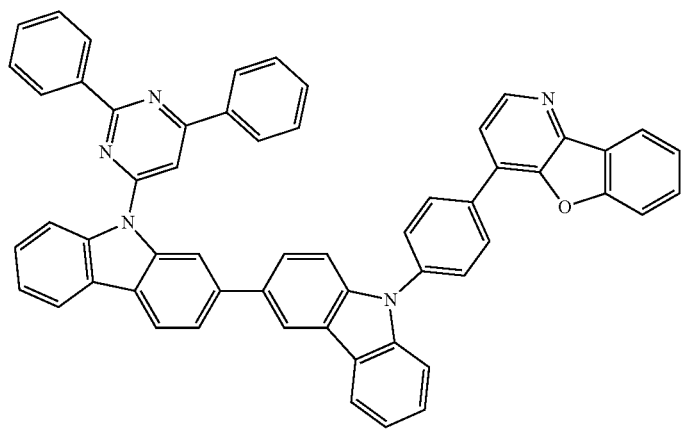
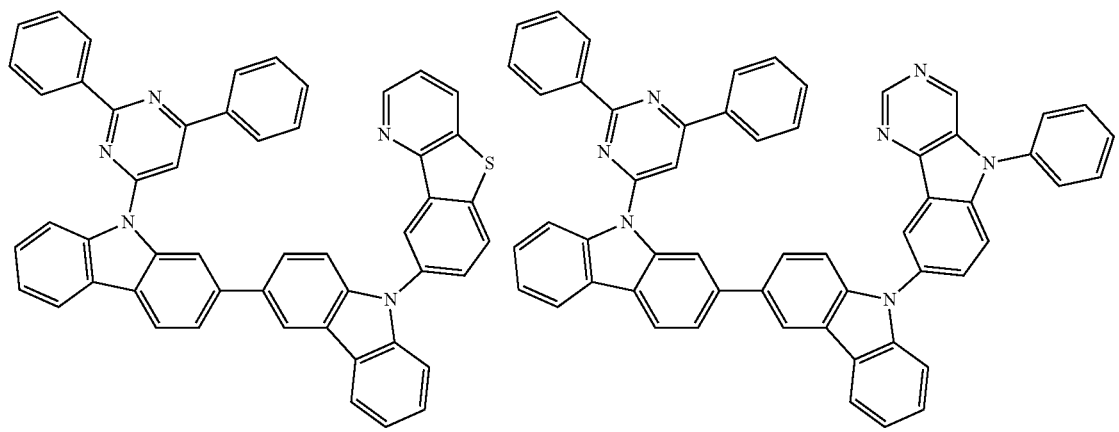
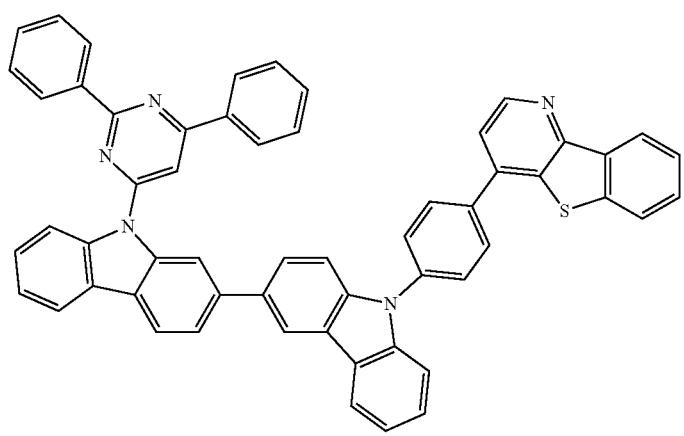

-continued
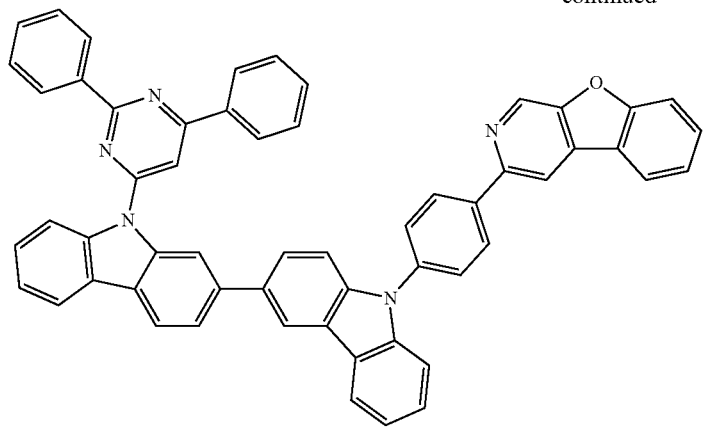
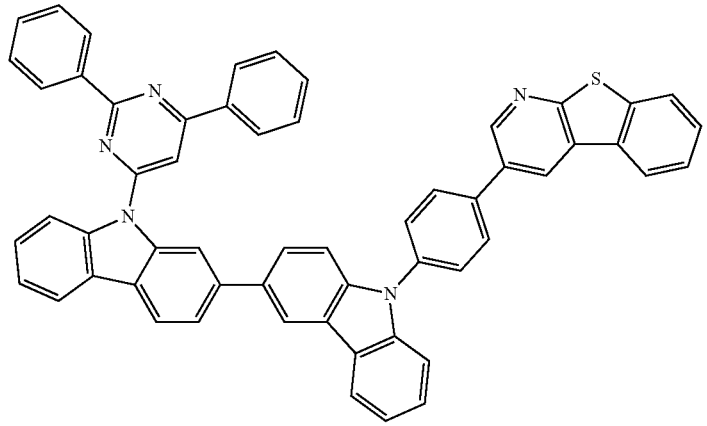

205 206
-continued
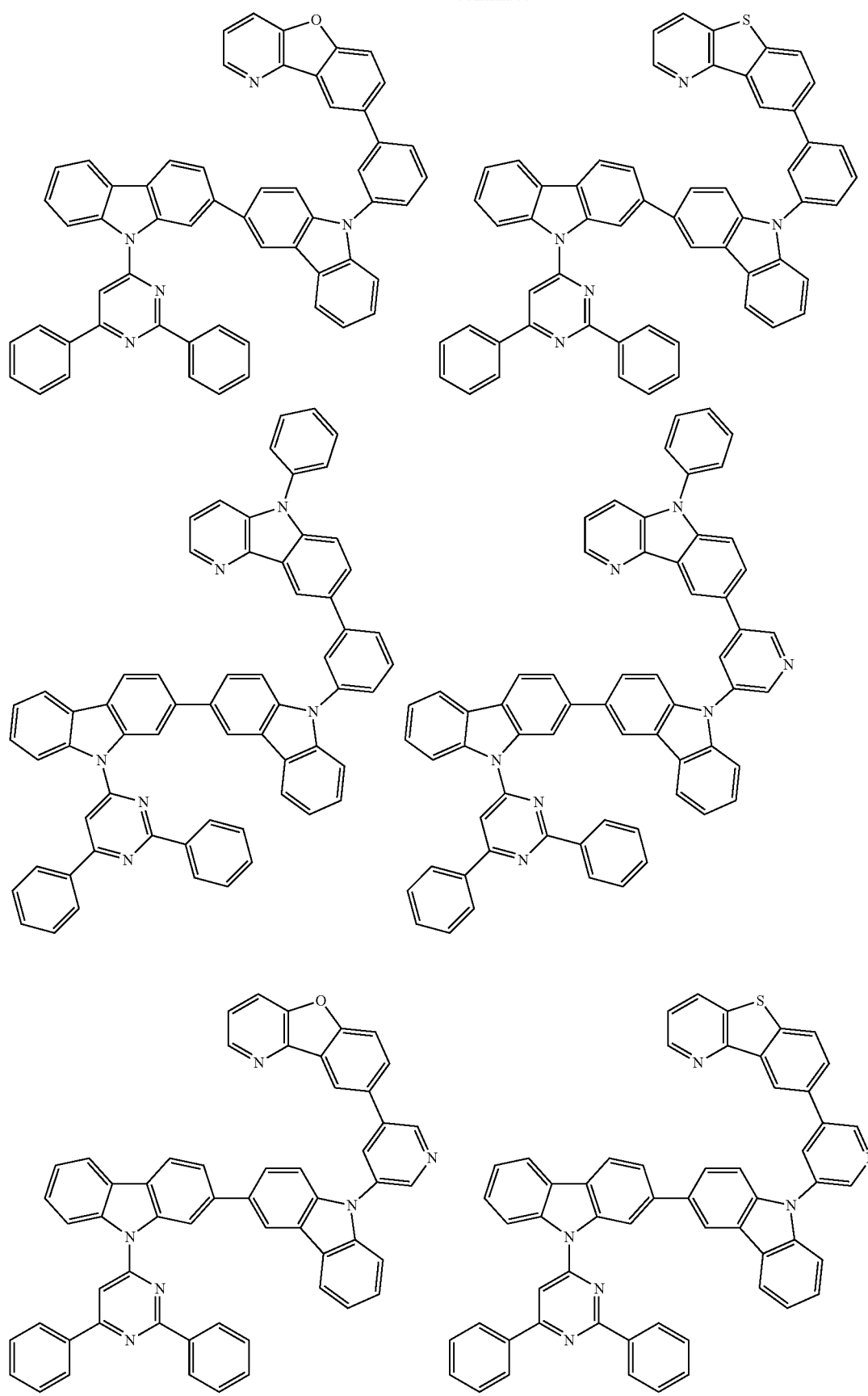

207 208
-continued
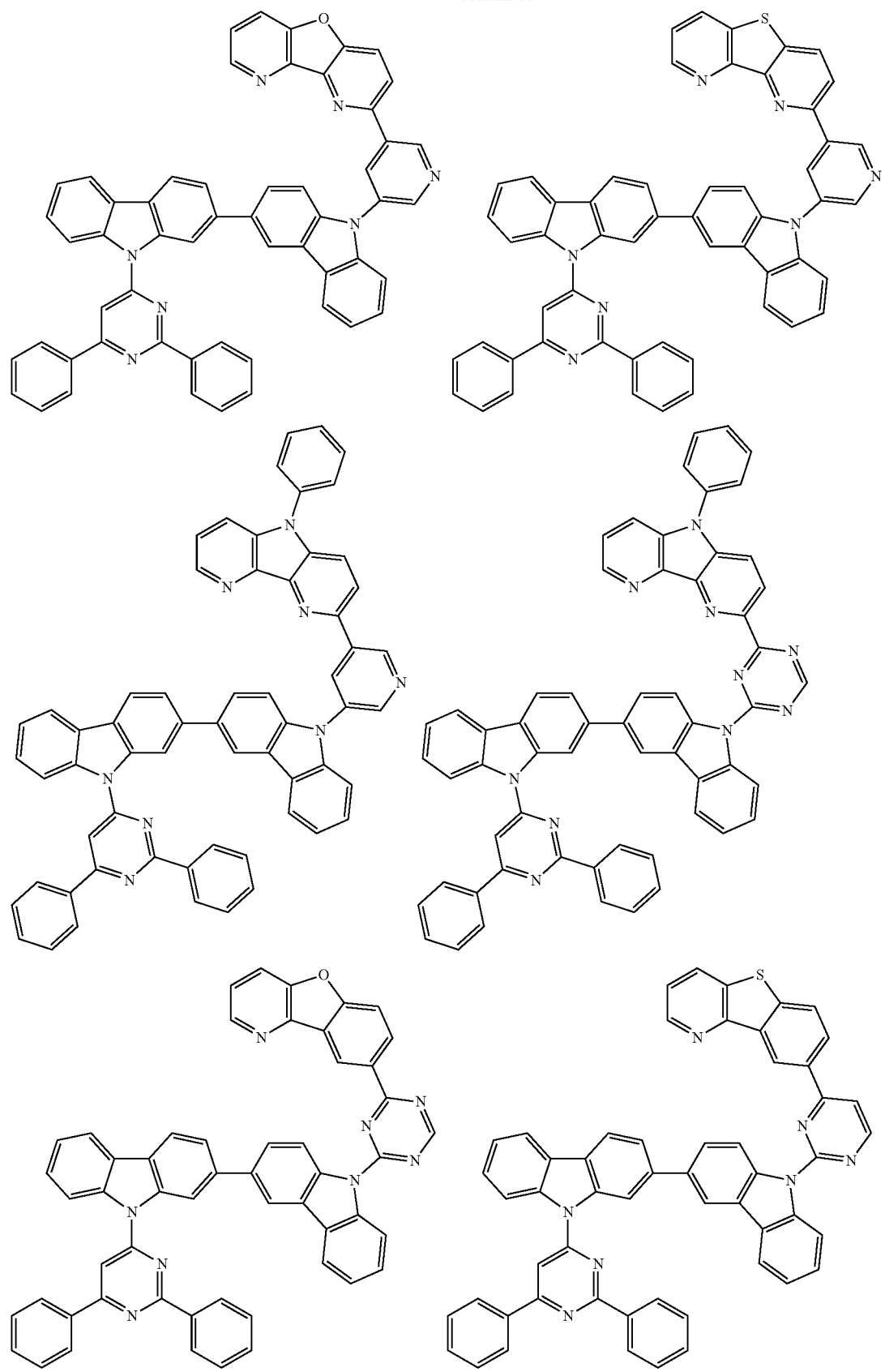

209
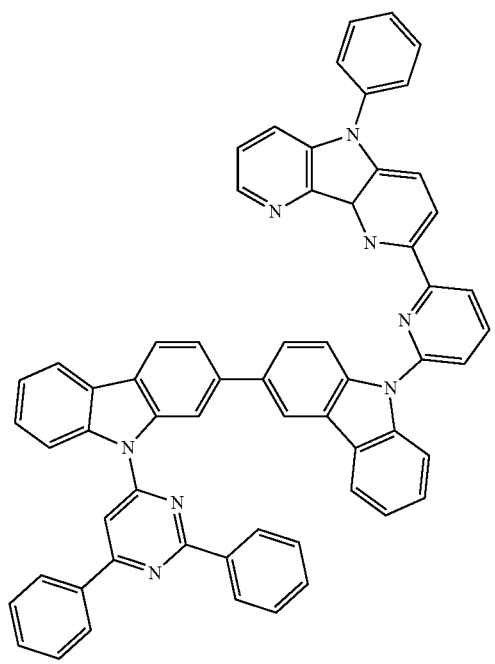
-continued
210
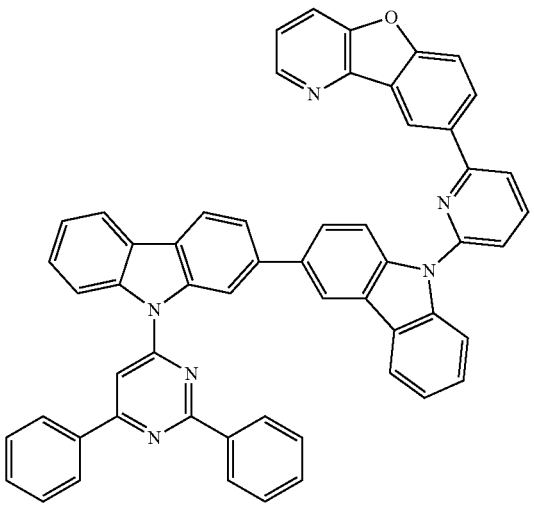
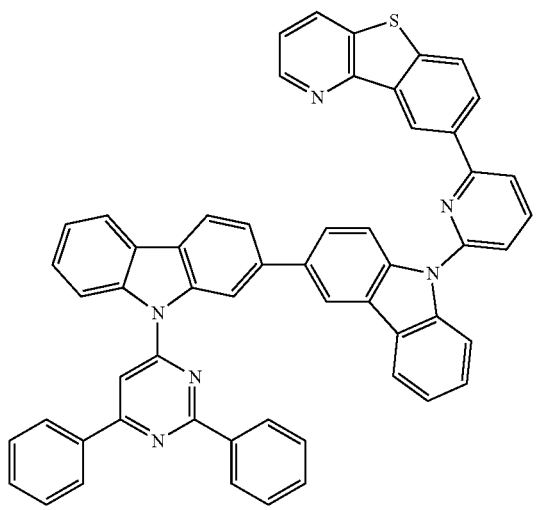

211 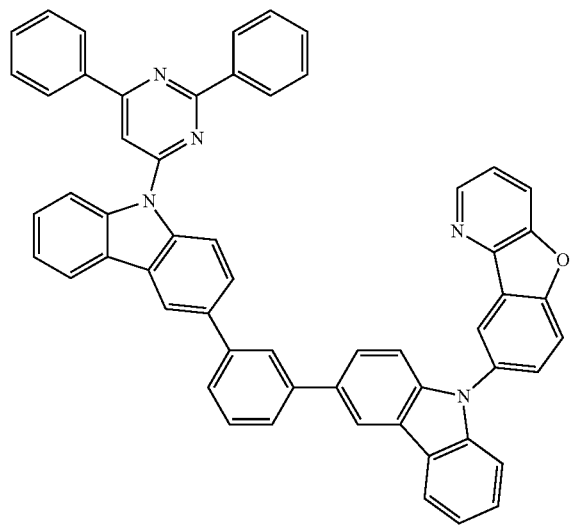 212 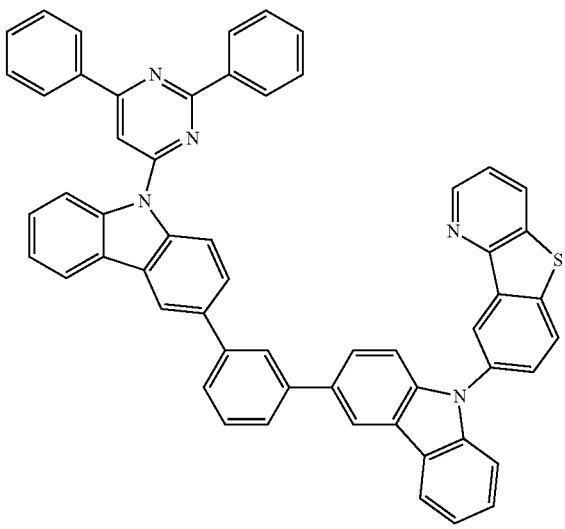
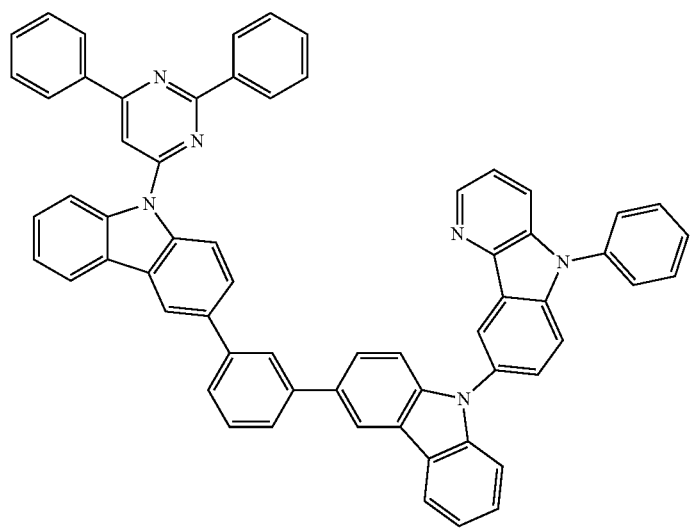
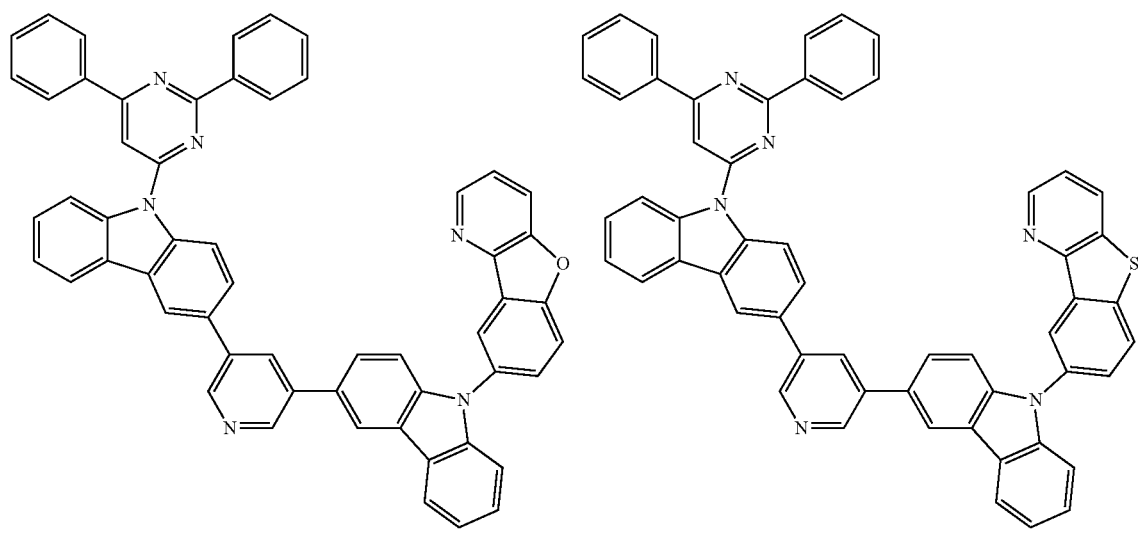

213
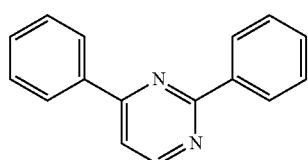
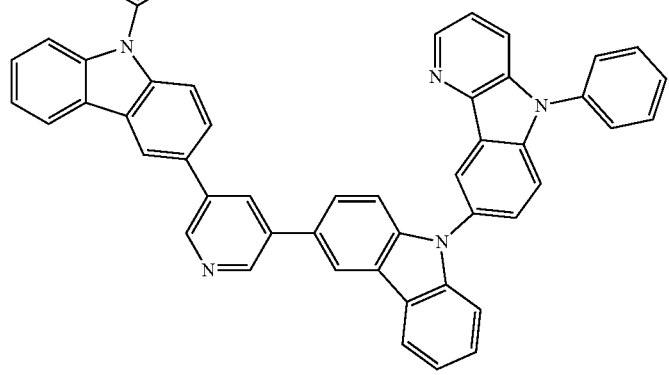
-continued
214
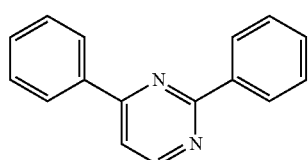
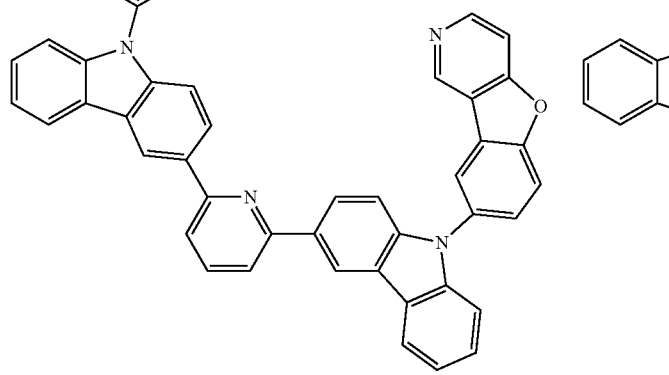
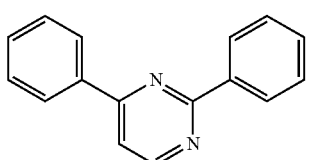
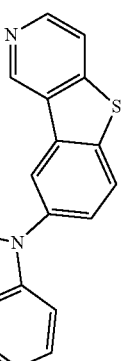
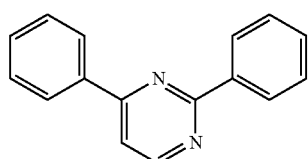
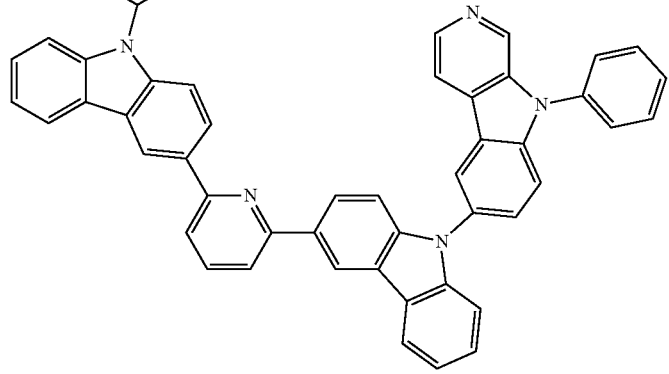

215
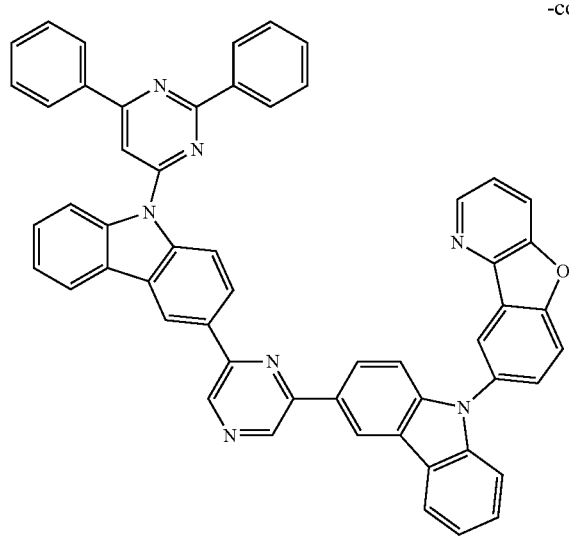
216
-continued
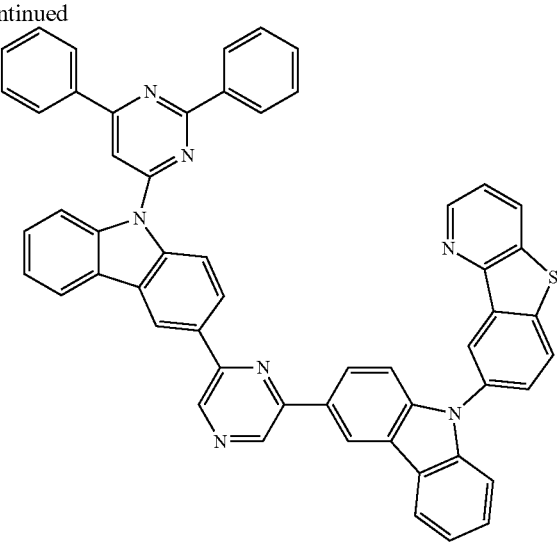
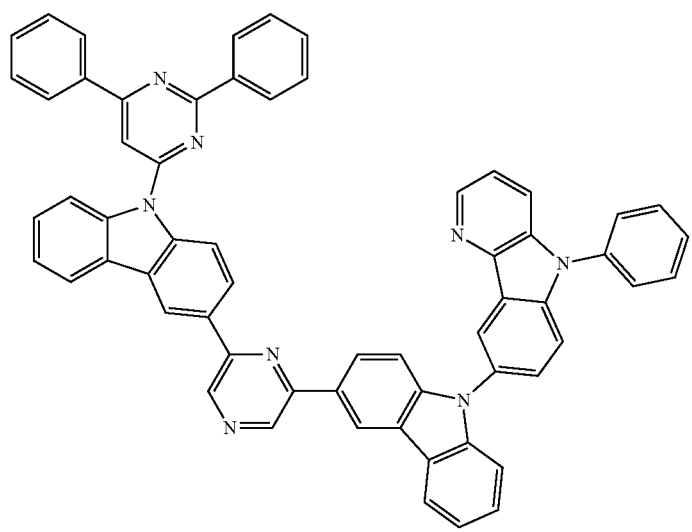
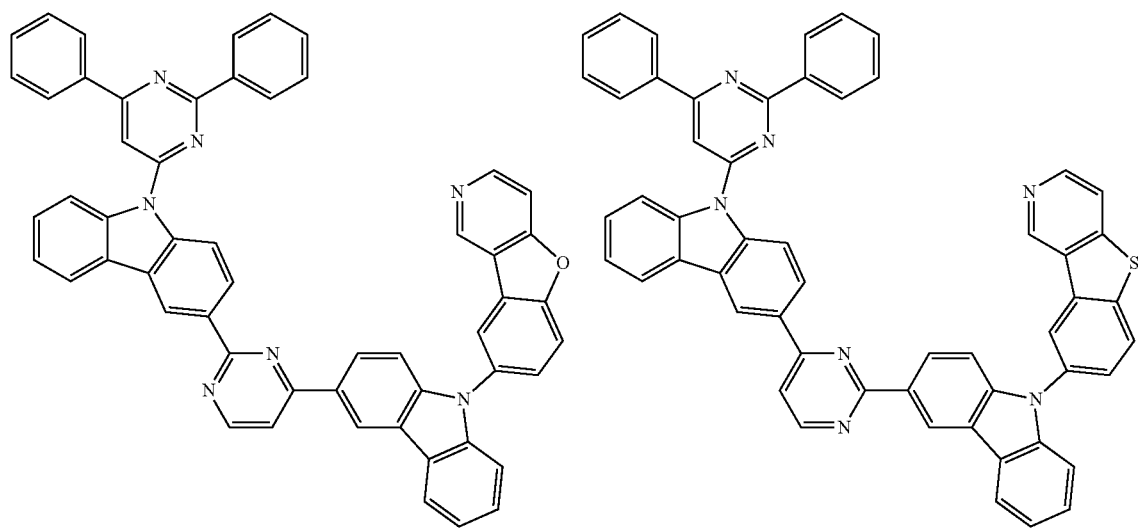

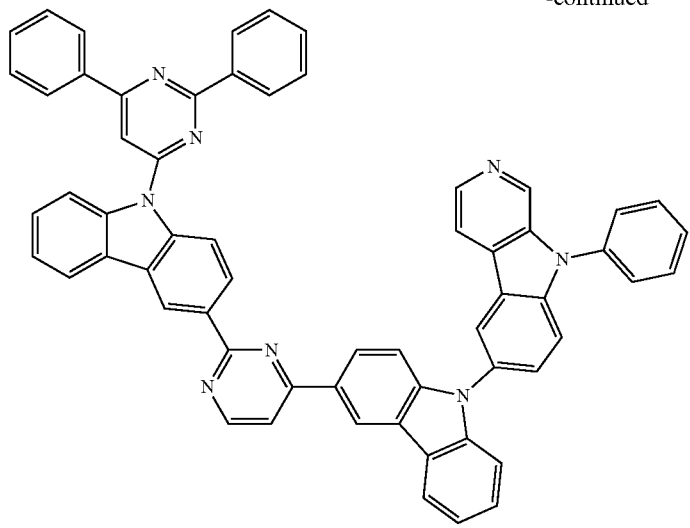
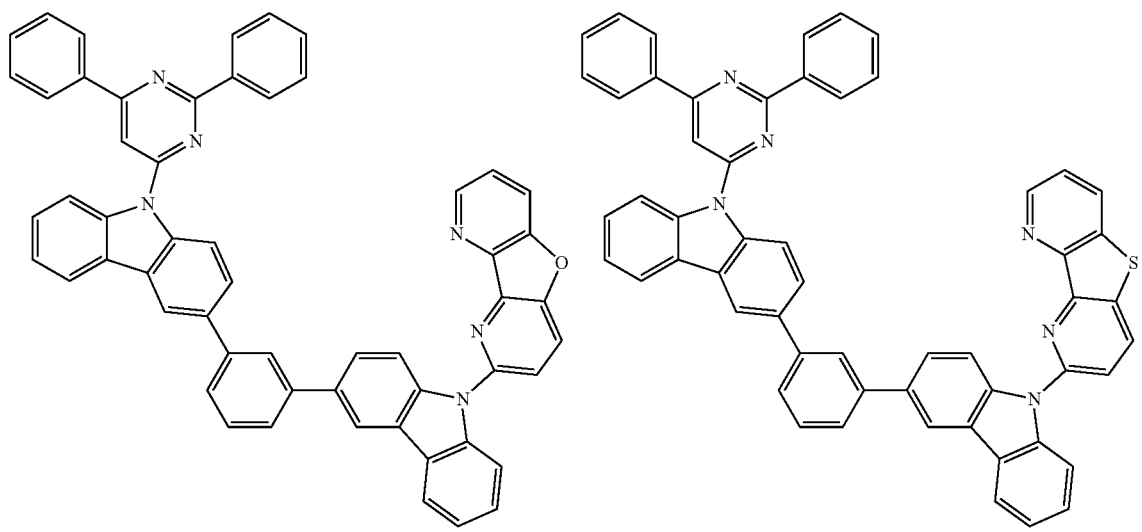
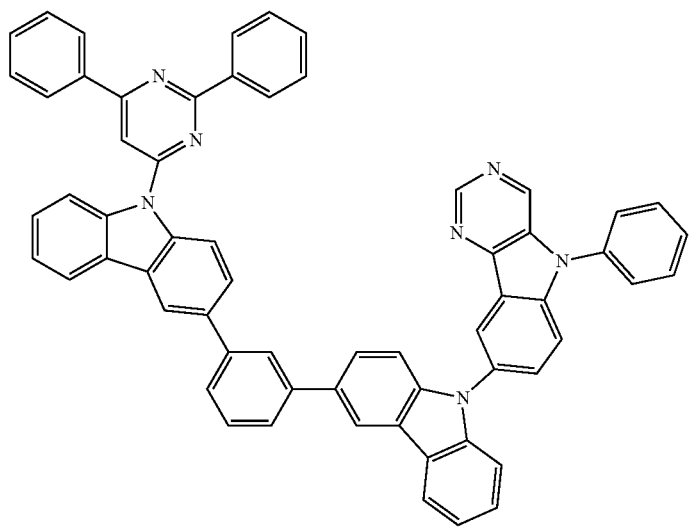

-continued
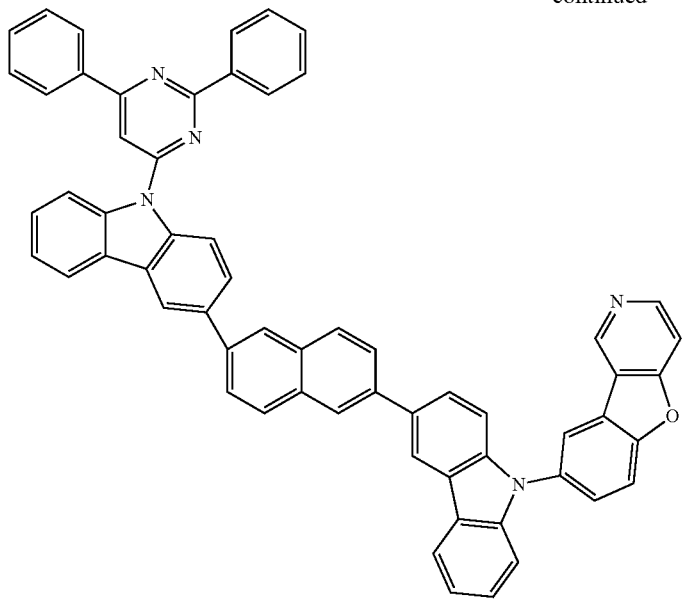
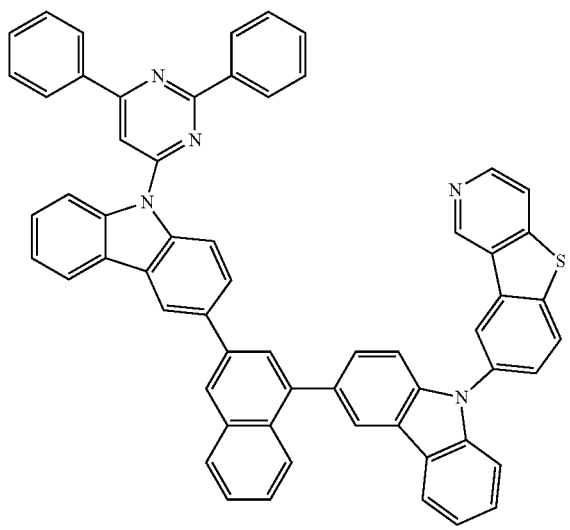
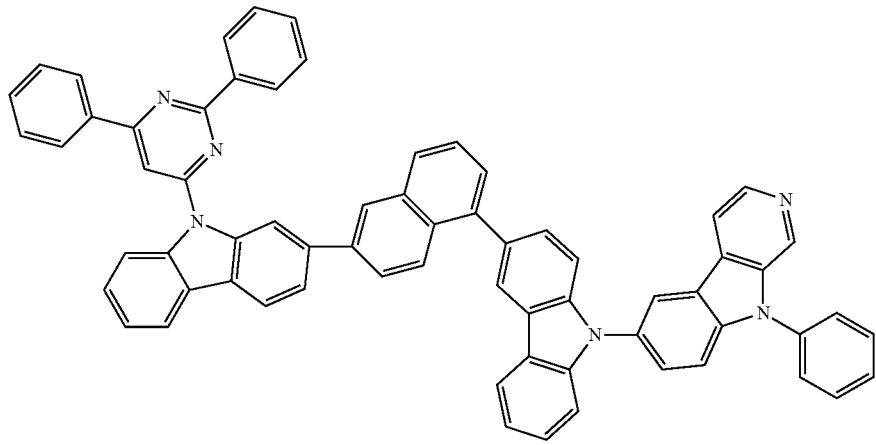

221
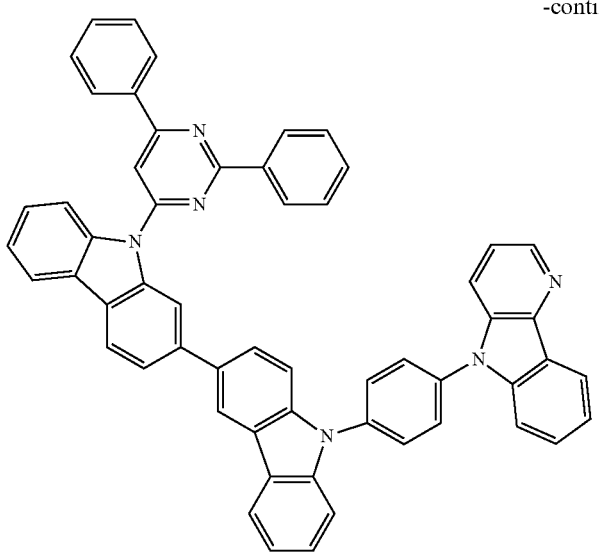
222
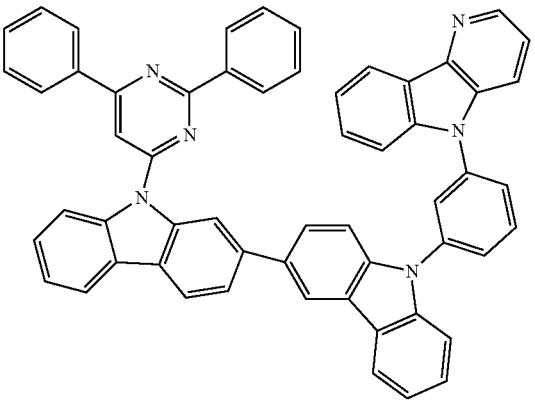
-continued
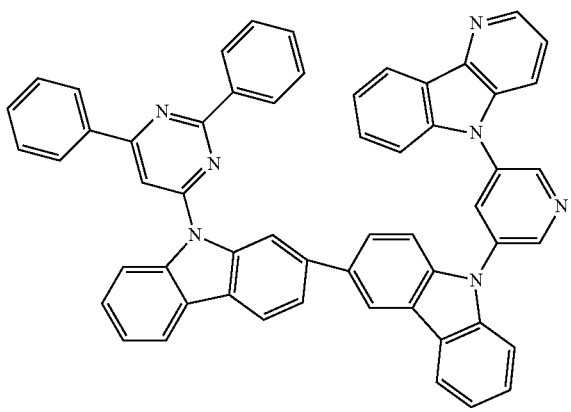
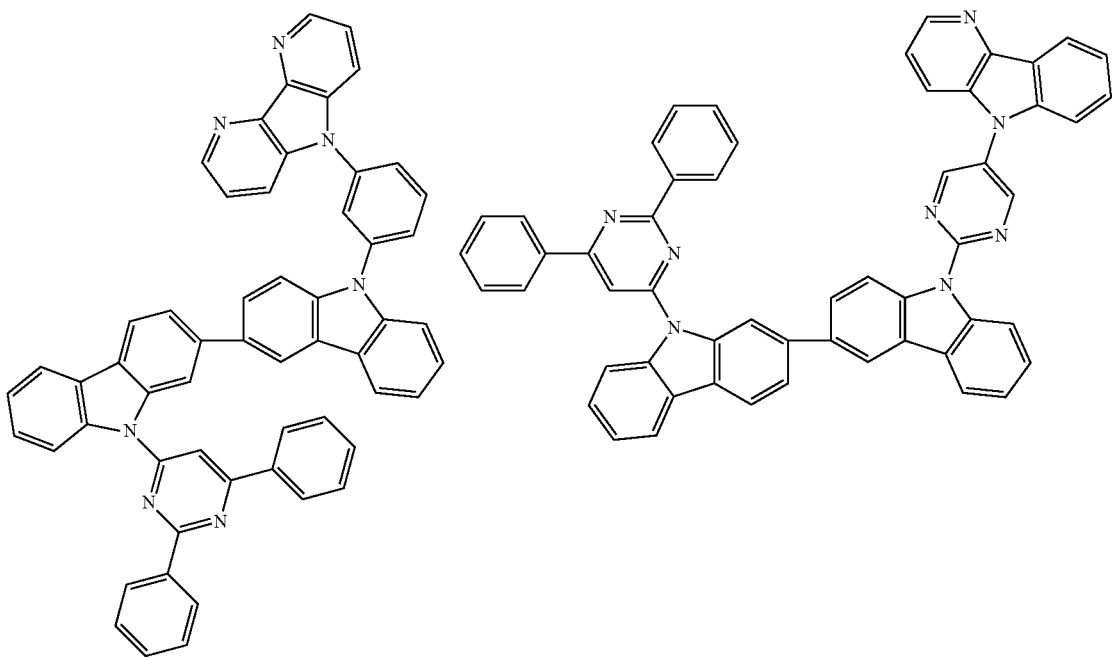

223 224
-continued
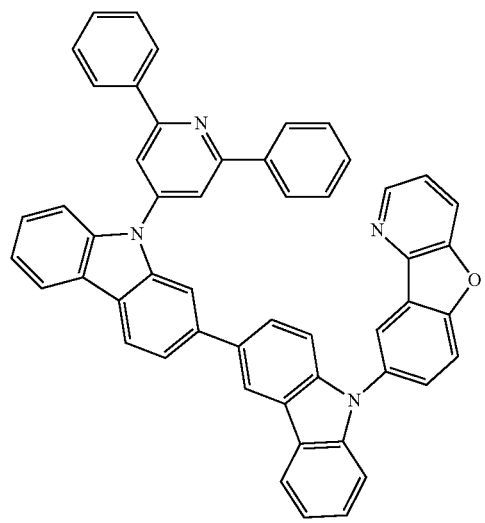
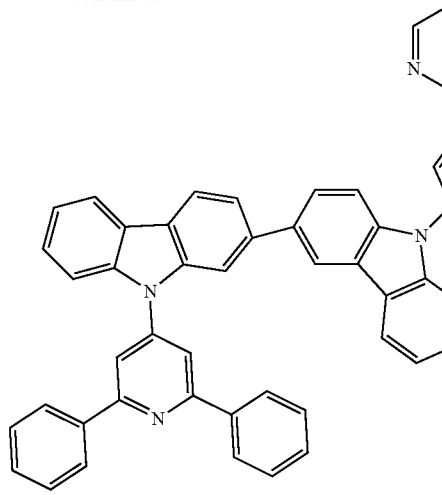
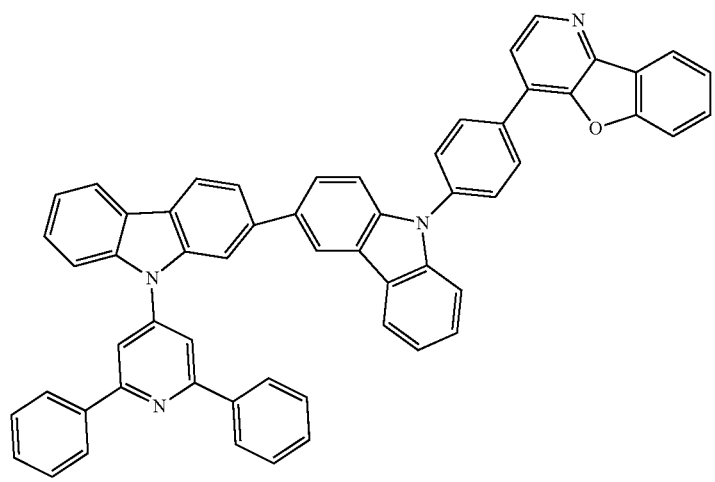
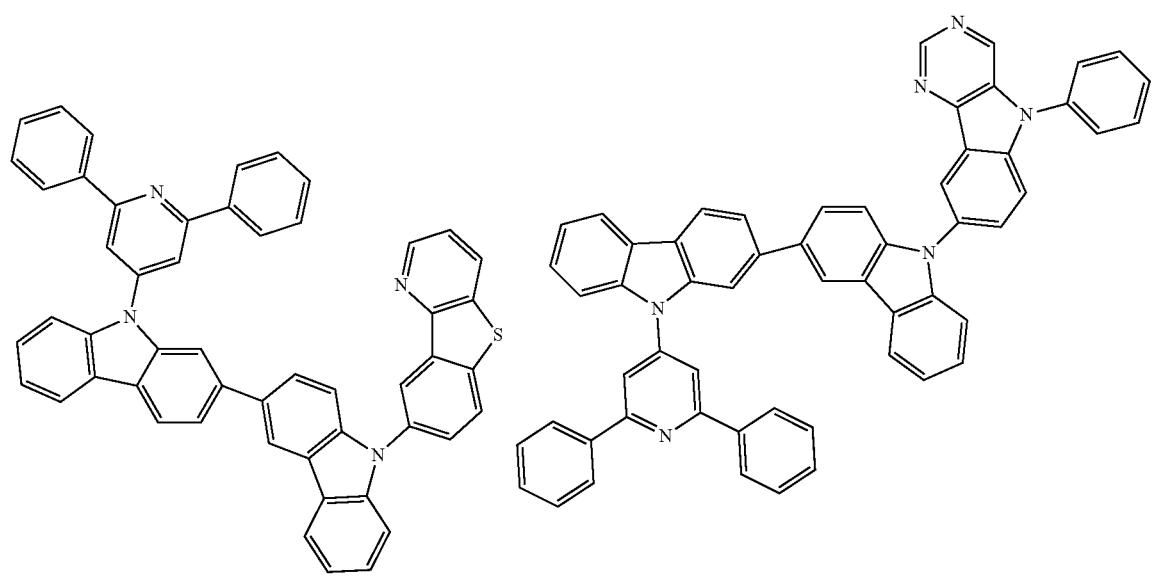

-continued
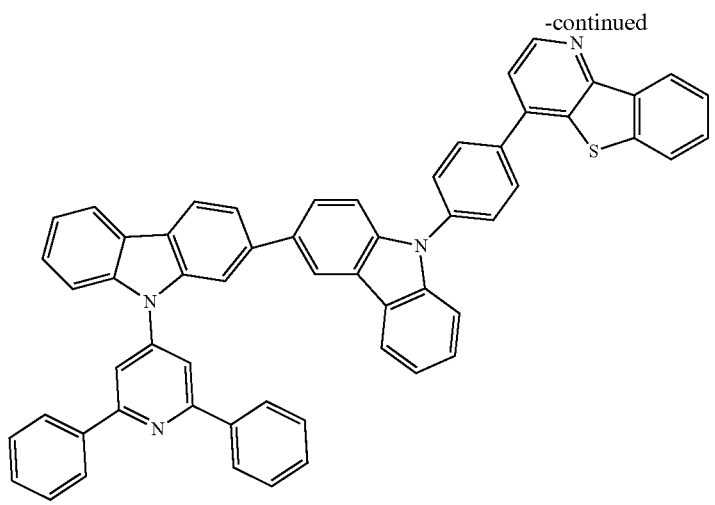
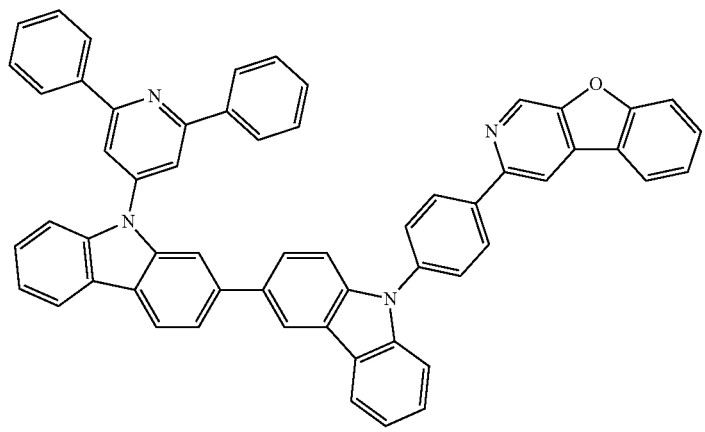
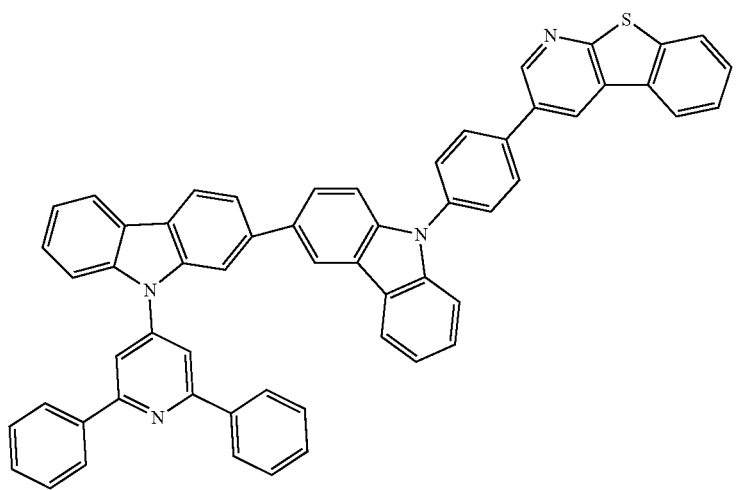

-continued
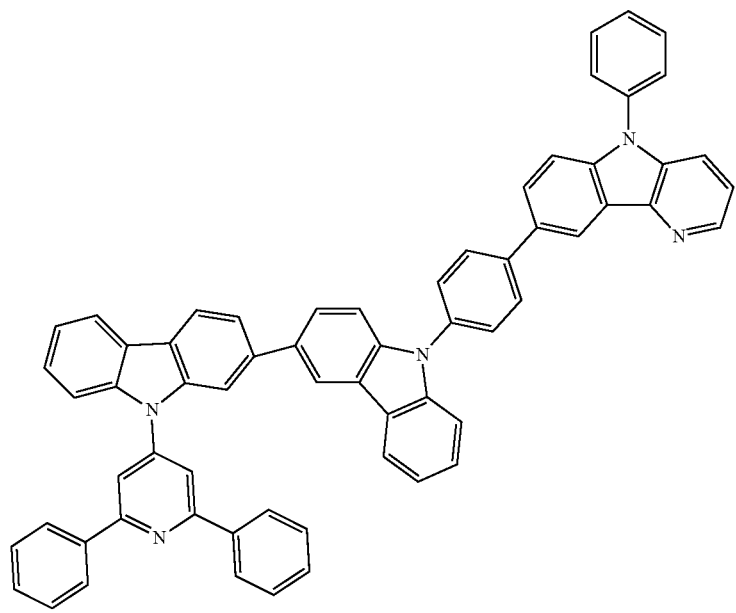
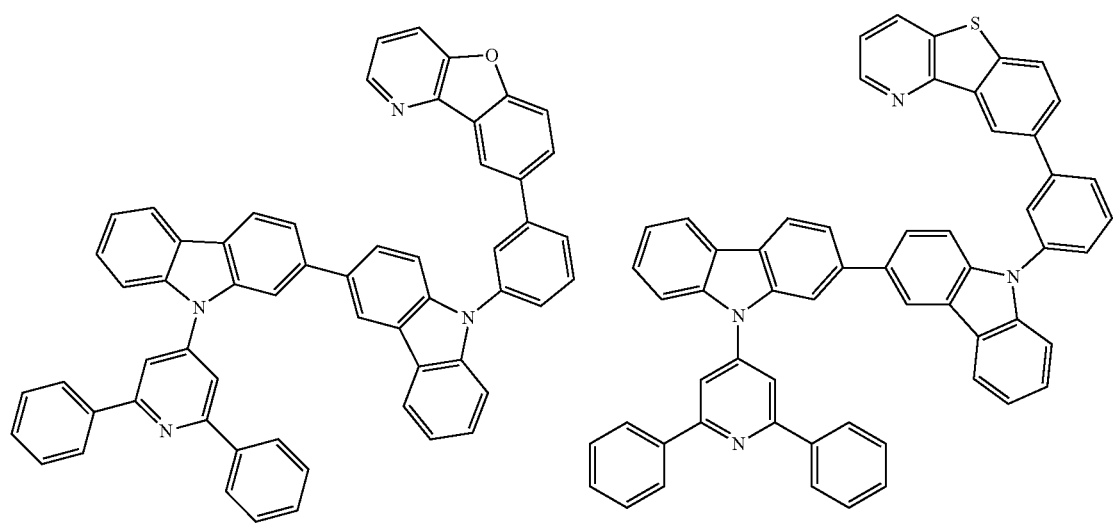

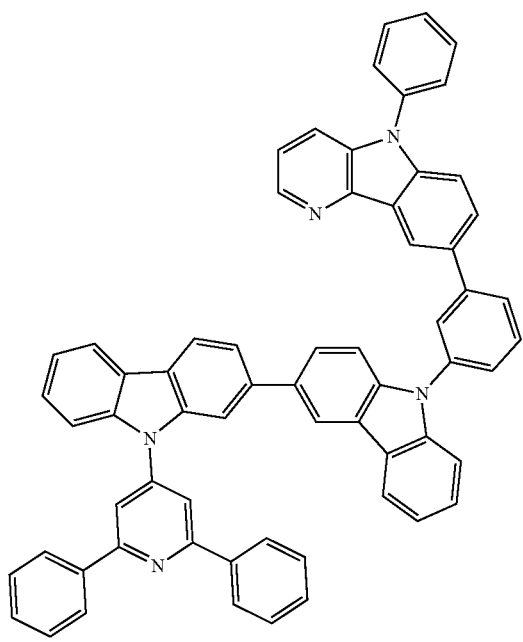
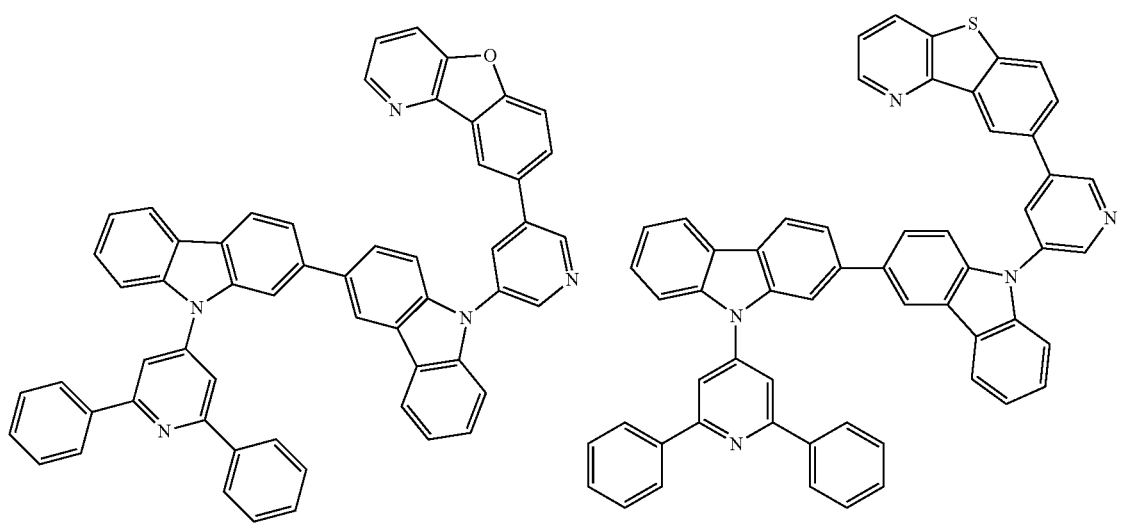

231 232
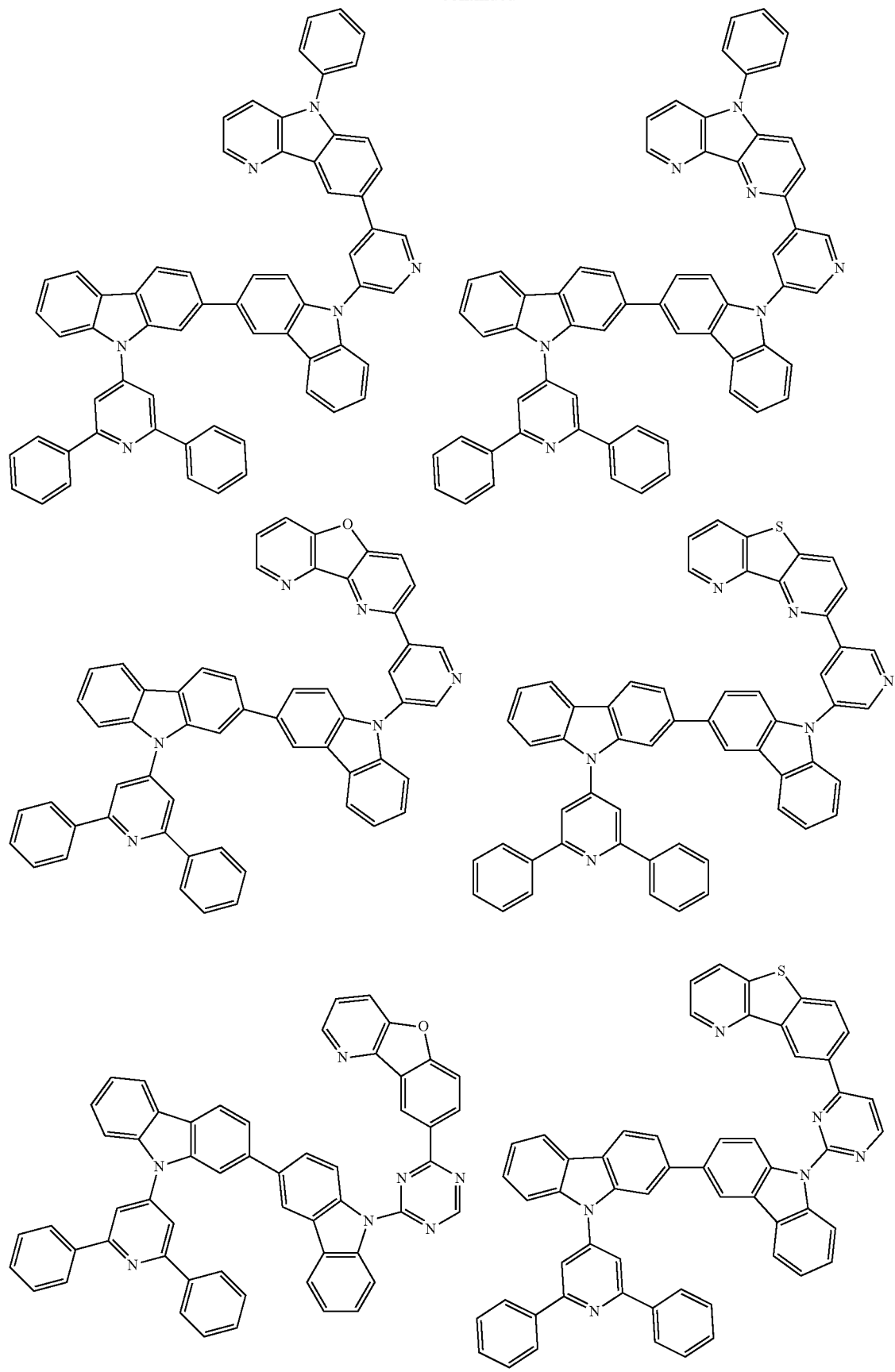

-continued
233
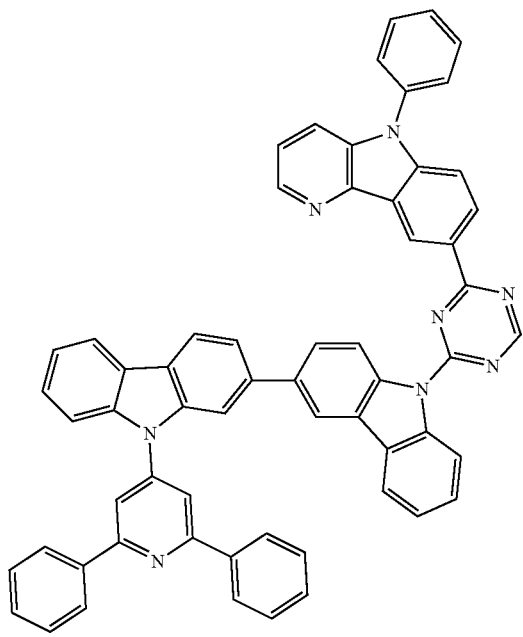
234
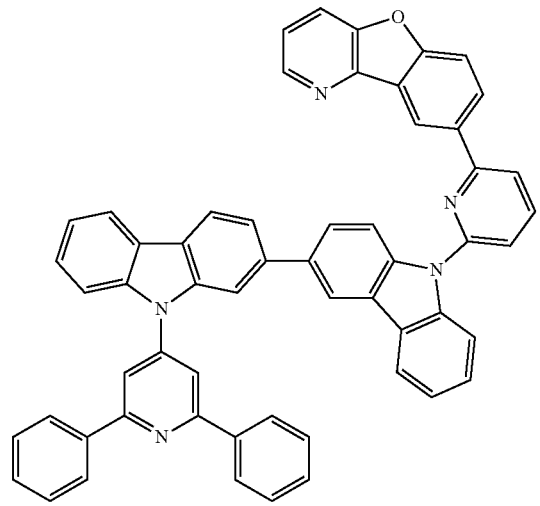
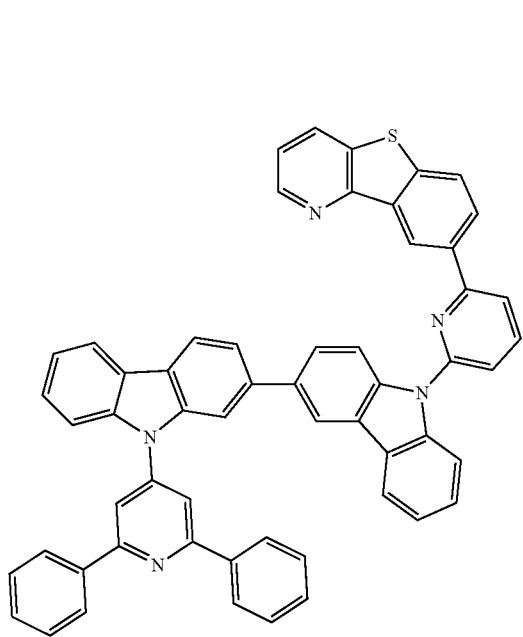
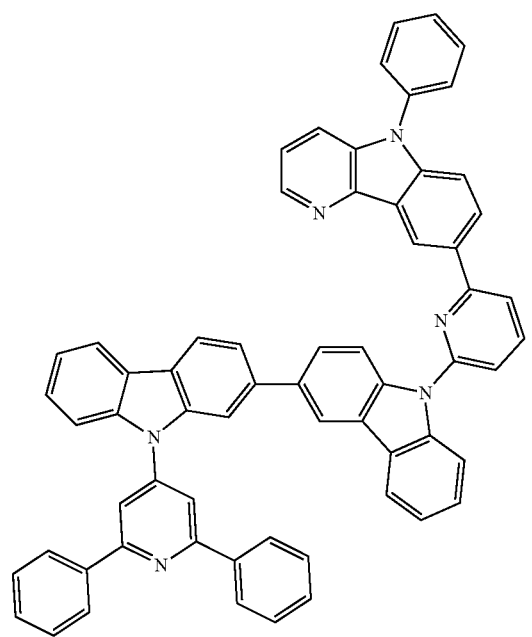

235
-continued
236
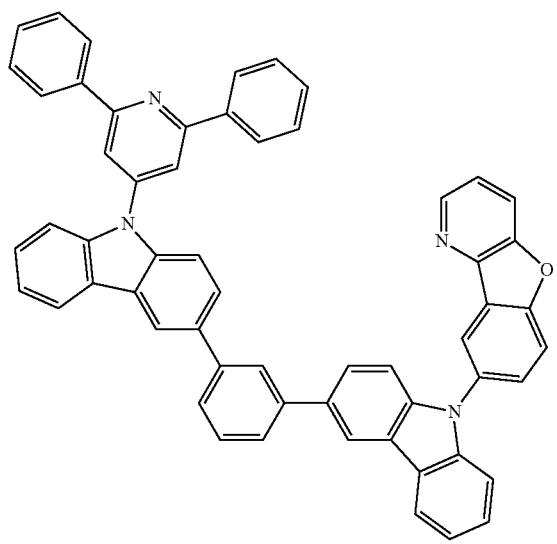
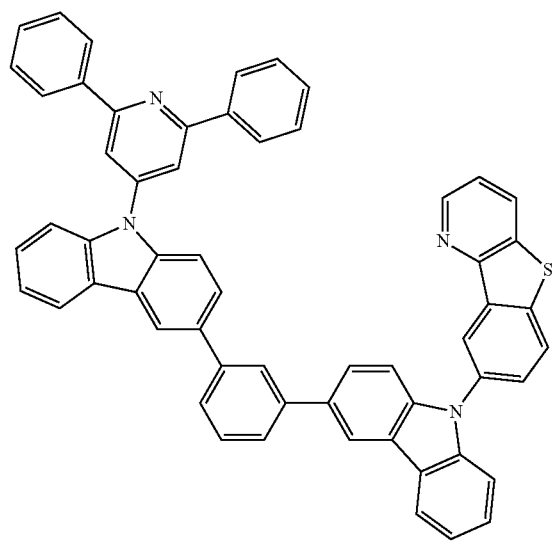
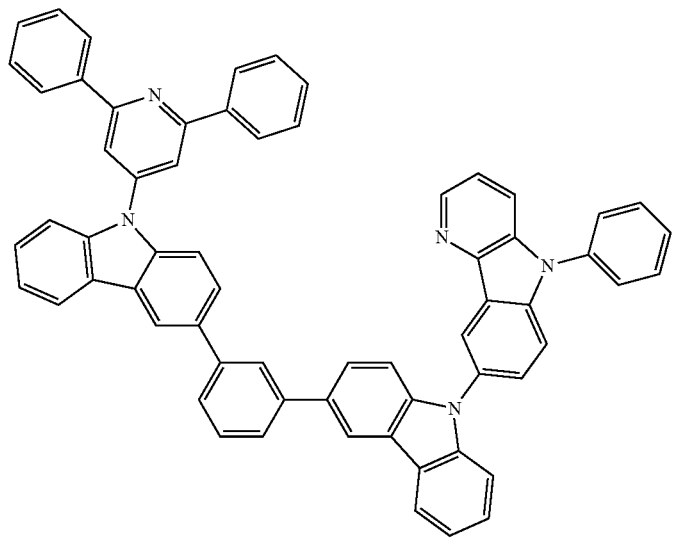
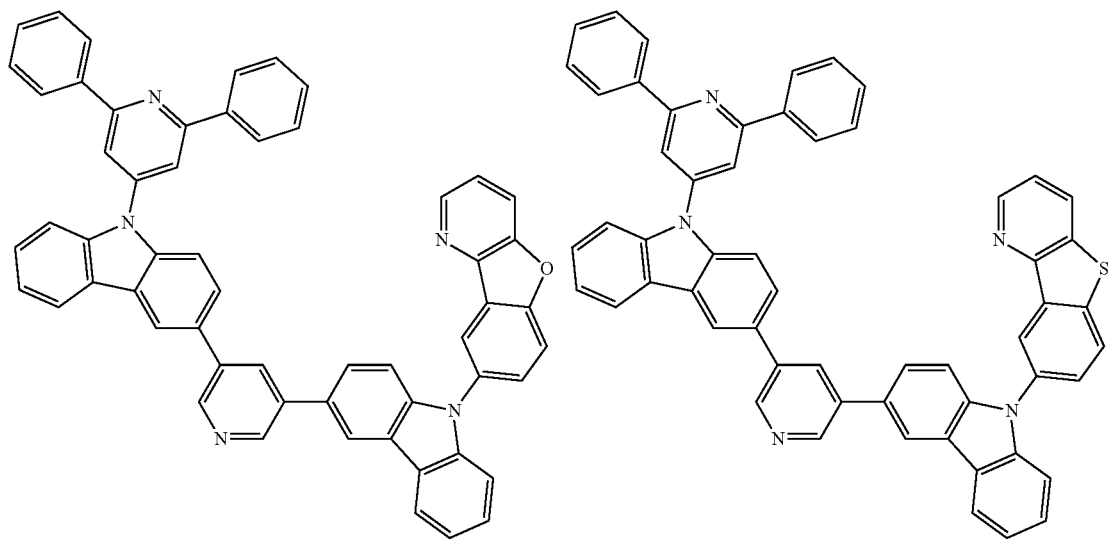

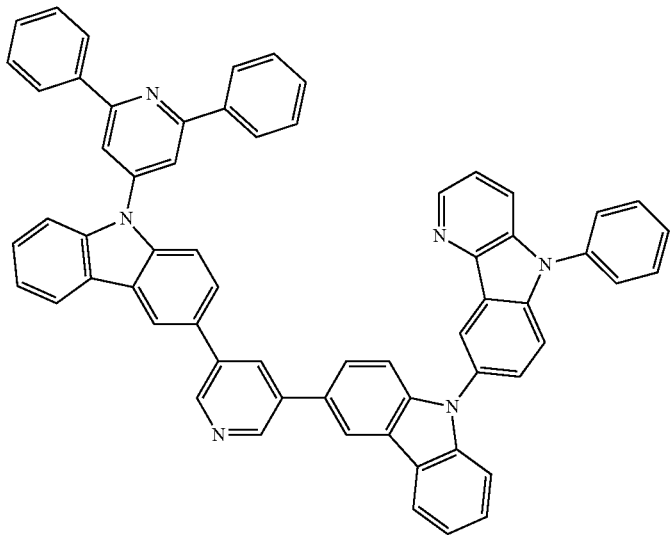
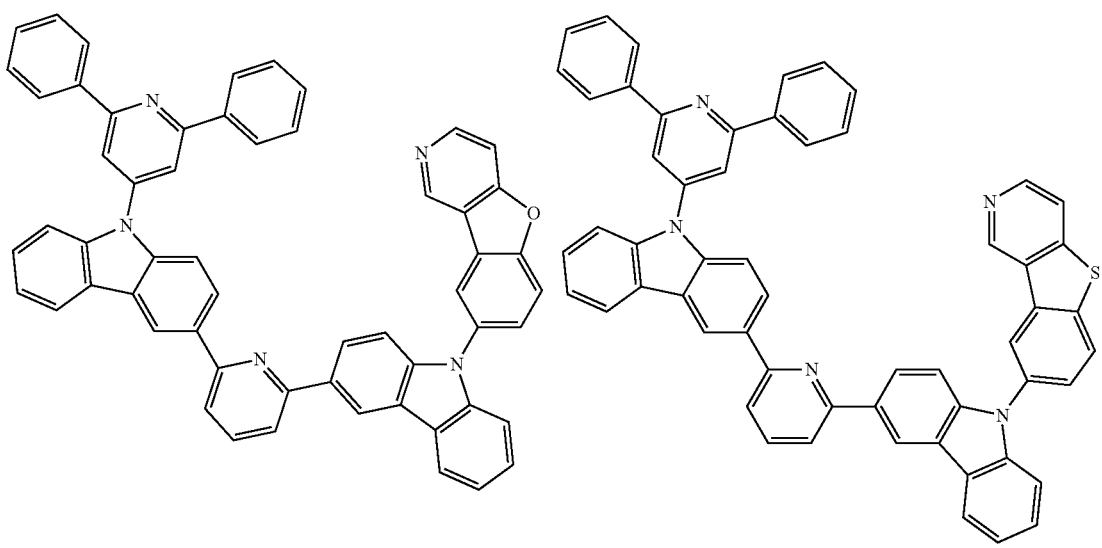
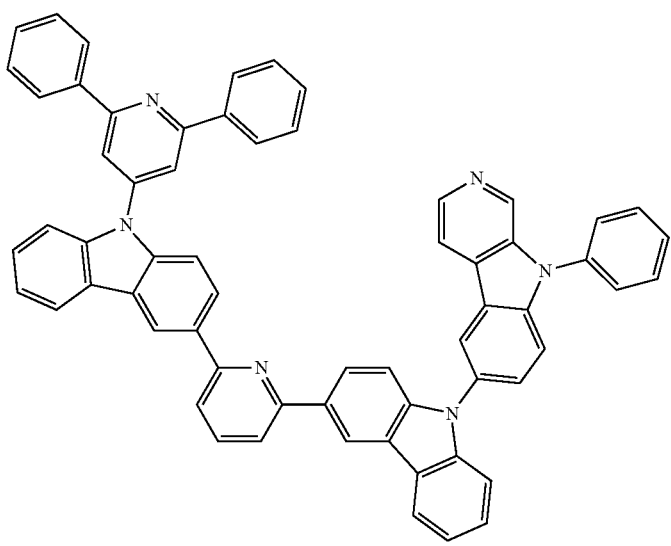

-continued
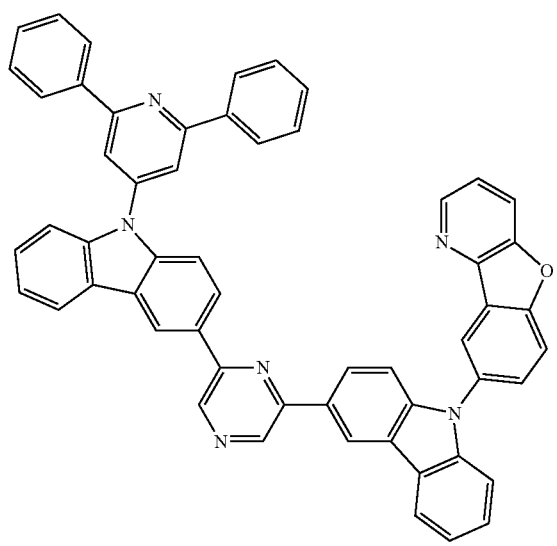
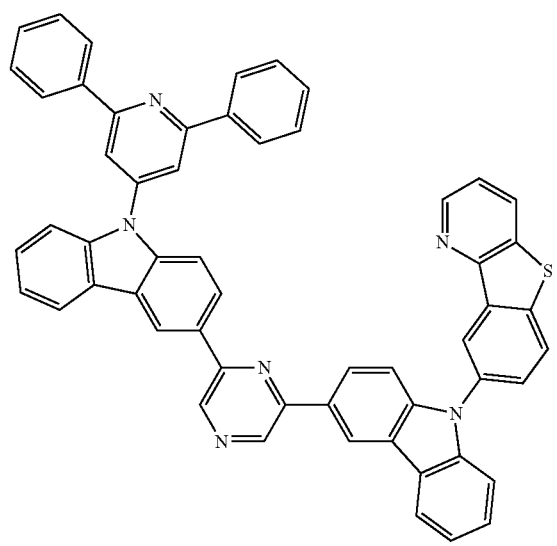
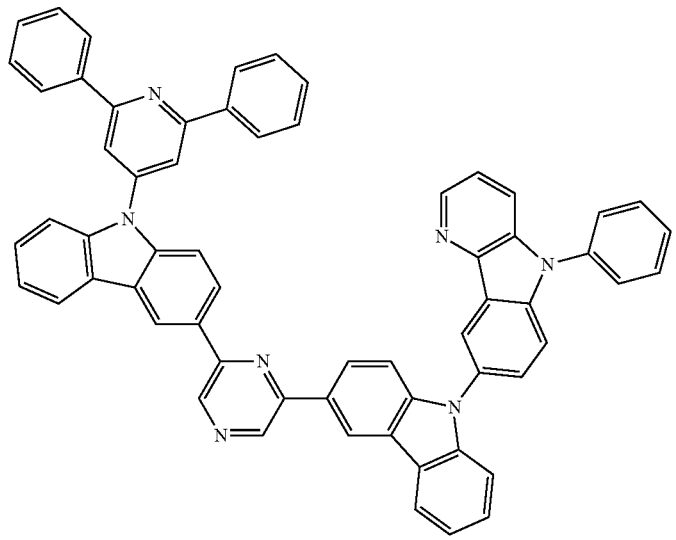
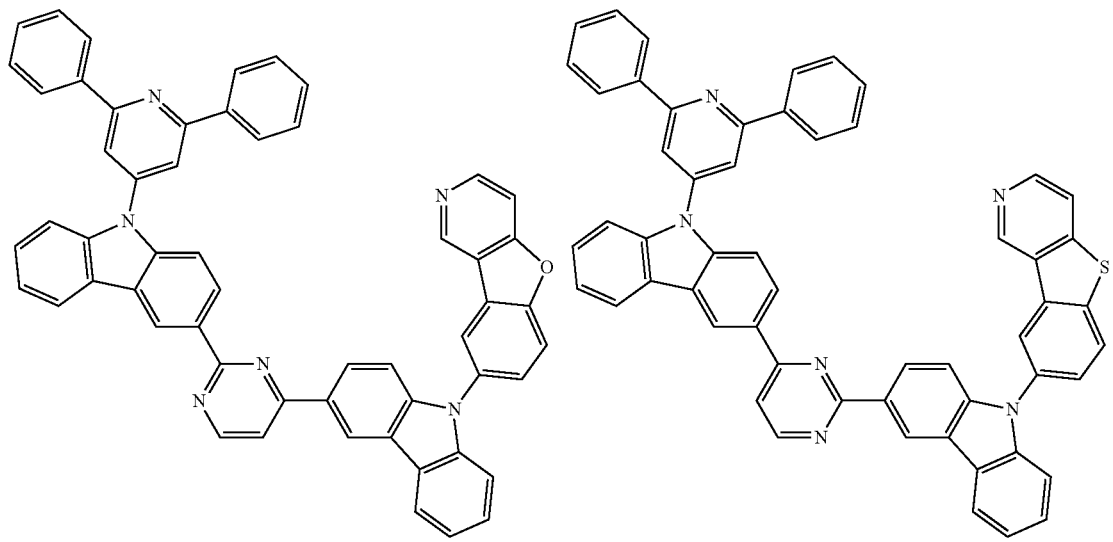

241
242
-continued
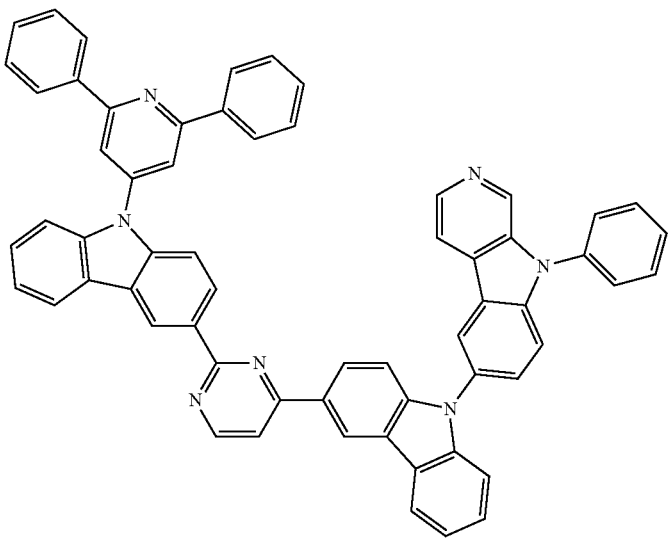
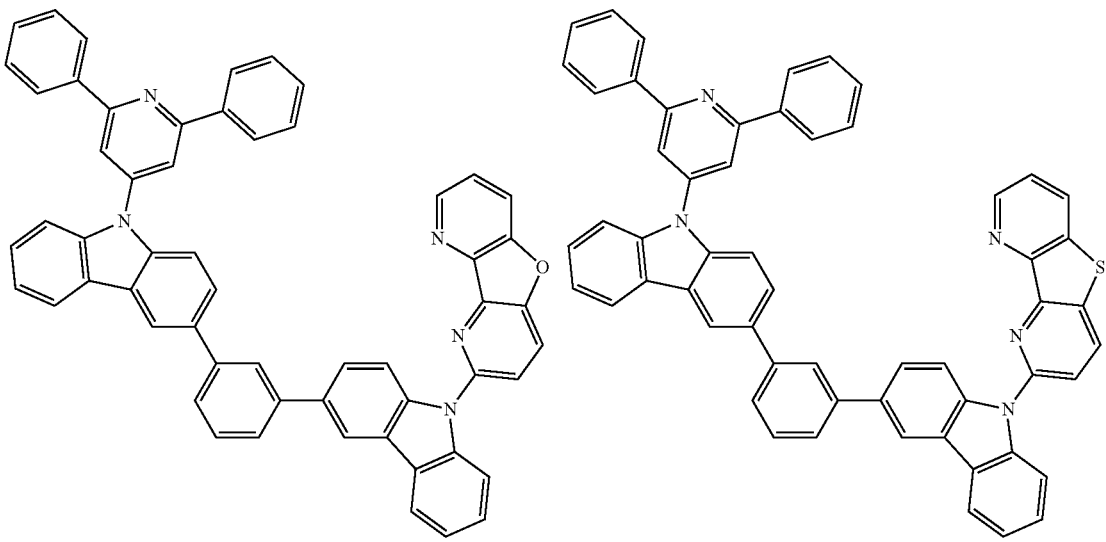
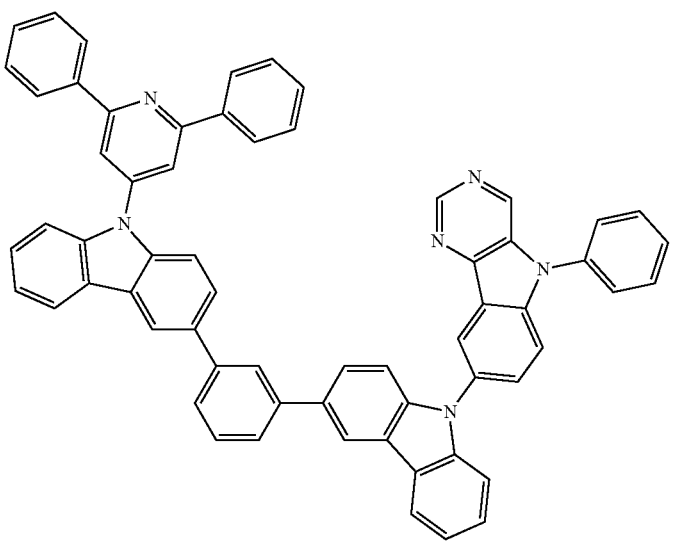

-continued
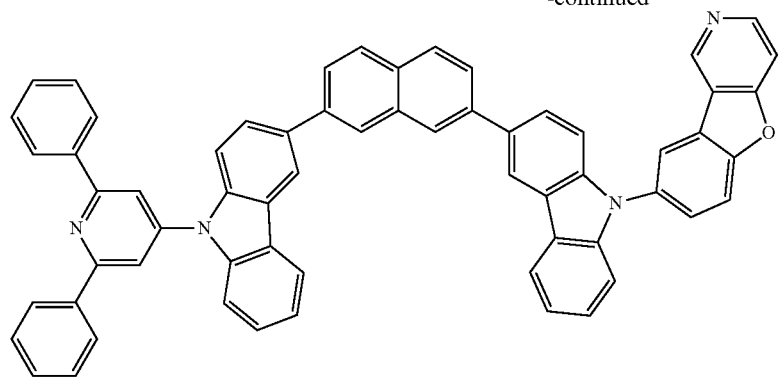
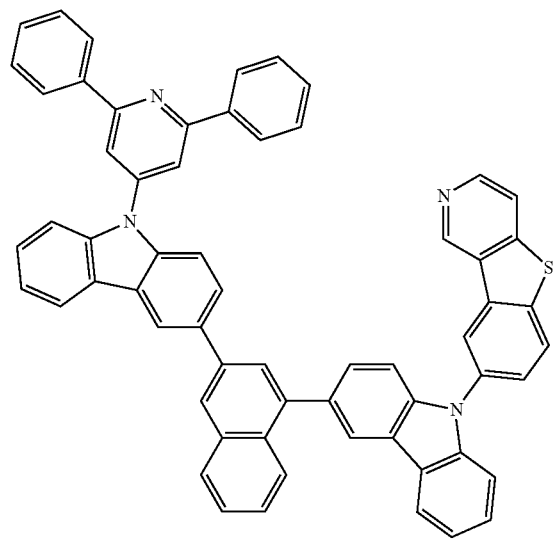
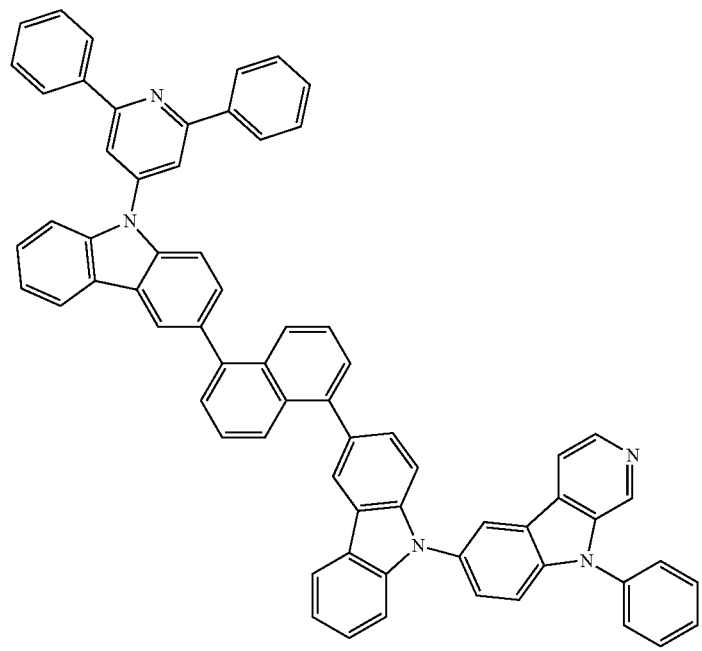

245
246
-continued
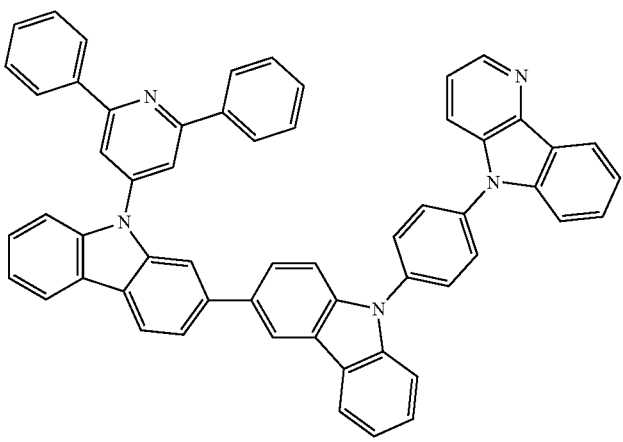
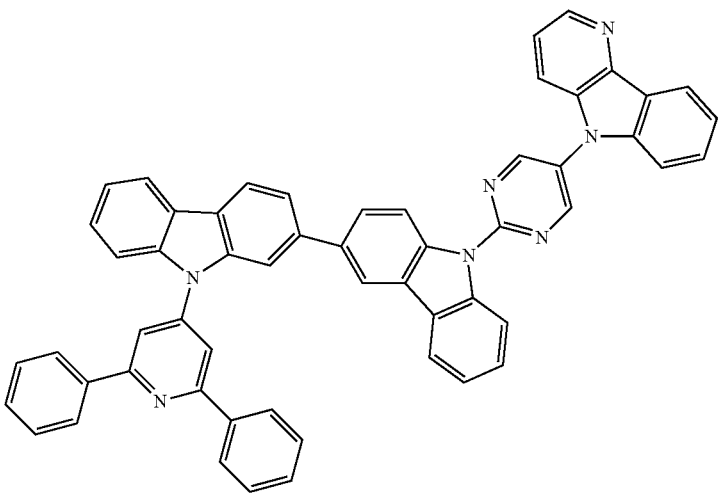
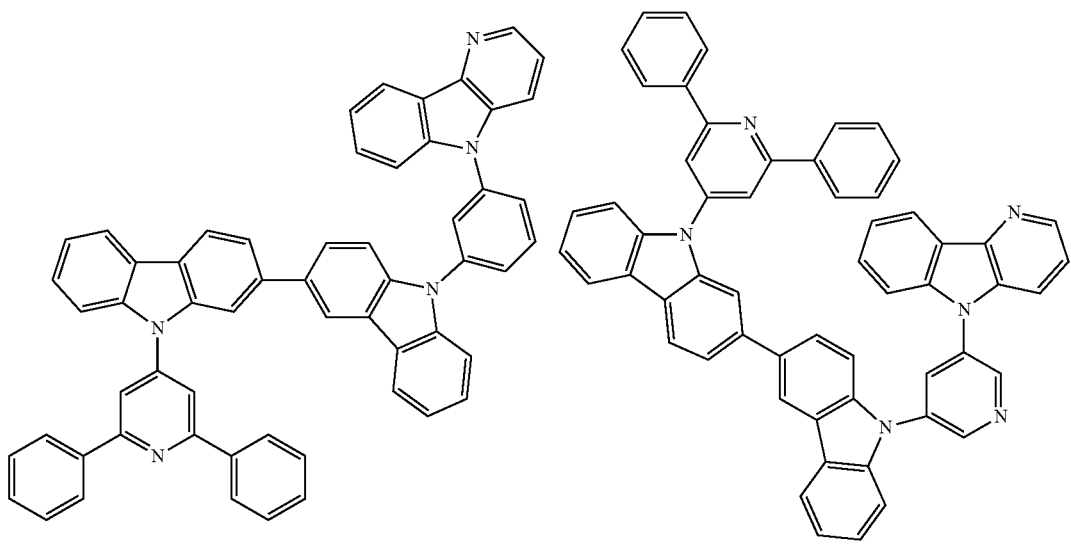

-continued
247 248
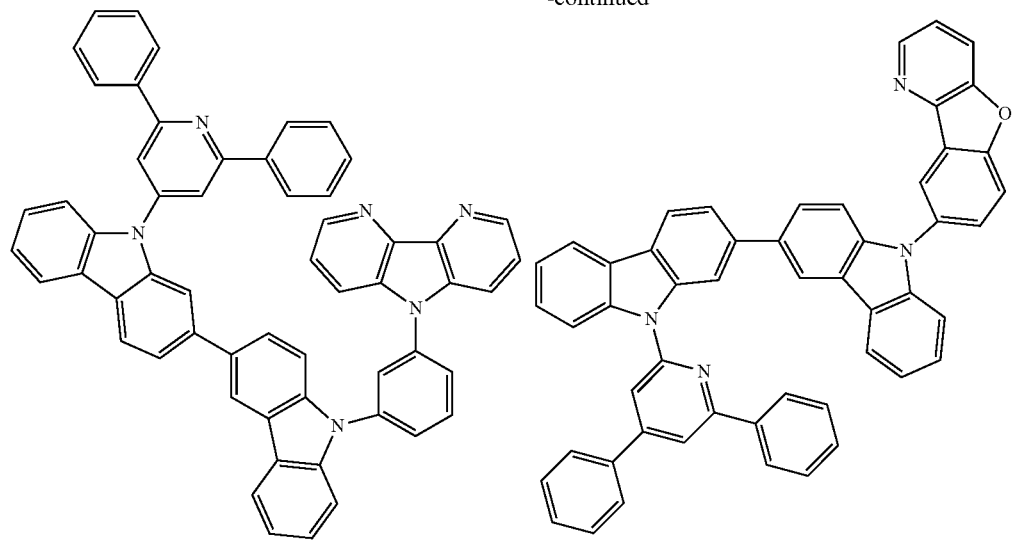
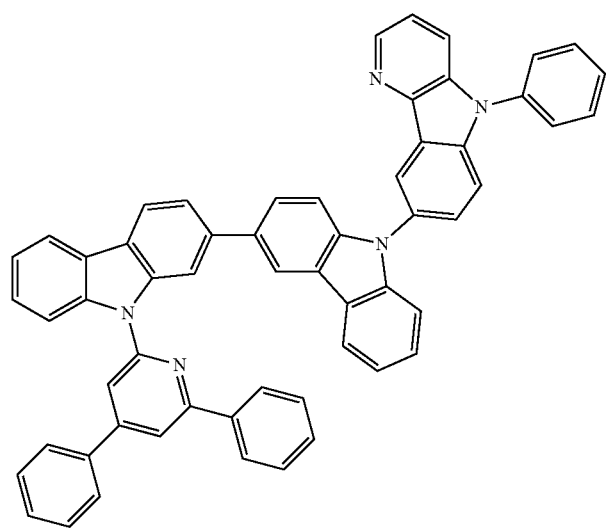
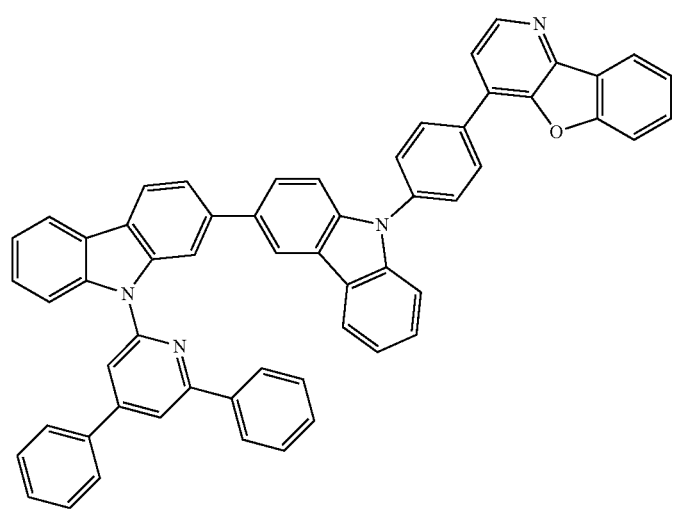 [SMILES: c1ccc(-c2cc(-c3ccccc3)nc(-n3c4ccccc4c4ccc(-c5ccc6c(c5)c5ccccc5n6-c5ccc(-c6ccnc7c6oc6ccccc67)cc5)cc43)c2)cc1]

249 250
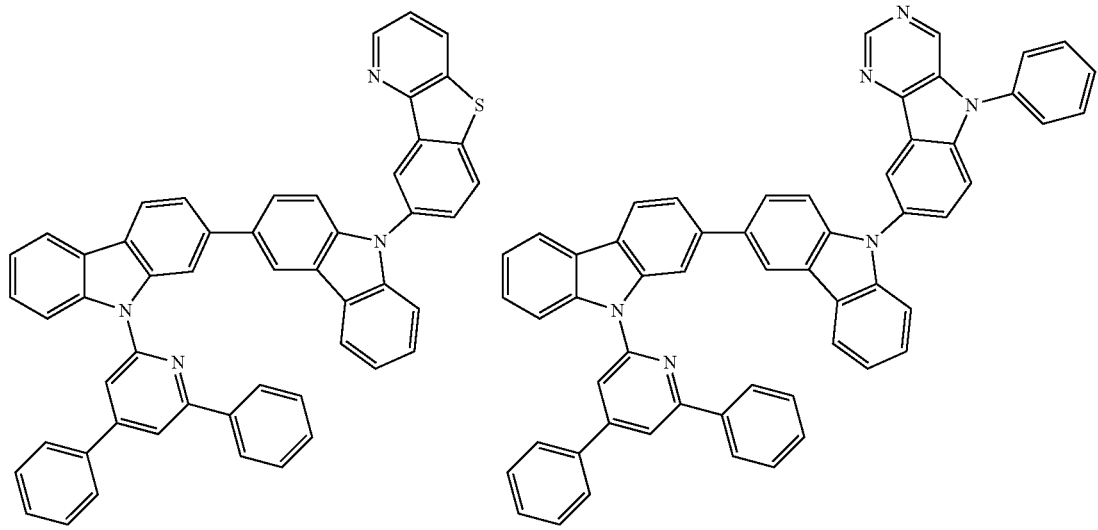
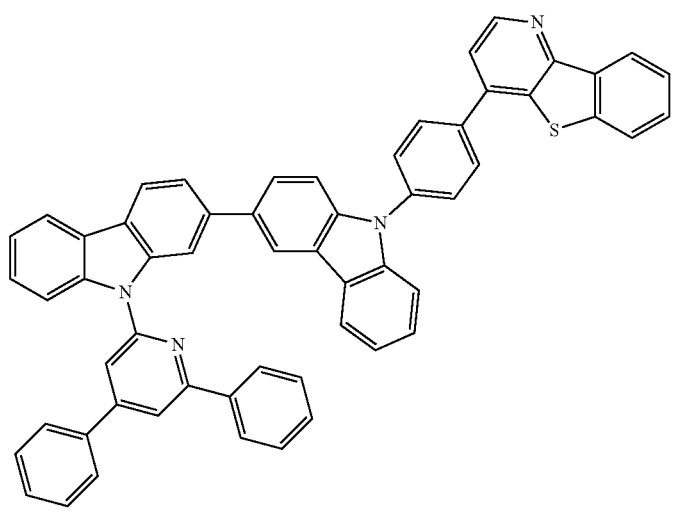
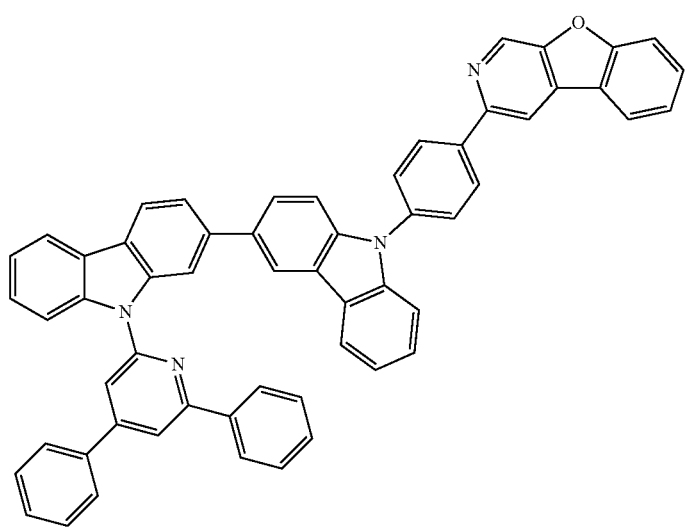

-continued
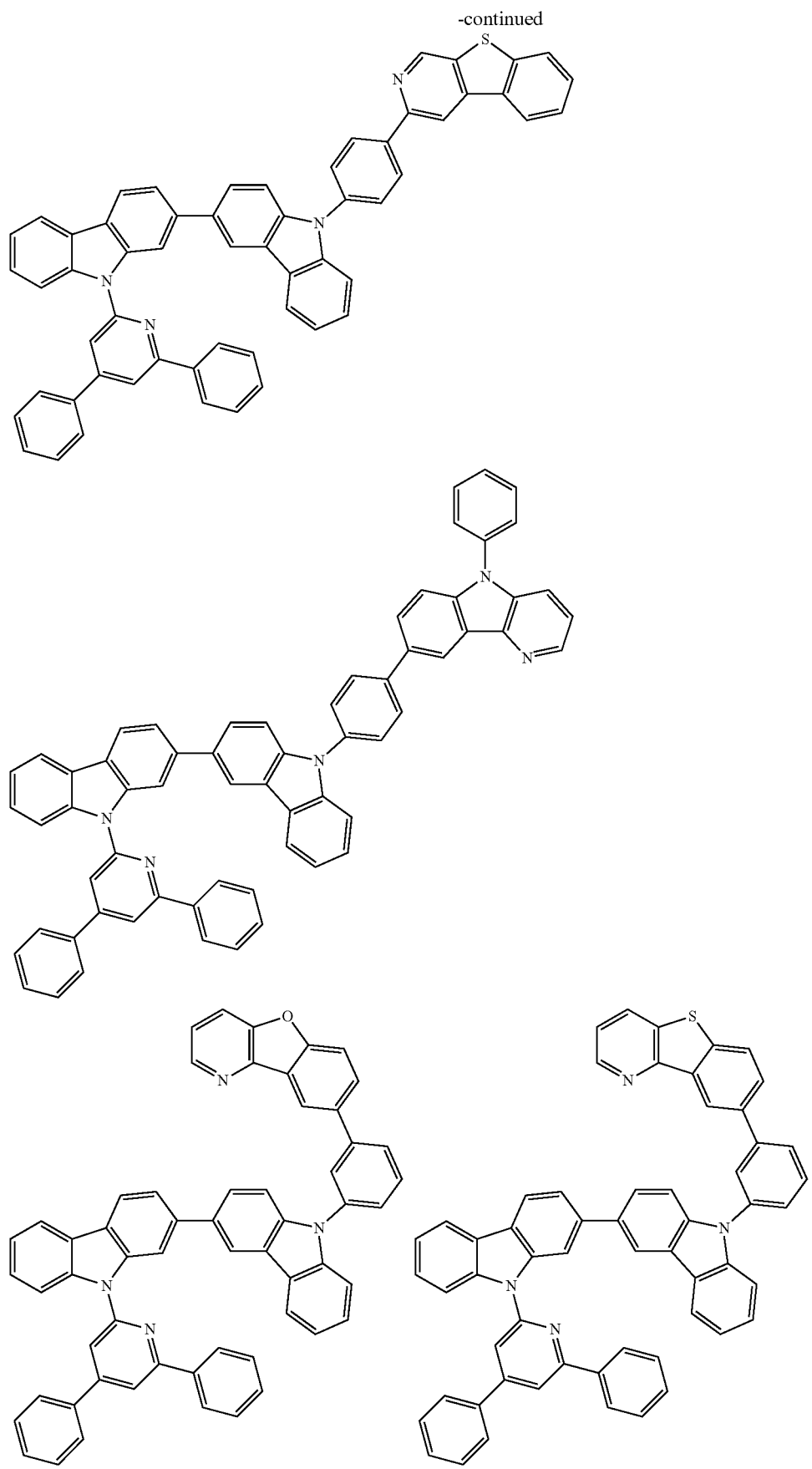

-continued
253
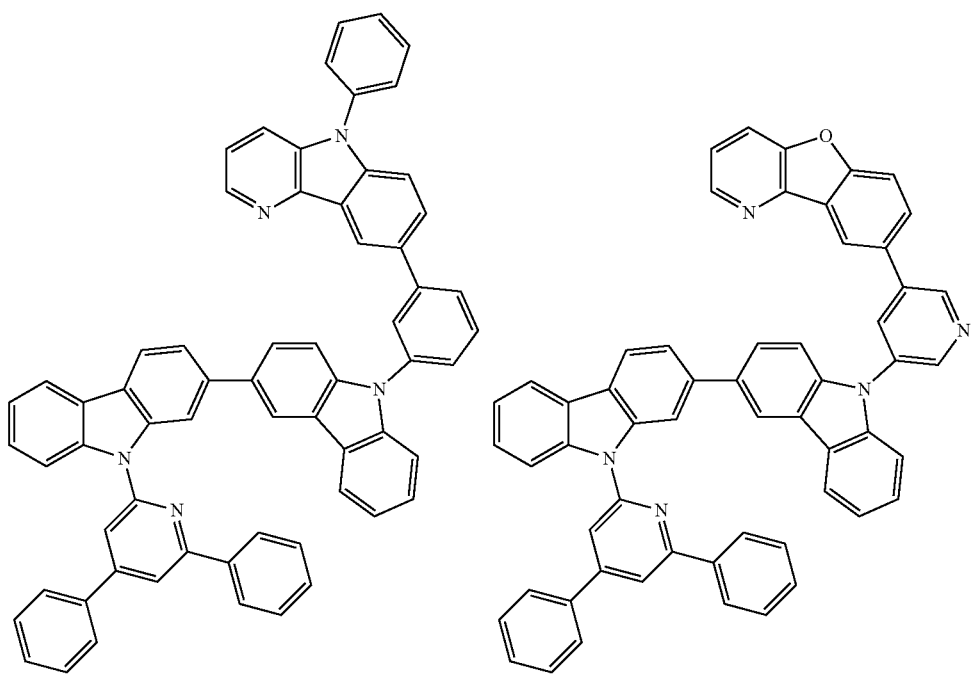
254
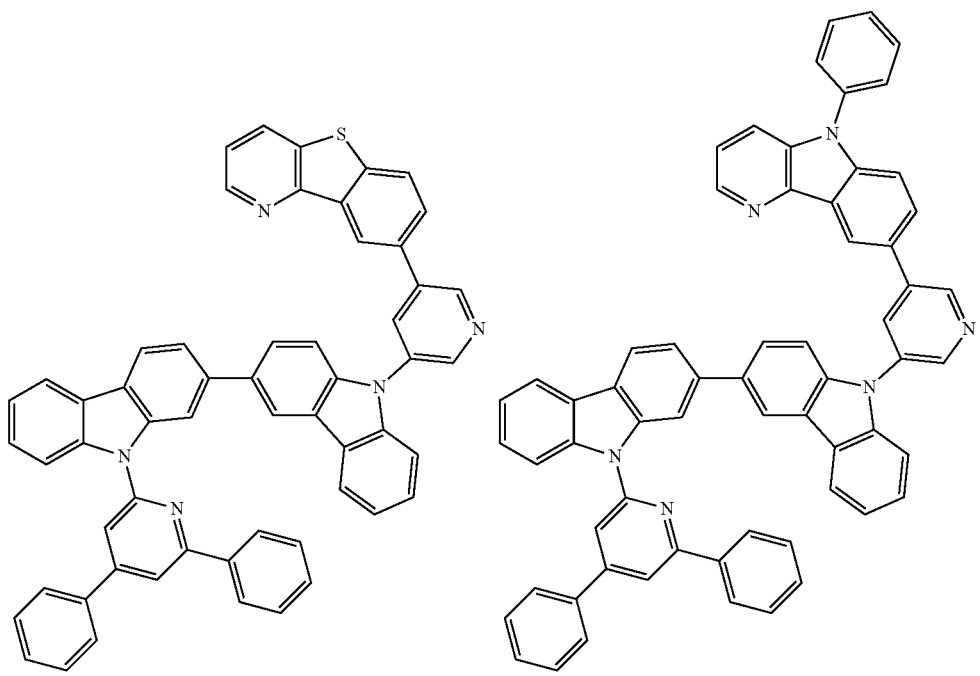

-continued
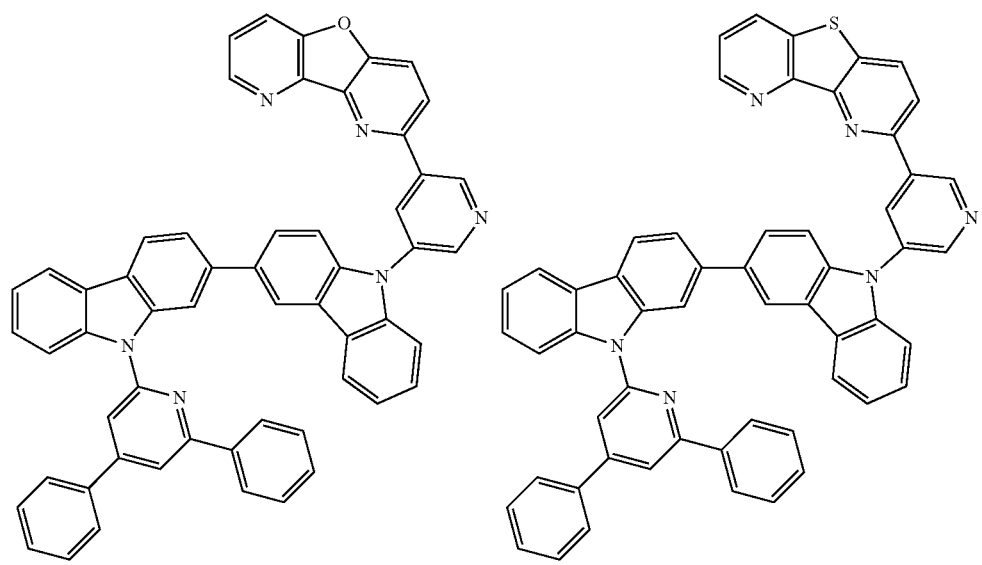
255
256
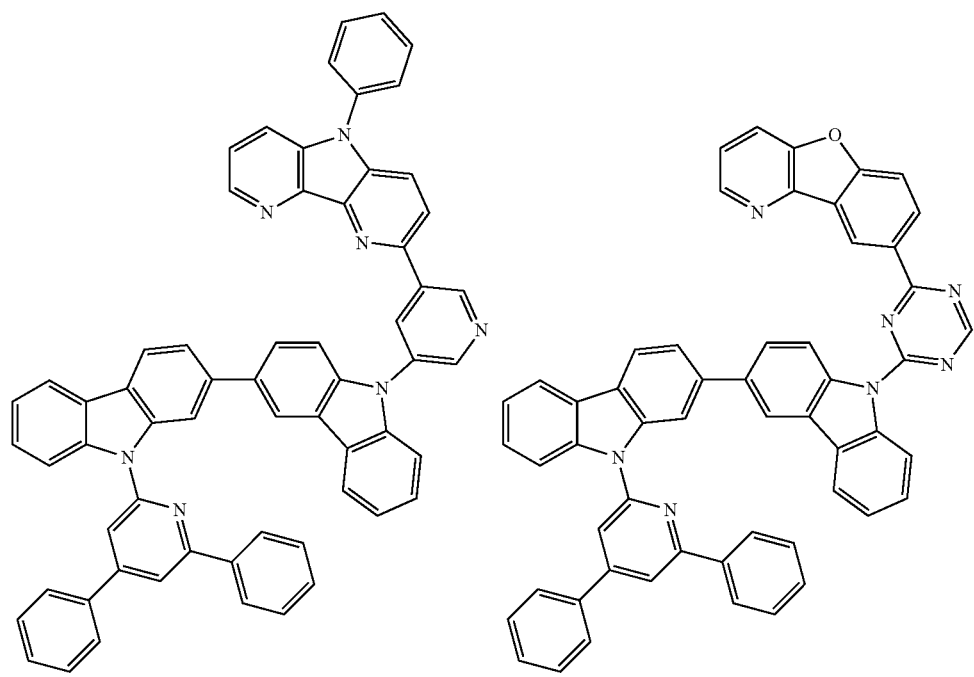

257 258
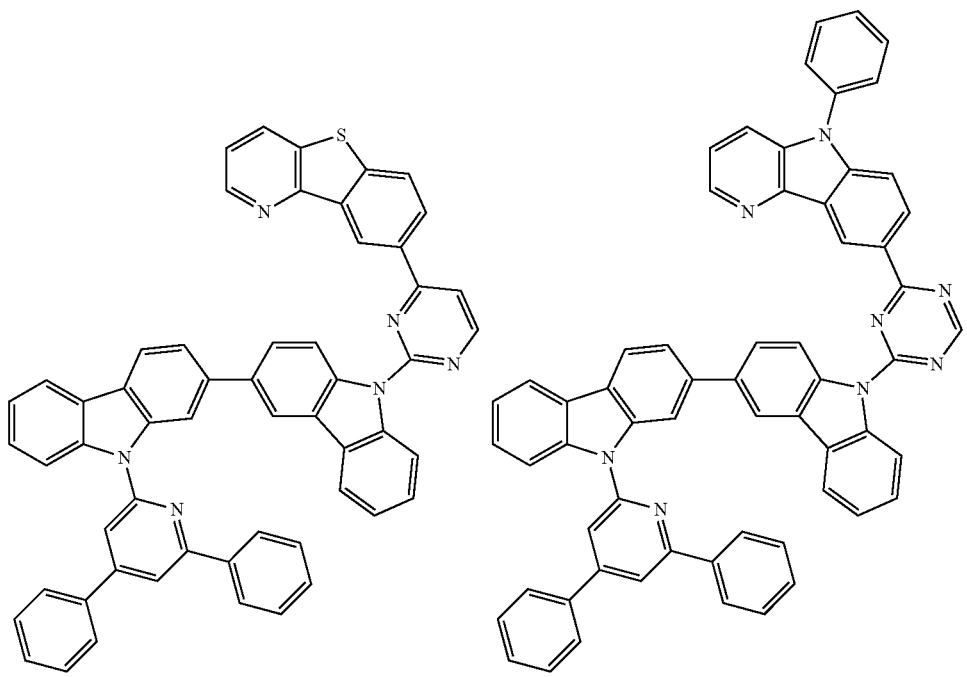
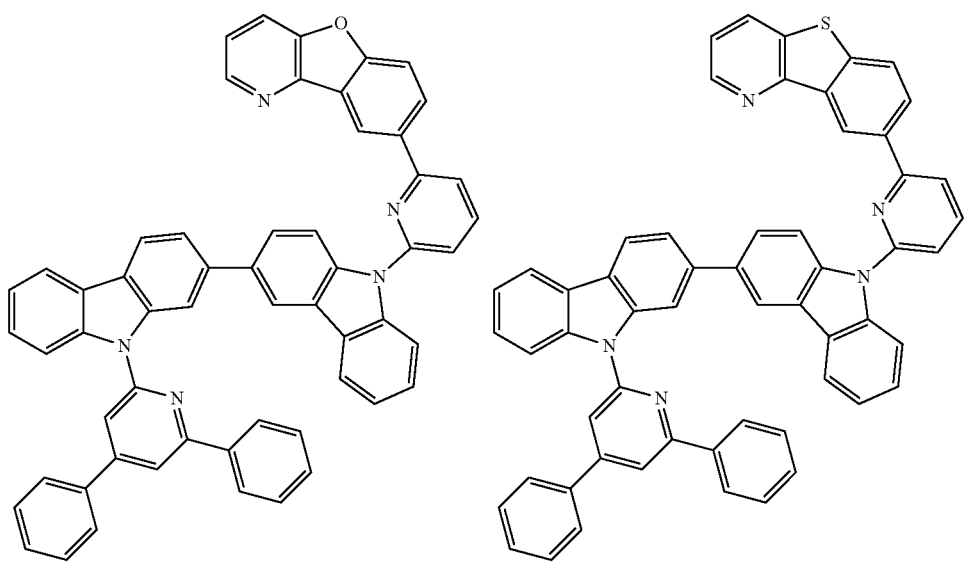

-continued
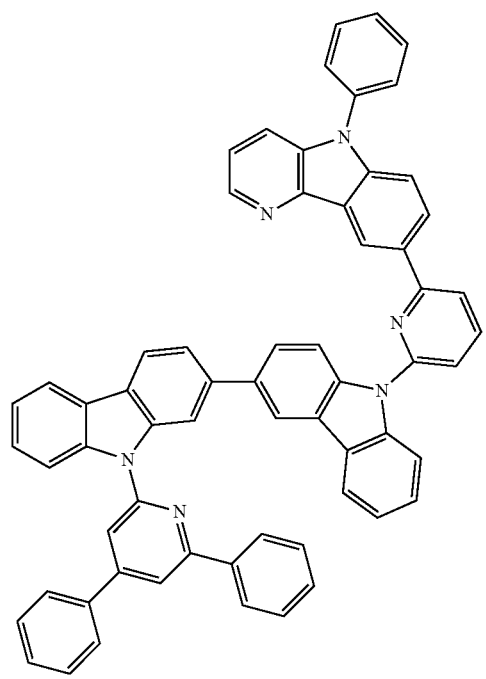
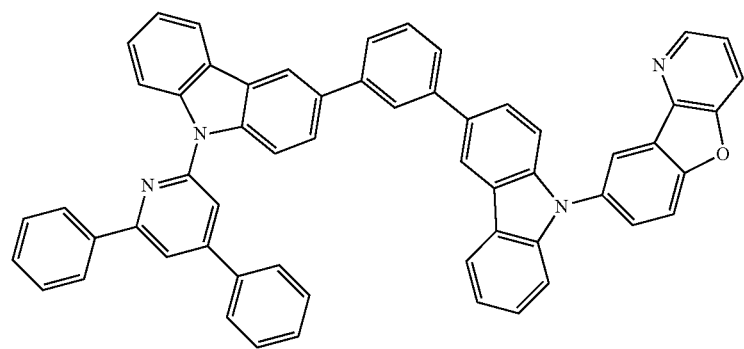
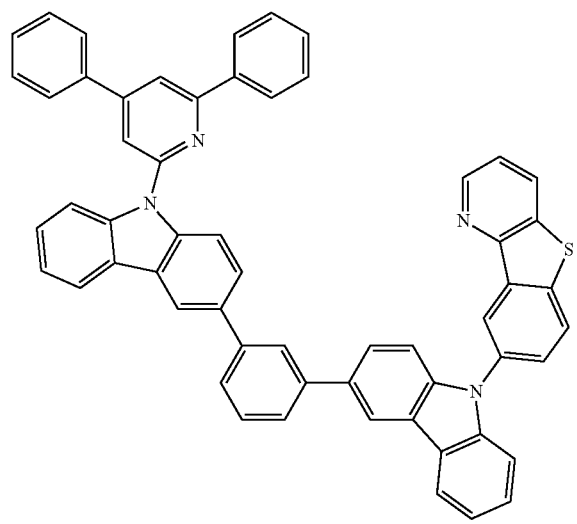

261
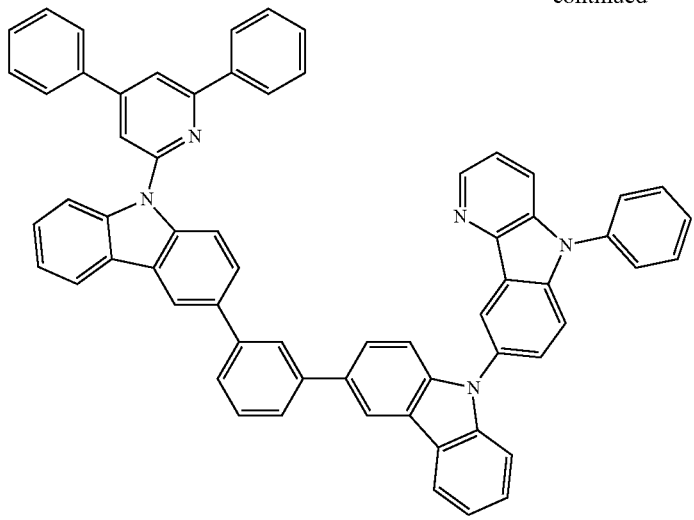
-continued
262
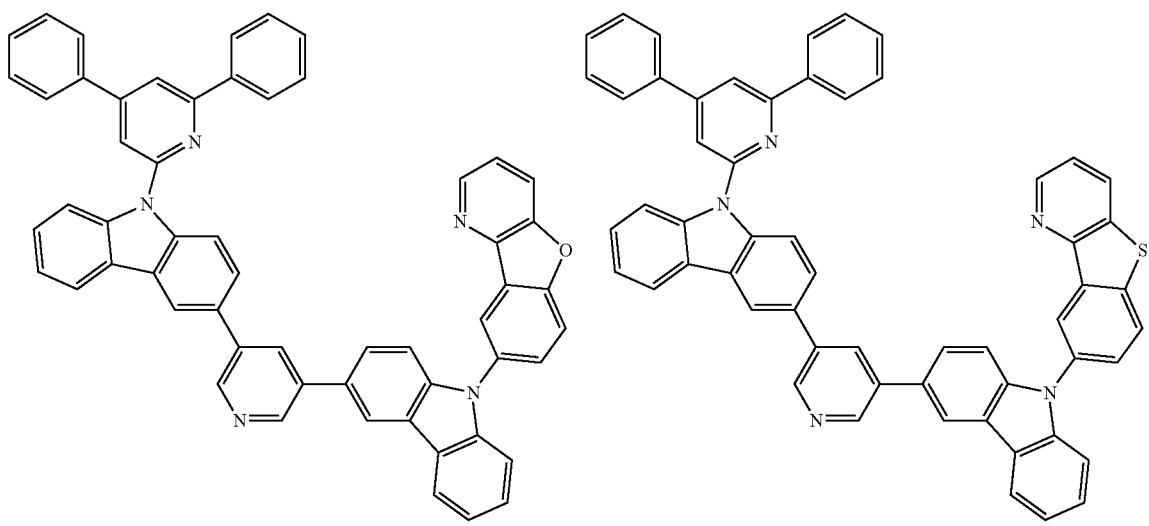
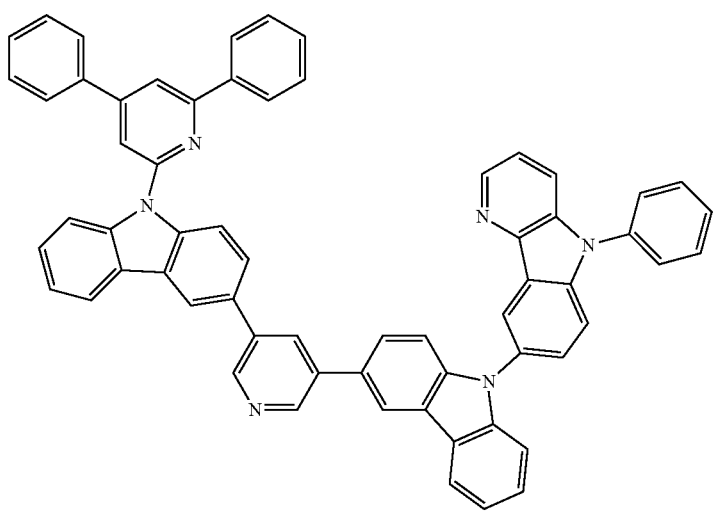

263
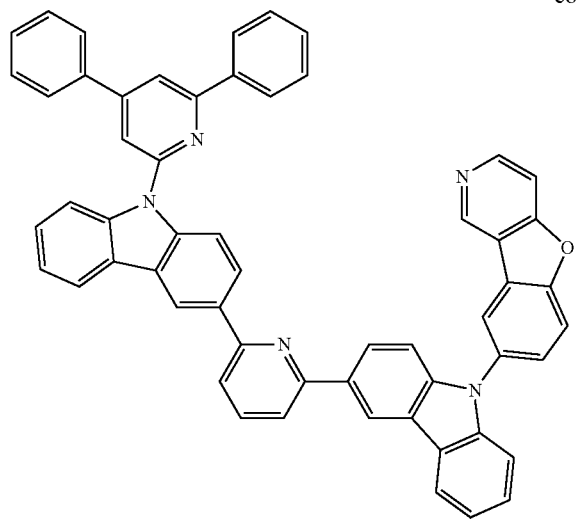
264
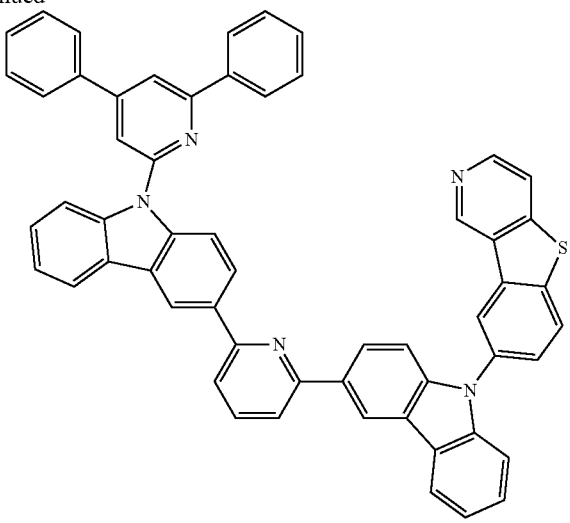
-continued
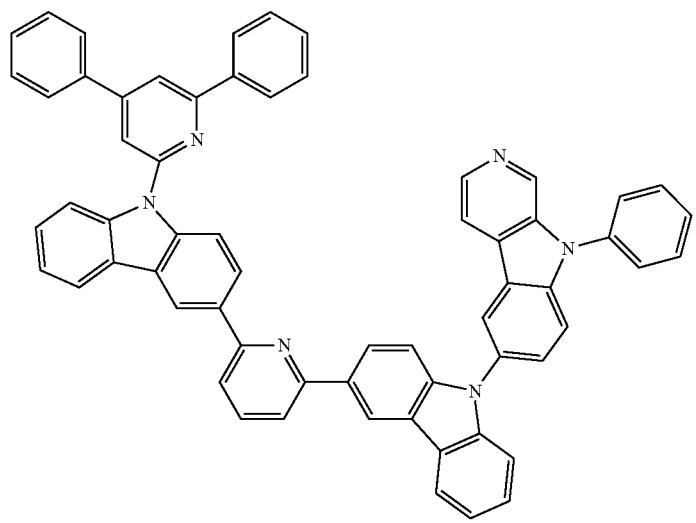
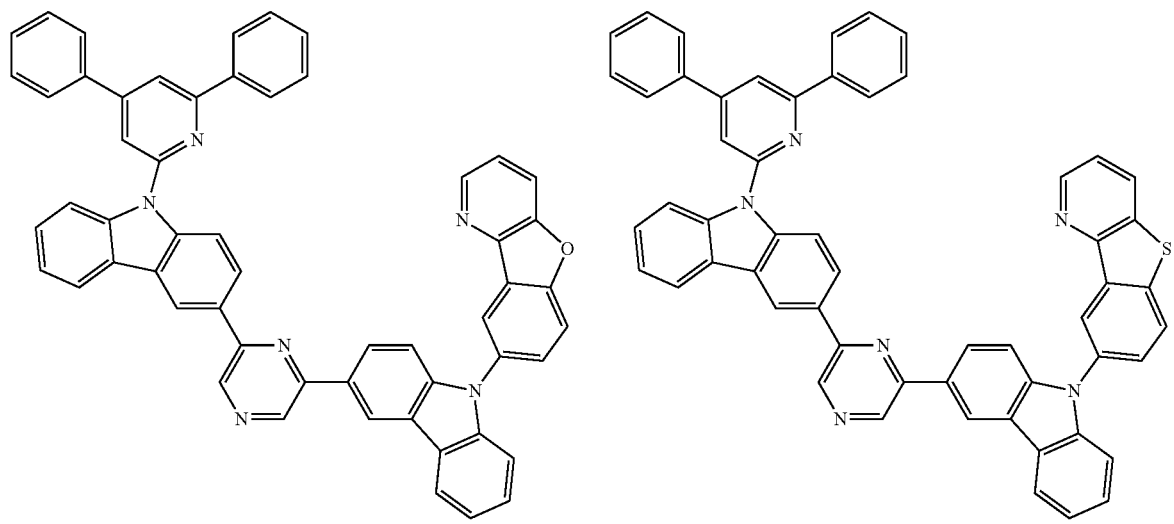

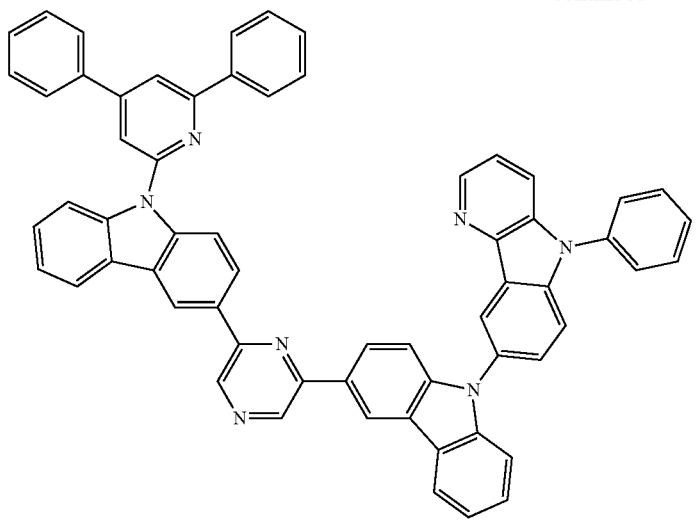
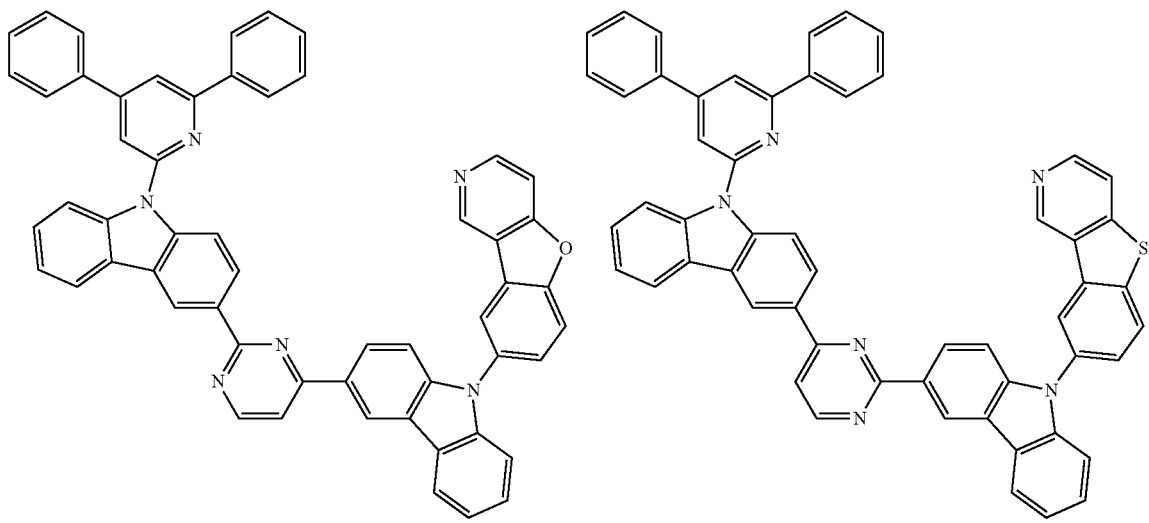
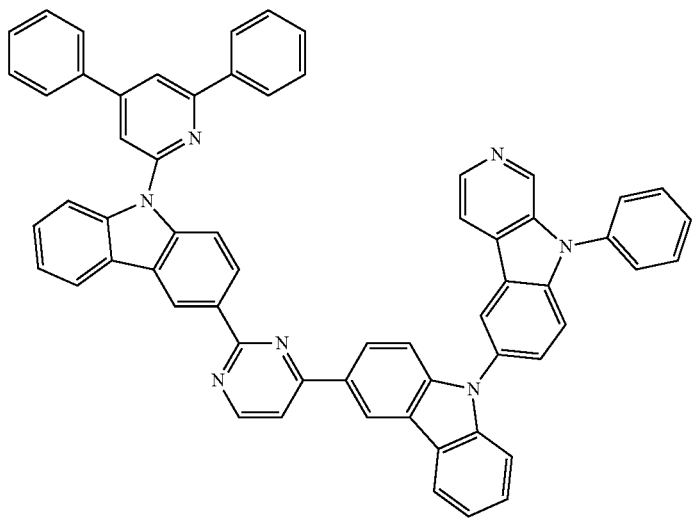

-continued
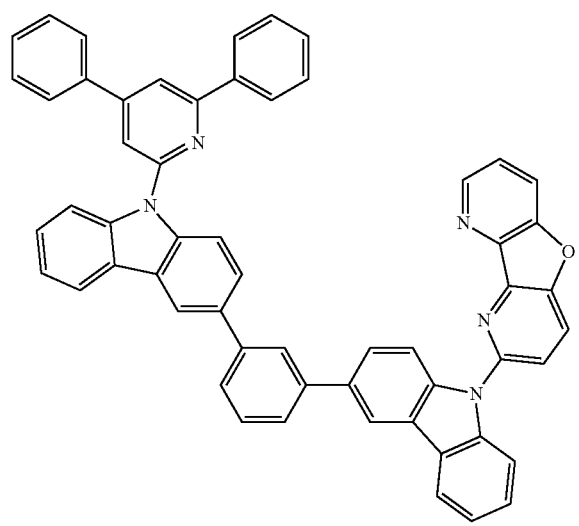
267
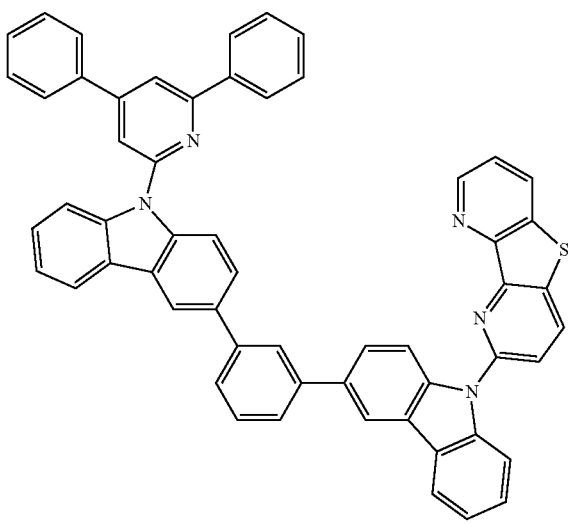
268
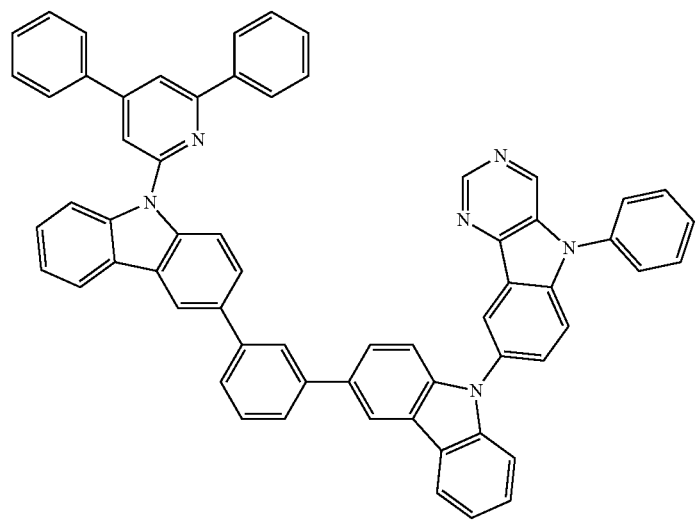
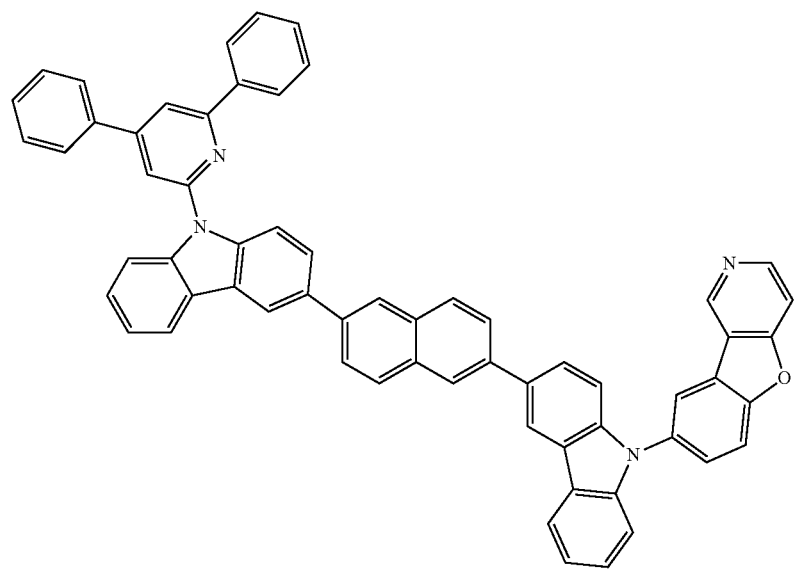

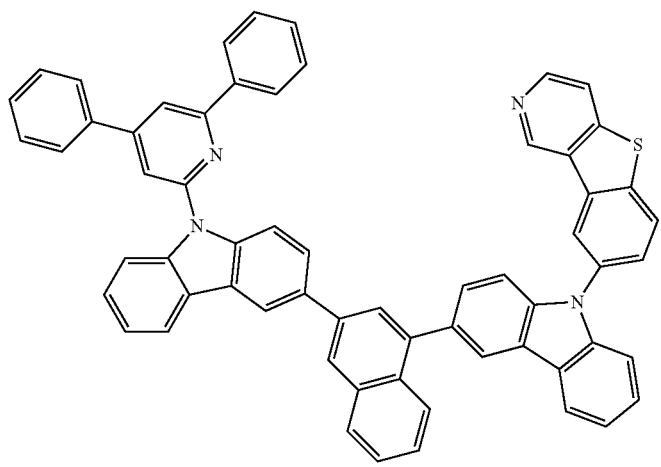
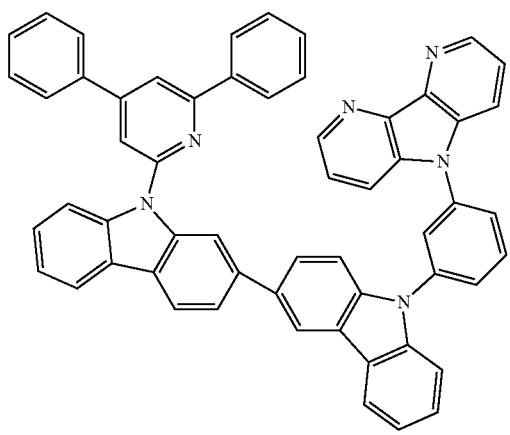
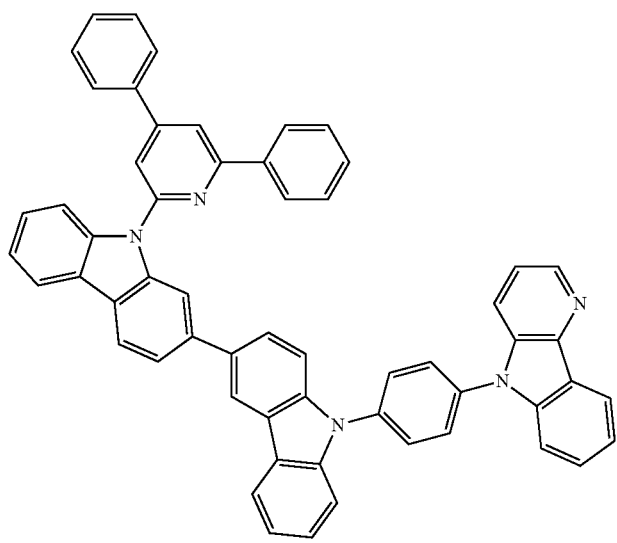

271 272
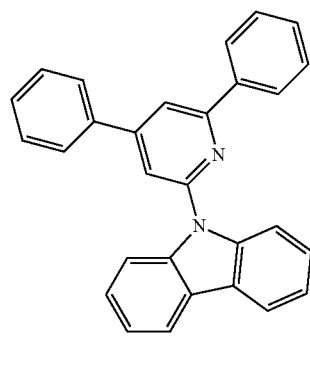 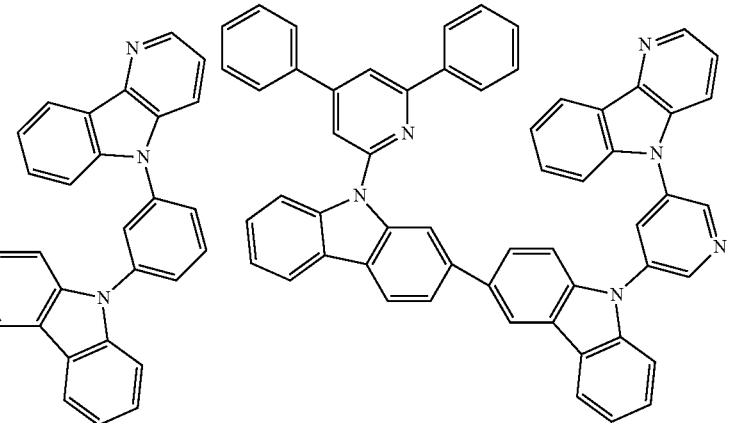
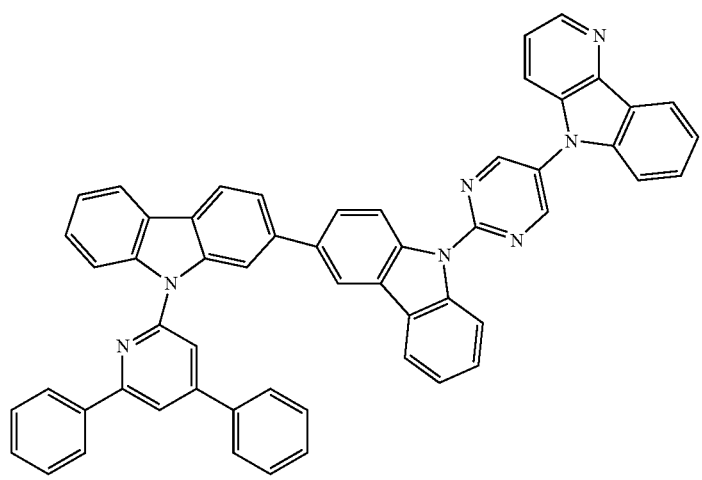
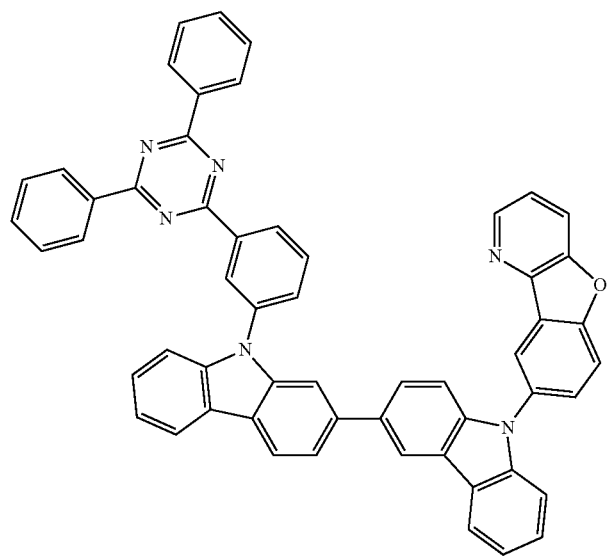

-continued
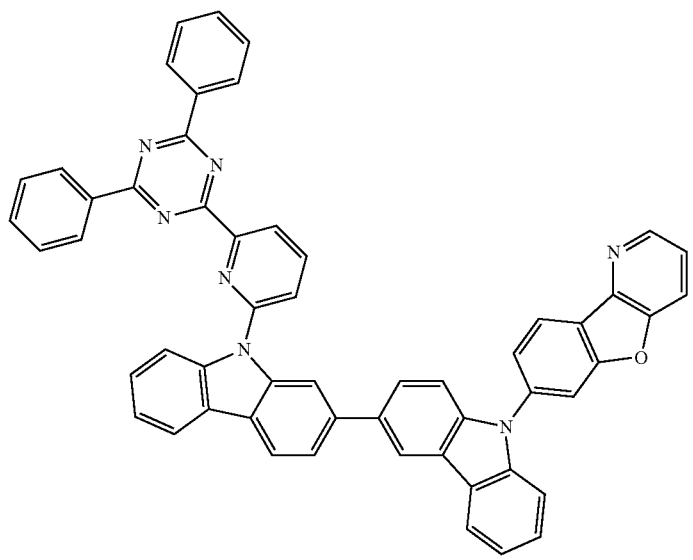

-continued
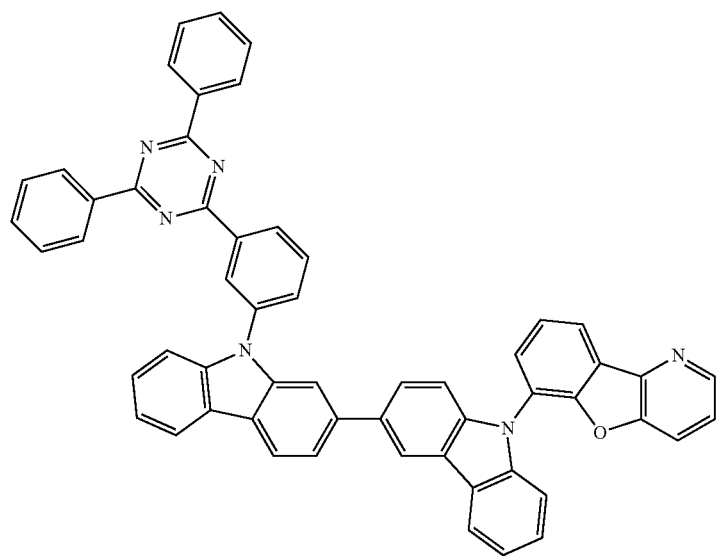
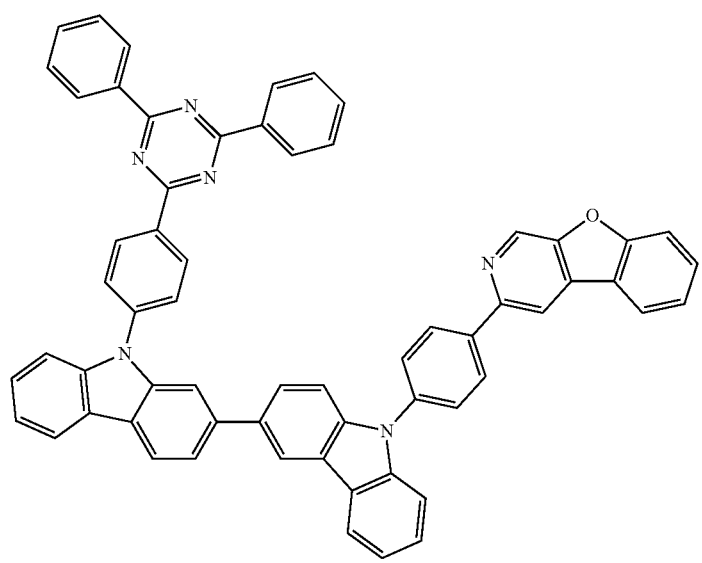

-continued
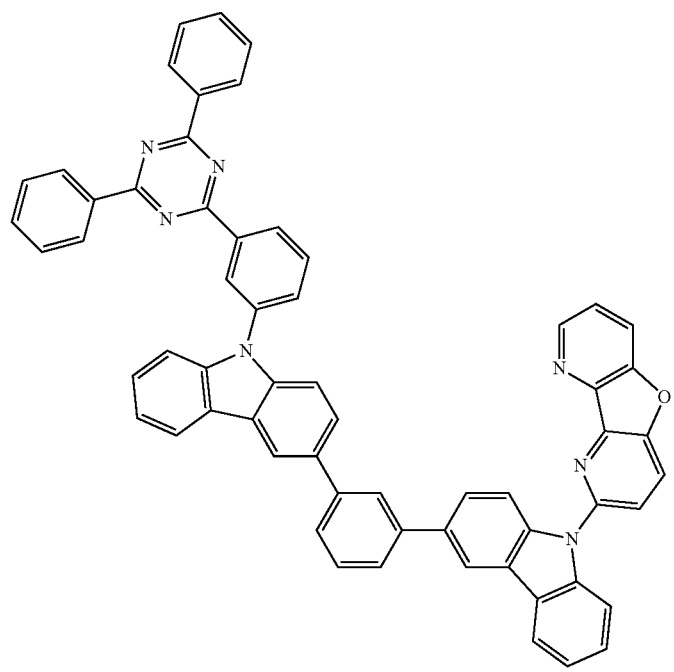
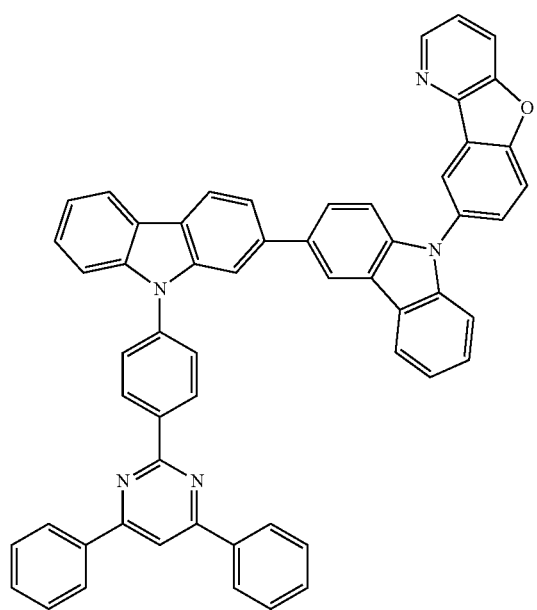

-continued
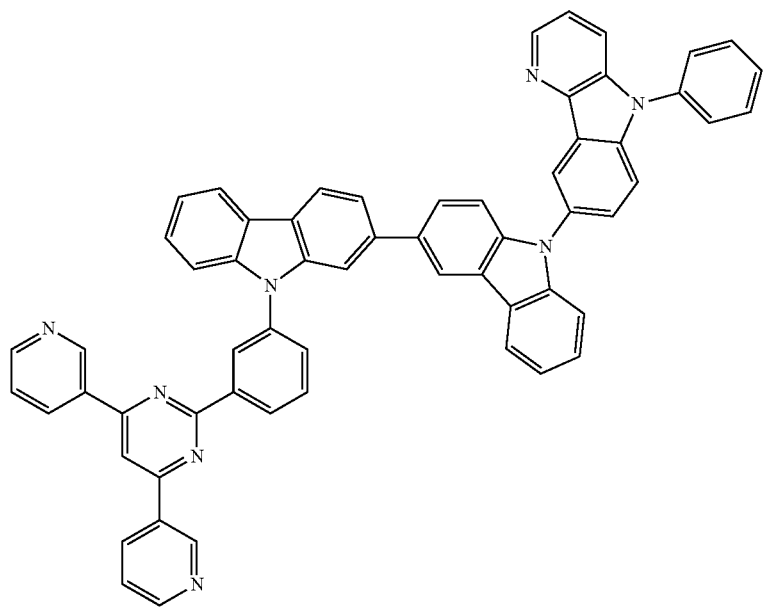
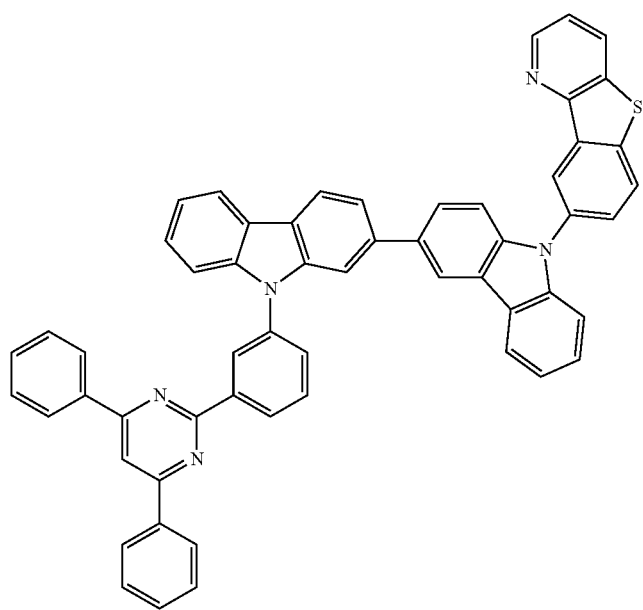

-continued
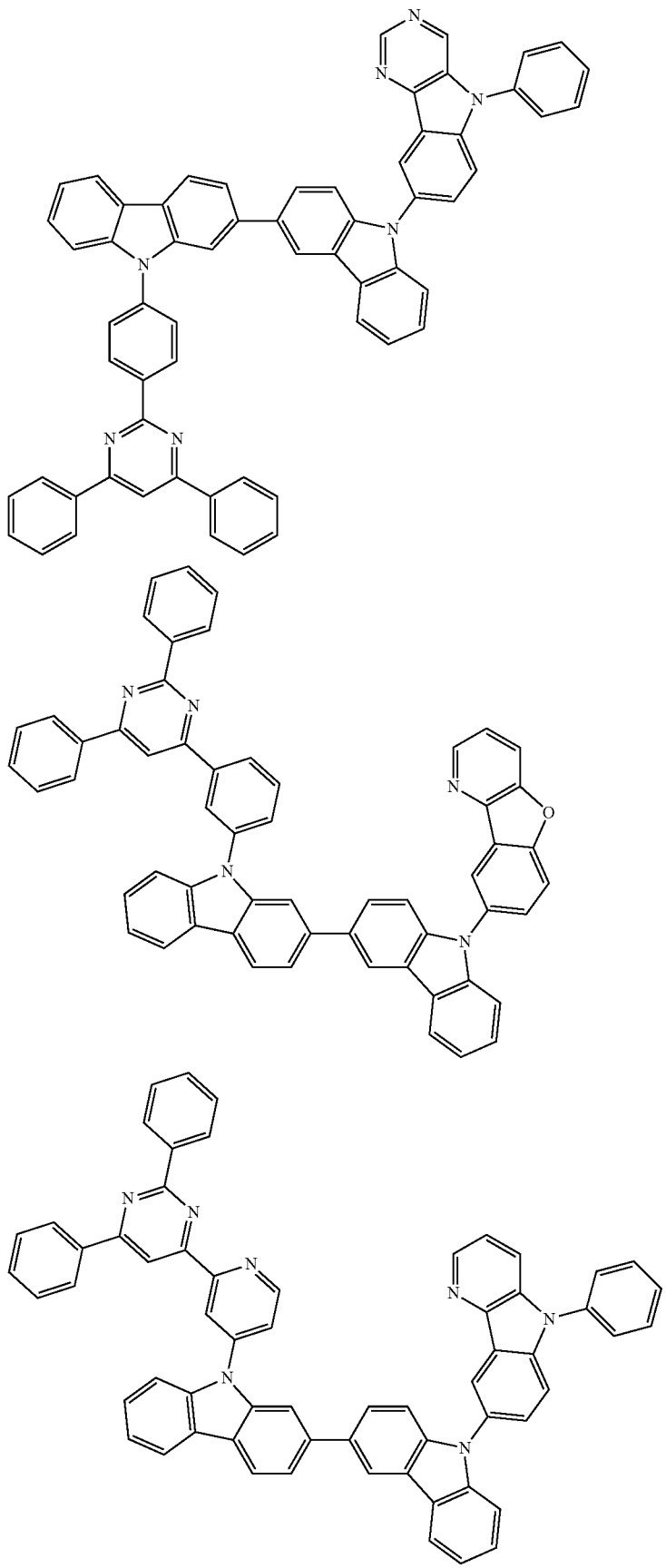

-continued
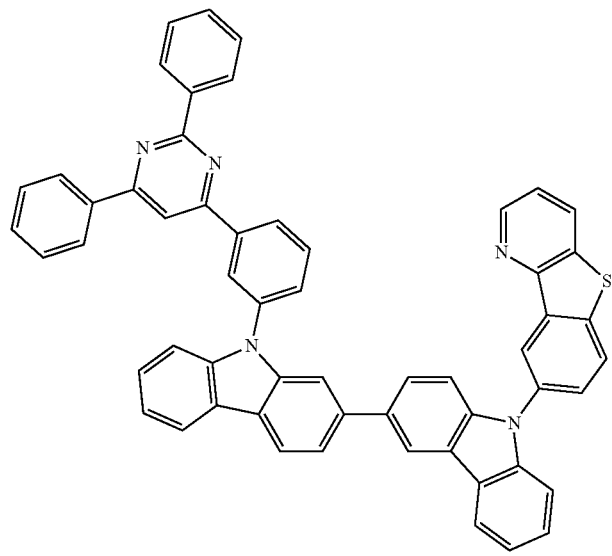
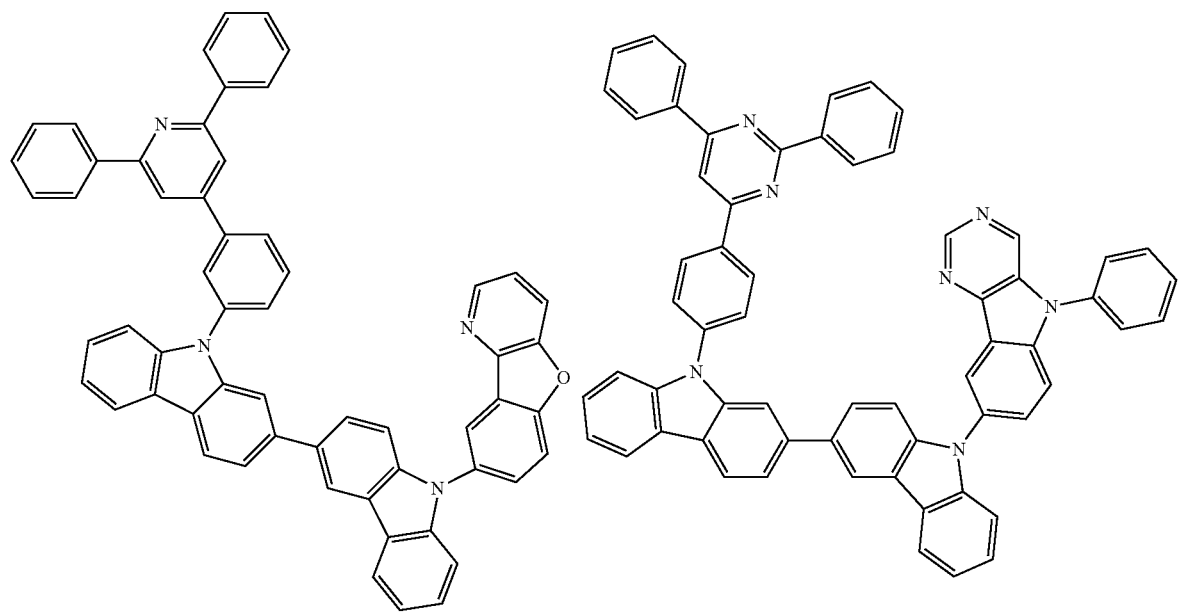

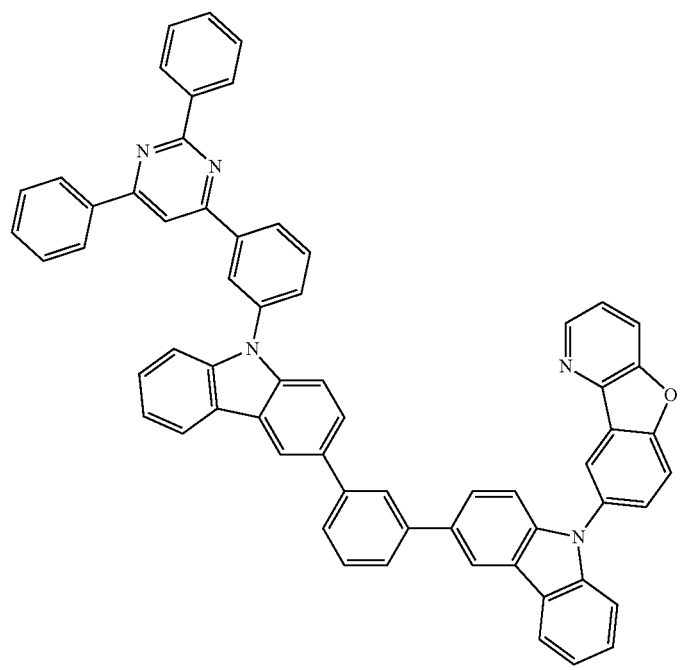
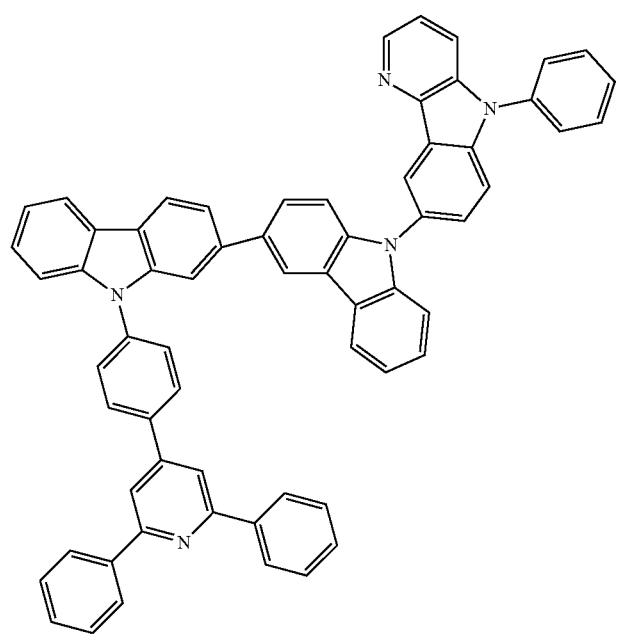

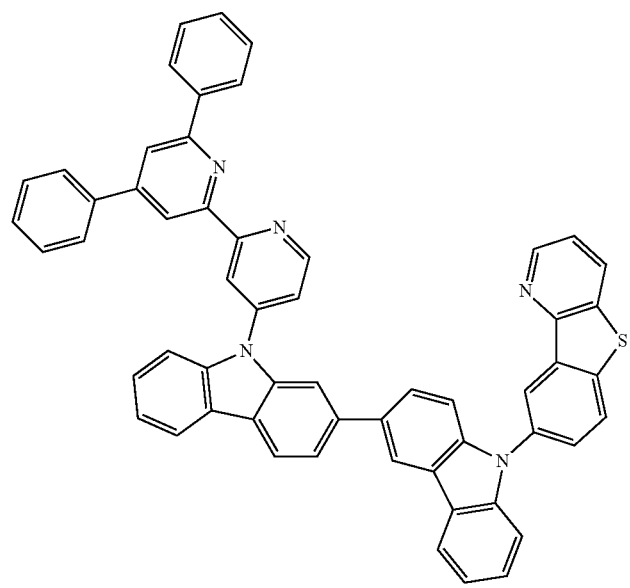
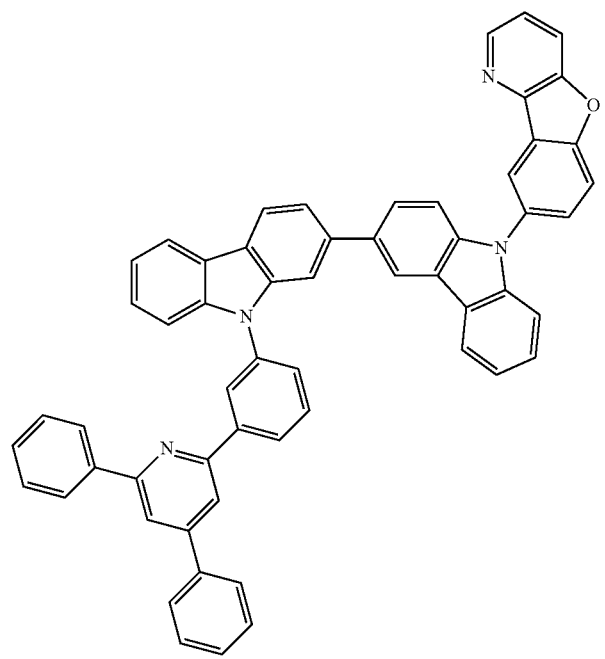

-continued
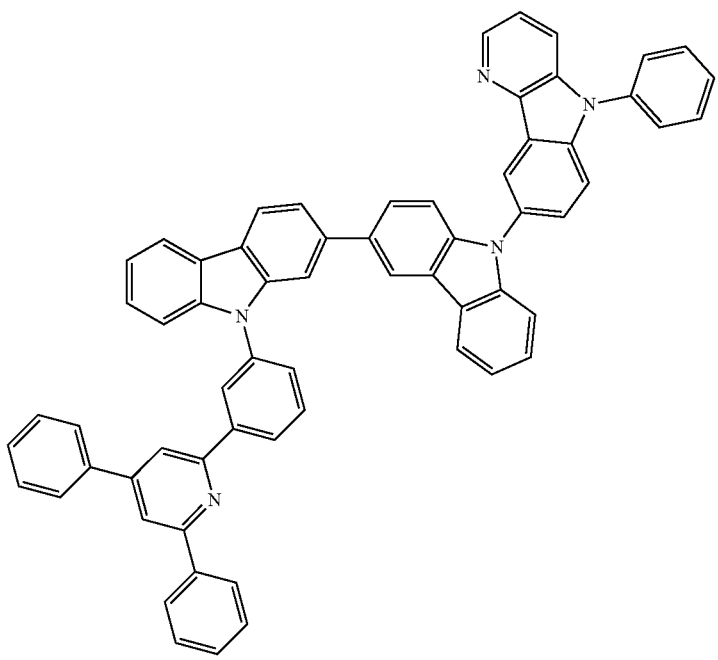
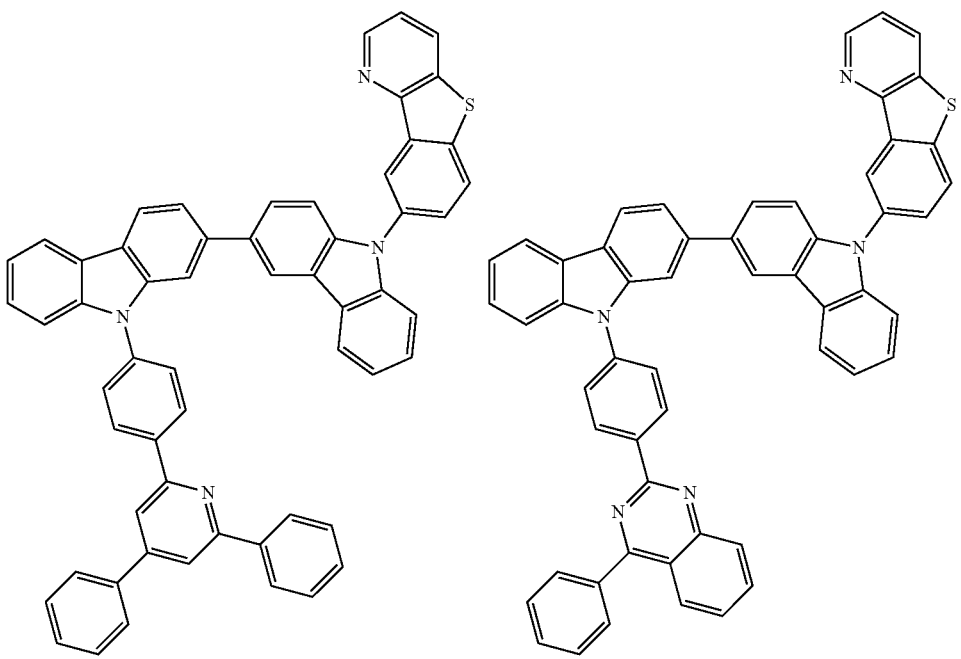

291 292
-continued
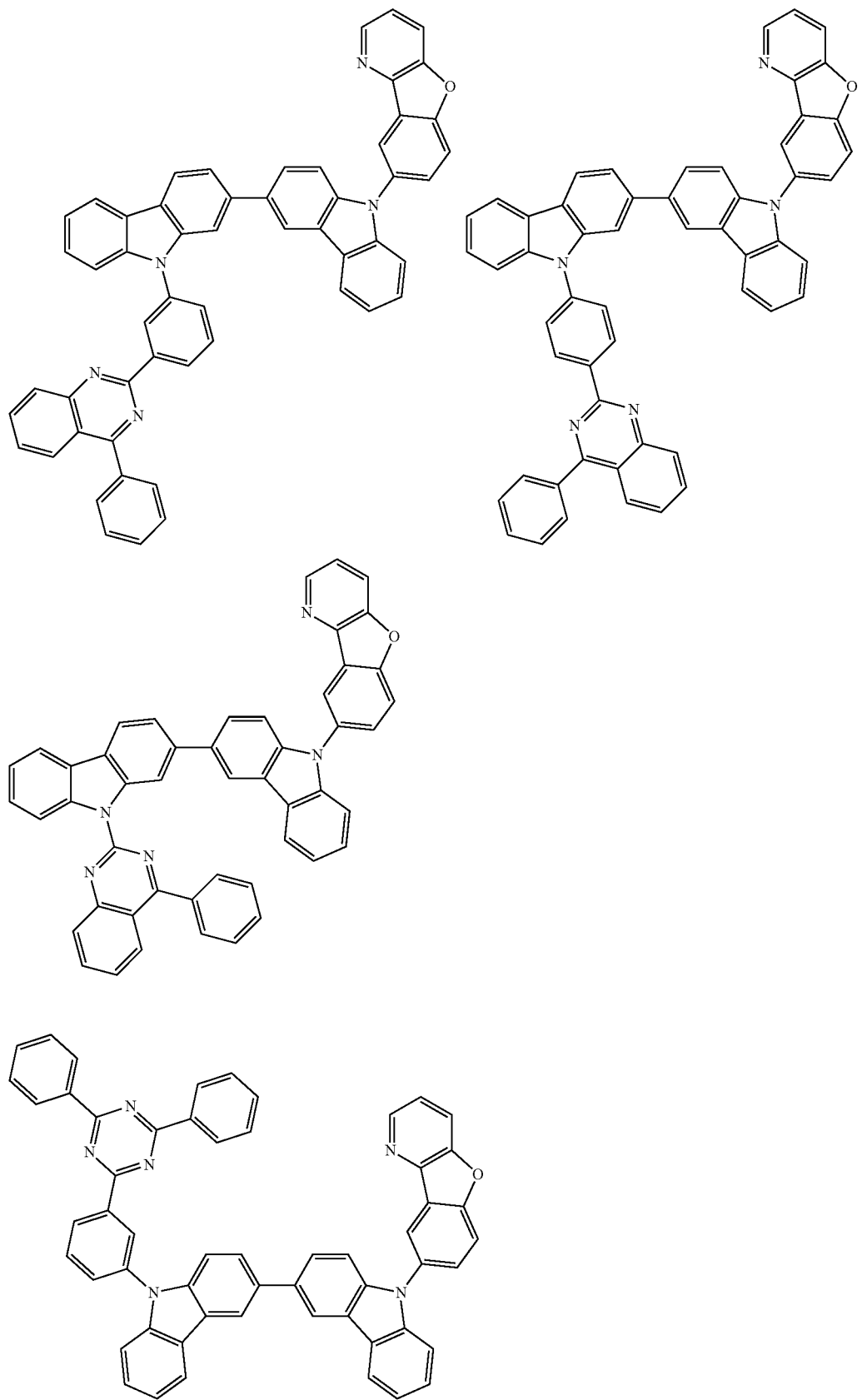 [SMILES: c1ccc(-c2nc(-c3cccc(-n4c5ccccc5c5ccc(-c6ccc7c(c6)c6ccccc6n7-c6ccc7oc8cccnc8c7c6)cc54)c3)nc3ccccc23)cc1 ; c1ccc(-c2nc(-c3ccc(-n4c5ccccc5c5ccc(-c6ccc7c(c6)c6ccccc6n7-c6ccc7oc8cccnc8c7c6)cc54)cc3)nc3ccccc23)cc1 ; c1ccc(-c2nc(-n3c4ccccc4c4ccc(-c5ccc6c(c5)c5ccccc5n6-c5ccc6oc7cccnc7c6c5)cc43)nc3ccccc23)cc1 ; c1ccc(-c2nc(-c3ccccc3)nc(-c3cccc(-n4c5ccccc5c5cc(-c6ccc7c(c6)c6ccccc6n7-c6ccc7oc8cccnc8c7c6)ccc54)c3)n2)cc1]

-continued
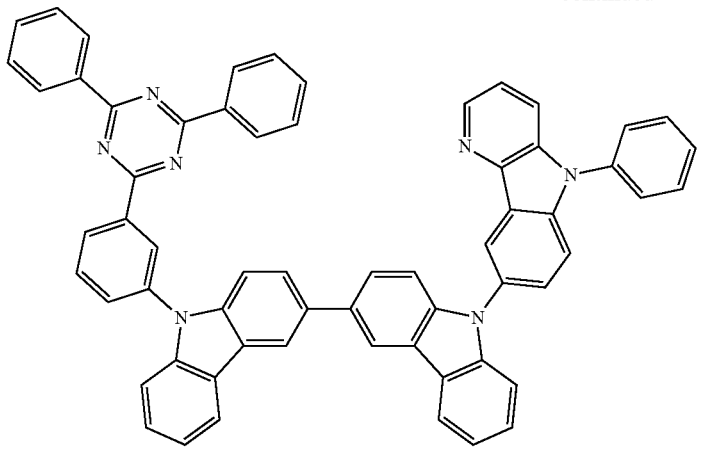
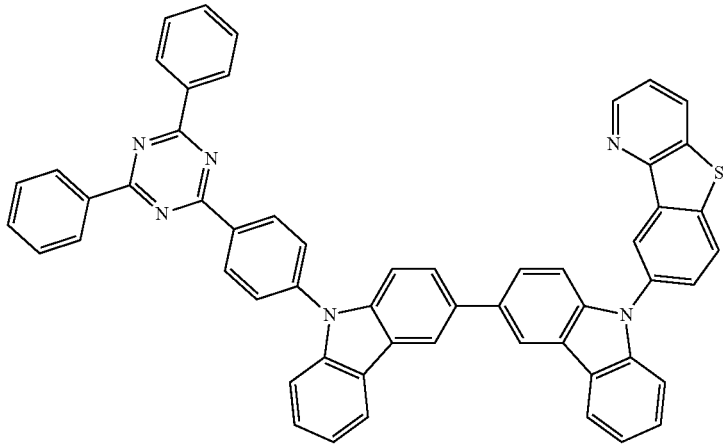
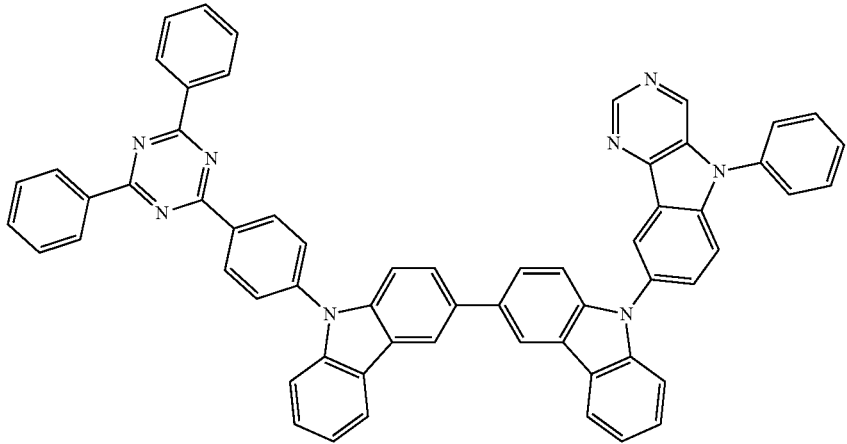
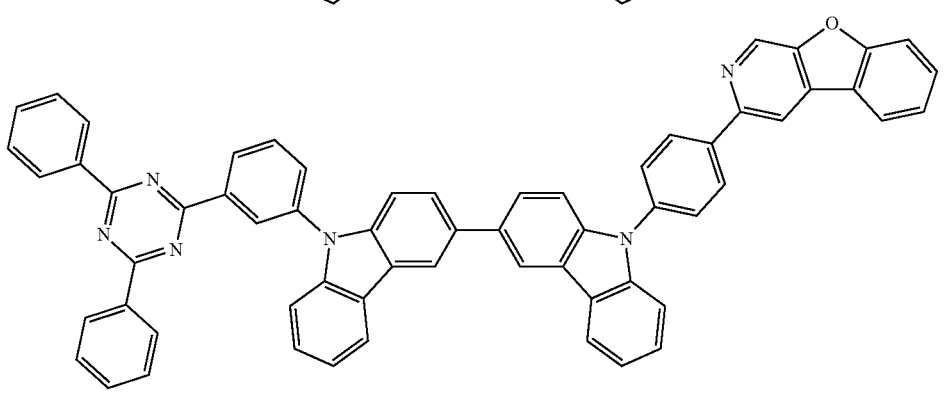

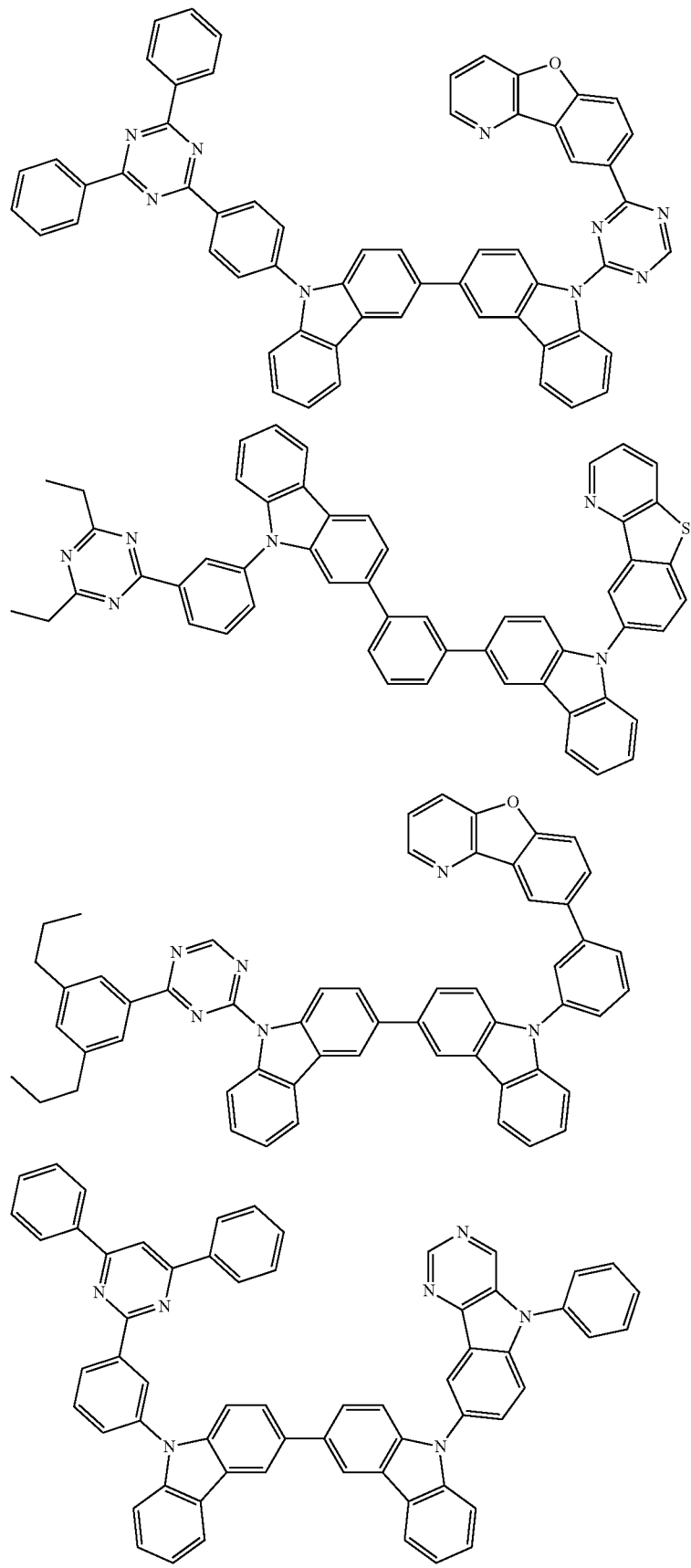

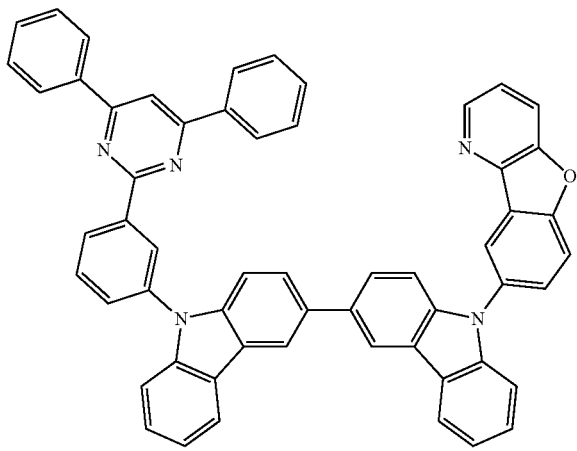
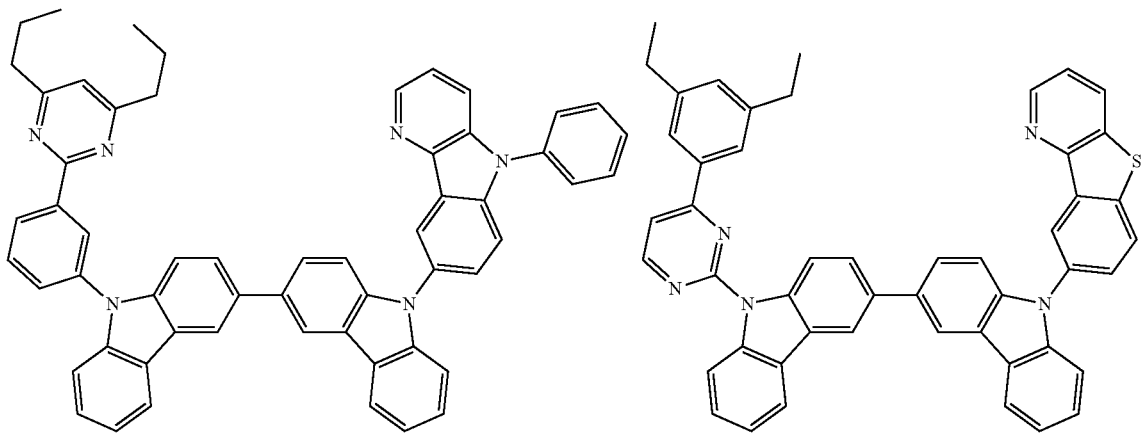
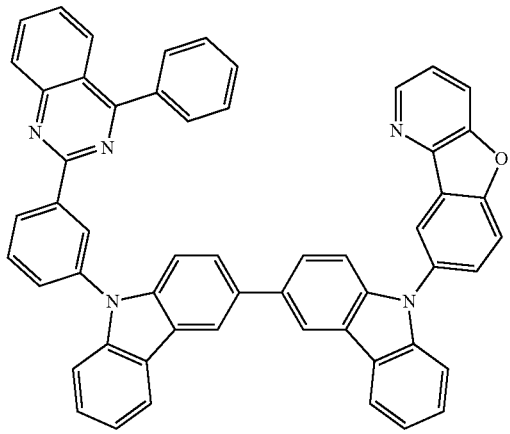
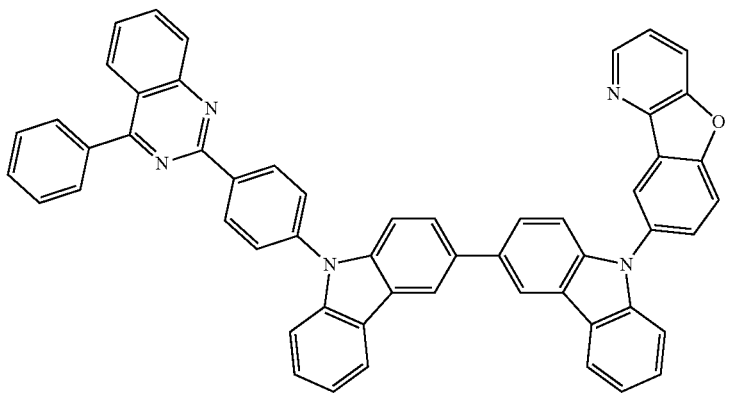

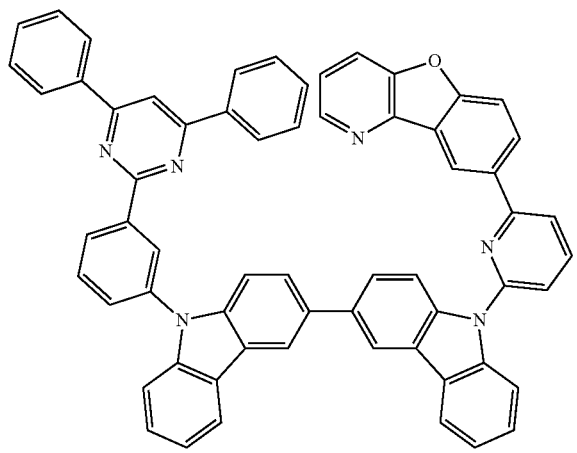
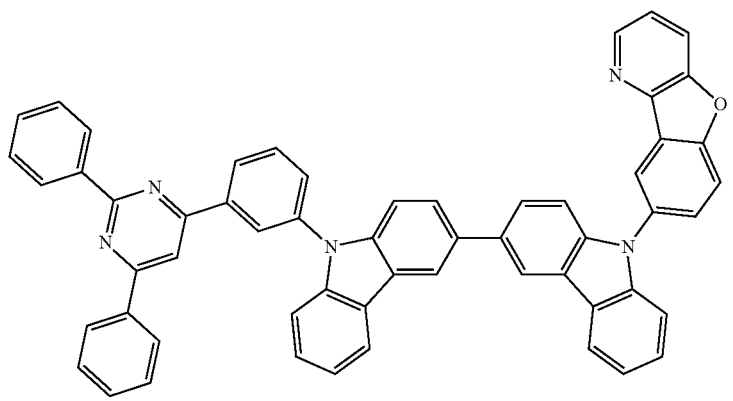
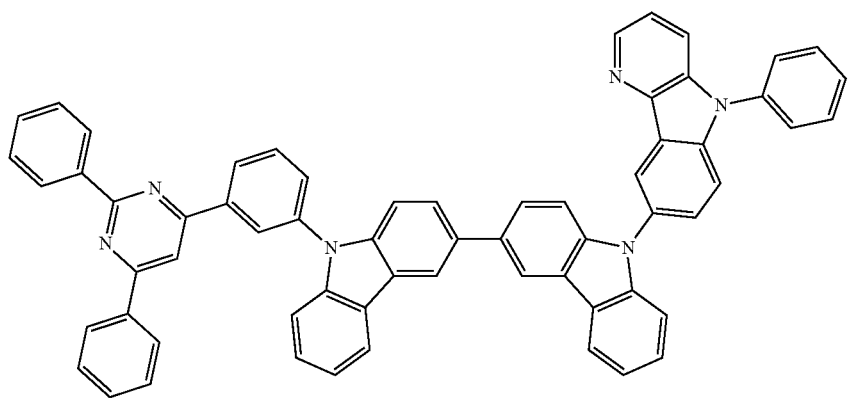
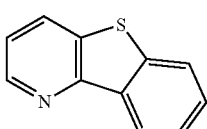
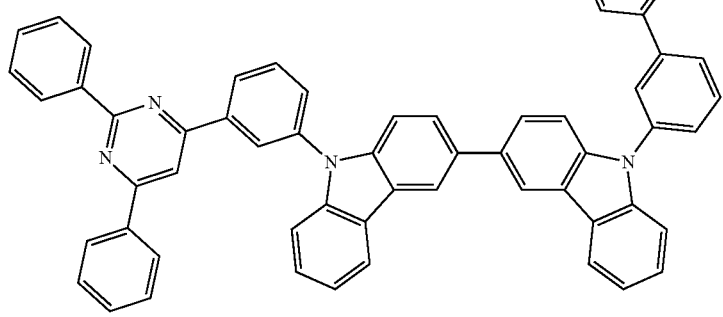

-continued
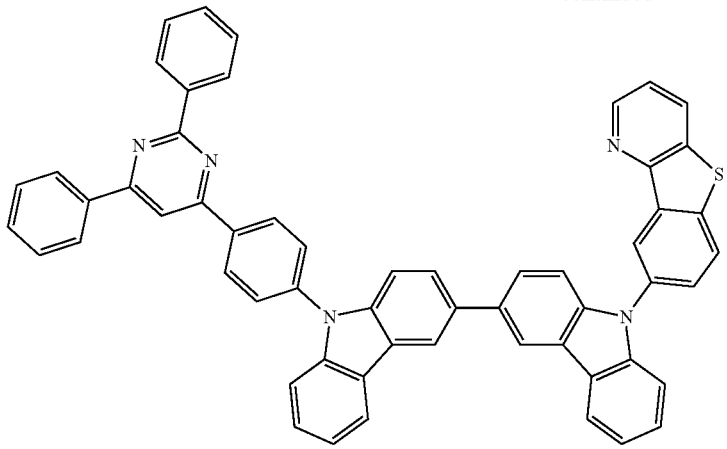
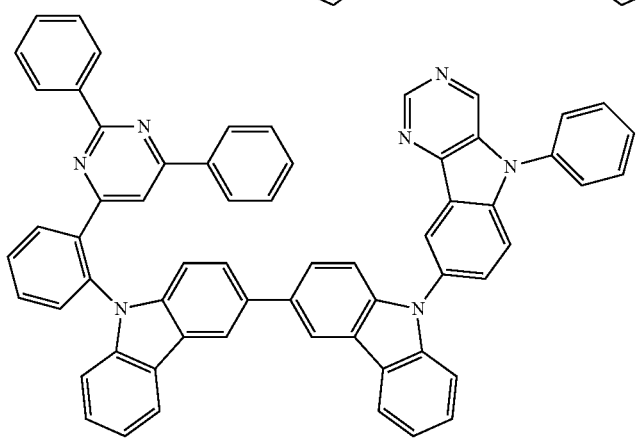
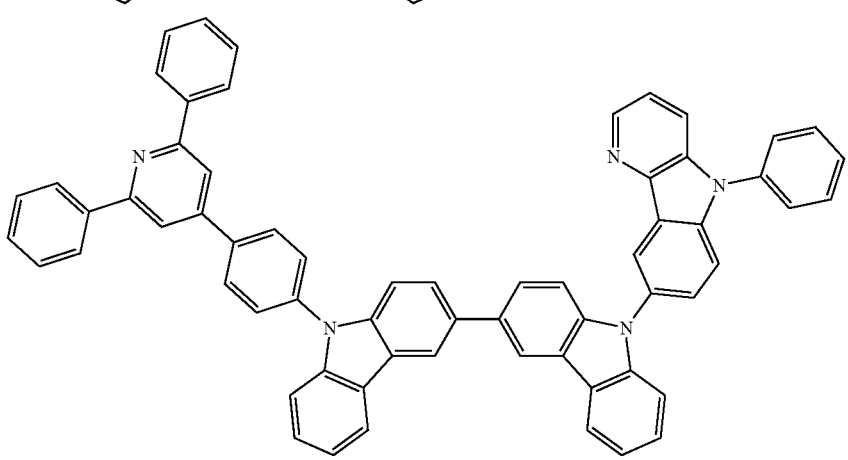
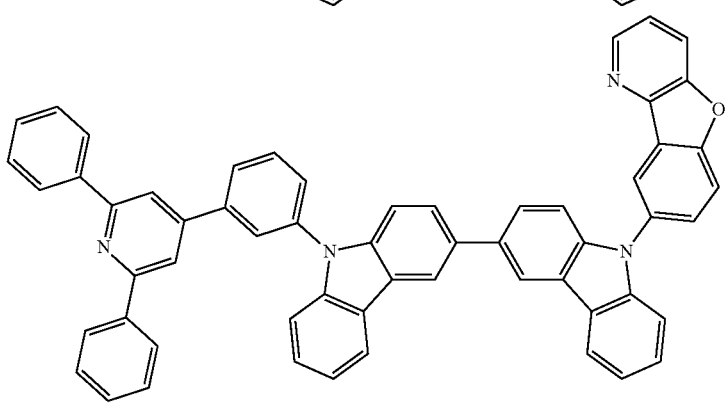

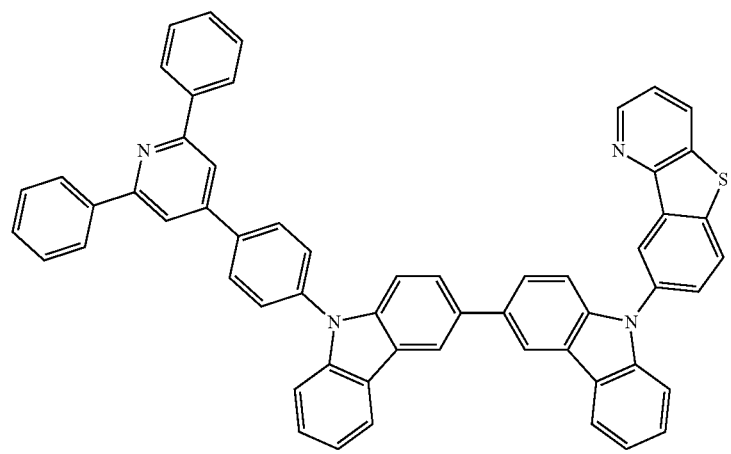
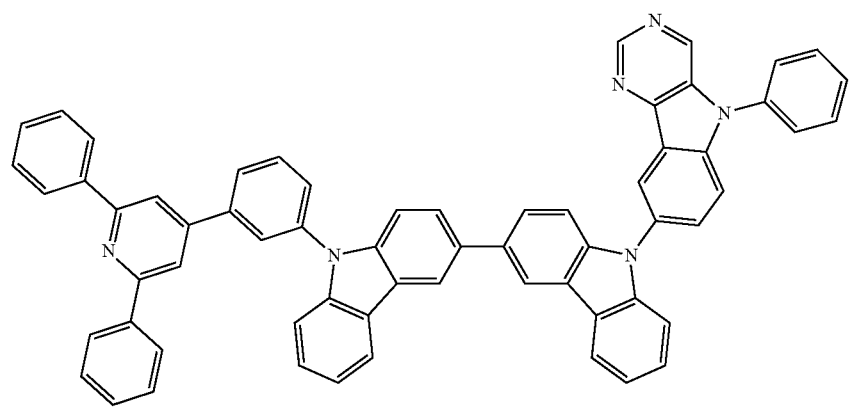
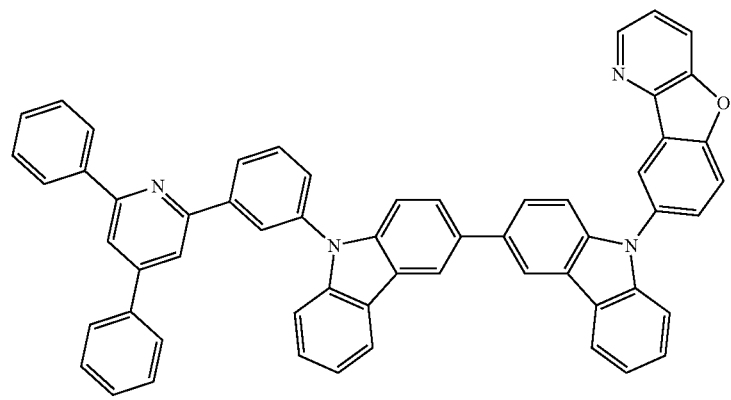
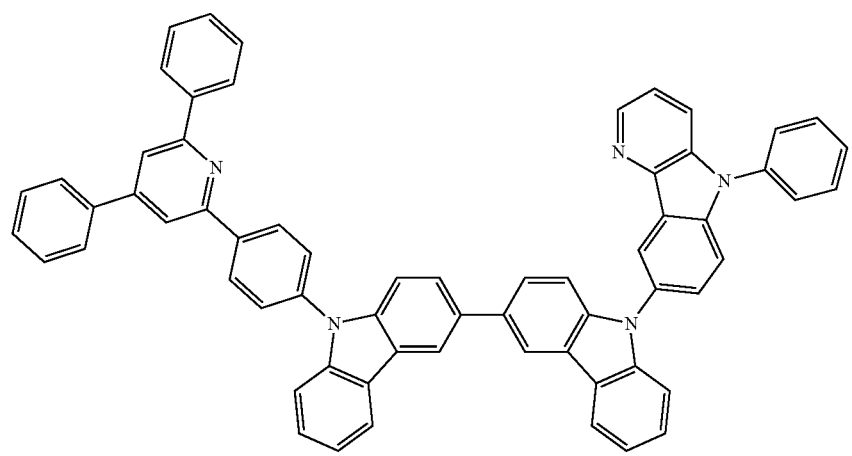

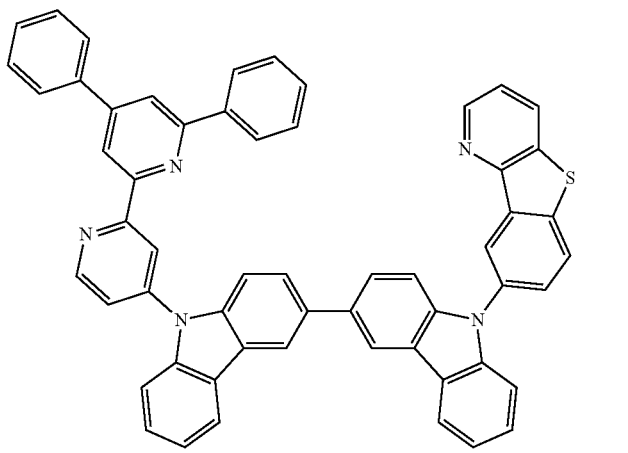
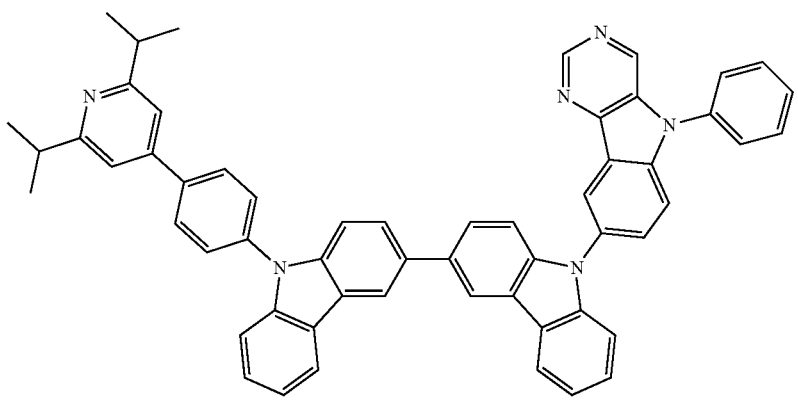
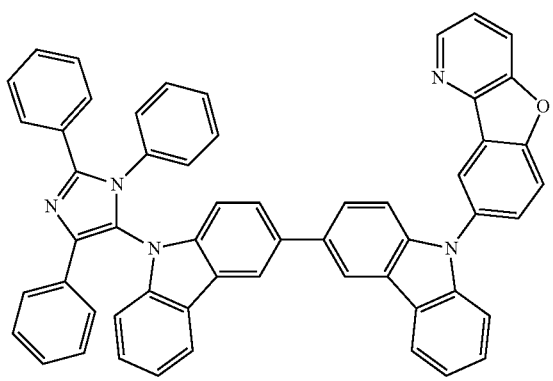
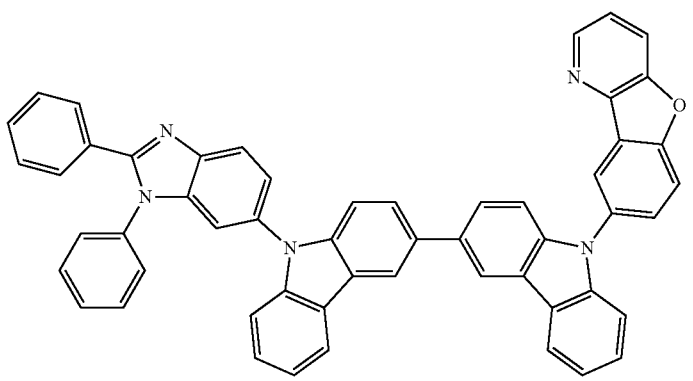

-continued
307
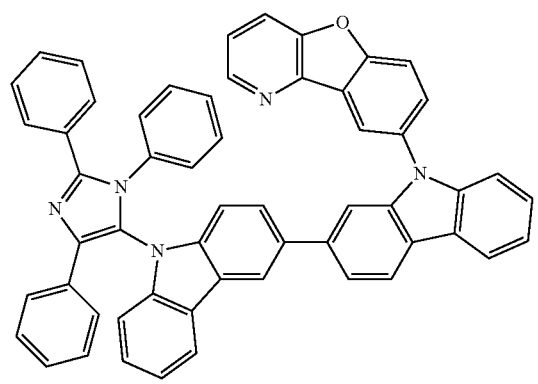
308
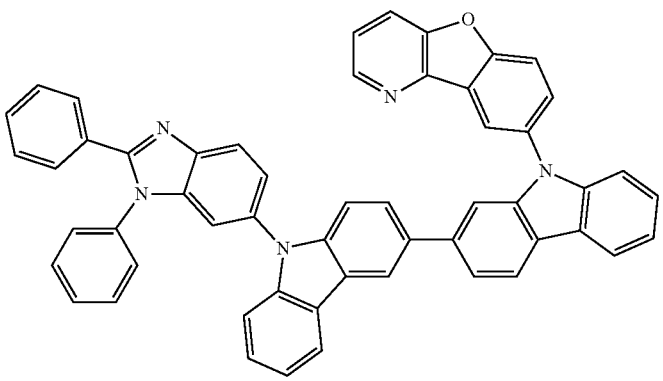
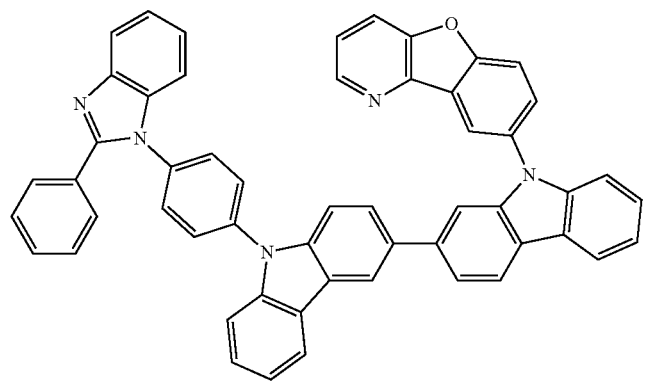
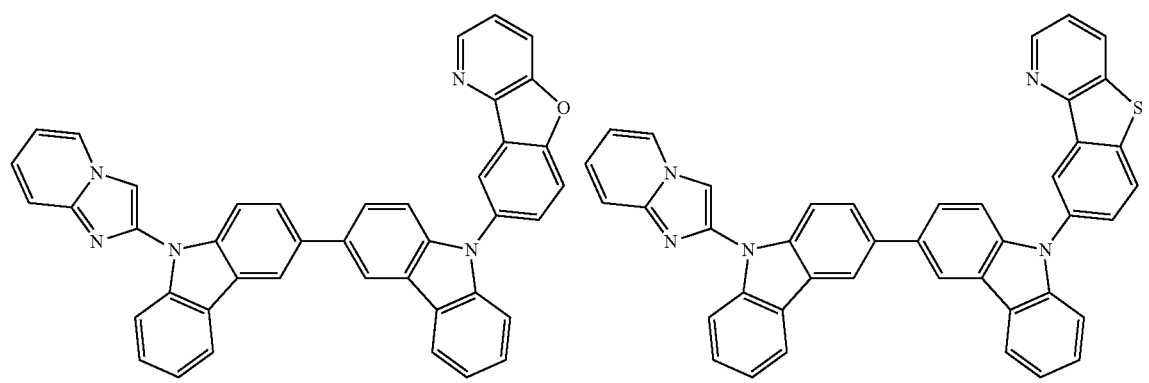

309
310
-continued
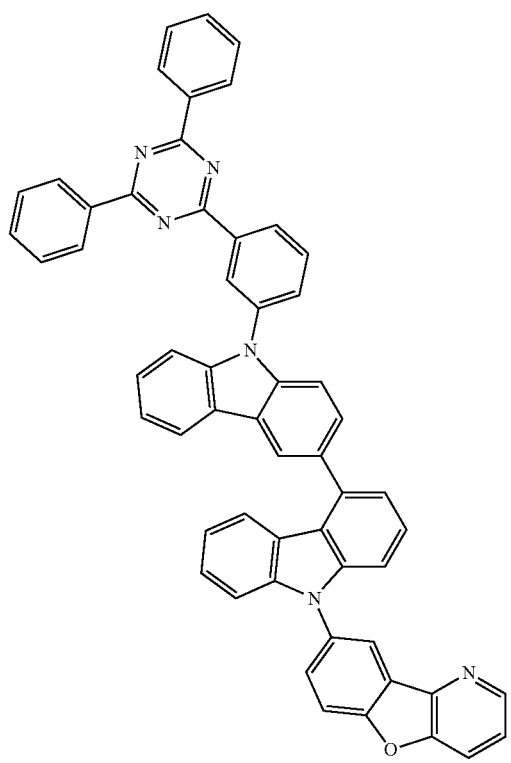
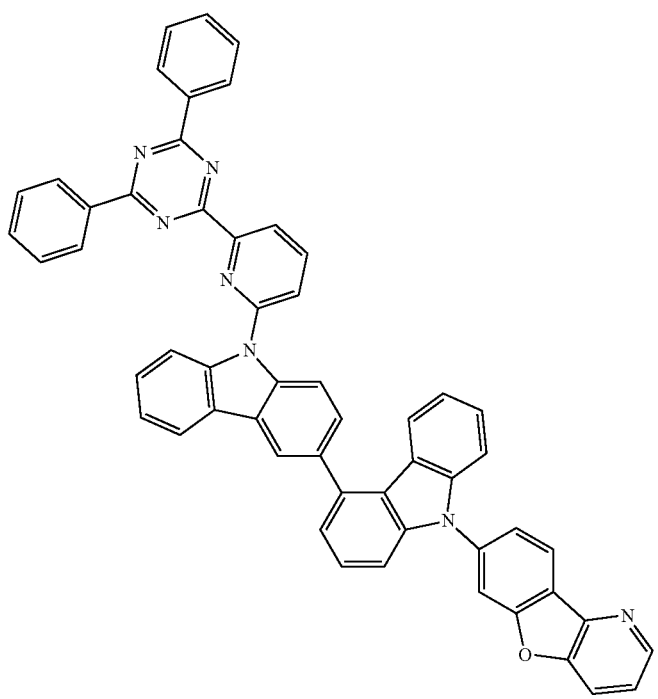
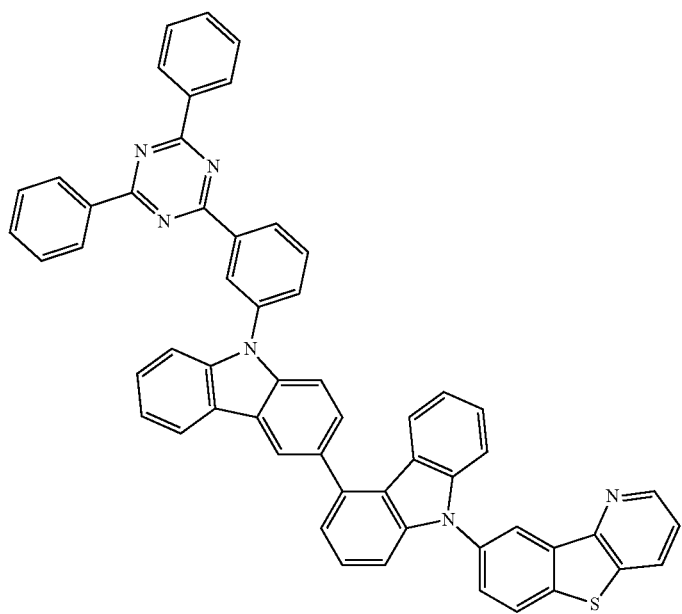

-continued
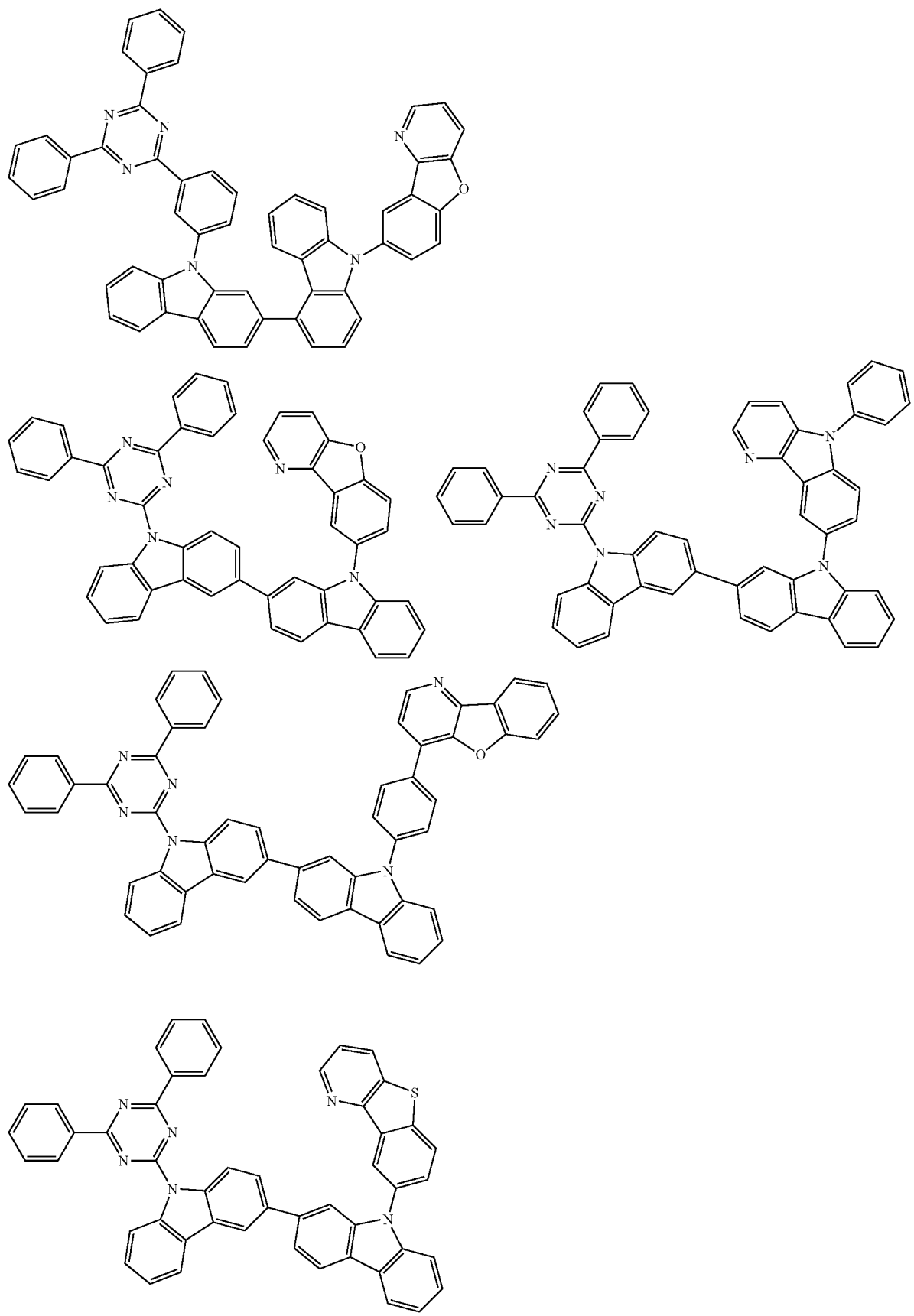

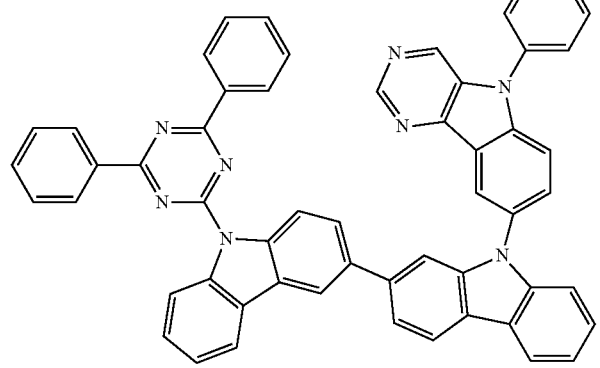
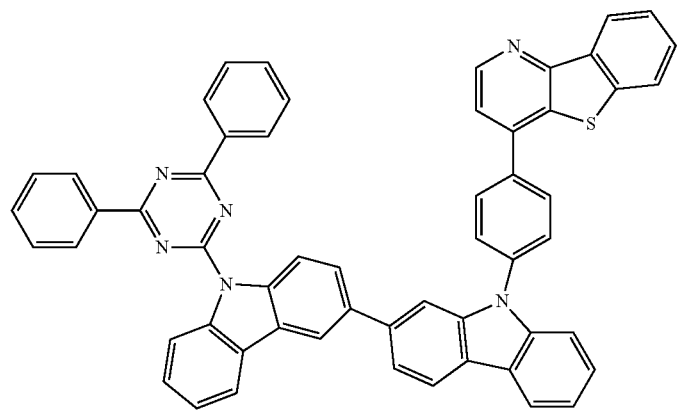
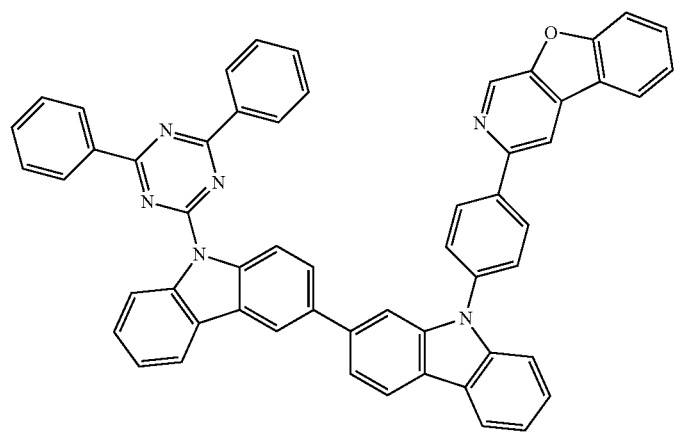
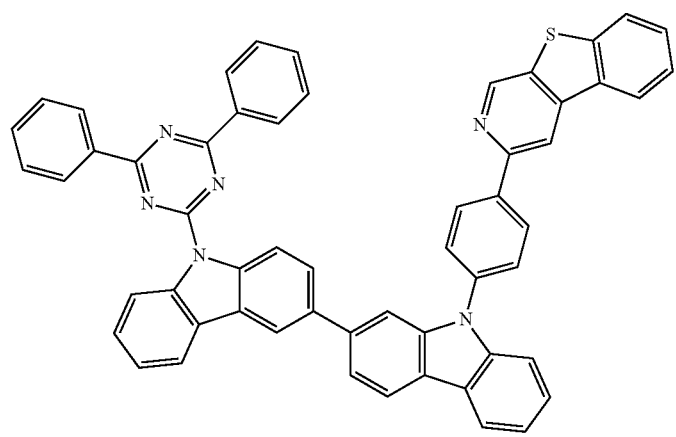

-continued
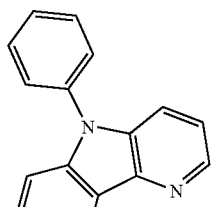
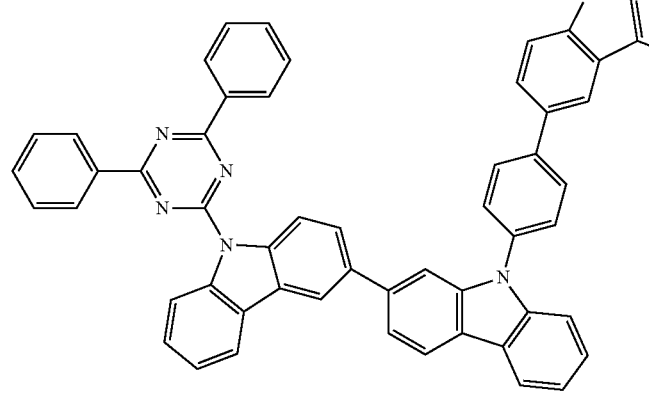
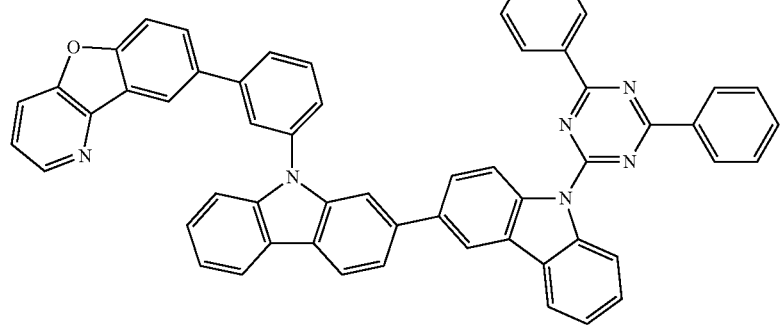
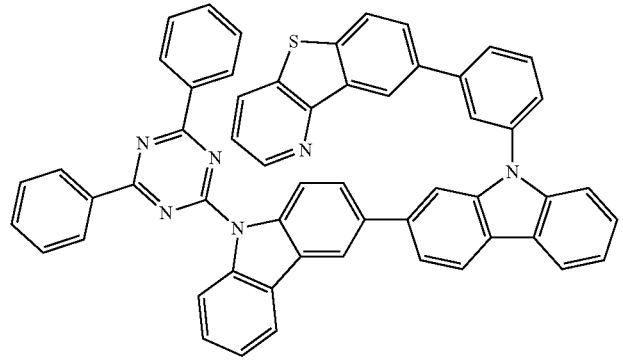
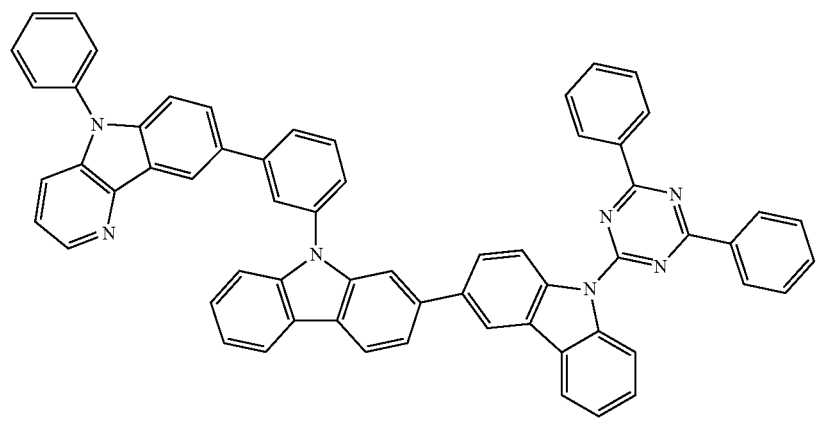

-continued
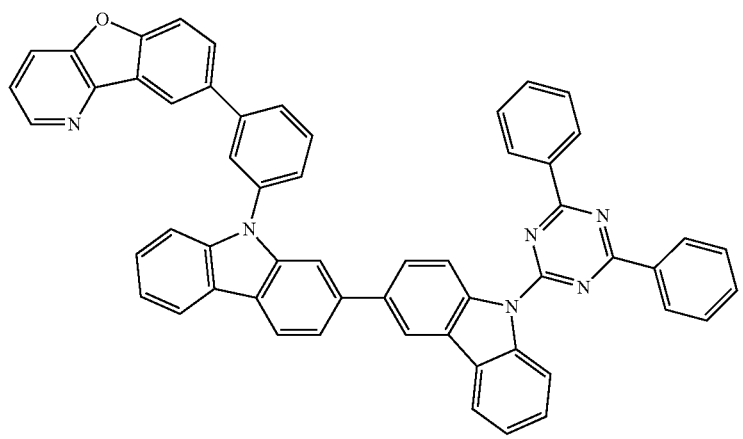
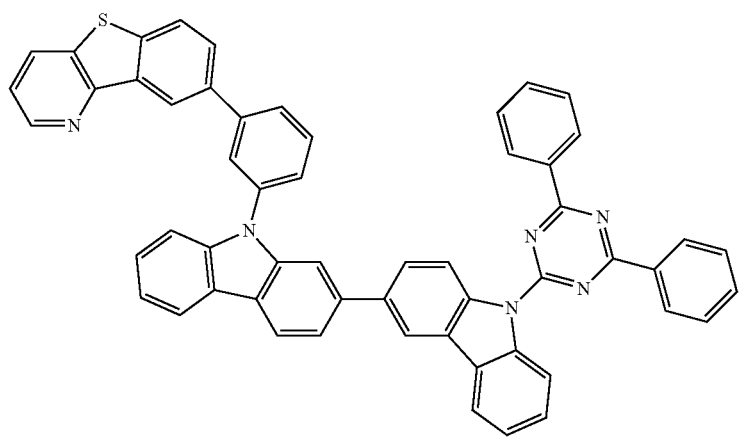
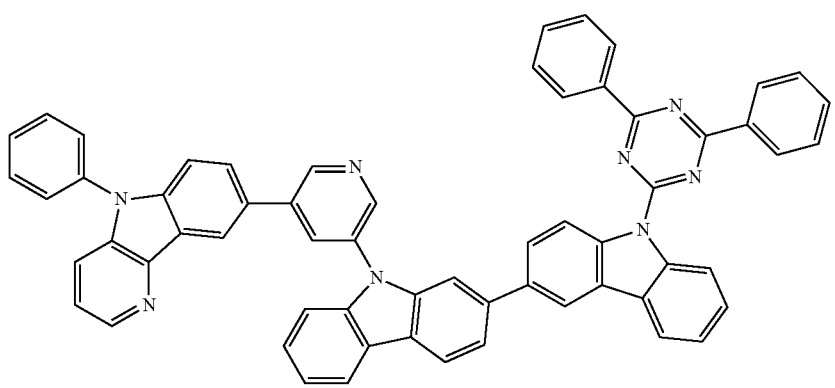
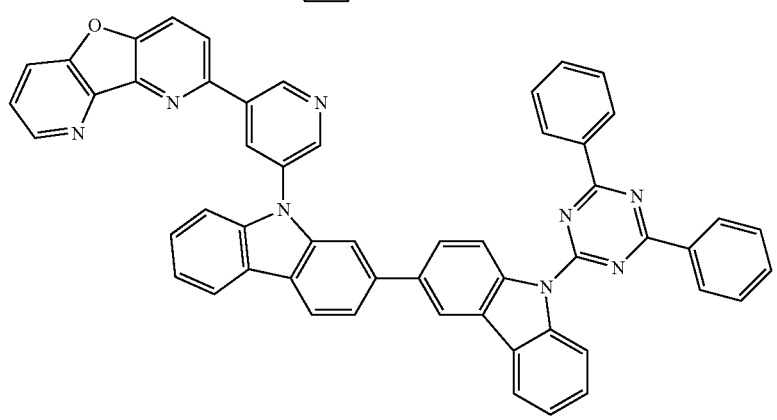

-continued
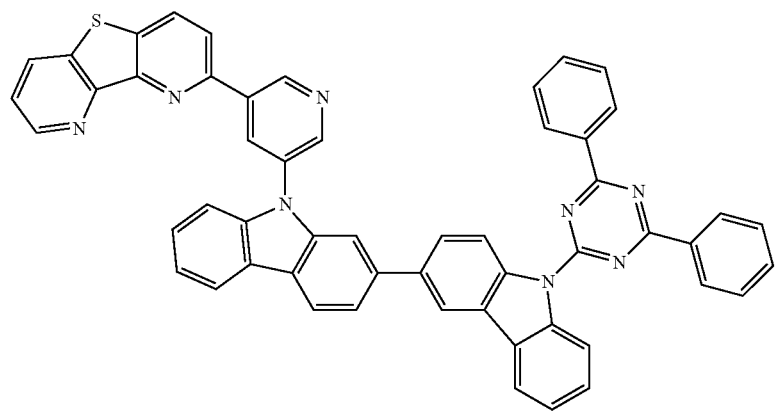
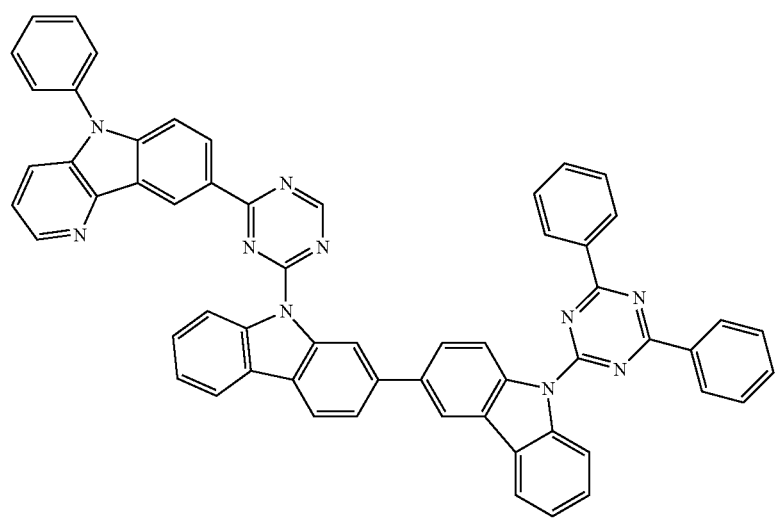
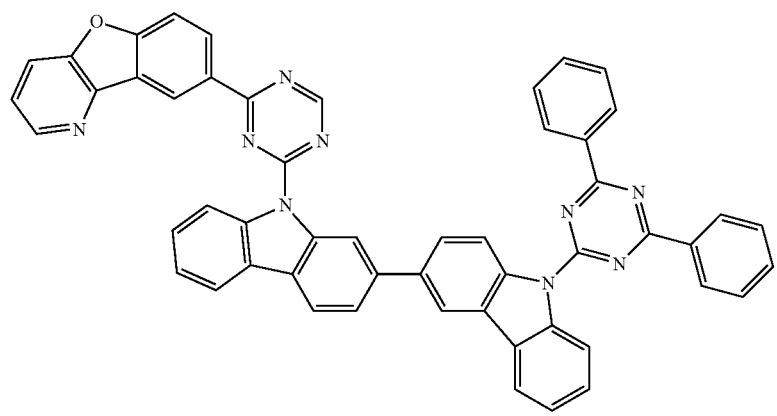

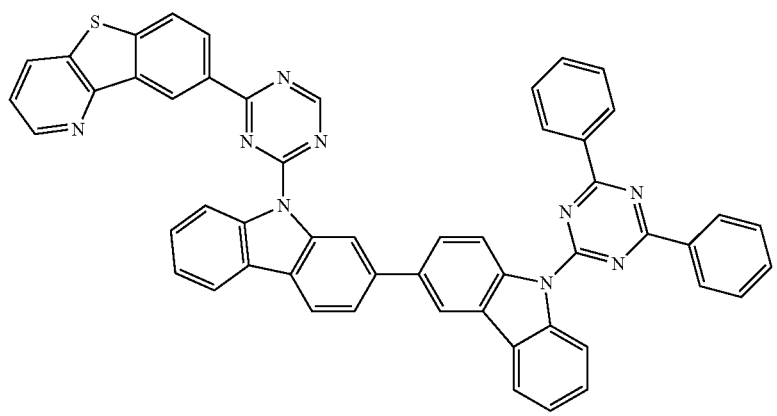
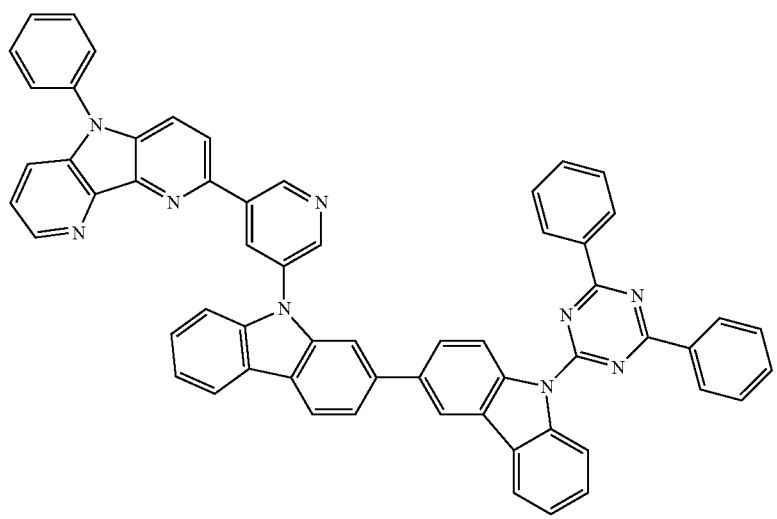
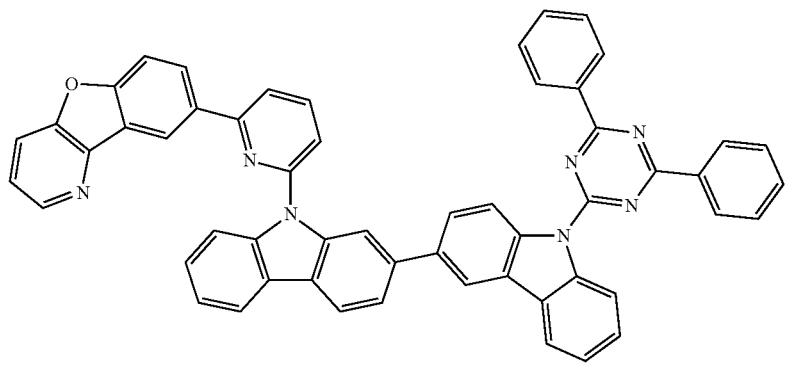

-continued
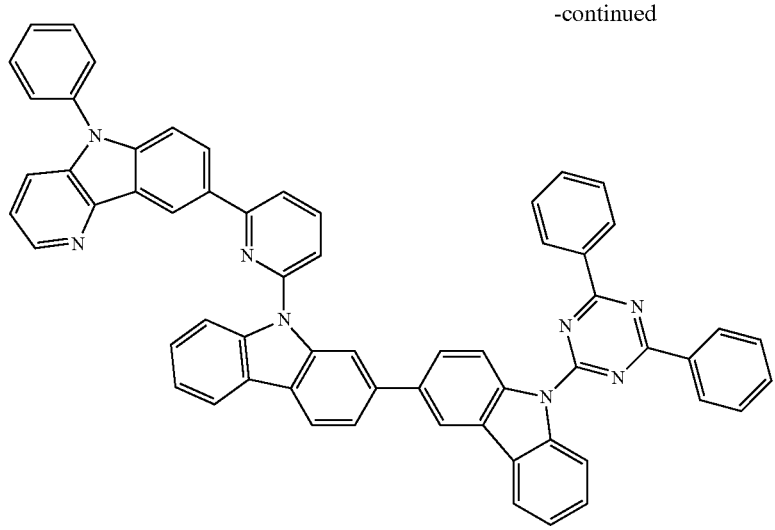
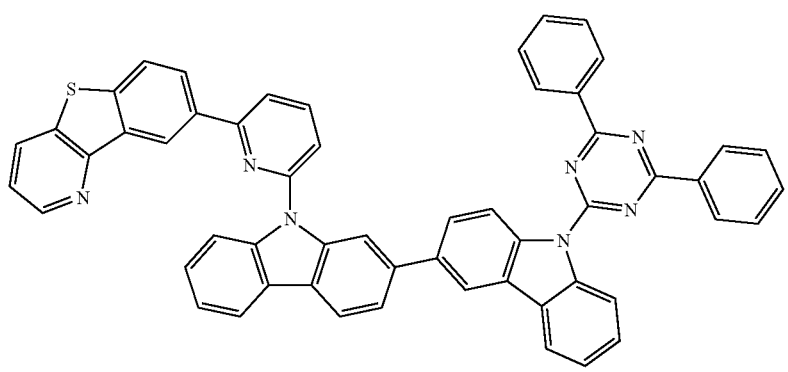 [SMILES: c1ccc(-c2nc(-c3ccccc3)nc(-n3c4ccccc4c4cc(-c5ccc6c7ccccc7n(-c7cccc(-c8ccc9sc%10cccnc%10c9c8)n7)c6c5)ccc43)n2)cc1]
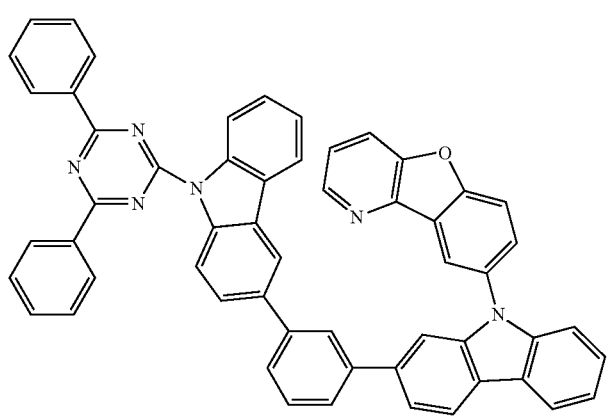

-continued
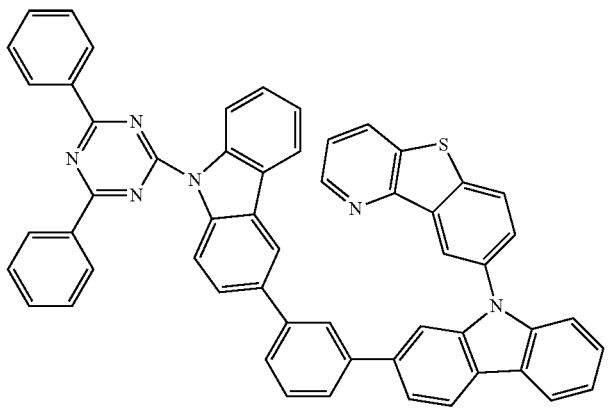
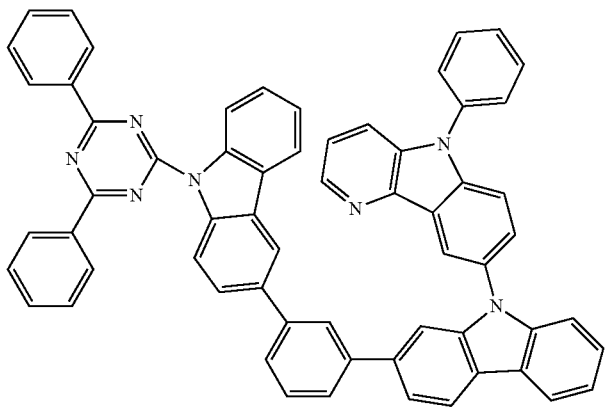
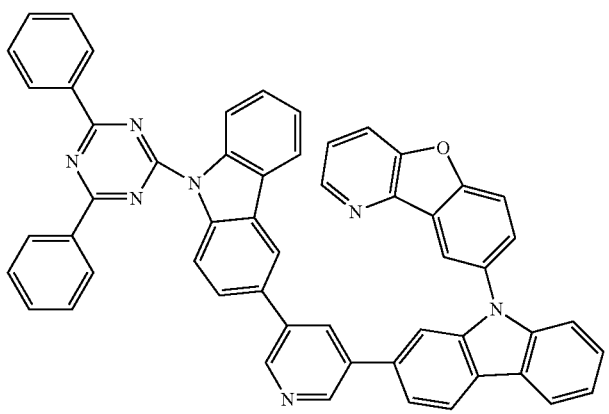
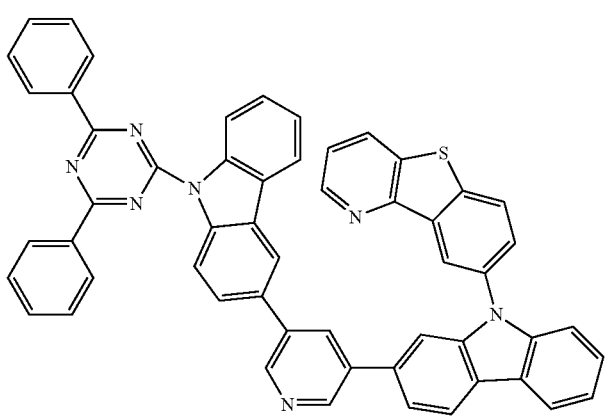

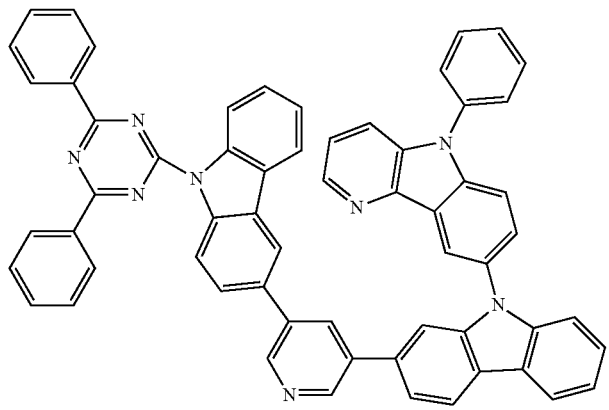
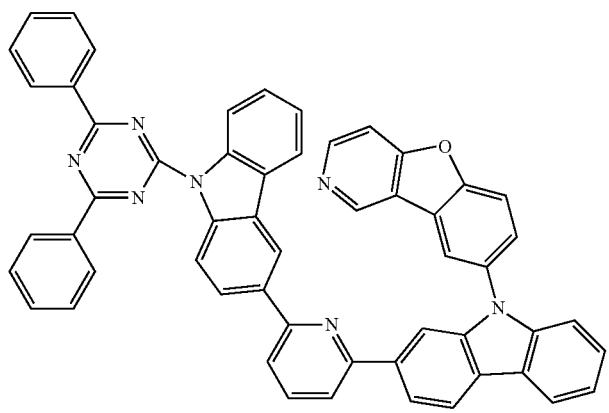
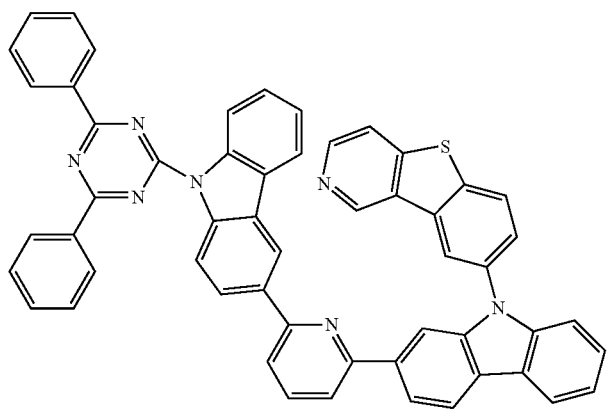
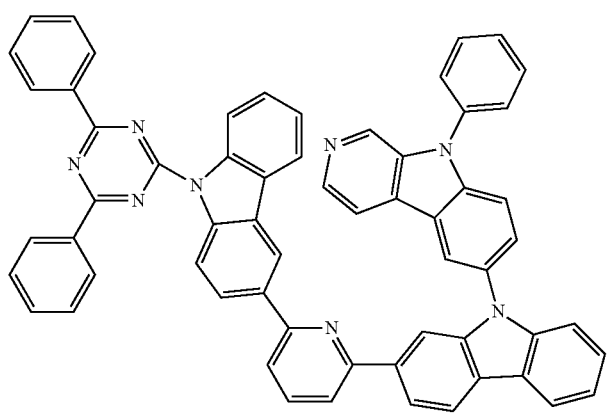

-continued
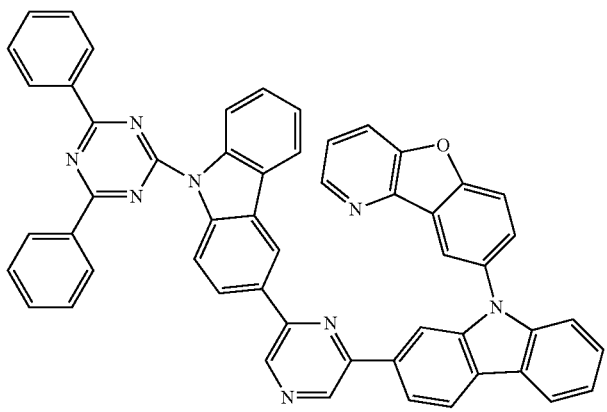
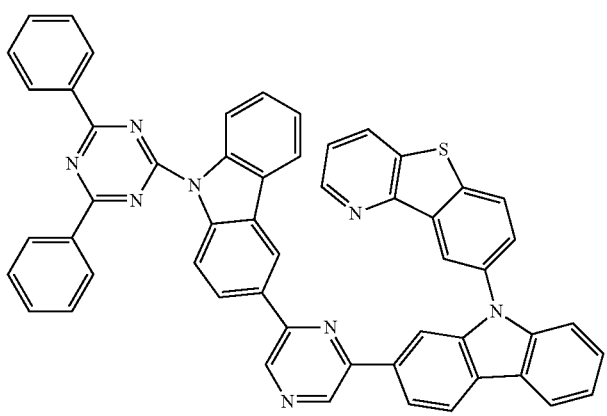
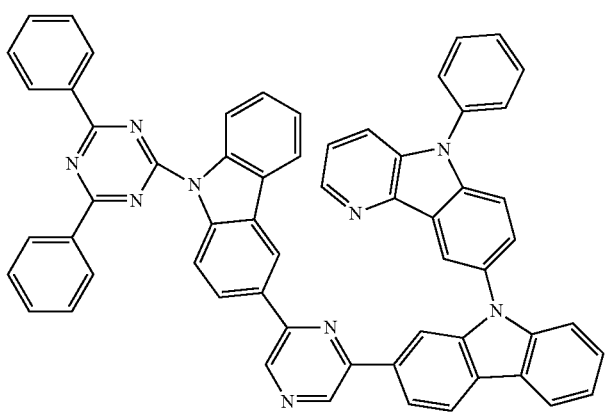
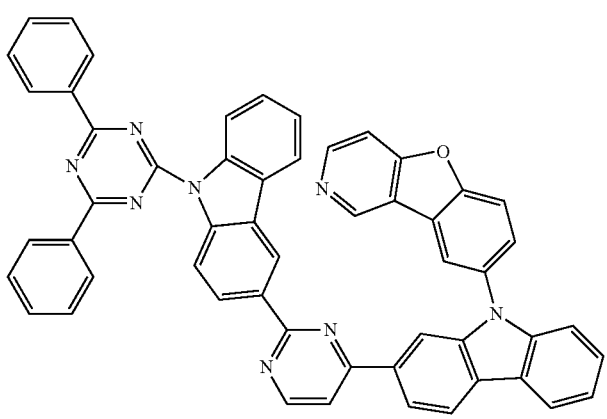

-continued
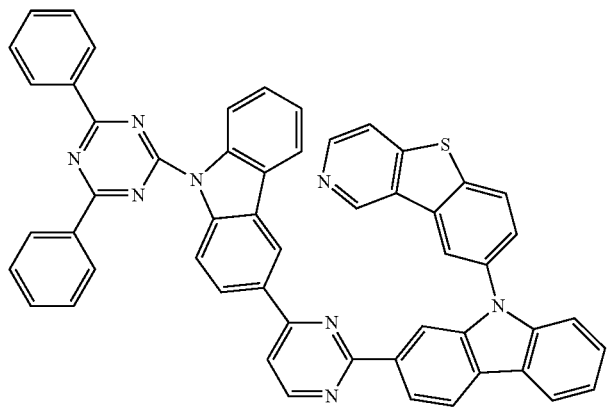
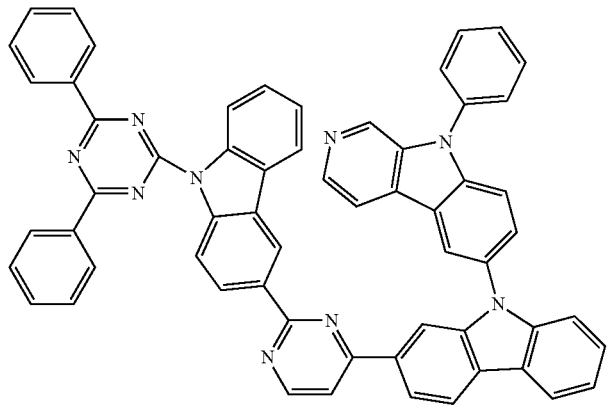
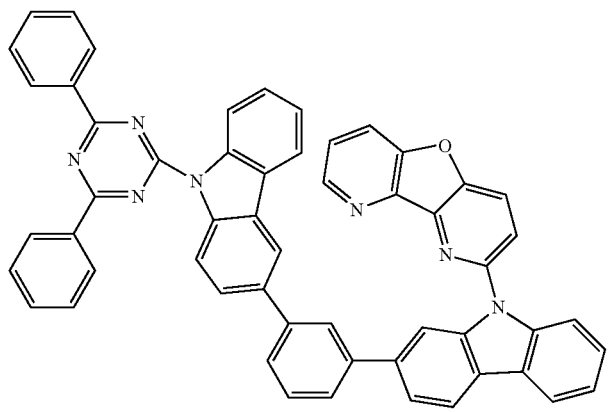
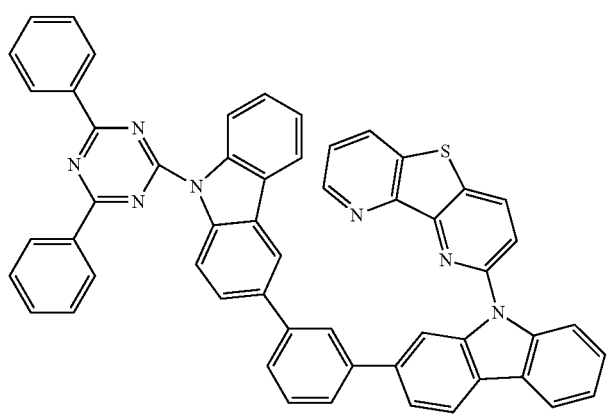

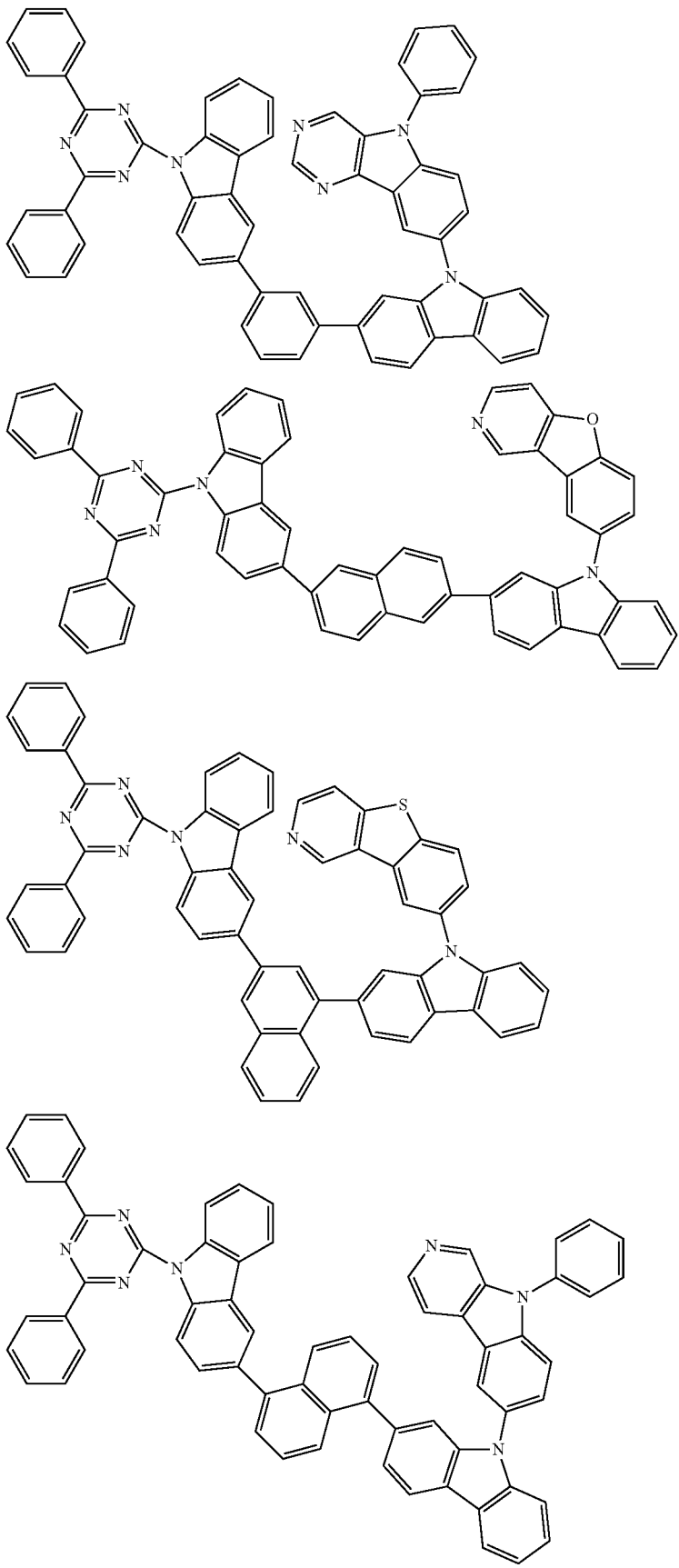

-continued
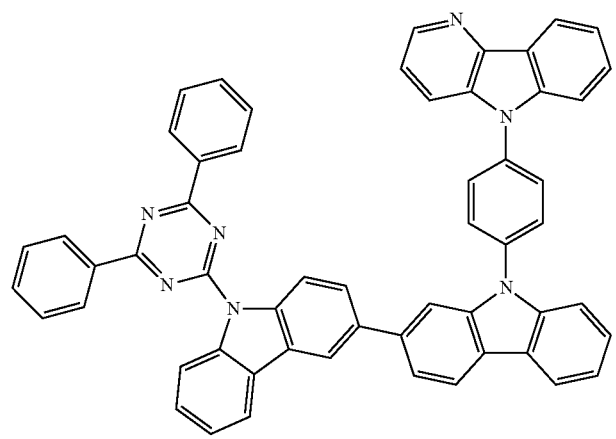
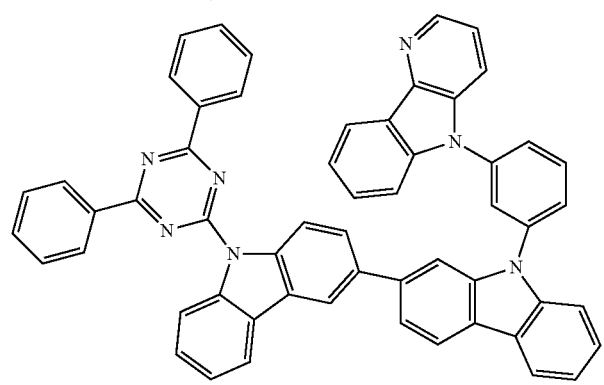
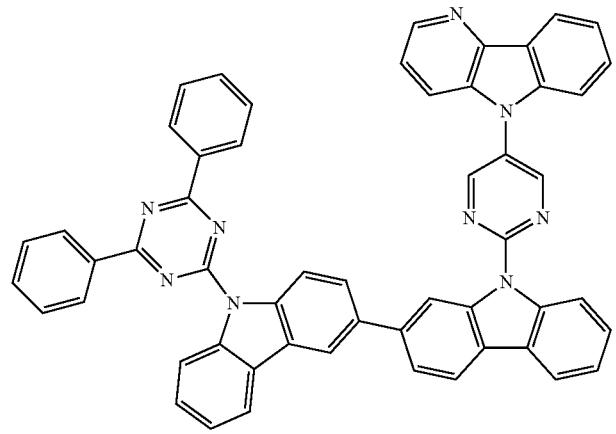
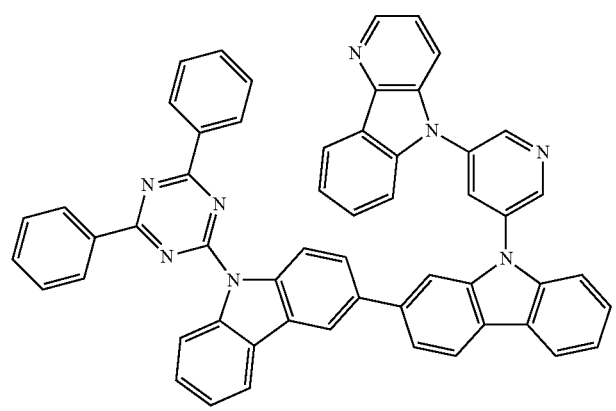

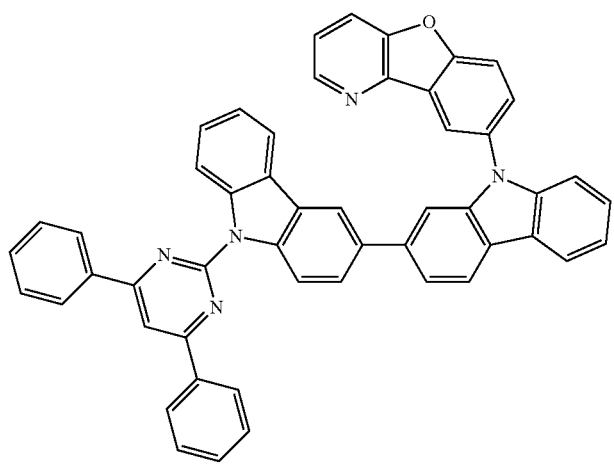
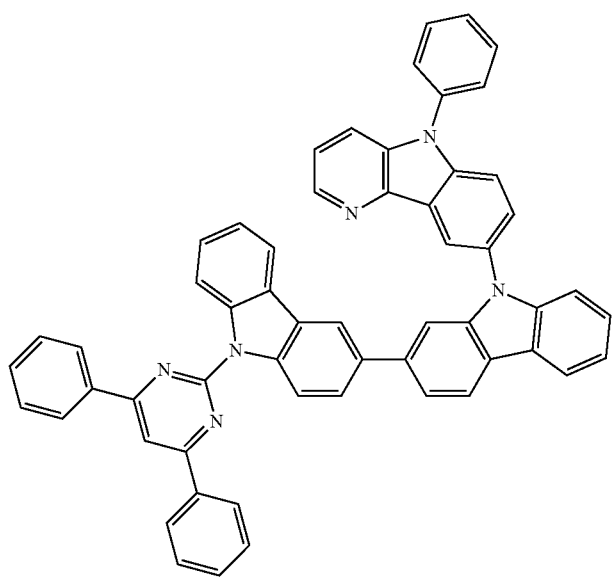
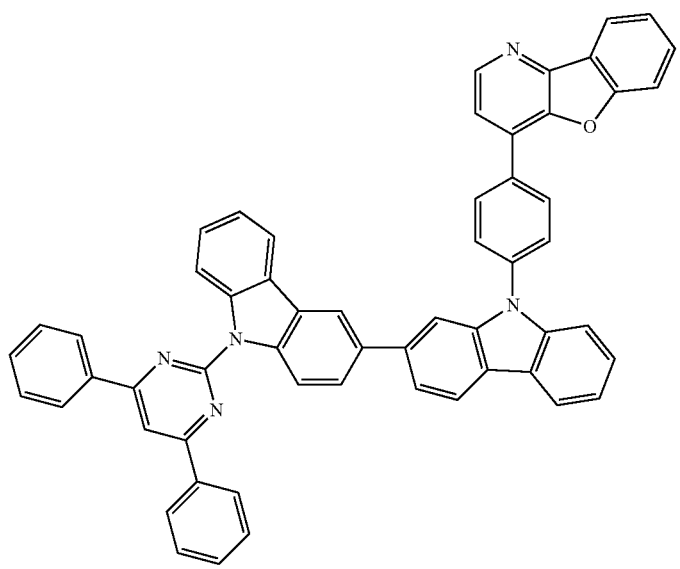

-continued
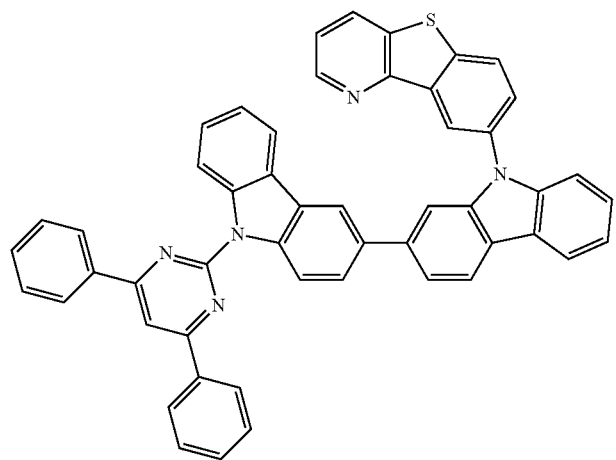
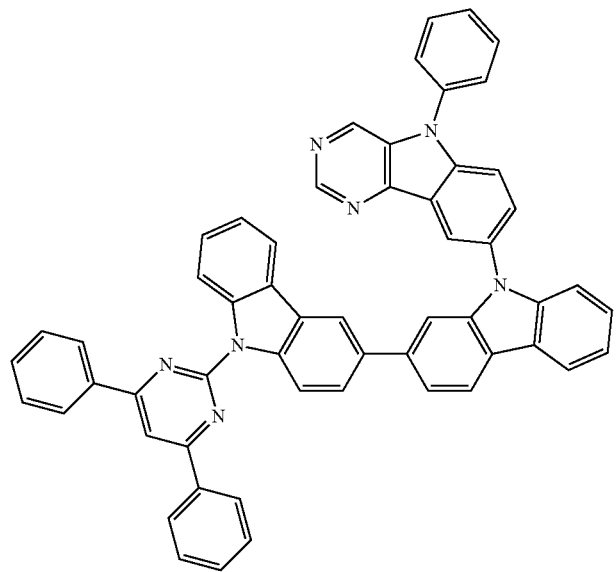
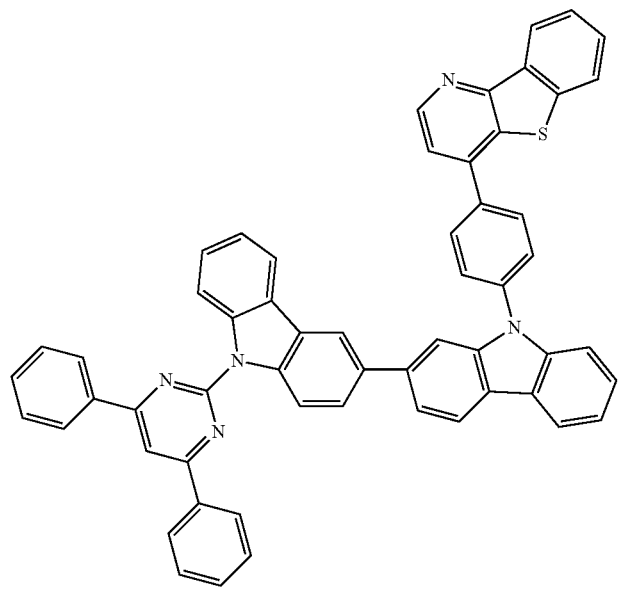

-continued
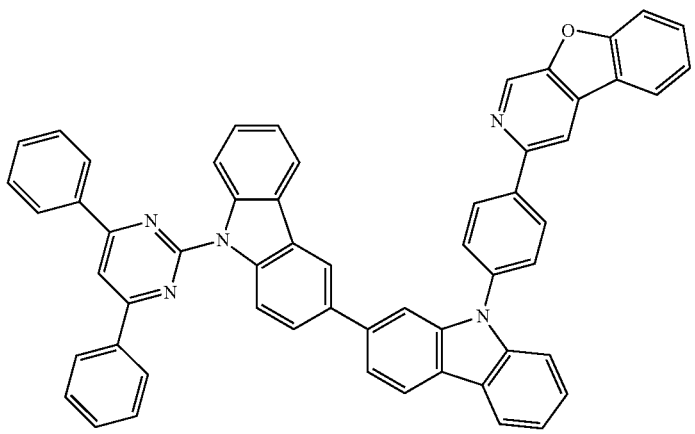
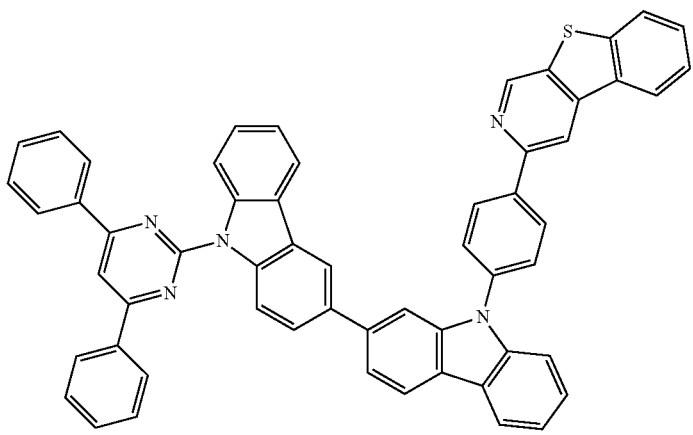
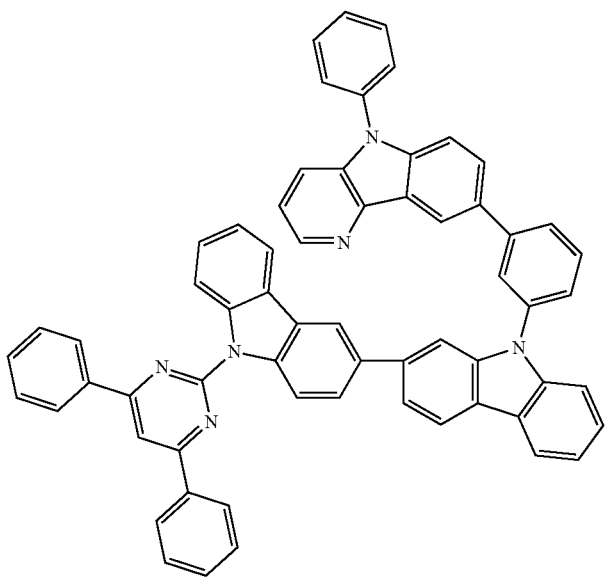

-continued
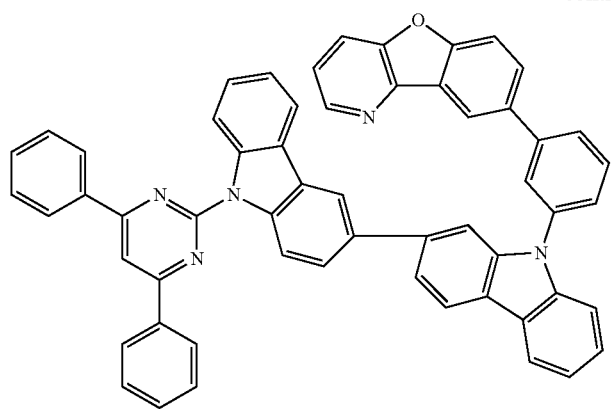
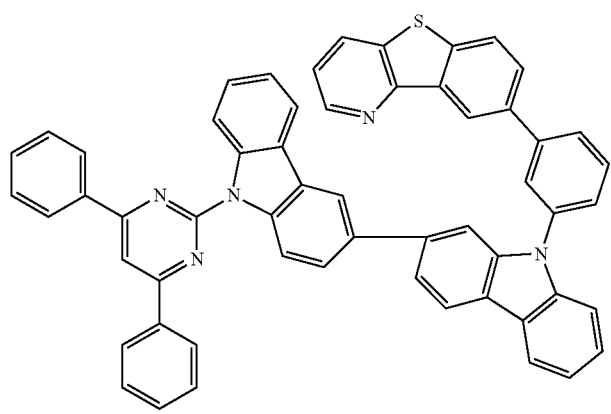
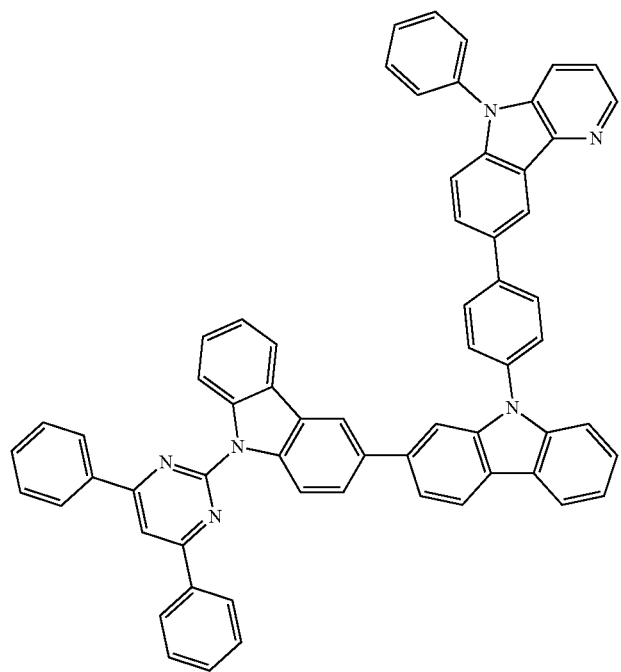

-continued
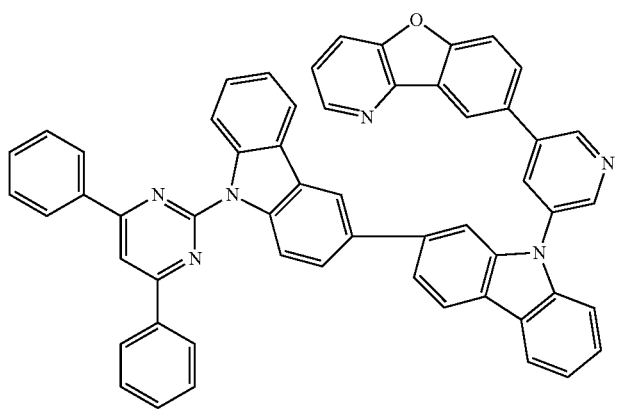
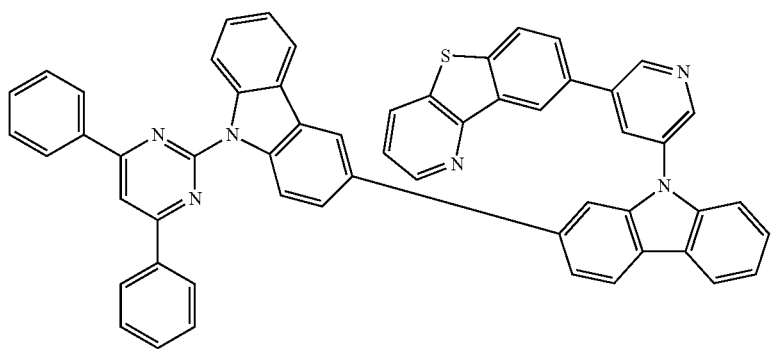
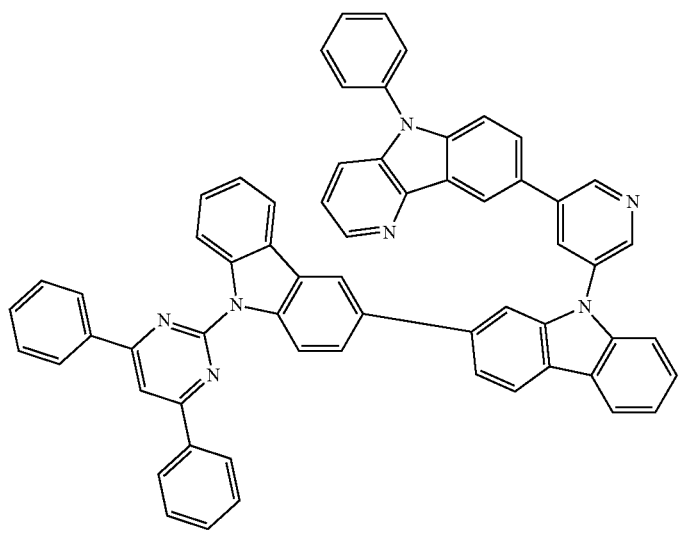

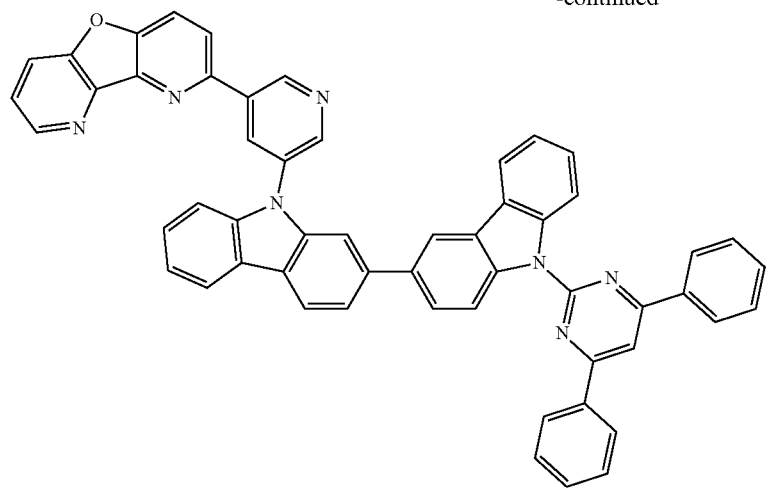
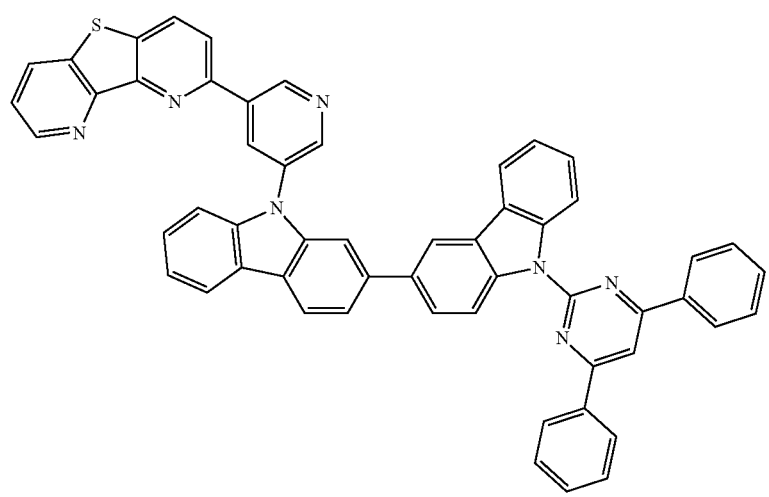
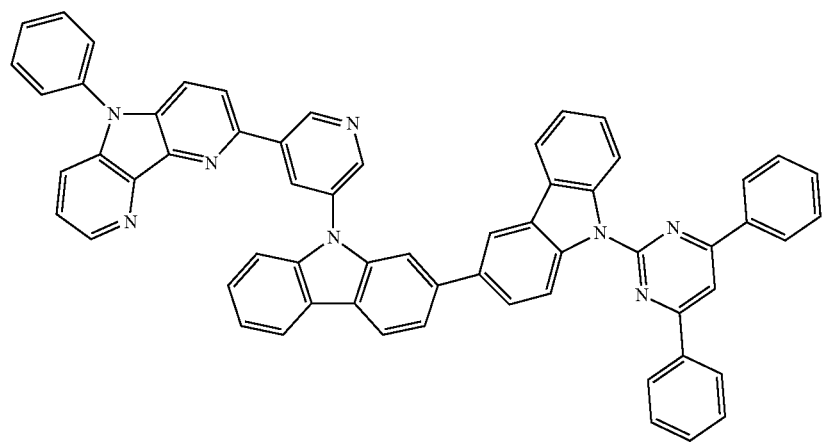

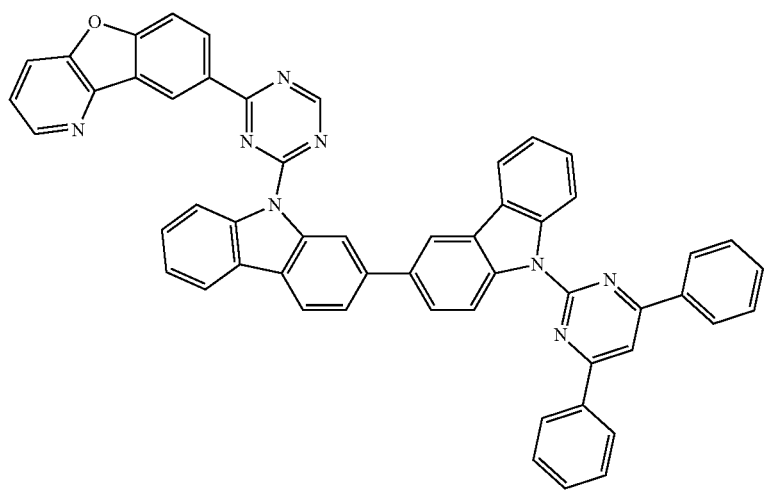
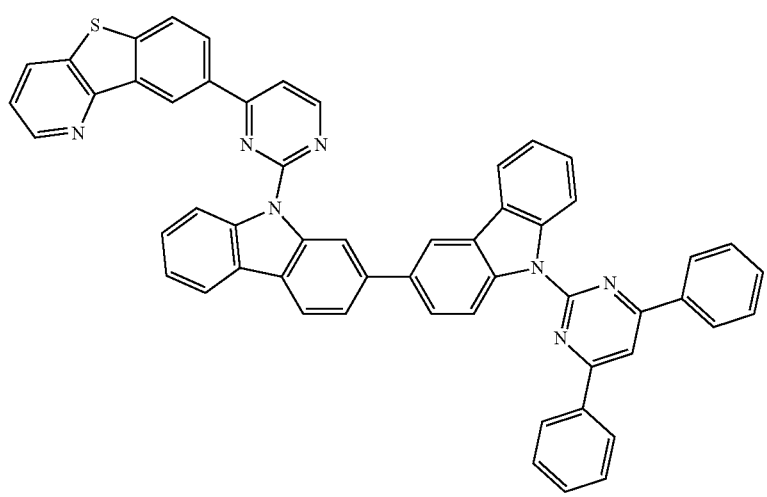
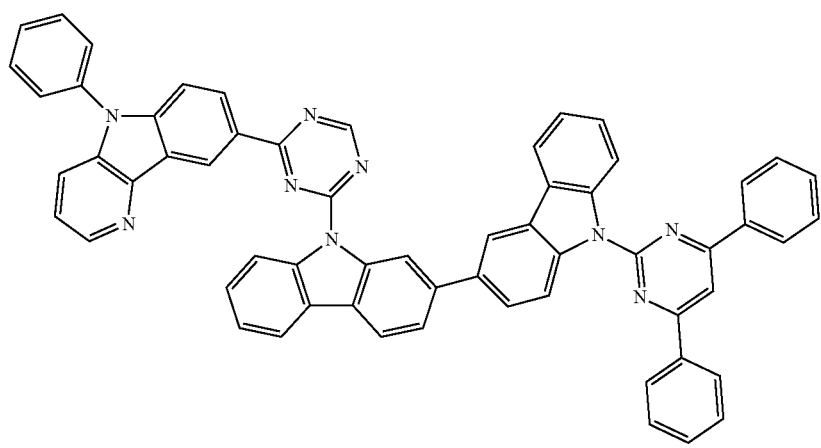

-continued
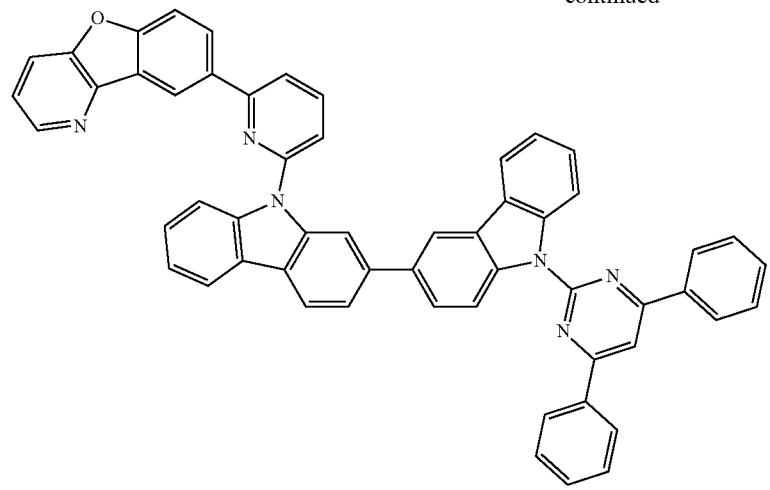
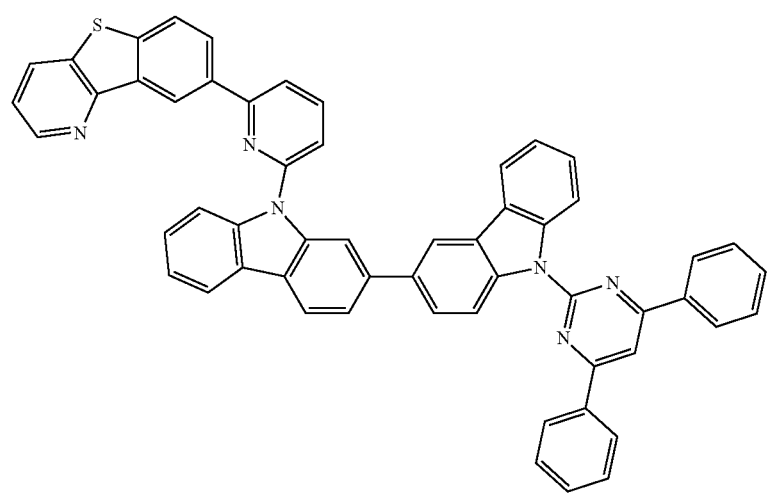
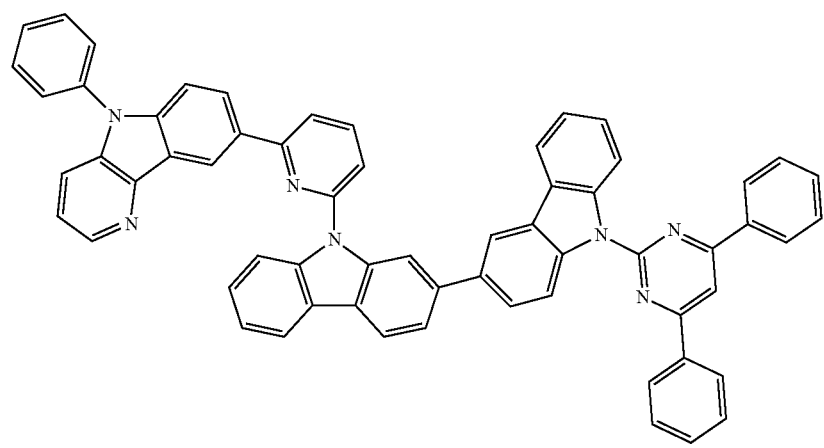

-continued
353
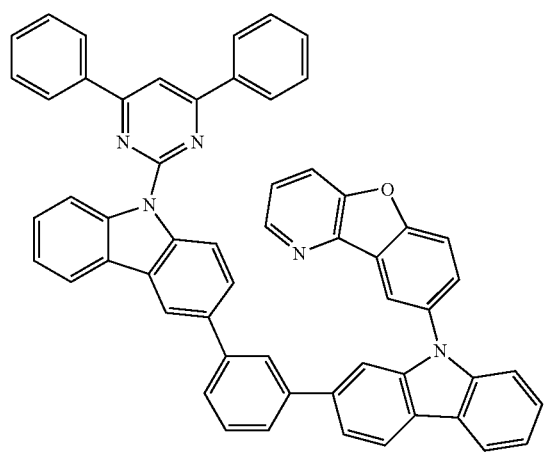
354
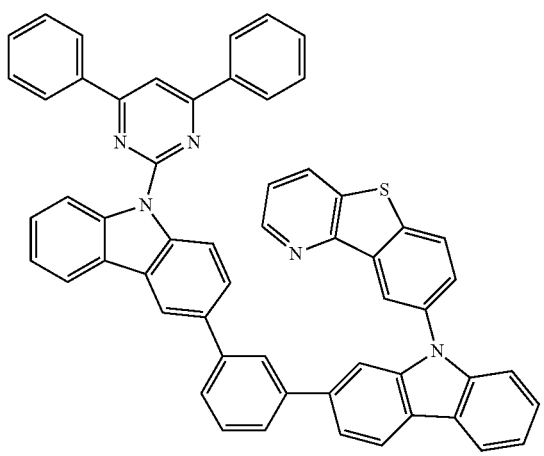
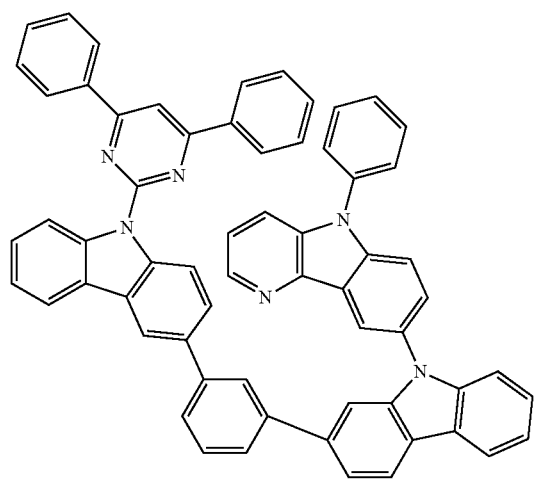
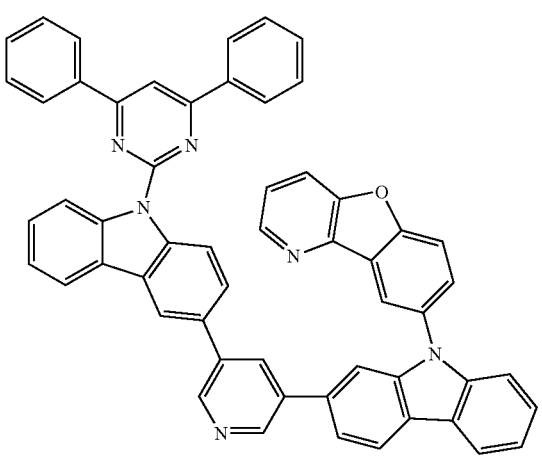
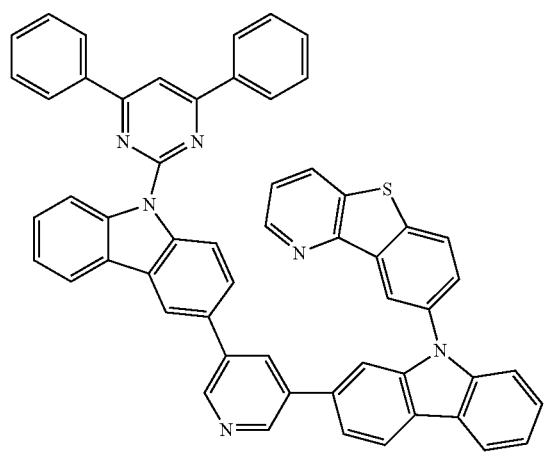
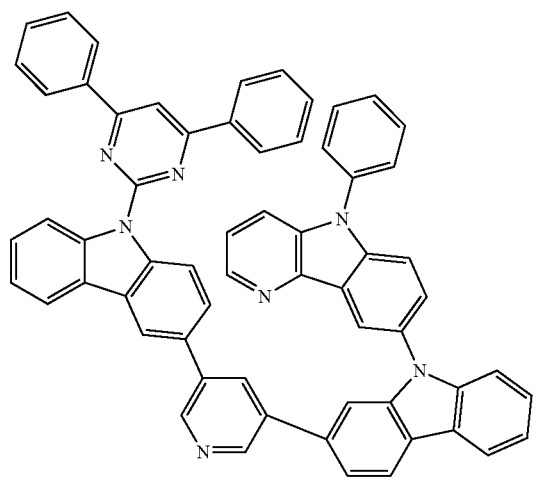

355
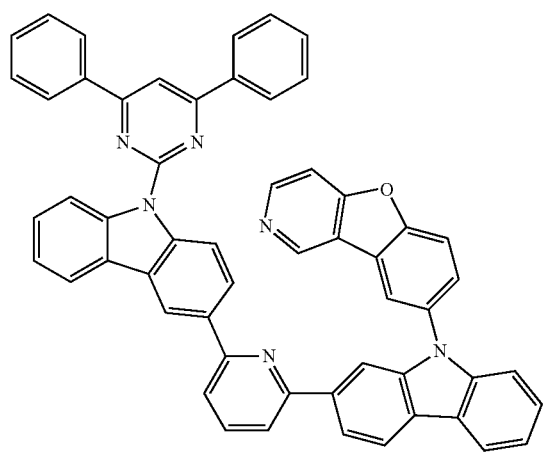
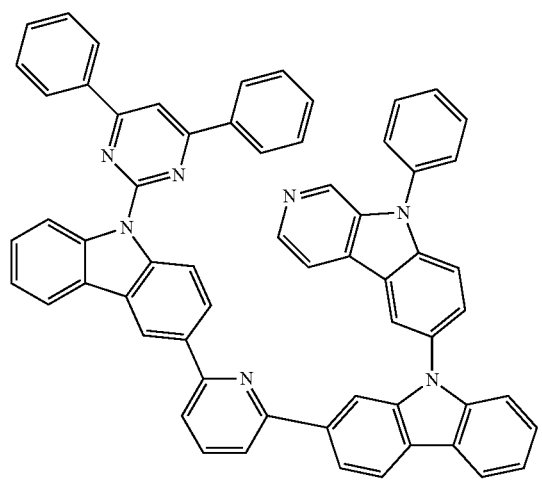
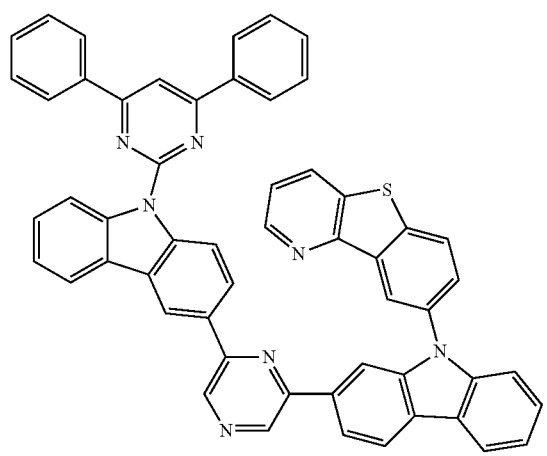
356
-continued
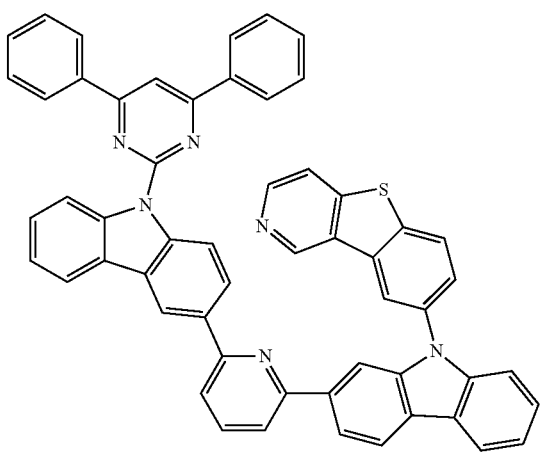
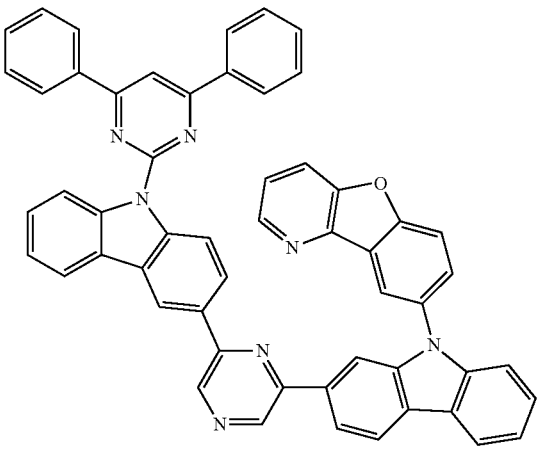
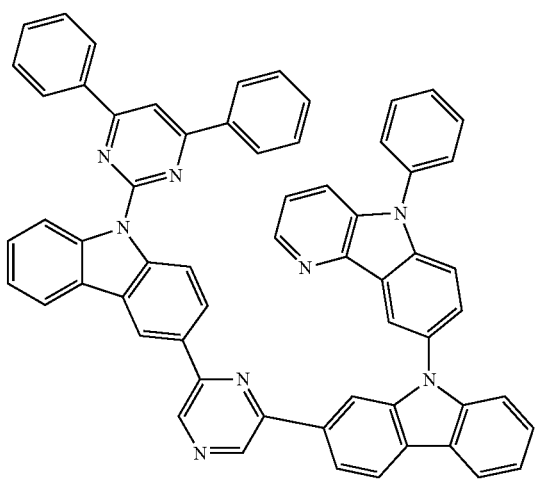

-continued
357
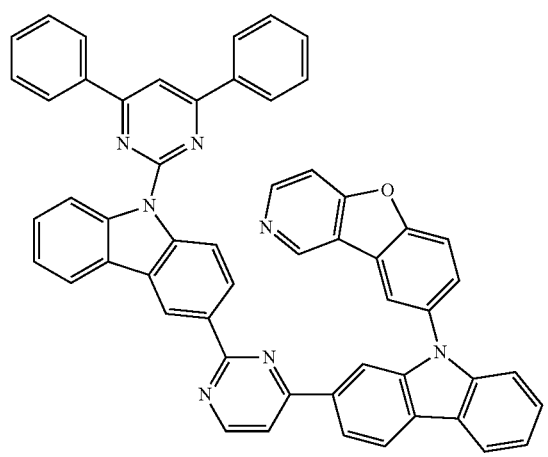
358
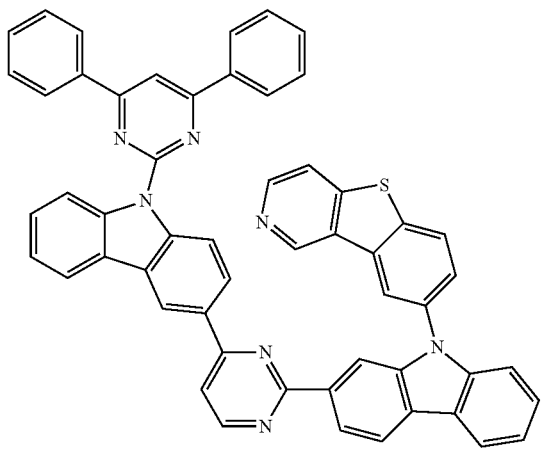
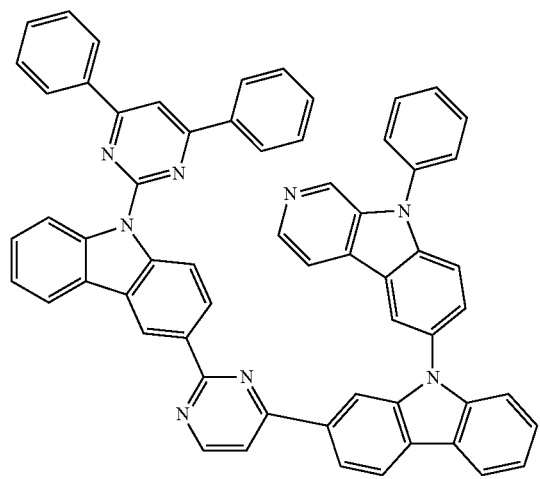
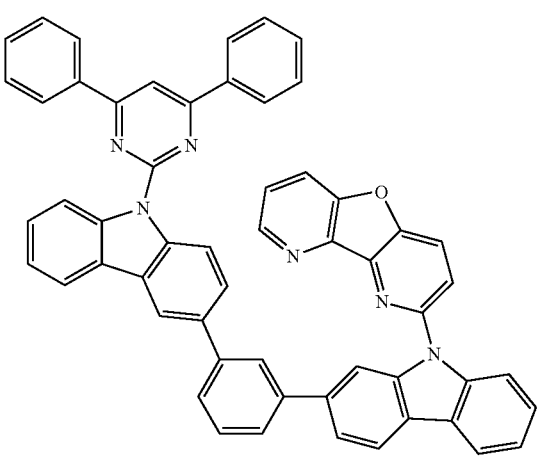
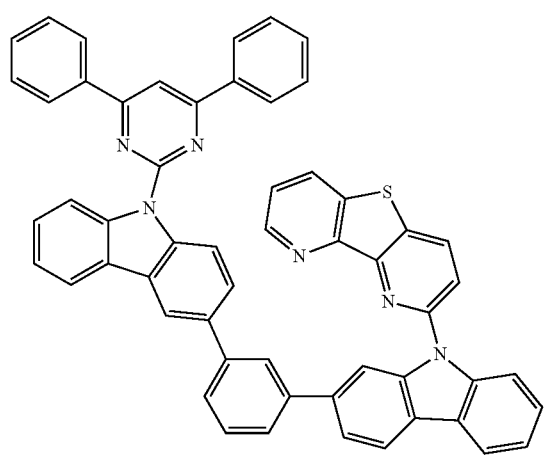
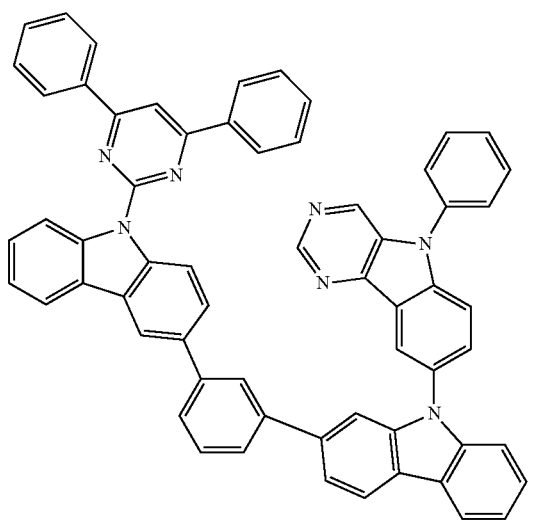

-continued
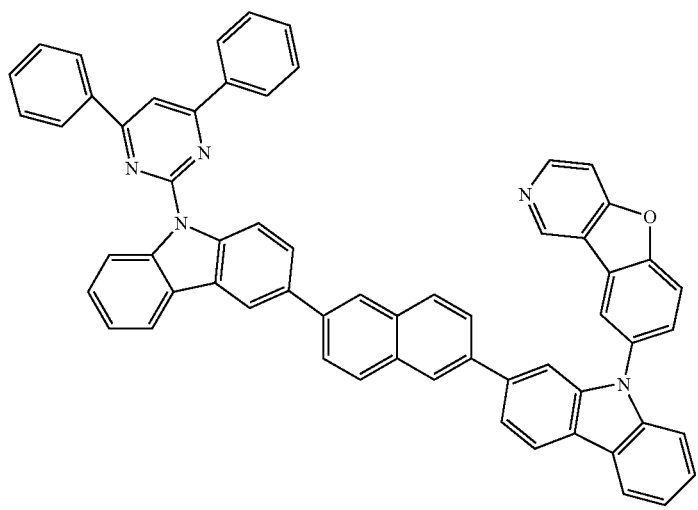

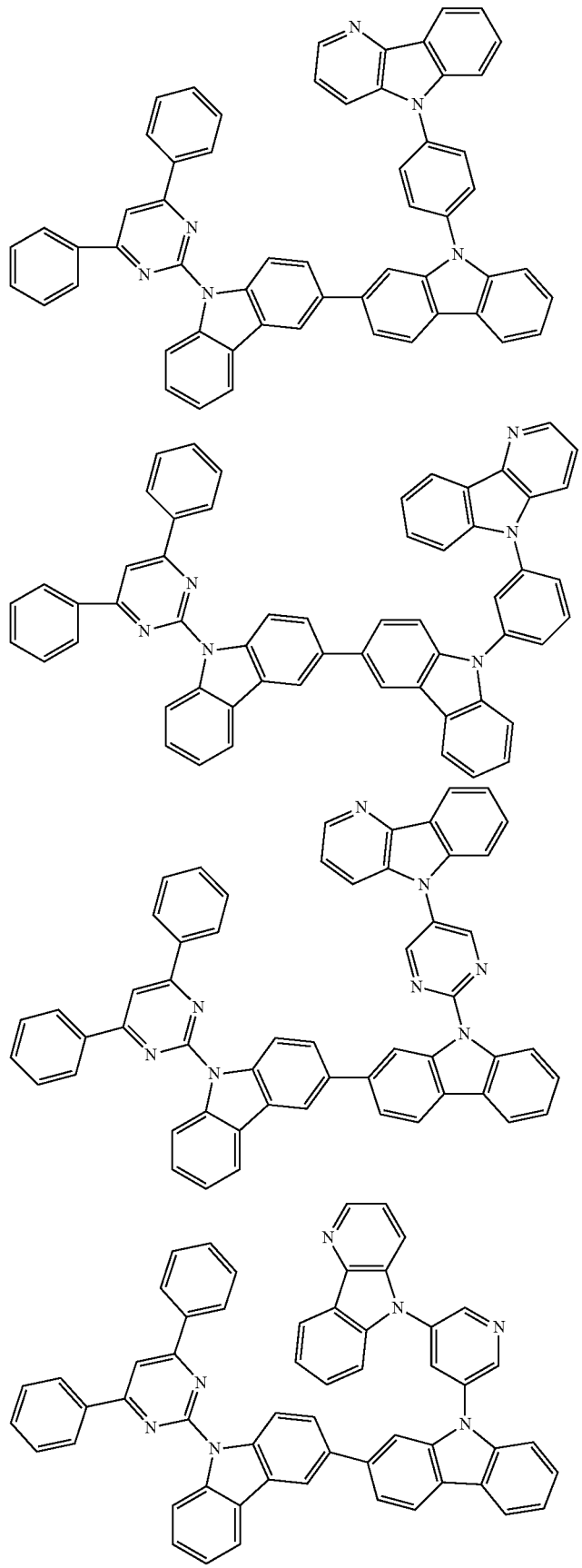

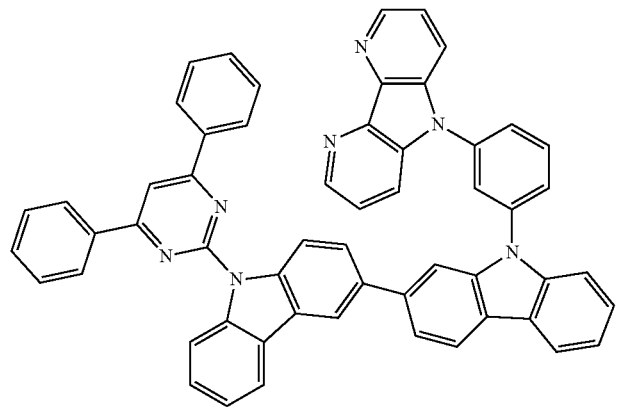
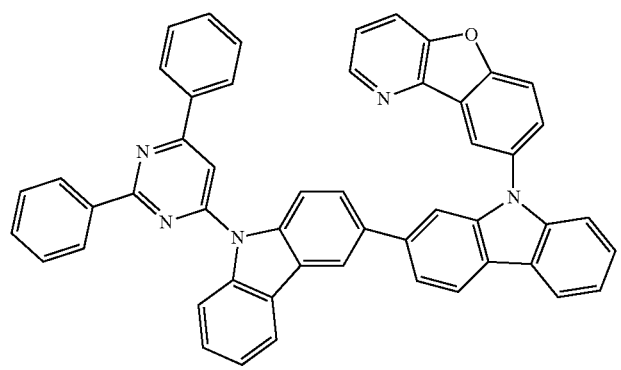
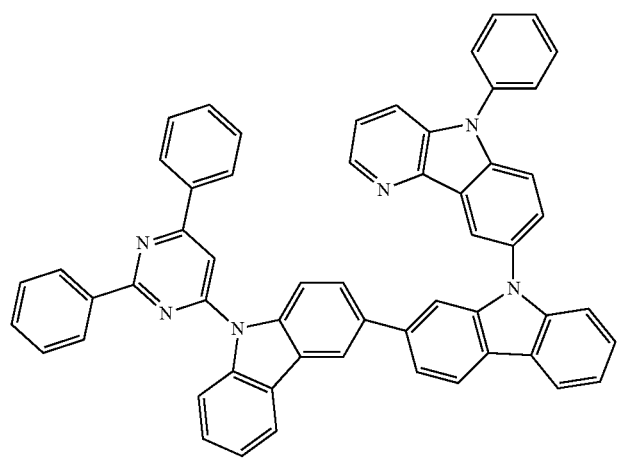
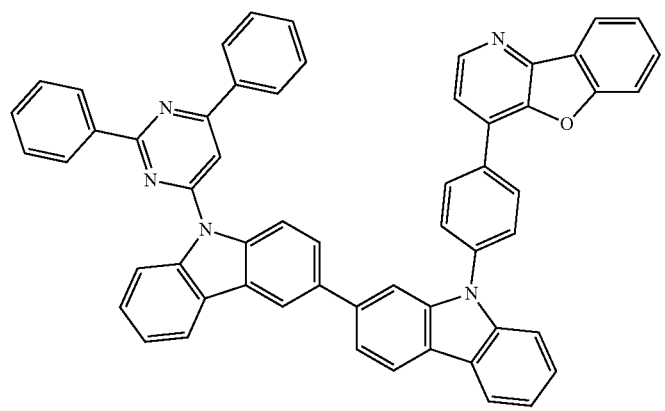

-continued
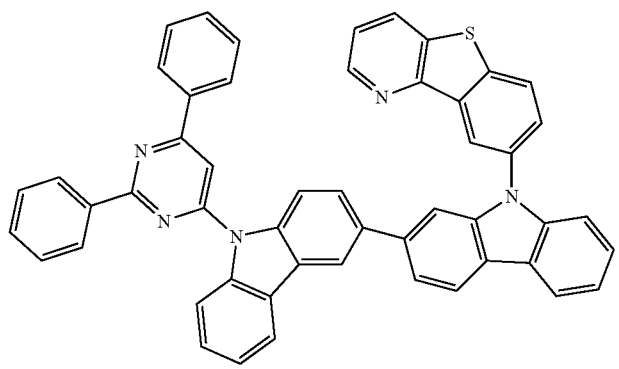
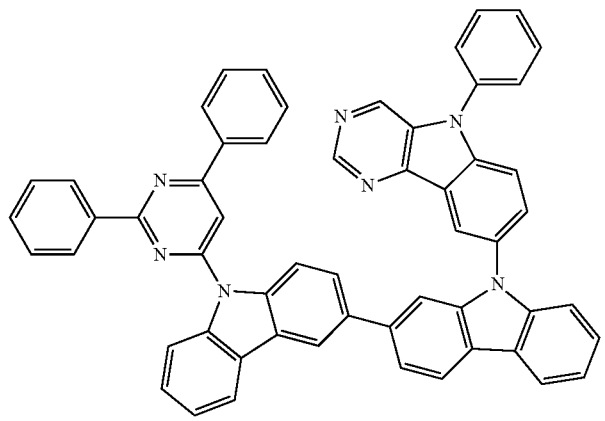
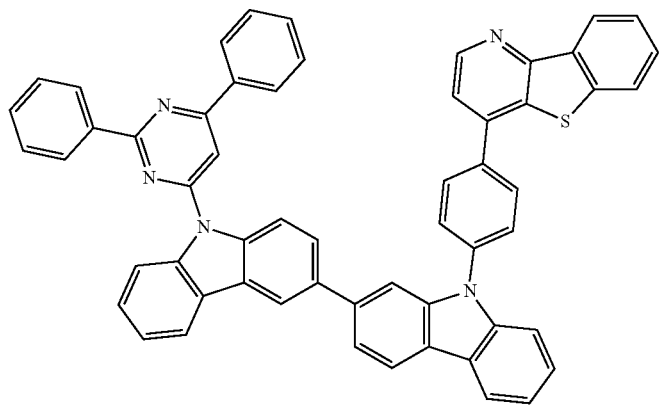
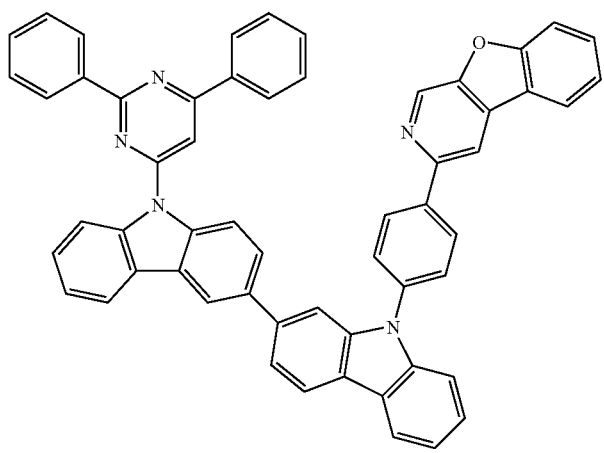

-continued
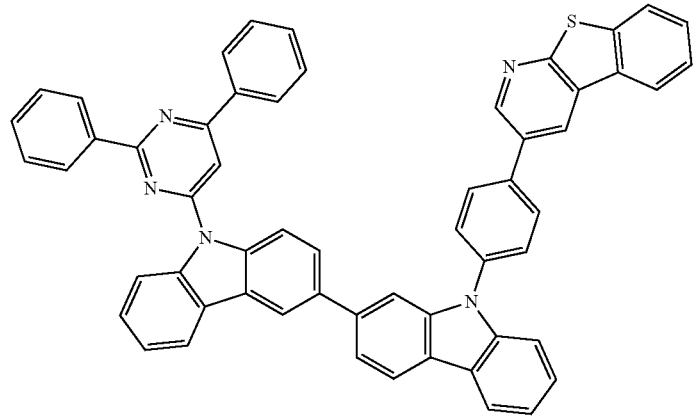
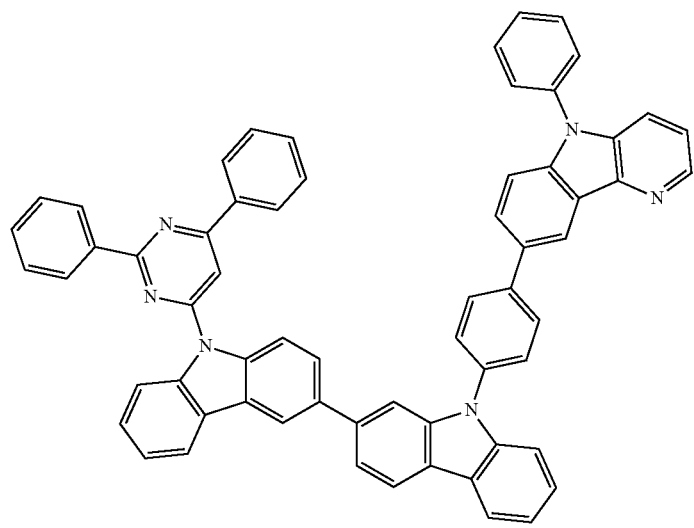
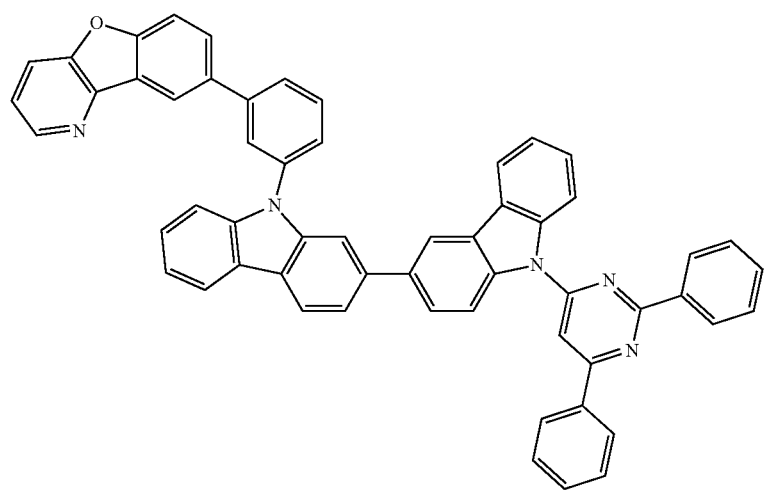

-continued
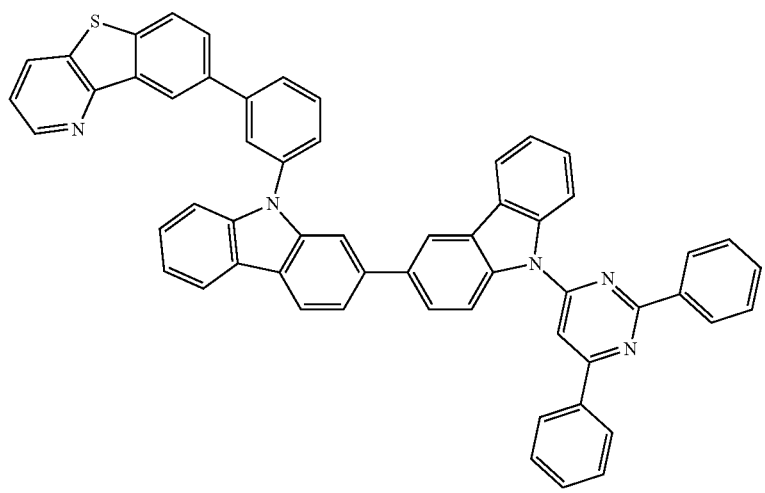
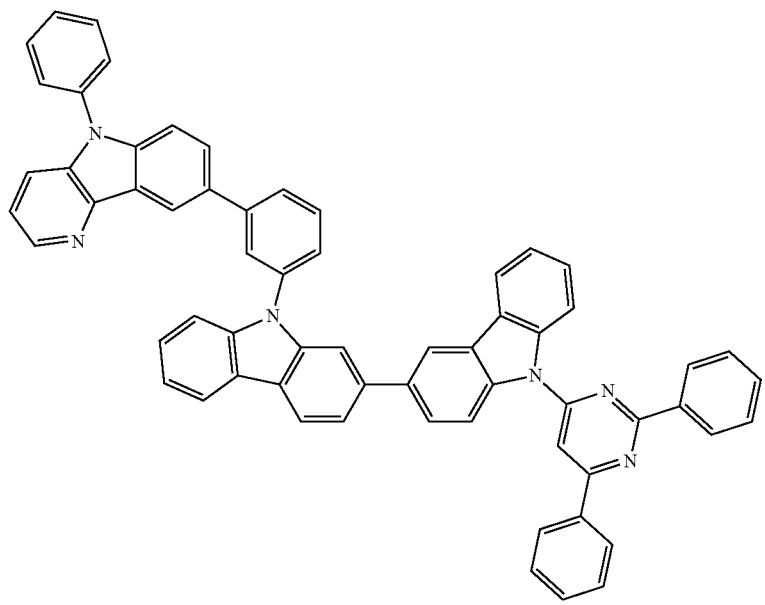
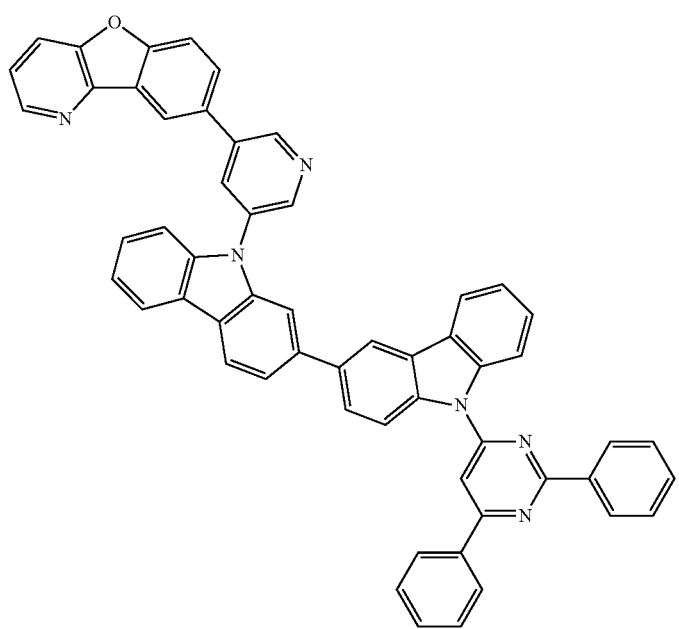

-continued
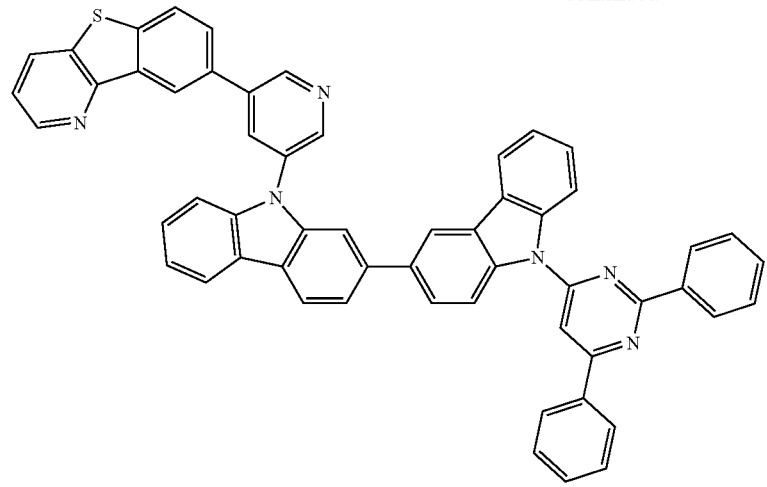
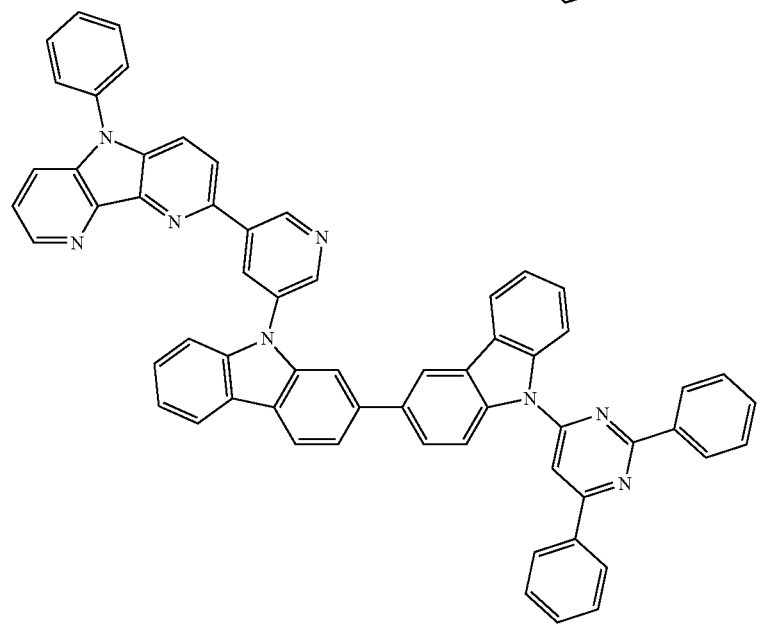
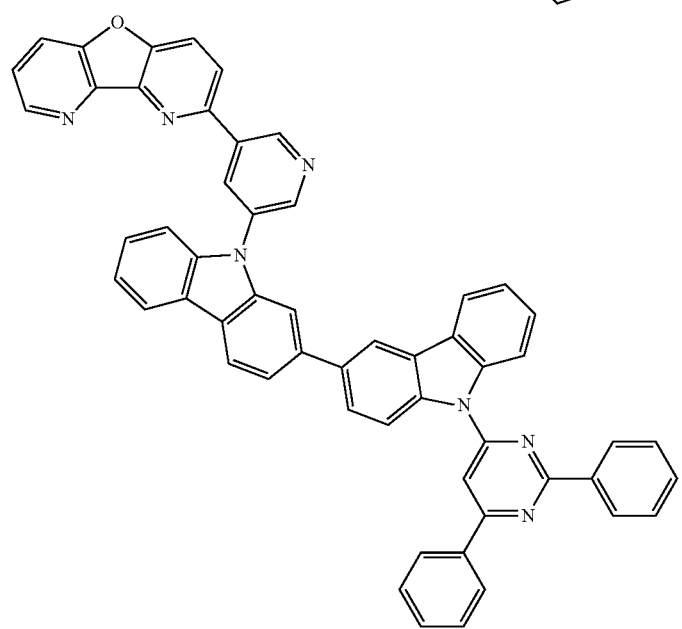

373 374
-continued
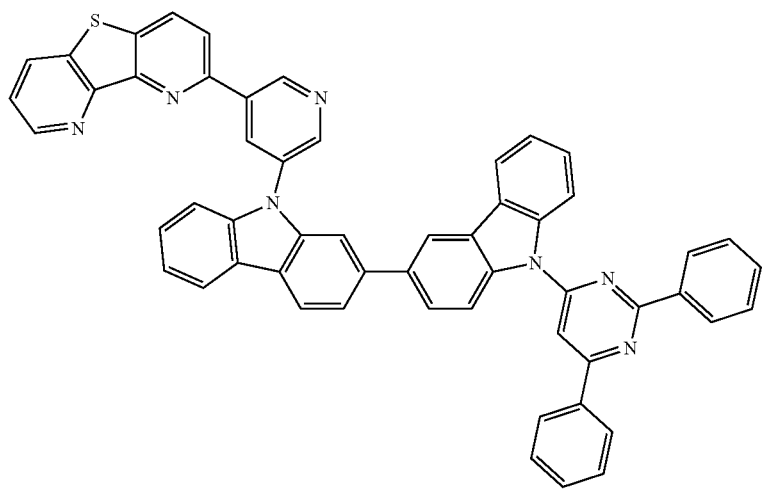
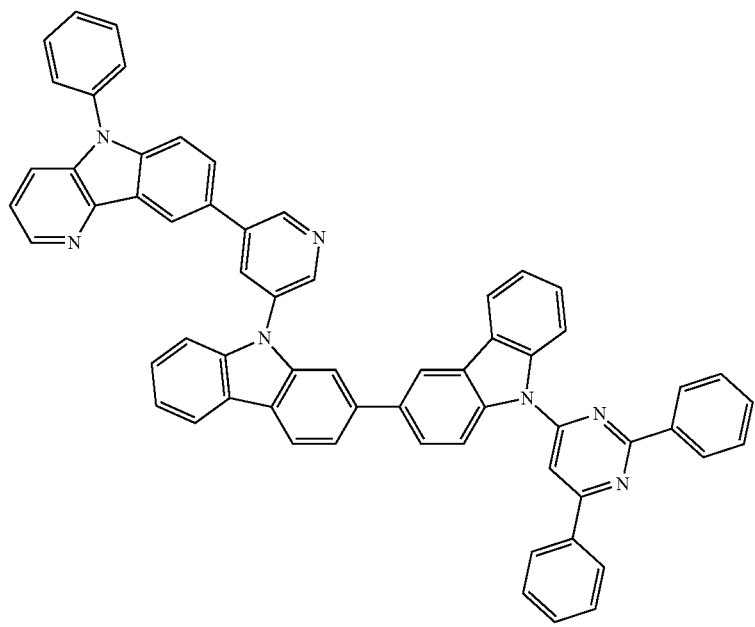
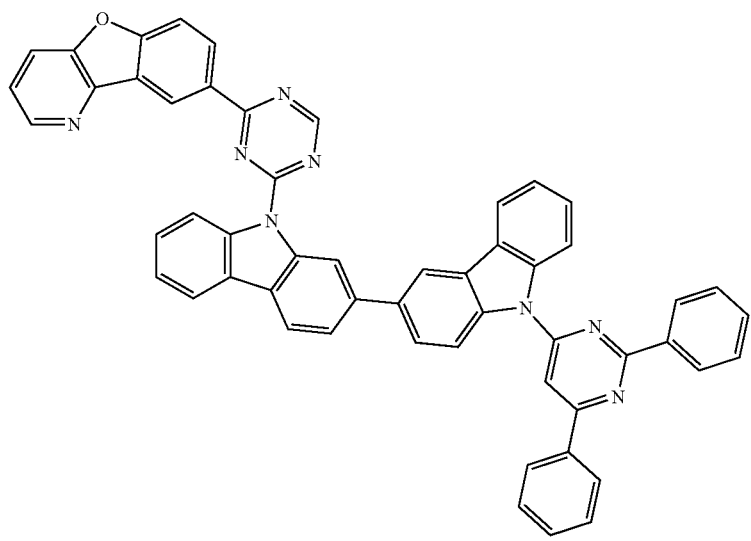

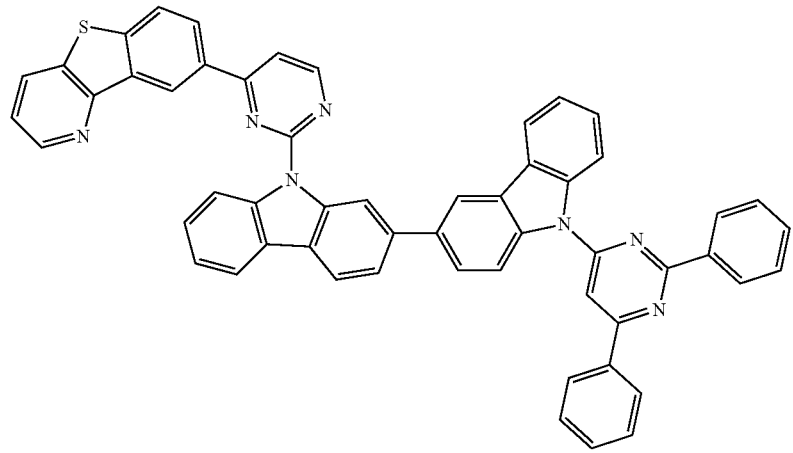
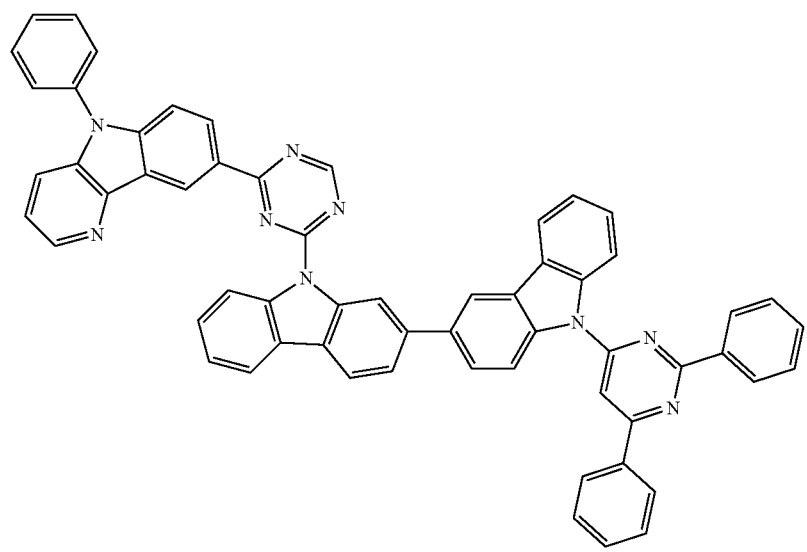
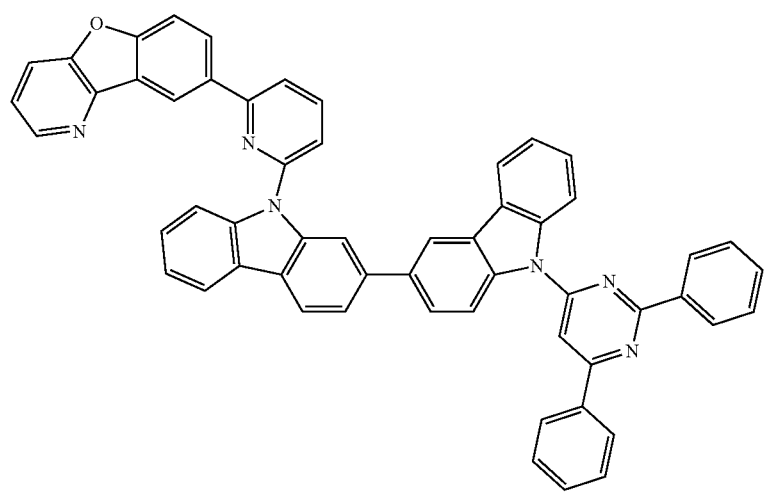

-continued
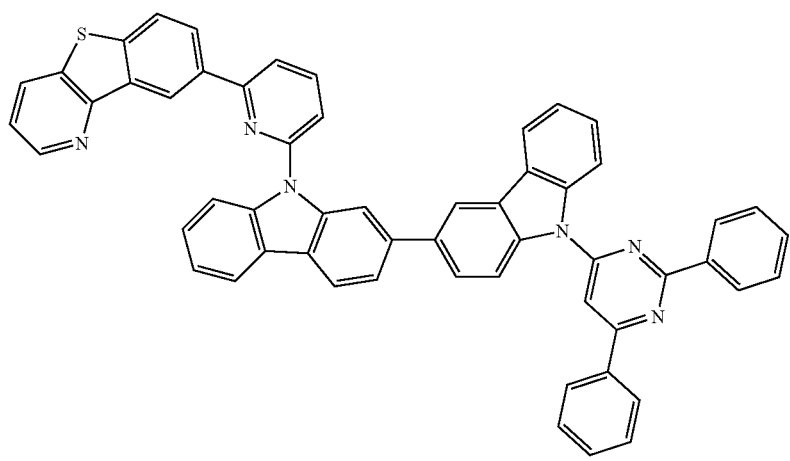
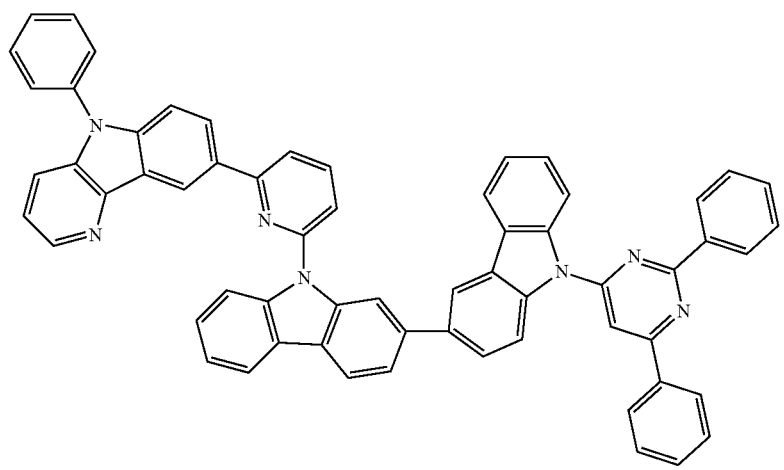
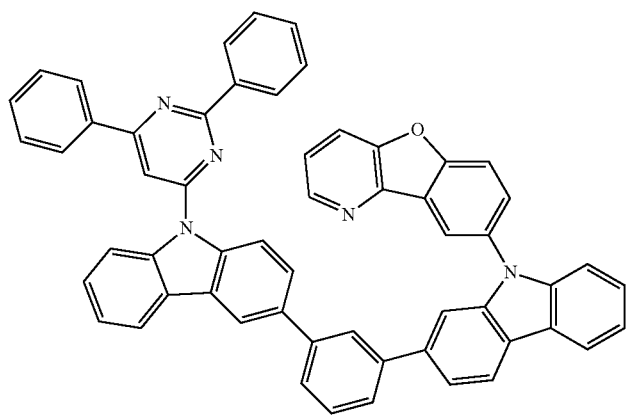

-continued
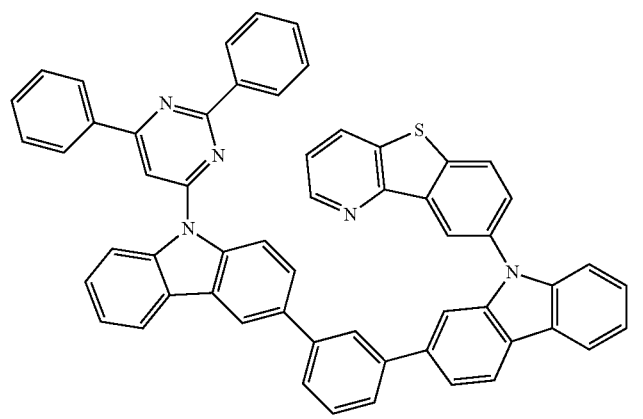
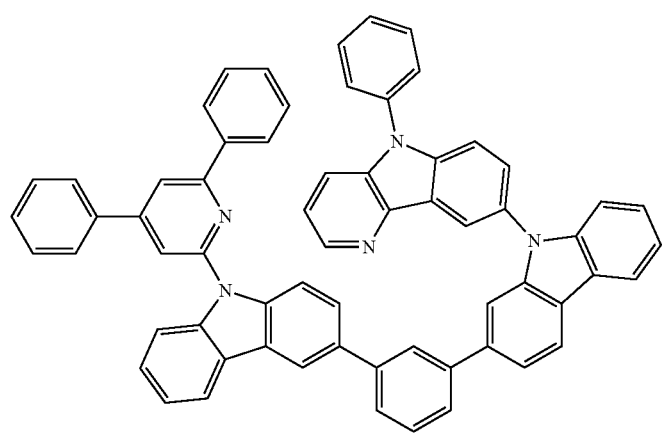
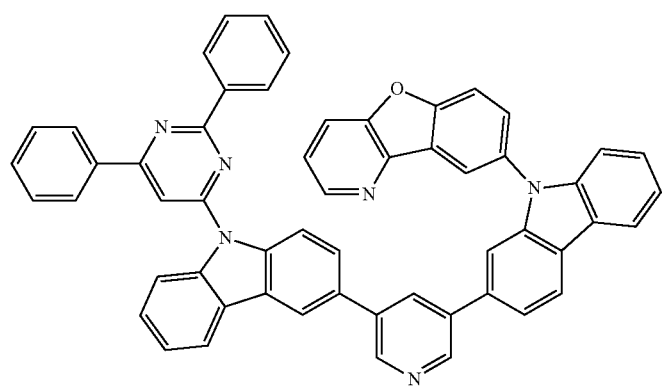
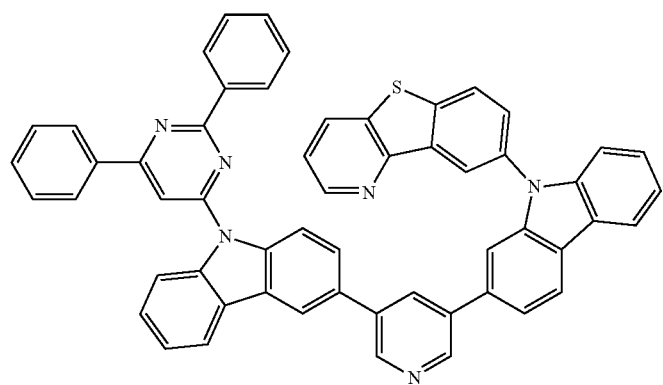

-continued
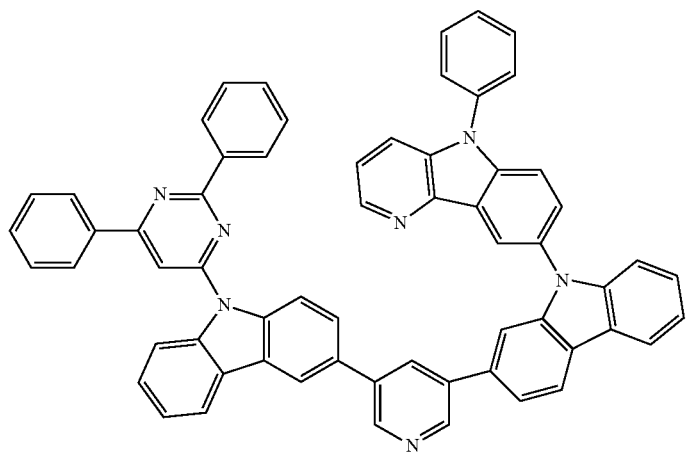
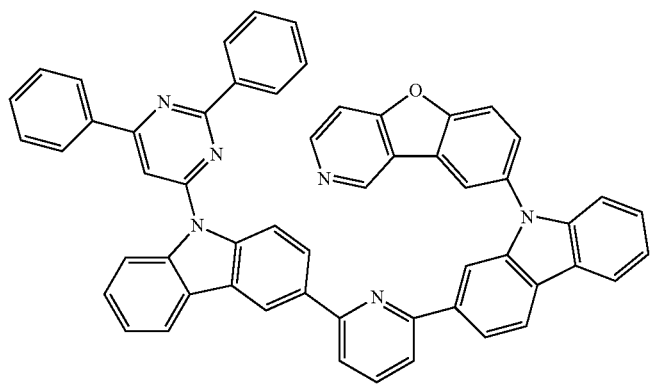
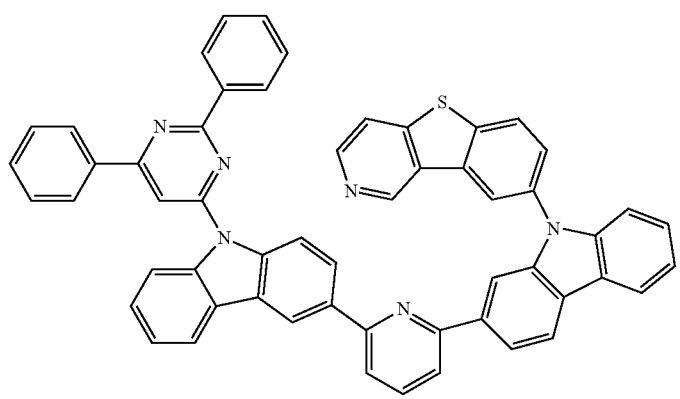
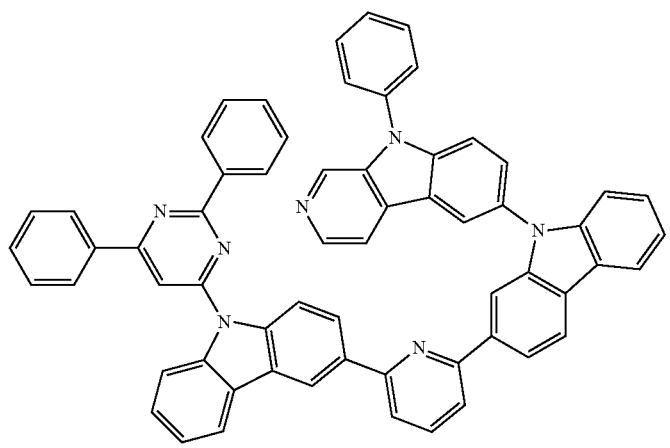

-continued
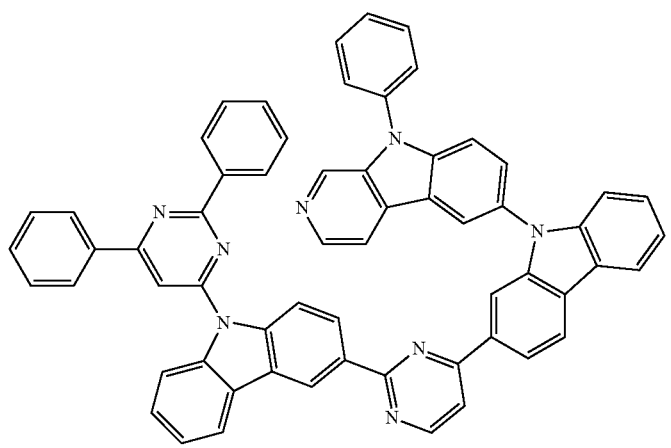
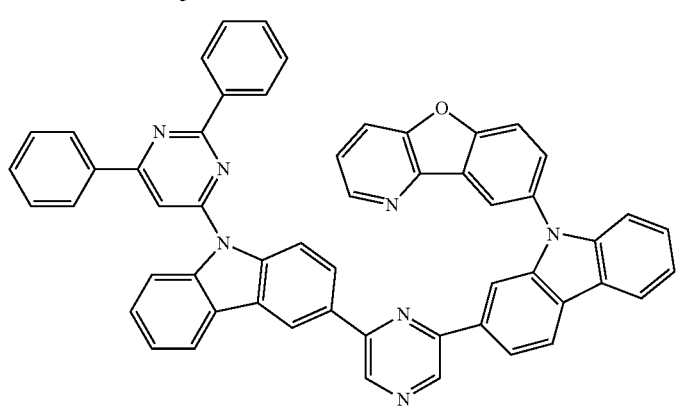
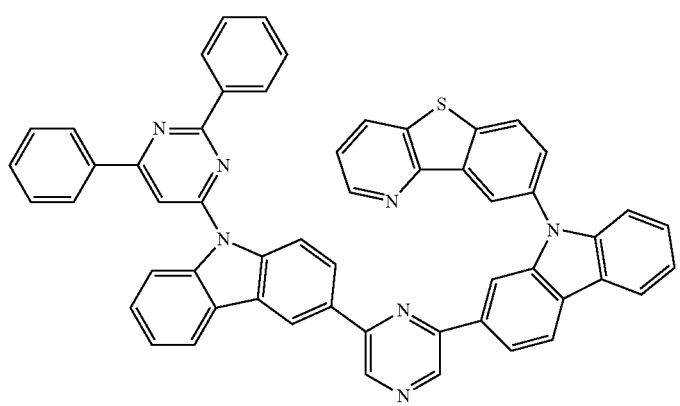
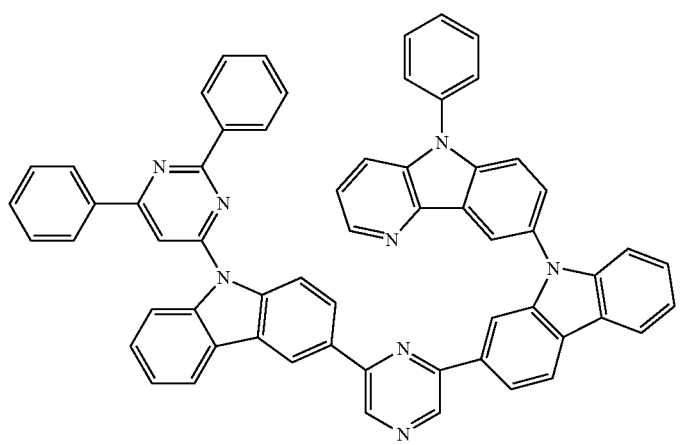

-continued
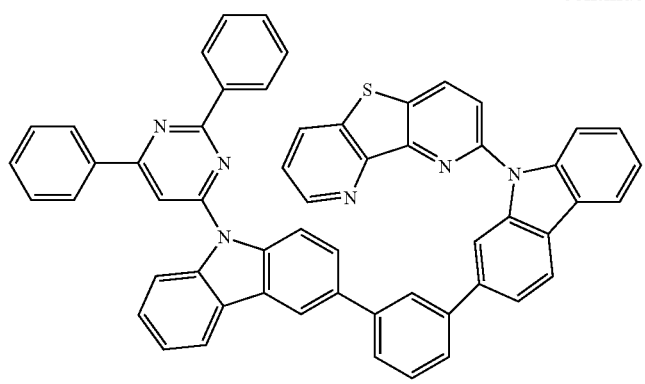

-continued
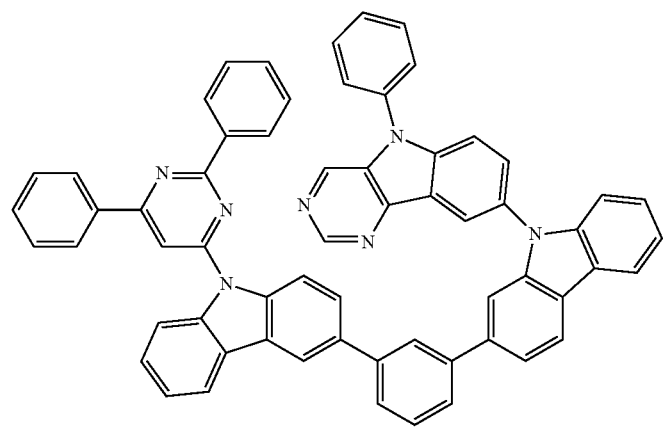
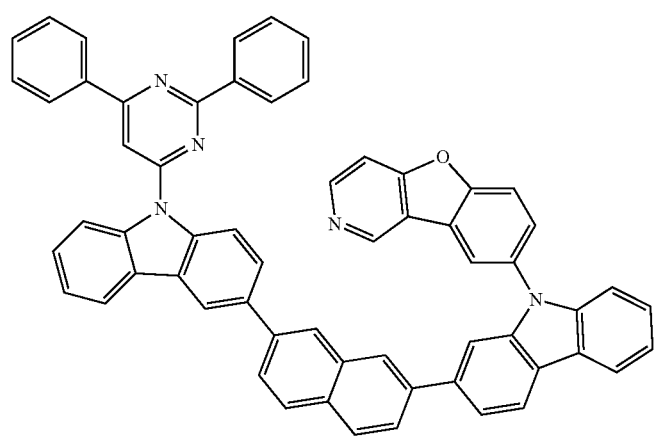
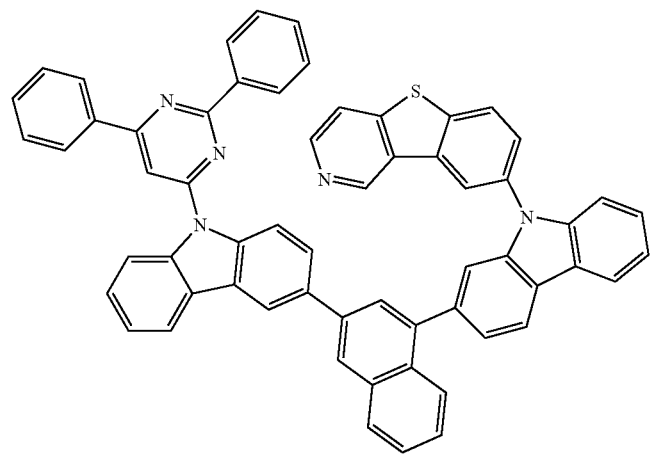

-continued
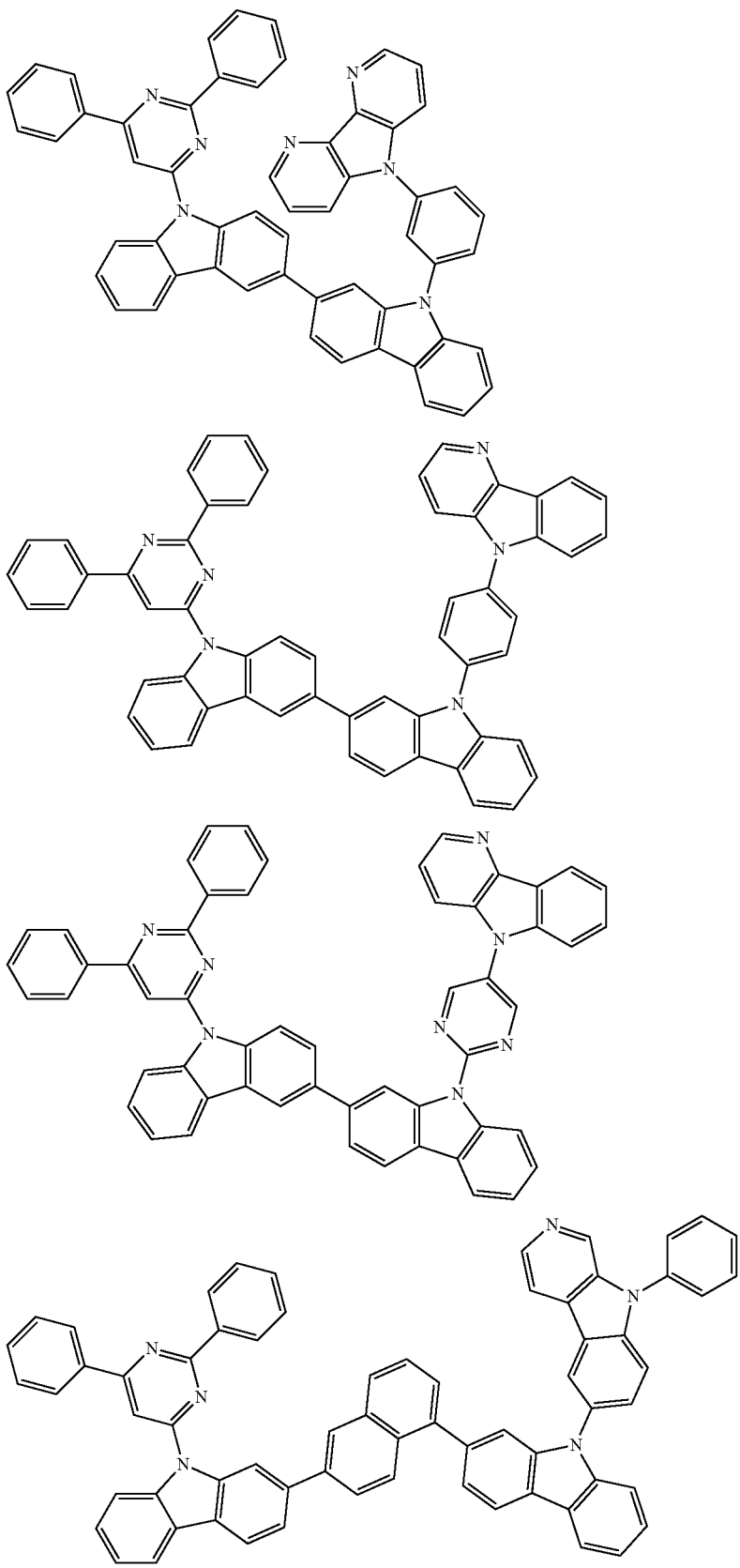

-continued
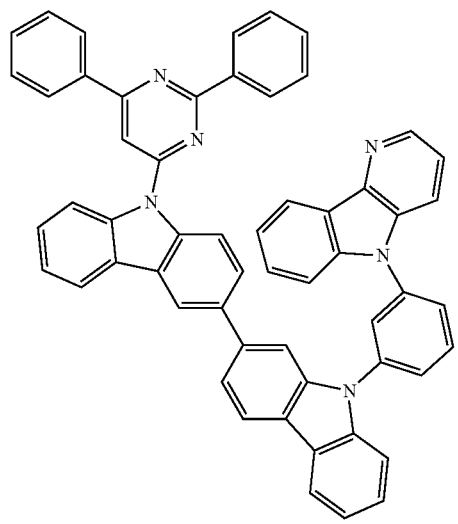
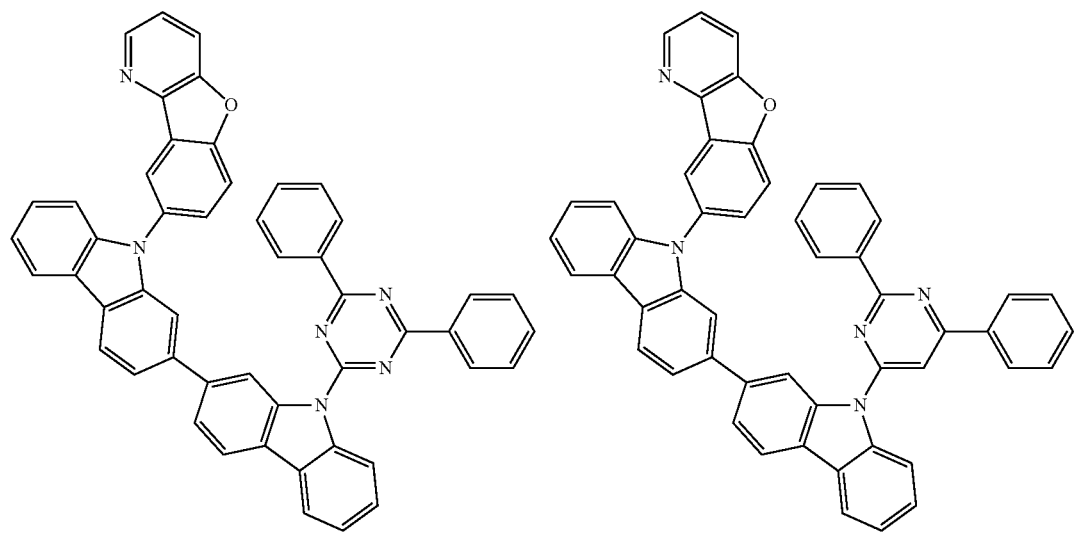
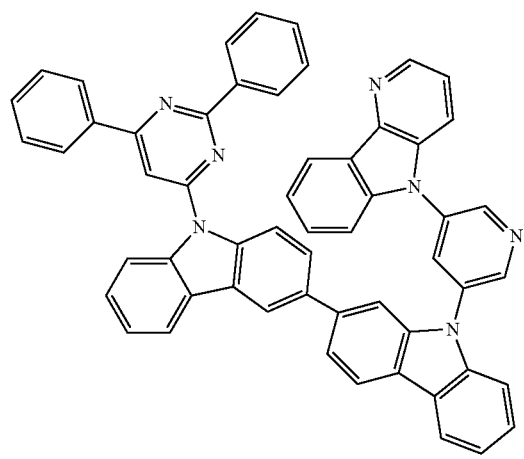

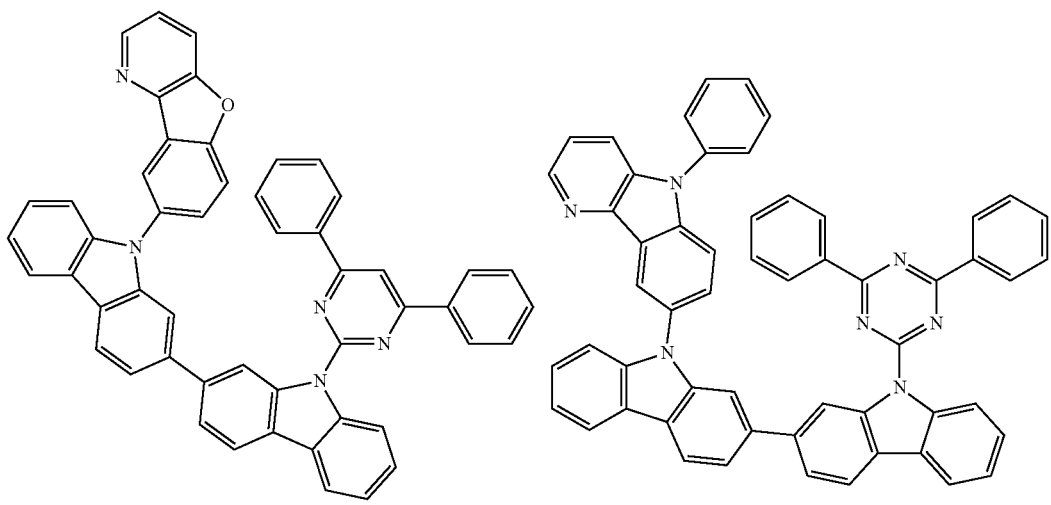
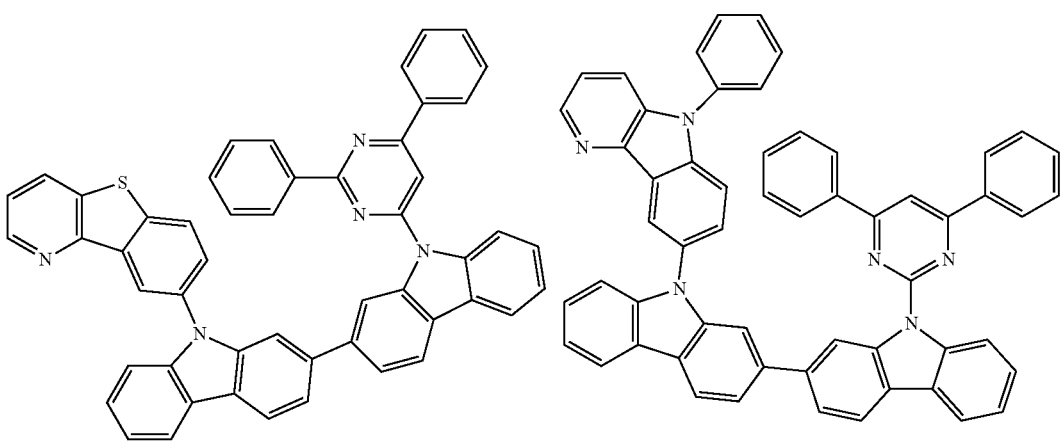
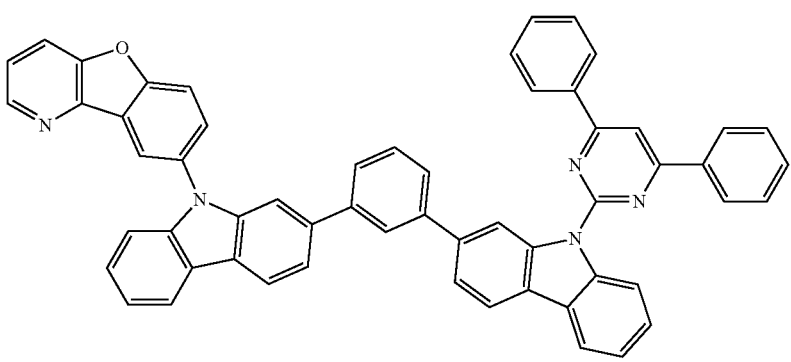

395 396
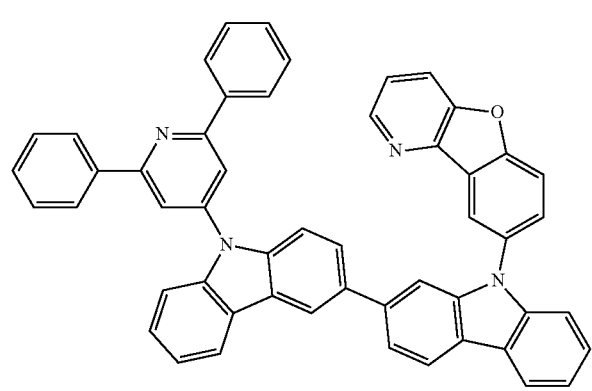 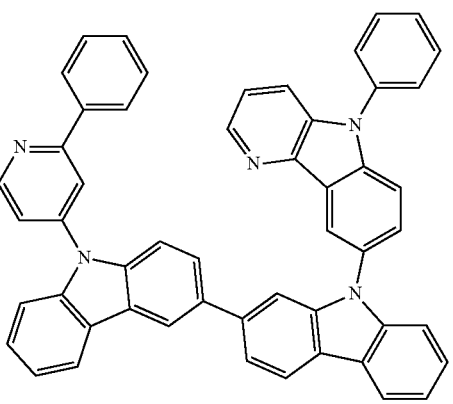
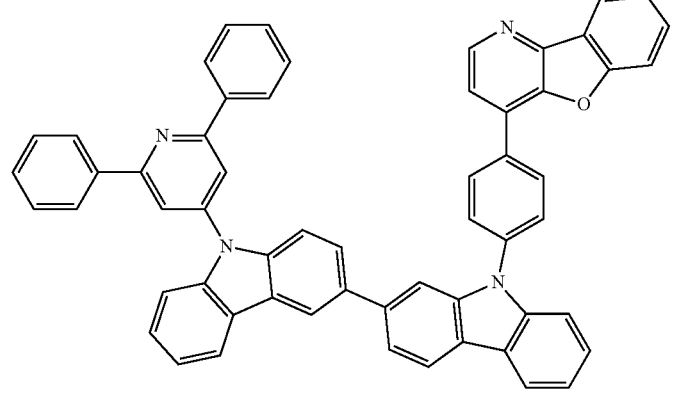
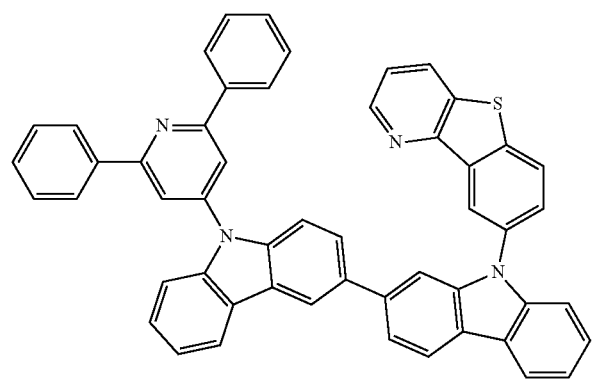
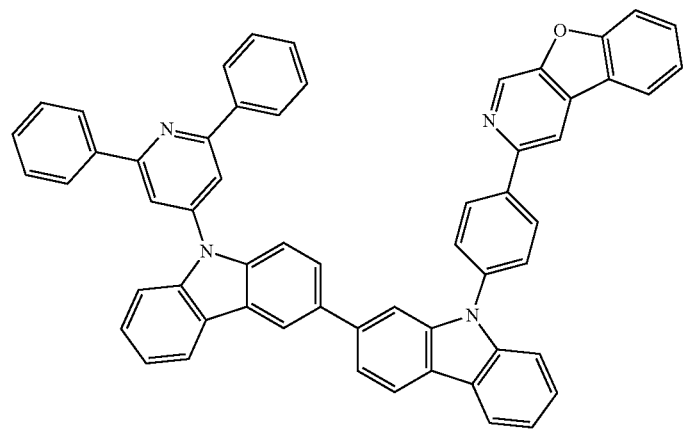

-continued
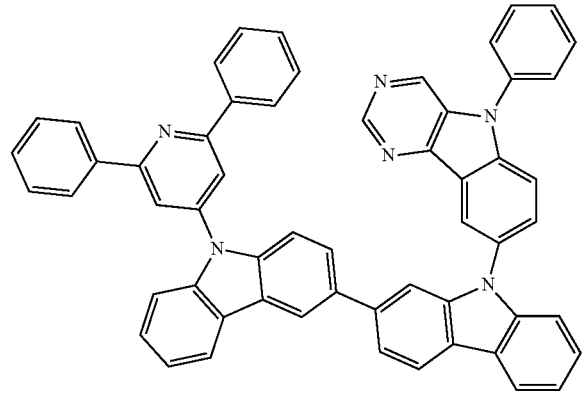
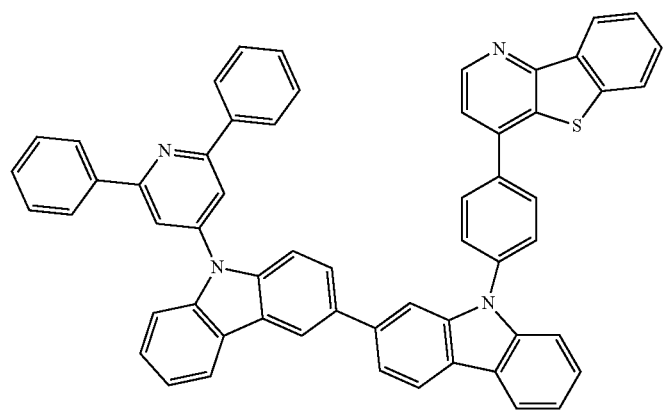
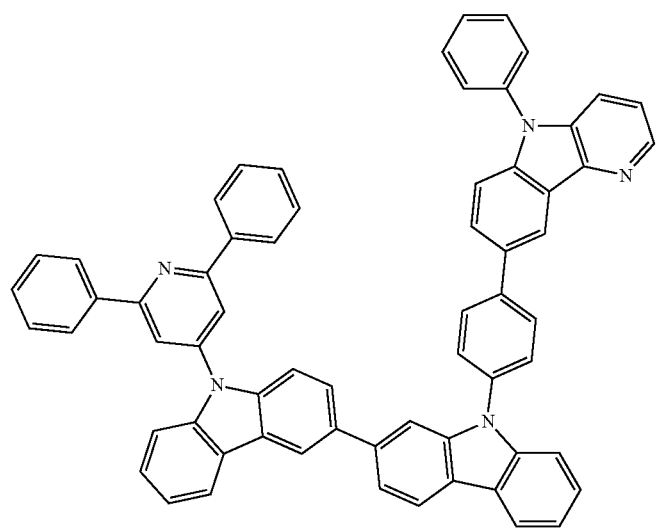

-continued
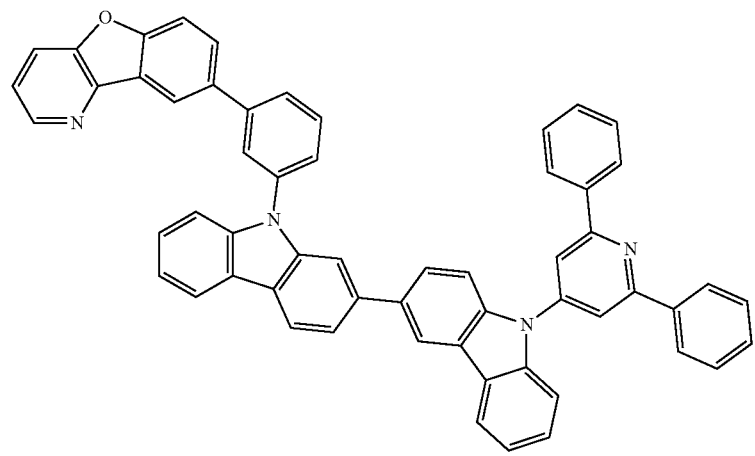
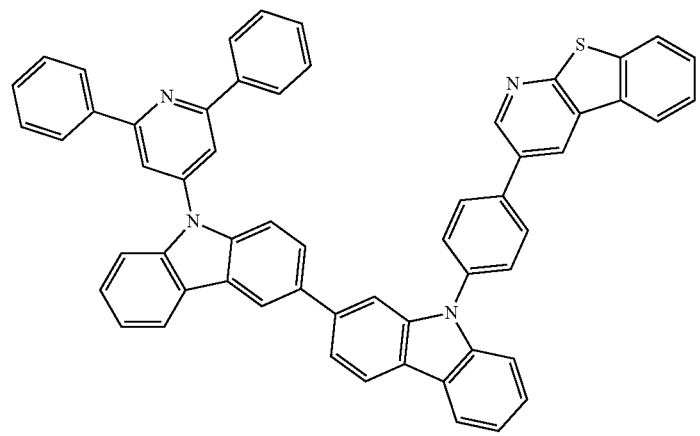
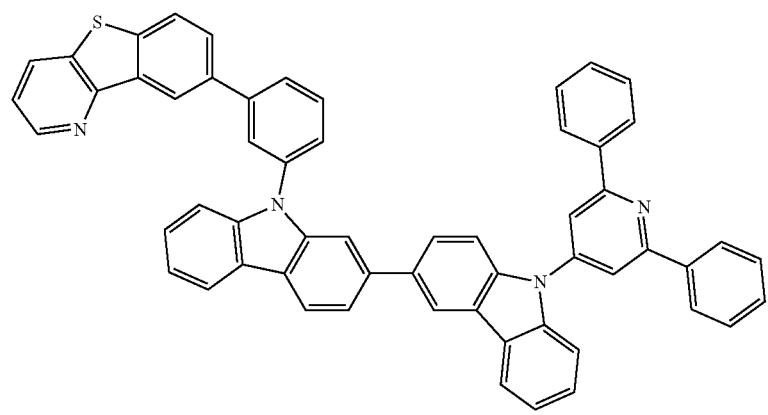
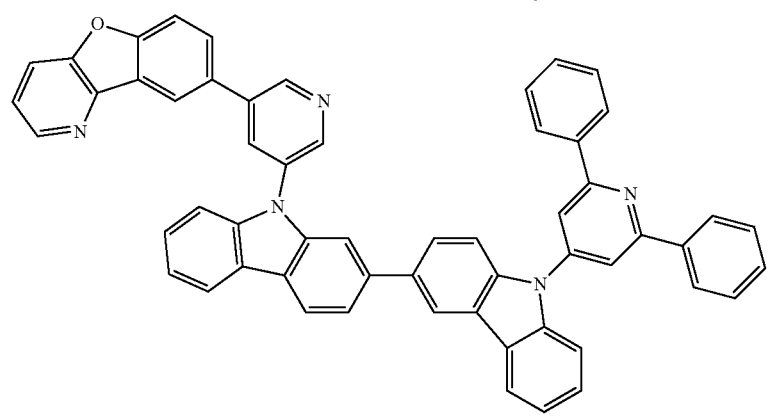

-continued
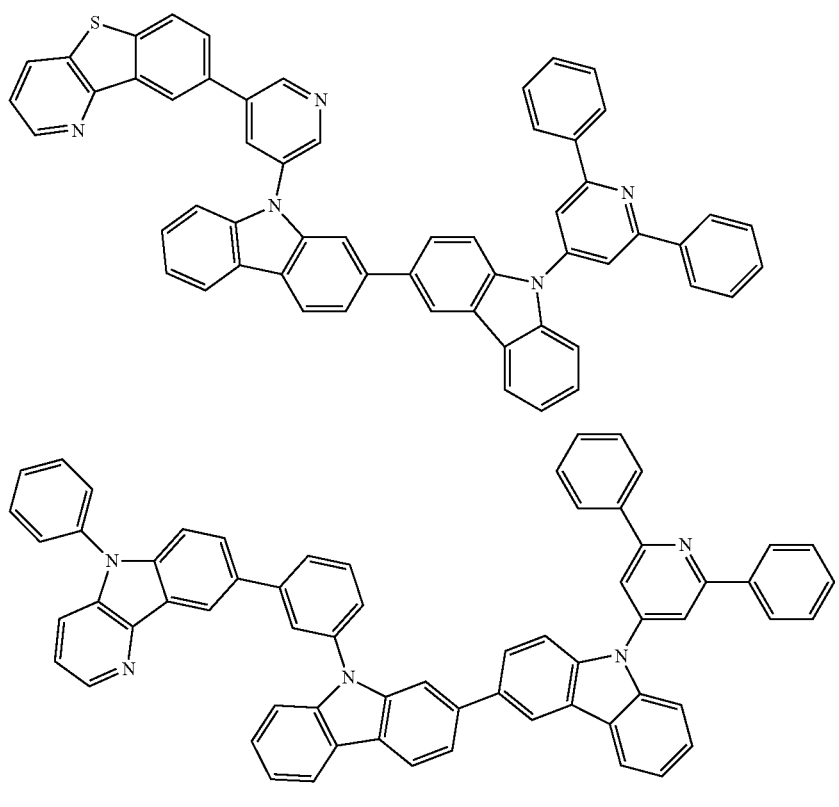
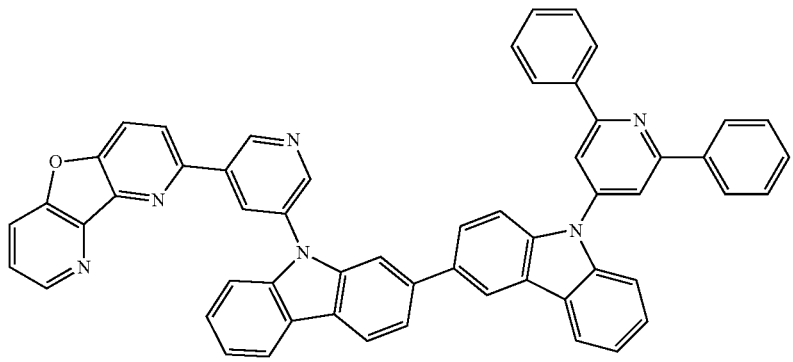
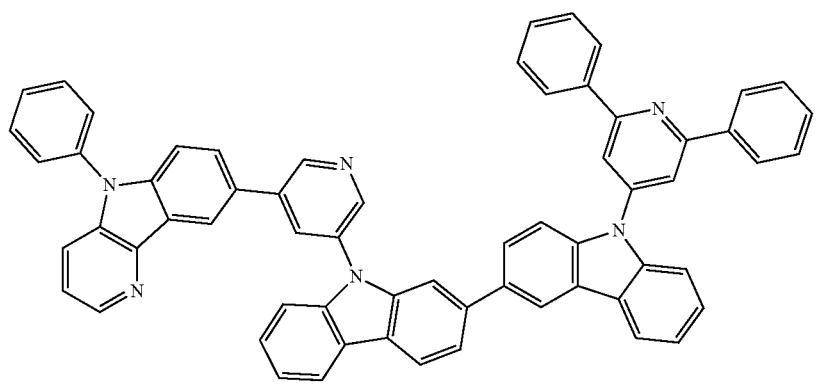

-continued
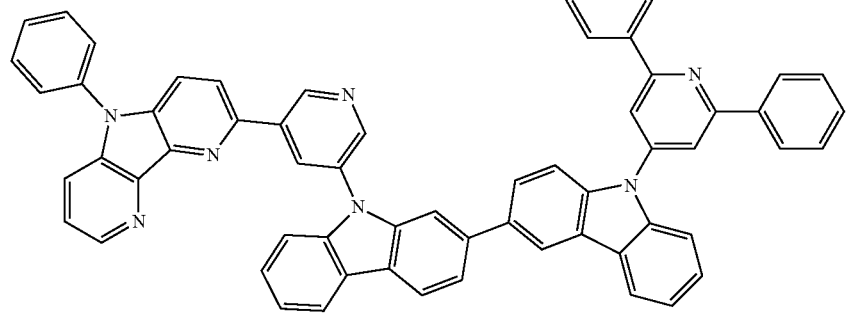
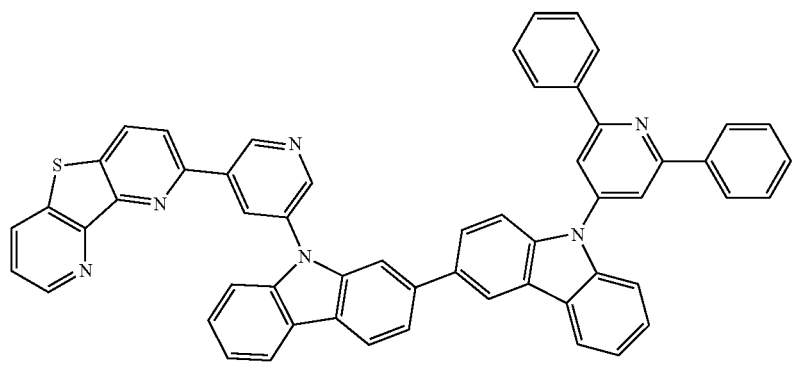
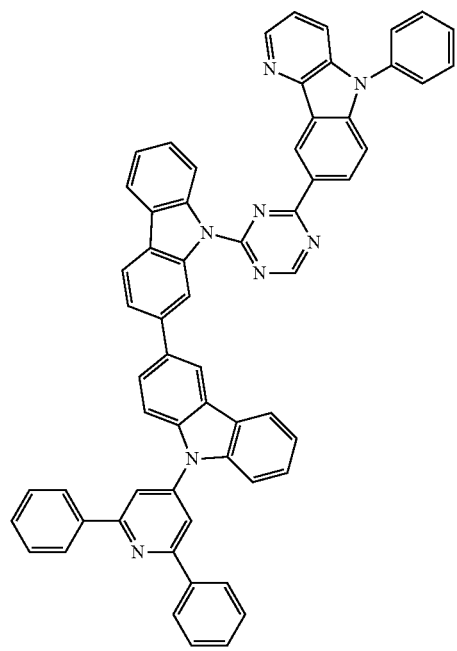

405
406
-continued
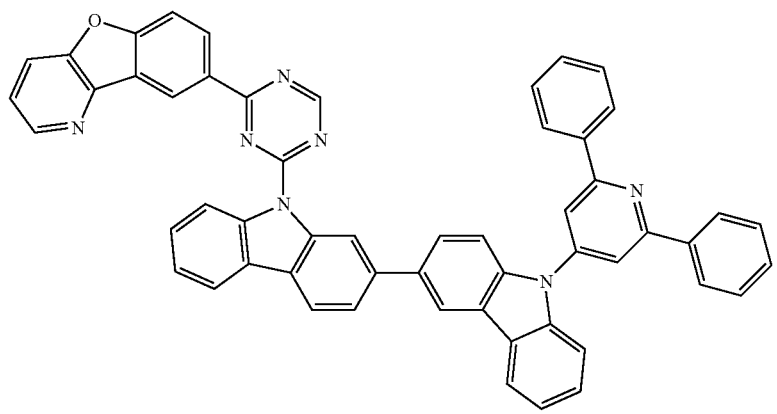
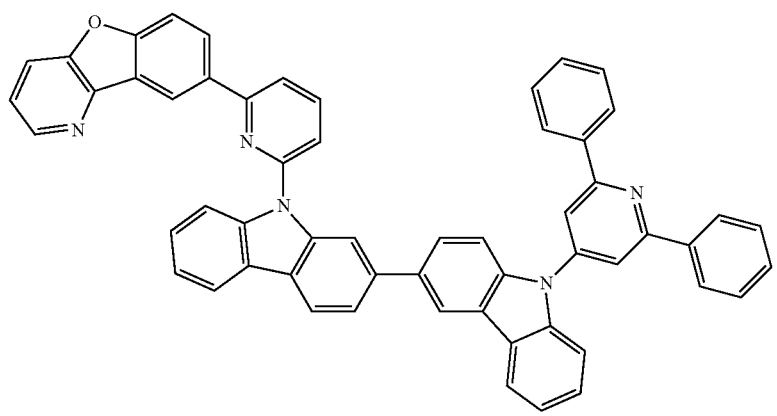
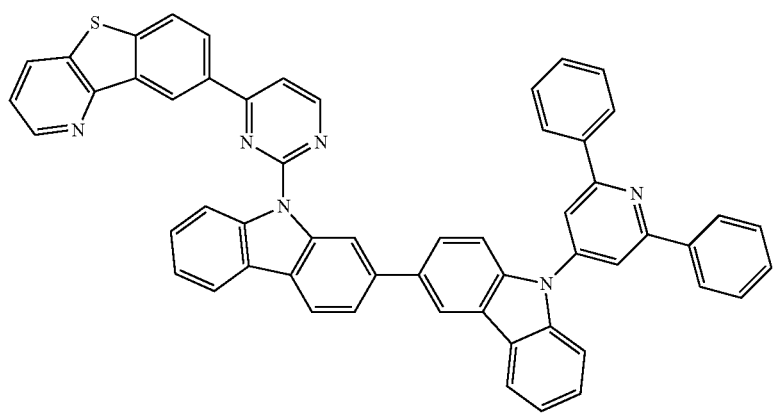
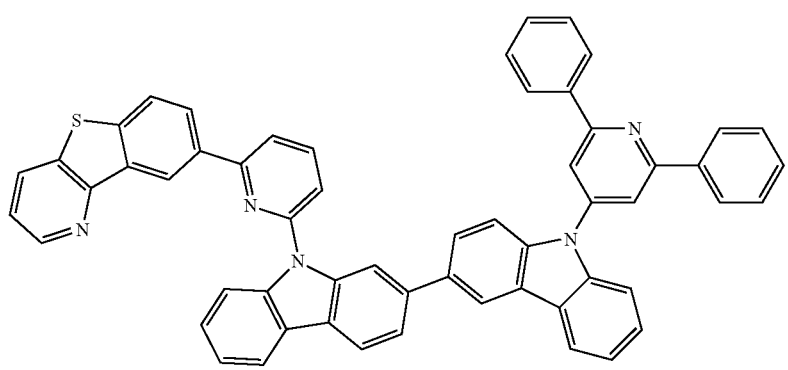

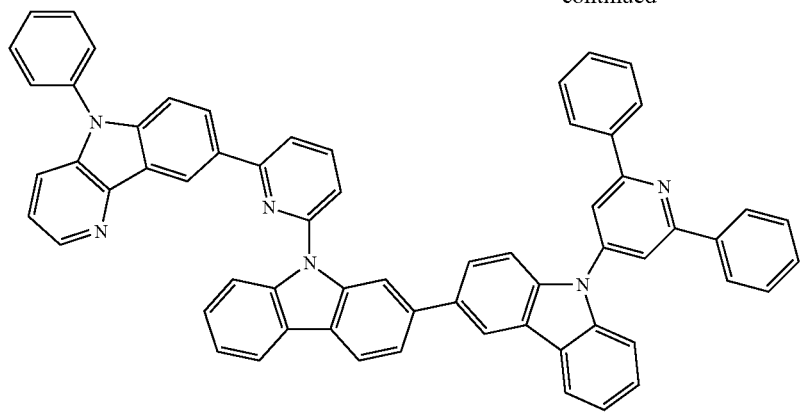
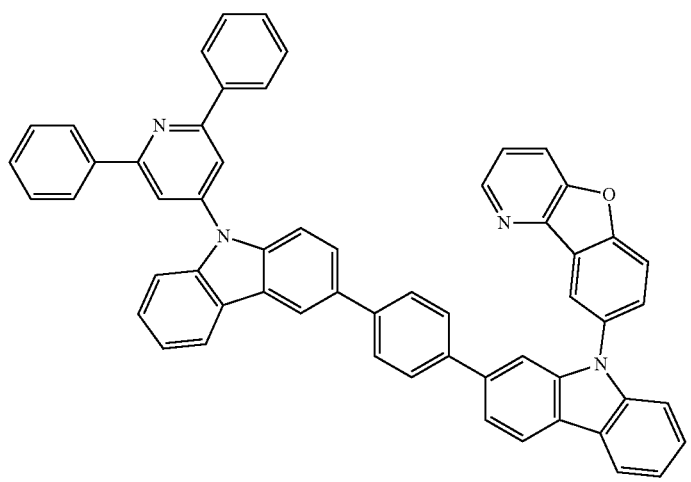
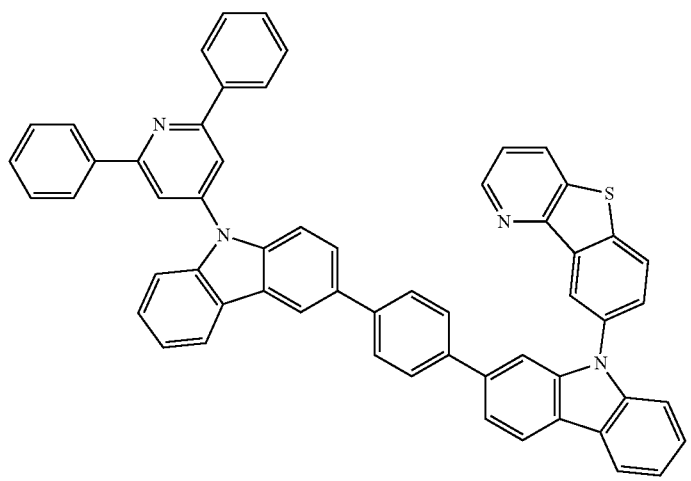

-continued
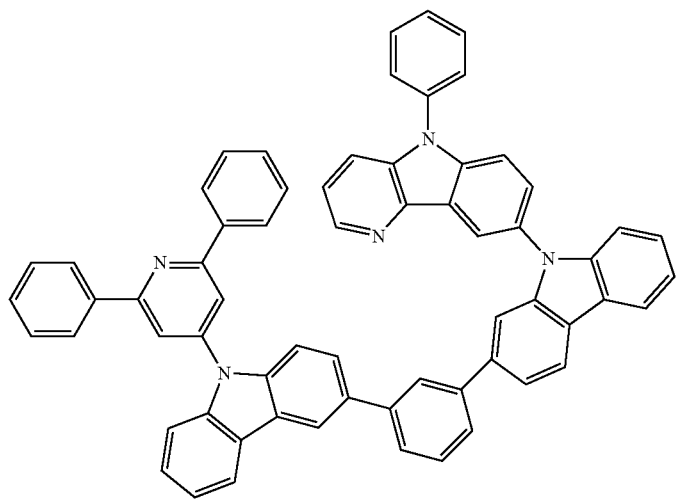
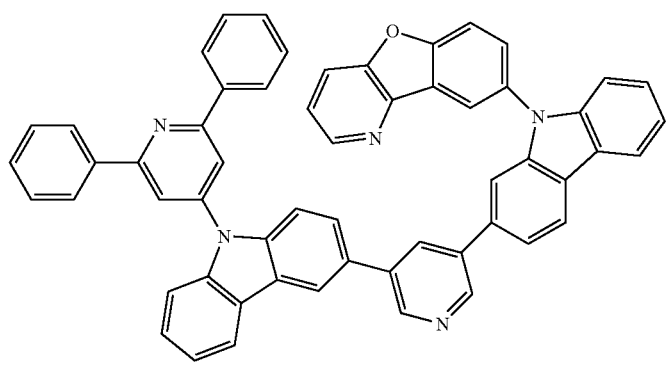
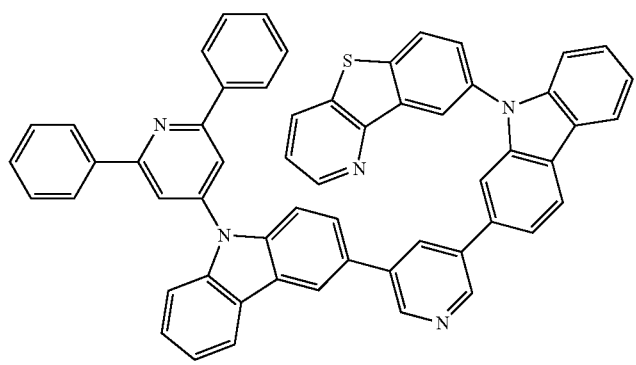
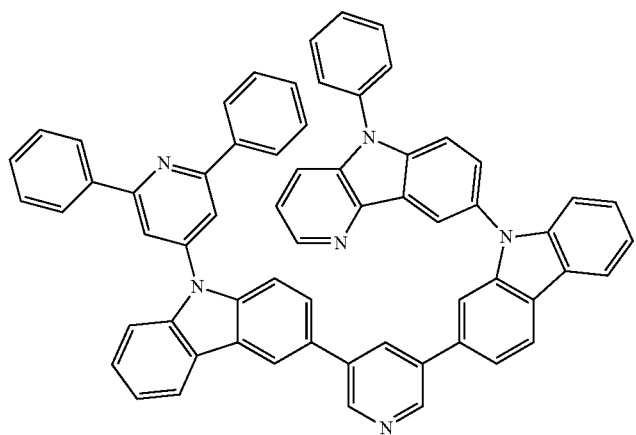

411 412
-continued
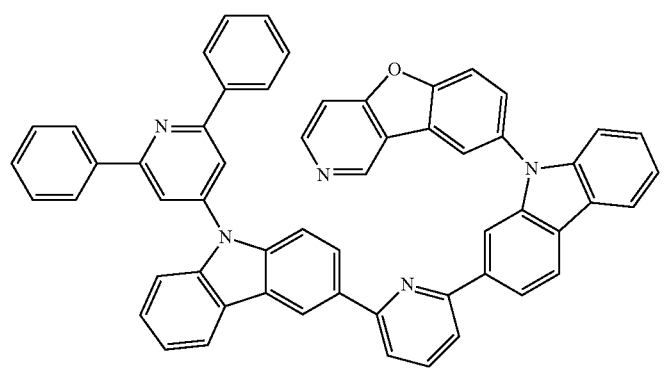
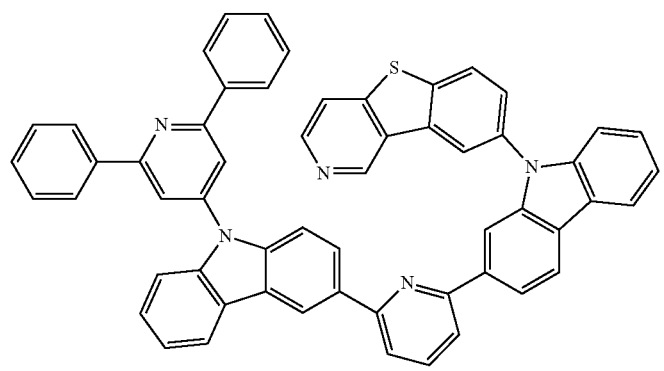
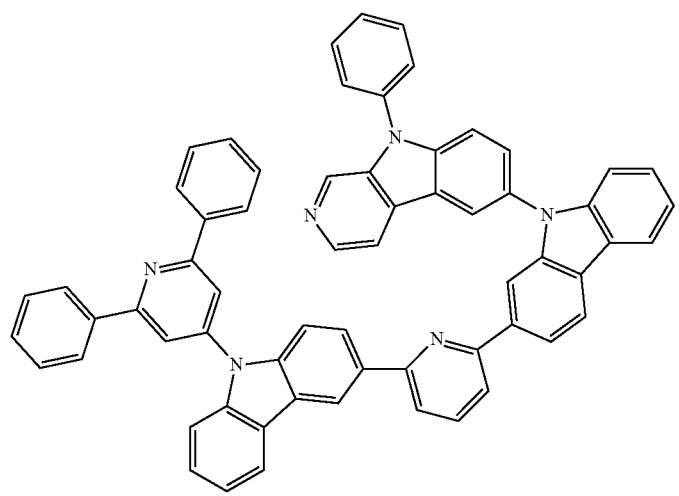
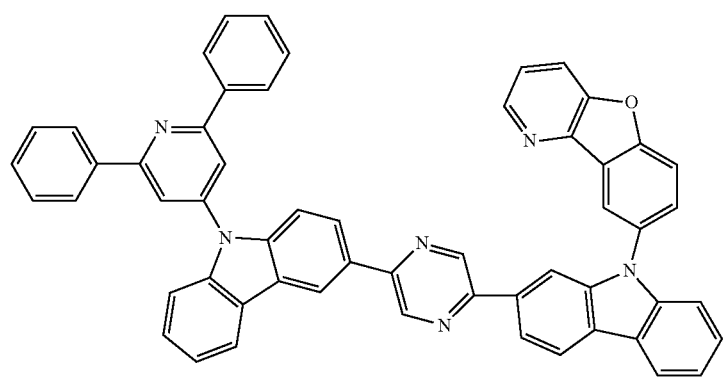

-continued
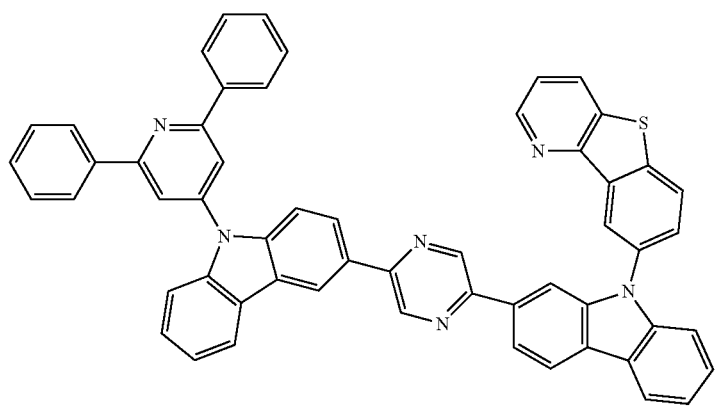
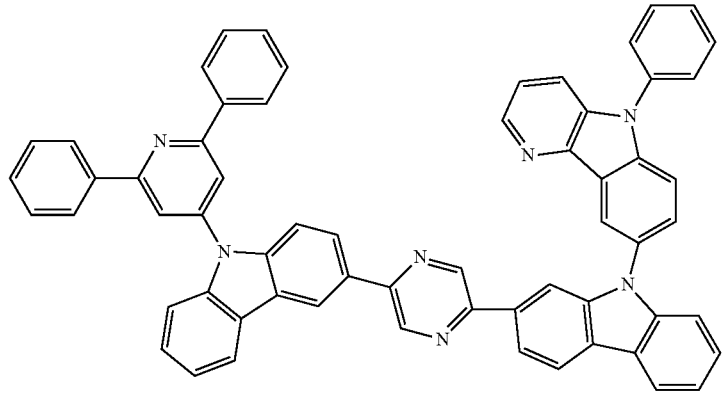
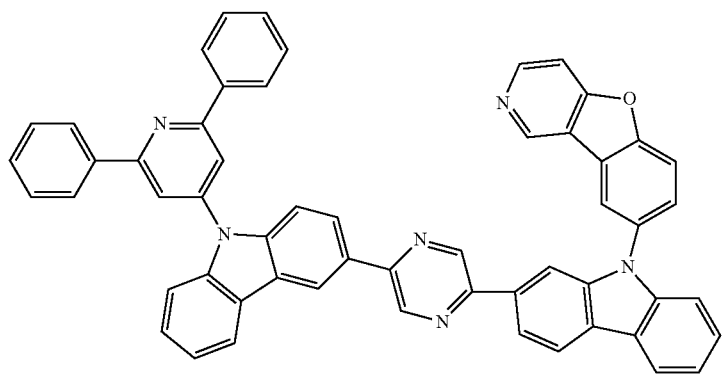
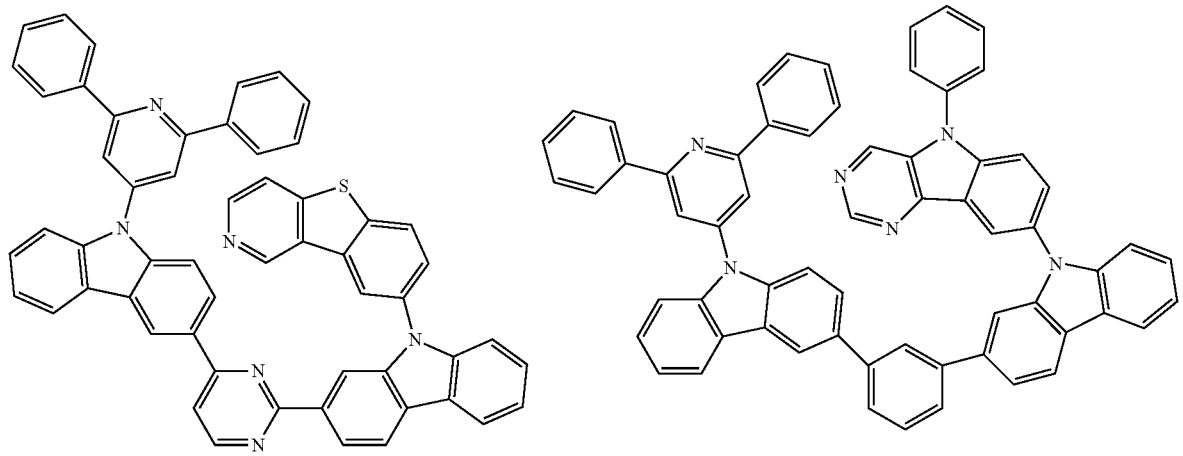

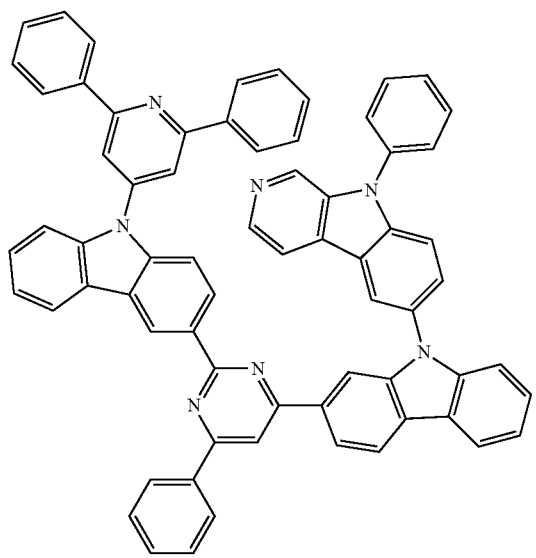
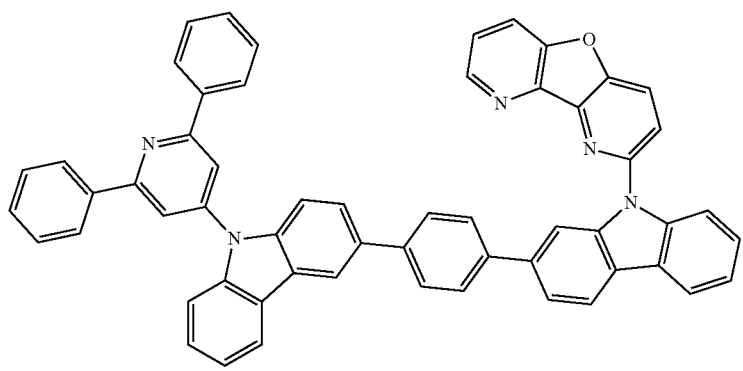
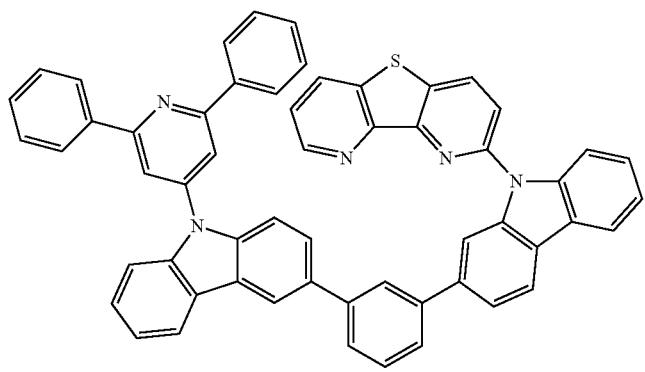

-continued
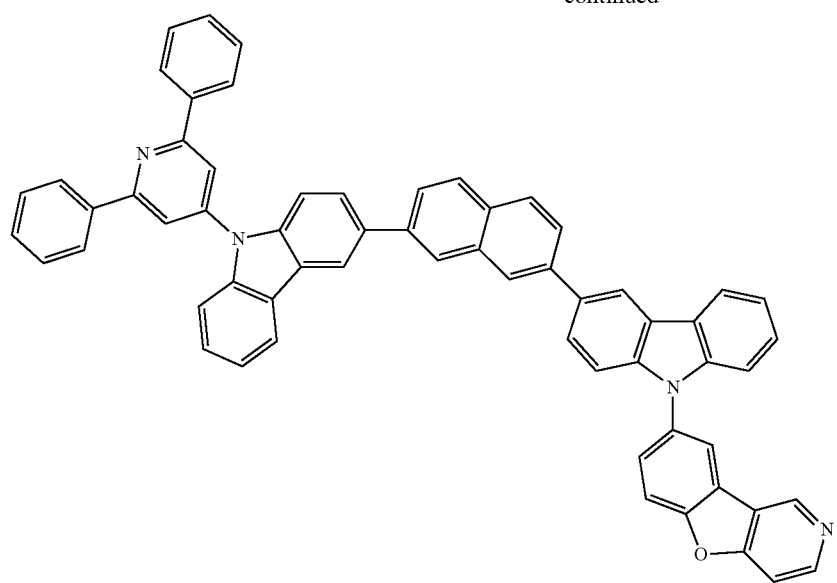
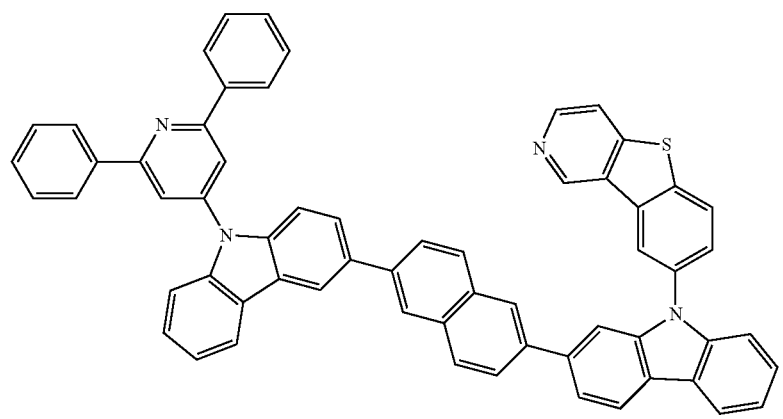
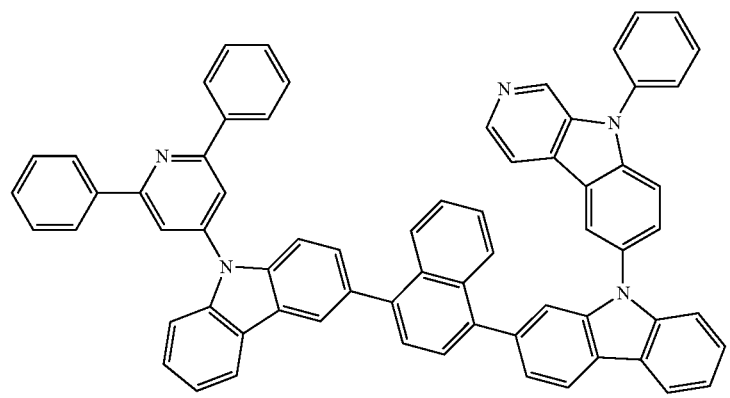

-continued
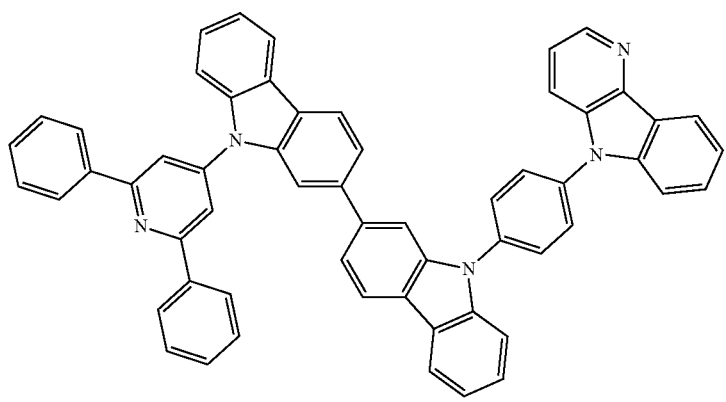
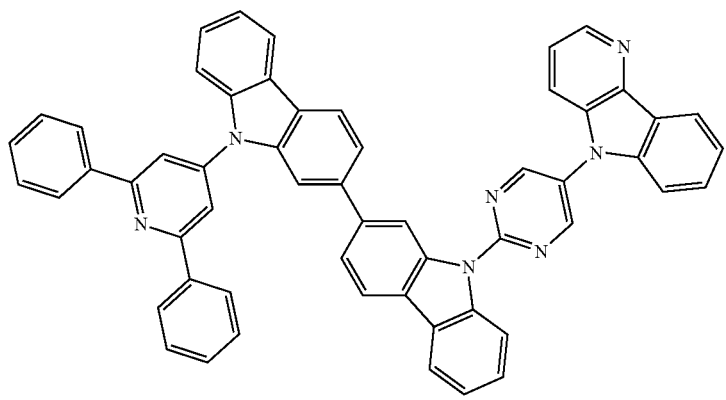
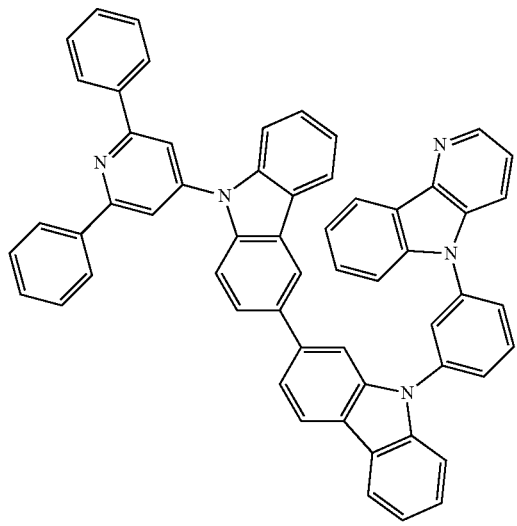
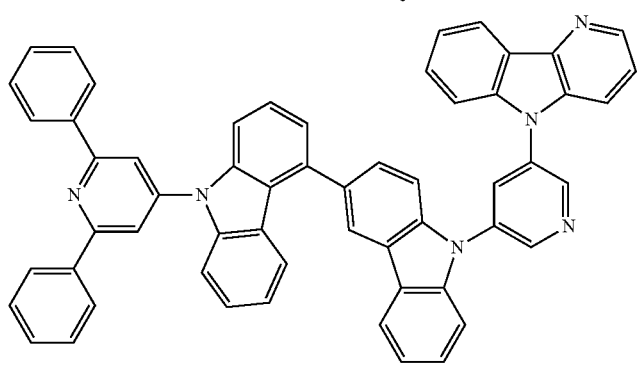

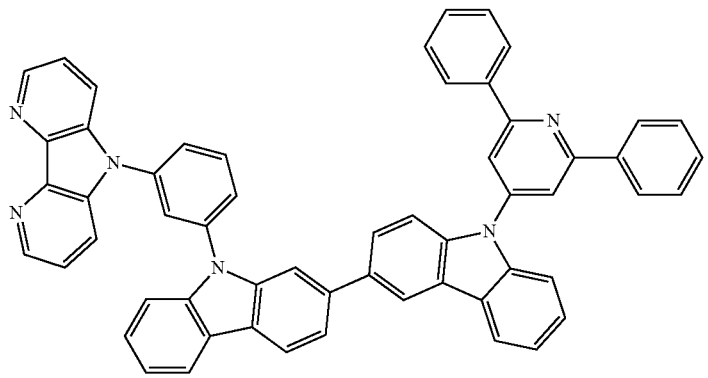
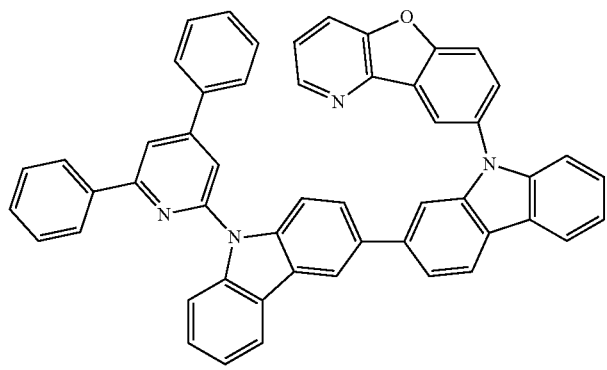
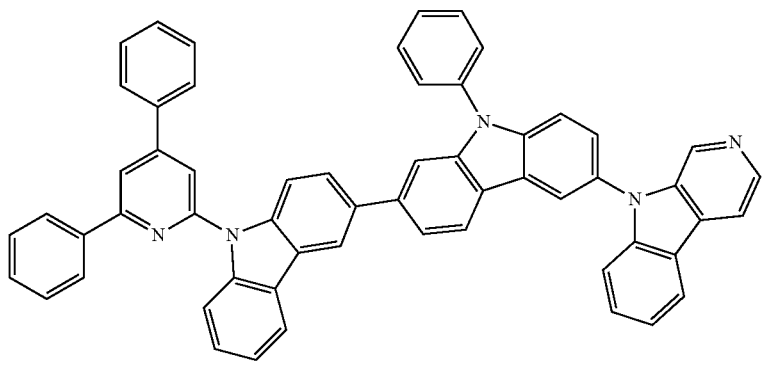
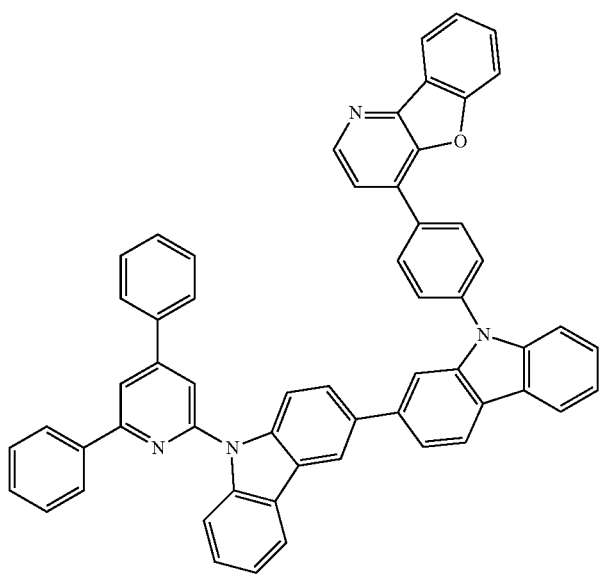

423 424
-continued
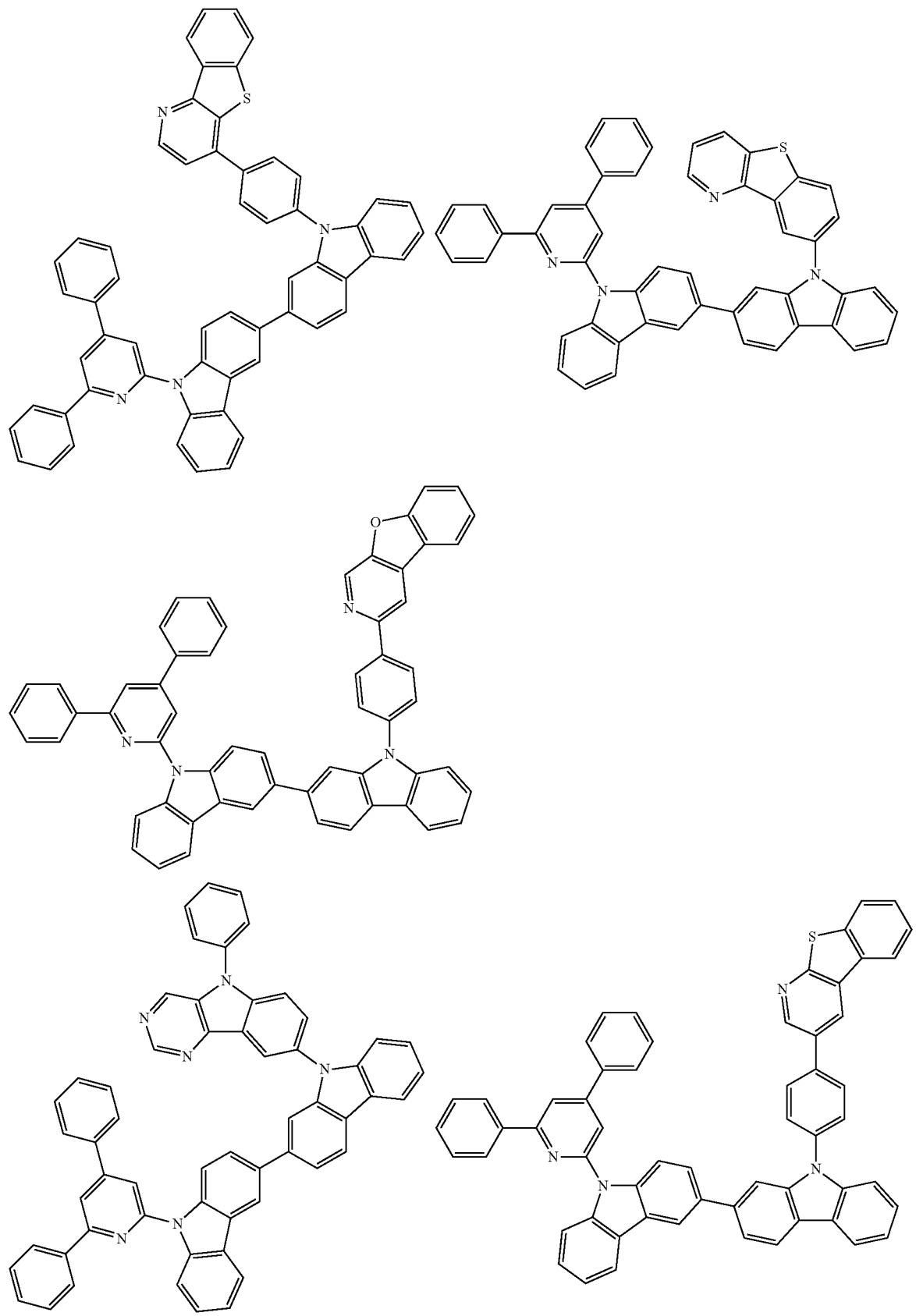

-continued
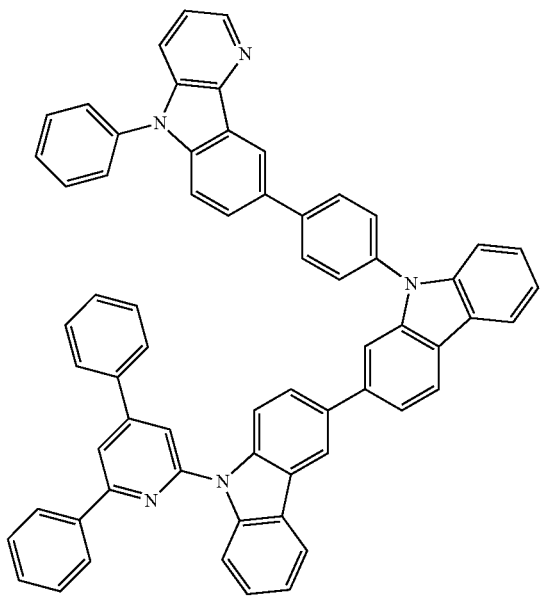
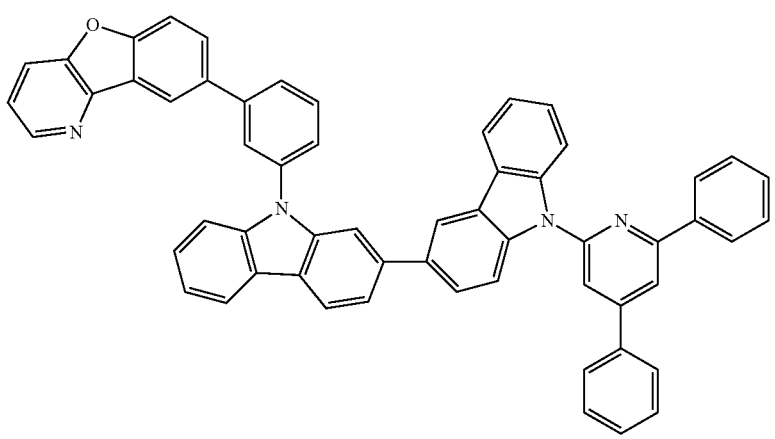
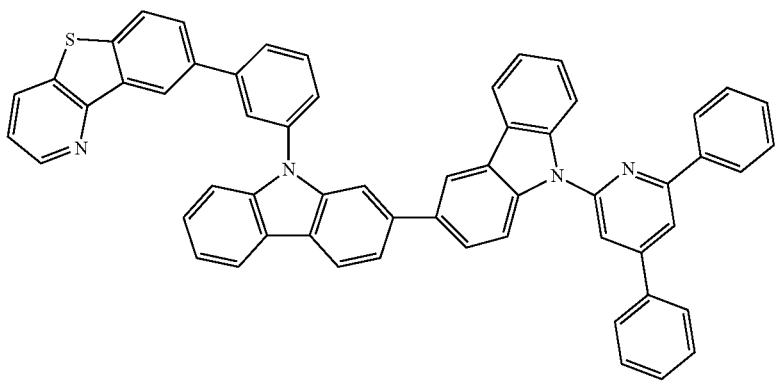

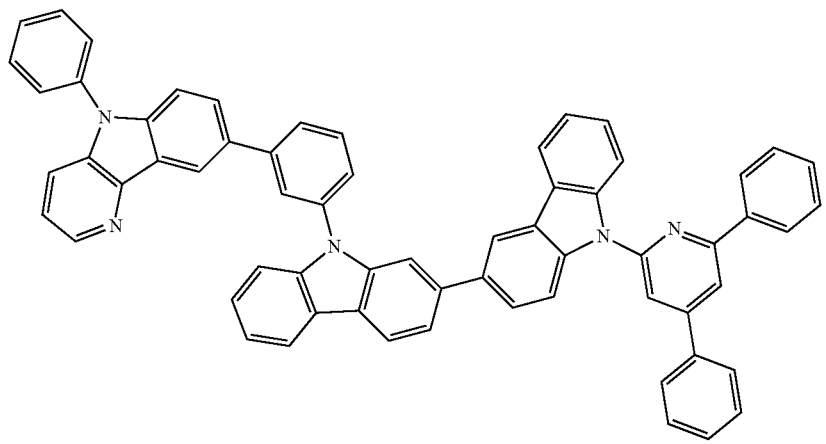
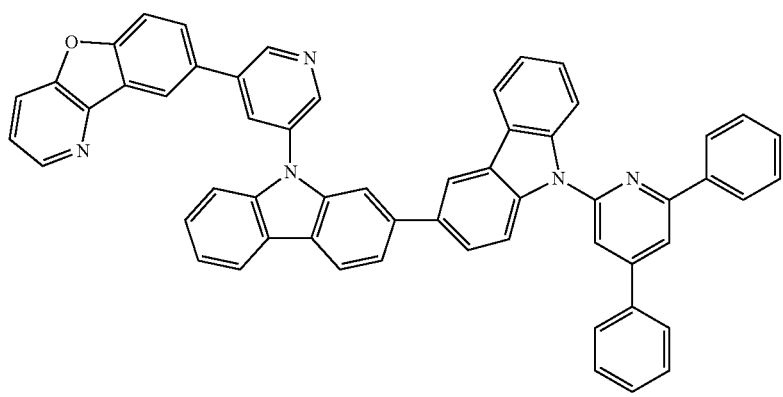
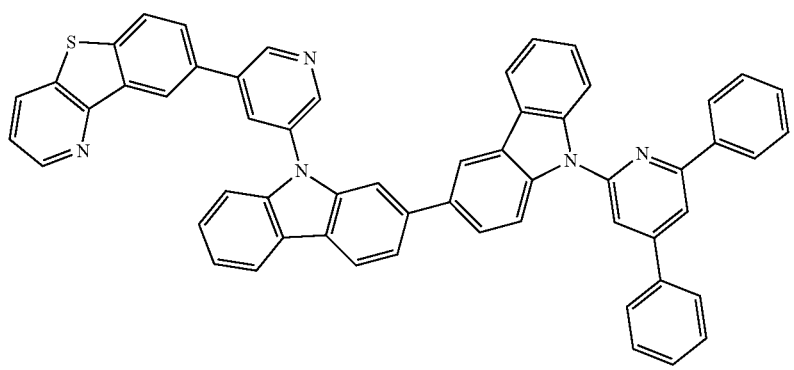
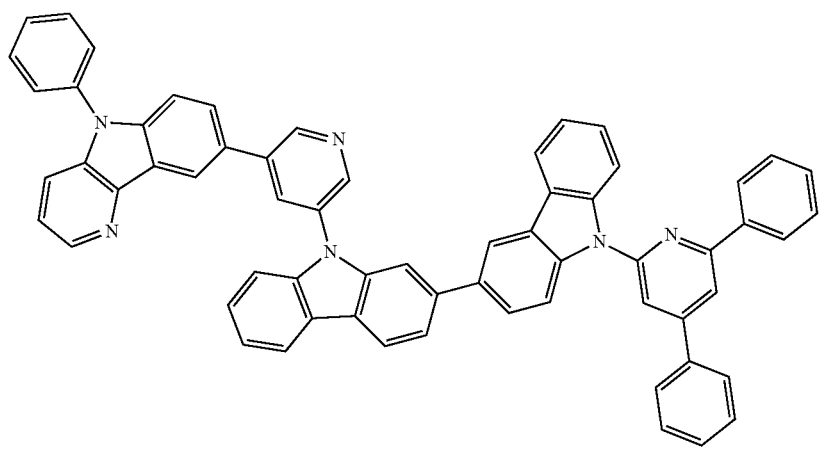

-continued
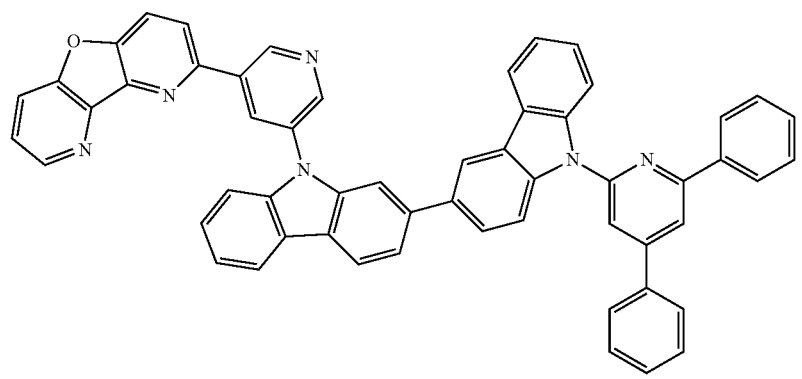
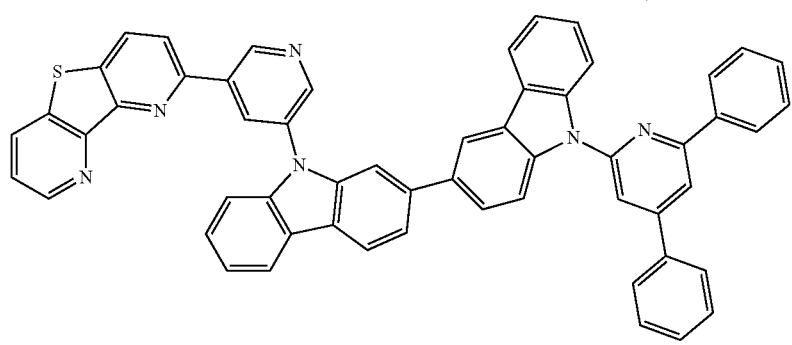
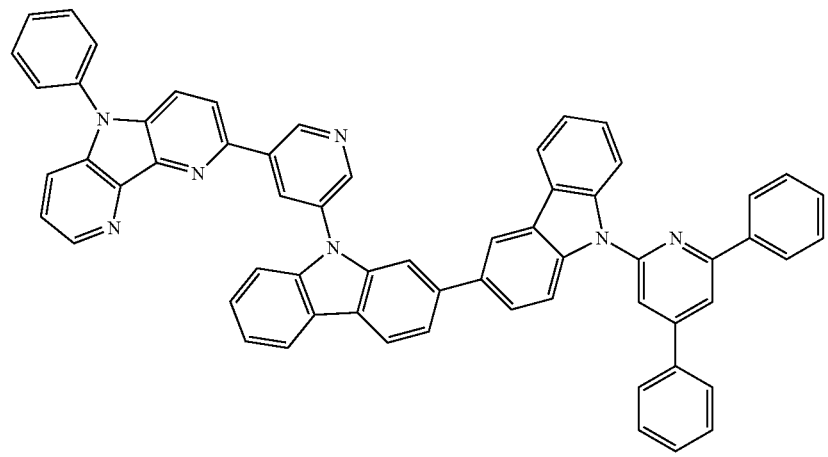
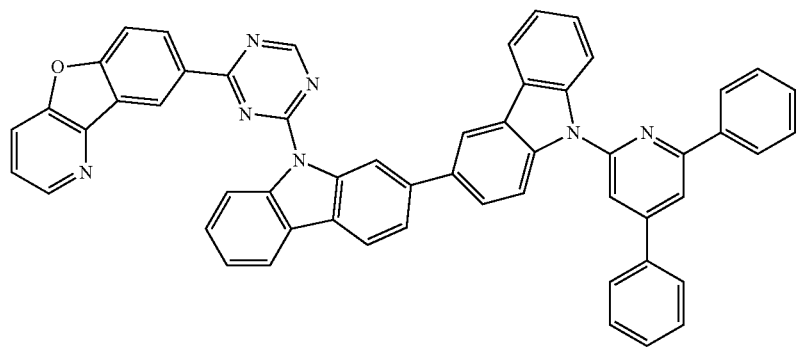

-continued
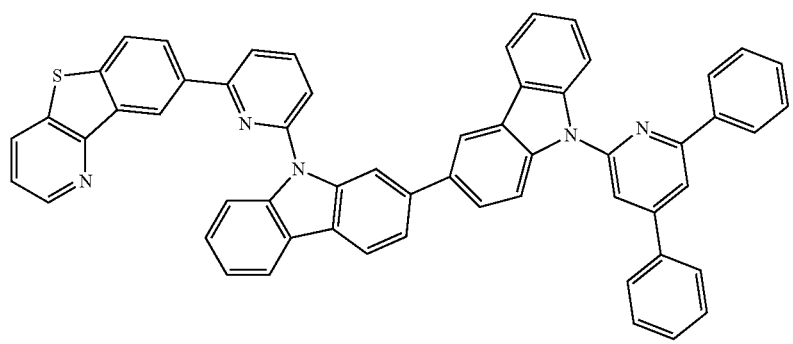
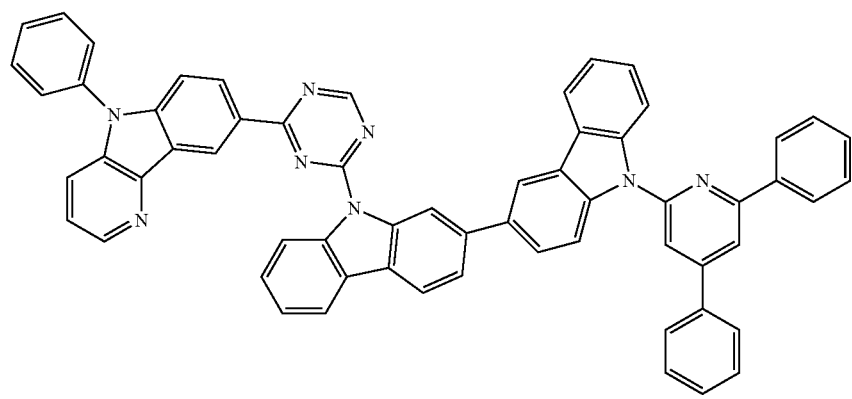
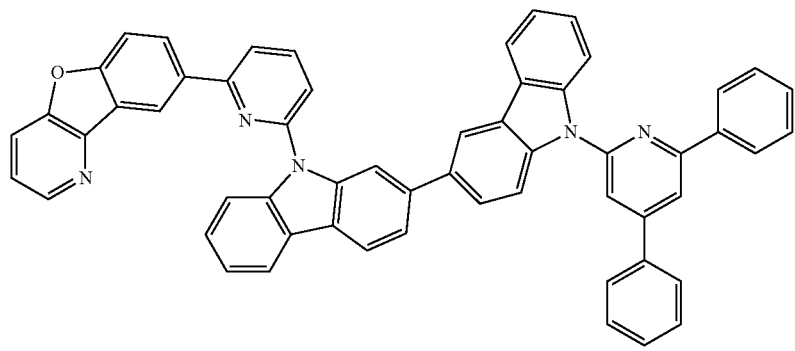
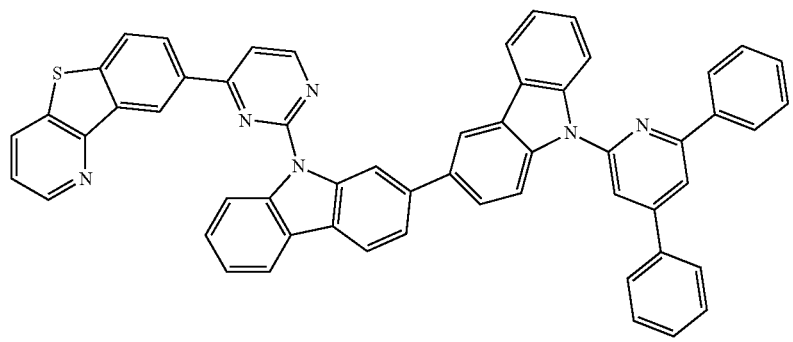

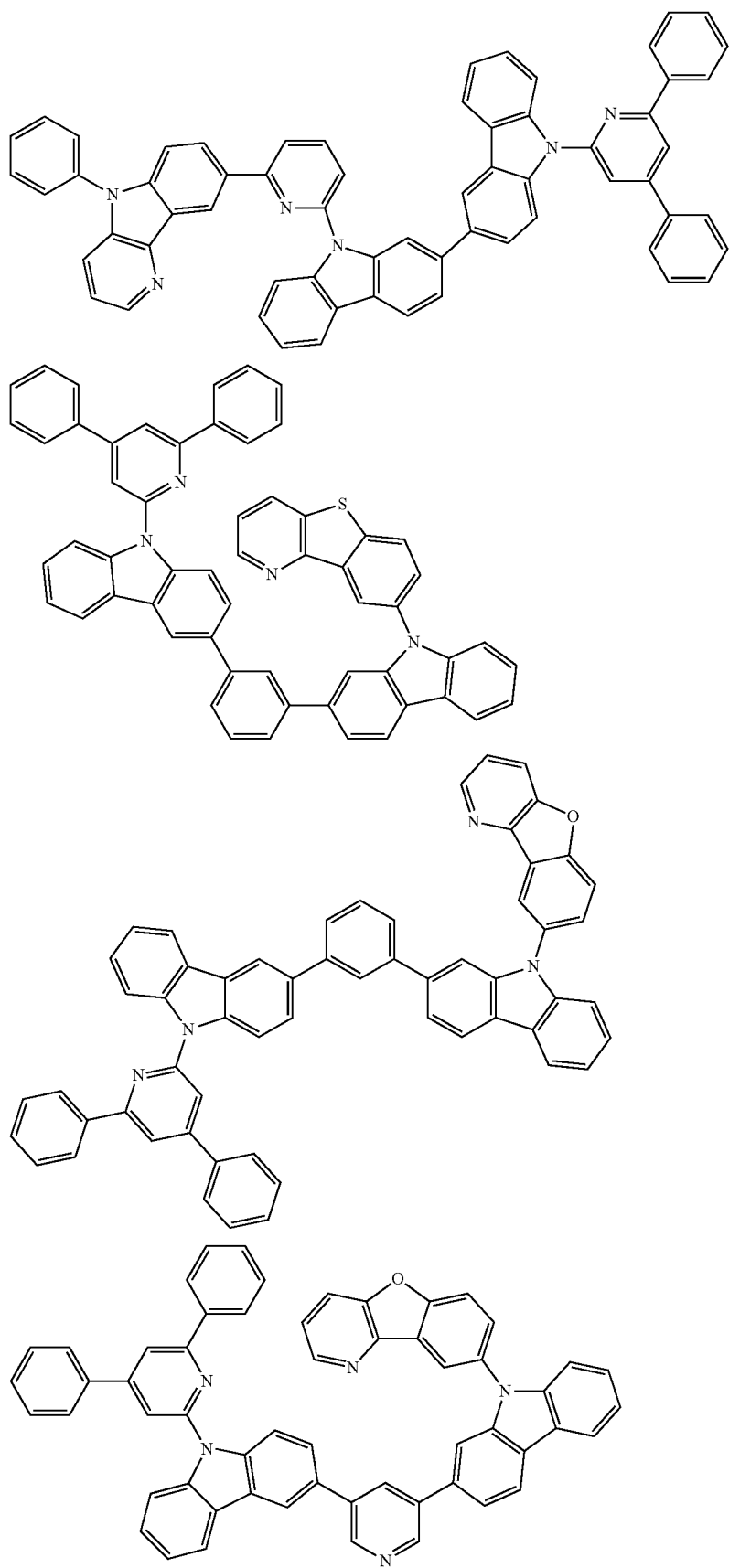

-continued
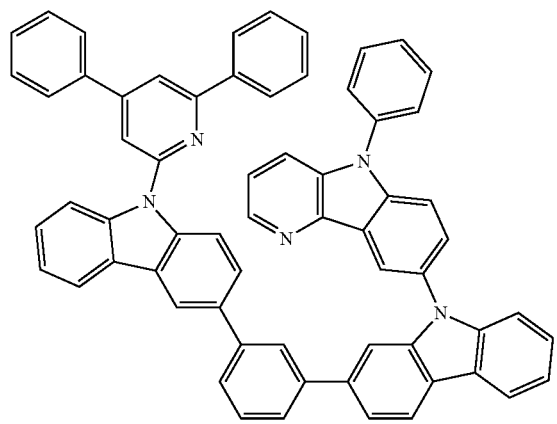
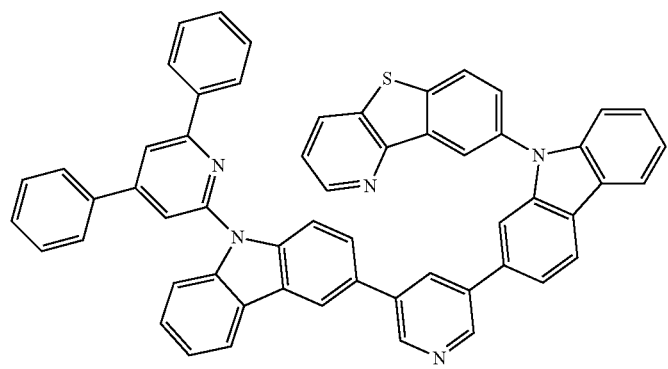
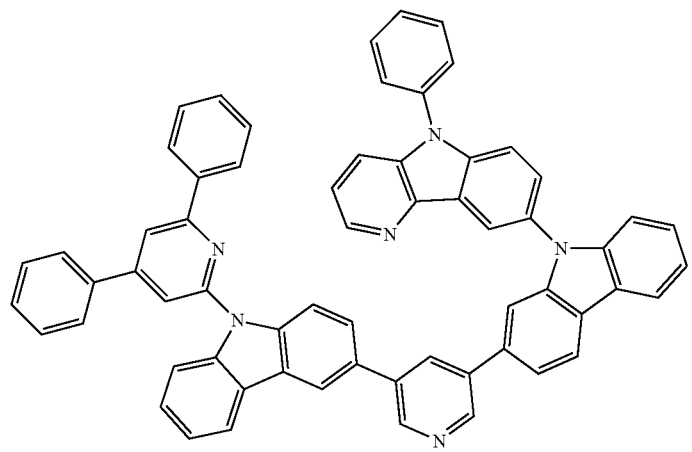
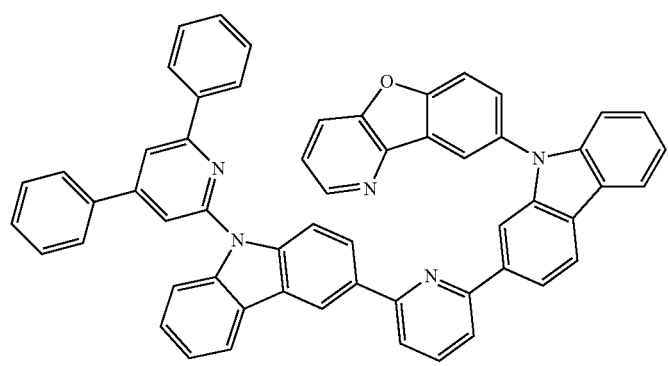

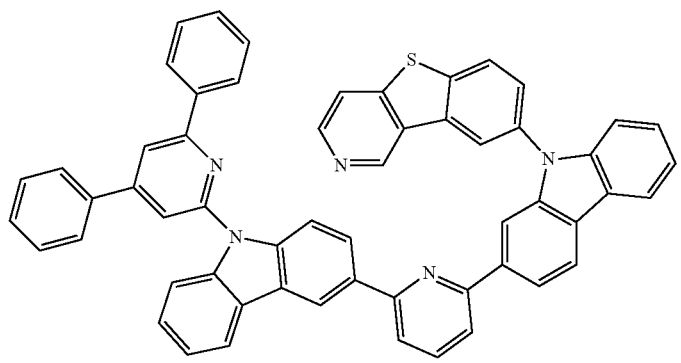
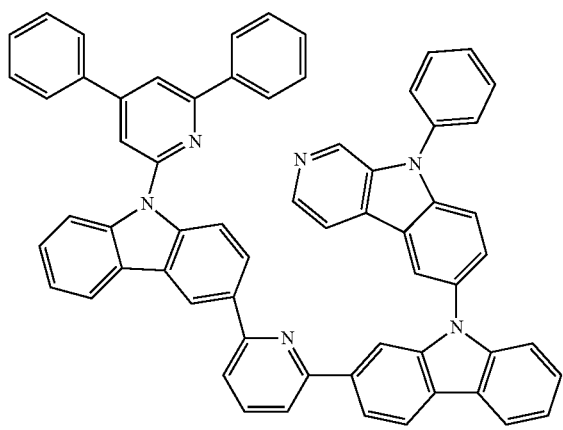
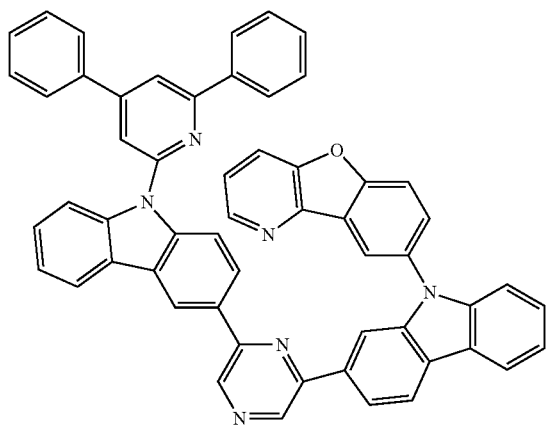

-continued
| 439 | 440 |
|---|---|
| 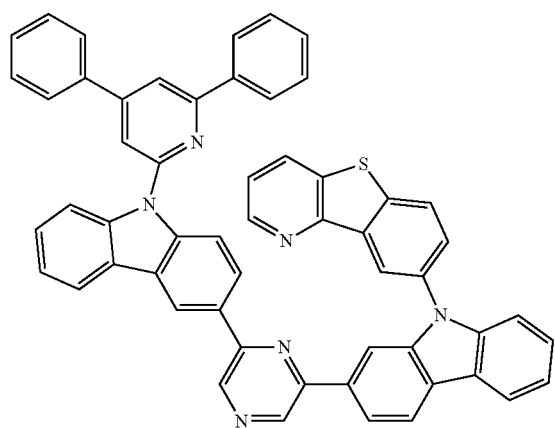 | 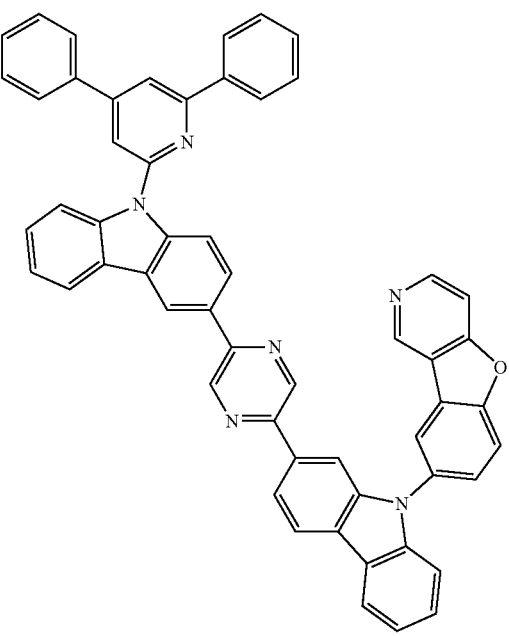 |
| 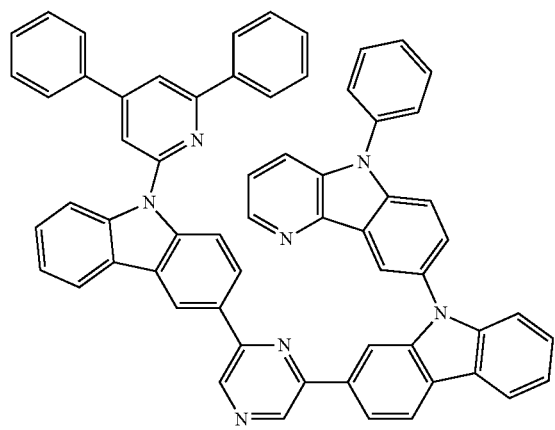 | 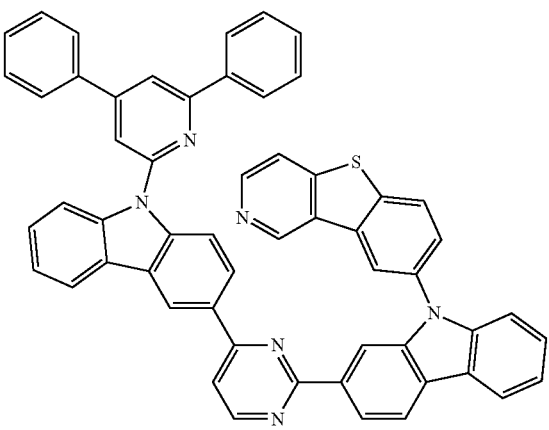 |
| 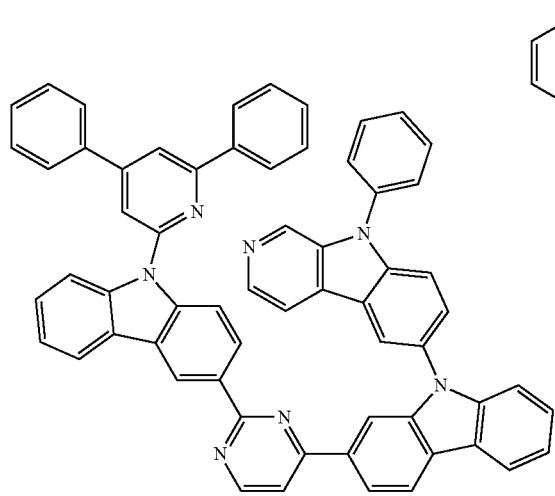 | 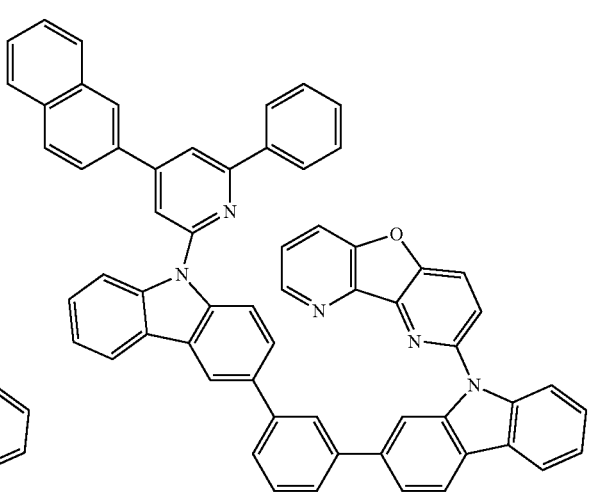 |

-continued
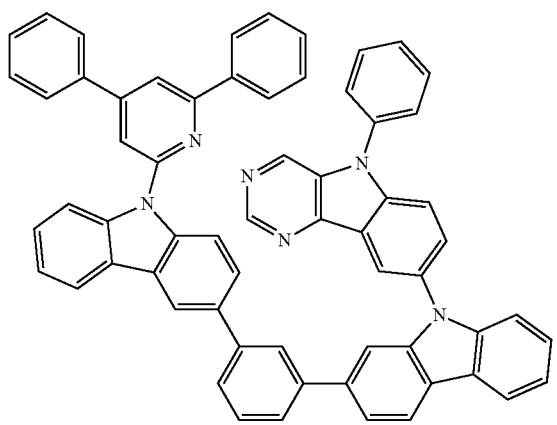
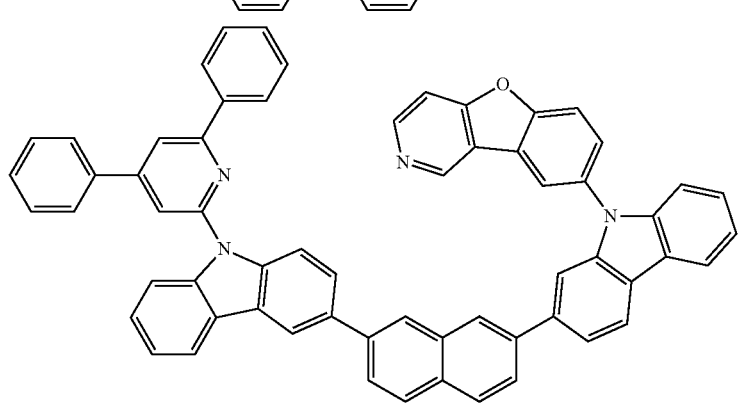
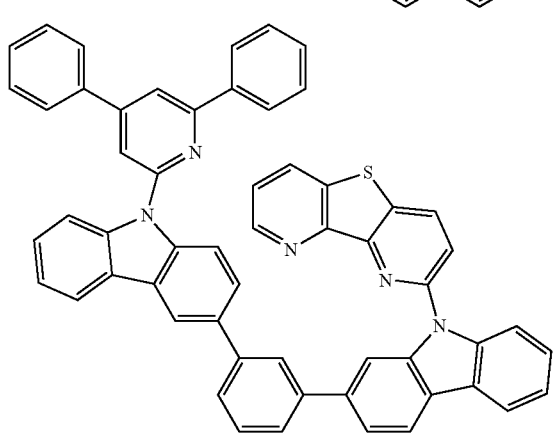
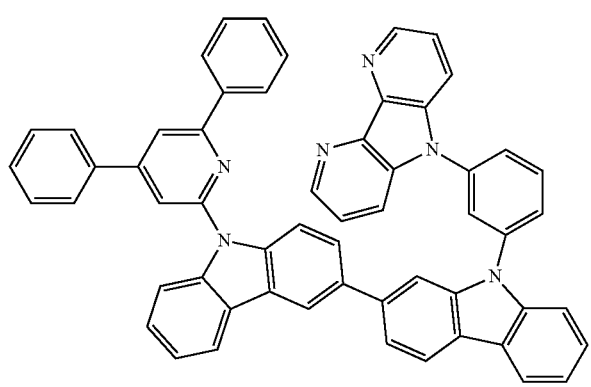

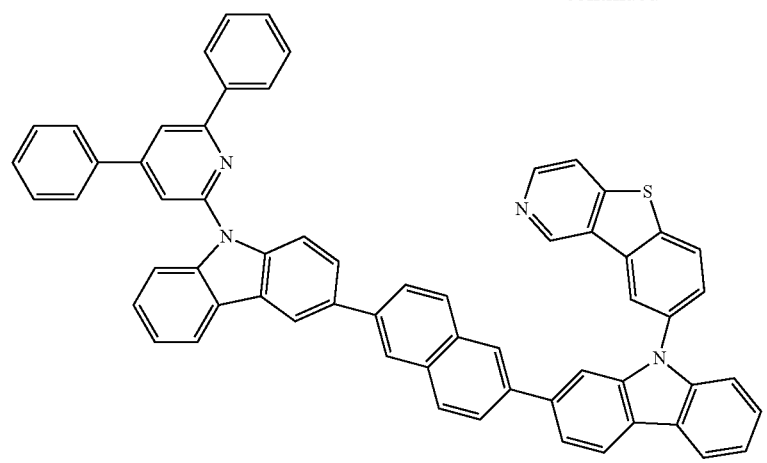
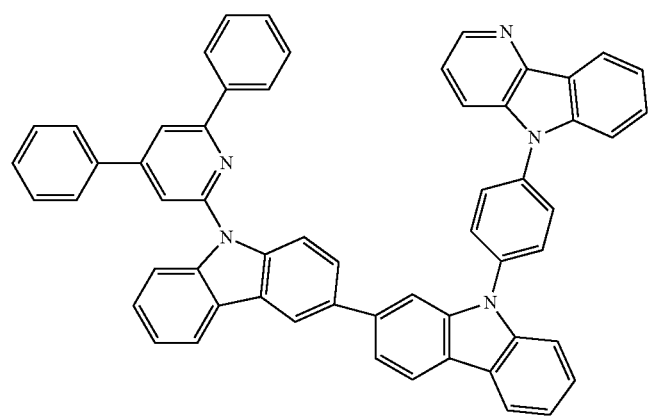
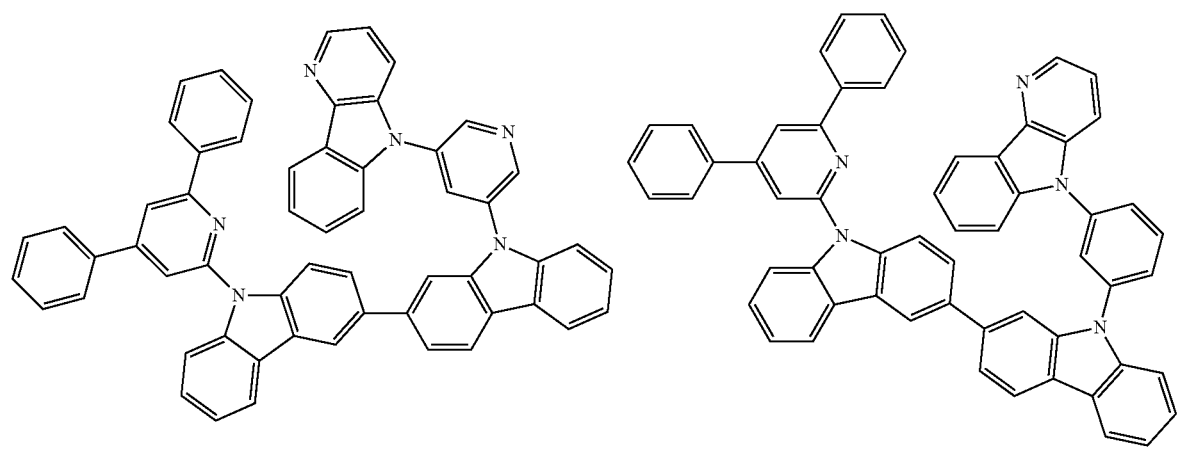
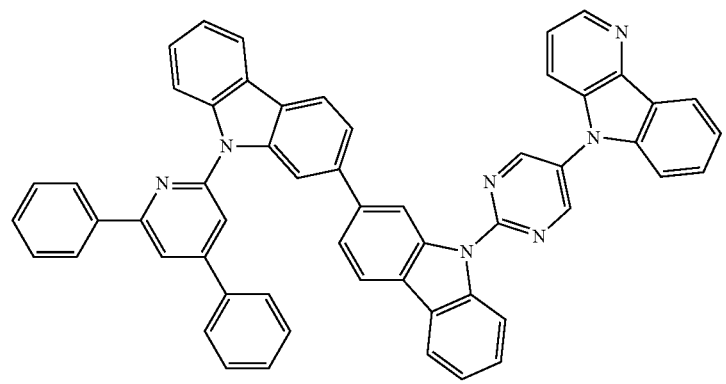

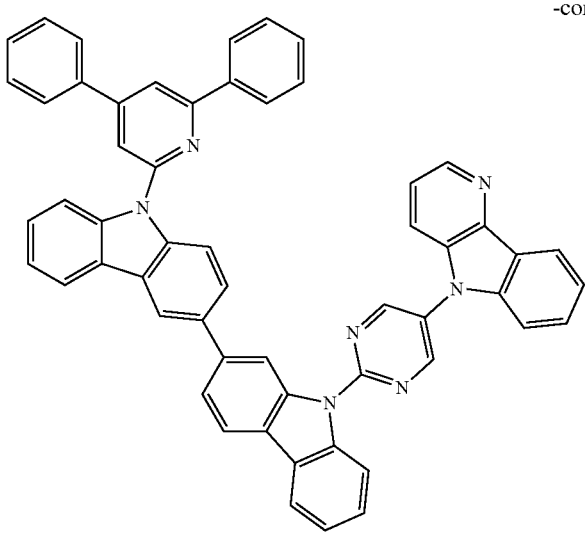

The compound of the invention can be produced in accordance with the following synthesis examples.

The compound of the invention can be suitably used as a material for an organic thin film layer constituting an organic EL device.

The compound of the invention is particularly preferable as a material for an emitting layer, and layers adjacent to an emitting layer, e.g. a hole-blocking layer or an electron blocking layer, in a phosphorescent organic EL device.

Subsequently, the organic EL device of the invention will be explained.

The organic EL device of the invention comprises one or more organic thin film layers including an emitting layer between an anode and a cathode. The material for an organic El device of the invention is contained in at least one of the organic thin film layers.

FIG. 1 is a schematic view showing a layer structure according to one embodiment of the organic EL device of the invention.

The organic EL device 1 has a construction in which an anode 20, a hole-transporting region 30, a phosphorescent emitting layer 40, an electron-transporting zone 50 and a cathode 60 are stacked on a substrate 10 in this order. The hole-transporting zone 30 means a hole-transporting layer, a hole-injecting layer, or the like. Similarly, the electron-transporting zone 50 means an electron-transporting layer, an electron-injecting layer or the like. Although these layers may not be formed, it is preferred that one or more layers be formed. In this device, each organic layer provided in the hole-transporting zone 30, a phosphorescent emitting layer 40 and each organic layer provided in the electron-transporting zone 50 correspond to the above-mentioned organic thin film layers. Among these organic thin film layers, at least one layer contains the material for an organic EL device of the invention. By this, the driving voltage of an organic EL device can be lowered.

Meanwhile, in the organic thin film layer containing the compound of the invention (hereinafter often referred to as "the material for an organic EL device of the invention"), the content of the material is preferably 1 to 100 wt %.

In the organic EL device of the invention, the material for an organic EL device of the invention is preferably contained in the phosphorescent emitting layer 40, and in particular, is preferably used as a host material in an emitting layer. Since the material of the invention has a sufficiently large triplet energy, even if a blue phosphorescent dopant material is used, the triplet energy of the phosphorescent dopant material can be efficiently confined in the emitting layer. Meanwhile, the material of the invention can be used not only in a blue emitting layer but also in an emitting layer which emits light having a longer wave length (green to red or the like).

In the invention, the maximum value of the emission wavelength of the device can be 430 nm or more and 720 nm or less.

The phosphorescent emitting layer contains a phosphorescent emitting material (phosphorescent dopant). As the phosphorescent dopant, metal complex compounds can be given. Preferable is a compound having a metal atom selected from Ir, Pt, Os, Au, Cu, Re and Ru and a ligand. The ligand preferably has an ortho-metal bond.

In respect of a high phosphorescent quantum yield and capability of improving external quantum yield of an emitting device, the phosphorescent dopant is preferably a compound having a metal atom selected from Ir, Os and Pt. Further preferable are a metal complex such as an iridium complex, an osmium complex and a platinum complex. Among them, an iridium complex and a platinum complex are more preferable, and an ortho-metalated iridium complex is most preferable. The dopant may be used singly or in combination of two or more.

It is preferred that the triplet energy of the phosphorescent material be 1.8 eV or more and less than 2.9 eV. With this range of triplet energy, red to blue emission having high purity can be obtained.

The concentration of a phosphorescent dopant added to a phosphorescent emitting layer is not particularly limited, but is preferably 0.1 to 30% by weight (wt %), with 0.1 to 20% by weight (wt %) being more preferable.

Moreover, it is preferred that the material of the invention be used in layers adjacent to the phosphorescent emitting layer 40. For example, in the device shown in FIG. 1, when layers containing the material of the invention (adjacent layers nearer to the anode) are formed between the hole-transporting zone 30 and the phosphorescent emitting layer 40, the layers function as an electron-blocking layer or an exciton-barrier layer.

On the other hand, when layers containing the material of the invention (adjacent layers near the cathode) are formed between the phosphorescent emitting layer 40 and the electron-transporting zone 50, the layers function as a hole-blocking layer or an exciton-barrier layer.

Meanwhile, the blocking (barrier) layer is a layer which blocks transporting of carriers or diffusion of excitons. The organic layer which prevents electrons from escaping from an emitting layer into a hole-transporting zone is mainly defined as the electron-blocking layer. The organic layer which prevents holes from leaking from an emitting layer into an electron-transporting zone is often defined as the hole-blocking layer. In addition, the organic layer which prevents triplet excitons generated in an emitting layer from diffusing to the peripheral layers having lower triplet energy than that of the emitting layer is often defined as the exciton-barrier layer (triplet-blocking layer).

Moreover, it is also possible to use the material of the invention in the layers adjacent to the phosphorescent emitting layer 40, and further in other organic thin film layers which bond to the adjacent layers.

Moreover, when two or more emitting layers are formed, the material of the invention can be suitably used in spacing layers formed between the emitting layers.

Figure 2:
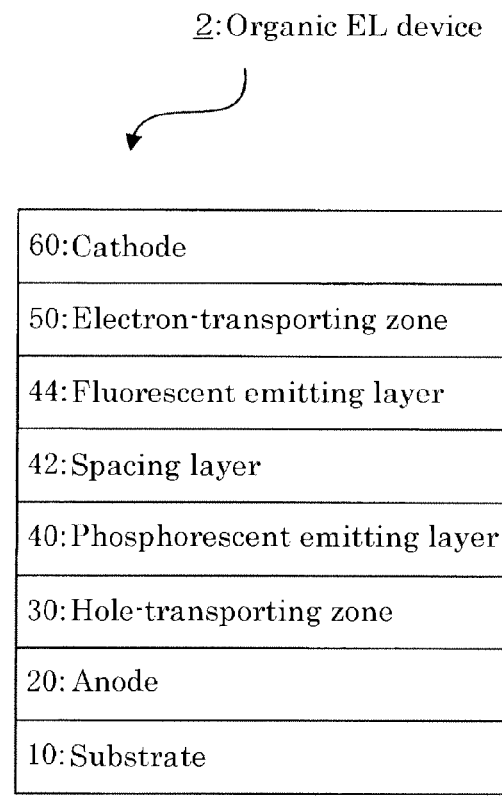
FIG. 2 is a schematic view showing the layer structure according to another embodiment of the organic EL device of the invention.

FIG. 2 is a schematic view showing the layer structure according to another embodiment of the organic EL device of the invention.

The organic EL device 2 is an example of a hybrid-type organic EL device, in which a phosphorescent emitting layer and a fluorescent emitting layer are stacked.

The organic EL device 2 has the same construction as the organic EL device 1 mentioned above, except that a spacing layer 42 and a fluorescent emitting layer 44 are formed between a phosphorescent emitting layer 40 and an electron-transporting zone 50. In the construction in which the phosphorescent emitting layer 40 and the fluorescent emitting layer 44 are stacked, for preventing excitons generated in the phosphorescent emitting layer 40 from diffusing into the fluorescent emitting layer 44, the spacing layer 42 may be provided between the fluorescent emitting layer 44 and the phosphorescent emitting layer 40. Since the material of the invention has a large triplet energy, it can function as a spacing layer.

In the organic EL device 2, for example, by allowing the phosphorescent emitting layer to emit yellow light and by allowing the fluorescent emitting layer to emit blue light, an organic EL device which emits white light can be obtained. Meanwhile, in this embodiment, the phosphorescent emitting layer and the fluorescent emitting layer are each formed as a single layer. However, the configuration is not limited thereto, and they may be each formed as two or more layers. Their manner of formation can be selected appropriately depending on the intended use such as lightning or a display device. For example, when a full-color emitting device is realized by utilizing white emitting devices and color filters, the phosphorescent emitting layer and the fluorescent emitting layer preferably include emissions in the plural wave length regions such as red, green and blue (RGB), or red, green, blue and yellow (RGBY) in respect of color rendering properties.

In addition to the above-mentioned embodiments, the organic EL device of the invention can employ various known structures. Further, the emission from an emitting layer can be outcoupled from the anode side, the cathode side or the both sides.

In the organic EL device of the invention, configurations of other layers than those in which the above-mentioned material for an organic EL device of the invention is used are not particularly restricted, and known materials or the like can be used. Hereinbelow, a brief explanation will be made on the layer of the device according to the embodiment 1. However, materials to be applied to the organic EL device of the invention are not limited to those mentioned below.

[Substrate]

As the substrate, a glass sheet, a polymer sheet or the like can be used.

Examples of materials of the glass sheet include soda lime glass, barium-strontium-containing glass, lead glass, aluminosilicate glass, borosilicate glass, barium borosilicate glass, quartz, and the like. Examples of materials of the polymer sheet include polycarbonate, acryl, polyethylene terephthalate, polyethersulfone, polysulfone, and the like.

[Anode]

The anode is formed of a conductive material, for example. A conductive material having a work function larger than 4 eV is suitable.

As the conductive material, carbon, aluminum, vanadium, iron, cobalt, nickel, tungsten, silver, gold, platinum, palladium, alloys thereof, an oxide metal such as tin oxide and indium oxide used in an ITO substrate and a NESA substrate and an organic conductive resin such as polythiophene and polypyrrole can be given.

If necessary, the anode may be formed of two or more layers.

[Cathode]

The cathode is formed of a conductive material, for example. A conductive material having a work function smaller than 4 eV is suitable.

As the conductive material, magnesium, calcium, tin, lead, titanium, yttrium, lithium, ruthenium, manganese, aluminum, lithium fluoride and alloys thereof can be given. The conductive material is not limited thereto.

As the alloy, a magnesium/silver alloy, a magnesium/indium alloy, a lithium/aluminum alloy or the like can be given as representative examples. The alloys are not limited thereto. The amount ratio of metals forming an alloy is controlled by the temperature of a deposition source, the atmosphere, the degree of vacuum or the like, and an appropriate ratio is selected.

If necessary, the cathode may be formed of two or more layers. The cathode can be formed by forming a thin film by subjecting the above-mentioned conductive material to a method such as deposition, sputtering or the like.

When outcoupling light from the emitting layer through the cathode, it is preferable that the cathode have a light transmittance of more than 10%.

The sheet resistance of the cathode is preferably several hundred $\Omega$/square or less. The thickness of the cathode is normally 10 nm to 1 μm, and preferably 50 to 200 nm.

[Emitting Layer]

When a phosphorescent emitting layer is formed by using materials other than the material for an organic EL device of the invention, materials which are known as a material for a phosphorescent emitting layer can be used. Specifically, reference can be made to the Japanese Patent Application No. 2005-517938 or the like.

The organic EL device of the invention may comprise a fluorescent emitting layer as the device shown in FIG. 2. As the fluorescent emitting layer, known materials can be used.

The emitting layer can be a double-host (often referred to as host/co-host) type. Specifically, in the emitting layer, an electron-transporting host and a hole-transporting host may be combined to control the carrier balance.

The emitting layer also can be of a double-dopant type. By incorporating two or more kinds of dopant materials having a high quantum yield to the emitting layer, each dopant emits. For example, there may be a case that a yellow emitting layer is realized by co-depositing a host, and a red dopant and a green dopant.

The emitting layer may be a single layer, or may have a stacked structure. When the emitting layer has a stacked structure, due to the accumulation of electrons and holes in the interface of the emitting layers, the recombination region can be concentrated in the interface of the emitting layers, thereby increasing the quantum efficiency.

[Hole-Injecting Layer and Hole-Transporting Layer]

The hole-injecting/transporting layer is a layer that helps holes to be injected to an emitting layer and transports the injected holes to an emitting region. It has a large hole mobility and normally a small ionization energy of 5.6 eV or less.

As the material for a hole-injecting/transporting layer, materials which can transport holes to an emitting layer at lower electric field intensity are preferable. In addition, it is preferred that the hole mobility be at least $10^{-4}$ cm$^2$/V·second when an electric field intensity of $10^4$ to $10^6$ V/cm is applied, for example.

Specific examples of materials for a hole-injecting layer and a hole-transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712, 47-25336 and 54-119925, and others), arylamine derivatives (see U.S. Pat. Nos. 3,567,450, 3,240,597, 3,658,520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), and aniline copolymers (JP-A-2-282263).

Further, an inorganic compound such as P-type Si and P-type SiC can be used as the hole-injecting material.

As the material for a hole-injecting/transporting layer, a cross-linking material can be used. As the cross-linking hole-injecting/transporting layer, a layer formed of the cross-linking agent disclosed in Chem. Mater. 2008, 20, 413-422, Chem. Mater. 2011, 23(3), 658-681, WO2008108430, WO2009102027, WO2009123269, WO2010016555, WO2010018813 or the like insolubilized by heat, light or the like can be given, for example.

[Electron-Injecting Layer and Electron-Transporting Layer]

The electron-injecting/transporting layer helps electrons to be injected to an emitting layer and transports the injected electrons to an emitting region. It has a large electron mobility.

In the organic EL device, it is known that since emitting light is reflected by an electrode (a cathode, for example), emission outcoupled directly from an anode interferes with emission after being reflected by the electrode. In order to utilize the interference effect efficiently, the film thickness of the electron injecting/transporting layer is appropriately selected to be several nm to several μm. When the film thickness is particularly large, it is preferred that the electron mobility be at least $10^{-6}$ cm$^2$/Vs or more at an applied electric field intensity of $10^4$ to $10^6$ V/cm in order to avoid an increase in voltage.

As the electron-transporting material used in the electron-injecting/transporting layer, an aromatic hetero ring compound containing one or more hetero atoms in the molecule is preferably used, with a nitrogen-containing ring derivative being particularly preferable. Further, as the nitrogen-containing ring derivative, a heteroaromatic hydrocarbon ring compound having a nitrogen-containing six-member ring or five-member ring skeleton, or a heterofused aromatic ring compound having a nitrogen-containing six-member ring or five-member ring skeleton is preferable. Examples thereof include compounds containing a pyridine ring, a pyrimidine ring, a triazine ring, a benzimidazole ring, a phenanthroline ring, a quinazoline ring or the like in the skeleton.

In addition, an organic layer with a semiconductor property may be formed by doping a donor material (n) or doping an acceptor material (p). Representative examples of N-doping include one obtained by doping an electron-transporting material with a metal such as Li or Cs. Representative examples of P-doping include one obtained by doping a hole-transporting material with an acceptor material such as F4TCNQ (see Japan Patent No. 3695714, for example).

In the invention, it is preferred that one or more electron-transporting layers (electron-injecting layer) be included and that at least one of the electron-transporting layers contain the compound of the invention.

As a result, an organic EL device having a low driving voltage can be realized.

Further, it is preferred that two or more electron-transporting layers (electron-injecting layers) be included; that at least one layer of the electron-transporting layers contain the compound of the invention; and that the same or other electron-transporting layers contain the above-mentioned heteroaromatic hydrocarbon ring compound having a nitrogen-containing six-member ring or five-member ring skeleton or a heterofused aromatic ring compound having a nitrogen-containing six-member ring or five-member ring skeleton. By this, an organic EL device having favorable electron injection property can be realized, leading to a lowering in driving voltage.

In the organic EL device, it is preferred that at least any of an electron-donating dopant and an organic metal complex be provided in an interfacial region of the cathode and the organic thin film layer.

Due to such a configuration, the organic EL device can have improved luminance and a prolonged lifetime.

As the electron-donating dopant, at least one selected from an alkali metal, an alkali metal compound, an alkaline-earth metal, an alkaline-earth metal compound, a rare-earth metal and a rare-earth metal compound can be given.

As the organic metal complex, at least one selected from an organic metal complex including an alkali metal, an organic metal complex including an alkaline-earth metal and an organic metal complex including a rare-earth metal can be given.

As the alkali metal, lithium (Li) (work function: 2.93 eV), sodium (Na) (work function: 2.36 eV), potassium (K) (work function: 2.28 eV), rubidium (Rb) (work function: 2.16 eV), cesium (Cs) (work function: 1.95 eV) and the like can be given. One having a work function of 2.9 eV or less is particularly preferable. Of these, K, Rb and Cs are preferable, Rb or Cs is further preferable, and Cs is most preferable.

As the alkaline-earth metal, calcium (Ca) (work function: 2.9 eV), strontium (Sr) (work function: 2.0 eV or more and 2.5 eV or less), barium (Ba) (work function: 2.52 eV) and the like can be given. One having a work function of 2.9 eV or less is particularly preferable.

As the rare-earth metal, scandium (Sc), yttrium (Y), cerium (Ce), terbium (Tb), ytterbium (Yb) and the like can be given. One having a work function of 2.9 eV or less is particularly preferable.

Among the above-mentioned metals, the preferable metals have a particularly high reducing ability, and hence can provide the resulting organic EL device with an improved luminance and a prolonged lifetime by adding a relative small amount to an electron-injecting region.

Examples of the alkali metal compound include an alkali oxide such as lithium oxide ($Li_2O$), cesium oxide ($Cs_2O$) or potassium oxide ($K_2O$), and an alkali halide such as lithium fluoride (LiF), sodium fluoride (NaF), cesium fluoride (CsF) or potassium fluoride (KF). Of these, lithium fluoride (LiF), lithium oxide ($Li_2O$) and sodium fluoride (NaF) are preferable.

Examples of the alkaline-earth metal compound include barium oxide (BaO), strontium oxide (SrO), calcium oxide (CaO), and mixtures thereof such as barium strontium acid ($Ba_xSr_{1-x}O$) (0<x<1) and barium calcium acid ($Ba_xCa_{1-x}O$) (0<x<1). Among these, BaO, SrO and CaO are preferred.

Examples of the rare-earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$). Among these, $YbF_3$, $ScF_3$ and $TbF_3$ are preferable.

The organic metal complexes are not particularly limited as long as they contain, as a metal ion, at least one of alkali metal ions, alkaline-earth metal ions, and rare-earth metal ions, as mentioned above. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

Regarding the addition form of the electron-donating dopant and the organic metal complex, it is preferred that the electron-donating dopant and the organic metal complex be formed in a shape of a layer or an island in the interfacial region. A preferred method for the formation is a method in which an organic substance as a light emitting material or an electron-injecting material for forming the interfacial region is deposited at the same time as at least one of the electron-donating dopant and the organic metal complex is deposited by a resistant heating deposition method, thereby dispersing at least one of the electron-donating dopant and the organic metal complex reducing dopant in the organic substance. The dispersion concentration by molar ratio of the organic substance to the electron-donating dopant and/or the organic metal complex is normally 100:1 to 1:100, preferably 5:1 to 1:5.

In a case where at least one of the electron-donating dopant and the organic metal complex is formed into the shape of a layer, the light emitting material or electron injecting material which serves as an organic layer in the interface is formed into the shape of a layer. After that, at least one of the electron-donating dopant and the organic metal complex is solely deposited by the resistant heating deposition method to form a layer preferably having a thickness of 0.1 nm or more and 15 nm or less.

In a case where at least one of the electron-donating dopant and the organic metal complex is formed into the shape of an island, the light emitting material or the electron injecting material which serves as an organic layer in the interface is formed into the shape of an island. After that, at least one of the electron-donating dopant and the organic metal complex is solely deposited by the resistant heating deposition method to form an island preferably having a thickness of 0.05 nm or more and 1 nm or less.

In addition, the ratio of the main component (the emitting material or the electron-injecting material) to at least one of the electron-donating dopant and the organic metal complex in the organic EL device of the invention is preferably 5:1 to 1:5, more preferably 2:1 to 1:2 in terms of molar ratio.

Each layer of the organic EL device of the invention can be formed by using known methods including the dry-type film formation such as vacuum deposition, sputtering, plasma, ion-plating or the like and the wet-type film formation such as spin coating, dipping, flow coating or the like.

The film thickness of each layer is not particularly limited, but should be set to be a proper thickness. If the film thickness is too large, a large voltage is required to be applied in order to obtain the predetermined light output, thereby leading to lowering in efficiency. If the film thickness is too small, due to generation of pinholes or the like, sufficient luminance cannot be obtained when an electric field is applied. Normally, the film thickness is preferably 5 nm to 10 μm, and the range of 10 nm to 0.2 μm is further preferable.

EXAMPLES

Synthesis of Compound

Synthesis Example 1

Compound 1 was synthesized by the following synthesis scheme.

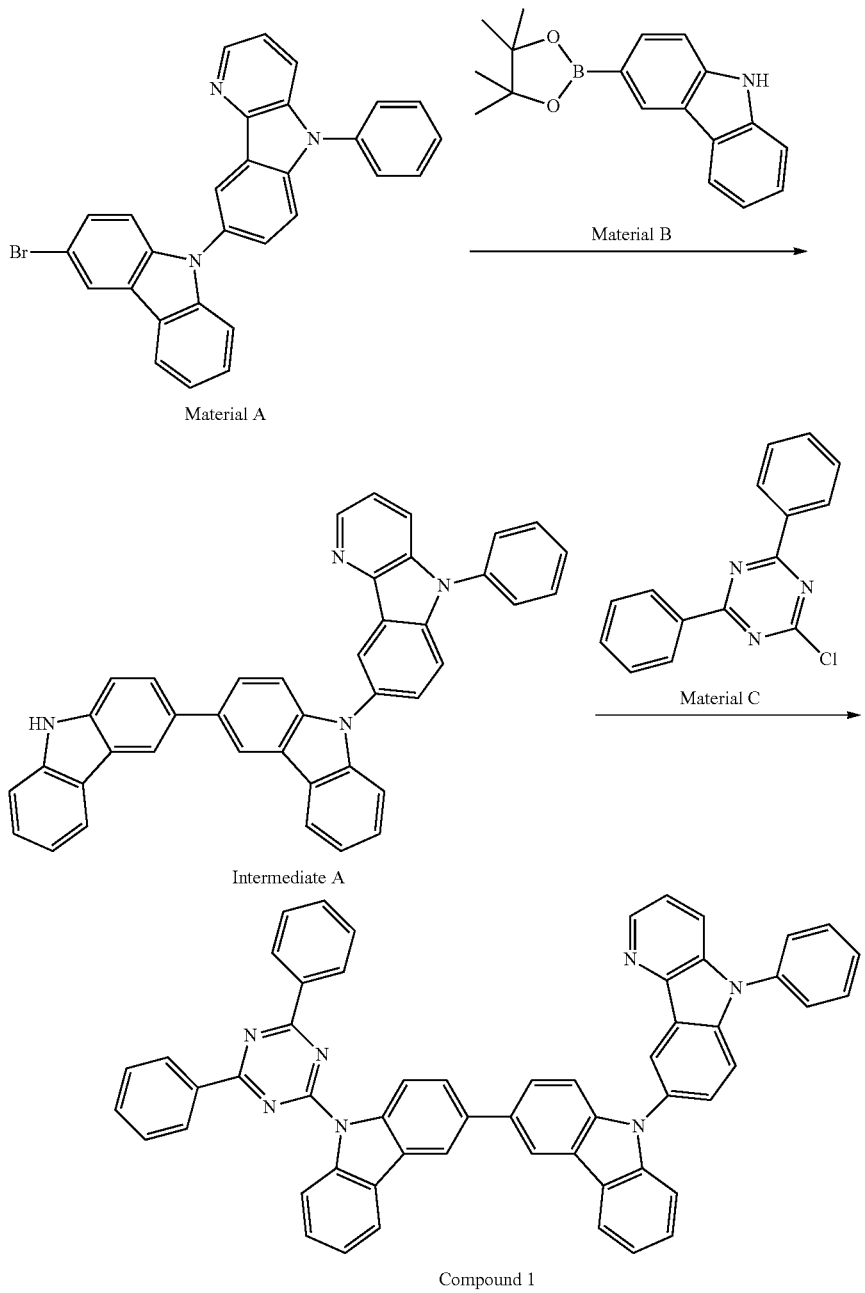

In an argon atmosphere, 4.9 g (10 mmol) of material A, 2.9 g (10 mmol) of material B, 460 mg (0.4 mmol) of tetrakis(triphenylphosphine)palladium(0), 3.2 g (30 mmol) of sodium carbonate, 15 ml of water and 60 mL of dimethoxyethane were put in a three-necked flask. The mixture was stirred while heating under reflux for 20 hours. The reaction mixture was cooled to room temperature, and water was added to the reaction mixture. The resulting mixture was stirred at room temperature for an hour, followed by addition of methanol. The resulting solids were taken out by filtration and purified by means of silica gel column chromatography to obtain 3.8 g (yield: 66%) of intermediate A.

In an argon atmosphere, 3.0 g (5.2 mmol) of intermediate A, 1.4 g (5.2 mmol) of intermediate C, 137 mg (0.150 mmol)

of tris(dibenzylideneacetone)dipalladium(0), 86 mg (0.3 mmol) of tri-t-butylphosphine tetrafluoroborate and 50 mL of dried xylene were put in a three-necked flask. The mixture was stirred while heating under reflux. To the mixture, 790 mg (7.28 mmol) of sodium t-butoxide was added and stirred for 12 hours. The reaction mixture was cooled to room temperature. By adding methanol, the precipitate obtained was taken out by filtration. The precipitate was purified by silica gel column chromatography and recrystallized to obtain 2.1 g (yield: 50%) of compound 1.

For the solids obtained, the molecular weight was measured by FD-mass spectrum. It was found to be 805.

Synthesis Example 2

Compound 2 was synthesized by the following synthesis scheme.

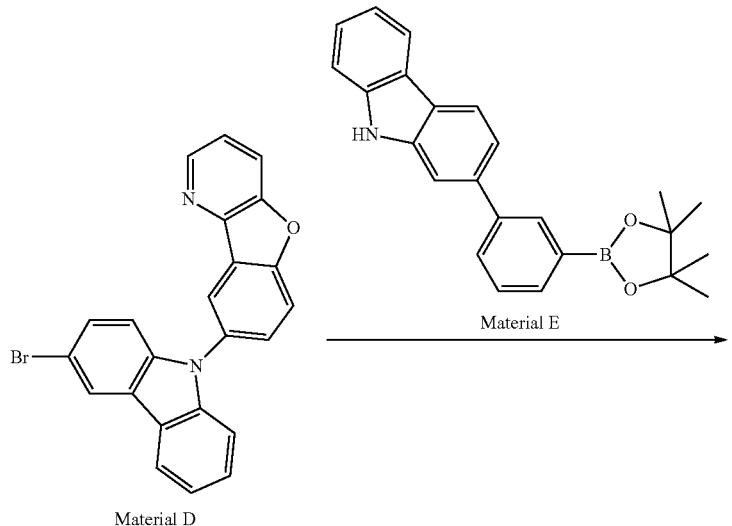

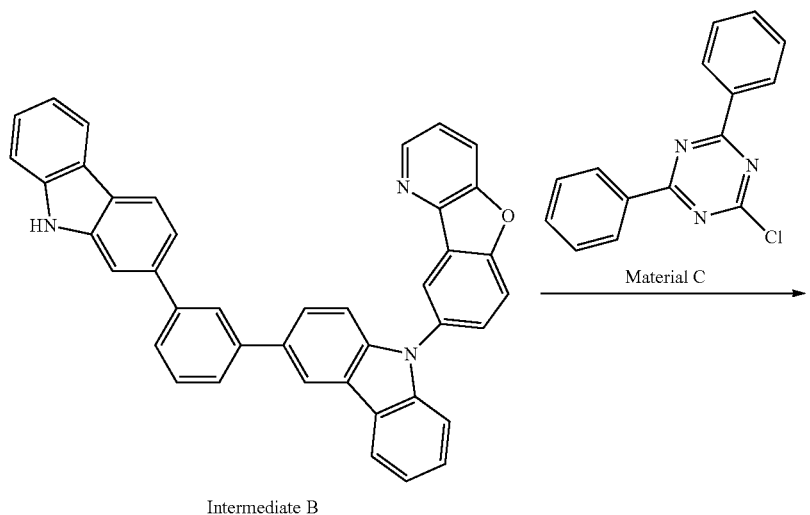

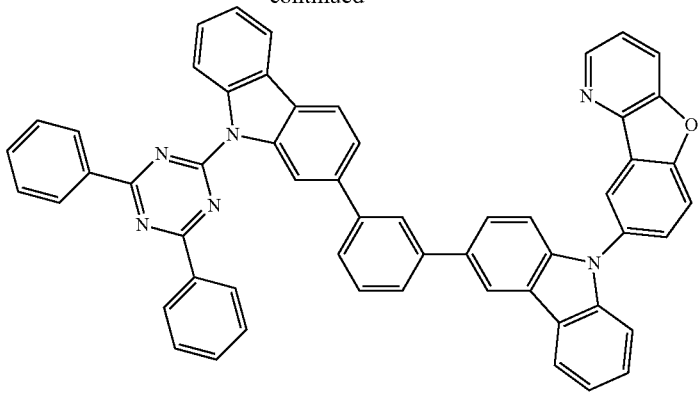

Compound 2

In an argon atmosphere, 4.1 g (10 mmol) of material D, 3.7 g (10 mmol) of material E, 460 mg (0.4 mmol) of tetrakis(triphenylphosphine)palladium(0), 3.2 g (30 mmol) of sodium carbonate, 15 ml of water and 80 mL of dimethoxyethane were put in a three-necked flask. The mixture was stirred while heating under reflux for 20 hours. The reaction mixture was cooled to room temperature, and water was added to the reaction mixture. The resulting mixture was stirred at room temperature for one hour, followed by addition of methanol. The resulting solids were taken out by filtration and purified by means of silica gel column chromatography to obtain 3.1 g (yield: 54%) of intermediate B.

In an argon atmosphere, 3.0 g (5.2 mmol) of intermediate B, 1.4 g (5.2 mmol) of intermediate C, 137 mg (0.150 mmol) of tris(dibenzylideneacetone)dipalladium(0), 86 mg (0.3 mmol) of tri-t-butylphosphine tetrafluoroborate and 50 mL of dried xylene were put in a three-necked flask. The mixture was stirred while heating under reflux. To the mixture, 790 mg (7.28 mmol) of sodium t-butoxide was added and stirred for 12 hours. The reaction mixture was cooled to room temperature. By adding methanol, the precipitate obtained was taken out by filtration. The precipitate was purified by silica gel column chromatography and recrystallized to obtain 2.0 g (yield: 47%) of compound 2.

For the solids obtained, the molecular weight was measured by FD-mass spectrum. It was found to be 806.

Synthesis Example 3

Compound 3 was synthesized by the following synthesis scheme.

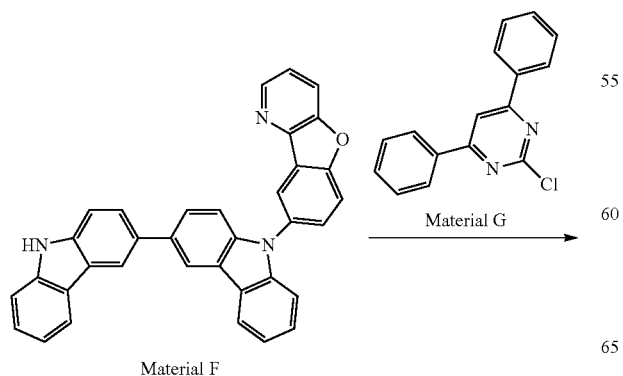

Material F

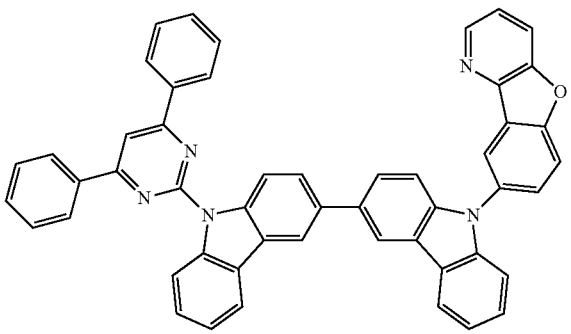

Compound 3

In an argon atmosphere, 3.0 g (6.0 mmol) of material F, 1.6 g (6.0 mmol) of material G, 164 mg (0.18 mmol) of tris(dibenzylideneacetone)dipalladium(0), 103 mg (0.36 mmol) of tri-t-butylphosphine tetrafluoroborate and 50 mL of dried xylene were put in a three-necked flask. The mixture was stirred while heating under reflux. To the mixture, 815 mg (8.48 mmol) of sodium t-butoxide was added and stirred for 4 hours. The reaction mixture was cooled to room temperature. By adding methanol, the precipitate obtained was taken out by filtration. The precipitate was purified by silica gel column chromatography and recrystallized to obtain 1.4 g (yield: 31%) of compound 3.

For the solids obtained, the molecular weight was measured by FD-mass spectrum. It was found to be 729.

Synthesis Example 4

Compound 4 was synthesized by the following synthesis scheme.

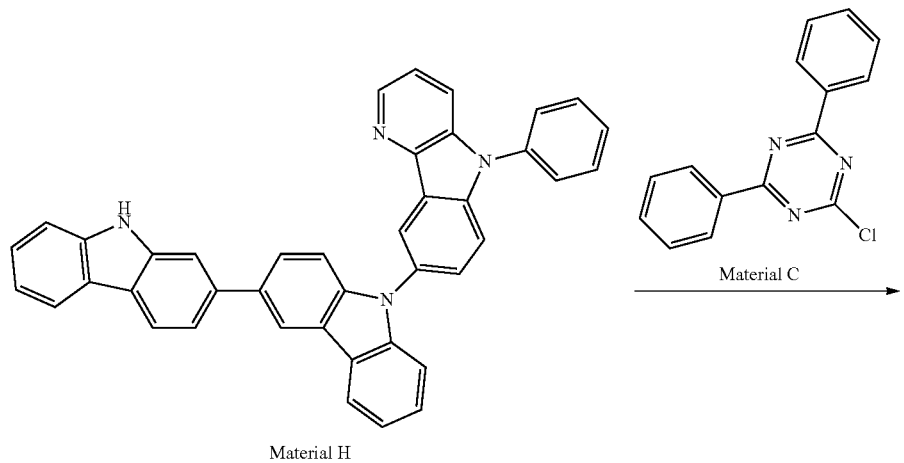

Material H

Material C

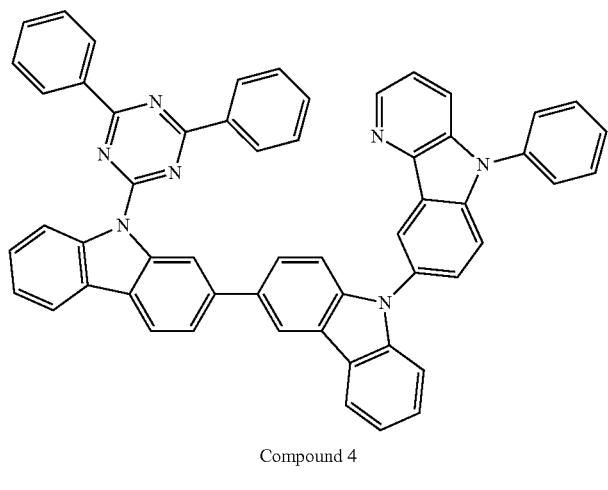

Compound 4

In an argon atmosphere, 3.0 g (5.2 mmol) of material H, 1.4 g (5.2 mmol) of material C, 137 mg (0.15 mmol) of tris(dibenzylideneacetone)dipalladium(0), 86 mg (0.3 mmol) of tri-t-butylphosphine tetrafluoroborate and 50 mL of dried xylene were put in a three-necked flask. The mixture was stirred while heating under reflux. To the mixture, 790 mg (7.28 mmol) of sodium t-butoxide was added and stirred for 12 hours. The reaction mixture was cooled to room temperature. By adding methanol, the precipitate obtained was taken out by filtration. The precipitate was purified by silica gel column chromatography and recrystallized to obtain 1.9 g (yield: 45%) of compound 4.

For the solids obtained, the molecular weight was measured by FD-mass spectrum. It was found to be 805.

Synthesis Example 5

Compound 5 was synthesized by the following synthesis scheme.

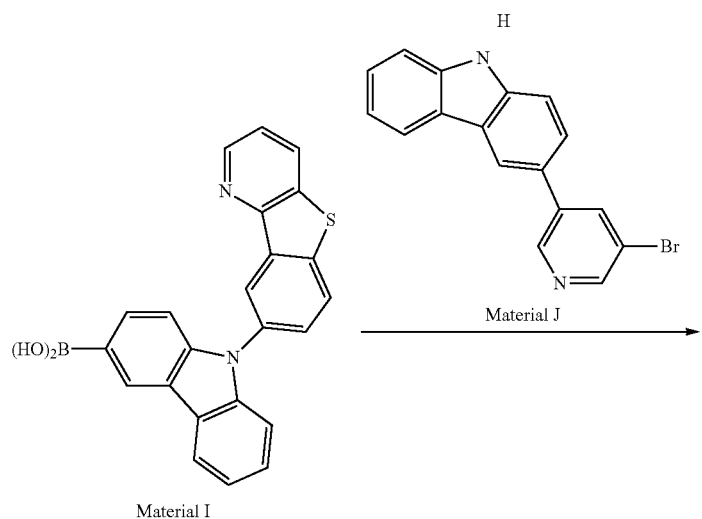
Material I
Material J
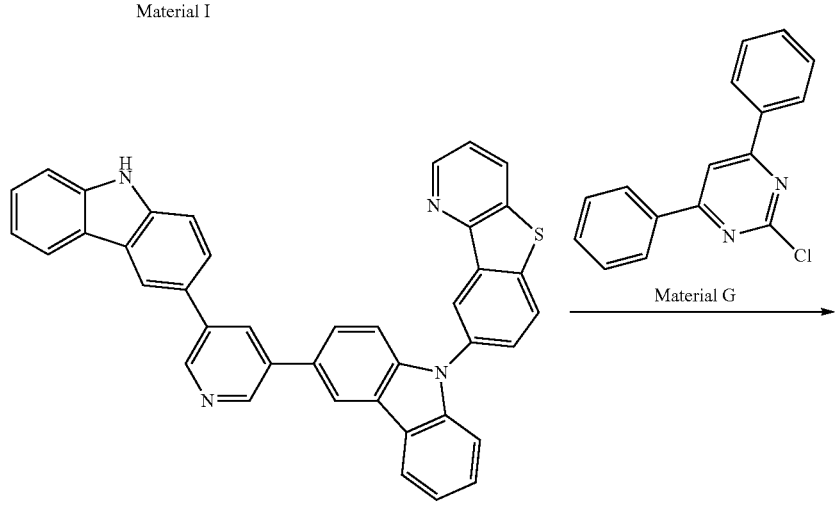
Intermediate C
Material G
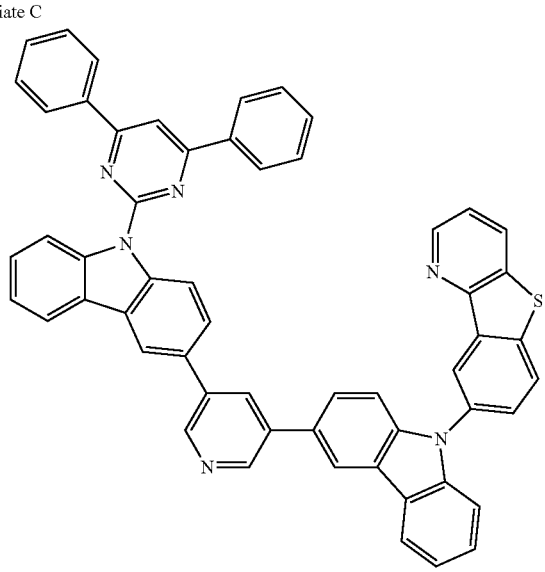
Compound 5
In an argon atmosphere, 3.9 g (10 mmol) of material I, 3.2 g (10 mmol) of material J, 462 mg (0.4 mmol) of tetrakis(triphenylphosphine)palladium(0), 80 ml of toluene, 40 mL of dimethoxyethane and 15.1 g of a 2M aqueous solution of sodium carbonate were mixed. The mixture was stirred for 12 hours at 85° C. The reaction mixture was cooled to room temperature and water was added to the reaction mixture. The resulting mixture was stirred for an hour. After filtration, the resultant was extracted with dichloromethane. The organic phase was washed with water, and then saturated saline. After drying with sodium sulfate, the solvent was distilled away under reduced pressure. The residue was purified by means of silica gel column chromatography and recrystallized to obtain 3.2 g (yield: 54%) of intermediate C.

In an argon atmosphere, 3.0 g (5.1 mmol) of intermediate C, 1.4 g (5.1 mmol) of material G, 137 mg (0.15 mmol) of tris(dibenzylideneacetone)dipalladium(0), 86 mg (0.30 mmol) of tri-t-buthylphosphine tetrafluoroborate and 50 mL of dried xylene were put in a three-necked flask. The mixture was stirred while heating under reflux. To the mixture, 680 mg (7.1 mmol) of sodium t-butoxide was added and stirred for 4 hours. The reaction mixture was cooled to room temperature. By adding methanol, the precipitate obtained was taken out by filtration. The precipitate was purified by silica gel column chromatography and recrystallized to obtain 1.6 g (yield: 38%) of compound 5.

For the solids obtained, the molecular weight was measured by FD-mass spectrum. It was found to be 822.

Synthesis Example 6

Compound 6 was synthesized by the following synthesis scheme.

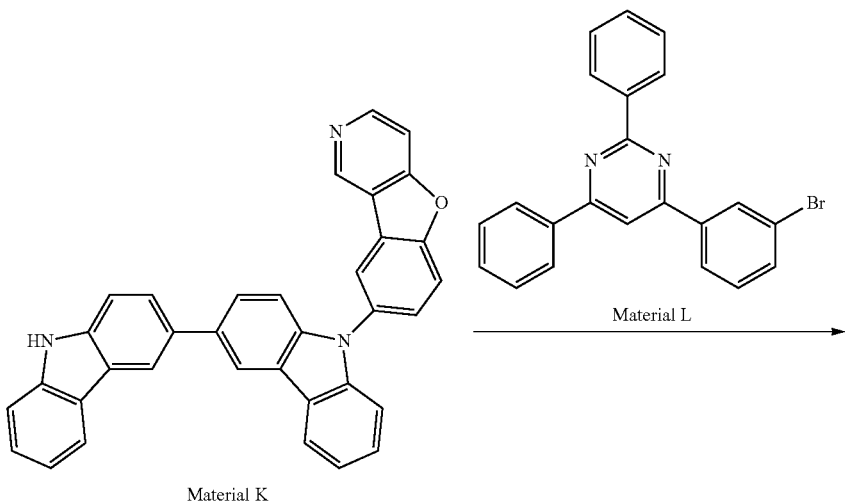

Material K

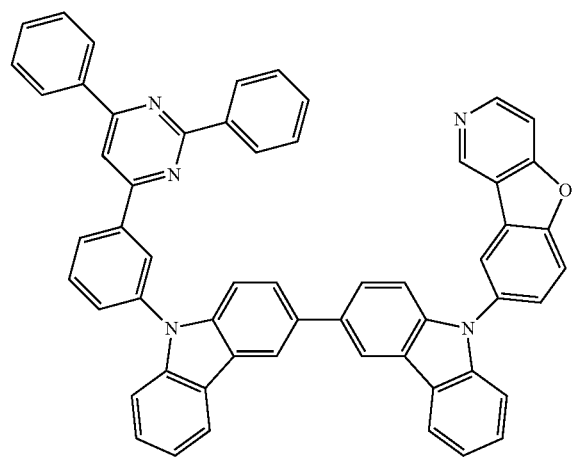

Compound 6

In an argon atmosphere, 3.0 g (6.0 mmol) of material K, 2.4 g (6.0 mmol) of material L, 330 mg (0.36 mmol) of tris(dibenzylideneacetone)dipalladium(0), 212 mg (0.72 mmol) of tri-t-butylphosphine tetrafluoroborate, 806 mg (8.4 mmol) of sodium t-butoxide and 70 mL of dried xylene were put in a three-necked flask. The mixture was stirred while heating under reflux for 16 hours. After the reaction mixture was cooled to room temperature and subjected to filtration with Celite™ (manufactured by Celite Corporation), the solvent was distilled away under reduced pressure. The residue was purified by means of silica gel column chromatography and recrystallized to obtain 1.8 g (yield: 37%) of compound 6.

For the solids obtained, the molecular weight was measured by FD-mass spectrum. It was found to be 805.

Synthesis Example 7

Compound 7 was synthesized by the followina synthesis scheme.

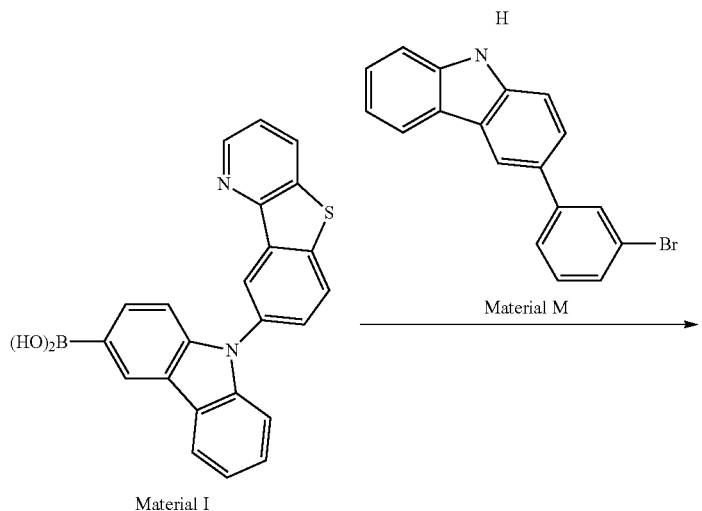

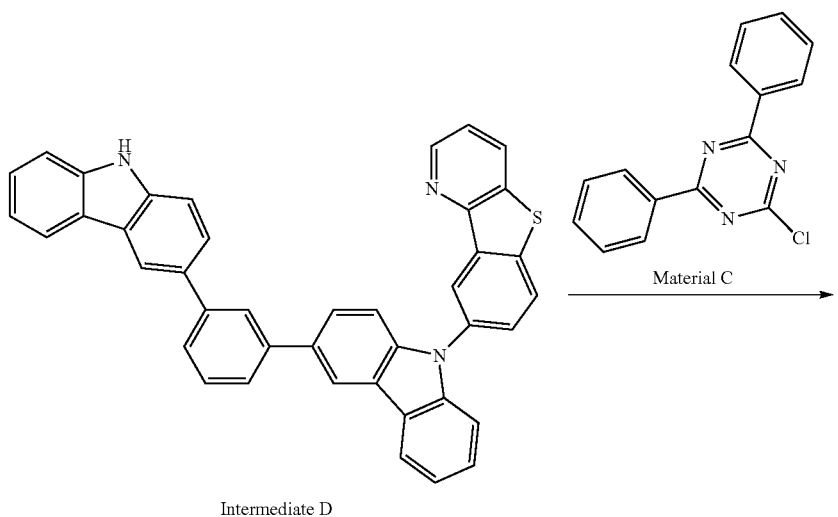

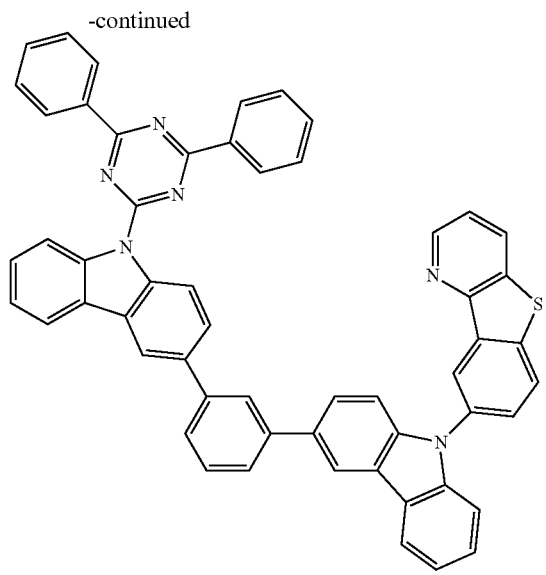

Compound 7

In an argon atmosphere, 3.9 g (10 mmol) of material I, 3.2 g (10 mmol) of material M, 462 mg (0.4 mmol) of tetrakis(triphenylphosphine)palladium(0), 80 ml of toluene, 40 mL of dimethoxyethane and 15.1 g of a 2M aqueous solution of sodium carbonate were mixed. The mixture was stirred for 12 hours at 85° C. The reaction mixture was cooled to room temperature, and water was added to the reaction mixture, followed by stirring for one hour. After filtration, the resultant was extracted with dichloromethane. The organic phase was washed with water, and then saturated saline. After drying with sodium sulfate, the solvent was distilled away under reduced pressure. The residue was purified by means of silica gel column chromatography and recrystallized to obtain 3.0 g (yield: 51%) of intermediate D.

In an argon atmosphere, 2.95 g (5.0 mmol) of intermediate D, 1.35 g (5.2 mmol) of material C, 137 mg (0.150 mmol) of tris(dibenzylideneacetone)dipalladium(0), 86 mg (0.3 mmol) of tri-t-butylphosphine tetrafluoroborate and 50 mL of dried xylene were put in a three-necked flask. The mixture was stirred while heating under reflux. To the mixture, 760 mg (7.0 mmol) of sodium t-butoxide was added and stirred for 12 hours. The reaction mixture was cooled to room temperature. By adding methanol, the precipitate obtained was taken out by filtration. The precipitate taken out was purified by silica gel column chromatography and recrystallized to obtain 1.8 g (yield: 44%) of compound 7.

For the solids obtained, the molecular weight was measured by FD-mass spectrum. It was found to be 822.

Synthesis Example 8

Compound 8 was synthesized by the following synthesis scheme.

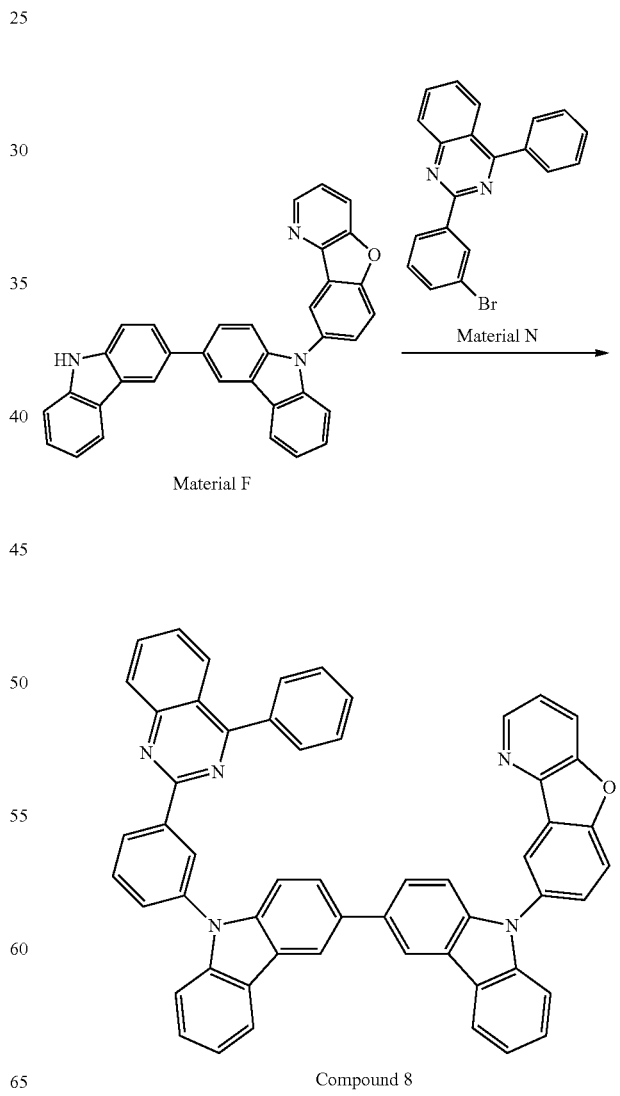

Material F

Material N

Compound 8

In an argon atmosphere, 3.0 g (6.0 mmol) of material F, 2.16 g (6.0 mmol) of material N, 330 mg (0.36 mmol) of tris(dibenzylideneacetone)dipalladium(0), 212 mg (0.72 mmol) of tri-t-butylphosphine tetrafluoroborate, 806 mg (8.4 mmol) of sodium t-butoxide and 70 mL of dried xylene were put in a three-necked flask. The mixture was heated under reflux while stirring for 14 hours. After the reaction mixture was cooled to room temperature and subjected to filtration with Celite, the solvent was distilled away under reduced pressure. The residue was purified by means of silica gel column chromatography and recrystallized to obtain 2.1 g (yield: 45%) of compound 8.

For the solids obtained, the molecular weight was measured by FD-mass spectrum. It was found to be 779.

Synthesis Example 9

Compound 9 was synthesized by the following synthesis scheme.

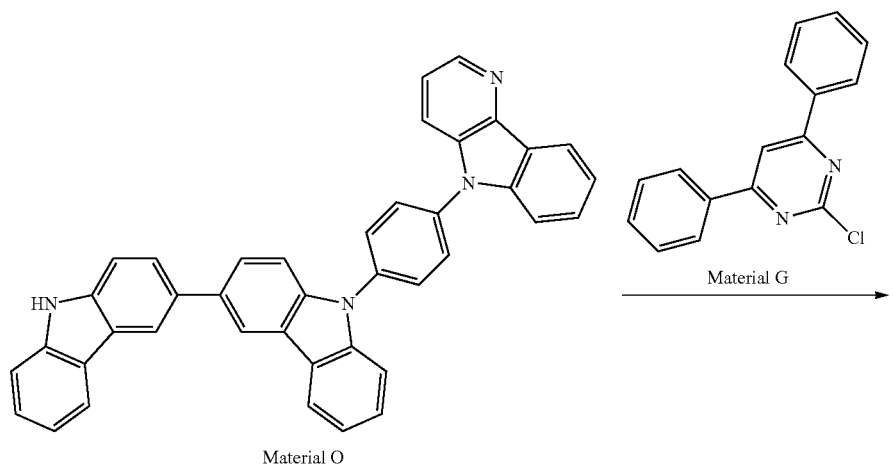

Material O · Material G

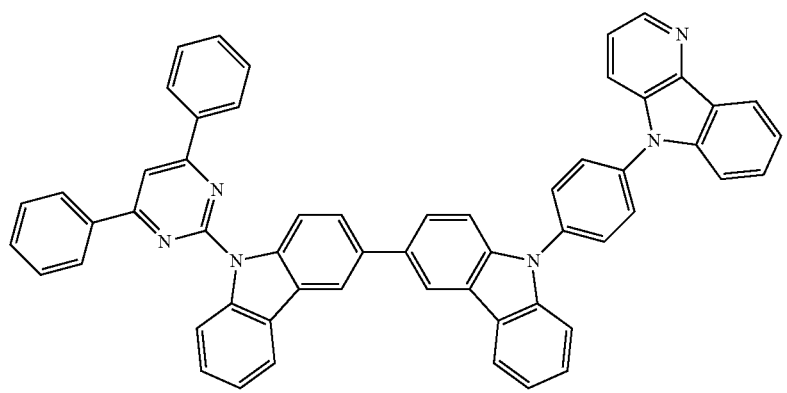

Compound 9

In an argon atmosphere, 3.4 g (6.0 mmol) of material O, 1.6 g (6.0 mmol) of material G, 164 mg (0.18 mmol) of tris(dibenzylideneacetone)dipalladium(0), 103 mg (0.36 mmol) of tri-t-butylphosphine tetrafluoroborate and 50 mL of dried xylene were put in a three-necked flask. The mixture was stirred while heating under reflux. To the resultant, 815 mg (8.48 mmol) of sodium t-butoxide was added, followed by stirring for 6 hours. After the reaction mixture was cooled to room temperature, the precipitate was taken out by filtration while adding methanol. The precipitate taken out was purified by means of silica gel column chromatography and recrystallized to obtain 1.9 g (yield: 39%) of compound 9.

For the solids obtained, the molecular weight was measured by FD-mass spectrum. It was found to be 804.

Synthesis Example 10

Compound 10 was synthesized by the following synthesis scheme.

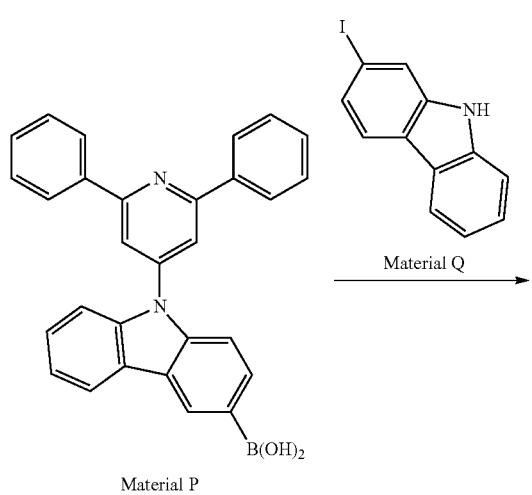

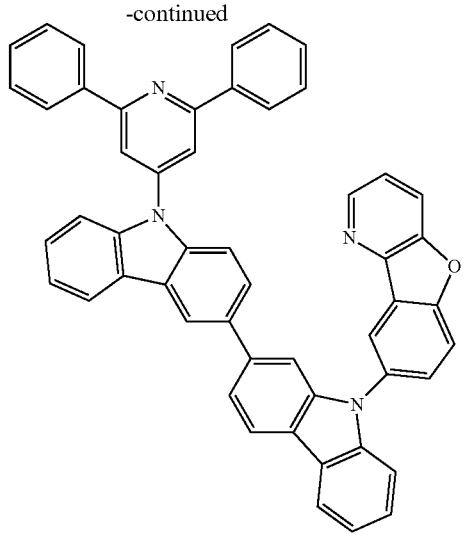

Compound 10

In an argon atmosphere, 3.0 g (6.8 mmol) of material P, 2.0 g (6.8 mmol) of material Q, 111 mg (0.136 mmol) of [1,1'-bis(diphenylphosphino)ferrocene]dichloropalladium (II), 2.16 g (20.4 mmol) of sodium carbonate, 10 ml of water and 80 mL of dried toluene were put in a three-necked flask. The mixture was heated under reflux while stirring for 18 hours. After the reaction mixture was cooled to room temperature and subjected to filtration with celite, the solvent was distilled away under reduced pressure. The residue was purified by means of silica gel column chromatography and recrystallized to obtain 2.5 g (yield: 66%) of intermediate E.

For the solids obtained, the molecular weight was measured by FD-mass spectrum. It was found to be 561.

In an argon atmosphere, 2.2 g (4.0 mmol) of intermediate E, 990 mg (4.0 mmol) of material R, 340 mg (0.372 mmol) of tris(dibenzylideneacetone)dipalladium(0), 218 mg (0.75 mmol) of tri-t-buthylphosphine tetrafluoroborate, 834 mg (8.68 mmol) of sodium t-butoxide and 50 mL of dried xylene were put in a three-necked flask. The mixture was heated under reflux while stirring for 20 hours. After the reaction mixture was cooled to room temperature and subjected to filtration with celite, the solvent was distilled away under reduced pressure. The residue was purified by means of silica gel column chromatography and recrystallized to obtain 1.5 g (yield: 51%) of compound 10.

For the solids obtained, the molecular weight was measured by FD-mass spectrum. It was found to be 782.

For the above-mentioned compounds 1 to 10, the triplet energy was determined. The triplet energy was measured using F-4500 (manufactured by Hitachi, Ltd.). The triplet energy was converted by the following expression:

Triplet Energy (eV)=1239.85/$\lambda_{mph}$

In the formula, "$\lambda_{ph}$ (unit: nm)" is determined as follows. When a tangent line is drawn against the rise in the shorter-wavelength side of the phosphorescence spectrum (vertical axis: phosphorescence intensity, horizontal axis: wavelength), "fledge" refers to the wavelength at the intersection of the tangent line and the horizontal axis.

Each compound was dissolved in a solvent (sample: 10 μmol/l, EPA (diethylether:isopentane:ethanol=5:5:5 (volume ratio), each solvent with a grade for spectroanalysis)) to obtain a sample for phosphorescent measurement. The sample for phosphorescent measurement put in a quartz cell was cooled to 77 (K) and irradiated with excitation light. The phosphorescence intensity was measured while changing wavelengths. The phosphorescence spectrum is plotted by taking phosphorescence intensities on the vertical axis and wavelengths on the horizontal axis.

A tangent line was drawn to the rise in the shorter-wavelength side of the phosphorescence spectrum, and a wavelength value $\lambda_{ph}$ (nm) at the intersection of the tangent line and the horizontal axis was obtained.

The tangent line to the rise in the shorter-wavelength side of the phosphorescence spectrum is drawn as follows. In a curve of phosphorescent spectrum, among the maximal values of the spectrum from the short-wavelength side to a maximal value in the shortest-wavelength side, a tangent line at each point on the curve towards the longer wavelength side is considered. The slope of each tangent line is increased with a rise in the curve (i.e. with an increase in vertical axis). A tangent line drawn at a point where the slope becomes maximum is defined as a tangent line to the rise on the short wavelength side of the phosphorescent spectrum.

Here, a maximal point having a peak intensity of 10% or less of the maximum peak intensity of the spectrum is not included in the above-mentioned maximal value in the shortest-wavelength side. The tangent line drawn to a point that is closest to the maximal point in the shortest-wavelength side and the value of whose slope becomes maximum is defined as the tangent line to the rise in the shorter-wavelength side of the phosphorescence spectrum.

The triplet energies for compounds 1 to 10 and the materials 4 and 6 as a phosphorescent material described later are shown in Table 1.

TABLE 1

| | Triplet Energy (eV) |
|---|---|
| Compound 1 | 2.9 |
| Compound 2 | 2.8 |
| Compound 3 | 2.9 |
| Compound 4 | 2.8 |
| Compound 5 | 2.8 |
| Compound 6 | 2.9 |
| Compound 7 | 2.9 |
| Compound 8 | 2.6 |
| Compound 9 | 2.8 |
| Compound 10 | 2.8 |
| Material 4 | 2.6 |
| Material 6 | 2.1 |

[Fabrication of Organic EL Device]

Organic EL devices were prepared using the compounds obtained in the above-mentioned Synthesis Examples. Materials used in the following Examples are shown below.

Material 1

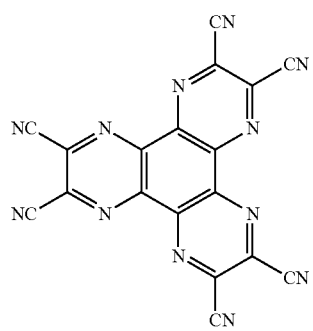

Material 2

Material 3

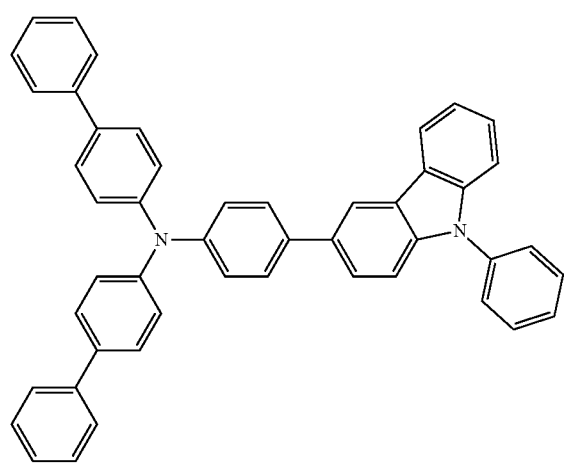

Material 4

-continued

Material 5

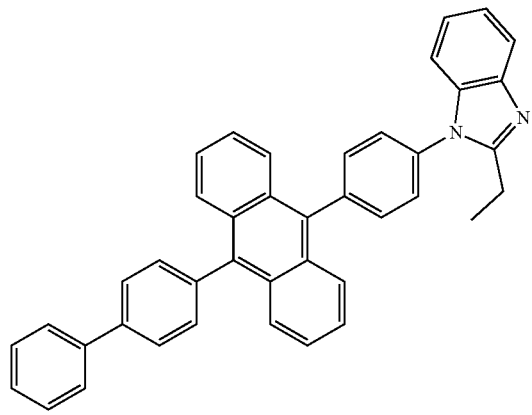

Material 6

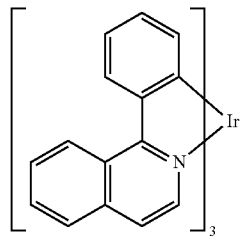

Material 7

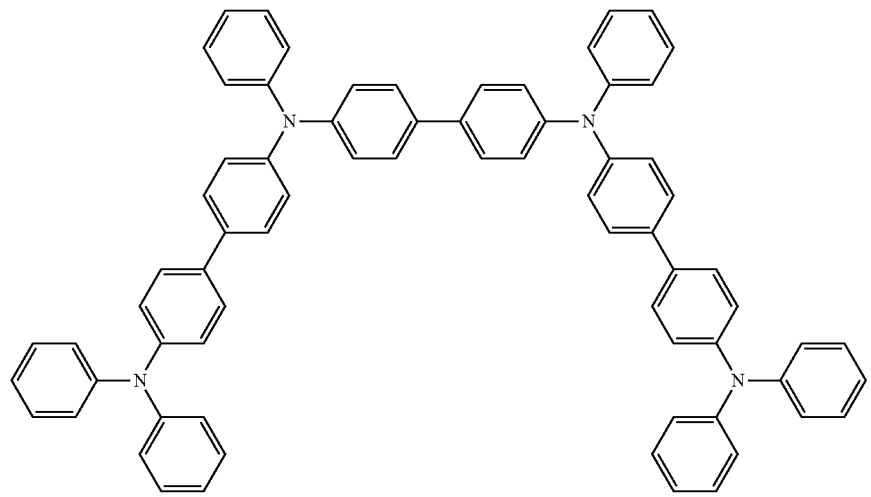

Material 8

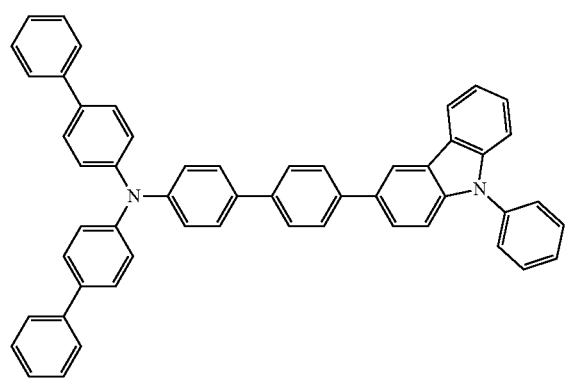

Material 9

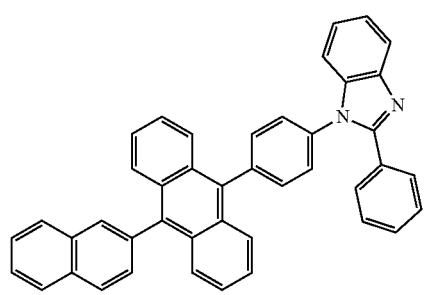

Example 1

A glass substrate (size: 25 mm×75 mm×1.1 mm thick, manufactured by Geomatec Co., Ltd.) having an ITO transparent electrode was subjected to ultrasonic-cleaning in isopropyl alcohol for five minutes, and then UV (Ultraviolet)/ozone-cleaning for 30 minutes. The film thickness of ITO was 70 nm.

The cleaned glass substrate having a transparent electrode was mounted on a substrate holder of a vacuum evaporation apparatus. Initially, material 1 was deposited on a surface of the glass substrate where the transparent electrode was provided so as to cover the transparent electrode, thereby forming a 5 nm-thick film of material 1. This film served as a hole-injecting layer. Next, on this film, material 2 was deposited to form a 65 nm-thick film, thereby to obtain a first hole-transporting layer. Subsequently, on this film, material 3 was deposited to form a 10 nm-thick film, thereby to obtain a second hole-transporting layer.

On the hole-transporting layer, compound 1 obtained in Synthesis Example 1 as a phosphorescent host material and material 4 (facial body) as a phosphorescent material were co-deposited to form a 25 nm-thick film, thereby to obtain a phosphorescent emitting layer. In the phosphorescent emitting layer, the concentration of compound 1 was 90% by mass, and the concentration of material 4 was 10% by mass.

Subsequently, on this phosphorescent emitting layer, material 5 was deposited to form a 35 nm-thick film, thereby to obtain an electron-transporting layer. Further, LiF and Al were stacked sequentially to form a 1 nm-thick film and an 80 nm-thick film, respectively, thereby to obtain a cathode. LiF, which is an electron-injecting electrode, was formed at a rate of 0.1 Å/min, whereby an organic EL device was prepared.

[Evaluation of Luminescent Performance of Organic EL Device]

The organic EL devices prepared were driven by DC current, thereby causing them to emit. Then, the luminance and the current density were measured, whereby the voltage and the luminous efficiency (external quantum efficiency) at a current density of 10 mA/cm$^2$ were determined. The results are shown in Table 2.

Examples 2 to 8

Organic EL devices were prepared and evaluated in the same manner as in Example 1, except that as the phosphorescent host material, the compounds shown in Table 2 were used instead of compound 1. The results are shown in Table 2.

Comparative Examples 1 and 2

Organic EL devices were prepared and evaluated in the same manner as in Example 1, except that as the phosphorescent host material, the following comparative compound 1 or 2 shown in Table 2 was used respectively instead of compound 1. The results are shown in Table 2.

Comparative Compound 1

Comparative Compound 2

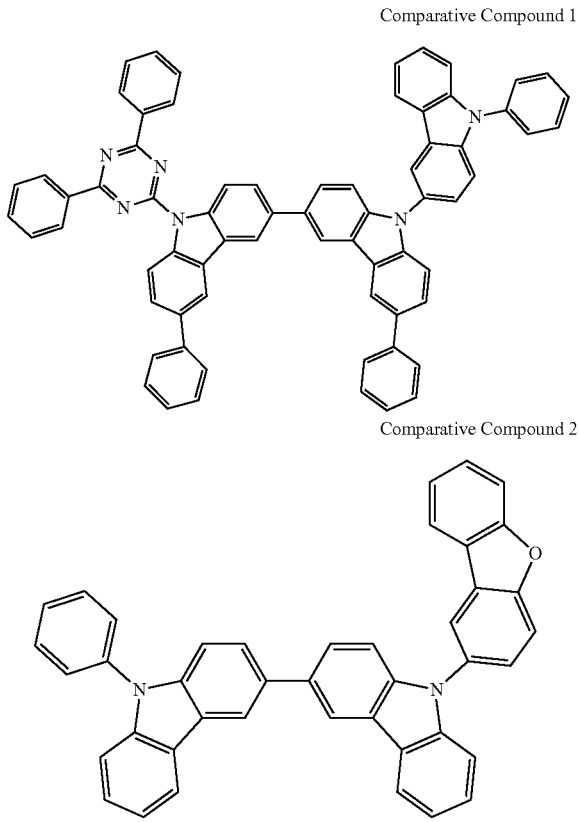

TABLE 2

| Emitting layer Host material | Voltage (V) | External quantum efficiency |
| --- | --- | --- |
| Example 1 | Compound 1 | 3.2 | 18.7 |
| Example 2 | Compound 2 | 3.3 | 17.8 |
| Example 3 | Compound 3 | 3.1 | 19.8 |
| Example 4 | Compound 4 | 3.0 | 17.3 |
| Example 5 | Compound 5 | 3.0 | 17.2 |
| Example 6 | Compound 6 | 3.3 | 17.5 |
| Example 7 | Compound 7 | 3.4 | 16.8 |
| Example 8 | Compound 9 | 3.3 | 18.2 |
| Com. Ex. 1 | Com. Compound 1 | 3.9 | 15.1 |
| Com. Ex. 2 | Com. Compound 2 | 4.0 | 17.2 |

Example 9

A glass substrate (size: 25 mm×75 mm×1.1 mm thick, manufactured by Geomatec Co., Ltd.) having an ITO transparent electrode was subjected to ultrasonic-cleaning in isopropyl alcohol for five minutes, and then UV(Ultraviolet)/ozone-cleaning for 30 minutes. The film thickness of ITO was 130 nm.

The cleaned glass substrate having the transparent electrode was mounted on a substrate holder of a vacuum evaporation apparatus. Initially, material 1 was deposited on a surface of the glass substrate where the transparent electrode was provided so as to cover the transparent electrode, thereby forming a 5 nm-thick film of material 1. This film served as a hole-injecting layer. Next, on this film, material 7 was deposited to form a 50 nm-thick film, thereby to obtain a first hole-transporting layer. Subsequently, on this film, material 8 was deposited to form a 60 nm-thick film, thereby to obtain a second hole-transporting layer.

On the hole-transporting layer, compound 4 obtained in Synthesis Example 4 as a phosphorescent host material and material 6 (facial body) as a phosphorescent material were co-deposited to form a 45 nm-thick film, thereby to obtain a phosphorescent emitting layer. In the phosphorescent emitting layer, the concentration of compound 4 was 92% by mass, and the concentration of material 6 was 8% by mass.

Subsequently, on this phosphorescent emitting layer, material 9 was deposited to form a 30 nm-thick film, thereby to obtain an electron-transporting layer. Further, LiF and Al were stacked sequentially to form a 1 nm-thick film and an 80 nm-thick film, respectively, thereby to obtain a cathode. LiF, which is an electron-injecting electrode, was formed at a rate of 0.1 Å/min, whereby an organic EL device was prepared.

[Evaluation of Luminescent Performance of Organic EL Device]

The organic EL devices prepared were driven by DC current, thereby causing them to emit at a luminance of 2000 cd/m$^2$. Then the voltage and luminous efficiency (cd/A) were determined. The results are shown in Table 3.

Examples 10 and 11

Organic EL devices were prepared and evaluated in the same manner as in Example 9, except that, as the phosphorescent host material, the compounds shown in Table 3 were used instead of compound 4. The results are shown in Table 3.

Comparative Examples 3 and 4

Organic EL devices were prepared and evaluated in the same manner as in Example 9, except that as the phosphorescent host material, the compounds shown in Table 3 were used instead of compound 4. The results are shown in Table 3.

TABLE 3

| | Emitting layer Host material | Emitting layer Emitting material | Voltage (V) | Luminous efficiency (cd/A) |
|---|---|---|---|---|
| Example 9 | Compound 4 | Material 6 | 3.4 | 10 |
| Example 10 | Compound 8 | Material 6 | 3.2 | 12 |
| Example 11 | Compound 10 | Material 6 | 3.2 | 11 |
| Com. Ex. 3 | Com. Compound 1 | Material 6 | 4.0 | 7.8 |
| Com. Ex. 4 | Com. Compound 2 | Material 6 | 4.2 | 5.6 |

From the results of Examples, it was confirmed that, by using of the compound of the invention in an emitting layer, a device which could be driven at a lower voltages and had a high efficiency as compared with those in Comparative Examples can be obtained.

INDUSTRIAL APPLICABILITY

The compound of the invention can be used in an organic EL device, an organic EL display, lightning, an organic semiconductor, an organic solar cell and the like.

The organic EL device of the invention can be used as a planar emitting body such as a flat panel display of a wall-hanging television, backlight of a copier, a printer, or a liquid crystal display, light sources for instruments, a display panel, a navigation light, and the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification and the Japanese patent applications claiming the priority under the Paris Convention to the invention are incorporated herein by reference in its entirety.

The invention claimed is:

1. An organic electroluminescence device comprising:
an emitting layer between a cathode and an anode; and
two or more electron-transporting layers between the emitting layer and the cathode;
wherein at least one of the electron-transporting layers comprises a compound represented by the following formula (1); and the identical or other electron-transporting layer comprises a heteroaromatic hydrocarbon ring compound including a nitrogen-containing six-member ring skeleton or a nitrogen-containing five-member ring skeleton, or a heterofused aromatic ring compound including a nitrogen-containing six-member ring skeleton or a nitrogen-containing five-member ring skeleton:

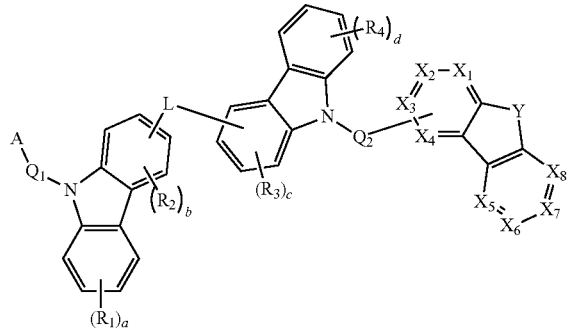

wherein in the formula (1),
L, $Q_1$ and $Q_2$ are independently a single bond or a linking group;
A is a substituted or unsubstituted nitrogen-containing heterocyclic group including 5 to 10 ring atoms;
$X_1$ to $X_8$ are independently a carbon atom that is bonded to $Q_2$, CH or N, provided that at least one of $X_1$ to $X_8$ is N;
Y is O, S, a nitrogen atom that is bonded to $Q_2$, or $NR_5$;
$R_1$ to $R_5$ are independently a substituted or unsubstituted aryl group including 6 to 18 ring carbon atoms, a substituted or unsubstituted heteroaryl group including 5 to 18 ring atoms, a substituted or unsubstituted alkyl group including 1 to 20 carbon atoms, a substituted or unsubstituted alkoxy group including 1 to 20 carbon atoms, a substituted or unsubstituted haloalkyl group including 1 to 20 carbon atoms, a substituted or unsubstituted haloalkoxy group including 1 to 20 carbon atoms, or a cyano group; and
a and d are independently an integer of 0 to 4, and b and c are independently an integer of 0 to 3 when a is 2 or more $R_1$s ma be the same or different from each other when b is 2 or more, $R_2$s may be the same or different from each other, when c is 2 or more, $R_3$s may be the same or different from each other, and when d is 2 or more, $R_4$s may be the same or different from each other.

2. The organic electroluminescence device according to claim 1, wherein A is a group including a substituted or unsubstituted pyridine ring, a substituted or unsubstituted pyrimidine ring, a substituted or unsubstituted triazine ring, a substituted or unsubstituted pyrazine ring or a substituted or unsubstituted quinazoline ring.

3. The organic electroluminescence device according to claim 1, wherein the emitting layer is a phosphorescent emitting layer.

4. The organic electroluminescence device according to claim 1, wherein the emitting layer comprises a fluorescent emitting layer.

5. The organic electroluminescence device according to claim 1, wherein the heteroaromatic hydrocarbon ring compound is a compound containing a pyridine ring, a pyrimidine ring, or a triazine ring in the skeleton.

6. The organic electroluminescence device according to claim 1, wherein the heteroaromatic hydrocarbon ring compound is a compound containing a benzimidazole ring, a phenanthroline ring, or a quinazoline ring in the skeleton.

7. The organic electroluminescence device according to claim 1, wherein the identical or other electron-transporting layer comprises an electron-donating dopant or an organic metal complex.

8. The organic electroluminescence device according to claim 7, wherein the electron-donating dopant is at least one selected from an alkali metal, an alkali metal compound, an alkaline-earth metal, an alkaline-earth metal compound, a rare-earth metal and a rare-earth metal compound.

9. The organic electroluminescence device according to claim 7, wherein the organic metal complex is at least one selected from an organic metal complex including an alkali metal, an organic metal complex including an alkaline-earth metal and an organic metal complex including a rare-earth metal.

10. The organic electroluminescence device according to claim 1, wherein a to d in the formula (1) are 0.

11. An organic electroluminescence device comprising:
an emitting layer between a cathode and an anode and;
two or more electron-transporting layers between the emitting layer and the cathode;
wherein at least one of the electron-transporting layers comprises a compound represented by the following formula (1):

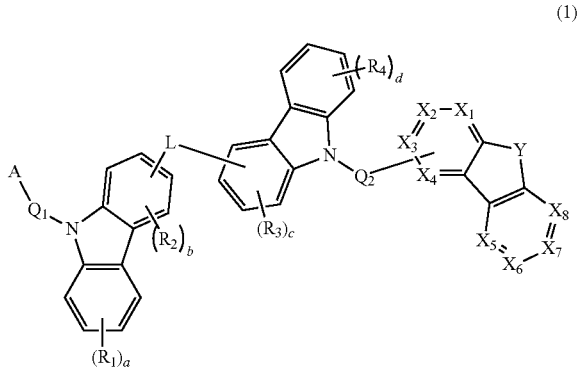

(1)

wherein in the formula (1),
L, $Q_1$ and $Q_2$ are independently a single bond or a linking group;
A is a substituted or unsubstituted nitrogen-containing heterocyclic group including 5 to 10 ring atoms;
$X_1$ to $X_8$ are independently a carbon atom that is bonded to $Q_2$, CH or N, provided that at least one of $X_1$ to $X_8$ is N;
Y is O, S, a nitrogen atom that is bonded to $Q_2$, or $NR_5$;
$R_1$ to $R_5$ are independently a substituted or unsubstituted aryl group including 6 to 18 ring carbon atoms, a substituted or unsubstituted heteroaryl group including 5 to 18 ring atoms, a substituted or unsubstituted alkyl group including 1 to 20 carbon atoms, a substituted or unsubstituted alkoxy group including 1 to 20 carbon atoms, a substituted or unsubstituted haloalkyl group including 1 to 20 carbon atoms, a substituted or unsubstituted haloalkoxy group including 1 to 20 carbon atoms, or a cyano group; and
a and d are independently an integer of 0 to 4, and b and c are independently an integer of 0 to 3, when a is 2 or more, $R_1$s may be the same or different from each other, when b is 2 or more, $R_2$s may be the same or different from each other, when c is 2 or more, $R_3$s may be the same or different from each other, and when d is 2 or more, $R_4$s may be the same or different from each other.

12. The organic electroluminescence device according to claim 11, wherein A is a group including a substituted or unsubstituted pyridine ring, a substituted or unsubstituted pyrimidine ring, a substituted or unsubstituted triazine ring, a substituted or unsubstituted pyrazine ring or a substituted or unsubstituted quinazoline ring.

13. The organic electroluminescence device according to claim 11, wherein the emitting layer is a phosphorescent emitting layer.

14. The organic electroluminescence device according to claim 11, wherein the emitting layer comprises a fluorescent emitting layer.

15. The organic electroluminescence device according to claim 11, wherein a to d in the formula (1) are 0.

16. The organic electroluminescence device according to claim 11, wherein the at least one of the electron-transporting layers comprising the compound represented by the formula (1) or other electron-transporting layer comprises an electron-donating dopant or an organic metal complex.

17. The organic electroluminescence device according to claim 16, wherein the electron-donating dopant is at least one selected from an alkali metal, an alkali metal compound, an alkaline-earth metal, an alkaline-earth metal compound, a rare-earth metal and a rare-earth metal compound.

18. The organic electroluminescence device according to claim 16, wherein the organic metal complex is at least one selected from an organic metal complex including an alkali metal, an organic metal complex including an alkaline-earth metal and an organic metal complex including a rare-earth metal.

* * * * *